United States Patent
Swairjo et al.

(10) Patent No.: US 8,328,934 B2
(45) Date of Patent: Dec. 11, 2012

(54) CRYSTAL OF GTP CYCLOHYDROLASE TYPE IB

(75) Inventors: Manal A. Swairjo, Pomona, CA (US); Dirk Iwata-Reuyl, Portland, OR (US); Valerie de Crecy-Lagard, Gainesville, FL (US)

(73) Assignee: Western University of Health Sciences, Pomona, CA (US)

( * ) Notice: Subject to any disclaimer, the term of this patent is extended or adjusted under 35 U.S.C. 154(b) by 7 days.

(21) Appl. No.: 12/756,617

(22) Filed: Apr. 8, 2010

(65) Prior Publication Data

US 2010/0291608 A1 Nov. 18, 2010

Related U.S. Application Data

(63) Continuation-in-part of application No. 12/670,438, filed as application No. PCT/US2008/071358 on Jul. 28, 2008, now abandoned.

(60) Provisional application No. 60/935,124, filed on Jul. 26, 2007.

(51) Int. Cl.
- *C30B 7/00* (2006.01)
- *G01N 31/00* (2006.01)
- *C12N 9/78* (2006.01)

(52) U.S. Cl. .............. 117/68; 436/4; 435/227
(58) Field of Classification Search .............. None
See application file for complete search history.

(56) References Cited

U.S. PATENT DOCUMENTS 7,629,141 B2 * 12/2009 Bruce et al. ............. 435/32
2008/0201123 A1 * 8/2008 Cosgrove ............. 703/11

OTHER PUBLICATIONS

McPherson, Eur. J. Biochem. 189:1-23, 1990.*
El Yacoubi et al., J. Biol. Chem. 281:37586-37593, 2006.*
Clugston et al., Biochem. J. 377:309-316, 2004.*
GenBank Accession No. CAB12128, Apr. 2005, 2 pages.*
Gaballa et al., J. Bacteriol. 184:6508-6514, 2002.*
Kako et al., Biochem. Biophys. Res. Comm. 324:1379-1385, 2004.*
Sankaran et al., J. Bacteriol. 191:6936-6949, 2009.*

* cited by examiner

*Primary Examiner* — David J Steadman
(74) *Attorney, Agent, or Firm* — J.A. Lindeman & Co., PLLC

(57) ABSTRACT

This invention relates to a novel, bacterial GTP Cyclohydrolase Type IB enzyme, and the crystal structure thereof.

6 Claims, 9 Drawing Sheets

```
Ec-GCYHIA                     β2        TTT              β3    ...            ααα
Ec-GCYHIA  95  VDENVIVRDITLTSTCEHH.......FVTIDGKAT...VAYIPKDSVIG...LSK
Tt-GCYHIA  93  GSENVVVKGVEFYSMCEHH.......LLPFFGKVH...IGYIPDGKILG...LSK
Hs-GCYHIA 126  HDENVIVKDIDMFSMCEHH.......LVPFVGKVH...IGYLPNKQVLG...LSK
Rn-GCYHIA 117  HDENVIVKDIDMFSMCEHH.......LVPFVGRVH...IGYLPNKQVLG...LSK
Tm-GCYHIB 129  FSFKILGVR.IPVHTLCPCSKEISDYGAHNQRAFVE...ITVKTR.KFIW...FED
Bs-GCYHIB 169  FKQRAGIS.AKVTILCPCSKEISEYSAHNQRGTVKHLGRIPTRA.ASLPSDVKED
Sa-GCYHIB 162  TRKELIIE.ATVTILCPCSKEISEYSAHNQRGVVT.VKIYINKD.QDIVDDYKNK
Ng-GCYHIB 133  YGHSMKVM.IPVTSLCPCSKEISQYGAHNQRSHVT...VSLTSD.ABVG...IEE
Ng-GCYHIB                  β5    ααααα         *          ...       ααα
                                  α3                         β6

Ec-GCYHIA           α6                             β4      α7
Ec-GCYHIA       εεεεεεε                        →    εεεεεεεεεεεεεε
Ec-GCYHIA 138  INRIVQFPAQ................RPQVQERLTQQILIALQILLGTNN
Tt-GCYHIA 135  FARIVDMFAR................RLQVQERLAVQIAEAIQRVLEPQG
Hs-GCYHIA 168  LARIVELYSR................KLQVQERLTKQIAVAITEALRPAG
Rn-GCYHIA 159  LARIVELYSR................RLQVQERLTKQIAVAITEALQPAG
Tm-GCYHIB 176  LVEIAEKNASSPLYTLLKRPDEKFVTEKAYENPRFVEDVARDVALELEKDPRITW
Bs-GCYHIB 222  LPHAAESMASARLHPVLKRPDEKAVTETAYENPRFVEDLARLIAADIFELEWVSA
Sa-GCYHIB 214  ILDAMEANASSILYPILKRPDEKRVTERAYENPRFVEDLIRLIAADIVEFDWLEG
Ng-GCYHIB 180  VIDIVERQASCQLYGLLKRPDEKYVTEKAYENPKFVEDMVRDVATSLIADKRIKS
Ng-GCYHIB       εεεεεε      →  εεεεεεεεεε      εεεεεεεεεε    TT
                  α4       β7               α5              α6

Ec-GCYHIA            β5    α8    TT             β6
Ec-GCYHIA       →     αααα
Ec-GCYHIA 172  VAVSIDAVHYCVKARGIRDATSATTTTSLG
Tt-GCYHIA 171  VGVVIEGVHLCMMRGVEKQHSRTVTSAML
Hs-GCYHIA 202  VGVVIEATHMCMVRGVQKMNSKTVTSIML
Rn-GCYHIA 193  VGVVIEATHMCMVRGVQKMNSKTVTSIML
Tm-GCYHIB 231  YRVIVESMESIH........NENAFACVEK
Bs-GCYHIB 277  FEIECMNEESIH........IHRCLCEVCP
Sa-GCYHIB 269  PDIECMNEESIH........QHDAFAKLKY
Ng-GCYHIB 235  FVWESIIFESIH........NLSAYAYLAY
Ng-GCYHIB       →       TT*     *          →
                  β8                         β9
```

FIG. 4

| BACTERIAL GENOMES | folE2 gene ID | Upstream gene in putative folE2 operon preceded by candidate Zur-binding site | Distance | Candidate Zur-binding site |
|---|---|---|---|---|
| PROTEOBACTERIA | Consensus Zur-binding site: | | | nAAATGTTATAnTATAACATTTn |
| Serratia marcescens | 4_0506 | - | -46 | GttATGTTATAATATAACAaaaC |
| Klebsiella pneumoniae (virulence plasmid pLVPK) | LV189 | LV190 | -50 | atgATGTTATgTTATAACgTTTt |
| Acinetobacter sp. ADP1 | ACIAD1740 | ACIAD1741 | -127 | tAtATGTTAcATTATAACATaaC |
| Methylococcus capsulatus | MCA2318 | MCA2321 | -142 | tAgtTGTTActTTATAACATaTa |
| Chromohalobacter salexigens DSM 3043 | Csal_0191 | Csal_0192 | -89 | agAATGTTATgGTATAACATaTC |
| Hahella chejuensis KCTC 2396 | HCH_01706 | HCH_01703 | -212 | aAAAaGaTATgATTAACgTaTC |
| Pseudoalteromonas atlantica T6c | Patl_1637 | Patl_1641 | -203 | GtgATGTTSTATTgTAtCATTTa |
| Pseudomonas aeruginosa | PA5539 | - | -64 | aAtAcGTTATATTATAACATTca |
| Pseudomonas entomophila L48 | PSEEN5514 | - | -68 | GcAATGTTATATTATAACAaTaC |
| Pseudomonas fluorescens Pf-5 | PFL_6177 | - | -51 | GcAtTGTTATAATATAACATgTg |
| Pseudomonas syringae | Psyr_2269 | - | -109 | ttAATGTTATAgTgTAACgaaTt |
| Pseudomonas putida | PP3324 | PP3321 | -4 | tAgATGTTATgTTATAACAcTTa |
| Azotobacter vinelandii | S8_0188 | - | -119 | ctttTGTTATgTTATAACAcaTa |
| Xanthomonas axonopodis | XAC1781 | XAC1780 | -154 | ttgATGTTActTTATAACACTTg |
| Xanthomonas campestris | XCC1764 | XCC1763 | -153 | ctAgTGTTACtTTATAACACTTg |
| Xylella fastidiosa | XF2196 | - | -195 | GttATGTATcTTATAACATaTt |
| Burkholderia cepacia R18194 | Bcep18194_B0317 | Bcep18194_B0316 | -9 | GaAATGATATgTTATATCgTTCC |
| Burkholderia cenocepacia AU 1054 | Bcen_3035 | Bcen_3034 | -8 | GaAATGATATgTTATATCgTaGC |
| Ralstonia metallidurans | Rmet0201011 | Rmet0201010 | -100 | gAAATCAACAAgGTTCATTTa |
| BACILLI | Consensus Zur-binding site: | | | TAAATCGTAATnATTACGATTTA |
| Bacillus subtilis | yciA | - | -45 | TAAATaGTAATtATACGATTTg |
| Bacillus licheniformis | BL02349 | - | -43 | TAAATaGgAActATTCGATTTA |
| Bacillus halodurans | BH098 | - | -40 | TAAATCGTAATtATTctTATTTA |

SEQUENCE LISTING

<160> NUMBER OF SEQ ID NOS: 33

<210> SEQ ID NO 1
<211> LENGTH: 106
<212> TYPE: PRT
<213> ORGANISM: Escherichia coli

<400> SEQUENCE: 1

```
Val Asp Glu Met Val Thr Val Arg Asp Ile Thr Leu Thr Ser Thr Cys
1               5                   10                  15

Glu His His Phe Val Thr Ile Asp Gly Lys Ala Thr Val Ala Tyr Ile
            20                  25                  30

Pro Lys Asp Ser Val Ile Gly Leu Ser Lys Ile Asn Arg Ile Val Gln
        35                  40                  45

Phe Phe Ala Gln Arg Pro Gln Val Gln Lys Arg Leu Thr Gln Gln Ile
    50                  55                  60

Leu Ile Ala Leu Gln Thr Leu Leu Gly Thr Asn Asn Val Ala Val Ser
65                  70                  75                  80

Ile Asp Ala Val His Tyr Cys Val Lys Ala Arg Gly Ile Arg Asp Ala
                85                  90                  95

Thr Ser Ala Thr Thr Thr Thr Ser Leu Gly
                100                 105
```

<210> SEQ ID NO 2
<211> LENGTH: 106
<212> TYPE: PRT
<213> ORGANISM: Thermus thermophilus

<400> SEQUENCE: 2

Gly Ser Glu Met Val Val Lys Gly Val Glu Phe Tyr Ser Met Cys
1               5                   10                  15

Glu His His Leu Leu Pro Phe Phe Gly Lys Val His Ile Gly Tyr Ile
                20                  25                  30

Pro Asp Gly Lys Ile Leu Gly Leu Ser Lys Phe Ala Arg Ile Val Asp
            35                  40                  45

Met Phe Ala Arg Arg Leu Gln Val Gln Lys Arg Leu Ala Val Gln Ile
    50                  55                  60

Ala Glu Ala Ile Gln Glu Val Leu Glu Pro Gln Gly Val Gln Val Val
65                  70                  75                  80

Val Glu Gly Val His Leu Cys Met Met Met Arg Gly Val Glu Lys Gln
                85                  90                  95

His Ser Arg Thr Val Thr Ser Ala Met Leu
                100                 105

<210> SEQ ID NO 3
<211> LENGTH: 106
<212> TYPE: PRT
<213> ORGANISM: Homo sapiens

<400> SEQUENCE: 3

His Asp Glu Met Val Ile Val Lys Asp Ile Asp Met Phe Ser Met Cys
1               5                   10                  15

Glu His His Leu Val Pro Phe Val Gly Lys Val His Ile Gly Tyr Leu
                20                  25                  30

Pro Asn Lys Gln Val Leu Gly Leu Ser Lys Leu Ala Arg Ile Val Glu
            35                  40                  45

Ile Tyr Ser Arg Arg Leu Gln Val Gln Lys Arg Leu Thr Lys Gln Ile
    50                  55                  60

Ala Val Ala Ile Thr Glu Ala Leu Arg Pro Ala Gly Val Gly Val Val
65                  70                  75                  80

Val Glu Ala Thr His Met Cys Met Val Met Arg Gly Val Gln Lys Met
                85                  90                  95

Asn Ser Lys Thr Val Thr Ser Thr Met Leu
                100                 105

<210> SEQ ID NO 4
<211> LENGTH: 106
<212> TYPE: PRT
<213> ORGANISM: Rattus norvegicus

<400> SEQUENCE: 4

His Asp Glu Met Val Ile Val Lys Asp Ile Asp Met Phe Ser Met Cys
1               5                   10                  15

Glu His His Leu Val Pro Phe Val Gly Arg Val His Ile Gly Tyr Leu
                20                  25                  30

Pro Asn Lys Gln Val Leu Gly Leu Ser Lys Leu Ala Arg Ile Val Glu
            35                  40                  45

Ile Tyr Ser Arg Arg Leu Gln Val Gln Lys Arg Leu Thr Lys Gln Ile
    50                  55                  60

Ala Val Ala Ile Thr Glu Ala Leu Gln Pro Ala Gly Val Gly Val Val
65                  70                  75                  80

Ile Glu Ala Thr His Met Cys Met Val Met Arg Gly Val Gln Lys Met
                85                  90                  95

Asn Ser Lys Thr Val Thr Ser Thr Met Leu

<210> SEQ ID NO 5
<211> LENGTH: 124
<212> TYPE: PRT
<213> ORGANISM: Thermotoga maritima

<400> SEQUENCE: 5

Phe Ser Phe Lys Ile Gly Val Arg Thr Pro Val His Thr Leu Cys Pro
1               5                   10                  15

Cys Ser Lys Glu Ile Ser Asp Tyr Gly Ala His Asn Gln Arg Ala Phe
            20                  25                  30

Val Glu Ile Thr Val Lys Thr Arg Lys Phe Ile Trp Phe Glu Asp Leu
        35                  40                  45

Val Glu Ile Ala Glu Lys Asn Ala Ser Ser Pro Leu Tyr Thr Leu Leu
    50                  55                  60

Lys Arg Pro Asp Glu Lys Phe Val Thr Glu Lys Ala Tyr Glu Asn Pro
65                  70                  75                  80

Arg Phe Val Lys Asp Val Ala Arg Asp Val Ala Leu Glu Leu Glu Lys
                85                  90                  95

Asp Pro Arg Ile Thr Trp Tyr Arg Val Tyr Val Glu Ser Met Glu Ser
            100                 105                 110

Ile His Asn His Asn Ala Phe Ala Cys Val Glu Lys
        115                 120

<210> SEQ ID NO 6
<211> LENGTH: 130
<212> TYPE: PRT
<213> ORGANISM: Bacillus subtilis

<400> SEQUENCE: 6

Phe Lys Gln Arg Ala Gly Ile Ser Ala Lys Val Thr Thr Leu Cys Pro
1               5                   10                  15

Cys Ser Lys Glu Ile Ser Glu Tyr Ser Ala His Asn Gln Arg Gly Thr
            20                  25                  30

Val Lys His Leu Gly Arg Ile Phe Thr Arg Ala Ala Ser Leu Pro Ser
        35                  40                  45

Asp Val Lys Ala Asp Leu Pro His Ala Ala Glu Ser Asn Ala Ser Ala
    50                  55                  60

Arg Leu His Pro Val Leu Lys Arg Pro Asp Glu Lys Ala Val Thr Glu
65                  70                  75                  80

Thr Ala Tyr Glu Asn Pro Arg Phe Val Lys Asp Leu Ala Arg Leu Ile
                85                  90                  95

Ala Ala Asp Leu Phe Glu Leu Glu Trp Val Ser Ala Phe Glu Ile Glu
            100                 105                 110

Cys Arg Asn Glu Glu Ser Ile His Leu His Arg Cys Leu Cys Glu Val
        115                 120                 125

Cys Phe
    130

<210> SEQ ID NO 7
<211> LENGTH: 129
<212> TYPE: PRT
<213> ORGANISM: Staphylococcus aureus

<400> SEQUENCE: 7

Thr Arg Lys Glu Leu Thr Ile Glu Ala Thr Val Thr Thr Leu Cys Pro
1               5                   10                  15

```
Cys Ser Lys Glu Ile Ser Glu Tyr Ser Ala His Asn Gln Arg Gly Val
            20                  25                  30

Val Thr Val Lys Thr Tyr Ile Asn Lys Asp Gln Asp Ile Val Asp Asp
        35                  40                  45

Tyr Lys Asn Lys Ile Leu Asp Ala Met Glu Ala Asn Ala Ser Ser Ile
    50                  55                  60

Leu Tyr Pro Ile Leu Lys Arg Pro Asp Glu Lys Arg Val Thr Glu Arg
 65                  70                  75                  80

Ala Tyr Glu Asn Pro Arg Pro Val Lys Asp Leu Ile Arg Leu Ile Ala
                85                  90                  95

Ala Asp Leu Val Glu Phe Asp Trp Leu Glu Gly Phe Asp Ile Glu Cys
            100                 105                 110

Arg Asn Glu Glu Ser Ile His Gln His Asp Ala Phe Ala Lys Leu Lys
        115                 120                 125

Tyr

<210> SEQ ID NO 8
<211> LENGTH: 124
<212> TYPE: PRT
<213> ORGANISM: Neisseria gonorrhoeae

<400> SEQUENCE: 8

Tyr Gly His Ser Met Lys Val Met Ile Pro Val Thr Ser Leu Cys Pro
 1               5                  10                  15

Cys Ser Lys Glu Ile Ser Gln Tyr Gly Ala His Asn Gln Arg Ser His
            20                  25                  30

Val Thr Val Ser Leu Thr Ser Asp Ala Glu Val Gly Ile Glu Glu Val
        35                  40                  45

Ile Asp Tyr Val Glu Thr Gln Ala Ser Cys Gln Leu Tyr Gly Leu Leu
    50                  55                  60

Lys Pro Arg Asp Glu Lys Tyr Val Thr Glu Lys Ala Tyr Glu Asn Pro
 65                  70                  75                  80

Lys Phe Val Lys Asp Met Val Arg Asp Val Ala Thr Ser Leu Ile Ala
                85                  90                  95

Asp Lys Arg Ile Lys Ser Phe Val Val Glu Ser Glu Asn Phe Glu Ser
            100                 105                 110

Ile His Asn His Ser Ala Tyr Ala Tyr Ile Ala Tyr
        115                 120

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other

<400> SEQUENCE: 9
naaatgttat antataacat ttn                                          23
```

```
<210> SEQ ID NO 10
<211> LENGTH: 23
<212> TYPE: DNA
<213> ORGANISM: Serratia marcescens

<400> SEQUENCE: 10
gttatgttat aatataacaa aac                                              23

<210> SEQ ID NO 11
<211> LENGTH: 23
<212> TYPE: DNA
<213> ORGANISM: Klebsiella pneumoniae

<400> SEQUENCE: 11
atgatgttat gttataacgt ttt                                              23

<210> SEQ ID NO 12
<211> LENGTH: 23
<212> TYPE: DNA
<213> ORGANISM: Acinetobacter sp.

<400> SEQUENCE: 12
tatatgttac attataacat aac                                              23

<210> SEQ ID NO 13
<211> LENGTH: 23
<212> TYPE: DNA
<213> ORGANISM: Methylococcus capsulatus

<400> SEQUENCE: 13
tagttgttac tttataacat ata                                              23

<210> SEQ ID NO 14
<211> LENGTH: 23
<212> TYPE: DNA
<213> ORGANISM: Chromohalobacter salexigens

<400> SEQUENCE: 14
agaatgttat ggtataacat atc                                              23

<210> SEQ ID NO 15
<211> LENGTH: 23
<212> TYPE: DNA
<213> ORGANISM: Hahella chejuensis

<400> SEQUENCE: 15
aaaaagatat gatataacgt atc                                              23

<210> SEQ ID NO 16
<211> LENGTH: 23
<212> TYPE: DNA
<213> ORGANISM: Pseudoalteromonas atlantica

<400> SEQUENCE: 16
gtgatgttat attgtatcat tta                                              23

<210> SEQ ID NO 17
<211> LENGTH: 23
<212> TYPE: DNA
<213> ORGANISM: Pseudomonas aeruginosa

<400> SEQUENCE: 17
aatacgttat attataacat tca                                              23
```

```
<210> SEQ ID NO 18
<211> LENGTH: 23
<212> TYPE: DNA
<213> ORGANISM: Pseudomonas entomophila

<400> SEQUENCE: 18
gcaatgttat attataacaa tac                                          23

<210> SEQ ID NO 19
<211> LENGTH: 23
<212> TYPE: DNA
<213> ORGANISM: Pseudomonas fluorescens

<400> SEQUENCE: 19
gcattgttat aatataacat gtg                                          23

<210> SEQ ID NO 20
<211> LENGTH: 23
<212> TYPE: DNA
<213> ORGANISM: Pseudomonas syringae

<400> SEQUENCE: 20
ttaatgttat agtgtaacga att                                          23

<210> SEQ ID NO 21
<211> LENGTH: 23
<212> TYPE: DNA
<213> ORGANISM: Pseudomonas putida

<400> SEQUENCE: 21
tagatgttat gttataacac tta                                          23

<210> SEQ ID NO 22
<211> LENGTH: 23
<212> TYPE: DNA
<213> ORGANISM: Azotobacter vinelandii

<400> SEQUENCE: 22
cttttgttat gttataacac ata                                          23

<210> SEQ ID NO 23
<211> LENGTH: 23
<212> TYPE: DNA
<213> ORGANISM: Xanthomonas axonopodis

<400> SEQUENCE: 23
ttgatgttac tttataacac ttg                                          23

<210> SEQ ID NO 24
<211> LENGTH: 23
<212> TYPE: DNA
<213> ORGANISM: Xanthomonas campestris

<400> SEQUENCE: 24
ctagtgttac tttataacac ttg                                          23

<210> SEQ ID NO 25
<211> LENGTH: 23
<212> TYPE: DNA
<213> ORGANISM: Xylella fastidiosa

<400> SEQUENCE: 25
gttatgttat tttataacat att                                          23
```

```
<210> SEQ ID NO 26
<211> LENGTH: 23
<212> TYPE: DNA
<213> ORGANISM: Burkholderia cepacia

<400> SEQUENCE: 26
gaaatgatat gttatatcgt tgc                                              23

<210> SEQ ID NO 27
<211> LENGTH: 23
<212> TYPE: DNA
<213> ORGANISM: Burkholderia cenocepacia

<400> SEQUENCE: 27
gaaatgatat gttatatcgt agc                                              23

<210> SEQ ID NO 28
<211> LENGTH: 23
<212> TYPE: DNA
<213> ORGANISM: Ralstonia metallidurans

<400> SEQUENCE: 28
gaaatgcaac aaggttgcat tta                                              23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (12)..(12)
<223> OTHER INFORMATION: a, c, t, g, unknown or other

<400> SEQUENCE: 29
taaatcgtaa tnattacgat tta                                              23

<210> SEQ ID NO 30
<211> LENGTH: 23
<212> TYPE: DNA
<213> ORGANISM: Bacillus subtilis

<400> SEQUENCE: 30
taaatagtaa ttattacgat ttg                                              23

<210> SEQ ID NO 31
<211> LENGTH: 23
<212> TYPE: DNA
<213> ORGANISM: Bacillus licheniformis

<400> SEQUENCE: 31
taaataggaa ctatttcgat tta                                              23

<210> SEQ ID NO 32
<211> LENGTH: 23
<212> TYPE: DNA
<213> ORGANISM: Bacillus halodurans

<400> SEQUENCE: 32
taaatcgtaa ttattcttat tta                                              23

<210> SEQ ID NO 33
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 33

His His His His His His
1               5
```

CRYSTAL OF GTP CYCLOHYDROLASE TYPE IB

RELATED APPLICATIONS

The present application is a continuation-in-part of U.S. patent application Ser. No. 12/670,438, filed Jan. 25, 2010; which is a U.S. national phase application of PCT/US08/71358, filed Jul. 28, 2008; and which is related to and claims the priority benefit of U.S. Provisional Patent Application Ser. No. 60/935,124, "entitled Novel GTP Cyclohydrolase Type IB," filed Jul. 26, 2007.

This invention was made with United States government support under Grant R01 GM70641-01 awarded by the National Institutes of Health, and Award No. MCB-0516948 awarded by the National Science Foundation. The Stanford Synchrotron Research Laboratory Structural Molecular Biology Program is supported by the Department of Energy, National Institutes of Health, and the National Institute of General Medical Sciences. The government has certain rights in the invention.

BACKGROUND

Bacterial diseases, such as those caused by *Neisseria gonorrhea* and *Staphylococcus aureus*, pose significant disease and health risks. *N. gonorrhoeae* is the causative agent of the sexually transmitted disease gonorrhea (infection of the genitalia, and urinary tract) and cause of pelvic inflammatory disease and infertility in one million women a year. Worldwide, there are an estimated 62 million new cases a year, with an average of 22 million cases at any given time. About 0.8 million new gonorrhea infections are reported each year in the U.S. primarily among teenage females and African Americans, costing $1.1 billion/year in treatment and related expenses. Importantly, gonorrhea infections increase the transmission and susceptibility to human immunodeficiency virus infection. Moreover, gonorrhea has become resistant to traditional treatments with quinolone (ciprofloxacin), tetracycline, penicillin, and sulfonamides. Currently, twenty percent of reported gonorrhea cases in the U.S. and Europe are resistant to all of these drugs, with the highest resistance seen among homosexual males. Although gonorrhea can now be treated with ultra high doses of azithromycin, resistance to that antibiotic is also emerging.

The *S. aureus* bacterium currently causes the most common and serious infections that occur in hospitalized patients. In recent years, *S. aureus* has become resistant to antibiotics (thus named Multidrug- or Methicillin-Resistant *S. aureus*, MRSA), causing a serious public health problem in the United States and worldwide. Sixty percent of intensive-care-unit infections in the U.S. are caused by MRSA, leading to significant mortality. The MRSA "superbug" multiplies very rapidly in the bloodstream causing toxic shock syndrome, and/or on the skin causing furuncles. Once an infection occurs, it is almost impossible to treat with existing antibiotics, especially in immune-compromised and elderly patients. When an incurable MRSA infection reaches the heart, it often causes fatal endocarditis.

Hence, there is a growing need for alternative treatments against such bacterial pathogens.

SUMMARY OF THE INVENTION

An object of the present invention provides for a novel avenue for combating bacterial pathogens by targeting specific enzymes that archaea and bacteria, but not eukarya, require. One embodiment of the present invention presents a novel, purified bacterial enzyme, GTP Cyclohydrolase Type IB (GCYH-IB).

Another embodiment provides for the crystalline structure of GCYH-IB. A related embodiments provides a GCYH-IB crystal. Yet another related embodiment provides for a computer-readable medium having GTP Cyclohydrolase Type IB crystal structure information stored thereon.

DESCRIPTION OF THE DRAWINGS

FIG. 4 presents structure-guided multi-sequence alignment of GCYH-IA and GCYH-IB in the shared T-fold region. For clarity, only four sequences are shown from each subfamily. Residue labels and secondary structure elements (from the crystal structures) are shown above and below the sequence alignment for enzyme subfamilies A and B, respectively. Secondary structure nomenclature is as in FIG. 3. Residues conserved between the two subfamilies are vertically outlined, with the strictly conserved residues (the substrate binding Glu and zinc binding Cys) highlighted in dark gray. Conserved regions within GCYH-IB subfamily are boxed. The zinc ion-ligandating side chains in each subfamily are labeled with gray stars. The Mn-ligandating side chains in GCYH-IB are labeled with black stars. # indicates a zinc ligandating side chain from the neighboring subunit. Ec: *Escherichia coli* (SEQ ID NO: 1), Tt: *Thermus thermophilus* (SEQ ID NO: 2), Hs: *Homo sapien* (SEQ ID NO: 3), Rn: *Rattus norvegicus* (SEQ ID NO: 4), Tm: *Thermotoga maritime* (SEQ ID NO: 5), Bs: *Bacillus subtilis* (SEQ ID NO: 6), Sa: *Staphylococcus aureus* (SEQ ID NO: 7), Ng: *Neisseria gonorrhoeae* (SEQ ID NO: 8).

FIG. 13 is a Table of candidate Zur-binding sites upstream of folE2 in bacterial genomes. Distance is given in nucleotides relative to the start codon of the downstream gene. The Table contains candidate Zur-binding sites for the following bacterial genomes: PROTEOBACTERIA Consensus Zur-binding site (SEQ ID NO: 9); *Serratia marcescens* (SEQ ID NO: 10); *Klebsiella pneumonia* (SEQ ID NO: 11); *Acinetobacter* sp. ADP I (SEQ ID NO: 12); *Methylococcus capsulatus* (SEQ ID NO: 13); *Chromohalobacter salexigens* DSM 3043 (SEQ ID NO: 14); *Hahella chejuensis* KCTC 2396 (SEQ ID NO: 15); *Pseudoalteromonas atlantica* T6c (SEQ ID NO: 16); *Pseudomonas aeruginosa* (SEQ ID NO: 17); *Pseudomonas entomophila* L48 (SEQ ID NO: 18); *Pseudomonas fluorescens* Pf 5 (SEQ ID NO: 19); *Pseudomonas syringae* (SEQ ID NO: 20); *Pseudomonas putida* (SEQ ID NO: 21); *Azotobacter vinelandii* (SEQ ID NO: 22); *Xanthomonas axonopodis* (SEQ ID NO: 23); *Xanthomonas campestris* (SEQ ID NO: 24); *Xylella fastidiosa* (SEQ ID NO: 25); *Burkholderia cepacia* R18194 (SEQ ID NO: 26); *Burkholderia cenocepacia* AU 1054 (SEQ ID NO: 27); *Ralstonia metallidurans* (SEQ ID NO: 28); BACILLI Consensus Zur-binding site (SEQ ID NO: 29); *Bacillus subtilis* (SEQ ID NO: 30); *Bacillus licheniformis* (SEQ ID NO: 31); *Bacillus halodurans* (SEQ ID NO: 32).

DETAILED DESCRIPTION

Figure 1:
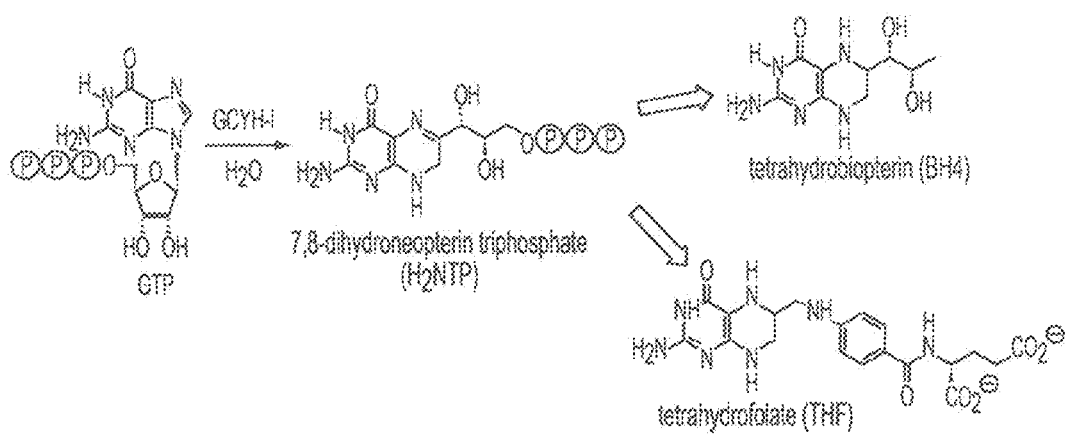
FIG. 1 presents a diagram of the reaction catalyzed by GTP Cyclohydrolase Type I (GCYH-I), and the metabolic fate of $H_2NTP$.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms "a," "an," and "the" include the plural reference and equivalents known to those skilled in the art unless the context clearly indicates otherwise. Other than in the operating examples, or where otherwise indicated, all numbers expressing quantities of ingredients or reaction conditions used herein should be understood as modified in all instances by the term "about."

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

Unless defined otherwise, all technical and scientific terms used herein have the same meaning as those commonly understood to one of ordinary skill in the art to which this invention pertains. When COG1469 is used in the context of a protein or gene family, it is synonymous with GCYH-IB protein or gene family.

Folic acid or folate is an essential metabolite in all life forms. It is used by all cells for the biosynthesis of purines (building blocks of DNA and RNA), amino acids, and vitamins. Unlike humans, who need folic acid as a dietary supplement, bacteria and yeast biosynthesize folic acid de novo. As a result, folate biosynthesis in bacteria and yeast has become an attractive target in antibacterial therapeutics. For example, sulfonamides, the first synthetic drugs developed with broad antibacterial activity, target a late step in the bacterial folate biosynthetic pathways. Emerging resistance to existing antibiotics spurs the quest for new and more effective target points along the pathway. One such point is the first step in folate biosynthesis: the conversion of GTP to 7,8-dihydroneopterin triphosphate by the enzyme GTP cyclohydrolase I (GCYH-I). The presence in humans of a homologous enzyme (required for making biopterin, another metabolic co-factor distinct from folate), complicated the development of bacterial GCYH-I as a drug target.

The present invention provides for a novel GCYH-I family of enzymes, called GCYH-IB, that has been identified in pathogenic bacteria. El Yacoubi et al., 281(49) J. Biol. Chem. 37586-93 (2006), incorporated fully herein by this reference. Importantly, GCYH-IB is absent in humans. The present invention identifies the biochemical properties and crystal structure of GCYH-IB from the pathogenic bacterium N. gonorrhoeae. The unique structure of the active center and the new metal dependency of this cyclohydrolase suggest an enzymatic mechanism distinct from that of the canonical GCYH-I. The differences in the active-site architecture and enzymatic mechanism of the two subtypes of GCYH-I enzymes can be exploited for the design of selective inhibitors of the bacteria-specific enzyme. Realization of such a goal allows for development of GCYH-IB as a therapeutic target for antibacterial pharmaceuticals. Furthermore, the presence of GCYH-IB as the sole GTP-cyclohydrolase in two clinically important human pathogens, N. gonorrhoeae and S. aureus, allows investigations of this enzyme as a potential drug target against the antibiotic resistant forms of gonorrhea and MRSA infections.

More specifically, regarding folate biosynthesis, folic acid in the form of various tetrahydrofolate (THF) derivatives serves as a cofactor in one-carbon transfer reactions during the synthesis of purines, thymidylate, pantothenate, glycine, serine and methionine, in all kingdoms of life. Nichol et al., 54 Ann. Rev. Biochem. 729-64 (1985). In bacteria, THF is also involved in the biosynthesis of the initiator formylmethionyl-tRNA. Clark & Marker, 17(2) J. Mol. Biol. 394-406 (1966). Plants, fungi, and most bacteria synthesize THF de novo from GTP and p-aminobenzoic acid (pABA). Green et al., in E. COLI & SALMONELLA, CELLULAR & MOLECULAR BIOL. 665-73 (Neidhart, ed., Am. Soc. Micro., Washington, D.C., 1996); Cossins & Chen, 45(3) Phytochem. 437-52 (1997); Hanson & Gregory, 5(3) Curr. Opin. Plant Biol. 244-49 (2002). Animals lack key enzymes of the folate biosynthetic pathway, and thus require a dietary source of folate for normal growth and development. Lucock, 71(1) Mol. Genet. Metab. 121-38 (2000).

GTP cyclohydrolase I (GCYH-I; EC 3.5.4.16) is the first enzyme of the de novo THF pathway (FIG. 1). Nichol et al., 1985. It is encoded in E. coli by the folE gene (Katzenmeier et al., 372(11) Biol. Chem. Hoppe Seyler 991-97 (1991); Schoedon et al., 210(2) Eur. J. Biochem. 561-68 (1992)), and catalyzes a complex reaction that begins with hydrolytic ring opening of the purine ring at $C_8$ to generate an N-formyl intermediate, which is then the site for a second hydrolysis with concomitant loss of $C_8$ as formic acid. Yim & Brown 251(16) J. Biol. Chem. 5087-94 (1976). In the subsequent steps of the reaction, the ribosyl moiety undergoes ring-opening and an Amidori rearrangement, followed by cyclization to generate the pterin ring in THF (FIG. 1). The product of GCYH-I, 7,8-dihydroneopterin triphosphate (H2NTP), is subsequently dephosphorylated to 7,8-dihydroneopterin by both specific and non specific phosphatases (Klaus et al., 280(7) J. Biol. Chem. 5274-80 (2005)), and the remainder of THF biosynthesis carried out by the enzymes encoded by the folBKPCA genes (in E. coli). Green et al., 1996.

The folate pathway has a storied history as an important target in antibacterial therapeutics and cancer chemotherapy. Dihydropteroate synthase is the target of the sulfonamides (Huovinen et al., 39(2) Antimicrobial Agents & Chemotherapeutics, 279-89 (1995)), and dihydrofolate reductase is the target of methotrexate, the first anticancer chemotherapy developed. A homologous GCYH-I is found in mammals and other higher eukaryotes, however, where it catalyzes the first step of the biopterin (BH4) pathway (FIG. 1), an essential cofactor in aromatic amino acid oxidation in the biosynthesis of tyrosine and neurotransmitters such as serotonin and L-DOPA. Thony et al., 347(1) Biochem. J. 1-16 (2000); Bonafe et al., 69(2) Am. J. Human Genet. 269-77 (2001). Although several enzymes in the folate pathway have proved important antimicrobial targets (Huovinen et al., 1995), the presence of homologous GCYH-I enzymes in both humans and bacteria has precluded the development of GCYH-I as a viable target.

The role of folate as an essential cofactor, coupled with the historical importance of the pathway in the development of antibacterial, antiparasitic, and anticancer therapies (Hoffbrand & Weir, 113(3) Brit. J. Haematol 579-89 (2001)), has led to folate metabolism being an especially well-characterized area of biology. The discovery of a novel, widely distributed folate biosynthetic enzyme, as described herein, illustrates the power of comparative genomic approaches to link genes and function. The signature genes of the de novo folate pathway, folP and folK, encode dihydropteroate synthase and 6-hydromethyl-7,8-dihydropterin pyrophosphokinase, respectively. All organisms that possess these two genes should have a homolog of the folE gene, because none of the metabolic intermediates from 7,8-dihydropterin triphosphate to 7,8-dihydro-hydroxymethylpterin pyrophosphate, are transported in bacteria. Skold, 3(3) Drug Resistance Update, 155-60 (2000).

The distribution of the folE/folE2 genes among the sequenced organisms in the SEED database (26 archaeal, 363 bacterial, and 29 eukaryeal more or less complete genomes) were analyzed. No FolE2 homolog was identified in the eukaryotic genomes, and there was significant variation in the distribution of the FolE/FolE2 genes among bacteria. Analysis of the distribution of the folE gene among all sequenced genomes that possessed folKP homologs revealed a large class of organisms that lacked folE homologs (Table 1), suggesting that folE was "locally missing" in these organisms. See also Koonin et al., 12(9) Trends Genet. 334-36 (1996); Suppl. data for El Yacoubi et al., 2006, available at JBC Online.

TABLE 1

Distribution of FolE, COG1469, FolK, and FolP homologs in a subset of sequenced genomes. The genomes used in the phylogenetic pattern search are in bold.

| Organism | FolE | COG1469 | FolK | FolP |
|---|---|---|---|---|
| *Escherichia coli* K12 | + | | + | + |
| *Bacillus subtilis* subsp. *subtilis* str. 168 | + | + | + | + |
| *Acinetobacter baylyi* | + | + | + | + |
| Bordatella bronchiseptica RB50 | | + | + | + |
| Neisseria gonorrhoeae FA 1090 | | + | + | + |
| Neisseria meningiditis MC58 | | + | + | + |
| Neisseria mengingiditis FAM18 | | + | + | + |
| Neisseria lactamica ST-640 | | + | + | + |
| Nitrosomonas europaea ATC 19718 | | + | + | + |
| Oceanobacillus iheyeniss HTE831 | | + | + | + |
| **Staphylococcus aureus subsp.*aureus* MW2** | | + | + | + |
| Staphylococcus haemolyticus JCSC1435 | | + | + | + |
| Staphylococcus saprophyticus | | + | + | + |
| Thermotaga maritime MSB8 | | + | + | + |
| Desulfotalea psychrophila LSv54 | | + | + | + |

TABLE 1-continued

Distribution of FolE, COG1469, FolK, and FolP homologs in a subset of sequenced genomes. The genomes used in the phylogenetic pattern search are in bold.

| Organism | FolE | COG1469 | FolK | FolP |
|---|---|---|---|---|
| *Desulfuromonas acetoxidans* | | + | + | + |
| *Exiguobacterium* sp. 255-15 | | + | + | + |
| *Geobacter sulferreducens* PCA | | + | + | + |
| *Geobacter metallireducens* GS-15 | | + | + | + |
| *Magnetococcus* sp. MC-1 | | + | + | + |
| *Methylobacillus flagellatus* KT | | + | + | + |
| *Silicobacter* sp. TM1040[B] | | + | + | + |
| *Rhodobacter sphaeroides* 2.4.1 | | + | + | + |
| *Idiomarina loihiensis* L2TR | | + | + | + |
| *Oceanicola batsensis* HTCC2597 | | + | + | + |
| *Rhodobacterales bacterium* HTCC2654 | | + | + | + |
| *Roseovarius nubinhibens* ISM [B] | | + | + | + |
| *Loktanella vestifoldensis* SKA53 | | + | + | + |
| *Thiomicrospira crunogena* XCL-2 | | + | + | + |
| *Sulfitobacter* sp. EE-36 | | + | + | + |
| *Roseobacter* sp. MED193 | | + | + | + |
| *Desulfovibrio vulgaris* | | + | + | + |

Using a SEED tool that allows identification of protein families that follow a defined phylogenetic distribution profile, a search was conducted of the available genomes for protein families that were present in organisms that lack folE homologs (Table 1, in bold) and absent in *E. coli*. Five protein families fulfilled those phylogenetic criteria, one of which, COG1469, was of unknown function. Members of this family clustered physically with folate metabolism genes in several organisms. The combination of phylogenetic distribution and clustering suggested that the COG1469 family might encode the missing GCYH-I enzyme.

Further regarding the variation of the distribution, the first and largest group, which includes *E. coli*, has only a folE homolog. A second group, which includes *S. aureus* and *N. gonorrhoeae*, has only a folE2 homolog. A third group, including *B. subtilis* and *A. baylyi*, has a homolog of each gene, whereas a fourth group can possess multiple copies of the two genes (e.g. *Pseudomonas aeruginosa* has two folE genes and one folE2 gene). The need for several genes encoding type I cyclohydrolase enzymes in many organisms may be due to differential expression under specific environmental conditions or their involvement in pathways other than folate biosynthesis: for example, a GTP cyclohydrolase has been implicated in the biosynthesis of 7-deazaguanosine derivatives, such as the modified tRNA nucleoside queuosine (Kuchino et al., 3 Nucl. Acids. Res. 393-98 (1976)), and the secondary metabolites toyocamycin and tubercidin. Suhadolnik & Uematsu, 245(17) J. Biol. Chem. 4365-71 (1970); Smulson & Suhadolnik, 242(12) J. Biol. Chem. 2872-76 (1967). In *B. subtilis*, it has been shown that the yciA gene is not essential (Gaballa et al., 184 J. Bacteriol. 6508-14 (2002)), because a folE gene (mtrA) is also present in this organism. Yakhin & Babitze, 64(3) Appl. Microbiol. Biotech. 382-86 (2004). No folE2 deletions are available in bacteria that do not have another identified folE gene; but construction of the corresponding *S. aureus* mutant is possible.

Most archaeal genomes possess either a folE or a folE2 homolog. See El Yacoubi et al., 2006, Suppl. Data. Several GTP-derived metabolites are synthesized in Archaea, including folate in the halophiles and Sulfolobii (White, 170(10) J. Bacteriol. 4608-12 (1988)), tetrahydromethanopterin in the methanogens (Graham et al., 41(50) Biochem. 15074-84 (2002)), and the 7-deazaguanosine tRNA-modified nucleoside archaeosine (Gregson et al., 268(14) J. Biol. Chem. 10076-86 (1993)), which is found in the majority of archaeal tRNA. The archaeal folE/folE2 genes may be involved in one or more of these biosynthetic pathways.

As noted above, GCYH-IB has been identified in a wide variety of bacteria using the techniques described herein. Table 2 illustrates some of this distribution:

TABLE 2

Distribution of genes encoding GCYH-1B in prokaryotes. Genome and gene ids are found in the SEED database.

| Genome ID | Organism | GCYH-IB |
|---|---|---|
| 272557.1 | *Aeropyrum pernix* K1 [A] | 1635 |
| 224325.1 | *Archaeoglobus fulgidus* DSM 4304 [A] | 1168 |
| 64091.1 | *Halobacterium* sp. NRC-1 [A] | 1638 |
| 348780.3 | *Nitrosamonas pharaonis* DSM 2160 [A] | 1042 |
| 18420.1 | *Methanothermobacter thermautotrophicus* str. Delta H [A] | 1179 |
| 243232.1 | *Methanocaldococcus jannaschii* DSM 2661 [A] | 797 |
| 267377.1 | *Methanococcus maripaludis* S2 [A] | 34 |
| 259564.1 | *Methanococcoides burtonii* DSM 6242 [A] | 34 |
| 188937.1 | *Methanosarcina acetivorans* C2A [A] | 4403 |
| 269797.3 | *Methanosarcina barkeri* str. fusaro [A] | 1194 |
| 2208.1 | *Methanosarcina barkeri* [A] | 3612 |
| 192952.1 | *Methanosarcina mazei* Go1 [A] | 1222 |
| 190192.1 | *Methanopyrus kandleri* AV19 [A] | 483 |
| 272844.1 | *Pyrococcus abyssi* GE5 [A] | 362 |
| 18497.1 | *Pyrococcus furiosus* DSM 3638 [A] | 1881 |
| 69014.3 | *Thermococcus kodakaraensis* [A] | 1153 |
| 263820.1 | *Picrophilus torridus* DSM 9790 [A] | 1009 |
| 273116.1 | *Thermoplasma volcanium* GSS1 [A] | 1214 |
| 273075.1 | *Thermoplasma acidophilum* DSM 1728 [A] | 1117 |

Importantly, in addition to *S. aureus* and *N. gonorrhoeae*, there are significant pathogens that have GCYH-IB but do not have GCYH-IA, as shown in Table 3:

TABLE 3

Clinically important pathogens with GCYH-IB and lacking GCYH-IA.

| Organism | Pathogenic Indication |
|---|---|
| *Bordetella parapertussis* 12822 | Mammalian pathogen, |
| *Bordetella parapertussis* 12822 | respiratory tract infection |
| *Bordetella pertussis* Tohama I | |
| *Neisseria gonorrhoeae* FA 1090 | Human pathogen, genital and urinary tract infection |
| *Neisseria meningitidis* FAM18 | Human pathogen, meningitis |
| *Neisseria meningitidis* MC58 | |
| *Neisseria meningitidis* ZZ491 | |
| *Staphylococcus aureus* RF122 | Human pathogen, blood and |
| *Staphylococcus aureus* subsp. *aureus* COL; subsp. *aureus* JH1; subsp. *aureus* MRSA252; subsp. *aureus* | skin infection, toxic shock syndrome |

TABLE 3-continued

Clinically important pathogens with GCYH-IB and lacking GCYH-IA.

| Organism | Pathogenic Indication |
| --- | --- |
| MSSA476; subsp. *aureus* MW2; subsp. *aureus* Mu50; subsp. *aureus* N315; subsp. *aureus* NCTC 8325; subsp. *aureus* USA300; subsp. *Aureus* | |
| *Staphylococcus epidermidis* ATCC 12228 | Human pathogen, blood, skin, |
| *Staphylococcus epidermidis* RP62A | and catheter infection |
| *Staphylococcus haemolyticus* JCSC1435 | Human pathogen, skin infection |
| *Staphylococcus saprophyticus* subsp. ATCC 15305 | Human pathogen, acute urinary tract infection |

The primary structure of GCYH-IB proteins presents no homology to any other known protein family. Direct alignment of GCYH-IB and GCYH-IA sequences yields no detectable similarity. Protein fold recognition analysis using 1- and 3-dimensional sequence profiles, however, coupled with secondary structure and solvation potential information (using the 3D-PSSM server available on-line from the Structural Bioinformatics Group at the Imperial College, UK; Kelley et al., 299(2) J. Mol. Biol. 499-520 (2000)), indicates potential three-dimensional structural homology with two tunnel-fold (T-fold) enzymes, a structural superfamily of enzymes that includes GCYH-IA. Colloc'h et al., 39(2) Proteins 142-54 (2000). T-fold enzymes bind planar purine and pterin-like substrates but catalyze disparate reactions (id.), and although they characteristically exhibit low sequence homology, their tertiary structural homology is very high.

Using the *N. gonorrhoeae* sequence as a bait, the N-terminal half of GCYH-IB is most similar in predicted tertiary structure to 7,8-dihydroneopterin triphosphate epimerase (Protein Data Bank code 1B9L (44), PSSM E value 0.39), whereas the C-terminal half is similar to 7,8-dihydroneopterin aldolase (DHNA; Protein Data Bank code 1NBU (45), PSSM E value 0.3). These were the only PSSM hits with a qualifying E value (i.e., lower than the detection threshold E value of 1.00). Both hits are folate biosynthetic enzymes with homo-octameric structures. Both the size of GCYH-IB proteins (250-300 amino acids) and the fact that two T-fold domains can be detected in their sequences suggest that GCYH-IB members belong to the bimodular subfamily of the T-fold superfamily, which includes urate oxidase (Colloc'h et al., 4(11) Nat. Struct'l Biol. 947-52 (1997)), the plant GCYH-IA enzyme (Basset et al., 99(19) PNAS 12489-94 (2002)), and the novel nitrile oxidoreductase (class 2; e.g. YqcD from *E. coli*) recently reported. Van Lanen et al., 102(2) PNAS 4264-69 (2005). Preliminary sedimentation velocity and crystallographic analyses of *N. gonorrhoeae* GCYH-IB suggest either a trimeric or a tetrameric quaternary structure.

Of the enzymes involved in folate and biopterin biosynthesis, GCYH-IA has attracted particular attention (Nar et al., 1995; Tanaka et al., 138(3) J. Biochem. (Tokyo) 263-75 (2005); Schramek et al., 316(3) J. Mol. Biol. 829-38 (2002); Bracher et al., 273(43) J. Biol. Chem. 28132-141 (1998); Wolf & Brown, 192(3) Biochem. Biophys. Acta 468-78 (1969)), due to the mechanistic complexity inherent in the conversion of GTP to H2NTP. GCYH-IA activity is dependent on a catalytic $Zn^{2+}$ atom (Auerbach et al., 97(25) PNAS 13567-72 (2000)), which functions as a Lewis acid in activating a water molecule for nucleophilic attack at C-8 of GTP in the initial hydrolytic step of the reaction. The $Zn^{2+}$ further serves to facilitate nucleophilic attack of the second water molecule by polarizing the resulting amide carbonyl. The zinc-binding site in GCYH-IA is made up of Cys110, His113, and Cys181 (*E. coli* numbering), with water occupying the fourth coordination site.

Hence, GCYH-IB was discovered in microbes (20% of bacteria and most archaea) that do not encode the canonical GCYH-I (renamed GCYH-IA), including several clinically important pathogens such as *N. gonorrhoeae* and *S. aureus*. El Yacoubi et al., 2006. Importantly, GCYH-IB is absent in eukarya, including humans. A prediction of the 3D structure of GCYH-IB showed that, like GCYH-IA, GCYH-IB enzymes are members of the tunnel-fold (T-fold) structural superfamily. GCYH-IB enzymes from *T. maritima, N. gonorrhoeae*, and *B. subtilis* have been cloned and functionally characterized in vitro. The metal dependency of GCYH-IB was analyzed in vitro and was found to be distinct from that of GCYH-IA, with manganese as the preferred metal cofactor. The preference for manganese of the *N. gonorrhoeae* enzyme is consistent with the fact that this pathogen had evolved unique and complex manganese-based cellular mechanisms for coping with the high oxidative stress environment imposed on it by the innate immune response of the female urogenital tract. Seib et al., 70(2) Bio. Reviews 344-61 (2006). The primary defenses used by *N. gonorrhoeae* against oxidative stress include the intracellular accumulation of manganese by the MntABC transport system and the unusually high manganese-dependent catalase and peroxidase activities. The discovery of a manganese-dependent folate biosynthesis enzyme in *N. gonorrhoeae* paves the way to a new approach in targeting the folate biosynthesis pathway for the development of anti-gonorrhea antibiotics.

The present invention provides for the crystal structures of *N. gonorrhoeae* GCYH-IB and of the manganese-remetallated form of the enzyme. The aspect of the present invention reveals the enyzme's active center, including a metal binding site, which are distinct from those of the canonical enzyme. The structural differences between human GCYH-IA and bacterial GCYH-IB in the active center, including those in the metal binding site, suggest distinct enzymatic mechanisms. These differences offer the unique opportunity to design and test inhibitors specific to the bacterial enzyme (GCYH-IB) that will not inhibit the human enzyme.

As noted above, the $Zn^{2+}$-dependent enzyme GTP cyclohydrolase I (GCYH-I; EC 3.5.4.16) is the first enzyme of the de novo tetrahydrofolate (THF) biosynthesis pathway (FIG. 1). Nichol et al., 54 Ann. Rev. Biochem. 729-64 (1985). THF is an essential cofactor in one-carbon transfer reactions in the synthesis of purines, thymidylate, pantothenate, glycine, serine, and methionine in all kingdoms of life (id.) and formylmethionyl-tRNA in bacteria. Clark & Marcker, 17 J. Mol. Biol. 394-406 (1966). GCYH-I is encoded in *E. coli* by the folE gene (Katzenmeier et al., 372 Biol. Chem. Hoppe Seyler 991-97 (1991)), and catalyzes the conversion of GTP to 7,8-dihydroneopterin triphosphate, a complex reaction that begins with hydrolytic opening of the purine ring at C-8 of GTP to generate an N-formyl intermediate, followed by deformylation and subsequent rearrangement and cyclization of the ribosyl moiety to generate the pterin ring in THF (FIG. 1). Yim & Brown, 251 J. Biol. Chem. 5087-94 (1976). An active-site $Zn^{2+}$ activates a water molecule for nucleophilic attack at C-8 in the first step of the reaction.

The distribution of folE (gene product renamed GCYH-IA) and folE2 (GCYH-IB) in microbes is diverse. El Yacoubi et al, 326 J. Mol. Biol. 503-516 (2006). The majority of organisms possess either a folE (65%, e.g., *E. coli*) or a folE2 gene (14%, e.g., *N. gonorrhoeae*). A significant number (12%, e.g., *B. subtilis*) possess both genes (a subset of 50 bacterial species is shown in FIG. 13), and 9% lack both genes, although members of the latter group are mainly intracellular or symbiotic bacteria that rely on external sources of folate.

TABLE 4

Distribution and candidate Zur-dependent regulation of alternative GCYH-I genes in bacteria[a]

| Organism | folE | 18 folE2 |
|---|---|---|
| Enterobacteria | | |
| *Escherichia coli* | + | − |
| *Salmonella typhimurium* | + | − |
| *Yersinia pestis* | + | + |
| *Klebsiella pneumoniae*[b] | + | + |
| *Serratia marcescens* | + | − |
| *Erwinia carotovora* | + | − |
| *Photorhabdus luminiscens* | + | − |
| *Proteus mirabilis* | + | − |
| Gamma-proteobacteria | | |
| *Vibrio cholerae* | + | − |
| *Acinetobacter* sp. ADP1 | + | + |
| *Pseudomonas aeruginosa* | + | + |
| *Pseudomonas entomophila* L48 | + | + |
| *Pseudomonas syringae* | + | + |
| *Pseudomonas putida* | + | + |
| *Hahella chejuensis* KCTC 2396 | + | + |
| *Chromohalobacter salexigens* DSM 3043 | + | + |
| *Methylococcus capsulatus* | + | + |
| *Xanthomonas axonopodis* | + | + |
| *Xanthomonas campestris* | + | + |
| *Xylella fastidiosa* | + | + |
| Idiomarina loihiensis[c] | − | + |
| *Colwellia psychrerythraea* | + | + |
| *Pseudoalteromonas atlantica* T6c | + | + |
| *Pseudoalteromonas haloplanktis* TAC125 | + | + |
| *Alteromonas macleodi* | + | − |
| *Nitrosococcus oceani* | + | + |
| *Legionella pneumophila* | + | − |
| *Francisella tularensis* | + | − |
| Beta-proteobacteria | | |
| *Chromobacterium violaceum* | + | − |
| Neisseria gonorrhoeae | − | + |
| *Burkholderia cepacia* R18194 | + | + |
| *Burkholderia cenocepacia* AU 1054 | + | + |
| *Burkholderia xenovorans* | + | − |
| *Burkholderia mallei* | + | − |
| Bordetella pertussis | − | + |
| *Ralstonia eutropha* JMP134 | + | − |
| *Ralstonia metallidurans* | + | + |
| *Ralstonia solanacearum* | + | − |
| Methylobacillus flagellatus | − | + |
| Nitrosomonas europeae | − | + |
| *Azoarcus* sp. | + | + |
| Bacilli/Clostridia | | |
| *Bacillus subtilis*[d] | + | + |
| *Bacillus licheniformis* | + | + |
| *Bacillus cereus* | + | − |

TABLE 4-continued

Distribution and candidate Zur-dependent regulation of alternative GCYH-I genes in bacteria[a]

| Organism | folE | 18 folE2 |
|---|---|---|
| *Bacillus halodurans* s | + | + |
| *Bacillus clausii* | + | − |
| *Geobacillu kaustophilus* | + | − |
| Oceanobacillus iheyensis | − | + |
| Staphylococcus aureus | − | + |

[a]Genes that are preceded by candidate Zur binding sites are on grey background;
[b]Zur-regulated cluster ison the virulence plasmid pLVPK;
[c]Examples of organisms with no folE genes are in bold;
[d]Zn-dependent regulation of *B. subtilis* folE2 by Zur was experimentally verified (Gaballa et al., 2002).

Expression of the folE2 *B. subtilis* gene, yciA, is controlled by the Zn-dependent Zur repressor and should thus be upregulated under Zn-limiting conditions. Gaballa et al. 184 J. Bacteriol., 6508-6514 (2002). Hence, the GCYH-IB family might utilize a metal other than Zn to allow growth in Zn-limiting environments. The metal dependence of *B. subtilis* GCYH-IB in vitro and in vivo was explored, revealing that that in organisms that contain both isozymes such as *B. subtilis*, only the Zn-dependent enzyme is expressed unless Zn becomes limiting. To gain a structural understanding of the metal dependence of GCYH-IB, the high-resolution crystal structures of $Zn^{2+}$- and $Mn^{2+}$-metallated forms of the *N. gonorrhoeae* ortholog were determined. The results shed light on the regulation of folate biosynthesis in organisms exposed to different metal environments and offer a structural understanding of this regulation.

GCYH-IB and GCYH-IA have different metal requirements in vitro. It is well established that GCYH-IA uses a bound $Zn^{2+}$ ion for activity. Nichol et al., 1985. To investigate the metal dependence of GCYH-IB, the purified recombinant *B. subtilis* enzyme was assayed for activity in the presence of a variety of metal ions or EDTA. Although no activity was observed in the presence of EDTA, the presence of several metal ions supported catalysis. To obtain unambiguous, quantitative data on the effect of various metal ions on catalytic activity, the enzyme was first demetallated by dialyzing against an EDTA/Chelex-containing buffer to generate the apoenzyme, which was then assayed in the presence of specific metal ions over a broad concentration range. As shown in Table 5, catalysis is supported by the metal ions $Mn^{2+}$, $Fe^{2+}$, $Mg^{2+}$, $Co^{2+}$, $Zn2^+$, and $Ni^{2+}$, conversely $Ca^{2+}$, $Cd^{2+}$, $Cu^{2+}$, $Co^{3+}$, and $Fe^{3+}$ fail to support activity:

TABLE 5

Metal dependence of *B. subtilis* GCYH-IB enzymatic activity

| Metal | [Metal][a] (µM) | Relative Activity (%) |
|---|---|---|
| No Metal | 0 | 0 |
| Mn(II) | 500 | 100 |
| Fe(II) | 1000 | 75 ± 8 |
| Mg(II) | 100 | 43 ± 4 |
| Co(II) | 100 | 24 ± 3 |
| Zn(II) | 50 | 14 ± 1 |
| Ni(II) | 100 | 9.8 ± 1.3 |
| Ca(II) | NA[b] | 0 |
| Cd(II) | NA | 0 |
| Cu(II) | NA | 0 |
| Co(III) | NA | 0 |
| Fe(III) | NA | 0 |

[a]The metal concentration for optimal activity.
[b]NA refers to no activity detected regardless of metal concentration.

Figure 10:
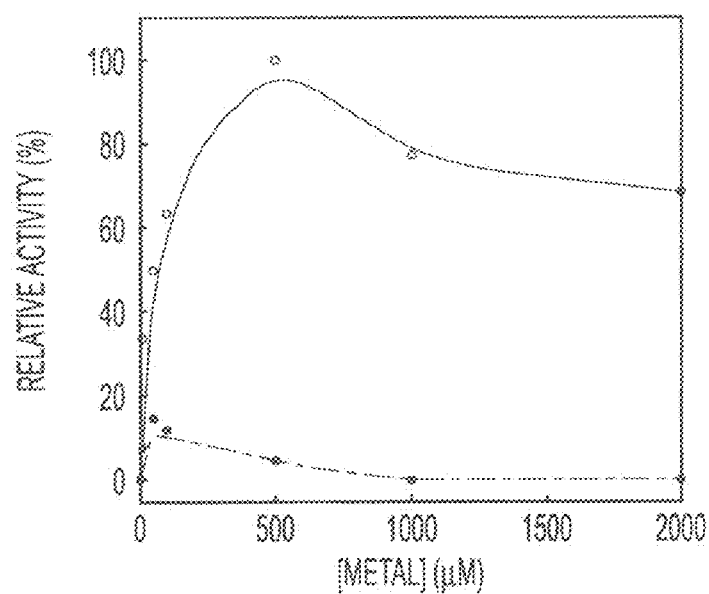
FIG. 10 presents *B. subtilis* GCYH-IB enzymatic activity versus [$Mn^{2+}$] (○) or [$Zn^{2+}$] (●). Each data point represents the average of four sets of triplicate assays.

Notably, although the enzyme exhibits some activity in the presence of $Zn^{2+}$, catalysis is significantly higher in the presence of $Mn^{2+}$, and to a lesser extent $Fe^{2+}$ and $Mg^{2+}$. Interestingly, the optimum metal concentration required for catalysis is roughly 10-fold lower for $Zn^{2+}$ than it is for $Mn^{2+}$ (FIG. 10, Table 5), suggesting that although $Mn^{2+}$ is more effective in supporting catalysis, it binds with lower affinity than does $Zn^{2+}$.

The presence of both $Zn^{2+}$ and $Mn^{2+}$ in a reaction assay results in diminished activity (i.e. $Zn^{2+}$ is an inhibitor versus $Mn^{2+}$, Table 6). All of the metals bind the enzymes with low affinity, such that running the protein over a G-25 column or dialyzing against metal free buffer removed the protein bound metal.

TABLE 6

The effect of zinc upon *B. subtilis* and *N. gonorrhoeae* GCYH-IB activity when assayed in the presence of 600 μM Mn(II). Data expressed as relative activity (%).

| [zinc] μM | B. subtilis | N. gonorrhoeae |
|---|---|---|
| 0 | 100 | 100 |
| 0.5 | 84 | 93 |
| 1 | 41 | 68 |
| 2 | 34 | 57 |
| 4 | 35 | 47 |
| 10 | 35 | 53 |
| 20 | 26 | 45 |
| 40 | 23 | 45 |

To understand the structural basis of the unique metal requirement of GCYH-IB, the crystal structure in two forms: one of the recombinant enzyme purified in solutions lacking added metal (GCYH-IB, PDB ID 3D1T), and one of the apoenzyme remetallated with manganese (GCYH-IB.Mn, PDB ID 3D2O) were determined. Enzymes from both *B. subtilis* and *N. gonorrhoeae* were pursued for crystallization, but only the *N. gonorrhoeae* ortholog produced diffracting crystals. The two orthologs are 64% similar and 35% identical in sequence and possess similar biochemical properties in vitro.

Figure 2A:
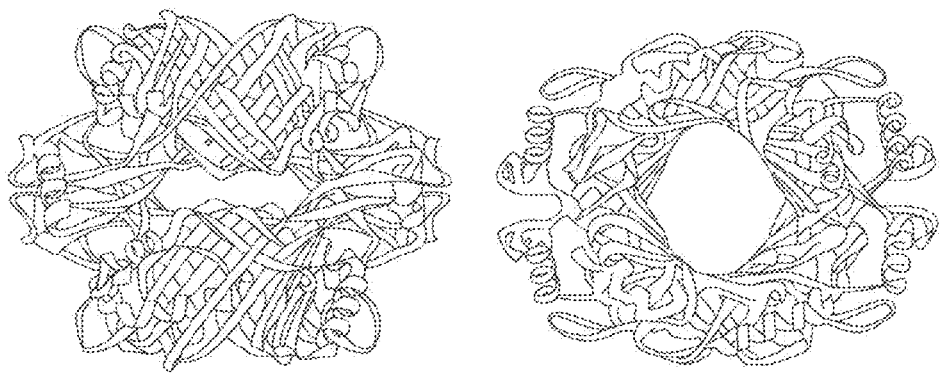
FIG. 2 shows the overall structure of GTP Cyclohydrolase Type IB (GCYH-IB). Panel 2A is a ribbon diagram showing a side view (left) and a top view (right) of the full biological tetramer. Panel 2B is a stereo view of a FOM-weighted experimental electron density map (resolution 2.2 Å, contour level 1.5 σ), calculated after solvent flattening, in the β-sheet region. The map is superimposed on the refined model. The figure was prepared with BobScript software. Esnouf, 55(4) Acta Crystallogr. D Biol. Crystallogr. 938-40 (1999).
Figure 2B:
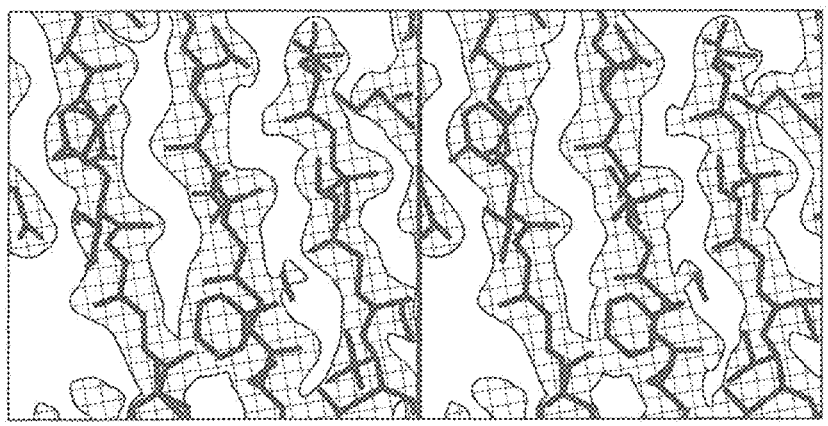

The crystal structure of GCYH-IB was determined by seleno-MAD methods (FIG. 2, Tables 7 and 9). Two monomers, A and B, were identified in the asymmetric unit. The final structure is missing residues 1-13 of monomer A and residues 1-14 of monomer B of the total 257 amino acids in each monomer, and contains two $Zn^{2+}$ ions and one acetate molecule. A homotetrameric complex representing the biological state of the enzyme. El Yacoubi et al. 281 J. Biol. Chem., 37586-37593 (2006) could be generated from the asymmetric-unit dimer by a crystallographic 2-fold rotation operation (FIG. 2A). (32% of the total monomeric surface is buried in the homotetramer). The monomer is a globular subunit composed of 9 β-strands and 6 α-helices (FIG. 3A), of which 8 sequential antiparallel β-strands (β1-β6, β8 and β9) and four antiparallel α-helices (α1, α2, α4 and α6) form a core with the classic tunneling fold (T-fold) architecture characteristic of bimodular pterin and purine binding enzymes. Colloc'h et al. 39 Proteins, 142-154 (2000). In this core, a highly twisted eight-stranded β-sheet is layered on its concave side with four antiparallel α-helices. The dimer of the asymmetric unit is constructed by a cyclic arrangement of the two eight-stranded β-sheets from the two monomers to form a sixteen-stranded antiparallel β-barrel. In the biological homotetramer, two β-barrels join together head-to-head to form a central tunnel that is 60 Å long and 17 Å in diameter (FIG. 2A).

A search for similar structures was done using the DALI search engine and the FSSP database (fold classification based on structure-structure alignment of proteins). Holm & Sander 233 J. Mol. Biol. 123-38 (1993). Several bimodular T-fold enzymes were identified, as well as GCYH-IA (FIG. 3C), a unimodular T-fold enzyme. The best fit was to *A. flavus* urate oxidase. Retailleau et al., 60 Acta Crystallogr. D 453-62 (2004) (PDB ID 1UOX, r.m.s.d. 3.4 Å over 197 $C_\alpha$ atoms, FIG. 3B) that follows a similar β8α4 topology.

Comparison of GCYH-IA and GCYH-IB structures shows that GCYH-IB is a homotetramer built around a bimodular β8α4 T-fold core and GCYH-IA is a homodecamer β4α2 unimodular T-fold enzyme. Pairwise structural comparison of the monomeric subunits of GCYH-IB and *E. coli* GCYH-IA (Rebelo et al., 326 J. Mol. Biol. 503-16 (2003)) (PDB ID 1FBX) using the DaliLite server (Holm & Park 16 Bioinformatics, 566-567 (2000)) yielded an alignment strictly in the four β-strands and two α-helices (β2, β3, β6, β7, α6, α7 of GCYH-IA, and β5, β6, β8, β9, α4, α6 of GCYH-IB) of the T-fold (r.m.s.d. 3.2 Å over 94 $C_\alpha$ atoms, FIG. 3C). Based on this alignment, a multi-sequence alignment of the two enzyme subfamilies in the shared core region was generated (15 sequences of each, FIG. 4). With the exception of a conserved cysteine involved in metal binding in both subfamilies (Cys147 in GCYH-IB), the new alignment differs significantly from previously reported alignment that was based on sequence information and predicted tertiary structure.

In the current alignment, the two subfamilies exhibit 28% sequence similarity and only two invariant residues; the metal and substrate liganding residues Cys147 and Glu216 (*N. gonorrhoeae* numbers), respectively. This unusually low primary structure homology, compared with 7%-17% identity and 39%-53% similarity between T-fold enzymes in general, explains improper annotation of GCYH-IB genes in genomic databases and limited success in previous attempts to generate a model of the tertiary structure by sequence-based homology modeling (El Yacoubi et al, 2006).

Figure 3:
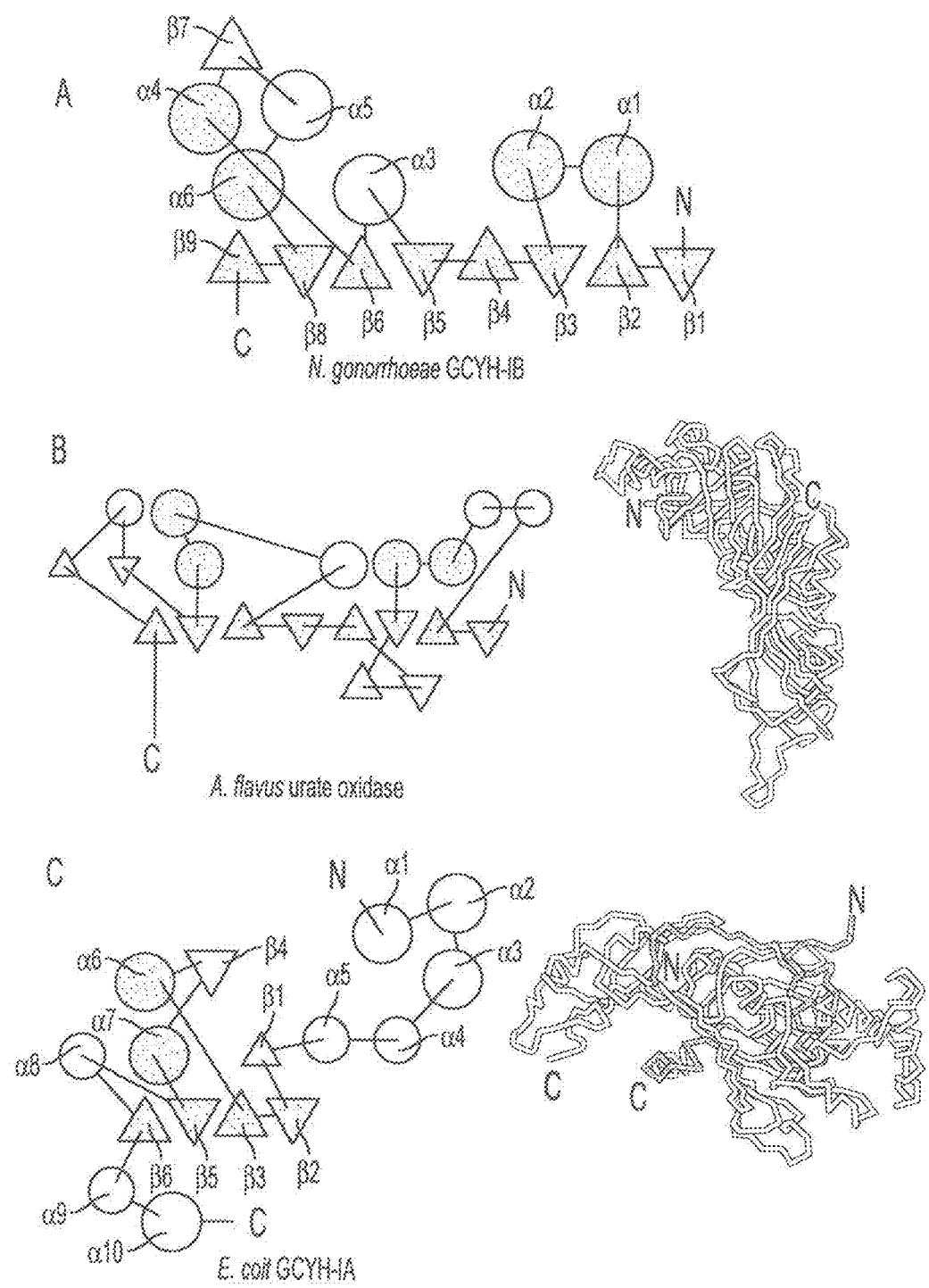
FIG. 3 depicts the topology of the GCYH-IB monomer and structural comparison with other T-fold enzymes. Panel 3A presents topology diagrams of *N. gonorrhoeae* GCYH-IB. Panel 3B: of *A. flavus* urate oxidase; Panel 3C: of *E. coli* GCYH-IA. Michalopoulos et al., 32 Nucleic Acids Res. D251-54 (2004). The N- and C-terminal modules of the core bimodular T-fold are colored in gray and light gray, respectively. $C_\alpha$ trace superpositions of the N- (gray) and C-terminal (light gray) modules of GCYH-IB with corresponding enzymes are shown in Panel B and panel C. Secondary structure nomenclature is shown for the two GCYH-I enzymes.

In addition to the absence in GCYH-IB of the N- and C-terminal domains found in GCYH-IA (FIGS. 3A and 3C), the following functionally important differences are seen in the T-fold domain, specifically in the active site: (a) insertion in GCYH-IB of a two turn α-helix (α3) between the first two strands (β5 and β6) of the common T-fold β-sheet (FIGS. 3A, 3C and FIG. 4). This change results in the loss of the $Zn^{2+}$ binding loop C110EHH113 found in GCYH-IA, with the exception of the Cys (FIG. 4); (b) Insertion in GCYH-IB of a β-strand (β7) and α-helix (α5) between the two α-helices (α4 and α6) of the T-fold (FIGS. 3A, 3C and FIG. 4). β7 and α5 are part of the inter-subunit interface that harbors the active site. Significantly, α5 provides the strictly conserved Glu201 as a carboxylate ligand to the active-site metal ion in GCYH-IB; and (c) Deletion in GCYH-IB of helix α8 found in the T-fold domain of GCYH-IA (FIGS. 3A, 3C, and FIG. 4). Importantly, α8 contains the second Cys ligand to $Zn^{2+}$ in GCYH-IA. This Cys is missing in GCYH-IB and the helix is replaced with a β-turn containing strictly conserved Glu243, His246 and His248.

Rearranged metal binding site and accommodation of $Mn^{2+}$; as in GCYH-IA, the active site of GCYH-IB is located at the interface between three subunits (Table 10 and Table 11). Two of the four active sites in the GCYH-IB homotetramer are partially disordered in the crystal. The active site encompasses the metal binding site and the putative GTP binding pocket with the conserved Glu216 that serves to anchor the substrate guanine moiety, a characteristic feature of all T-fold proteins (Colloc'h et al, 2000).

Figure 5:
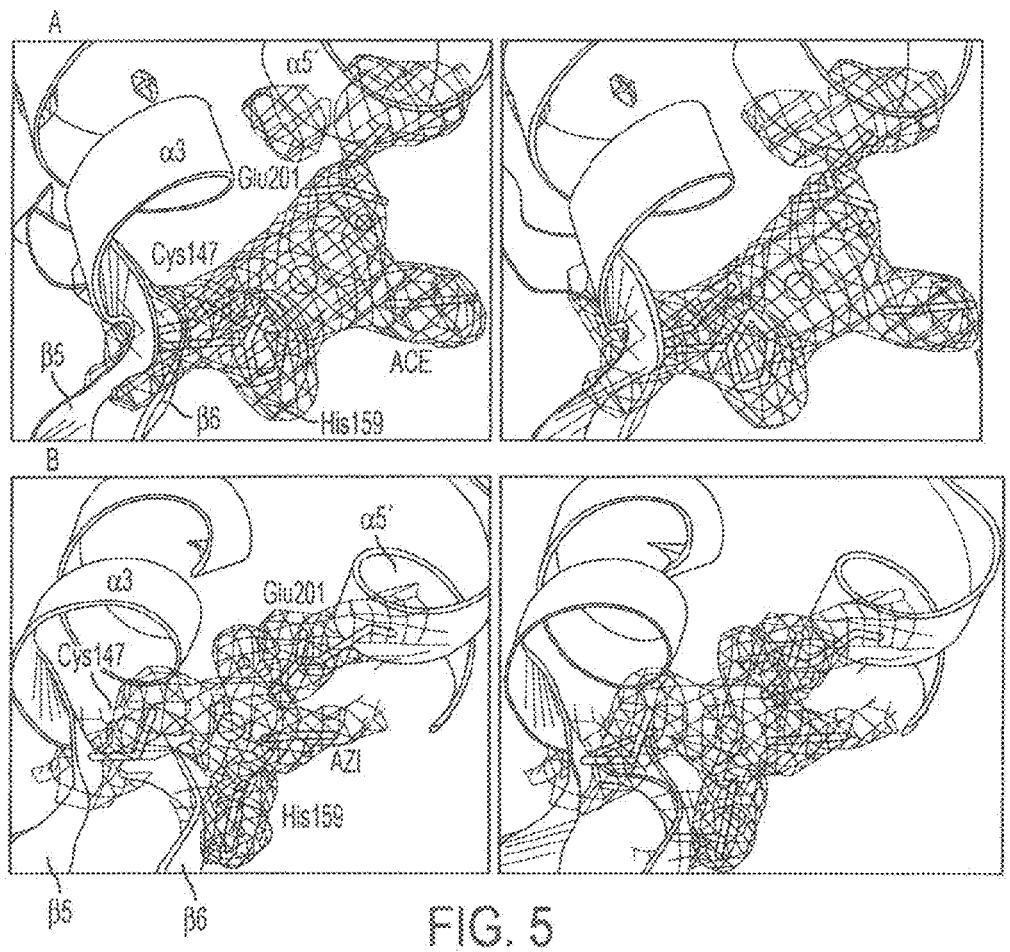
FIG. 5 depicts the metal site in GCYH-IB. Panel A shows a stereoview of annealed Fo-Fc electron density map (1500 K, 2.2 Å, 2.5 σ, $Zn^{2+}$ and its ligands omitted from the phase calculation) superimposed on the model. Panel B shows the $Mn^{2+}$-occupied metal site in the GCYH-IB.$Mn^{2+}$ complex. Stereoview of annealed omit Fo-Fc electron density map (1500 K, 2.04 Å, 2.5 σ, $Mn^{2+}$ and its ligands omitted from phase calculation) superposed on the model. Metal ions and water molecules are shown as spheres. Secondary structure elements in GCYH-IB are labeled.
Figure 6:
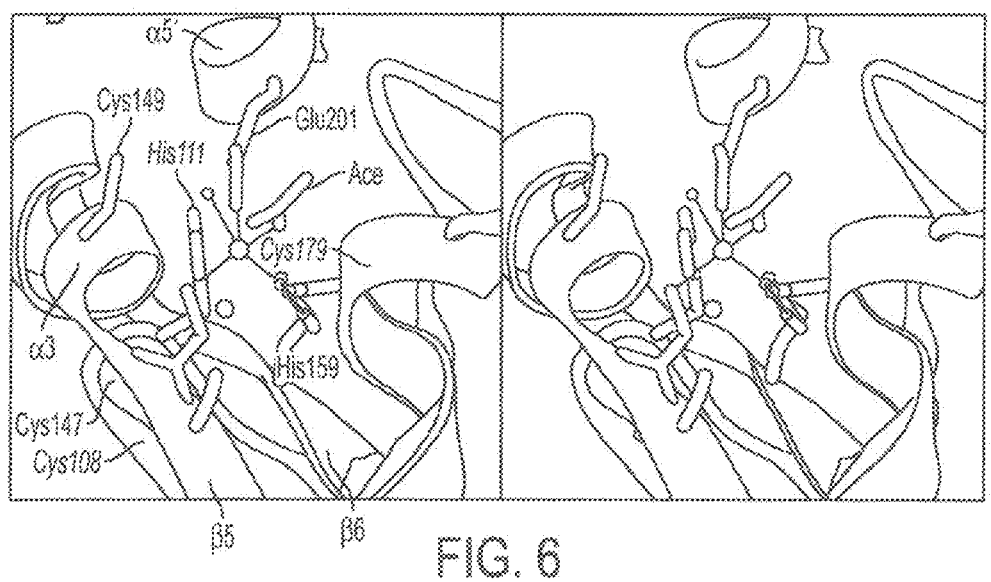
FIG. 6 presents a 3D alignment of GCYH-IB (regular labels) and *T. thermophilus* GCYH-IA (italic labels) in the active-site region. Strictly conserved Cys149 in the metal binding loop of GCYH-IB is shown although it does not interact with the bound metal.
Figure 7:
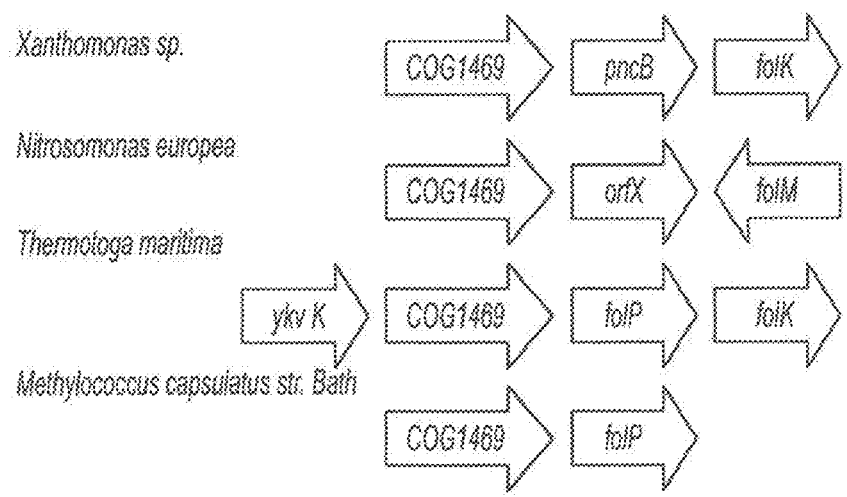
FIG. 7 illustrates the physical clustering of GCYH-IB (labeled COG1469) encoding genes with folate biosynthetic genes, such as folK, folP, and folM (an alternative dihydrofolate reductase gene). Rebelo et al., 326(2) J. Mol. Biol. 503-16 (2003).
Figure 12:
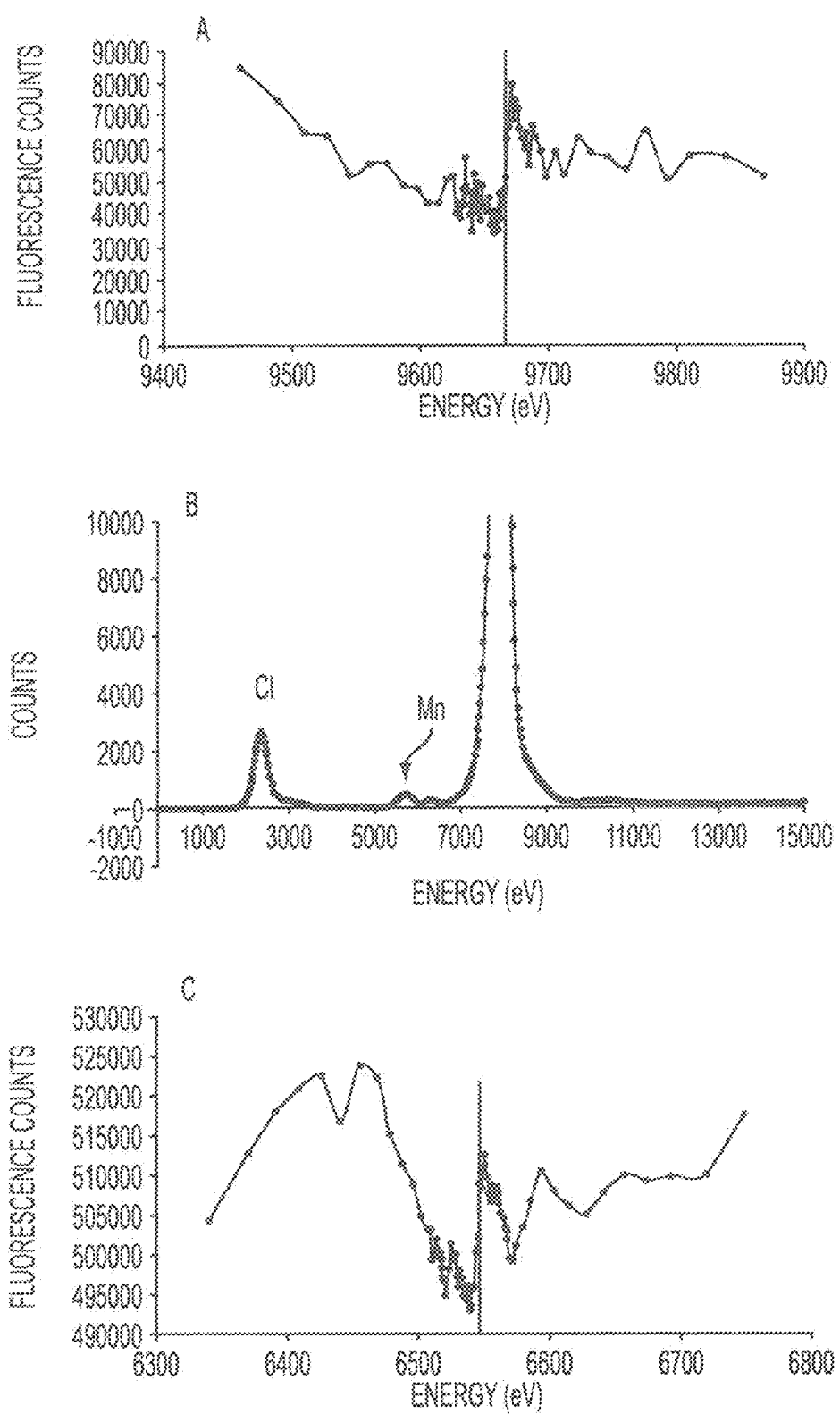
FIG. 12 shows data from X-ray emission and fluorescence scans of bound metals in GCYH-IB crystals. Panel A reflects the fluorescence spectrum from GCYH-IB crystal taken near the zinc absorption edge. Panels B and C are emission scan and fluorescence spectrum, respectively, from GCYH-IB.$Mn^{2+}$ crystal taken near the manganese K-shell absorption edge. Inflection points in the fluorescence spectra are indicated with vertical lines. The large peak in panel B corresponds to scattering from the main beam.

The presence of bound $Zn^{2+}$ in the GCYH-IB crystal (grown with no additional Zn in the crystallization buffer) was confirmed by an X-ray fluorescence scan near the Zn absorption edge (see FIG. 12A) and an omit Fo-Fc map (FIG. 5A). $Zn^{2+}$ is bound in a trigonal bipyramidal geometry and is coordinated by the thiol group of Cys147, side-chain oxygen atom of Glu201 from the neighboring subunit, and an oxygen atom from a bound acetate molecule (present in the protein sample at 50 mM) as equatorial ligands, and Nε of His159 and a water molecule as the bottom and top axial ligands, respectively (FIGS. 5A and 6 and Table 10). The average $Zn^{2+}$-to-ligand distance is 2.4 Å. In its current position, the acetate molecule may mimic one of the cyclohydrolase reaction transition states that are subsequent of the opening of the substrate guanosine ring. The liganding side chains, their positions in the $Zn^{2+}$ coordination sphere and the protein secondary structure elements in which they lie are different from those seen in GCYH-IA (FIGS. 4, 6, and Table 10). In *T. thermophilus* and *E. coli* GCYH-IA (PDB ID 1WM9, Rebelo et al., 326 J. Mol. Biol. 503-516 (2003); Tanaka et al., 138 J. Biochem. 263-275 (2005)), $Zn^{2+}$ is coordinated by two thiol groups and a histidine side chain (Cys110, Cys181, His113 in *E. coli* residue numbers), all from the same subunit. These side chains come from the loop between the first two β-strands of the T-fold (β2 and β3 in Ec-GCYH-IA nomenclature) and a short α-helix (α8) (FIG. 4). In GCYH-IB, the metal binding site is formed by the helix-loop insertion (α3) between the first two β strands of the T-fold (β5 and β6) and the helical insertion α5 from the neighboring subunit.

Crystals of GCYH-IB remetallated with $Mn^{2+}$ (GCYH-IB.Mn) were grown using Zn-free reagents. The presence of bound $Mn^{2+}$ was confirmed with an X-ray emission spectrum and fluorescence scan near the Mn absorption edge following a wash and 1-hr back-soak of the crystal in metal-free solution (see FIGS. 12B and 12C). The crystal structure was determined by difference Fourier methods using model phases from the $Zn^{2+}$-metallated structure (Tables 7 and 9 and Table 11). The two structures are similar and superpose with r.m.s.d. 0.3 Å over 486 Cα atoms. Metal coordination and distances are also similar except for the replacement of acetate with azide (added to the acetate-free protein sample at 12 mM concentration prior to crystallization) as an equatorial ligand to $Mn^{2+}$ (FIG. 5B and Table 11).

The Zur dependent regulation of folE2 is conserved across bacterial species. The biochemical and structural analyses of *B. subtilis* and *N. gonorrhoeae* GCYH-IB suggest that Zn is not the physiological metal for this family of cyclohydrolases. The expression of GCYH-IB in *B. subtilis* is controlled by the Zn-dependent Zur repressor and is thus up-regulated under Zn-limiting conditions. Gelfand et al., 1 Brief Bioinform 357-71 (2000). To check if orthologs of folE2 in other bacteria are similarly subject to Zur-mediated control, bacterial regulons were analyzed using a comparative genomics approach. Gelfand et al, 2000; Rodionov, 107 Chem. Rev. 3467-97 (2007). Annotation of the folE and folE2 genes in available genomes had been performed previously. Two position-specific weight matrices (PWMs) were constructed for known Zur binding sites from Gram-positive and Gram-negative bacteria (Panina et al., 100 Proc Natl Acad Sci USA 9912-17 (2003)), and were used to scan for candidate Zur binding sites in 5'-untranslated regions (UTRs) of folE2 and neighbor genes in bacterial genomes. To account for possible operon structures, UTRs of genes located immediately upstream of folE2 in the genomes were also analyzed.

Strong Zur operator sites were identified upstream of folE2 genes in twenty-one bacterial genomes (Table 4, FIG. 13). This unique regulatory feature is conserved across phyla including examples in fifteen γ-proteobacteria (Pseudomonadales, Xanthomonadales, some *Enterobacteria*, and other lineages), three β-proteobacteria (some Burkholderiales), and three *Bacillus* species. Notably, all organisms that have the Zur-regulated folE2 gene also contain a copy of folE (e.g., *B. subtilis*). Similarly, no Zur regulatory sites were found upstream of folE2 genes in those organisms that lack the Zn-dependent GCYH-IA isozyme (e.g., *N. gonorrhoeae*). These results show that Zur regulation of GCYH-IB is widespread and suggest that, in some bacteria, the GCYH-IB isozyme is expressed under Zn-limiting conditions to replace the Zn-dependent GCYH-IA.

Figure 11:
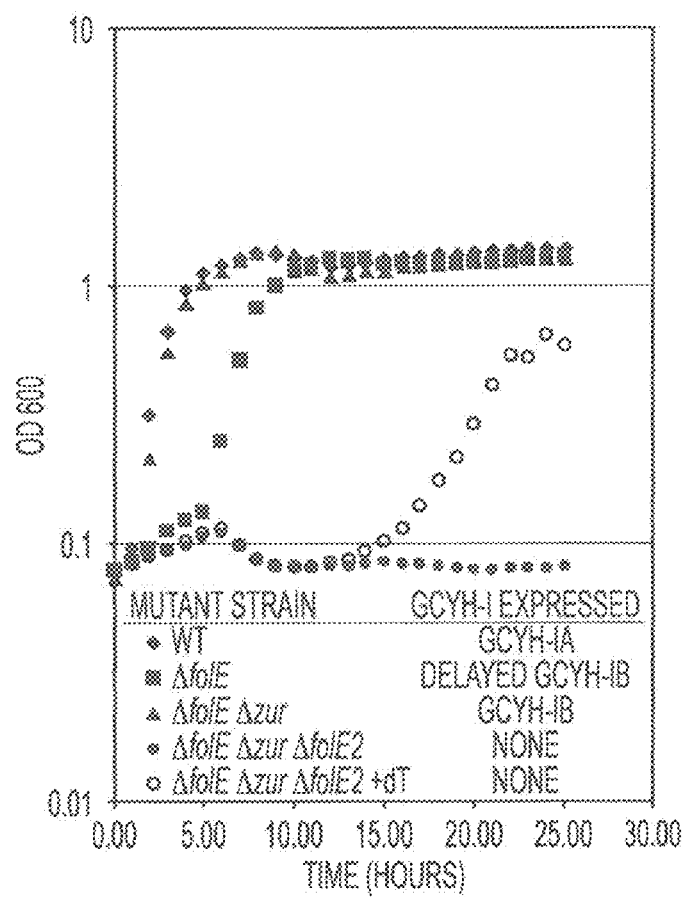
FIG. 11 reflects GCYH-IB-dependent complementation of the *B. subtilis* ΔfolE mutant strain. Growth curves in rich medium of wild type (WT) and mutant *B. subtilis* strains expressing either type of GCYH-I. Strains and their corresponding expressed GCYH-I isozyme are listed.

GCYH-IB can functionally replace GCYH-IA in *B. subtilis*, which has both the folE and folE2 genes (also known as mtrA and yciA, respectively). To determine whether GCYH-IB can functionally replace GCYH-IA, a *B. subtilis* ΔfolE mutant strain was constructed and its complementation with GCYH-IB investigated. Wild-type *B. subtilis* grows well in rich (LB) medium (FIG. 11, diamonds). As reported previously (Babitzke et al., 174 J, Bacteriol. 2059-64 (1992)), the ΔfolE mutant strain, expressing only GCYH-IB, is a thymidine (dT) auxotroph. In the absence of dT, it grows only with a reproducible lag in rich medium (FIG. 11, squares). Poor growth of the ΔfolE mutant strain in log phase is consistent with repression of GCYH-IB expression under these conditions. Growth commences in stationary phase and reflects derepression of GCYH-IB when cells become Zn-starved and Zur repression is released. Indeed, deleting the zur gene, as in the Δzur ΔfolE double mutant where GCYH-IB is constitutively expressed, eliminates the growth lag in rich medium (FIG. 11, triangles). As expected, the ΔfolE Δzur ΔfolE2 triple mutant strain, expressing no GCYH-I, is unable to grow (FIG. 11, closed circles), nor is the ΔfolE ΔfolE2 double mutant strain. For either strain, growth can only be partially restored by the addition of dT (FIG. 11, open circles) or all of the folate-derived metabolites. The rather poor dT rescue of these two mutant strains may be due to deficient formylated methionine biosynthesis. These results indicate that GCYH-IB functionally replaces GCYH-IA in *B. subtilis* under Zn-limiting conditions.

Sequence conservation indicates that metal-dependent catalysis is a property of the GCYH-IB enzyme family in general, with $Mn^{2+}$, not $Zn^{2+}$, possibly the preferred metal in vitro. Indeed, metal catalysis has been observed with GCYH-IB orthologs from *N. gonorrhoeae* and *T. maritima*, and from *M. jannaschii* (Grochowski et al., 46 Biochem. 6658-67 (2007)), which exhibits optimal activity in the presence of $Fe^{2+}$. The structural differences between GCYH-IA and -IB enzymes in the active-site region contribute to creating a new metal functionality in GCYH-IB. For example, the introduction of an acidic side chain (Glu201) in the metal site of GCYH-IB allows accommodation of $Mn^{2+}$ which favors oxygen ligands more than $Zn^{2+}$. Further, the contribution of a neighboring subunit to the metal site suggests possible post-translational regulation by metal-induced oligomerization as seen in DHNA. Goulding et al., 349 J. Mol. Biol. 61-72 (2005). The metal ion likely serves to activate the nucleophile water molecule in the first step of the reaction and to stabilize the formyl intermediate, as in GCYH-IA. Tanaka et al, 2005.

The differences in the active-site architecture and associated metal dependence between GCYH-IA and -IB may reflect differences in catalytic strategies for the two enzyme families. The presence of acetate and azide as exogenous metal ligands in the $Zn^{2+}$- and $Mn^{2+}$-metallated enzyme structures, respectively, is a result of sample preparation conditions and does not reflect specificity to the type of metal. The acetate ligand may mimic the reaction formyl intermediate or formic acid as a leaving group. The azide ligand may represent a moiety in a transition-state intermediate occurring in a later step, e.g., during the Amadori rearrangement that takes place after guanine and ribose ring opening.

Zinc is an essential cofactor for numerous proteins. In Bacteria and Eukaryotes, cellular $Zn^{2+}$ levels are sensed by specific transcription factors (the repressor Zur in *B. subtilis* and *E. coli*, the activator Zap1p in *S. cerevisiae*). Hantke, 8 Curr. Opin. Microbiol. 196-202 (2005); Lyons et al., 97 Proc. Nat'l Acad. Sci. USA 7957-62 (2000); Moore & Heimann, 8 Curr. Opin. Microbiol. 188-195 (2005). Cellular responses to low $Zn^{2+}$ conditions include increased expression of high-affinity $Zn^{2+}$ transporters such as ZnuABC, and substitution of $Zn^{2+}$-dependent enzymes with alternative isozymes that do not rely on this metal ion as a cofactor. Examples of the latter strategy include $Zn^{2+}$-dependent regulation of the alcohol dehydrogenase isozyme ADH4 in yeast (Lyons et al., 2000), and paralogs of ribosomal proteins (e.g., L31 and L33) in *B. subtilis* and *Streptomyces coelicolor*. Nanamiya et al., 52 Mol. Microbiol. 273-83 (2004); Panina et al, 2003; Shin et al., 189 J. Bacteriol. 4070-77 (2007).

Similarly, results from the work presented herein indicate that the upregulation of *B. subtilis* GCYH-IB when $Zn^{2+}$ is low serves to allow utilization of metal ions other than $Zn^{2+}$ for folate synthesis. On the other hand, *N. gonorrhoeae* (and several other pathogens) do not possess the Zn-dependent GCYH-IA isozyme and instead rely solely on GCYH-IB for folate synthesis. Consistently, they do not have Zur regulatory sites upstream of the folE2 gene. *N. gonorrhoeae* live in the highly oxidizing environment created by the host immune response and, to survive in this challenging environment, they accumulate millimolar levels of manganese, an effective scavenger of reactive oxygen species (ROS), in the cytoplasm. Seib et al., 70 Microbiol. Mol. Biol. Rev. 344-61 (2006). A similar utilization of Mn to fight ROS damage resulting from radiation exposure occurs in *D. radiodurans*. Daly et al., 306 Science 1025-28 (2004). Presumably, the ready availability of $Mn^{2+}$ makes a Mn-dependent folate biosynthesis pathway more advantageous for these organisms. Further, a recent report shows that the innate immune system in mice fights *S. aureus* infections by inhibiting microbial growth in tissue abscesses through chelation of $Mn^{2+}$ and $Zn^{2+}$ by the neutrophil-derived protein calprotectin, depriving the bacteria of essential nutrients. Corbin et al., 319 Science 962-65 (2008). It is possible that this defense strategy targets, among other cellular processes, folate synthesis in *S. aureus*, an organism that depends solely on GCYH-IB for folate synthesis and lacks GCYH-IA (FIG. 13). Hence, the distinct structure and metal dependence of GCYH-IB and its absence in humans may make it an attractive target for the development of new antibiotic agents.

The structural information disclosed herein is useful analysis of binding interactions with a ligand, e.g., for discovery of small molecule antibiotic agents. Such data is useful for a number of purposes, including the generation of structures to analyse the mechanisms of action and/or to discover or perform rational drug design of active compounds. For example, a search of several small-molecule structural data bases such as Available Chemicals Directory, Cambridge Crystallographic Database, Fine Chemical Database and CONCORD database is carried out using parameters derived from the crystal structure. The search can be 2-dimensional, 3-dimensional or both and can be done using a combination of software such as UNITY version 2.3.1 (Tripos, Inc.), MACCS 3D, CAVEAT and DOCK. Conformational flexibility of the small molecules is allowed. The strategy for conducting the search takes into account conformations and/or key residues in the combining site.

As discussed above, the structural information can be stored on a computer-readable medium. The invention therefore provides systems, particularly a computer system, the systems containing the atomic co-ordinate data of any one of the tables below, or selected co-ordinates thereof. The computer system may comprise: (i) a computer-readable data storage medium comprising data storage material encoded with the computer-readable data; (ii) a working memory for storing instructions for processing said computer-readable data; and (iii) a central-processing unit coupled to said working memory and to the computer-readable data storage medium for processing said computer-readable data and thereby generating structures and/or performing rational drug design. The computer system may further comprise a display coupled to the central-processing unit for displaying said structures. The computer system may contain one or more remote devices. The remote device may comprise e.g. a computer system or computer readable media of one of the previous aspects of the invention. The device may be in a different country or jurisdiction from where the computer-readable data is received. The communication with a remote device may be via the internet, intranet, e-mail etc, transmitted through wires or by wireless means such as by terrestrial radio or by satellite. Typically the communication will be electronic in nature, but some, or all, of the communication pathway may be optical, for example, over optical fibers. The data received may then be used in a computer-based method for the analysis of the interaction of a ligand as discussed above.

EXAMPLES

Example 1

Bioinformatics

Analysis of the folate subsystem was performed in the SEED data base (Overbeek et al., 33(17) Nucl. Acids Res. 5691-5702 (2005)) with SEED version cvs.1144925141 (05: 45:41 on Apr. 13, 2006) (available on the internet at, for example, the ".org" site of the National Microbial Pathogen Data Resource (NMPDR). Results are made available in the "Folate Biosynthesis Subsystem" on the publicly available server (available on the internet at the SEED cite of the University of Chicago). The phylogenetic pattern search was performed on the SEED server located on the NMPDR website.

Example 2

Cloning of *Thermotoga maritima, Neisseria gonorrhoeae*, and *Bacillus subtilis* COG1469 Genes for GCYH-IB Protein Expression The COG1469 genes from *T. maritima* (TM0039; GenBank™ accession number gi|15642814), *N. gonorrhoeae* (ngo0387; GenBank™ accession number gi|59800831), and *B. subtilis* (yciA; GenBank™ accession number gi|2632620) were amplified by PCR from genomic DNA of the respective organisms. The primers have been included in Ser. No. 60/935,124 and published in El Yacoubi et al., 2006.

The PCRs contained 500 ng of genomic DNA, 200 µM dNTPs, 50 pmol of the sense and antisense primers, 1×Pfu Ultra buffer (supplied by the manufacturer), and 2.5 units of Pfu Ultra DNA polymerase in a final volume of 50 µl. A three-step PCR thermocycling protocol was utilized: (1) 94° C. for 1 min; (2) 30 cycles of denaturation at 94° C. for 1 min, annealing at 50° C. for 2 min, and extension at 72° C. for 1 min; (3) 72° C. for 4 min. The PCR product was purified from a 1% agarose gel containing ethidium bromide using the Qiagen Inc. PCR purification kit and cloned into a linearized pET-30 Xa/LIC expression vector (Novagen). The primary structures of the resulting constructs, pSAB-7-189 (*T. maritima*), pSAB-8-142 (*N. gonorrhoeae*), and pSAB-9-61 (*B. subtilis*), were confirmed by sequencing.

Example 3

Cloning of the *T. maritima*, *Acinetobacter baylyi*, and *B. subtilis* COG1469 Genes for Complementation pTM0039 expressing the TM0039 gene under PBAD control (Klock et al., 6(2-3) J. Struct. Genomics 89-94 (2005)) was a kind gift of the Joint Center for Structural Genomics (La Jolla, Calif.). The COG1469 genes from *B. subtilis* (yciA) and *A. baylyi* (ACIAD1740 gi|50084892) were cloned in pBAD24. Guzman et al., 177(14) J. Bact. 4121-30 (1995). The primers have been included in Ser. No. 60/935,124 and published in El Yacoubi et al., 2006. PCR products were obtained and purified as described above and then digested with NcoI/XbaI before ligation into plasmid pBAD24 (Guzman et al., 1995) digested with the same endonucleases and transformed into Topo10 cells (Invitrogen). The primary structures of the resulting constructs, pBY142.1 (expressing *A. baylyi* ACIAD1740) and pBY143.1 (expressing *B. subtilis* yciA), were confirmed by sequencing.

These plasmids, as well as pBAD24 and pTM0039, were transformed into the *E. coli* folE::KanR strain. Klaus et al., 280(46) J. Biol. Chem. 38457-63 (2005). The transformants were plated on LB supplemented with dT, ampicillin and kanamycin, and screened for the capacity to grow on LB without dT in the presence of various concentrations of arabinose. To confirm the presence of the folE::Kan$^R$ allele and of the pBAD derivatives in the transformants, the colonies were analyzed by PCR using the oligonucleotides located upstream and downstream from the folE gene and ChkDfolEol2 or located upstream and downstream of the polylinker in the pBAD derivatives and pBADol5 as described in Ser. No. 60/935,124 and published in El Yacoubi et al., 2006.

Example 4

Purification and Overexpression of Recombinant *T. maritima*, *N. gonorrhoeae*, and *B. subtilis* GCYH-IB Proteins The plasmids pSAB-7-189, pSAB-8-142, and pSAB-9-61 were transformed into *E. coli* BL21 (DE3) for expression of His6 tag (SEQ ID NO: 33) fusion proteins. Cultures of the transformed cells were grown at 37° C. with shaking (250 rpm) until an A600 of 0.9 was attained. Isopropyl-D-thiogalactopyranoside was added to a final concentration of 0.1 mM, and the cultures were incubated for an additional 4 h at 37° C. with shaking (250 rpm). The cells were harvested by centrifugation at 5000×g for 10 min at 4° C. The cell paste was flash frozen in liquid nitrogen and stored at −80° C. until needed.

Frozen cell paste was thawed and suspended in lysis buffer (50 mM Tris acetate (pH 8.0), 50 mM KCl, and 1 mM-mercaptoethanol) at a concentration of 250 mg/ml. The cells were lysed by the addition of lysozyme and DNase to a final concentration of 0.25 mg/ml and 10 μg/ml, respectively. The lysate was centrifuged at 15,000×g for 30 min at 4° C., and the resulting supernatant was filtered (low protein binding, 0.45 μm). The cell-free extract was loaded onto an Ni$^{2+}$-nitrilotriacetic acid-agarose column (Qiagen) that had been equilibrated with Buffer A (100 mM Tris-acetate (pH 8.0), 300 mM KCl, 2 mM β-mercaptoethanol, 1% Triton X-100, 1 mM phenylmethylsulfonyl fluoride, and 10% glycerol). The column was washed with five column volumes of Buffer A, five column volumes of Buffer B (100 mM Tris acetate (pH 8.0), 300 mM KCl, 2 mM β-mercaptoethanol, 1% Triton X-100, 1 mM phenylmethylsulfonyl fluoride, 10% glycerol, and 20 mM imidazole), and finally five column volumes of Buffer C (100 mM Tris acetate (pH 8.0), 300 mM KCl, 2 mM-mercaptoethanol, 10% glycerol, and 20 mM imidazole). The protein was eluted from the column with ten column volumes of Buffer C containing 250 mM imidazole. The protein was concentrated in a Centricon YM-10 ultracentrifugation device and dialyzed at 4° C. against 50 mM Tris acetate (pH 8.0), 50 mM KCl, and 4 mM dithiothreitol.

The His6 tag (SEQ ID NO: 33) was cleaved from the *T. maritima*, *N. gonorrhoeae*, and *B. subtilis* GCYH-IB proteins in reactions that contained fusion protein (20 mg), Factor Xa protease (20 μg), 50 mM Tris acetate (pH 8.0), 100 mM KCl, 2 mM CaCl$_2$ in a final volume of 1 ml. After incubating for 20 h at room temperature, the reactions were loaded onto a column containing 2 ml of Ni2+-nitrilotriacetic acid-agarose equilibrated in Buffer A. Wild-type protein was eluted from the column with ten column volumes of Buffer A. The protein was concentrated and dialyzed against 50 mM Tris acetate (pH 8.0), 50 mM KCl, and 10% glycerol.

Example 5

COG1469 Genes Complement an *E. coli* folE Mutant

Because folate is not transported in most bacteria (Skold et al., 2000), it can not be supplied in the medium to enable growth of a folate auxotroph. On rich medium, however, all of the folate-derived metabolites are present in sufficient quantities except for dT, allowing a folE mutant to be maintained on LB/dT. Klaus et al., 2005; Yakhin & Babitzke, 2004. Nevertheless, the *E. coli* folE::KanR strain has a slow growth phenotype on LB/dT (colonies take two days instead of one day to form at 37° C.), presumably due to the absence of formylation of the initiator tRNA. The folE::KanR strain was transformed with pBAD derivatives expressing the COG1469 homolog from *T. maritime* (TM0039).

Figure 8:
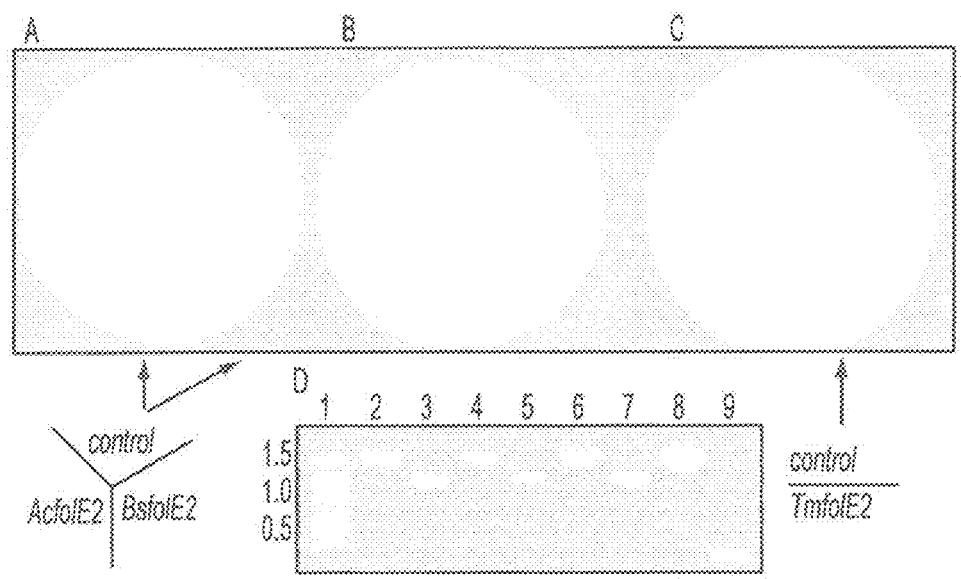
FIG. 8 depicts various complementation data of the dT auxotrophy on LB (Panel A) or the slow growth phenotype on LB dT (Panel B) of the *E. coli* folE::KanR by pBAD derivatives expressing the GCYH-IB genes from *B. subtilis* (BsfolE2) and *A. baylyi* (AcfolE2). Panel C shows complementation of the slow growth on LB in the presence of dT of the *E. coli* folE::KanR by a plasmid expressing TM0039 (TmfolE2). The control is folE::KanR transformed by pBAD24. The plates were incubated at 37° C. for 48 h. Panel D presents PCR amplification to check for the presence of the folE::KanR allele (lanes 2, 4, 6, and 8) and to check for the presence of an insert of the expected size in the pBAD derivatives (lanes 3, 5, 7, and 9) was performed on the folE::KanR strain transformed with plasmids expressing AcfolE2 (lanes 2 and 3), BsfolE2 (lanes 4 and 5), and TmfolE2 (lanes 6 and 7) and with the pBAD24 control (lanes 8 and 9). The expected size of the PCR product detecting folE::KanR is about 3.5 kb, whereas the same primers amplify a 2.5-kb product in the wild type strain. The sizes of the PCR products resulting from having AcfolE2, BsfolE2, or TmfolE2 in pBAD24 are 1072, 1105, and 960 bp, respectively.

Although complementation of both the dT auxotrophy and the slow growth phenotype was observed (FIG. 8C), was not robust, and depended on high arabinose levels. This is not surprising because *T. maritima* is a thermophile, and many of the enzymes from thermophiles exhibit low activity at 37° C. To achieve better complementation, the COG1469 orthologs from the mesophiles *B. subtilis* and *A. baylyi* (formally known as *Acinetobacter* sp. ADP1) were cloned and transformed into the *E. coli* folE::KanR strain. Robust complementation of dT auxotrophy (FIG. 8A) and poor growth (FIG. 8B) were observed with these constructs, which is consistent with GCYH-IB family proteins catalyzing GCYH-I activity.

Example 6

GCYH-IB Proteins have GCYH-I Activity In Vitro

In parallel with the in vivo experiments, COG1469 genes were cloned into protein expression vectors to allow unambiguous assignment of catalytic function through the direct investigation of putative GTP cyclohydrolase I activity with in vitro enzymatic assays of purified proteins. Thus, the genes encoding GCYH-IB proteins from *T. maritima*, *N. gonorrhoeae*, and *B. subtilis* were cloned from genomic DNA into the pET30 system, and the recombinant His6 fusion proteins were overproduced and purified. All three of the recombinant proteins were obtained as soluble, active enzymes both as the His6 fusion and the cleaved wild type.

Figure 9:
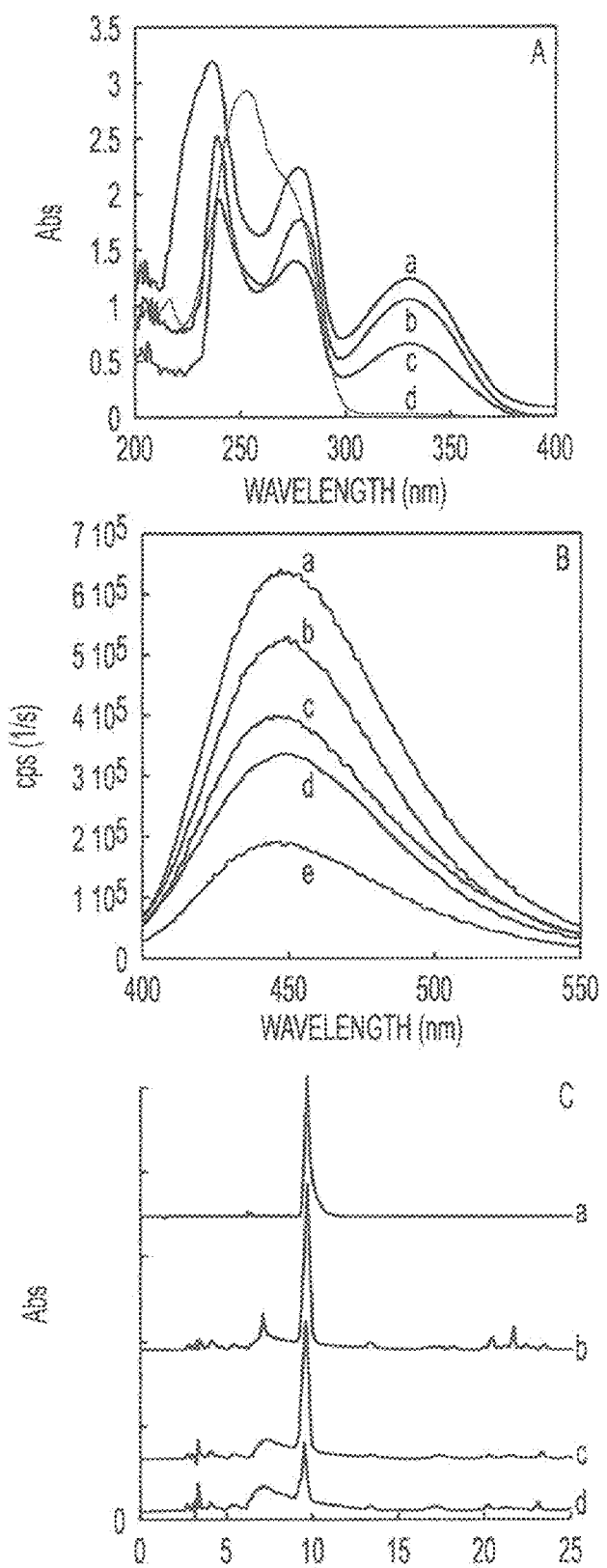
FIG. 9 graphically depicts GCYH-I activity assays. Panel 9A shows UV-visible spectra of cyclohydrolase assays. Line a, *E. coli* FolE; b, GCYH-IB protein from *N. gonorrhoeae*; c, GCYH-IB protein from *B. subtilis*; d, no enzyme. Panel 9B reflects fluorescence spectra of authentic neopterin and cyclohydrolase assays following post-reaction dephosphorylation and oxidation. Fluorescence was measured with excitation at 365 nm. Line a, *T. maritima* GCYH-IB; b, *B. subtilis* GCYH-IB; line c, *E. coli* FolE; d, authentic neopterin; e, *N. gonorrhoeae* GCYH-IB. Panel 9C presents HPLC chromatograms of authentic neopterin (line a) and cyclohydrolase assays with *E. coli* FolE (line b), *B. subtilis* GCYH-IB added to authentic neopterin (line c), and *B. subtilis* GCYH-IB alone (line d). Enzyme assays were subjected to postreaction dephosphorylation and oxidation.

Radiochemical assays using [8-$^{14}$C]GTP (Yim et al., 1976), of each of the GCYH-IB proteins, along with *E. coli* FolE as a positive control, demonstrated that [$^{14}$C]formate was released in each assay and that its production was both time- and enzyme-dependent, consistent with enzyme-catalyzed hydrolytic ring opening and deformylation at C-8 of GTP. From these data, specific activities of 2.3 min$^{-1}$ mg$^{-1}$ to 5.3 nmol min mg$^{-1}$ were calculated for the GCYH-IB proteins, roughly an order of magnitude lower than that reported for FolE (Bracher et al., 274 J. Biol. Chem. 16727-35 (1999); Kolinsky & Gross, 279(39) J. Biol. Chem. 40677-82 (2004); Rebelo et al., 326(2) J. Mol. Biol. 503-16 (2003)) and the FolE control. To confirm that the product of the GCYH-IB catalyzed reactions was in fact 7,8-dihydroneopterin triphosphate, the enzyme assays were analyzed with UV-visible (Bracher et al., 40(26) Biochem. 7896-902 (2001)) and fluorescence spectroscopy. (Hatakeyama & Yoneyama, 100 Methods Mol. Biol. 265-72 (1998)). FIG. 9A shows UV-visible spectra for enzyme assays of *E. coli* FolE and GCYH-IB proteins under standard GTP cyclohydrolase 1 assay conditions. The spectra are essentially identical, with the characteristic absorption spectrum of GTP replaced by that of H2NTP. Bracher et al., 2001. When enzyme assays were subjected to post-reaction dephosphorylation and oxidation to convert the putative enzymatically produced H2NTP to the fluorescent neopterin, the fluorescent spectra from the GCYH-IB assays were identical to the spectrum of the *E. coli* FolE assay (FIG. 9B) and to that of authentic neopterin. Hatakeyama & Yoneyama, 1998.

Furthermore, HPLC analysis of the enzyme assays after dephosphorylation showed that the product from each enzyme-catalyzed reaction had the same retention time as authentic neopterin (under the analysis conditions dihydroneopterin is oxidized to neopterin) (FIG. 9C). Finally, mass spectrometry analysis of the *E. coli* FolE and *N. gonorrhoeae* GCYH-IB reactions revealed identical constituents, with ions corresponding to GTP (m/z 522, M-H$^-$; m/z 544, M-2H$^-$+ Na$^+$; m/z 566, M-3H$^{-2}$Na$^+$), neopterin triphosphate (m/z 492, M-H$^-$; under the conditions of the analysis dihydroneopterin is oxidized to neopterin), and neopterin cyclic monophosphate (m/z 314, M-H$^-$; it has been previously documented that under the alkaline conditions of the work-up neopterin triphosphate is converted to the cyclic monophosphate. Basset et al., 99(19) PNAS 12489-94 (2002); Cone & Guroff, 246(4) J. Biol. Chem. 979-85 (1971); Plowman et al., 249(17) J. Biol. Chem. 5559-64 (1974).

Taken together, the data clearly demonstrate that the GCYH-IB proteins catalyze GTP cyclohydrolase I activity, and thus they represent a new structural class of GTP cyclohydrolase enzymes, distinct from the canonical GCYH-I enzyme exemplified by human and *E. coli* FolE. To differentiate these two cyclohydrolase families, the canonical type I cyclohydrolase may be renamed GCYH-IA, that the COG1469 family be named GCYH-IB, and that their corresponding genes be denoted as folE and folE2, respectively.

Example 7

Over-Expression and Purification of Selenomethionine (SeMet)-Labeled *N. gonorrhoeae* GCYH-IB (Ng-GCYH-IB)

Ng-GCYH-IB was cloned in pET-30 Xa/LIC expression vector (Novagen, San Diego, Calif.) as described previously. El Yacoubi et al., 2006. SeMet-labeled Ng-GCYH-IB was over-expressed in the *E. coli* methionine auxotroph B834 (DE3) (Novagen) following standard methods. Hendrickson et al., 9(5) Eur. Mole. Biol. Org. J. 1665-72 (1990). The His6-tagged protein (SEQ ID NO: 33) was purified on Ni-NTA resin (washed with Tris acetate (100 mM, pH 8.0), KCl (300 mM), β-mercaptoethariol (2 mM), glycerol (10%), and imidazole (20 mM)), and eluted with the same buffer containing 250 mM imidazole. After concentration and dialysis against Tris acetate (50 mM, pH 8.0), KCl (50 mM), and dithiothreitol (4 mM), the His6 tag (SEQ ID NO: 33) was cleaved from the enzyme with Factor Xa as described previously (E1 Yacoubi et al., 2006) and SeMet-labeled wild-type Ng-GCYH-1B was further purified on a Ni-NTA column and eluted with ten column volumes of Tris-acetate (100 mM, pH 8.0), KCl (300 mM), β-mercaptoethanol (2 mM), Triton X-100 (1%), phenylmethylsulfonyl fluoride (1 mM), and glycerol (10%). After concentrating to 5.5 mg/mL, the protein was dialyzed against Tris-Acetate (50 mM, pH 8.0), KCl (100 mM) and β-mercaptoethanol (5 mM) and further concentrated to 9 mg/mL. Selenium substitution was verified with mass spectrometry using MALDI-TOF analysis.

Example 8

Crystallization and X-Ray Data Collection

SeMet-labeled GCYH-IB was crystallized at 20° C. by vapor diffusion in 2 μL sitting drops containing enzyme (9 mg/mL in 50 mM Tris-Acetate, 100 mM KCl, 5 mM BME, pH 8.0), polyethylene glycol 6000 (10-16%), LiCl (1-1.4 M), Tris (50 mM, pH 9.0) and Tris-HCl (50 mM, pH 7.0). The Mn-reconstituted enzyme (10 mg/mL in 50 mM Tris-HCl, 50 mM KCl, 1 mM DTT, pH 8.0) was crystallized under similar conditions but using metal-free reagents (Chelex-100-pretreated Milli-Q water and ultra pure reagents from Hampton, Inc.) with 1-10 mM MnCl$_2$ and 12 mM sodium azide (as a preservative) added to the protein solution prior to crystallization. Crystals were cryo-protected in mother liquor plus ethylene glycol (25%) and flash cooled in liquid nitrogen. For the SeMet-labelled enzyme, a three-wavelength selenium dataset was collected at the Advanced Light Source (ALS, Berkeley, Calif.) beamline 8.2.2. For the GCYH-IB.Mn$^{2+}$ complex, crystals were back-soaked in metal-free reservoir solution for 1 hr prior to cryo protection and a single-wavelength dataset was collected from a single crystal at the Stanford Synchrotron Radiation Laboratory (SSRL, Stanford, Calif.) beamline 7-1. X-ray data were processed in HKL2000. Otwinowski, Z. & Minor, W. 276 Methods Enzymol., 307-326 (1997).

Example 9

Structure Determination

The crystal structure of Ng-GCYH-IB was determined by the multi-wavelength anomalous dispersion (MAD) method using selenium as the anomalous scatterer. An initial heavy-atom substructure consisting of 15 selenium sites was identified using the Phenix-hyss program. Adams et al., 11 J. Synchrotron Rad. 53-55 (2004). Heavy atom positions, occupancies, and atomic displacement parameters were then refined in the SHARP maximum likelihood program (*Maximum-likelihood heavy atom parameter refinement in the MIR and MAD methods*, in METHODS IN ENZYMOLOGY (de La Fortelle & Bricogne, eds., Acad. Press, San Diego, Calif., 1997)), and initial phases were calculated using all Se sites. Phases were improved by density modification with DM (Cowtan, 31 Joint CCP4 & ESF-EACBM Newslett. Protein Crystallography, 34-38 (1994)), and SOLOMON (Abrahams & Leslie, 52 Acta Crystallographica 30-42 (1996)), of the CCP4 suite (Collaborative Computational Proj., N.4, D50 Acta Crystallographica 760-63 (1994)), using data in the resolution range 50 Å to 2.2 Å and solvent content of 47%.

With solvent flattening, the mean figure of merit increased from 0.34 to 0.85. The 2.2 Å FoFOM map was calculated and auto-traced in ARP/wARP (Perrakis et al., 6 Nature Structural Bio. 458-63 (1999)), where 418 of the 514 residues in the asymmetric unit were built. The model was manually completed and partially rebuilt in COOT (Emsley & Cowtan, D60 Acta Crystallographica 2126-32 (2004)), utilizing the two-fold non-crystallographic symmetry (NCS) relation. Subsequent crystallographic refinement was carried out with Phenix-refine (Adams et al. 11 *J. Synchr. Radiat.*, 53-55 (2004)), using NCS restraints and Twin Lattice Symmetry parameterization that included 3 domains per monomer. (Isotropic B-group constraints were applied to disordered parts of the model). Finally, the f and f' were refined in Phenix to final values of −6.4 and 5.6, −5.4 and 4.9, and −5.6 and 3.5, for the peak, inflection, and remote wavelength, respectively. Solvent molecules and ions were added, the structure was further refined in Crystallography and NMR Systems (CNS, Adams et al., 8(5) Curr. Opin. Struct. Biol. 606-11 (1998)), after removal of NCS restraints, and was validated using Procheck software. Vaguine et al., 55 Acta Crystallographica D, 191-205 (1999). The electron density for residues 146-160 and 188-210 of monomer A was weak with refined b-factors >60 Å$^2$, indicating that this region is disordered.

The crystal structure of the GCYH-IB.Mn$^{2+}$ complex was determined by direct difference Fourier calculation in which a protein model based on the crystal structure of the Zn$^{2+}$-metallated enzyme was used to calculate phases. The structure was rigid-body refined in CNS, then refined in the program refmac from CCP4 (Michalopoulos, et al. 32 Nucl. Acids Res., 251-254 (2004)) while applying NCS restraints and solvent flattening. NCS restraints were removed in a second refmac run. Ligands and solvent molecules were modeled in Coot (Emsley, P. & Cowtan, K. 60 *Acta Crystallogr. Biol. Crystallogr. D*, 2126-2132 (2004)) and final refinement in refmac.

TABLE 7

| Dataset | Se$_{peak}$ | Se$_{inflection}$ | Se$_{remote}$ |
|---|---|---|---|
| GCYH-IB X-ray data collection and phasing statistics | | | |
| Data collection | | | |
| Unit cell (Å) | 91.7, 100.3, 114.1 | 91.7, 100.2, 114.0 | 91.8, 100.4, 114.1 |
| Wavelength (Å) | 0.9793 | 0.9795 | 0.9747 |
| Resolution (Å) | 50.0-2.20 | 50.0-2.20 | 50.0-2.20 |
| Unique reflections (ano) | 26,689 (26,567)[1] | 26,724 (26,675) | 26,490 (25,691) |
| Completeness (%) | 99.8 (99.0) | 99.8 (100.0) | 99.0 (92.0) |
| Redundancy | 5.7 (5.0) | 5.8 (5.7) | 5.4 (3.5) |
| Rmerge (%)[2] | 8.7 (61) | 7.5 (36.9) | 84 (89.1) |
| <I/σ(I)> | 16.3 | 17.6 | 15.0 |
| X-ray data collection, phasing, and structure refinement statistics (con't) | | | |
| Phasing statistics (29-2.30 Å) | | | |
| R$_{der}$[3] | 0.074[4] | 0.137 | |
| R$_{anom}$[5] | 0.069 | 0.059 | 0.058 |
| R$_{cullis}$[6] (iso[4]/ano) | 0.49/0.73 | 0.83/0.72 | 0.84/0.86 |
| Phasing power[7] | | | |
| Centric | 0.06 | 0.11 | 0.16 |
| Acentric iso[4] | 0.06 | 0.09 | 0.15 |
| Acentric ano | 1.20 | 1.46 | 1.10 |
| FOM[8], overall | 0.34 | | |
| after DM | 0.83 | | |
| after Solomon | 0.85 | | |
| Number of Se sites | 15 | | |

[1]Highest-resolution shell (2.2-2.28 Å) information in parentheses.

[2]R$_{merge}$ = 100 × ($\Sigma_h \Sigma_i$|<I(h)> − I(h)$_i$|)/$\Sigma_h \Sigma_i$ I(h)$_i$, where I(h)$_i$ is the i$^{th}$ observation of reflection h and <I(h)> is the mean intensity of all observations of reflection h.

[3]R$_{der}$ = $\Sigma_h$|F$_{PH}$ − F$_P$|/$\Sigma_h$|F$_P$|, where |F$_P$| and |F$_{PH}$| are the observed structure factor amplitudes of the native and the derivative, respectively.

[4]The dispersive differences were treated as isomorphous replacement information where the data collected at wavelength 0.9747 Å are treated as native data (Terwilliger 1994).

[5]R$_{anom}$ = $\Sigma_h$|F$_{PH+}$ − F$_{PH−}$|/$\Sigma_h$|<F$_{PH}$>|, where |F$_{PH+}$| and |F$_{PH−}$| are the Friedel-pair observed structure factor amplitudes of the derivative at a given wavelength, and <F$_{PH}$> is their average.

[6]R$_{Cullis}$ = $\Sigma_h$[|F$_H$| − (|F$_{PH}$| − |F$_P$|)]/$\Sigma_h$(|F$_{PH}$| − |F$_P$|), where |F$_H$| is the calculated heavy-atom structure factor for reflection h.

[7]PP$_{disp}$ = (1/N$_{refl}$)$\Sigma_h$ [||F$_{PH}$| − |F$_P$||/$\int_0^{2\pi}$ (|F$_{PH}$−F$_{PH}^{calc}$|) P(φ) d(φ)], where P(φ) is the probability of a phase value of φ for reflection h. PP$_{ano}$ = (1/N$_{refl}$)$\Sigma_h$[|Δ$_{obs}^{ANO}$|/$\int_0^{2\pi}$(|Δ$_{obs}^{ANO}$ − Δ$_{calc}^{ANO}$|) P(φ), d(), where Δ$_{obs}^{ANO}$ and Δ$_{calc}^{ANO}$ are the Friedel-pair differences in the observed and calculated structure-factor amplitudes, respectively, for reflection h.

[8]FOM: figure of merit.

TABLE 8

GCYH-IB•Mn$^{2+}$ X-ray data collection
GCYH-IB•Mn$^{2+}$

| Spacegroup | C222$_1$ |
| --- | --- |
| Dataset | |
| Unit cell (Å) | 92.2, 100.4, 113.9 |
| Wavelength (Å) | 0.97607 |
| Resolution (Å) | 30.33-2.04 |
| Unique reflections (ano) | 33,675 (3,314)[1] |
| Completeness (%) | 99.8 (99.9) |
| Redundancy | 4.5 (4.5) |
| Rmerge (%) | 7.1 (42.8) |
| <I/σ(I)> | 11.0 |

[1]Highest-resolution shell (2.04-2.11 Å) information in parentheses.

TABLE 9

Structure refinement of GCYH-IB and GCYH-IB•Mn$^{2+}$
Structure refinement

| | GCYH-IB | GCYH-IB•Mn$^{2+}$ |
| --- | --- | --- |
| Resolution range | 45.9-2.2 Å[9] | 30.33-2.04 |
| Number of reflections | | |
| working/free | 42,833[10]/4,631 [10] | 31,937/1,710 |
| Number of atoms | | |
| protein/water | 3,829/133 | 3,829/261 |
| active site metal ions | 2 | 2 |
| other ions | 1 | 2 |
| other ligands | 4 | 3 |
| R-cryst[11]/R-free[12] (%) | 0.20/0.25 | 0.19/0.26 |
| Rmsd bond lengths (Å) | 0.007 | 0.019 |
| Rmsd bond angles (Å) | 0.825 | 1.754 |
| Ramachandran Plot (%) | | |
| favored | 93.2 | 96.9 |
| allowed | 6.8 | 3.1 |
| Wilson B-factor (Å$^2$) | 40.3 | 37.4 |

[9]During density modification, structure factors were calculated for remote-wavelength data in the resolution range 2.3-2.2 Å.
[10]Anomalous pairs treated as separate reflections.
[11]Crystallographic R-factor = 100 × (Σh||Fobs(h)| − |Fcalc(h)||)/Σh |Fobs(h)|, where Fobs (h) and Fcalc(h) are the observed structure factor amplitude and the structurefactor amplitude calculated from the model, respectively.
[12]The free R-factor was calculated by using 90% and 95% of the data for GCYH-IB and GCYH-IB•Mn$^{2+}$, respectively.

TABLE 10

Three-Dimensional Coordinates of *Neisseria gonorrhoeae* GCYH-IB (SEQ. ID. No. 8)

| ATOM | 1 | N | ARG | 14 | 50.990 | 37.265 | 26.073 | 1.00 | 56.18 |
| --- | --- | --- | --- | --- | --- | --- | --- | --- | --- |
| ATOM | 2 | CA | ARG | 14 | 50.011 | 36.185 | 25.960 | 1.00 | 93.83 |
| ATOM | 3 | C | ARG | 14 | 49.059 | 36.319 | 24.779 | 1.00 | 0.95 |
| ATOM | 4 | O | ARG | 14 | 48.591 | 37.409 | 24.432 | 1.00 | 0.99 |
| ATOM | 5 | CB | ARG | 14 | 49.303 | 35.895 | 27.281 | 1.00 | 91.72 |
| ATOM | 6 | CG | ARG | 14 | 49.942 | 34.713 | 27.967 | 1.00 | 98.01 |
| ATOM | 7 | CD | ARG | 14 | 51.285 | 34.426 | 27.304 | 1.00 | 0.59 |
| ATOM | 8 | NE | ARG | 14 | 51.414 | 33.039 | 26.865 | 1.00 | 0.30 |
| ATOM | 9 | CZ | ARG | 14 | 52.447 | 32.573 | 26.171 | 1.00 | 0.57 |
| ATOM | 10 | NH1 | ARG | 14 | 53.439 | 33.390 | 25.833 | 1.00 | 0.47 |
| ATOM | 11 | NH2 | ARG | 14 | 52.489 | 31.293 | 25.814 | 1.00 | 0.76 |
| ATOM | 12 | N | ASN | 15 | 48.763 | 35.156 | 24.216 | 1.00 | 0.82 |
| ATOM | 13 | CA | ASN | 15 | 48.731 | 34.960 | 22.775 | 1.00 | 0.69 |
| ATOM | 14 | C | ASN | 15 | 47.386 | 34.873 | 22.064 | 1.00 | 0.82 |
| ATOM | 15 | O | ASN | 15 | 47.347 | 34.785 | 20.840 | 1.00 | 0.58 |
| ATOM | 16 | CB | ASN | 15 | 49.542 | 33.711 | 22.446 | 1.00 | 0.43 |
| ATOM | 17 | CG | ASN | 15 | 50.905 | 34.038 | 21.890 | 1.00 | 0.83 |
| ATOM | 18 | OD1 | ASN | 15 | 51.045 | 34.928 | 21.057 | 1.00 | 0.77 |
| ATOM | 19 | ND2 | ASN | 15 | 51.914 | 33.309 | 22.326 | 1.00 | 0.18 |
| ATOM | 20 | N | LEU | 16 | 46.303 | 34.863 | 22.829 | 1.00 | 93.09 |
| ATOM | 21 | CA | LEU | 16 | 44.939 | 34.936 | 22.298 | 1.00 | 61.91 |
| ATOM | 22 | C | LEU | 16 | 44.622 | 34.166 | 21.008 | 1.00 | 56.02 |
| ATOM | 23 | O | LEU | 16 | 45.138 | 34.469 | 19.932 | 1.00 | 38.84 |
| ATOM | 24 | CB | LEU | 16 | 44.489 | 36.387 | 22.186 | 1.00 | 59.10 |
| ATOM | 25 | CG | LEU | 16 | 43.830 | 36.989 | 23.430 | 1.00 | 70.01 |
| ATOM | 26 | CD1 | LEU | 16 | 44.738 | 36.859 | 24.627 | 1.00 | 95.51 |
| ATOM | 27 | CD2 | LEU | 16 | 43.495 | 38.446 | 23.180 | 1.00 | 64.01 |
| ATOM | 28 | N | PRO | 17 | 43.757 | 33.151 | 21.121 | 1.00 | 46.50 |
| ATOM | 29 | CA | PRO | 17 | 43.251 | 32.480 | 19.919 | 1.00 | 51.15 |
| ATOM | 30 | C | PRO | 17 | 42.355 | 33.456 | 19.159 | 1.00 | 50.11 |
| ATOM | 31 | O | PRO | 17 | 41.764 | 34.343 | 19.781 | 1.00 | 53.59 |
| ATOM | 32 | CB | PRO | 17 | 42.371 | 31.359 | 20.477 | 1.00 | 48.36 |
| ATOM | 33 | CG | PRO | 17 | 42.657 | 31.288 | 21.920 | 1.00 | 47.75 |
| ATOM | 34 | CD | PRO | 17 | 43.193 | 32.595 | 22.362 | 1.00 | 35.50 |
| ATOM | 35 | N | ILE | 18 | 42.269 | 33.309 | 17.840 | 1.00 | 37.05 |
| ATOM | 36 | CA | ILE | 18 | 41.329 | 34.091 | 17.045 | 1.00 | 44.06 |
| ATOM | 37 | C | ILE | 18 | 40.165 | 33.183 | 16.623 | 1.00 | 37.56 |
| ATOM | 38 | O | ILE | 18 | 40.365 | 32.151 | 15.989 | 1.00 | 33.36 |
| ATOM | 39 | CB | ILE | 18 | 42.022 | 34.736 | 15.835 | 1.00 | 40.66 |
| ATOM | 40 | CG1 | ILE | 18 | 43.083 | 35.747 | 16.310 | 1.00 | 47.12 |
| ATOM | 41 | CG2 | ILE | 18 | 41.009 | 35.427 | 14.932 | 1.00 | 45.97 |
| ATOM | 42 | CD1 | ILE | 18 | 44.084 | 36.146 | 15.235 | 1.00 | 36.80 |
| ATOM | 43 | N | LEU | 51 | 42.102 | 30.092 | 14.708 | 1.00 | 39.41 |
| ATOM | 44 | CA | LEU | 51 | 43.542 | 30.191 | 14.783 | 1.00 | 40.03 |
| ATOM | 45 | C | LEU | 51 | 43.945 | 30.049 | 16.241 | 1.00 | 49.59 |
| ATOM | 46 | O | LEU | 51 | 43.620 | 30.892 | 17.048 | 1.00 | 35.47 |

TABLE 10-continued

Three-Dimensional Coordinates of *Neisseria gonorrhoeae* GCYH-IB (SEQ. ID. No. 8)

| ATOM | 47 | CB | LEU | 51 | 44.031 | 31.523 | 14.227 | 1.00 | 43.30 |
|---|---|---|---|---|---|---|---|---|---|
| ATOM | 48 | CG | LEU | 51 | 45.544 | 31.592 | 14.050 | 1.00 | 47.56 |
| ATOM | 49 | CD1 | LEU | 51 | 45.938 | 30.629 | 12.934 | 1.00 | 46.53 |
| ATOM | 50 | CD2 | LEU | 51 | 46.047 | 33.017 | 13.741 | 1.00 | 36.00 |
| ATOM | 51 | N | PRO | 52 | 44.626 | 28.949 | 16.581 | 1.00 | 47.01 |
| ATOM | 52 | CA | PRO | 52 | 45.190 | 28.656 | 17.906 | 1.00 | 54.47 |
| ATOM | 53 | C | PRO | 52 | 46.064 | 29.798 | 18.441 | 1.00 | 47.94 |
| ATOM | 54 | O | PRO | 52 | 46.671 | 30.515 | 17.665 | 1.00 | 42.41 |
| ATOM | 55 | CB | PRO | 52 | 46.074 | 27.435 | 17.643 | 1.00 | 45.04 |
| ATOM | 56 | CG | PRO | 52 | 45.583 | 26.838 | 16.384 | 1.00 | 58.50 |
| ATOM | 57 | CD | PRO | 52 | 45.024 | 27.960 | 15.569 | 1.00 | 44.63 |
| ATOM | 58 | N | ALA | 53 | 46.140 | 29.938 | 19.754 | 1.00 | 48.98 |
| ATOM | 59 | CA | ALA | 53 | 46.895 | 31.025 | 20.372 | 1.00 | 58.53 |
| ATOM | 60 | C | ALA | 53 | 48.293 | 31.269 | 19.809 | 1.00 | 62.49 |
| ATOM | 61 | O | ALA | 53 | 48.705 | 32.414 | 19.618 | 1.00 | 65.81 |
| ATOM | 62 | CB | ALA | 53 | 46.968 | 30.817 | 21.866 | 1.00 | 53.72 |
| ATOM | 63 | N | GLU | 54 | 49.045 | 30.206 | 19.556 | 1.00 | 72.43 |
| ATOM | 64 | CA | GLU | 54 | 50.444 | 30.426 | 19.208 | 1.00 | 0.41 |
| ATOM | 65 | C | GLU | 54 | 50.782 | 30.220 | 17.740 | 1.00 | 90.42 |
| ATOM | 66 | O | GLU | 54 | 51.950 | 30.167 | 17.369 | 1.00 | 95.32 |
| ATOM | 67 | CB | GLU | 54 | 51.388 | 29.642 | 20.125 | 1.00 | 0.46 |
| ATOM | 68 | CG | GLU | 54 | 51.661 | 28.215 | 19.713 | 1.00 | 0.78 |
| ATOM | 69 | CD | GLU | 54 | 52.565 | 27.509 | 20.707 | 1.00 | 0.22 |
| ATOM | 70 | OE1 | GLU | 54 | 52.165 | 27.386 | 21.885 | 1.00 | 0.86 |
| ATOM | 71 | OE2 | GLU | 54 | 53.675 | 27.080 | 20.317 | 1.00 | 0.17 |
| ATOM | 72 | N | GLN | 55 | 49.757 | 30.122 | 16.905 | 1.00 | 74.01 |
| ATOM | 73 | CA | GLN | 55 | 49.960 | 30.205 | 15.468 | 1.00 | 65.50 |
| ATOM | 74 | C | GLN | 55 | 49.842 | 31.683 | 15.100 | 1.00 | 60.70 |
| ATOM | 75 | O | GLN | 55 | 48.917 | 32.349 | 15.541 | 1.00 | 63.86 |
| ATOM | 76 | CB | GLN | 55 | 48.915 | 29.362 | 14.736 | 1.00 | 64.04 |
| ATOM | 77 | CG | GLN | 55 | 49.232 | 29.077 | 13.274 | 1.00 | 67.10 |
| ATOM | 78 | CD | GLN | 55 | 48.245 | 28.102 | 12.656 | 1.00 | 78.01 |
| ATOM | 79 | OE1 | GLN | 55 | 47.694 | 27.243 | 13.344 | 1.00 | 86.83 |
| ATOM | 80 | NE2 | GLN | 55 | 48.020 | 28.230 | 11.349 | 1.00 | 66.25 |
| ATOM | 81 | N | LYS | 56 | 50.785 | 32.197 | 14.316 | 1.00 | 58.08 |
| ATOM | 82 | CA | LYS | 56 | 50.833 | 33.629 | 14.040 | 1.00 | 68.32 |
| ATOM | 83 | C | LYS | 56 | 49.826 | 34.047 | 12.981 | 1.00 | 68.10 |
| ATOM | 84 | O | LYS | 56 | 49.327 | 35.168 | 13.007 | 1.00 | 70.15 |
| ATOM | 85 | CB | LYS | 56 | 52.240 | 34.063 | 13.606 | 1.00 | 86.98 |
| ATOM | 86 | CG | LYS | 56 | 52.324 | 35.528 | 13.177 | 1.00 | 0.17 |
| ATOM | 87 | CD | LYS | 56 | 53.736 | 35.934 | 12.796 | 1.00 | 0.61 |
| ATOM | 88 | CE | LYS | 56 | 54.133 | 35.369 | 11.443 | 1.00 | 0.08 |
| ATOM | 89 | NZ | LYS | 56 | 55.504 | 35.801 | 11.051 | 1.00 | 0.69 |
| ATOM | 90 | N | GLY | 57 | 49.550 | 33.142 | 12.044 | 1.00 | 53.87 |
| ATOM | 91 | CA | GLY | 57 | 48.726 | 33.462 | 10.893 | 1.00 | 62.82 |
| ATOM | 92 | C | GLY | 57 | 48.122 | 32.238 | 10.237 | 1.00 | 69.86 |
| ATOM | 93 | O | GLY | 57 | 48.528 | 31.114 | 10.513 | 1.00 | 61.08 |
| ATOM | 94 | N | THR | 58 | 47.134 | 32.456 | 9.376 | 1.00 | 69.78 |
| ATOM | 95 | CA | THR | 58 | 46.546 | 31.375 | 8.602 | 1.00 | 71.47 |
| ATOM | 96 | C | THR | 58 | 47.141 | 31.433 | 7.205 | 1.00 | 55.97 |
| ATOM | 97 | O | THR | 58 | 48.036 | 32.244 | 6.951 | 1.00 | 59.93 |
| ATOM | 98 | CB | THR | 58 | 44.996 | 31.491 | 8.551 | 1.00 | 71.04 |
| ATOM | 99 | OG1 | THR | 58 | 44.438 | 30.260 | 8.090 | 1.00 | 77.37 |
| ATOM | 100 | CG2 | THR | 58 | 44.553 | 32.634 | 7.635 | 1.00 | 65.11 |
| ATOM | 101 | N | HIS | 59 | 46.646 | 30.597 | 6.297 | 1.00 | 58.22 |
| ATOM | 102 | CA | HIS | 59 | 47.133 | 30.614 | 4.921 | 1.00 | 64.81 |
| ATOM | 103 | C | HIS | 59 | 46.042 | 31.111 | 3.982 | 1.00 | 61.25 |
| ATOM | 104 | O | HIS | 59 | 45.196 | 30.337 | 3.553 | 1.00 | 68.43 |
| ATOM | 105 | CB | HIS | 59 | 47.617 | 29.219 | 4.529 | 1.00 | 66.44 |
| ATOM | 106 | CG | HIS | 59 | 48.517 | 28.597 | 5.553 | 1.00 | 72.69 |
| ATOM | 107 | ND1 | HIS | 59 | 48.032 | 27.906 | 6.639 | 1.00 | 76.25 |
| ATOM | 108 | CD2 | HIS | 59 | 49.864 | 28.598 | 5.667 | 1.00 | 76.00 |
| ATOM | 109 | CE1 | HIS | 59 | 49.048 | 27.489 | 7.377 | 1.00 | 85.64 |
| ATOM | 110 | NE2 | HIS | 59 | 50.168 | 27.892 | 6.811 | 1.00 | 86.98 |
| ATOM | 111 | N | MSE | 60 | 46.076 | 32.402 | 3.661 | 1.00 | 65.09 |
| ATOM | 112 | CA | MSE | 60 | 44.944 | 33.083 | 3.033 | 1.00 | 58.00 |
| ATOM | 113 | C | MSE | 60 | 44.570 | 32.565 | 1.654 | 1.00 | 50.50 |
| ATOM | 114 | O | MSE | 60 | 43.381 | 32.500 | 1.314 | 1.00 | 53.78 |
| ATOM | 115 | CB | MSE | 60 | 45.194 | 34.591 | 2.971 | 1.00 | 62.77 |
| ATOM | 116 | CG | MSE | 60 | 45.200 | 35.270 | 4.331 | 1.00 | 87.09 |
| ATOM | 117 | SE | MSE | 60 | 43.419 | 35.392 | 5.187 | 1.00 | 78.03 |
| ATOM | 118 | CE | MSE | 60 | 43.904 | 36.431 | 6.770 | 1.00 | 92.20 |
| ATOM | 119 | N | SER | 61 | 45.581 | 32.191 | 0.870 | 1.00 | 45.42 |
| ATOM | 120 | CA | SER | 61 | 45.372 | 31.744 | −0.512 | 1.00 | 47.54 |
| ATOM | 121 | C | SER | 61 | 44.668 | 30.391 | −0.647 | 1.00 | 55.39 |
| ATOM | 122 | O | SER | 61 | 44.049 | 30.106 | −1.677 | 1.00 | 61.05 |
| ATOM | 123 | CB | SER | 61 | 46.682 | 31.749 | −1.310 | 1.00 | 57.85 |
| ATOM | 124 | OG | SER | 61 | 47.430 | 30.578 | −1.078 | 1.00 | 61.24 |

TABLE 10-continued

Three-Dimensional Coordinates of *Neisseria gonorrhoeae* GCYH-IB (SEQ. ID. No. 8)

| ATOM | 125 | N | ARG | 62 | 44.750 | 29.559 | 0.383 | 1.00 | 50.58 |
|------|-----|-----|-----|-----|--------|--------|--------|------|-------|
| ATOM | 126 | CA | ARG | 62 | 44.031 | 28.279 | 0.363 | 1.00 | 51.01 |
| ATOM | 127 | C | ARG | 62 | 42.498 | 28.410 | 0.275 | 1.00 | 41.04 |
| ATOM | 128 | O | ARG | 62 | 41.844 | 27.611 | −0.363 | 1.00 | 44.23 |
| ATOM | 129 | CB | ARG | 62 | 44.429 | 27.432 | 1.569 | 1.00 | 50.03 |
| ATOM | 130 | CG | ARG | 62 | 45.869 | 26.931 | 1.485 | 1.00 | 50.73 |
| ATOM | 131 | CD | ARG | 62 | 46.291 | 26.230 | 2.754 | 1.00 | 47.50 |
| ATOM | 132 | NE | ARG | 62 | 47.747 | 26.097 | 2.827 | 1.00 | 72.17 |
| ATOM | 133 | CZ | ARG | 62 | 48.391 | 25.436 | 3.779 | 1.00 | 68.28 |
| ATOM | 134 | NH1 | ARG | 62 | 47.707 | 24.837 | 4.742 | 1.00 | 59.95 |
| ATOM | 135 | NH2 | ARG | 62 | 49.714 | 25.375 | 3.768 | 1.00 | 79.31 |
| ATOM | 136 | N | PHE | 63 | 41.940 | 29.427 | 0.917 | 1.00 | 41.97 |
| ATOM | 137 | CA | PHE | 63 | 40.503 | 29.668 | 0.879 | 1.00 | 44.58 |
| ATOM | 138 | C | PHE | 63 | 40.028 | 29.808 | −0.557 | 1.00 | 49.40 |
| ATOM | 139 | O | PHE | 63 | 39.061 | 29.168 | −0.957 | 1.00 | 39.22 |
| ATOM | 140 | CB | PHE | 63 | 40.142 | 30.920 | 1.655 | 1.00 | 40.89 |
| ATOM | 141 | CG | PHE | 63 | 40.396 | 30.816 | 3.121 | 1.00 | 28.93 |
| ATOM | 142 | CD1 | PHE | 63 | 39.581 | 30.031 | 3.914 | 1.00 | 38.88 |
| ATOM | 143 | CD2 | PHE | 63 | 41.431 | 31.517 | 3.706 | 1.00 | 35.68 |
| ATOM | 144 | CE1 | PHE | 63 | 39.790 | 29.946 | 5.262 | 1.00 | 36.00 |
| ATOM | 145 | CE2 | PHE | 63 | 41.649 | 31.445 | 5.051 | 1.00 | 44.36 |
| ATOM | 146 | CZ | PHE | 63 | 40.829 | 30.669 | 5.838 | 1.00 | 30.89 |
| ATOM | 147 | N | ALA | 65 | 41.881 | 28.991 | −3.386 | 1.00 | 31.61 |
| ATOM | 148 | CA | ALA | 65 | 42.210 | 27.754 | −4.104 | 1.00 | 46.10 |
| ATOM | 149 | C | ALA | 65 | 41.122 | 26.698 | −3.901 | 1.00 | 50.34 |
| ATOM | 150 | O | ALA | 65 | 40.794 | 25.957 | −4.815 | 1.00 | 45.89 |
| ATOM | 151 | CB | ALA | 65 | 43.597 | 27.186 | −3.664 | 1.00 | 43.69 |
| ATOM | 152 | N | LEU | 89 | 42.214 | 21.349 | 4.987 | 1.00 | 56.45 |
| ATOM | 153 | CA | LEU | 89 | 43.163 | 22.013 | 4.115 | 1.00 | 52.29 |
| ATOM | 154 | C | LEU | 89 | 43.946 | 23.137 | 4.829 | 1.00 | 59.53 |
| ATOM | 155 | O | LEU | 89 | 45.146 | 23.299 | 4.615 | 1.00 | 40.19 |
| ATOM | 156 | CB | LEU | 89 | 42.421 | 22.578 | 2.905 | 1.00 | 53.20 |
| ATOM | 157 | CG | LEU | 89 | 43.248 | 23.410 | 1.928 | 1.00 | 60.26 |
| ATOM | 158 | CD1 | LEU | 89 | 44.138 | 22.497 | 1.126 | 1.00 | 43.38 |
| ATOM | 159 | CD2 | LEU | 89 | 42.353 | 24.204 | 1.011 | 1.00 | 58.43 |
| ATOM | 160 | N | LEU | 90 | 43.268 | 23.916 | 5.666 | 1.00 | 49.78 |
| ATOM | 161 | CA | LEU | 90 | 43.935 | 24.970 | 6.421 | 1.00 | 62.35 |
| ATOM | 162 | C | LEU | 90 | 44.539 | 24.469 | 7.733 | 1.00 | 64.62 |
| ATOM | 163 | O | LEU | 90 | 45.059 | 25.243 | 8.539 | 1.00 | 60.89 |
| ATOM | 164 | CB | LEU | 90 | 42.973 | 26.124 | 6.657 | 1.00 | 47.33 |
| ATOM | 165 | CG | LEU | 90 | 43.040 | 27.025 | 5.431 | 1.00 | 59.03 |
| ATOM | 166 | CD1 | LEU | 90 | 41.833 | 26.865 | 4.532 | 1.00 | 36.20 |
| ATOM | 167 | CD2 | LEU | 90 | 43.199 | 28.447 | 5.854 | 1.00 | 69.47 |
| ATOM | 168 | N | ASP | 91 | 44.466 | 23.159 | 7.928 | 1.00 | 62.53 |
| ATOM | 169 | CA | ASP | 91 | 45.047 | 22.520 | 9.096 | 1.00 | 74.18 |
| ATOM | 170 | C | ASP | 91 | 44.501 | 23.155 | 10.370 | 1.00 | 64.49 |
| ATOM | 171 | O | ASP | 91 | 45.269 | 23.640 | 11.196 | 1.00 | 49.15 |
| ATOM | 172 | CB | ASP | 91 | 46.574 | 22.632 | 9.041 | 1.00 | 79.82 |
| ATOM | 173 | CG | ASP | 91 | 47.201 | 21.658 | 8.051 | 1.00 | 0.54 |
| ATOM | 174 | OD1 | ASP | 91 | 46.457 | 20.880 | 7.417 | 1.00 | 0.33 |
| ATOM | 175 | OD2 | ASP | 91 | 48.445 | 21.657 | 7.918 | 1.00 | 0.26 |
| ATOM | 176 | N | SER | 92 | 43.176 | 23.153 | 10.523 | 1.00 | 57.69 |
| ATOM | 177 | CA | SER | 92 | 42.553 | 23.776 | 11.687 | 1.00 | 45.90 |
| ATOM | 178 | C | SER | 92 | 41.470 | 22.934 | 12.389 | 1.00 | 51.56 |
| ATOM | 179 | O | SER | 92 | 40.897 | 22.048 | 11.805 | 1.00 | 45.21 |
| ATOM | 180 | CB | SER | 92 | 41.987 | 25.143 | 11.299 | 1.00 | 50.32 |
| ATOM | 181 | OG | SER | 92 | 41.420 | 25.786 | 12.424 | 1.00 | 54.21 |
| ATOM | 182 | N | ARG | 105 | 35.965 | 63.521 | 15.017 | 1.00 | 33.07 |
| ATOM | 183 | CA | ARG | 105 | 36.979 | 63.849 | 15.997 | 1.00 | 29.88 |
| ATOM | 184 | C | ARG | 105 | 38.125 | 64.607 | 15.317 | 1.00 | 32.84 |
| ATOM | 185 | O | ARG | 105 | 38.619 | 64.208 | 14.260 | 1.00 | 36.69 |
| ATOM | 186 | CB | ARG | 105 | 37.493 | 62.590 | 16.668 | 1.00 | 29.04 |
| ATOM | 187 | CG | ARG | 105 | 38.351 | 62.846 | 17.863 | 1.00 | 48.37 |
| ATOM | 188 | CD | ARG | 105 | 39.092 | 61.594 | 18.287 | 1.00 | 47.10 |
| ATOM | 189 | NE | ARG | 105 | 39.543 | 61.665 | 19.671 | 1.00 | 44.80 |
| ATOM | 190 | CZ | ARG | 105 | 40.409 | 60.822 | 20.222 | 1.00 | 56.34 |
| ATOM | 191 | NH1 | ARG | 105 | 40.945 | 59.847 | 19.494 | 1.00 | 36.07 |
| ATOM | 192 | NH2 | ARG | 105 | 40.747 | 60.953 | 21.503 | 1.00 | 43.89 |
| ATOM | 193 | N | LYS | 106 | 38.492 | 65.735 | 15.908 | 1.00 | 38.84 |
| ATOM | 194 | CA | LYS | 106 | 39.620 | 66.529 | 15.447 | 1.00 | 52.88 |
| ATOM | 195 | C | LYS | 106 | 40.929 | 65.782 | 15.718 | 1.00 | 42.47 |
| ATOM | 196 | O | LYS | 106 | 41.179 | 65.301 | 16.828 | 1.00 | 53.64 |
| ATOM | 197 | CB | LYS | 106 | 39.610 | 67.901 | 16.128 | 1.00 | 46.81 |
| ATOM | 198 | CG | LYS | 106 | 40.099 | 69.022 | 15.248 | 1.00 | 69.34 |
| ATOM | 199 | CD | LYS | 106 | 39.127 | 70.188 | 15.285 | 1.00 | 90.51 |
| ATOM | 200 | CE | LYS | 106 | 39.855 | 71.518 | 15.320 | 1.00 | 0.04 |
| ATOM | 201 | NZ | LYS | 106 | 40.925 | 71.586 | 14.292 | 1.00 | 0.37 |
| ATOM | 202 | N | LYS | 107 | 41.732 | 65.658 | 14.670 | 1.00 | 34.97 |

TABLE 10-continued

Three-Dimensional Coordinates of *Neisseria gonorrhoeae* GCYH-IB (SEQ. ID. No. 8)

| ATOM | 203 | CA | LYS | 107 | 43.065 | 65.060 | 14.759 | 1.00 | 52.25 |
|------|-----|-----|-----|-----|--------|--------|--------|------|-------|
| ATOM | 204 | C | LYS | 107 | 44.181 | 66.034 | 14.370 | 1.00 | 51.78 |
| ATOM | 205 | O | LYS | 107 | 43.937 | 67.035 | 13.709 | 1.00 | 50.24 |
| ATOM | 206 | CB | LYS | 107 | 43.145 | 63.819 | 13.880 | 1.00 | 46.87 |
| ATOM | 207 | CG | LYS | 107 | 42.805 | 62.570 | 14.628 | 1.00 | 73.11 |
| ATOM | 208 | CD | LYS | 107 | 41.862 | 61.713 | 13.838 | 1.00 | 52.85 |
| ATOM | 209 | CE | LYS | 107 | 42.594 | 60.754 | 12.936 | 1.00 | 74.85 |
| ATOM | 210 | NZ | LYS | 107 | 43.478 | 59.816 | 13.679 | 1.00 | 60.74 |
| ATOM | 211 | N | THR | 108 | 45.406 | 65.706 | 14.768 | 1.00 | 39.92 |
| ATOM | 212 | CA | THR | 108 | 46.595 | 66.510 | 14.453 | 1.00 | 51.78 |
| ATOM | 213 | C | THR | 108 | 47.620 | 65.753 | 13.599 | 1.00 | 56.01 |
| ATOM | 214 | O | THR | 108 | 48.046 | 64.670 | 13.972 | 1.00 | 48.49 |
| ATOM | 215 | CB | THR | 108 | 47.265 | 66.962 | 15.743 | 1.00 | 58.98 |
| ATOM | 216 | OG1 | THR | 108 | 46.367 | 67.820 | 16.453 | 1.00 | 76.08 |
| ATOM | 217 | CG2 | THR | 108 | 48.565 | 67.713 | 15.439 | 1.00 | 63.78 |
| ATOM | 218 | N | ALA | 109 | 48.009 | 66.319 | 12.457 | 1.00 | 51.19 |
| ATOM | 219 | CA | ALA | 109 | 48.981 | 65.674 | 11.577 | 1.00 | 47.51 |
| ATOM | 220 | C | ALA | 109 | 50.292 | 65.456 | 12.332 | 1.00 | 56.59 |
| ATOM | 221 | O | ALA | 109 | 50.692 | 66.287 | 13.122 | 1.00 | 58.26 |
| ATOM | 222 | CB | ALA | 109 | 49.198 | 66.489 | 10.318 | 1.00 | 52.79 |
| ATOM | 223 | N | PRO | 110 | 50.940 | 64.306 | 12.120 | 1.00 | 60.88 |
| ATOM | 224 | CA | PRO | 110 | 52.063 | 63.857 | 12.954 | 1.00 | 54.80 |
| ATOM | 225 | C | PRO | 110 | 53.369 | 64.686 | 12.855 | 1.00 | 73.41 |
| ATOM | 226 | O | PRO | 110 | 54.163 | 64.643 | 13.794 | 1.00 | 94.80 |
| ATOM | 227 | CB | PRO | 110 | 52.284 | 62.420 | 12.469 | 1.00 | 59.86 |
| ATOM | 228 | CG | PRO | 110 | 51.694 | 62.406 | 11.099 | 1.00 | 62.30 |
| ATOM | 229 | CD | PRO | 110 | 50.486 | 63.240 | 11.220 | 1.00 | 65.45 |
| ATOM | 230 | N | VAL | 111 | 53.586 | 65.414 | 11.759 | 1.00 | 63.03 |
| ATOM | 231 | CA | VAL | 111 | 54.752 | 66.292 | 11.640 | 1.00 | 67.64 |
| ATOM | 232 | C | VAL | 111 | 54.375 | 67.780 | 11.620 | 1.00 | 74.71 |
| ATOM | 233 | O | VAL | 111 | 54.850 | 68.549 | 12.447 | 1.00 | 70.73 |
| ATOM | 234 | CB | VAL | 111 | 55.618 | 65.937 | 10.406 | 1.00 | 71.63 |
| ATOM | 235 | CG1 | VAL | 111 | 56.663 | 67.006 | 10.150 | 1.00 | 85.60 |
| ATOM | 236 | CG2 | VAL | 111 | 56.284 | 64.605 | 10.607 | 1.00 | 80.10 |
| ATOM | 237 | N | SER | 112 | 53.508 | 68.170 | 10.689 | 1.00 | 78.75 |
| ATOM | 238 | CA | SER | 112 | 53.131 | 69.567 | 10.506 | 1.00 | 75.70 |
| ATOM | 239 | C | SER | 112 | 52.215 | 70.105 | 11.605 | 1.00 | 69.51 |
| ATOM | 240 | O | SER | 112 | 52.104 | 71.327 | 11.801 | 1.00 | 49.35 |
| ATOM | 241 | CB | SER | 112 | 52.460 | 69.758 | 9.146 | 1.00 | 52.06 |
| ATOM | 242 | OG | SER | 112 | 51.115 | 69.326 | 9.190 | 1.00 | 56.21 |
| ATOM | 243 | N | GLY | 113 | 51.551 | 69.189 | 12.304 | 1.00 | 52.71 |
| ATOM | 244 | CA | GLY | 113 | 50.584 | 69.545 | 13.330 | 1.00 | 53.69 |
| ATOM | 245 | C | GLY | 113 | 49.263 | 70.121 | 12.828 | 1.00 | 57.78 |
| ATOM | 246 | O | GLY | 113 | 48.436 | 70.534 | 13.636 | 1.00 | 46.82 |
| ATOM | 247 | N | ILE | 114 | 49.067 | 70.165 | 11.509 | 1.00 | 48.95 |
| ATOM | 248 | CA | ILE | 114 | 47.827 | 70.689 | 10.954 | 1.00 | 62.98 |
| ATOM | 249 | C | ILE | 114 | 46.650 | 69.813 | 11.372 | 1.00 | 62.30 |
| ATOM | 250 | O | ILE | 114 | 46.718 | 68.582 | 11.321 | 1.00 | 62.97 |
| ATOM | 251 | CB | ILE | 114 | 47.875 | 70.826 | 9.417 | 1.00 | 74.53 |
| ATOM | 252 | CG1 | ILE | 114 | 49.070 | 71.677 | 8.990 | 1.00 | 89.66 |
| ATOM | 253 | CG2 | ILE | 114 | 46.597 | 71.473 | 8.904 | 1.00 | 60.35 |
| ATOM | 254 | CD1 | ILE | 114 | 49.088 | 71.999 | 7.508 | 1.00 | 0.82 |
| ATOM | 255 | N | ARG | 115 | 45.581 | 70.461 | 11.809 | 1.00 | 58.21 |
| ATOM | 256 | CA | ARG | 115 | 44.416 | 69.765 | 12.333 | 1.00 | 66.68 |
| ATOM | 257 | C | ARG | 115 | 43.330 | 69.540 | 11.287 | 1.00 | 57.62 |
| ATOM | 258 | O | ARG | 115 | 43.135 | 70.350 | 10.377 | 1.00 | 46.10 |
| ATOM | 259 | CB | ARG | 115 | 43.858 | 70.514 | 13.536 | 1.00 | 68.26 |
| ATOM | 260 | CG | ARG | 115 | 44.883 | 70.668 | 14.648 | 1.00 | 96.72 |
| ATOM | 261 | CD | ARG | 115 | 44.398 | 71.606 | 15.733 | 1.00 | 0.68 |
| ATOM | 262 | NE | ARG | 115 | 43.474 | 70.954 | 16.653 | 1.00 | 0.03 |
| ATOM | 263 | CZ | ARG | 115 | 42.717 | 71.604 | 17.530 | 1.00 | 0.61 |
| ATOM | 264 | NH1 | ARG | 115 | 42.768 | 72.927 | 17.601 | 1.00 | 0.15 |
| ATOM | 265 | NH2 | ARG | 115 | 41.903 | 70.932 | 18.331 | 1.00 | 0.32 |
| ATOM | 266 | N | SER | 116 | 42.647 | 68.407 | 11.413 | 1.00 | 42.68 |
| ATOM | 267 | CA | SER | 116 | 41.529 | 68.076 | 10.535 | 1.00 | 43.53 |
| ATOM | 268 | C | SER | 116 | 40.657 | 67.039 | 11.224 | 1.00 | 43.72 |
| ATOM | 269 | O | SER | 116 | 41.096 | 66.350 | 12.142 | 1.00 | 45.98 |
| ATOM | 270 | CB | SER | 116 | 42.026 | 67.562 | 9.184 | 1.00 | 62.92 |
| ATOM | 271 | OG | SER | 116 | 42.807 | 66.390 | 9.331 | 1.00 | 72.92 |
| ATOM | 272 | N | LEU | 117 | 39.411 | 66.949 | 10.796 | 1.00 | 45.79 |
| ATOM | 273 | CA | LEU | 117 | 38.468 | 66.030 | 11.393 | 1.00 | 41.01 |
| ATOM | 274 | C | LEU | 117 | 38.604 | 64.680 | 10.718 | 1.00 | 30.98 |
| ATOM | 275 | O | LEU | 117 | 38.923 | 64.602 | 9.534 | 1.00 | 36.37 |
| ATOM | 276 | CB | LEU | 117 | 37.051 | 66.528 | 11.164 | 1.00 | 27.67 |
| ATOM | 277 | CG | LEU | 117 | 36.540 | 67.797 | 11.834 | 1.00 | 46.81 |
| ATOM | 278 | CD1 | LEU | 117 | 35.225 | 68.156 | 11.179 | 1.00 | 42.43 |
| ATOM | 279 | CD2 | LEU | 117 | 36.379 | 67.617 | 13.334 | 1.00 | 33.79 |
| ATOM | 280 | N | LEU | 118 | 38.363 | 63.616 | 11.471 | 1.00 | 36.49 |

TABLE 10-continued

Three-Dimensional Coordinates of *Neisseria gonorrhoeae* GCYH-IB (SEQ. ID. No. 8)

| ATOM | 281 | CA | LEU | 118 | 38.123 | 62.309 | 10.869 | 1.00 | 34.89 |
|---|---|---|---|---|---|---|---|---|---|
| ATOM | 282 | C | LEU | 118 | 36.754 | 61.798 | 11.335 | 1.00 | 43.06 |
| ATOM | 283 | O | LEU | 118 | 36.329 | 62.065 | 12.465 | 1.00 | 27.18 |
| ATOM | 284 | CB | LEU | 118 | 39.216 | 61.307 | 11.257 | 1.00 | 37.46 |
| ATOM | 285 | CG | LEU | 118 | 39.256 | 60.025 | 10.399 | 1.00 | 51.69 |
| ATOM | 286 | CD1 | LEU | 118 | 39.805 | 60.313 | 9.021 | 1.00 | 47.89 |
| ATOM | 287 | CD2 | LEU | 118 | 40.055 | 58.916 | 11.031 | 1.00 | 55.80 |
| ATOM | 288 | N | PRO | 142 | 38.424 | 53.420 | 10.783 | 1.00 | 23.25 |
| ATOM | 289 | CA | PRO | 142 | 39.252 | 53.150 | 9.606 | 1.00 | 26.43 |
| ATOM | 290 | C | PRO | 142 | 40.728 | 53.367 | 9.970 | 1.00 | 33.52 |
| ATOM | 291 | O | PRO | 142 | 41.004 | 54.347 | 10.649 | 1.00 | 34.13 |
| ATOM | 292 | CB | PRO | 142 | 38.856 | 54.257 | 8.632 | 1.00 | 33.09 |
| ATOM | 293 | CG | PRO | 142 | 37.937 | 55.197 | 9.398 | 1.00 | 36.83 |
| ATOM | 294 | CD | PRO | 142 | 37.951 | 54.809 | 10.830 | 1.00 | 33.30 |
| ATOM | 295 | N | VAL | 143 | 41.629 | 52.489 | 9.535 | 1.00 | 29.80 |
| ATOM | 296 | CA | VAL | 143 | 43.062 | 52.644 | 9.755 | 1.00 | 29.02 |
| ATOM | 297 | C | VAL | 143 | 43.816 | 52.138 | 8.533 | 1.00 | 37.92 |
| ATOM | 298 | O | VAL | 143 | 43.207 | 51.728 | 7.551 | 1.00 | 42.12 |
| ATOM | 299 | CB | VAL | 143 | 43.547 | 51.867 | 10.977 | 1.00 | 45.56 |
| ATOM | 300 | CG1 | VAL | 143 | 42.719 | 52.247 | 12.211 | 1.00 | 32.69 |
| ATOM | 301 | CG2 | VAL | 143 | 43.500 | 50.365 | 10.696 | 1.00 | 46.28 |
| ATOM | 302 | N | THR | 144 | 45.145 | 52.193 | 8.601 | 1.00 | 40.29 |
| ATOM | 303 | CA | THR | 144 | 46.019 | 51.692 | 7.543 | 1.00 | 58.11 |
| ATOM | 304 | C | THR | 144 | 46.639 | 50.402 | 8.022 | 1.00 | 45.82 |
| ATOM | 305 | O | THR | 144 | 47.059 | 50.298 | 9.178 | 1.00 | 41.15 |
| ATOM | 306 | CB | THR | 144 | 47.182 | 52.666 | 7.239 | 1.00 | 76.98 |
| ATOM | 307 | OG1 | THR | 144 | 46.679 | 53.997 | 7.072 | 1.00 | 84.02 |
| ATOM | 308 | CG2 | THR | 144 | 47.933 | 52.234 | 5.985 | 1.00 | 83.55 |
| ATOM | 309 | N | SER | 145 | 46.701 | 49.415 | 7.145 | 1.00 | 36.24 |
| ATOM | 310 | CA | SER | 145 | 47.395 | 48.183 | 7.473 | 1.00 | 52.43 |
| ATOM | 311 | C | SER | 145 | 48.464 | 47.925 | 6.424 | 1.00 | 54.50 |
| ATOM | 312 | O | SER | 145 | 48.248 | 48.158 | 5.250 | 1.00 | 43.53 |
| ATOM | 313 | CB | SER | 145 | 46.416 | 47.009 | 7.539 | 1.00 | 64.86 |
| ATOM | 314 | OG | SER | 145 | 45.730 | 46.851 | 6.309 | 1.00 | 68.39 |
| ATOM | 315 | N | LEU | 146 | 49.621 | 47.452 | 6.852 | 1.00 | 56.00 |
| ATOM | 316 | CA | LEU | 146 | 50.691 | 47.139 | 5.919 | 1.00 | 62.10 |
| ATOM | 317 | C | LEU | 146 | 51.116 | 45.682 | 6.109 | 1.00 | 44.80 |
| ATOM | 318 | O | LEU | 146 | 51.243 | 45.211 | 7.229 | 1.00 | 49.94 |
| ATOM | 319 | CB | LEU | 146 | 51.872 | 48.103 | 6.111 | 1.00 | 66.77 |
| ATOM | 320 | CG | LEU | 146 | 53.014 | 47.984 | 5.089 | 1.00 | 65.46 |
| ATOM | 321 | CD1 | LEU | 146 | 53.480 | 49.346 | 4.611 | 1.00 | 57.34 |
| ATOM | 322 | CD2 | LEU | 146 | 54.166 | 47.156 | 5.653 | 1.00 | 61.66 |
| ATOM | 323 | N | CYS | 147 | 51.339 | 44.976 | 5.012 | 1.00 | 33.12 |
| ATOM | 324 | CA | CYS | 147 | 51.537 | 43.531 | 5.062 | 1.00 | 53.22 |
| ATOM | 325 | C | CYS | 147 | 52.978 | 43.105 | 5.361 | 1.00 | 49.05 |
| ATOM | 326 | O | CYS | 147 | 53.874 | 43.354 | 4.568 | 1.00 | 43.23 |
| ATOM | 327 | CB | CYS | 147 | 51.095 | 42.891 | 3.753 | 1.00 | 44.07 |
| ATOM | 328 | SG | CYS | 147 | 51.253 | 41.076 | 3.766 | 1.00 | 43.71 |
| ATOM | 329 | N | PRO | 148 | 53.185 | 42.411 | 6.485 | 1.00 | 76.53 |
| ATOM | 330 | CA | PRO | 148 | 54.521 | 41.952 | 6.877 | 1.00 | 83.85 |
| ATOM | 331 | C | PRO | 148 | 55.120 | 40.977 | 5.869 | 1.00 | 74.03 |
| ATOM | 332 | O | PRO | 148 | 56.284 | 41.115 | 5.550 | 1.00 | 61.76 |
| ATOM | 333 | CB | PRO | 148 | 54.274 | 41.256 | 8.215 | 1.00 | 84.26 |
| ATOM | 334 | CG | PRO | 148 | 52.968 | 41.783 | 8.690 | 1.00 | 73.26 |
| ATOM | 335 | CD | PRO | 148 | 52.165 | 42.004 | 7.458 | 1.00 | 71.33 |
| ATOM | 336 | N | CYS | 149 | 54.340 | 40.025 | 5.369 | 1.00 | 75.80 |
| ATOM | 337 | CA | CYS | 149 | 54.833 | 39.072 | 4.379 | 1.00 | 74.27 |
| ATOM | 338 | C | CYS | 149 | 55.272 | 39.756 | 3.091 | 1.00 | 78.06 |
| ATOM | 339 | O | CYS | 149 | 56.307 | 39.421 | 2.536 | 1.00 | 46.90 |
| ATOM | 340 | CB | CYS | 149 | 53.772 | 38.010 | 4.067 | 1.00 | 95.66 |
| ATOM | 341 | SG | CYS | 149 | 54.170 | 36.925 | 2.670 | 1.00 | 84.40 |
| ATOM | 342 | N | SER | 150 | 54.470 | 40.706 | 2.625 | 1.00 | 80.75 |
| ATOM | 343 | CA | SER | 150 | 54.775 | 41.480 | 1.431 | 1.00 | 64.38 |
| ATOM | 344 | C | SER | 150 | 56.102 | 42.224 | 1.569 | 1.00 | 54.94 |
| ATOM | 345 | O | SER | 150 | 56.914 | 42.224 | 0.646 | 1.00 | 38.94 |
| ATOM | 346 | CB | SER | 150 | 53.651 | 42.484 | 1.173 | 1.00 | 69.77 |
| ATOM | 347 | OG | SER | 150 | 53.899 | 43.263 | 0.023 | 1.00 | 33.31 |
| ATOM | 348 | N | LYS | 151 | 56.300 | 42.885 | 2.708 | 1.00 | 33.12 |
| ATOM | 349 | CA | LYS | 151 | 57.547 | 43.593 | 2.989 | 1.00 | 68.45 |
| ATOM | 350 | C | LYS | 151 | 58.748 | 42.633 | 3.032 | 1.00 | 66.78 |
| ATOM | 351 | O | LYS | 151 | 59.751 | 42.833 | 2.357 | 1.00 | 57.85 |
| ATOM | 352 | CB | LYS | 151 | 57.428 | 44.328 | 4.320 | 1.00 | 71.24 |
| ATOM | 353 | CG | LYS | 151 | 58.697 | 45.032 | 4.746 | 1.00 | 76.97 |
| ATOM | 354 | CD | LYS | 151 | 58.592 | 45.599 | 6.148 | 1.00 | 68.20 |
| ATOM | 355 | CE | LYS | 151 | 59.889 | 46.271 | 6.539 | 1.00 | 58.17 |
| ATOM | 356 | NZ | LYS | 151 | 59.812 | 46.823 | 7.902 | 1.00 | 59.77 |
| ATOM | 357 | N | GLU | 152 | 58.613 | 41.585 | 3.829 | 1.00 | 78.41 |
| ATOM | 358 | CA | GLU | 152 | 59.640 | 40.561 | 4.021 | 1.00 | 92.52 |

TABLE 10-continued

Three-Dimensional Coordinates of *Neisseria gonorrhoeae* GCYH-IB (SEQ. ID. No. 8)

| ATOM | 359 | C | GLU | 152 | 60.153 | 39.905 | 2.735 | 1.00 | 79.43 |
|---|---|---|---|---|---|---|---|---|---|
| ATOM | 360 | O | GLU | 152 | 61.339 | 39.649 | 2.602 | 1.00 | 69.31 |
| ATOM | 361 | CB | GLU | 152 | 59.091 | 39.489 | 4.962 | 1.00 | 0.08 |
| ATOM | 362 | CG | GLU | 152 | 60.011 | 38.331 | 5.246 | 1.00 | 0.79 |
| ATOM | 363 | CD | GLU | 152 | 59.323 | 37.258 | 6.072 | 1.00 | 0.24 |
| ATOM | 364 | OE1 | GLU | 152 | 58.216 | 36.827 | 5.688 | 1.00 | 0.23 |
| ATOM | 365 | OE2 | GLU | 152 | 59.884 | 36.848 | 7.108 | 1.00 | 0.86 |
| ATOM | 366 | N | ILE | 153 | 59.262 | 39.634 | 1.790 | 1.00 | 89.96 |
| ATOM | 367 | CA | ILE | 153 | 59.642 | 38.882 | 0.597 | 1.00 | 92.18 |
| ATOM | 368 | C | ILE | 153 | 60.114 | 39.737 | −0.576 | 1.00 | 88.22 |
| ATOM | 369 | O | ILE | 153 | 60.802 | 39.239 | −1.457 | 1.00 | 82.43 |
| ATOM | 370 | CB | ILE | 153 | 58.513 | 37.932 | 0.108 | 1.00 | 86.38 |
| ATOM | 371 | CG1 | ILE | 153 | 57.298 | 38.733 | −0.386 | 1.00 | 77.79 |
| ATOM | 372 | CG2 | ILE | 153 | 58.133 | 36.944 | 1.202 | 1.00 | 83.92 |
| ATOM | 373 | CD1 | ILE | 153 | 56.227 | 37.894 | −1.037 | 1.00 | 62.29 |
| ATOM | 374 | N | SER | 154 | 59.745 | 41.013 | −0.609 | 1.00 | 88.01 |
| ATOM | 375 | CA | SER | 154 | 60.133 | 41.853 | −1.742 | 1.00 | 86.91 |
| ATOM | 376 | C | SER | 154 | 61.351 | 42.710 | −1.418 | 1.00 | 67.99 |
| ATOM | 377 | O | SER | 154 | 61.612 | 43.017 | −0.263 | 1.00 | 52.76 |
| ATOM | 378 | CB | SER | 154 | 58.960 | 42.701 | −2.253 | 1.00 | 78.98 |
| ATOM | 379 | OG | SER | 154 | 58.304 | 43.363 | −1.197 | 1.00 | 77.89 |
| ATOM | 380 | N | GLN | 155 | 62.102 | 43.079 | −2.448 | 1.00 | 68.23 |
| ATOM | 381 | CA | GLN | 155 | 63.334 | 43.837 | −2.252 | 1.00 | 87.17 |
| ATOM | 382 | C | GLN | 155 | 63.032 | 45.299 | −1.942 | 1.00 | 86.25 |
| ATOM | 383 | O | GLN | 155 | 63.870 | 46.020 | −1.408 | 1.00 | 67.23 |
| ATOM | 384 | CB | GLN | 155 | 64.269 | 43.704 | −3.460 | 1.00 | 96.47 |
| ATOM | 385 | CG | GLN | 155 | 63.654 | 44.106 | −4.786 | 1.00 | 0.52 |
| ATOM | 386 | CD | GLN | 155 | 64.638 | 44.006 | −5.936 | 1.00 | 0.43 |
| ATOM | 387 | OE1 | GLN | 155 | 65.818 | 44.328 | −5.789 | 1.00 | 0.25 |
| ATOM | 388 | NE2 | GLN | 155 | 64.156 | 43.559 | −7.090 | 1.00 | 0.08 |
| ATOM | 389 | N | TYR | 156 | 61.822 | 45.723 | −2.284 | 1.00 | 82.97 |
| ATOM | 390 | CA | TYR | 156 | 61.318 | 47.030 | −1.884 | 1.00 | 80.96 |
| ATOM | 391 | C | TYR | 156 | 59.800 | 47.062 | −1.963 | 1.00 | 80.92 |
| ATOM | 392 | O | TYR | 156 | 59.193 | 46.208 | −2.600 | 1.00 | 47.73 |
| ATOM | 393 | CB | TYR | 156 | 61.929 | 48.158 | −2.723 | 1.00 | 65.47 |
| ATOM | 394 | CG | TYR | 156 | 62.164 | 47.832 | −4.181 | 1.00 | 85.68 |
| ATOM | 395 | CD1 | TYR | 156 | 61.111 | 47.526 | −5.027 | 1.00 | 77.03 |
| ATOM | 396 | CD2 | TYR | 156 | 63.447 | 47.853 | −4.715 | 1.00 | 90.55 |
| ATOM | 397 | CE1 | TYR | 156 | 61.328 | 47.238 | −6.361 | 1.00 | 99.10 |
| ATOM | 398 | CE2 | TYR | 156 | 63.672 | 47.566 | −6.044 | 1.00 | 96.22 |
| ATOM | 399 | CZ | TYR | 156 | 62.611 | 47.260 | −6.862 | 1.00 | 0.08 |
| ATOM | 400 | OH | TYR | 156 | 62.837 | 46.976 | −8.186 | 1.00 | 90.79 |
| ATOM | 401 | N | GLY | 157 | 59.196 | 48.044 | −1.304 | 1.00 | 72.73 |
| ATOM | 402 | CA | GLY | 157 | 57.754 | 48.188 | −1.307 | 1.00 | 58.71 |
| ATOM | 403 | C | GLY | 157 | 57.062 | 47.167 | −0.424 | 1.00 | 52.06 |
| ATOM | 404 | O | GLY | 157 | 57.631 | 46.138 | −0.078 | 1.00 | 47.90 |
| ATOM | 405 | N | ALA | 158 | 55.824 | 47.471 | −0.046 | 1.00 | 33.39 |
| ATOM | 406 | CA | ALA | 158 | 54.953 | 46.536 | 0.669 | 1.00 | 56.02 |
| ATOM | 407 | C | ALA | 158 | 53.518 | 46.951 | 0.406 | 1.00 | 62.89 |
| ATOM | 408 | O | ALA | 158 | 53.168 | 48.113 | 0.567 | 1.00 | 42.34 |
| ATOM | 409 | CB | ALA | 158 | 55.239 | 46.546 | 2.164 | 1.00 | 50.98 |
| ATOM | 410 | N | HIS | 159 | 52.675 | 46.023 | −0.016 | 1.00 | 53.10 |
| ATOM | 411 | CA | HIS | 159 | 51.307 | 46.421 | −0.280 | 1.00 | 50.36 |
| ATOM | 412 | C | HIS | 159 | 50.642 | 46.805 | 1.043 | 1.00 | 46.60 |
| ATOM | 413 | O | HIS | 159 | 50.840 | 46.156 | 2.077 | 1.00 | 42.85 |
| ATOM | 414 | CB | HIS | 159 | 50.528 | 45.359 | −1.061 | 1.00 | 69.62 |
| ATOM | 415 | CG | HIS | 159 | 50.007 | 44.242 | −0.218 | 1.00 | 64.17 |
| ATOM | 416 | ND1 | HIS | 159 | 48.869 | 44.363 | 0.549 | 1.00 | 65.54 |
| ATOM | 417 | CD2 | HIS | 159 | 50.456 | 42.985 | −0.031 | 1.00 | 51.87 |
| ATOM | 418 | CE1 | HIS | 159 | 48.648 | 43.223 | 1.182 | 1.00 | 52.61 |
| ATOM | 419 | NE2 | HIS | 159 | 49.595 | 42.373 | 0.846 | 1.00 | 61.55 |
| ATOM | 420 | N | ASN | 160 | 49.913 | 47.915 | 1.011 | 1.00 | 39.47 |
| ATOM | 421 | CA | ASN | 160 | 49.141 | 48.362 | 2.156 | 1.00 | 41.24 |
| ATOM | 422 | C | ASN | 160 | 47.750 | 48.703 | 1.673 | 1.00 | 36.77 |
| ATOM | 423 | O | ASN | 160 | 47.495 | 48.705 | 0.481 | 1.00 | 37.08 |
| ATOM | 424 | CB | ASN | 160 | 49.819 | 49.545 | 2.865 | 1.00 | 40.95 |
| ATOM | 425 | CG | ASN | 160 | 50.298 | 50.619 | 1.900 | 1.00 | 68.88 |
| ATOM | 426 | OD1 | ASN | 160 | 51.460 | 50.618 | 1.484 | 1.00 | 66.81 |
| ATOM | 427 | ND2 | ASN | 160 | 49.411 | 51.546 | 1.545 | 1.00 | 28.56 |
| ATOM | 428 | N | GLN | 161 | 46.855 | 49.012 | 2.591 | 1.00 | 26.40 |
| ATOM | 429 | CA | GLN | 161 | 45.458 | 49.252 | 2.236 | 1.00 | 43.83 |
| ATOM | 430 | C | GLN | 161 | 44.713 | 49.794 | 3.417 | 1.00 | 49.46 |
| ATOM | 431 | O | GLN | 161 | 45.198 | 49.738 | 4.542 | 1.00 | 43.92 |
| ATOM | 432 | CB | GLN | 161 | 44.775 | 47.962 | 1.777 | 1.00 | 57.27 |
| ATOM | 433 | CG | GLN | 161 | 44.857 | 46.852 | 2.784 | 1.00 | 60.87 |
| ATOM | 434 | CD | GLN | 161 | 46.158 | 46.068 | 2.695 | 1.00 | 52.87 |
| ATOM | 435 | OE1 | GLN | 161 | 46.634 | 45.738 | 1.601 | 1.00 | 41.97 |
| ATOM | 436 | NE2 | GLN | 161 | 46.725 | 45.746 | 3.850 | 1.00 | 38.64 |

TABLE 10-continued

Three-Dimensional Coordinates of *Neisseria gonorrhoeae* GCYH-IB (SEQ. ID. No. 8)

| ATOM | 437 | N | ARG | 162 | 43.522 | 50.312 | 3.158 | 1.00 | 52.54 |
|------|-----|-----|-----|-----|--------|--------|-------|------|-------|
| ATOM | 438 | CA | ARG | 162 | 42.648 | 50.738 | 4.232 | 1.00 | 46.71 |
| ATOM | 439 | C | ARG | 162 | 42.082 | 49.501 | 4.904 | 1.00 | 59.05 |
| ATOM | 440 | O | ARG | 162 | 41.814 | 48.496 | 4.270 | 1.00 | 42.45 |
| ATOM | 441 | CB | ARG | 162 | 41.524 | 51.644 | 3.711 | 1.00 | 54.51 |
| ATOM | 442 | CG | ARG | 162 | 41.034 | 52.664 | 4.718 | 1.00 | 71.10 |
| ATOM | 443 | CD | ARG | 162 | 39.975 | 53.579 | 4.129 | 1.00 | 86.06 |
| ATOM | 444 | NE | ARG | 162 | 40.524 | 54.548 | 3.190 | 1.00 | 68.39 |
| ATOM | 445 | CZ | ARG | 162 | 39.800 | 55.199 | 2.290 | 1.00 | 75.71 |
| ATOM | 446 | NH1 | ARG | 162 | 38.499 | 54.973 | 2.206 | 1.00 | 62.22 |
| ATOM | 447 | NH2 | ARG | 162 | 40.375 | 56.065 | 1.471 | 1.00 | 70.75 |
| ATOM | 448 | N | SER | 163 | 41.938 | 49.587 | 6.211 | 1.00 | 37.48 |
| ATOM | 449 | CA | SER | 163 | 41.365 | 48.527 | 7.016 | 1.00 | 34.90 |
| ATOM | 450 | C | SER | 163 | 40.248 | 49.125 | 7.885 | 1.00 | 42.81 |
| ATOM | 451 | O | SER | 163 | 40.317 | 50.265 | 8.350 | 1.00 | 29.13 |
| ATOM | 452 | CB | SER | 163 | 42.466 | 47.877 | 7.862 | 1.00 | 43.38 |
| ATOM | 453 | OG | SER | 163 | 41.956 | 47.004 | 8.840 | 1.00 | 73.12 |
| ATOM | 454 | N | HIS | 164 | 39.167 | 48.383 | 8.050 | 1.00 | 25.58 |
| ATOM | 455 | CA | HIS | 164 | 38.147 | 48.793 | 9.003 | 1.00 | 27.06 |
| ATOM | 456 | C | HIS | 164 | 38.230 | 47.893 | 10.208 | 1.00 | 36.62 |
| ATOM | 457 | O | HIS | 164 | 38.126 | 46.676 | 10.089 | 1.00 | 35.13 |
| ATOM | 458 | CB | HIS | 164 | 36.748 | 48.713 | 8.377 | 1.00 | 33.69 |
| ATOM | 459 | CG | HIS | 164 | 36.524 | 49.686 | 7.266 | 1.00 | 64.30 |
| ATOM | 460 | ND1 | HIS | 164 | 35.667 | 49.443 | 6.221 | 1.00 | 73.91 |
| ATOM | 461 | CD2 | HIS | 164 | 37.058 | 50.917 | 7.034 | 1.00 | 61.84 |
| ATOM | 462 | CE1 | HIS | 164 | 35.671 | 50.475 | 5.393 | 1.00 | 72.47 |
| ATOM | 463 | NE2 | HIS | 164 | 36.512 | 51.379 | 5.866 | 1.00 | 59.98 |
| ATOM | 464 | N | GLU | 178 | 35.857 | 58.012 | 22.387 | 1.00 | 39.25 |
| ATOM | 465 | CA | GLU | 178 | 37.222 | 58.396 | 22.054 | 1.00 | 38.39 |
| ATOM | 466 | C | GLU | 178 | 38.207 | 57.420 | 22.669 | 1.00 | 48.57 |
| ATOM | 467 | O | GLU | 178 | 39.273 | 57.172 | 22.104 | 1.00 | 46.83 |
| ATOM | 468 | CB | GLU | 178 | 37.512 | 59.842 | 22.484 | 1.00 | 42.73 |
| ATOM | 469 | CG | GLU | 178 | 37.664 | 60.049 | 23.993 | 1.00 | 64.81 |
| ATOM | 470 | CD | GLU | 178 | 36.370 | 59.881 | 24.781 | 1.00 | 66.63 |
| ATOM | 471 | OE1 | GLU | 178 | 35.270 | 60.027 | 24.197 | 1.00 | 60.52 |
| ATOM | 472 | OE2 | GLU | 178 | 36.461 | 59.611 | 25.997 | 1.00 | 61.01 |
| ATOM | 473 | N | GLU | 179 | 37.840 | 56.840 | 23.808 | 1.00 | 37.21 |
| ATOM | 474 | CA | GLU | 179 | 38.661 | 55.782 | 24.407 | 1.00 | 40.17 |
| ATOM | 475 | C | GLU | 179 | 38.751 | 54.560 | 23.517 | 1.00 | 36.90 |
| ATOM | 476 | O | GLU | 179 | 39.825 | 53.985 | 23.374 | 1.00 | 51.37 |
| ATOM | 477 | CB | GLU | 179 | 38.129 | 55.350 | 25.773 | 1.00 | 43.49 |
| ATOM | 478 | CG | GLU | 179 | 38.141 | 56.416 | 26.843 | 1.00 | 57.74 |
| ATOM | 479 | CD | GLU | 179 | 37.805 | 55.843 | 28.214 | 1.00 | 74.66 |
| ATOM | 480 | OE1 | GLU | 179 | 38.687 | 55.202 | 28.841 | 1.00 | 60.84 |
| ATOM | 481 | OE2 | GLU | 179 | 36.653 | 56.032 | 28.660 | 1.00 | 68.81 |
| ATOM | 482 | N | ILE | 181 | 38.345 | 54.507 | 20.306 | 1.00 | 27.44 |
| ATOM | 483 | CA | ILE | 181 | 39.097 | 54.884 | 19.126 | 1.00 | 29.36 |
| ATOM | 484 | C | ILE | 181 | 40.614 | 54.834 | 19.407 | 1.00 | 50.07 |
| ATOM | 485 | O | ILE | 181 | 41.397 | 54.383 | 18.564 | 1.00 | 40.42 |
| ATOM | 486 | CB | ILE | 181 | 38.699 | 56.265 | 18.613 | 1.00 | 30.81 |
| ATOM | 487 | CG1 | ILE | 181 | 37.266 | 56.212 | 18.047 | 1.00 | 37.62 |
| ATOM | 488 | CG2 | ILE | 181 | 39.754 | 56.774 | 17.599 | 1.00 | 29.95 |
| ATOM | 489 | CD1 | ILE | 181 | 36.677 | 57.558 | 17.652 | 1.00 | 39.81 |
| ATOM | 490 | N | ASP | 182 | 41.004 | 55.282 | 20.598 | 1.00 | 29.14 |
| ATOM | 491 | CA | ASP | 182 | 42.401 | 55.313 | 21.019 | 1.00 | 37.82 |
| ATOM | 492 | C | ASP | 182 | 42.982 | 53.891 | 21.154 | 1.00 | 43.42 |
| ATOM | 493 | O | ASP | 182 | 44.074 | 53.610 | 20.662 | 1.00 | 47.73 |
| ATOM | 494 | CB | ASP | 182 | 42.558 | 56.092 | 22.331 | 1.00 | 36.01 |
| ATOM | 495 | CG | ASP | 182 | 42.444 | 57.614 | 22.149 | 1.00 | 52.83 |
| ATOM | 496 | OD1 | ASP | 182 | 42.697 | 58.124 | 21.032 | 1.00 | 49.45 |
| ATOM | 497 | OD2 | ASP | 182 | 42.108 | 58.306 | 23.144 | 1.00 | 54.83 |
| ATOM | 498 | N | TYR | 183 | 42.257 | 52.988 | 21.807 | 1.00 | 37.63 |
| ATOM | 499 | CA | TYR | 183 | 42.705 | 51.598 | 21.887 | 1.00 | 25.05 |
| ATOM | 500 | C | TYR | 183 | 43.036 | 51.059 | 20.493 | 1.00 | 47.61 |
| ATOM | 501 | O | TYR | 183 | 43.943 | 50.254 | 20.326 | 1.00 | 41.37 |
| ATOM | 502 | CB | TYR | 183 | 41.645 | 50.700 | 22.527 | 1.00 | 33.40 |
| ATOM | 503 | CG | TYR | 183 | 41.497 | 50.812 | 24.026 | 1.00 | 47.28 |
| ATOM | 504 | CD1 | TYR | 183 | 42.600 | 50.998 | 24.836 | 1.00 | 56.26 |
| ATOM | 505 | CD2 | TYR | 183 | 40.252 | 50.681 | 24.633 | 1.00 | 38.98 |
| ATOM | 506 | CE1 | TYR | 183 | 42.477 | 51.075 | 26.207 | 1.00 | 67.80 |
| ATOM | 507 | CE2 | TYR | 183 | 40.115 | 50.753 | 26.001 | 1.00 | 55.22 |
| ATOM | 508 | CZ | TYR | 183 | 41.233 | 50.955 | 26.789 | 1.00 | 67.84 |
| ATOM | 509 | OH | TYR | 183 | 41.117 | 51.036 | 28.160 | 1.00 | 69.73 |
| ATOM | 510 | N | VAL | 184 | 42.294 | 51.485 | 19.480 | 1.00 | 32.30 |
| ATOM | 511 | CA | VAL | 184 | 42.513 | 50.910 | 18.168 | 1.00 | 34.08 |
| ATOM | 512 | C | VAL | 184 | 43.614 | 51.617 | 17.387 | 1.00 | 36.57 |
| ATOM | 513 | O | VAL | 184 | 44.448 | 50.970 | 16.789 | 1.00 | 35.67 |
| ATOM | 514 | CB | VAL | 184 | 41.228 | 50.851 | 17.308 | 1.00 | 40.81 |

TABLE 10-continued

Three-Dimensional Coordinates of *Neisseria gonorrhoeae* GCYH-IB (SEQ. ID. No. 8)

| ATOM | 515 | CG1 | VAL | 184 | 41.578 | 50.500 | 15.876 | 1.00 | 41.01 |
|---|---|---|---|---|---|---|---|---|---|
| ATOM | 516 | CG2 | VAL | 184 | 40.222 | 49.820 | 17.875 | 1.00 | 29.23 |
| ATOM | 517 | N | GLU | 185 | 43.610 | 52.941 | 17.391 | 1.00 | 40.28 |
| ATOM | 518 | CA | GLU | 185 | 44.548 | 53.689 | 16.562 | 1.00 | 39.88 |
| ATOM | 519 | C | GLU | 185 | 45.993 | 53.527 | 17.037 | 1.00 | 49.88 |
| ATOM | 520 | O | GLU | 185 | 46.913 | 53.496 | 16.236 | 1.00 | 56.83 |
| ATOM | 521 | CB | GLU | 185 | 44.119 | 55.154 | 16.470 | 1.00 | 28.85 |
| ATOM | 522 | CG | GLU | 185 | 42.883 | 55.365 | 15.585 | 1.00 | 48.56 |
| ATOM | 523 | CD | GLU | 185 | 42.538 | 56.833 | 15.405 | 1.00 | 52.66 |
| ATOM | 524 | OE1 | GLU | 185 | 42.974 | 57.633 | 16.251 | 1.00 | 43.17 |
| ATOM | 525 | OE2 | GLU | 185 | 41.836 | 57.191 | 14.430 | 1.00 | 39.75 |
| ATOM | 526 | N | THR | 186 | 46.158 | 53.416 | 18.348 | 1.00 | 56.19 |
| ATOM | 527 | CA | THR | 186 | 47.419 | 53.065 | 18.988 | 1.00 | 60.74 |
| ATOM | 528 | C | THR | 186 | 48.080 | 51.839 | 18.356 | 1.00 | 54.76 |
| ATOM | 529 | O | THR | 186 | 49.286 | 51.803 | 18.152 | 1.00 | 53.36 |
| ATOM | 530 | CB | THR | 186 | 47.188 | 52.794 | 20.494 | 1.00 | 59.55 |
| ATOM | 531 | OG1 | THR | 186 | 47.159 | 54.038 | 21.195 | 1.00 | 64.84 |
| ATOM | 532 | CG2 | THR | 186 | 48.287 | 51.920 | 21.078 | 1.00 | 66.33 |
| ATOM | 533 | N | GLN | 187 | 47.274 | 50.843 | 18.028 | 1.00 | 54.99 |
| ATOM | 534 | CA | GLN | 187 | 47.774 | 49.561 | 17.551 | 1.00 | 53.27 |
| ATOM | 535 | C | GLN | 187 | 47.868 | 49.431 | 16.034 | 1.00 | 47.18 |
| ATOM | 536 | O | GLN | 187 | 48.309 | 48.411 | 15.541 | 1.00 | 56.60 |
| ATOM | 537 | CB | GLN | 187 | 46.862 | 48.446 | 18.054 | 1.00 | 45.99 |
| ATOM | 538 | CG | GLN | 187 | 46.659 | 48.444 | 19.536 | 1.00 | 53.53 |
| ATOM | 539 | CD | GLN | 187 | 47.920 | 48.065 | 20.252 | 1.00 | 60.81 |
| ATOM | 540 | OE1 | GLN | 187 | 48.807 | 47.435 | 19.670 | 1.00 | 55.31 |
| ATOM | 541 | NE2 | GLN | 187 | 48.015 | 48.432 | 21.520 | 1.00 | 47.26 |
| ATOM | 542 | N | ALA | 188 | 47.427 | 50.426 | 15.283 | 1.00 | 44.02 |
| ATOM | 543 | CA | ALA | 188 | 47.445 | 50.290 | 13.834 | 1.00 | 52.84 |
| ATOM | 544 | C | ALA | 188 | 48.853 | 50.496 | 13.242 | 1.00 | 61.50 |
| ATOM | 545 | O | ALA | 188 | 49.666 | 51.203 | 13.820 | 1.00 | 45.67 |
| ATOM | 546 | CB | ALA | 188 | 46.466 | 51.254 | 13.219 | 1.00 | 42.42 |
| ATOM | 547 | N | SER | 189 | 49.135 | 49.860 | 12.103 | 1.00 | 36.67 |
| ATOM | 548 | CA | SER | 189 | 50.352 | 50.130 | 11.336 | 1.00 | 49.39 |
| ATOM | 549 | C | SER | 189 | 50.511 | 51.630 | 11.189 | 1.00 | 62.48 |
| ATOM | 550 | O | SER | 189 | 51.589 | 52.169 | 11.411 | 1.00 | 51.33 |
| ATOM | 551 | CB | SER | 189 | 50.289 | 49.483 | 9.953 | 1.00 | 35.57 |
| ATOM | 552 | OG | SER | 189 | 50.524 | 48.091 | 10.040 | 1.00 | 49.82 |
| ATOM | 553 | N | CYS | 190 | 49.420 | 52.285 | 10.796 | 1.00 | 43.06 |
| ATOM | 554 | CA | CYS | 190 | 49.286 | 53.728 | 10.919 | 1.00 | 42.62 |
| ATOM | 555 | C | CYS | 190 | 47.816 | 54.169 | 10.820 | 1.00 | 49.00 |
| ATOM | 556 | O | CYS | 190 | 46.973 | 53.488 | 10.259 | 1.00 | 43.56 |
| ATOM | 557 | CB | CYS | 190 | 50.158 | 54.486 | 9.912 | 1.00 | 80.65 |
| ATOM | 558 | SG | CYS | 190 | 50.699 | 56.108 | 10.542 | 1.00 | 74.68 |
| ATOM | 559 | N | GLN | 191 | 47.510 | 55.311 | 11.396 | 1.00 | 39.65 |
| ATOM | 560 | CA | GLN | 191 | 46.148 | 55.797 | 11.388 | 1.00 | 60.24 |
| ATOM | 561 | C | GLN | 191 | 45.908 | 56.730 | 10.210 | 1.00 | 52.12 |
| ATOM | 562 | O | GLN | 191 | 46.837 | 57.102 | 9.515 | 1.00 | 49.03 |
| ATOM | 563 | CB | GLN | 191 | 45.831 | 56.475 | 12.715 | 1.00 | 61.86 |
| ATOM | 564 | CG | GLN | 191 | 46.995 | 57.198 | 13.327 | 1.00 | 60.94 |
| ATOM | 565 | CD | GLN | 191 | 46.670 | 57.707 | 14.698 | 1.00 | 63.14 |
| ATOM | 566 | OE1 | GLN | 191 | 45.933 | 58.674 | 14.849 | 1.00 | 54.80 |
| ATOM | 567 | NE2 | GLN | 191 | 47.211 | 57.055 | 15.713 | 1.00 | 66.82 |
| ATOM | 568 | N | LEU | 192 | 44.655 | 57.086 | 9.984 | 1.00 | 50.72 |
| ATOM | 569 | CA | LEU | 192 | 44.289 | 57.926 | 8.860 | 1.00 | 41.55 |
| ATOM | 570 | C | LEU | 192 | 44.159 | 59.371 | 9.315 | 1.00 | 50.00 |
| ATOM | 571 | O | LEU | 192 | 43.876 | 59.621 | 10.475 | 1.00 | 36.32 |
| ATOM | 572 | CB | LEU | 192 | 42.966 | 57.446 | 8.255 | 1.00 | 39.35 |
| ATOM | 573 | CG | LEU | 192 | 42.940 | 56.019 | 7.727 | 1.00 | 46.42 |
| ATOM | 574 | CD1 | LEU | 192 | 41.593 | 55.684 | 7.117 | 1.00 | 41.02 |
| ATOM | 575 | CD2 | LEU | 192 | 44.044 | 55.836 | 6.701 | 1.00 | 49.16 |
| ATOM | 576 | N | TYR | 193 | 44.386 | 60.307 | 8.394 | 1.00 | 41.05 |
| ATOM | 577 | CA | TYR | 193 | 44.156 | 61.731 | 8.618 | 1.00 | 41.75 |
| ATOM | 578 | C | TYR | 193 | 43.434 | 62.327 | 7.416 | 1.00 | 45.03 |
| ATOM | 579 | O | TYR | 193 | 43.612 | 61.860 | 6.290 | 1.00 | 56.48 |
| ATOM | 580 | CB | TYR | 193 | 45.482 | 62.471 | 8.851 | 1.00 | 46.33 |
| ATOM | 581 | CG | TYR | 193 | 46.279 | 61.953 | 10.022 | 1.00 | 52.84 |
| ATOM | 582 | CD1 | TYR | 193 | 46.090 | 62.483 | 11.290 | 1.00 | 47.66 |
| ATOM | 583 | CD2 | TYR | 193 | 47.222 | 60.925 | 9.863 | 1.00 | 49.49 |
| ATOM | 584 | CE1 | TYR | 193 | 46.804 | 62.018 | 12.366 | 1.00 | 57.04 |
| ATOM | 585 | CE2 | TYR | 193 | 47.944 | 60.452 | 10.941 | 1.00 | 51.34 |
| ATOM | 586 | CZ | TYR | 193 | 47.730 | 61.010 | 12.187 | 1.00 | 59.22 |
| ATOM | 587 | OH | TYR | 193 | 48.427 | 60.569 | 13.273 | 1.00 | 45.64 |
| ATOM | 588 | N | GLY | 194 | 42.625 | 63.357 | 7.649 | 1.00 | 47.68 |
| ATOM | 589 | CA | GLY | 194 | 41.953 | 64.039 | 6.563 | 1.00 | 45.00 |
| ATOM | 590 | C | GLY | 194 | 42.902 | 64.941 | 5.783 | 1.00 | 55.57 |
| ATOM | 591 | O | GLY | 194 | 42.802 | 65.059 | 4.562 | 1.00 | 73.94 |
| ATOM | 592 | N | LEU | 195 | 43.828 | 65.576 | 6.495 | 1.00 | 56.69 |

TABLE 10-continued

Three-Dimensional Coordinates of *Neisseria gonorrhoeae* GCYH-IB (SEQ. ID. No. 8)

| ATOM | 593 | CA | LEU | 195 | 44.748 | 66.545 | 5.903 | 1.00 | 68.95 |
|------|-----|-----|-----|-----|--------|--------|-------|------|-------|
| ATOM | 594 | C | LEU | 195 | 46.190 | 66.203 | 6.238 | 1.00 | 68.24 |
| ATOM | 595 | O | LEU | 195 | 46.552 | 66.162 | 7.408 | 1.00 | 53.14 |
| ATOM | 596 | CB | LEU | 195 | 44.431 | 67.941 | 6.431 | 1.00 | 55.82 |
| ATOM | 597 | CG | LEU | 195 | 44.860 | 69.144 | 5.603 | 1.00 | 63.65 |
| ATOM | 598 | CD1 | LEU | 195 | 44.173 | 70.395 | 6.124 | 1.00 | 53.17 |
| ATOM | 599 | CD2 | LEU | 195 | 46.371 | 69.303 | 5.634 | 1.00 | 83.63 |
| ATOM | 600 | N | LEU | 196 | 47.000 | 65.960 | 5.208 | 1.00 | 49.64 |
| ATOM | 601 | CA | LEU | 196 | 48.437 | 65.714 | 5.370 | 1.00 | 47.59 |
| ATOM | 602 | C | LEU | 196 | 49.267 | 66.548 | 4.411 | 1.00 | 55.36 |
| ATOM | 603 | O | LEU | 196 | 48.957 | 66.624 | 3.222 | 1.00 | 59.50 |
| ATOM | 604 | CB | LEU | 196 | 48.768 | 64.246 | 5.111 | 1.00 | 47.54 |
| ATOM | 605 | CG | LEU | 196 | 48.082 | 63.238 | 6.027 | 1.00 | 58.31 |
| ATOM | 606 | CD1 | LEU | 196 | 48.266 | 61.841 | 5.517 | 1.00 | 54.87 |
| ATOM | 607 | CD2 | LEU | 196 | 48.630 | 63.386 | 7.419 | 1.00 | 37.88 |
| ATOM | 608 | N | LYS | 197 | 50.338 | 67.146 | 4.923 | 1.00 | 48.39 |
| ATOM | 609 | CA | LYS | 197 | 51.311 | 67.836 | 4.083 | 1.00 | 75.76 |
| ATOM | 610 | C | LYS | 197 | 52.429 | 66.865 | 3.703 | 1.00 | 71.25 |
| ATOM | 611 | O | LYS | 197 | 52.485 | 65.749 | 4.228 | 1.00 | 49.06 |
| ATOM | 612 | CB | LYS | 197 | 51.880 | 69.060 | 4.807 | 1.00 | 81.92 |
| ATOM | 613 | CG | LYS | 197 | 50.855 | 70.153 | 5.073 | 1.00 | 88.40 |
| ATOM | 614 | CD | LYS | 197 | 49.784 | 70.161 | 3.999 | 1.00 | 0.78 |
| ATOM | 615 | CE | LYS | 197 | 49.135 | 71.520 | 3.846 | 1.00 | 0.41 |
| ATOM | 616 | NZ | LYS | 197 | 49.905 | 72.367 | 2.897 | 1.00 | 0.26 |
| ATOM | 617 | N | ARG | 198 | 53.307 | 67.287 | 2.795 | 1.00 | 61.35 |
| ATOM | 618 | CA | ARG | 198 | 54.429 | 66.455 | 2.340 | 1.00 | 78.19 |
| ATOM | 619 | C | ARG | 198 | 55.195 | 65.744 | 3.462 | 1.00 | 75.65 |
| ATOM | 620 | O | ARG | 198 | 55.372 | 64.533 | 3.408 | 1.00 | 52.93 |
| ATOM | 621 | CB | ARG | 198 | 55.403 | 67.271 | 1.491 | 1.00 | 91.33 |
| ATOM | 622 | CG | ARG | 198 | 55.218 | 67.126 | −0.001 | 1.00 | 0.83 |
| ATOM | 623 | CD | ARG | 198 | 56.126 | 68.092 | −0.738 | 1.00 | 0.91 |
| ATOM | 624 | NE | ARG | 198 | 56.610 | 67.533 | −1.995 | 1.00 | 0.29 |
| ATOM | 625 | CZ | ARG | 198 | 57.805 | 66.973 | −2.152 | 1.00 | 0.90 |
| ATOM | 626 | NH1 | ARG | 198 | 58.646 | 66.902 | −1.128 | 1.00 | 0.09 |
| ATOM | 627 | NH2 | ARG | 198 | 58.162 | 66.488 | −3.334 | 1.00 | 0.42 |
| ATOM | 628 | N | PRO | 199 | 55.669 | 66.494 | 4.471 | 1.00 | 70.03 |
| ATOM | 629 | CA | PRO | 199 | 56.397 | 65.866 | 5.579 | 1.00 | 66.36 |
| ATOM | 630 | C | PRO | 199 | 55.541 | 64.867 | 6.351 | 1.00 | 71.38 |
| ATOM | 631 | O | PRO | 199 | 56.103 | 63.892 | 6.843 | 1.00 | 55.95 |
| ATOM | 632 | CB | PRO | 199 | 56.757 | 67.059 | 6.482 | 1.00 | 64.71 |
| ATOM | 633 | CG | PRO | 199 | 55.798 | 68.123 | 6.082 | 1.00 | 73.47 |
| ATOM | 634 | CD | PRO | 199 | 55.666 | 67.957 | 4.609 | 1.00 | 77.02 |
| ATOM | 635 | N | ASP | 200 | 54.227 | 65.115 | 6.456 | 1.00 | 60.82 |
| ATOM | 636 | CA | ASP | 200 | 53.290 | 64.211 | 7.142 | 1.00 | 63.99 |
| ATOM | 637 | C | ASP | 200 | 53.146 | 62.886 | 6.410 | 1.00 | 61.39 |
| ATOM | 638 | O | ASP | 200 | 53.208 | 61.814 | 7.003 | 1.00 | 53.71 |
| ATOM | 639 | CB | ASP | 200 | 51.899 | 64.838 | 7.228 | 1.00 | 50.68 |
| ATOM | 640 | CG | ASP | 200 | 51.852 | 66.035 | 8.145 | 1.00 | 70.50 |
| ATOM | 641 | OD1 | ASP | 200 | 52.439 | 65.955 | 9.241 | 1.00 | 53.74 |
| ATOM | 642 | OD2 | ASP | 200 | 51.215 | 67.045 | 7.773 | 1.00 | 75.96 |
| ATOM | 643 | N | GLU | 201 | 52.926 | 62.986 | 5.109 | 1.00 | 44.34 |
| ATOM | 644 | CA | GLU | 201 | 52.811 | 61.827 | 4.255 | 1.00 | 68.64 |
| ATOM | 645 | C | GLU | 201 | 54.094 | 61.003 | 4.267 | 1.00 | 64.75 |
| ATOM | 646 | O | GLU | 201 | 54.046 | 59.787 | 4.319 | 1.00 | 40.48 |
| ATOM | 647 | CB | GLU | 201 | 52.469 | 62.247 | 2.830 | 1.00 | 44.67 |
| ATOM | 648 | CG | GLU | 201 | 52.608 | 61.122 | 1.836 | 1.00 | 71.92 |
| ATOM | 649 | CD | GLU | 201 | 51.777 | 61.334 | 0.595 | 1.00 | 76.03 |
| ATOM | 650 | OE1 | GLU | 201 | 51.495 | 62.494 | 0.255 | 1.00 | 87.45 |
| ATOM | 651 | OE2 | GLU | 201 | 51.404 | 60.336 | −0.043 | 1.00 | 64.60 |
| ATOM | 652 | N | LYS | 202 | 55.243 | 61.661 | 4.206 | 1.00 | 50.01 |
| ATOM | 653 | CA | LYS | 202 | 56.513 | 60.957 | 4.314 | 1.00 | 53.02 |
| ATOM | 654 | C | LYS | 202 | 56.564 | 60.157 | 5.628 | 1.00 | 42.78 |
| ATOM | 655 | O | LYS | 202 | 56.876 | 58.973 | 5.640 | 1.00 | 43.49 |
| ATOM | 656 | CB | LYS | 202 | 57.685 | 61.948 | 4.227 | 1.00 | 45.02 |
| ATOM | 657 | CG | LYS | 202 | 59.008 | 61.344 | 4.615 | 1.00 | 59.66 |
| ATOM | 658 | CD | LYS | 202 | 60.147 | 62.359 | 4.555 | 1.00 | 54.22 |
| ATOM | 659 | CE | LYS | 202 | 61.395 | 61.732 | 5.112 | 1.00 | 46.69 |
| ATOM | 660 | NZ | LYS | 202 | 62.492 | 62.730 | 5.135 | 1.00 | 0.21 |
| ATOM | 661 | N | TYR | 203 | 56.261 | 60.827 | 6.729 | 1.00 | 53.09 |
| ATOM | 662 | CA | TYR | 203 | 56.204 | 60.202 | 8.045 | 1.00 | 64.50 |
| ATOM | 663 | C | TYR | 203 | 55.245 | 59.002 | 8.106 | 1.00 | 61.81 |
| ATOM | 664 | O | TYR | 203 | 55.568 | 57.969 | 8.685 | 1.00 | 65.84 |
| ATOM | 665 | CB | TYR | 203 | 55.783 | 61.245 | 9.075 | 1.00 | 67.81 |
| ATOM | 666 | CG | TYR | 203 | 55.679 | 60.723 | 10.477 | 1.00 | 64.72 |
| ATOM | 667 | CD1 | TYR | 203 | 56.748 | 60.819 | 11.345 | 1.00 | 52.12 |
| ATOM | 668 | CD2 | TYR | 203 | 54.513 | 60.137 | 10.940 | 1.00 | 53.63 |
| ATOM | 669 | CE1 | TYR | 203 | 56.664 | 60.356 | 12.633 | 1.00 | 60.02 |
| ATOM | 670 | CE2 | TYR | 203 | 54.421 | 59.662 | 12.241 | 1.00 | 64.08 |

TABLE 10-continued

Three-Dimensional Coordinates of *Neisseria gonorrhoeae* GCYH-IB (SEQ. ID. No. 8)

| ATOM | 671 | CZ | TYR | 203 | 55.506 | 59.781 | 13.079 | 1.00 | 69.98 |
|---|---|---|---|---|---|---|---|---|---|
| ATOM | 672 | OH | TYR | 203 | 55.444 | 59.316 | 14.365 | 1.00 | 69.48 |
| ATOM | 673 | N | VAL | 204 | 54.068 | 59.141 | 7.506 | 1.00 | 60.20 |
| ATOM | 674 | CA | VAL | 204 | 53.038 | 58.088 | 7.576 | 1.00 | 78.24 |
| ATOM | 675 | C | VAL | 204 | 53.422 | 56.850 | 6.723 | 1.00 | 47.17 |
| ATOM | 676 | O | VAL | 204 | 53.315 | 55.712 | 7.181 | 1.00 | 43.11 |
| ATOM | 677 | CB | VAL | 204 | 51.612 | 58.669 | 7.250 | 1.00 | 43.63 |
| ATOM | 678 | CG1 | VAL | 204 | 51.277 | 58.534 | 5.775 | 1.00 | 47.36 |
| ATOM | 679 | CG2 | VAL | 204 | 50.563 | 58.049 | 8.102 | 1.00 | 71.25 |
| ATOM | 680 | N | THR | 205 | 53.905 | 57.086 | 5.506 | 1.00 | 44.47 |
| ATOM | 681 | CA | THR | 205 | 54.461 | 56.047 | 4.633 | 1.00 | 52.60 |
| ATOM | 682 | C | THR | 205 | 55.540 | 55.208 | 5.338 | 1.00 | 57.12 |
| ATOM | 683 | O | THR | 205 | 55.508 | 53.963 | 5.330 | 1.00 | 41.28 |
| ATOM | 684 | CB | THR | 205 | 55.107 | 56.681 | 3.363 | 1.00 | 61.74 |
| ATOM | 685 | OG1 | THR | 205 | 54.153 | 57.493 | 2.669 | 1.00 | 49.23 |
| ATOM | 686 | CG2 | THR | 205 | 55.642 | 55.616 | 2.418 | 1.00 | 57.92 |
| ATOM | 687 | N | GLU | 206 | 56.501 | 55.905 | 5.939 | 1.00 | 51.43 |
| ATOM | 688 | CA | GLU | 206 | 57.652 | 55.270 | 6.587 | 1.00 | 49.67 |
| ATOM | 689 | C | GLU | 206 | 57.274 | 54.507 | 7.859 | 1.00 | 42.78 |
| ATOM | 690 | O | GLU | 206 | 57.708 | 53.380 | 8.056 | 1.00 | 46.60 |
| ATOM | 691 | CB | GLU | 206 | 58.753 | 56.312 | 6.872 | 1.00 | 32.43 |
| ATOM | 692 | CG | GLU | 206 | 59.406 | 56.840 | 5.608 | 1.00 | 67.25 |
| ATOM | 693 | CD | GLU | 206 | 60.333 | 58.014 | 5.874 | 1.00 | 94.44 |
| ATOM | 694 | OE1 | GLU | 206 | 60.462 | 58.439 | 7.044 | 1.00 | 0.36 |
| ATOM | 695 | OE2 | GLU | 206 | 60.933 | 58.514 | 4.904 | 1.00 | 89.69 |
| ATOM | 696 | N | LYS | 207 | 56.460 | 55.129 | 8.703 | 1.00 | 46.45 |
| ATOM | 697 | CA | LYS | 207 | 56.052 | 54.550 | 9.968 | 1.00 | 62.72 |
| ATOM | 698 | C | LYS | 207 | 55.270 | 53.262 | 9.746 | 1.00 | 63.15 |
| ATOM | 699 | O | LYS | 207 | 55.445 | 52.296 | 10.483 | 1.00 | 51.88 |
| ATOM | 700 | CB | LYS | 207 | 55.237 | 55.571 | 10.776 | 1.00 | 72.67 |
| ATOM | 701 | CG | LYS | 207 | 54.342 | 54.977 | 11.858 | 1.00 | 0.74 |
| ATOM | 702 | CD | LYS | 207 | 55.121 | 54.624 | 13.113 | 1.00 | 0.57 |
| ATOM | 703 | CE | LYS | 207 | 54.183 | 54.307 | 14.272 | 1.00 | 0.12 |
| ATOM | 704 | NZ | LYS | 207 | 54.926 | 54.061 | 15.540 | 1.00 | 0.37 |
| ATOM | 705 | N | ALA | 208 | 54.419 | 53.247 | 8.721 | 1.00 | 51.93 |
| ATOM | 706 | CA | ALA | 208 | 53.653 | 52.046 | 8.383 | 1.00 | 52.25 |
| ATOM | 707 | C | ALA | 208 | 54.595 | 50.951 | 7.896 | 1.00 | 57.98 |
| ATOM | 708 | O | ALA | 208 | 54.459 | 49.779 | 8.252 | 1.00 | 36.09 |
| ATOM | 709 | CB | ALA | 208 | 52.598 | 52.353 | 7.319 | 1.00 | 38.82 |
| ATOM | 710 | N | TYR | 209 | 55.565 | 51.343 | 7.077 | 1.00 | 52.31 |
| ATOM | 711 | CA | TYR | 209 | 56.567 | 50.407 | 6.594 | 1.00 | 56.68 |
| ATOM | 712 | C | TYR | 209 | 57.336 | 49.761 | 7.761 | 1.00 | 64.16 |
| ATOM | 713 | O | TYR | 209 | 57.634 | 48.581 | 7.726 | 1.00 | 52.26 |
| ATOM | 714 | CB | TYR | 209 | 57.510 | 51.099 | 5.615 | 1.00 | 51.72 |
| ATOM | 715 | CG | TYR | 209 | 58.410 | 50.162 | 4.833 | 1.00 | 63.67 |
| ATOM | 716 | CD1 | TYR | 209 | 57.999 | 49.632 | 3.608 | 1.00 | 59.18 |
| ATOM | 717 | CD2 | TYR | 209 | 59.667 | 49.813 | 5.309 | 1.00 | 67.39 |
| ATOM | 718 | CE1 | TYR | 209 | 58.809 | 48.792 | 2.885 | 1.00 | 74.90 |
| ATOM | 719 | CE2 | TYR | 209 | 60.490 | 48.966 | 4.586 | 1.00 | 55.98 |
| ATOM | 720 | CZ | TYR | 209 | 60.053 | 48.459 | 3.378 | 1.00 | 78.85 |
| ATOM | 721 | OH | TYR | 209 | 60.859 | 47.615 | 2.659 | 1.00 | 69.89 |
| ATOM | 722 | N | GLU | 210 | 57.623 | 50.527 | 8.806 | 1.00 | 59.87 |
| ATOM | 723 | CA | GLU | 210 | 58.365 | 50.004 | 9.952 | 1.00 | 55.94 |
| ATOM | 724 | C | GLU | 210 | 57.461 | 49.241 | 10.920 | 1.00 | 69.29 |
| ATOM | 725 | O | GLU | 210 | 57.948 | 48.571 | 11.819 | 1.00 | 56.02 |
| ATOM | 726 | CB | GLU | 210 | 59.066 | 51.136 | 10.702 | 1.00 | 55.80 |
| ATOM | 727 | CG | GLU | 210 | 59.989 | 51.979 | 9.849 | 1.00 | 71.30 |
| ATOM | 728 | CD | GLU | 210 | 60.235 | 53.368 | 10.426 | 1.00 | 87.58 |
| ATOM | 729 | OE1 | GLU | 210 | 59.759 | 53.668 | 11.546 | 1.00 | 73.11 |
| ATOM | 730 | OE2 | GLU | 210 | 60.903 | 54.171 | 9.748 | 1.00 | 93.13 |
| ATOM | 731 | N | ASN | 211 | 56.144 | 49.348 | 10.751 | 1.00 | 52.95 |
| ATOM | 732 | CA | ASN | 211 | 55.228 | 48.666 | 11.660 | 1.00 | 72.66 |
| ATOM | 733 | C | ASN | 211 | 54.204 | 47.800 | 10.915 | 1.00 | 72.42 |
| ATOM | 734 | O | ASN | 211 | 53.002 | 48.024 | 11.008 | 1.00 | 55.20 |
| ATOM | 735 | CB | ASN | 211 | 54.537 | 49.677 | 12.586 | 1.00 | 82.34 |
| ATOM | 736 | CG | ASN | 211 | 53.763 | 49.010 | 13.711 | 1.00 | 96.40 |
| ATOM | 737 | OD1 | ASN | 211 | 54.164 | 47.965 | 14.228 | 1.00 | 0.40 |
| ATOM | 738 | ND2 | ASN | 211 | 52.645 | 49.617 | 14.097 | 1.00 | 93.22 |
| ATOM | 739 | N | PRO | 212 | 54.685 | 46.797 | 10.171 | 1.00 | 55.52 |
| ATOM | 740 | CA | PRO | 212 | 53.771 | 45.938 | 9.417 | 1.00 | 50.78 |
| ATOM | 741 | C | PRO | 212 | 52.908 | 45.098 | 10.357 | 1.00 | 62.47 |
| ATOM | 742 | O | PRO | 212 | 53.390 | 44.658 | 11.396 | 1.00 | 43.99 |
| ATOM | 743 | CB | PRO | 212 | 54.717 | 45.020 | 8.633 | 1.00 | 44.67 |
| ATOM | 744 | CG | PRO | 212 | 56.099 | 45.617 | 8.786 | 1.00 | 53.75 |
| ATOM | 745 | CD | PRO | 212 | 56.078 | 46.322 | 10.087 | 1.00 | 52.24 |
| ATOM | 746 | N | LYS | 213 | 51.647 | 44.889 | 10.000 | 1.00 | 50.06 |
| ATOM | 747 | CA | LYS | 213 | 50.733 | 44.089 | 10.821 | 1.00 | 60.06 |
| ATOM | 748 | C | LYS | 213 | 49.698 | 43.345 | 9.986 | 1.00 | 37.78 |

TABLE 10-continued

Three-Dimensional Coordinates of *Neisseria gonorrhoeae* GCYH-IB (SEQ. ID. No. 8)

| ATOM | 749 | O | LYS | 213 | 48.985 | 43.940 | 9.184 | 1.00 | 49.66 |
|---|---|---|---|---|---|---|---|---|---|
| ATOM | 750 | CB | LYS | 213 | 50.019 | 44.947 | 11.877 | 1.00 | 59.67 |
| ATOM | 751 | CG | LYS | 213 | 50.842 | 45.204 | 13.119 | 1.00 | 67.39 |
| ATOM | 752 | CD | LYS | 213 | 50.009 | 45.756 | 14.255 | 1.00 | 71.54 |
| ATOM | 753 | CE | LYS | 213 | 50.909 | 46.303 | 15.349 | 1.00 | 66.53 |
| ATOM | 754 | NZ | LYS | 213 | 50.180 | 46.690 | 16.586 | 1.00 | 54.59 |
| ATOM | 755 | N | PHE | 214 | 49.644 | 42.037 | 10.189 | 1.00 | 44.37 |
| ATOM | 756 | CA | PHE | 214 | 48.577 | 41.197 | 9.666 | 1.00 | 57.67 |
| ATOM | 757 | C | PHE | 214 | 47.257 | 41.532 | 10.339 | 1.00 | 50.58 |
| ATOM | 758 | O | PHE | 214 | 47.235 | 42.124 | 11.414 | 1.00 | 52.80 |
| ATOM | 759 | CB | PHE | 214 | 48.882 | 39.721 | 9.950 | 1.00 | 53.34 |
| ATOM | 760 | CG | PHE | 214 | 49.983 | 39.148 | 9.112 | 1.00 | 60.66 |
| ATOM | 761 | CD1 | PHE | 214 | 49.924 | 39.198 | 7.730 | 1.00 | 75.57 |
| ATOM | 762 | CD2 | PHE | 214 | 51.063 | 38.528 | 9.708 | 1.00 | 74.87 |
| ATOM | 763 | CE1 | PHE | 214 | 50.932 | 38.660 | 6.959 | 1.00 | 68.54 |
| ATOM | 764 | CE2 | PHE | 214 | 52.075 | 37.984 | 8.943 | 1.00 | 73.49 |
| ATOM | 765 | CZ | PHE | 214 | 52.009 | 38.051 | 7.565 | 1.00 | 65.16 |
| ATOM | 766 | N | VAL | 215 | 46.161 | 41.102 | 9.721 | 1.00 | 50.21 |
| ATOM | 767 | CA | VAL | 215 | 44.838 | 41.218 | 10.332 | 1.00 | 32.24 |
| ATOM | 768 | C | VAL | 215 | 44.760 | 40.429 | 11.663 | 1.00 | 39.63 |
| ATOM | 769 | O | VAL | 215 | 44.097 | 40.842 | 12.616 | 1.00 | 34.93 |
| ATOM | 770 | CB | VAL | 215 | 43.736 | 40.829 | 9.328 | 1.00 | 49.44 |
| ATOM | 771 | CG1 | VAL | 215 | 43.564 | 39.327 | 9.245 | 1.00 | 40.48 |
| ATOM | 772 | CG2 | VAL | 215 | 42.442 | 41.477 | 9.698 | 1.00 | 43.26 |
| ATOM | 773 | N | GLU | 216 | 45.483 | 39.315 | 11.741 | 1.00 | 31.87 |
| ATOM | 774 | CA | GLU | 216 | 45.604 | 38.551 | 12.985 | 1.00 | 37.07 |
| ATOM | 775 | C | GLU | 216 | 46.236 | 39.343 | 14.124 | 1.00 | 42.58 |
| ATOM | 776 | O | GLU | 216 | 45.774 | 39.286 | 15.267 | 1.00 | 37.19 |
| ATOM | 777 | CB | GLU | 216 | 46.392 | 37.253 | 12.760 | 1.00 | 37.27 |
| ATOM | 778 | CG | GLU | 216 | 45.753 | 36.309 | 11.734 | 1.00 | 55.63 |
| ATOM | 779 | CD | GLU | 216 | 46.293 | 36.491 | 10.315 | 1.00 | 64.24 |
| ATOM | 780 | OE1 | GLU | 216 | 46.794 | 37.581 | 9.987 | 1.00 | 72.74 |
| ATOM | 781 | OE2 | GLU | 216 | 46.212 | 35.541 | 9.514 | 1.00 | 72.11 |
| ATOM | 782 | N | ASP | 217 | 47.297 | 40.082 | 13.821 | 1.00 | 42.79 |
| ATOM | 783 | CA | ASP | 217 | 47.967 | 40.880 | 14.846 | 1.00 | 48.33 |
| ATOM | 784 | C | ASP | 217 | 47.118 | 42.054 | 15.292 | 1.00 | 43.56 |
| ATOM | 785 | O | ASP | 217 | 47.070 | 42.373 | 16.475 | 1.00 | 45.97 |
| ATOM | 786 | CB | ASP | 217 | 49.316 | 41.364 | 14.338 | 1.00 | 53.19 |
| ATOM | 787 | CG | ASP | 217 | 50.191 | 40.226 | 13.902 | 1.00 | 69.65 |
| ATOM | 788 | OD1 | ASP | 217 | 50.265 | 39.231 | 14.662 | 1.00 | 73.54 |
| ATOM | 789 | OD2 | ASP | 217 | 50.782 | 40.314 | 12.801 | 1.00 | 68.83 |
| ATOM | 790 | N | MSE | 218 | 46.443 | 42.682 | 14.336 | 1.00 | 37.35 |
| ATOM | 791 | CA | MSE | 218 | 45.542 | 43.788 | 14.634 | 1.00 | 39.78 |
| ATOM | 792 | C | MSE | 218 | 44.546 | 43.395 | 15.734 | 1.00 | 24.72 |
| ATOM | 793 | O | MSE | 218 | 44.499 | 44.012 | 16.796 | 1.00 | 29.59 |
| ATOM | 794 | CB | MSE | 218 | 44.810 | 44.241 | 13.362 | 1.00 | 58.79 |
| ATOM | 795 | CG | MSE | 218 | 44.073 | 45.573 | 13.480 | 1.00 | 77.38 |
| ATOM | 796 | SE | MSE | 218 | 45.130 | 46.991 | 14.337 | 1.00 | 0.47 |
| ATOM | 797 | CE | MSE | 218 | 44.023 | 48.546 | 13.914 | 1.00 | 0.92 |
| ATOM | 798 | N | VAL | 219 | 43.774 | 42.337 | 15.494 | 1.00 | 29.59 |
| ATOM | 799 | CA | VAL | 219 | 42.719 | 41.980 | 16.429 | 1.00 | 26.43 |
| ATOM | 800 | C | VAL | 219 | 43.272 | 41.489 | 17.751 | 1.00 | 27.62 |
| ATOM | 801 | O | VAL | 219 | 42.717 | 41.787 | 18.809 | 1.00 | 32.99 |
| ATOM | 802 | CB | VAL | 219 | 41.705 | 40.955 | 15.837 | 1.00 | 36.95 |
| ATOM | 803 | CG1 | VAL | 219 | 41.063 | 41.525 | 14.612 | 1.00 | 35.83 |
| ATOM | 804 | CG2 | VAL | 219 | 42.391 | 39.657 | 15.492 | 1.00 | 30.34 |
| ATOM | 805 | N | ARG | 220 | 44.362 | 40.734 | 17.691 | 1.00 | 30.45 |
| ATOM | 806 | CA | ARG | 220 | 45.024 | 40.300 | 18.917 | 1.00 | 43.29 |
| ATOM | 807 | C | ARG | 220 | 45.473 | 41.480 | 19.757 | 1.00 | 39.78 |
| ATOM | 808 | O | ARG | 220 | 45.241 | 41.506 | 20.961 | 1.00 | 49.09 |
| ATOM | 809 | CB | ARG | 220 | 46.204 | 39.392 | 18.606 | 1.00 | 37.68 |
| ATOM | 810 | CG | ARG | 220 | 45.787 | 37.957 | 18.434 | 1.00 | 41.30 |
| ATOM | 811 | CD | ARG | 220 | 46.922 | 37.107 | 17.877 | 1.00 | 37.85 |
| ATOM | 812 | NE | ARG | 220 | 46.562 | 35.704 | 18.004 | 1.00 | 44.94 |
| ATOM | 813 | CZ | ARG | 220 | 47.039 | 34.723 | 17.253 | 1.00 | 47.83 |
| ATOM | 814 | NH1 | ARG | 220 | 47.911 | 34.976 | 16.293 | 1.00 | 39.44 |
| ATOM | 815 | NH2 | ARG | 220 | 46.630 | 33.483 | 17.468 | 1.00 | 46.76 |
| ATOM | 816 | N | ASP | 221 | 46.091 | 42.466 | 19.116 | 1.00 | 30.84 |
| ATOM | 817 | CA | ASP | 221 | 46.593 | 43.628 | 19.863 | 1.00 | 39.37 |
| ATOM | 818 | C | ASP | 221 | 45.487 | 44.506 | 20.456 | 1.00 | 39.67 |
| ATOM | 819 | O | ASP | 221 | 45.582 | 44.958 | 21.584 | 1.00 | 44.32 |
| ATOM | 820 | CB | ASP | 221 | 47.527 | 44.451 | 18.990 | 1.00 | 50.33 |
| ATOM | 821 | CG | ASP | 221 | 48.803 | 43.695 | 18.628 | 1.00 | 76.67 |
| ATOM | 822 | OD1 | ASP | 221 | 49.064 | 42.623 | 19.227 | 1.00 | 84.23 |
| ATOM | 823 | OD2 | ASP | 221 | 49.549 | 44.170 | 17.741 | 1.00 | 61.34 |
| ATOM | 824 | N | VAL | 222 | 44.411 | 44.721 | 19.707 | 1.00 | 35.67 |
| ATOM | 825 | CA | VAL | 222 | 43.286 | 45.490 | 20.242 | 1.00 | 37.76 |
| ATOM | 826 | C | VAL | 222 | 42.568 | 44.737 | 21.366 | 1.00 | 32.07 |

TABLE 10-continued

Three-Dimensional Coordinates of *Neisseria gonorrhoeae* GCYH-IB (SEQ. ID. No. 8)

| ATOM | 827 | O | VAL | 222 | 42.181 | 45.332 | 22.366 | 1.00 | 38.73 |
|------|-----|-----|-----|-----|--------|--------|--------|------|-------|
| ATOM | 828 | CB | VAL | 222 | 42.265 | 45.817 | 19.163 | 1.00 | 30.54 |
| ATOM | 829 | CG1 | VAL | 222 | 41.055 | 46.485 | 19.798 | 1.00 | 34.98 |
| ATOM | 830 | CG2 | VAL | 222 | 42.880 | 46.682 | 18.116 | 1.00 | 31.33 |
| ATOM | 831 | N | ALA | 223 | 42.408 | 43.424 | 21.189 | 1.00 | 27.50 |
| ATOM | 832 | CA | ALA | 223 | 41.684 | 42.595 | 22.152 | 1.00 | 38.49 |
| ATOM | 833 | C | ALA | 223 | 42.393 | 42.585 | 23.496 | 1.00 | 41.28 |
| ATOM | 834 | O | ALA | 223 | 41.755 | 42.586 | 24.540 | 1.00 | 35.49 |
| ATOM | 835 | CB | ALA | 223 | 41.531 | 41.189 | 21.634 | 1.00 | 32.48 |
| ATOM | 836 | N | THR | 224 | 43.722 | 42.571 | 23.457 | 1.00 | 38.65 |
| ATOM | 837 | CA | THR | 224 | 44.515 | 42.572 | 24.679 | 1.00 | 41.10 |
| ATOM | 838 | C | THR | 224 | 44.251 | 43.847 | 25.487 | 1.00 | 40.22 |
| ATOM | 839 | O | THR | 224 | 44.079 | 43.801 | 26.702 | 1.00 | 44.23 |
| ATOM | 840 | CB | THR | 224 | 45.997 | 42.444 | 24.361 | 1.00 | 34.72 |
| ATOM | 841 | OG1 | THR | 224 | 46.230 | 41.196 | 23.701 | 1.00 | 47.19 |
| ATOM | 842 | CG2 | THR | 224 | 46.809 | 42.504 | 25.634 | 1.00 | 51.18 |
| ATOM | 843 | N | SER | 225 | 44.206 | 44.985 | 24.803 | 1.00 | 35.60 |
| ATOM | 844 | CA | SER | 225 | 43.861 | 46.250 | 25.456 | 1.00 | 47.00 |
| ATOM | 845 | C | SER | 225 | 42.478 | 46.229 | 26.070 | 1.00 | 45.84 |
| ATOM | 846 | O | SER | 225 | 42.288 | 46.755 | 27.161 | 1.00 | 42.17 |
| ATOM | 847 | CB | SER | 225 | 43.921 | 47.413 | 24.479 | 1.00 | 42.92 |
| ATOM | 848 | OG | SER | 225 | 45.122 | 47.392 | 23.754 | 1.00 | 48.51 |
| ATOM | 849 | N | LEU | 226 | 41.518 | 45.629 | 25.370 | 1.00 | 37.09 |
| ATOM | 850 | CA | LEU | 226 | 40.133 | 45.605 | 25.853 | 1.00 | 36.24 |
| ATOM | 851 | C | LEU | 226 | 40.008 | 44.659 | 27.036 | 1.00 | 37.89 |
| ATOM | 852 | O | LEU | 226 | 39.325 | 44.973 | 28.006 | 1.00 | 43.78 |
| ATOM | 853 | CB | LEU | 226 | 39.165 | 45.210 | 24.729 | 1.00 | 34.97 |
| ATOM | 854 | CG | LEU | 226 | 39.134 | 46.090 | 23.479 | 1.00 | 33.84 |
| ATOM | 855 | CD1 | LEU | 226 | 38.220 | 45.489 | 22.430 | 1.00 | 50.41 |
| ATOM | 856 | CD2 | LEU | 226 | 38.715 | 47.542 | 23.789 | 1.00 | 39.51 |
| ATOM | 857 | N | ILE | 227 | 40.697 | 43.517 | 26.953 | 1.00 | 36.57 |
| ATOM | 858 | CA | ILE | 227 | 40.717 | 42.519 | 28.015 | 1.00 | 45.24 |
| ATOM | 859 | C | ILE | 227 | 41.250 | 43.119 | 29.305 | 1.00 | 47.23 |
| ATOM | 860 | O | ILE | 227 | 40.767 | 42.806 | 30.391 | 1.00 | 49.27 |
| ATOM | 861 | CB | ILE | 227 | 41.584 | 41.309 | 27.644 | 1.00 | 47.34 |
| ATOM | 862 | CG1 | ILE | 227 | 40.827 | 40.398 | 26.683 | 1.00 | 43.33 |
| ATOM | 863 | CG2 | ILE | 227 | 42.004 | 40.532 | 28.913 | 1.00 | 38.95 |
| ATOM | 864 | CD1 | ILE | 227 | 41.690 | 39.392 | 26.055 | 1.00 | 47.18 |
| ATOM | 865 | N | ALA | 228 | 42.242 | 43.995 | 29.169 | 1.00 | 33.22 |
| ATOM | 866 | CA | ALA | 228 | 42.793 | 44.696 | 30.316 | 1.00 | 51.83 |
| ATOM | 867 | C | ALA | 228 | 41.791 | 45.649 | 30.994 | 1.00 | 62.10 |
| ATOM | 868 | O | ALA | 228 | 41.712 | 45.706 | 32.215 | 1.00 | 60.35 |
| ATOM | 869 | CB | ALA | 228 | 44.061 | 45.427 | 29.931 | 1.00 | 49.81 |
| ATOM | 870 | N | ASP | 229 | 41.017 | 46.383 | 30.207 | 1.00 | 48.90 |
| ATOM | 871 | CA | ASP | 229 | 40.031 | 47.312 | 30.765 | 1.00 | 44.21 |
| ATOM | 872 | C | ASP | 229 | 38.912 | 46.607 | 31.570 | 1.00 | 52.96 |
| ATOM | 873 | O | ASP | 229 | 38.167 | 45.795 | 31.024 | 1.00 | 56.32 |
| ATOM | 874 | CB | ASP | 229 | 39.422 | 48.142 | 29.638 | 1.00 | 63.61 |
| ATOM | 875 | CG | ASP | 229 | 38.777 | 49.411 | 30.137 | 1.00 | 71.21 |
| ATOM | 876 | OD1 | ASP | 229 | 37.992 | 49.364 | 31.117 | 1.00 | 54.93 |
| ATOM | 877 | OD2 | ASP | 229 | 39.065 | 50.462 | 29.541 | 1.00 | 59.40 |
| ATOM | 878 | N | LYS | 230 | 38.797 | 46.931 | 32.858 | 1.00 | 59.01 |
| ATOM | 879 | CA | LYS | 230 | 37.898 | 46.203 | 33.757 | 1.00 | 60.43 |
| ATOM | 880 | C | LYS | 230 | 36.423 | 46.579 | 33.583 | 1.00 | 51.76 |
| ATOM | 881 | O | LYS | 230 | 35.540 | 45.878 | 34.083 | 1.00 | 60.37 |
| ATOM | 882 | CB | LYS | 230 | 38.306 | 46.402 | 35.220 | 1.00 | 66.12 |
| ATOM | 883 | CG | LYS | 230 | 39.779 | 46.128 | 35.521 | 1.00 | 90.89 |
| ATOM | 884 | CD | LYS | 230 | 40.171 | 44.685 | 35.229 | 1.00 | 94.28 |
| ATOM | 885 | CE | LYS | 230 | 41.592 | 44.381 | 35.704 | 1.00 | 89.21 |
| ATOM | 886 | NZ | LYS | 230 | 42.710 | 44.902 | 34.842 | 1.00 | 72.91 |
| ATOM | 887 | N | ASN | 241 | 40.511 | 43.782 | 6.157 | 1.00 | 35.37 |
| ATOM | 888 | CA | ASN | 241 | 41.557 | 44.396 | 5.336 | 1.00 | 35.84 |
| ATOM | 889 | C | ASN | 241 | 41.181 | 44.360 | 3.868 | 1.00 | 44.30 |
| ATOM | 890 | O | ASN | 241 | 41.131 | 43.285 | 3.277 | 1.00 | 35.87 |
| ATOM | 891 | CB | ASN | 241 | 42.846 | 43.596 | 5.458 | 1.00 | 59.50 |
| ATOM | 892 | CG | ASN | 241 | 43.834 | 44.211 | 6.385 | 1.00 | 74.07 |
| ATOM | 893 | OD1 | ASN | 241 | 45.033 | 44.132 | 6.144 | 1.00 | 83.92 |
| ATOM | 894 | ND2 | ASN | 241 | 43.353 | 44.817 | 7.461 | 1.00 | 73.43 |
| ATOM | 895 | N | PHE | 242 | 40.947 | 45.512 | 3.261 | 1.00 | 34.18 |
| ATOM | 896 | CA | PHE | 242 | 40.648 | 45.561 | 1.835 | 1.00 | 54.06 |
| ATOM | 897 | C | PHE | 242 | 41.932 | 45.486 | 1.029 | 1.00 | 43.36 |
| ATOM | 898 | O | PHE | 242 | 42.298 | 46.430 | 0.319 | 1.00 | 42.57 |
| ATOM | 899 | CB | PHE | 242 | 39.837 | 46.812 | 1.491 | 1.00 | 49.71 |
| ATOM | 900 | CG | PHE | 242 | 38.579 | 46.943 | 2.307 | 1.00 | 54.48 |
| ATOM | 901 | CD1 | PHE | 242 | 37.400 | 46.327 | 1.899 | 1.00 | 48.92 |
| ATOM | 902 | CD2 | PHE | 242 | 38.587 | 47.658 | 3.500 | 1.00 | 50.08 |
| ATOM | 903 | CE1 | PHE | 242 | 36.249 | 46.426 | 2.662 | 1.00 | 44.33 |
| ATOM | 904 | CE2 | PHE | 242 | 37.446 | 47.768 | 4.265 | 1.00 | 56.26 |

TABLE 10-continued

Three-Dimensional Coordinates of *Neisseria gonorrhoeae* GCYH-IB (SEQ. ID. No. 8)

| ATOM | 905 | CZ | PHE | 242 | 36.269 | 47.147 | 3.847 | 1.00 | 48.67 |
|---|---|---|---|---|---|---|---|---|---|
| ATOM | 906 | N | GLU | 243 | 42.603 | 44.341 | 1.149 | 1.00 | 43.70 |
| ATOM | 907 | CA | GLU | 243 | 43.938 | 44.146 | 0.598 | 1.00 | 53.80 |
| ATOM | 908 | C | GLU | 243 | 44.041 | 44.634 | −0.836 | 1.00 | 54.72 |
| ATOM | 909 | O | GLU | 243 | 43.155 | 44.399 | −1.662 | 1.00 | 36.12 |
| ATOM | 910 | CB | GLU | 243 | 44.409 | 42.691 | 0.753 | 1.00 | 62.42 |
| ATOM | 911 | CG | GLU | 243 | 43.409 | 41.659 | 0.338 | 1.00 | 98.18 |
| ATOM | 912 | CD | GLU | 243 | 43.956 | 40.259 | 0.486 | 1.00 | 0.38 |
| ATOM | 913 | OE1 | GLU | 243 | 43.160 | 39.296 | 0.471 | 1.00 | 0.85 |
| ATOM | 914 | OE2 | GLU | 243 | 45.189 | 40.123 | 0.625 | 1.00 | 0.45 |
| ATOM | 915 | N | SER | 244 | 45.126 | 45.345 | −1.110 | 1.00 | 48.15 |
| ATOM | 916 | CA | SER | 244 | 45.254 | 46.091 | −2.349 | 1.00 | 48.27 |
| ATOM | 917 | C | SER | 244 | 45.764 | 45.216 | −3.487 | 1.00 | 43.29 |
| ATOM | 918 | O | SER | 244 | 45.999 | 45.711 | −4.582 | 1.00 | 54.30 |
| ATOM | 919 | CB | SER | 244 | 46.178 | 47.290 | −2.154 | 1.00 | 50.70 |
| ATOM | 920 | OG | SER | 244 | 47.495 | 46.834 | −1.924 | 1.00 | 57.31 |
| ATOM | 921 | N | ILE | 245 | 45.938 | 43.921 | −3.225 | 1.00 | 38.50 |
| ATOM | 922 | CA | ILE | 245 | 46.367 | 42.985 | −4.273 | 1.00 | 54.46 |
| ATOM | 923 | C | ILE | 245 | 45.290 | 41.961 | −4.654 | 1.00 | 49.60 |
| ATOM | 924 | O | ILE | 245 | 45.474 | 41.190 | −5.595 | 1.00 | 39.53 |
| ATOM | 925 | CB | ILE | 245 | 47.658 | 42.234 | −3.879 | 1.00 | 54.37 |
| ATOM | 926 | CG1 | ILE | 245 | 47.401 | 41.334 | −2.669 | 1.00 | 54.44 |
| ATOM | 927 | CG2 | ILE | 245 | 48.758 | 43.216 | −3.577 | 1.00 | 37.95 |
| ATOM | 928 | CD1 | ILE | 245 | 48.629 | 40.583 | −2.192 | 1.00 | 73.40 |
| ATOM | 929 | N | HIS | 246 | 44.188 | 41.940 | −3.908 | 1.00 | 43.91 |
| ATOM | 930 | CA | HIS | 246 | 43.058 | 41.050 | −4.206 | 1.00 | 49.94 |
| ATOM | 931 | C | HIS | 246 | 41.770 | 41.862 | −4.355 | 1.00 | 57.65 |
| ATOM | 932 | O | HIS | 246 | 41.754 | 43.043 | −4.058 | 1.00 | 47.46 |
| ATOM | 933 | CB | HIS | 246 | 42.893 | 40.005 | −3.104 | 1.00 | 40.63 |
| ATOM | 934 | CG | HIS | 246 | 44.038 | 39.038 | −3.001 | 1.00 | 63.27 |
| ATOM | 935 | ND1 | HIS | 246 | 44.749 | 38.845 | −1.831 | 1.00 | 58.15 |
| ATOM | 936 | CD2 | HIS | 246 | 44.585 | 38.202 | −3.912 | 1.00 | 61.44 |
| ATOM | 937 | CE1 | HIS | 246 | 45.683 | 37.933 | −2.032 | 1.00 | 69.99 |
| ATOM | 938 | NE2 | HIS | 246 | 45.609 | 37.532 | −3.288 | 1.00 | 70.61 |
| ATOM | 939 | N | ASN | 247 | 40.699 | 41.241 | −4.831 | 1.00 | 45.02 |
| ATOM | 940 | CA | ASN | 247 | 39.407 | 41.904 | −4.820 | 1.00 | 41.42 |
| ATOM | 941 | C | ASN | 247 | 38.445 | 41.358 | −3.747 | 1.00 | 46.46 |
| ATOM | 942 | O | ASN | 247 | 37.230 | 41.355 | −3.930 | 1.00 | 59.35 |
| ATOM | 943 | CB | ASN | 247 | 38.748 | 41.892 | −6.206 | 1.00 | 48.65 |
| ATOM | 944 | CG | ASN | 247 | 37.673 | 42.965 | −6.343 | 1.00 | 49.46 |
| ATOM | 945 | OD1 | ASN | 247 | 37.815 | 44.041 | −5.800 | 1.00 | 34.71 |
| ATOM | 946 | ND2 | ASN | 247 | 36.602 | 42.670 | −7.065 | 1.00 | 32.52 |
| TER | | | | | | | | | |
| ATOM | 947 | ZN | ZN2 B | 258 | 50.203 | 40.407 | 1.793 | 1.00 | 35.76 |
| ATOM | 948 | C | ACY B | 259 | 47.704 | 37.868 | 1.932 | 1.00 | 65.42 |
| ATOM | 949 | O | ACY B | 259 | 47.758 | 37.530 | 3.162 | 1.00 | 54.29 |
| ATOM | 950 | OXT | ACY B | 259 | 48.249 | 38.912 | 1.482 | 1.00 | 52.67 |
| ATOM | 951 | CH3 | ACY B | 259 | 46.973 | 37.009 | 0.925 | 1.00 | 47.10 |
| TER | | | | | | | | | |
| ATOM | 952 | N | ARG | 14 | 50.990 | 63.026 | −26.073 | 1.00 | 56.18 |
| ATOM | 953 | CA | ARG | 14 | 50.011 | 64.106 | −25.960 | 1.00 | 93.83 |
| ATOM | 954 | C | ARG | 14 | 49.059 | 63.972 | −24.779 | 1.00 | 0.95 |
| ATOM | 955 | O | ARG | 14 | 48.591 | 62.882 | −24.432 | 1.00 | 0.99 |
| ATOM | 956 | CB | ARG | 14 | 49.303 | 64.396 | −27.281 | 1.00 | 91.72 |
| ATOM | 957 | CG | ARG | 14 | 49.942 | 65.578 | −27.967 | 1.00 | 98.01 |
| ATOM | 958 | CD | ARG | 14 | 51.285 | 65.865 | −27.304 | 1.00 | 0.59 |
| ATOM | 959 | NE | ARG | 14 | 51.414 | 67.252 | −26.865 | 1.00 | 0.30 |
| ATOM | 960 | CZ | ARG | 14 | 52.447 | 67.718 | −26.171 | 1.00 | 0.57 |
| ATOM | 961 | NH1 | ARG | 14 | 53.439 | 66.901 | −25.833 | 1.00 | 0.47 |
| ATOM | 962 | NH2 | ARG | 14 | 52.489 | 68.998 | −25.814 | 1.00 | 0.76 |
| ATOM | 963 | N | ASN | 15 | 48.763 | 65.135 | −24.216 | 1.00 | 0.82 |
| ATOM | 964 | CA | ASN | 15 | 48.731 | 65.331 | −22.775 | 1.00 | 0.69 |
| ATOM | 965 | C | ASN | 15 | 47.386 | 65.418 | −22.064 | 1.00 | 0.82 |
| ATOM | 966 | O | ASN | 15 | 47.347 | 65.506 | −20.840 | 1.00 | 0.58 |
| ATOM | 967 | CB | ASN | 15 | 49.542 | 66.580 | −22.446 | 1.00 | 0.43 |
| ATOM | 968 | CG | ASN | 15 | 50.905 | 66.253 | −21.890 | 1.00 | 0.83 |
| ATOM | 969 | OD1 | ASN | 15 | 51.045 | 65.363 | −21.057 | 1.00 | 0.77 |
| ATOM | 970 | ND2 | ASN | 15 | 51.914 | 66.982 | −22.326 | 1.00 | 0.18 |
| ATOM | 971 | N | LEU | 16 | 46.303 | 65.428 | −22.829 | 1.00 | 93.09 |
| ATOM | 972 | CA | LEU | 16 | 44.939 | 65.355 | −22.298 | 1.00 | 61.91 |
| ATOM | 973 | C | LEU | 16 | 44.622 | 66.125 | −21.008 | 1.00 | 56.02 |
| ATOM | 974 | O | LEU | 16 | 45.138 | 65.822 | −19.932 | 1.00 | 38.84 |
| ATOM | 975 | CB | LEU | 16 | 44.489 | 63.904 | −22.186 | 1.00 | 59.10 |
| ATOM | 976 | CG | LEU | 16 | 43.830 | 63.302 | −23.430 | 1.00 | 70.01 |
| ATOM | 977 | CD1 | LEU | 16 | 44.738 | 63.432 | −24.627 | 1.00 | 95.51 |
| ATOM | 978 | CD2 | LEU | 16 | 43.495 | 61.845 | −23.180 | 1.00 | 64.01 |
| ATOM | 979 | N | PRO | 17 | 43.757 | 67.140 | −21.121 | 1.00 | 46.50 |
| ATOM | 980 | CA | PRO | 17 | 43.251 | 67.811 | −19.919 | 1.00 | 51.15 |

TABLE 10-continued

Three-Dimensional Coordinates of *Neisseria gonorrhoeae* GCYH-IB (SEQ. ID. No. 8)

| ATOM | 981 | C | PRO | 17 | 42.355 | 66.835 | −19.159 | 1.00 | 50.11 |
|---|---|---|---|---|---|---|---|---|---|
| ATOM | 982 | O | PRO | 17 | 41.764 | 65.948 | −19.781 | 1.00 | 53.59 |
| ATOM | 983 | CB | PRO | 17 | 42.371 | 68.932 | −20.477 | 1.00 | 48.36 |
| ATOM | 984 | CG | PRO | 17 | 42.657 | 69.003 | −21.920 | 1.00 | 47.75 |
| ATOM | 985 | CD | PRO | 17 | 43.193 | 67.696 | −22.362 | 1.00 | 35.50 |
| ATOM | 986 | N | ILE | 18 | 42.269 | 66.982 | −17.840 | 1.00 | 37.05 |
| ATOM | 987 | CA | ILE | 18 | 41.329 | 66.200 | −17.045 | 1.00 | 44.06 |
| ATOM | 988 | C | ILE | 18 | 40.165 | 67.108 | −16.623 | 1.00 | 37.56 |
| ATOM | 989 | O | ILE | 18 | 40.365 | 68.140 | −15.989 | 1.00 | 33.36 |
| ATOM | 990 | CB | ILE | 18 | 42.022 | 65.555 | −15.835 | 1.00 | 40.66 |
| ATOM | 991 | CG1 | ILE | 18 | 43.083 | 64.544 | −16.310 | 1.00 | 47.12 |
| ATOM | 992 | CG2 | ILE | 18 | 41.009 | 64.864 | −14.932 | 1.00 | 45.97 |
| ATOM | 993 | CD1 | ILE | 18 | 44.084 | 64.145 | −15.235 | 1.00 | 36.80 |
| ATOM | 994 | N | ASN | 19 | 38.963 | 66.745 | −17.035 | 1.00 | 32.51 |
| ATOM | 995 | CA | ASN | 19 | 37.764 | 67.513 | −16.705 | 1.00 | 35.21 |
| ATOM | 996 | C | ASN | 19 | 37.639 | 67.863 | −15.230 | 1.00 | 40.29 |
| ATOM | 997 | O | ASN | 19 | 37.423 | 69.016 | −14.893 | 1.00 | 34.49 |
| ATOM | 998 | CB | ASN | 19 | 36.511 | 66.771 | −17.157 | 1.00 | 47.76 |
| ATOM | 999 | CG | ASN | 19 | 36.476 | 66.555 | −18.648 | 1.00 | 51.75 |
| ATOM | 1000 | OD1 | ASN | 19 | 35.652 | 67.140 | −19.335 | 1.00 | 61.29 |
| ATOM | 1001 | ND2 | ASN | 19 | 37.372 | 65.715 | −19.160 | 1.00 | 31.66 |
| ATOM | 1002 | N | GLN | 20 | 37.795 | 66.879 | −14.348 | 1.00 | 36.73 |
| ATOM | 1003 | CA | GLN | 20 | 37.707 | 67.140 | −12.919 | 1.00 | 33.67 |
| ATOM | 1004 | C | GLN | 20 | 38.670 | 66.226 | −12.183 | 1.00 | 35.95 |
| ATOM | 1005 | O | GLN | 20 | 38.703 | 65.023 | −12.421 | 1.00 | 30.38 |
| ATOM | 1006 | CB | GLN | 20 | 36.272 | 66.916 | −12.376 | 1.00 | 35.50 |
| ATOM | 1007 | CG | GLN | 20 | 35.140 | 67.729 | −13.030 | 1.00 | 36.99 |
| ATOM | 1008 | CD | GLN | 20 | 35.230 | 69.213 | −12.750 | 1.00 | 47.86 |
| ATOM | 1009 | OE1 | GLN | 20 | 35.841 | 69.622 | −11.771 | 1.00 | 44.72 |
| ATOM | 1010 | NE2 | GLN | 20 | 34.636 | 70.029 | −13.622 | 1.00 | 48.95 |
| ATOM | 1011 | N | VAL | 21 | 39.437 | 66.796 | −11.267 | 1.00 | 30.12 |
| ATOM | 1012 | CA | VAL | 21 | 40.238 | 65.974 | −10.397 | 1.00 | 34.50 |
| ATOM | 1013 | C | VAL | 21 | 40.183 | 66.600 | −9.031 | 1.00 | 38.21 |
| ATOM | 1014 | O | VAL | 21 | 40.161 | 67.827 | −8.905 | 1.00 | 43.19 |
| ATOM | 1015 | CB | VAL | 21 | 41.699 | 65.873 | −10.883 | 1.00 | 38.43 |
| ATOM | 1016 | CG1 | VAL | 21 | 42.278 | 67.249 | −11.082 | 1.00 | 32.73 |
| ATOM | 1017 | CG2 | VAL | 21 | 42.535 | 65.141 | −9.876 | 1.00 | 35.82 |
| ATOM | 1018 | N | GLY | 22 | 40.160 | 65.758 | −8.010 | 1.00 | 28.80 |
| ATOM | 1019 | CA | GLY | 22 | 40.140 | 66.202 | −6.630 | 1.00 | 28.65 |
| ATOM | 1020 | C | GLY | 22 | 39.756 | 65.068 | −5.713 | 1.00 | 41.36 |
| ATOM | 1021 | O | GLY | 22 | 40.296 | 63.954 | −5.820 | 1.00 | 37.38 |
| ATOM | 1022 | N | ILE | 23 | 38.813 | 65.339 | −4.822 | 1.00 | 28.55 |
| ATOM | 1023 | CA | ILE | 23 | 38.422 | 64.370 | −3.802 | 1.00 | 30.09 |
| ATOM | 1024 | C | ILE | 23 | 36.941 | 64.073 | −3.808 | 1.00 | 32.04 |
| ATOM | 1025 | O | ILE | 23 | 36.112 | 64.890 | −4.211 | 1.00 | 34.87 |
| ATOM | 1026 | CB | ILE | 23 | 38.819 | 64.839 | −2.378 | 1.00 | 28.66 |
| ATOM | 1027 | CG1 | ILE | 23 | 38.014 | 66.074 | −1.975 | 1.00 | 30.62 |
| ATOM | 1028 | CG2 | ILE | 23 | 40.303 | 65.120 | −2.308 | 1.00 | 40.70 |
| ATOM | 1029 | CD1 | ILE | 23 | 38.023 | 66.347 | −0.511 | 1.00 | 43.09 |
| ATOM | 1030 | N | THR | 48 | 36.389 | 69.073 | −6.903 | 1.00 | 24.29 |
| ATOM | 1031 | CA | THR | 48 | 37.274 | 68.785 | −8.006 | 1.00 | 31.42 |
| ATOM | 1032 | C | THR | 48 | 37.590 | 70.085 | −8.785 | 1.00 | 41.99 |
| ATOM | 1033 | O | THR | 48 | 36.853 | 71.081 | −8.699 | 1.00 | 34.59 |
| ATOM | 1034 | CB | THR | 48 | 36.617 | 67.751 | −8.950 | 1.00 | 43.46 |
| ATOM | 1035 | OG1 | THR | 48 | 35.426 | 68.302 | −9.502 | 1.00 | 43.17 |
| ATOM | 1036 | CG2 | THR | 48 | 36.281 | 66.445 | −8.216 | 1.00 | 41.57 |
| ATOM | 1037 | N | VAL | 49 | 38.683 | 70.085 | −9.537 | 1.00 | 34.12 |
| ATOM | 1038 | CA | VAL | 49 | 38.973 | 71.194 | −10.463 | 1.00 | 29.96 |
| ATOM | 1039 | C | VAL | 49 | 39.461 | 70.666 | −11.801 | 1.00 | 39.64 |
| ATOM | 1040 | O | VAL | 49 | 39.885 | 69.522 | −11.914 | 1.00 | 34.16 |
| ATOM | 1041 | CB | VAL | 49 | 40.050 | 72.148 | −9.917 | 1.00 | 28.70 |
| ATOM | 1042 | CG1 | VAL | 49 | 39.613 | 72.760 | −8.609 | 1.00 | 34.65 |
| ATOM | 1043 | CG2 | VAL | 49 | 41.401 | 71.413 | −9.736 | 1.00 | 34.78 |
| ATOM | 1044 | N | TYR | 50 | 39.410 | 71.515 | −12.811 | 1.00 | 35.35 |
| ATOM | 1045 | CA | TYR | 50 | 39.965 | 71.222 | −14.128 | 1.00 | 36.36 |
| ATOM | 1046 | C | TYR | 50 | 41.498 | 71.212 | −14.090 | 1.00 | 30.60 |
| ATOM | 1047 | O | TYR | 50 | 42.117 | 72.076 | −13.476 | 1.00 | 48.28 |
| ATOM | 1048 | CB | TYR | 50 | 39.477 | 72.281 | −15.104 | 1.00 | 43.69 |
| ATOM | 1049 | CG | TYR | 50 | 40.034 | 72.207 | −16.498 | 1.00 | 44.11 |
| ATOM | 1050 | CD1 | TYR | 50 | 39.424 | 71.435 | −17.459 | 1.00 | 35.06 |
| ATOM | 1051 | CD2 | TYR | 50 | 41.138 | 72.972 | −16.871 | 1.00 | 47.58 |
| ATOM | 1052 | CE1 | TYR | 50 | 39.915 | 71.378 | −18.761 | 1.00 | 48.54 |
| ATOM | 1053 | CE2 | TYR | 50 | 41.642 | 72.926 | −18.166 | 1.00 | 60.18 |
| ATOM | 1054 | CZ | TYR | 50 | 41.024 | 72.130 | −19.108 | 1.00 | 64.39 |
| ATOM | 1055 | OH | TYR | 50 | 41.514 | 72.087 | −20.393 | 1.00 | 57.90 |
| ATOM | 1056 | N | LEU | 51 | 42.102 | 70.199 | −14.708 | 1.00 | 39.41 |
| ATOM | 1057 | CA | LEU | 51 | 43.542 | 70.100 | −14.783 | 1.00 | 40.03 |
| ATOM | 1058 | C | LEU | 51 | 43.945 | 70.242 | −16.241 | 1.00 | 49.59 |

TABLE 10-continued

Three-Dimensional Coordinates of *Neisseria gonorrhoeae* GCYH-IB (SEQ. ID. No. 8)

| ATOM | 1059 | O | LEU | 51 | 43.620 | 69.399 | −17.048 | 1.00 | 35.47 |
|------|------|------|-----|----|--------|--------|---------|------|-------|
| ATOM | 1060 | CB | LEU | 51 | 44.031 | 68.768 | −14.227 | 1.00 | 43.30 |
| ATOM | 1061 | CG | LEU | 51 | 45.544 | 68.699 | −14.050 | 1.00 | 47.56 |
| ATOM | 1062 | CD1 | LEU | 51 | 45.938 | 69.662 | −12.934 | 1.00 | 46.53 |
| ATOM | 1063 | CD2 | LEU | 51 | 46.047 | 67.274 | −13.741 | 1.00 | 36.00 |
| ATOM | 1064 | N | PRO | 52 | 44.626 | 71.342 | −16.581 | 1.00 | 47.01 |
| ATOM | 1065 | CA | PRO | 52 | 45.190 | 71.635 | −17.906 | 1.00 | 54.47 |
| ATOM | 1066 | C | PRO | 52 | 46.064 | 70.493 | −18.441 | 1.00 | 47.94 |
| ATOM | 1067 | O | PRO | 52 | 46.671 | 69.776 | −17.665 | 1.00 | 42.41 |
| ATOM | 1068 | CB | PRO | 52 | 46.074 | 72.856 | −17.643 | 1.00 | 45.04 |
| ATOM | 1069 | CG | PRO | 52 | 45.583 | 73.453 | −16.384 | 1.00 | 58.50 |
| ATOM | 1070 | CD | PRO | 52 | 45.024 | 72.331 | −15.569 | 1.00 | 44.63 |
| ATOM | 1071 | N | ALA | 53 | 46.140 | 70.353 | −19.754 | 1.00 | 48.98 |
| ATOM | 1072 | CA | ALA | 53 | 46.895 | 69.266 | −20.372 | 1.00 | 58.53 |
| ATOM | 1073 | C | ALA | 53 | 48.293 | 69.022 | −19.809 | 1.00 | 62.49 |
| ATOM | 1074 | O | ALA | 53 | 48.705 | 67.877 | −19.618 | 1.00 | 65.81 |
| ATOM | 1075 | CB | ALA | 53 | 46.968 | 69.474 | −21.866 | 1.00 | 53.72 |
| ATOM | 1076 | N | GLU | 54 | 49.045 | 70.085 | −19.556 | 1.00 | 72.43 |
| ATOM | 1077 | CA | GLU | 54 | 50.444 | 69.865 | −19.208 | 1.00 | 0.41 |
| ATOM | 1078 | C | GLU | 54 | 50.782 | 70.071 | −17.740 | 1.00 | 90.42 |
| ATOM | 1079 | O | GLU | 54 | 51.950 | 70.124 | −17.369 | 1.00 | 95.32 |
| ATOM | 1080 | CB | GLU | 54 | 51.388 | 70.649 | −20.125 | 1.00 | 0.46 |
| ATOM | 1081 | CG | GLU | 54 | 51.661 | 72.076 | −19.713 | 1.00 | 0.78 |
| ATOM | 1082 | CD | GLU | 54 | 52.565 | 72.782 | −20.707 | 1.00 | 0.22 |
| ATOM | 1083 | OE1 | GLU | 54 | 52.165 | 72.905 | −21.885 | 1.00 | 0.86 |
| ATOM | 1084 | OE2 | GLU | 54 | 53.675 | 73.211 | −20.317 | 1.00 | 0.17 |
| ATOM | 1085 | N | GLN | 55 | 49.757 | 70.169 | −16.905 | 1.00 | 74.01 |
| ATOM | 1086 | CA | GLN | 55 | 49.960 | 70.086 | −15.468 | 1.00 | 65.50 |
| ATOM | 1087 | C | GLN | 55 | 49.842 | 68.608 | −15.100 | 1.00 | 60.70 |
| ATOM | 1088 | O | GLN | 55 | 48.917 | 67.942 | −15.541 | 1.00 | 63.86 |
| ATOM | 1089 | CB | GLN | 55 | 48.915 | 70.929 | −14.736 | 1.00 | 64.04 |
| ATOM | 1090 | CG | GLN | 55 | 49.232 | 71.214 | −13.274 | 1.00 | 67.10 |
| ATOM | 1091 | CD | GLN | 55 | 48.245 | 72.189 | −12.656 | 1.00 | 78.01 |
| ATOM | 1092 | OE1 | GLN | 55 | 47.694 | 73.048 | −13.344 | 1.00 | 86.83 |
| ATOM | 1093 | NE2 | GLN | 55 | 48.020 | 72.061 | −11.349 | 1.00 | 66.25 |
| ATOM | 1094 | N | LYS | 56 | 50.785 | 68.094 | −14.316 | 1.00 | 58.08 |
| ATOM | 1095 | CA | LYS | 56 | 50.833 | 66.662 | −14.040 | 1.00 | 68.32 |
| ATOM | 1096 | C | LYS | 56 | 49.826 | 66.244 | −12.981 | 1.00 | 68.10 |
| ATOM | 1097 | O | LYS | 56 | 49.327 | 65.123 | −13.007 | 1.00 | 70.15 |
| ATOM | 1098 | CB | LYS | 56 | 52.240 | 66.228 | −13.606 | 1.00 | 86.98 |
| ATOM | 1099 | CG | LYS | 56 | 52.324 | 64.763 | −13.177 | 1.00 | 0.17 |
| ATOM | 1100 | CD | LYS | 56 | 53.736 | 64.357 | −12.796 | 1.00 | 0.61 |
| ATOM | 1101 | CE | LYS | 56 | 54.133 | 64.922 | −11.443 | 1.00 | 0.08 |
| ATOM | 1102 | NZ | LYS | 56 | 55.504 | 64.490 | −11.051 | 1.00 | 0.69 |
| ATOM | 1103 | N | GLY | 57 | 49.550 | 67.149 | −12.044 | 1.00 | 53.87 |
| ATOM | 1104 | CA | GLY | 57 | 48.726 | 66.829 | −10.893 | 1.00 | 62.82 |
| ATOM | 1105 | C | GLY | 57 | 48.122 | 68.053 | −10.237 | 1.00 | 69.86 |
| ATOM | 1106 | O | GLY | 57 | 48.528 | 69.177 | −10.513 | 1.00 | 61.08 |
| ATOM | 1107 | N | THR | 58 | 47.134 | 67.835 | −9.376 | 1.00 | 69.78 |
| ATOM | 1108 | CA | THR | 58 | 46.546 | 68.916 | −8.602 | 1.00 | 71.47 |
| ATOM | 1109 | C | THR | 58 | 47.141 | 68.858 | −7.205 | 1.00 | 55.97 |
| ATOM | 1110 | O | THR | 58 | 48.036 | 68.047 | −6.951 | 1.00 | 59.93 |
| ATOM | 1111 | CB | THR | 58 | 44.996 | 68.800 | −8.551 | 1.00 | 71.04 |
| ATOM | 1112 | OG1 | THR | 58 | 44.438 | 70.031 | −8.090 | 1.00 | 77.37 |
| ATOM | 1113 | CG2 | THR | 58 | 44.553 | 67.657 | −7.635 | 1.00 | 65.11 |
| ATOM | 1114 | N | HIS | 59 | 46.646 | 69.694 | −6.297 | 1.00 | 58.22 |
| ATOM | 1115 | CA | HIS | 59 | 47.133 | 69.677 | −4.921 | 1.00 | 64.81 |
| ATOM | 1116 | C | HIS | 59 | 46.042 | 69.180 | −3.982 | 1.00 | 61.25 |
| ATOM | 1117 | O | HIS | 59 | 45.196 | 69.954 | −3.553 | 1.00 | 68.43 |
| ATOM | 1118 | CB | HIS | 59 | 47.617 | 71.072 | −4.529 | 1.00 | 66.44 |
| ATOM | 1119 | CG | HIS | 59 | 48.517 | 71.694 | −5.553 | 1.00 | 72.69 |
| ATOM | 1120 | ND1 | HIS | 59 | 48.032 | 72.385 | −6.639 | 1.00 | 76.25 |
| ATOM | 1121 | CD2 | HIS | 59 | 49.864 | 71.693 | −5.667 | 1.00 | 76.00 |
| ATOM | 1122 | CE1 | HIS | 59 | 49.048 | 72.802 | −7.377 | 1.00 | 85.64 |
| ATOM | 1123 | NE2 | HIS | 59 | 50.168 | 72.399 | −6.811 | 1.00 | 86.98 |
| ATOM | 1124 | N | MSE | 60 | 46.076 | 67.889 | −3.661 | 1.00 | 65.09 |
| ATOM | 1125 | CA | MSE | 60 | 44.944 | 67.208 | −3.033 | 1.00 | 58.00 |
| ATOM | 1126 | C | MSE | 60 | 44.570 | 67.726 | −1.654 | 1.00 | 50.50 |
| ATOM | 1127 | O | MSE | 60 | 43.381 | 67.791 | −1.314 | 1.00 | 53.78 |
| ATOM | 1128 | CB | MSE | 60 | 45.194 | 65.700 | −2.971 | 1.00 | 62.77 |
| ATOM | 1129 | CG | MSE | 60 | 45.200 | 65.021 | −4.331 | 1.00 | 87.09 |
| ATOM | 1130 | SE | MSE | 60 | 43.419 | 64.899 | −5.187 | 1.00 | 78.03 |
| ATOM | 1131 | CE | MSE | 60 | 43.904 | 63.860 | −6.770 | 1.00 | 92.20 |
| ATOM | 1132 | N | SER | 61 | 45.581 | 68.100 | −0.870 | 1.00 | 45.42 |
| ATOM | 1133 | CA | SER | 61 | 45.372 | 68.547 | 0.512 | 1.00 | 47.54 |
| ATOM | 1134 | C | SER | 61 | 44.668 | 69.900 | 0.647 | 1.00 | 55.39 |
| ATOM | 1135 | O | SER | 61 | 44.049 | 70.185 | 1.677 | 1.00 | 61.05 |
| ATOM | 1136 | CB | SER | 61 | 46.682 | 68.542 | 1.310 | 1.00 | 57.85 |

TABLE 10-continued

Three-Dimensional Coordinates of *Neisseria gonorrhoeae* GCYH-IB (SEQ. ID. No. 8)

| ATOM | 1137 | OG | SER | 61 | 47.430 | 69.713 | 1.078 | 1.00 | 61.24 |
|---|---|---|---|---|---|---|---|---|---|
| ATOM | 1138 | N | ARG | 62 | 44.750 | 70.732 | −0.383 | 1.00 | 50.58 |
| ATOM | 1139 | CA | ARG | 62 | 44.031 | 72.012 | −0.363 | 1.00 | 51.01 |
| ATOM | 1140 | C | ARG | 62 | 42.498 | 71.881 | −0.275 | 1.00 | 41.04 |
| ATOM | 1141 | O | ARG | 62 | 41.844 | 72.680 | 0.363 | 1.00 | 44.23 |
| ATOM | 1142 | CB | ARG | 62 | 44.429 | 72.859 | −1.569 | 1.00 | 50.03 |
| ATOM | 1143 | CG | ARG | 62 | 45.869 | 73.360 | −1.485 | 1.00 | 50.73 |
| ATOM | 1144 | CD | ARG | 62 | 46.291 | 74.061 | −2.754 | 1.00 | 47.50 |
| ATOM | 1145 | NE | ARG | 62 | 47.747 | 74.194 | −2.827 | 1.00 | 72.17 |
| ATOM | 1146 | CZ | ARG | 62 | 48.391 | 74.855 | −3.779 | 1.00 | 68.28 |
| ATOM | 1147 | NH1 | ARG | 62 | 47.707 | 75.454 | −4.742 | 1.00 | 59.95 |
| ATOM | 1148 | NH2 | ARG | 62 | 49.714 | 74.916 | −3.768 | 1.00 | 79.31 |
| ATOM | 1149 | N | PHE | 63 | 41.940 | 70.864 | −0.917 | 1.00 | 41.97 |
| ATOM | 1150 | CA | PHE | 63 | 40.503 | 70.623 | −0.879 | 1.00 | 44.58 |
| ATOM | 1151 | C | PHE | 63 | 40.028 | 70.483 | 0.557 | 1.00 | 49.40 |
| ATOM | 1152 | O | PHE | 63 | 39.061 | 71.123 | 0.957 | 1.00 | 39.22 |
| ATOM | 1153 | CB | PHE | 63 | 40.142 | 69.371 | −1.655 | 1.00 | 40.89 |
| ATOM | 1154 | CG | PHE | 63 | 40.396 | 69.475 | −3.121 | 1.00 | 28.93 |
| ATOM | 1155 | CD1 | PHE | 63 | 39.581 | 70.260 | −3.914 | 1.00 | 38.88 |
| ATOM | 1156 | CD2 | PHE | 63 | 41.431 | 68.774 | −3.706 | 1.00 | 35.68 |
| ATOM | 1157 | CE1 | PHE | 63 | 39.790 | 70.345 | −5.262 | 1.00 | 36.00 |
| ATOM | 1158 | CE2 | PHE | 63 | 41.649 | 68.846 | −5.051 | 1.00 | 44.36 |
| ATOM | 1159 | CZ | PHE | 63 | 40.829 | 69.622 | −5.838 | 1.00 | 30.89 |
| ATOM | 1160 | N | VAL | 64 | 40.732 | 69.655 | 1.321 | 1.00 | 38.51 |
| ATOM | 1161 | CA | VAL | 64 | 40.438 | 69.431 | 2.723 | 1.00 | 36.46 |
| ATOM | 1162 | C | VAL | 64 | 40.702 | 70.690 | 3.547 | 1.00 | 44.40 |
| ATOM | 1163 | O | VAL | 64 | 39.850 | 71.084 | 4.335 | 1.00 | 40.10 |
| ATOM | 1164 | CB | VAL | 64 | 41.266 | 68.289 | 3.305 | 1.00 | 54.00 |
| ATOM | 1165 | CG1 | VAL | 64 | 40.964 | 68.118 | 4.766 | 1.00 | 60.44 |
| ATOM | 1166 | CG2 | VAL | 64 | 40.994 | 67.015 | 2.546 | 1.00 | 63.75 |
| ATOM | 1167 | N | ALA | 65 | 41.881 | 71.300 | 3.386 | 1.00 | 31.61 |
| ATOM | 1168 | CA | ALA | 65 | 42.210 | 72.537 | 4.104 | 1.00 | 46.10 |
| ATOM | 1169 | C | ALA | 65 | 41.122 | 73.593 | 3.901 | 1.00 | 50.34 |
| ATOM | 1170 | O | ALA | 65 | 40.794 | 74.334 | 4.815 | 1.00 | 45.89 |
| ATOM | 1171 | CB | ALA | 65 | 43.597 | 73.105 | 3.664 | 1.00 | 43.69 |
| ATOM | 1172 | N | LEU | 66 | 40.574 | 73.650 | 2.691 | 1.00 | 43.19 |
| ATOM | 1173 | CA | LEU | 66 | 39.556 | 74.640 | 2.360 | 1.00 | 41.61 |
| ATOM | 1174 | C | LEU | 66 | 38.341 | 74.405 | 3.250 | 1.00 | 55.17 |
| ATOM | 1175 | O | LEU | 66 | 37.801 | 75.328 | 3.841 | 1.00 | 52.31 |
| ATOM | 1176 | CB | LEU | 66 | 39.194 | 74.538 | 0.883 | 1.00 | 58.42 |
| ATOM | 1177 | CG | LEU | 66 | 38.117 | 75.513 | 0.426 | 1.00 | 64.87 |
| ATOM | 1178 | CD1 | LEU | 66 | 38.717 | 76.886 | 0.319 | 1.00 | 65.34 |
| ATOM | 1179 | CD2 | LEU | 66 | 37.506 | 75.098 | −0.901 | 1.00 | 68.63 |
| ATOM | 1180 | N | MSE | 67 | 37.948 | 73.147 | 3.386 | 1.00 | 52.78 |
| ATOM | 1181 | CA | MSE | 67 | 36.836 | 72.771 | 4.261 | 1.00 | 43.01 |
| ATOM | 1182 | C | MSE | 67 | 37.085 | 73.021 | 5.746 | 1.00 | 48.38 |
| ATOM | 1183 | O | MSE | 67 | 36.207 | 73.512 | 6.447 | 1.00 | 45.66 |
| ATOM | 1184 | CB | MSE | 67 | 36.457 | 71.301 | 4.053 | 1.00 | 47.95 |
| ATOM | 1185 | CG | MSE | 67 | 35.691 | 71.069 | 2.776 | 1.00 | 70.03 |
| ATOM | 1186 | SE | MSE | 67 | 34.340 | 72.453 | 2.495 | 1.00 | 0.69 |
| ATOM | 1187 | CE | MSE | 67 | 33.466 | 71.739 | 0.906 | 1.00 | 0.86 |
| ATOM | 1188 | N | GLU | 68 | 38.267 | 72.661 | 6.231 | 1.00 | 40.76 |
| ATOM | 1189 | CA | GLU | 68 | 38.577 | 72.843 | 7.641 | 1.00 | 48.85 |
| ATOM | 1190 | C | GLU | 68 | 38.543 | 74.316 | 8.043 | 1.00 | 60.66 |
| ATOM | 1191 | O | GLU | 68 | 38.178 | 74.657 | 9.173 | 1.00 | 58.50 |
| ATOM | 1192 | CB | GLU | 68 | 39.937 | 72.238 | 7.979 | 1.00 | 54.20 |
| ATOM | 1193 | CG | GLU | 68 | 40.048 | 70.756 | 7.675 | 1.00 | 71.81 |
| ATOM | 1194 | CD | GLU | 68 | 39.261 | 69.901 | 8.646 | 1.00 | 93.47 |
| ATOM | 1195 | OE1 | GLU | 68 | 38.577 | 70.470 | 9.522 | 1.00 | 92.19 |
| ATOM | 1196 | OE2 | GLU | 68 | 39.323 | 68.658 | 8.535 | 1.00 | 0.36 |
| ATOM | 1197 | N | GLN | 69 | 38.904 | 75.188 | 7.108 | 1.00 | 76.80 |
| ATOM | 1198 | CA | GLN | 69 | 39.078 | 76.602 | 7.419 | 1.00 | 92.12 |
| ATOM | 1199 | C | GLN | 69 | 37.768 | 77.374 | 7.328 | 1.00 | 88.66 |
| ATOM | 1200 | O | GLN | 69 | 37.662 | 78.502 | 7.804 | 1.00 | 92.08 |
| ATOM | 1201 | CB | GLN | 69 | 40.112 | 77.231 | 6.492 | 1.00 | 0.48 |
| ATOM | 1202 | CG | GLN | 69 | 40.744 | 78.483 | 7.064 | 1.00 | 0.89 |
| ATOM | 1203 | CD | GLN | 69 | 41.389 | 79.351 | 6.003 | 1.00 | 0.27 |
| ATOM | 1204 | OE1 | GLN | 69 | 40.999 | 79.315 | 4.834 | 1.00 | 0.95 |
| ATOM | 1205 | NE2 | GLN | 69 | 42.378 | 80.145 | 6.407 | 1.00 | 0.89 |
| ATOM | 1206 | N | HIS | 70 | 36.771 | 76.758 | 6.712 | 1.00 | 88.30 |
| ATOM | 1207 | CA | HIS | 70 | 35.480 | 77.402 | 6.522 | 1.00 | 91.96 |
| ATOM | 1208 | C | HIS | 70 | 34.461 | 76.908 | 7.543 | 1.00 | 90.90 |
| ATOM | 1209 | O | HIS | 70 | 33.859 | 75.852 | 7.374 | 1.00 | 0.38 |
| ATOM | 1210 | CB | HIS | 70 | 34.994 | 77.164 | 5.092 | 1.00 | 0.30 |
| ATOM | 1211 | CG | HIS | 70 | 33.507 | 77.153 | 4.946 | 1.00 | 0.41 |
| ATOM | 1212 | ND1 | HIS | 70 | 32.749 | 76.030 | 5.177 | 1.00 | 0.00 |
| ATOM | 1213 | CD2 | HIS | 70 | 32.641 | 78.125 | 4.574 | 1.00 | 0.21 |
| ATOM | 1214 | CE1 | HIS | 70 | 31.475 | 76.309 | 4.967 | 1.00 | 0.57 |

TABLE 10-continued

Three-Dimensional Coordinates of *Neisseria gonorrhoeae* GCYH-IB (SEQ. ID. No. 8)

| ATOM | 1215 | NE2 | HIS | 70 | 31.383 | 77.573 | 4.597 | 1.00 | 0.16 |
|---|---|---|---|---|---|---|---|---|---|
| ATOM | 1216 | N | ALA | 84 | 34.316 | 79.531 | −5.688 | 1.00 | 33.25 |
| ATOM | 1217 | CA | ALA | 84 | 35.233 | 80.497 | −6.283 | 1.00 | 48.28 |
| ATOM | 1218 | C | ALA | 84 | 36.546 | 80.459 | −5.531 | 1.00 | 39.13 |
| ATOM | 1219 | O | ALA | 84 | 37.599 | 80.477 | −6.121 | 1.00 | 50.56 |
| ATOM | 1220 | CB | ALA | 84 | 34.646 | 81.896 | −6.227 | 1.00 | 31.09 |
| ATOM | 1221 | N | GLU | 85 | 36.455 | 80.428 | −4.207 | 1.00 | 35.63 |
| ATOM | 1222 | CA | GLU | 85 | 37.616 | 80.417 | −3.351 | 1.00 | 37.98 |
| ATOM | 1223 | C | GLU | 85 | 38.447 | 79.157 | −3.599 | 1.00 | 46.30 |
| ATOM | 1224 | O | GLU | 85 | 39.666 | 79.170 | −3.460 | 1.00 | 53.61 |
| ATOM | 1225 | CB | GLU | 85 | 37.171 | 80.501 | −1.896 | 1.00 | 42.29 |
| ATOM | 1226 | CG | GLU | 85 | 38.298 | 80.701 | −0.924 | 1.00 | 80.83 |
| ATOM | 1227 | CD | GLU | 85 | 37.814 | 81.190 | 0.415 | 1.00 | 0.90 |
| ATOM | 1228 | OE1 | GLU | 85 | 36.587 | 81.377 | 0.562 | 1.00 | 0.66 |
| ATOM | 1229 | OE2 | GLU | 85 | 38.658 | 81.390 | 1.316 | 1.00 | 0.63 |
| ATOM | 1230 | N | MSE | 86 | 37.777 | 78.073 | −3.981 | 1.00 | 34.35 |
| ATOM | 1231 | CA | MSE | 86 | 38.455 | 76.797 | −4.253 | 1.00 | 38.80 |
| ATOM | 1232 | C | MSE | 86 | 39.232 | 76.811 | −5.562 | 1.00 | 43.36 |
| ATOM | 1233 | O | MSE | 86 | 40.388 | 76.407 | −5.585 | 1.00 | 49.32 |
| ATOM | 1234 | CB | MSE | 86 | 37.471 | 75.622 | −4.279 | 1.00 | 32.54 |
| ATOM | 1235 | CG | MSE | 86 | 38.089 | 74.354 | −4.852 | 1.00 | 44.97 |
| ATOM | 1236 | SE | MSE | 86 | 36.780 | 72.927 | −5.113 | 1.00 | 63.68 |
| ATOM | 1237 | CE | MSE | 86 | 36.010 | 73.458 | −6.821 | 1.00 | 28.92 |
| ATOM | 1238 | N | VAL | 87 | 38.600 | 77.253 | −6.651 | 1.00 | 38.65 |
| ATOM | 1239 | CA | VAL | 87 | 39.295 | 77.311 | −7.933 | 1.00 | 34.36 |
| ATOM | 1240 | C | VAL | 87 | 40.490 | 78.256 | −7.825 | 1.00 | 47.21 |
| ATOM | 1241 | O | VAL | 87 | 41.540 | 78.009 | −8.444 | 1.00 | 48.22 |
| ATOM | 1242 | CB | VAL | 87 | 38.391 | 77.728 | −9.107 | 1.00 | 46.20 |
| ATOM | 1243 | CG1 | VAL | 87 | 37.200 | 76.772 | −9.251 | 1.00 | 40.79 |
| ATOM | 1244 | CG2 | VAL | 87 | 37.909 | 79.116 | −8.920 | 1.00 | 49.33 |
| ATOM | 1245 | N | ALA | 88 | 40.345 | 79.313 | −7.021 | 1.00 | 37.66 |
| ATOM | 1246 | CA | ALA | 88 | 41.443 | 80.285 | −6.838 | 1.00 | 52.91 |
| ATOM | 1247 | C | ALA | 88 | 42.581 | 79.670 | −6.038 | 1.00 | 61.51 |
| ATOM | 1248 | O | ALA | 88 | 43.749 | 79.856 | −6.360 | 1.00 | 60.52 |
| ATOM | 1249 | CB | ALA | 88 | 40.957 | 81.523 | −6.135 | 1.00 | 46.70 |
| ATOM | 1250 | N | LEU | 89 | 42.214 | 78.942 | −4.987 | 1.00 | 56.45 |
| ATOM | 1251 | CA | LEU | 89 | 43.163 | 78.278 | −4.115 | 1.00 | 52.29 |
| ATOM | 1252 | C | LEU | 89 | 43.946 | 77.154 | −4.829 | 1.00 | 59.53 |
| ATOM | 1253 | O | LEU | 89 | 45.146 | 76.992 | −4.615 | 1.00 | 40.19 |
| ATOM | 1254 | CB | LEU | 89 | 42.421 | 77.713 | −2.905 | 1.00 | 53.20 |
| ATOM | 1255 | CG | LEU | 89 | 43.248 | 76.881 | −1.928 | 1.00 | 60.26 |
| ATOM | 1256 | CD1 | LEU | 89 | 44.138 | 77.794 | −1.126 | 1.00 | 43.38 |
| ATOM | 1257 | CD2 | LEU | 89 | 42.353 | 76.087 | −1.011 | 1.00 | 58.43 |
| ATOM | 1258 | N | LEU | 90 | 43.268 | 76.375 | −5.666 | 1.00 | 49.78 |
| ATOM | 1259 | CA | LEU | 90 | 43.935 | 75.321 | −6.421 | 1.00 | 62.35 |
| ATOM | 1260 | C | LEU | 90 | 44.539 | 75.822 | −7.733 | 1.00 | 64.62 |
| ATOM | 1261 | O | LEU | 90 | 45.059 | 75.048 | −8.539 | 1.00 | 60.89 |
| ATOM | 1262 | CB | LEU | 90 | 42.973 | 74.167 | −6.657 | 1.00 | 47.33 |
| ATOM | 1263 | CG | LEU | 90 | 43.040 | 73.266 | −5.431 | 1.00 | 59.03 |
| ATOM | 1264 | CD1 | LEU | 90 | 41.833 | 73.426 | −4.532 | 1.00 | 36.20 |
| ATOM | 1265 | CD2 | LEU | 90 | 43.199 | 71.844 | −5.854 | 1.00 | 69.47 |
| ATOM | 1266 | N | ASP | 91 | 44.466 | 77.132 | −7.928 | 1.00 | 62.53 |
| ATOM | 1267 | CA | ASP | 91 | 45.047 | 77.771 | −9.096 | 1.00 | 74.18 |
| ATOM | 1268 | C | ASP | 91 | 44.501 | 77.136 | −10.370 | 1.00 | 64.49 |
| ATOM | 1269 | O | ASP | 91 | 45.269 | 76.651 | −11.196 | 1.00 | 49.15 |
| ATOM | 1270 | CB | ASP | 91 | 46.574 | 77.659 | −9.041 | 1.00 | 79.82 |
| ATOM | 1271 | CG | ASP | 91 | 47.201 | 78.633 | −8.051 | 1.00 | 0.54 |
| ATOM | 1272 | OD1 | ASP | 91 | 46.457 | 79.411 | −7.417 | 1.00 | 0.33 |
| ATOM | 1273 | OD2 | ASP | 91 | 48.445 | 78.634 | −7.918 | 1.00 | 0.26 |
| ATOM | 1274 | N | SER | 92 | 43.176 | 77.138 | −10.523 | 1.00 | 57.69 |
| ATOM | 1275 | CA | SER | 92 | 42.553 | 76.515 | −11.687 | 1.00 | 45.90 |
| ATOM | 1276 | C | SER | 92 | 41.470 | 77.357 | −12.389 | 1.00 | 51.56 |
| ATOM | 1277 | O | SER | 92 | 40.897 | 78.243 | −11.805 | 1.00 | 45.21 |
| ATOM | 1278 | CB | SER | 92 | 41.987 | 75.148 | −11.299 | 1.00 | 50.32 |
| ATOM | 1279 | OG | SER | 92 | 41.420 | 74.505 | −12.424 | 1.00 | 54.21 |
| ATOM | 1280 | N | ARG | 93 | 41.174 | 77.010 | −13.637 | 1.00 | 60.08 |
| ATOM | 1281 | CA | ARG | 93 | 40.214 | 77.712 | −14.486 | 1.00 | 47.03 |
| ATOM | 1282 | C | ARG | 93 | 38.743 | 77.357 | −14.182 | 1.00 | 59.53 |
| ATOM | 1283 | O | ARG | 93 | 37.830 | 78.115 | −14.507 | 1.00 | 62.26 |
| ATOM | 1284 | CB | ARG | 93 | 40.534 | 77.354 | −15.942 | 1.00 | 60.51 |
| ATOM | 1285 | CG | ARG | 93 | 39.779 | 78.116 | −16.998 | 1.00 | 79.56 |
| ATOM | 1286 | CD | ARG | 93 | 40.076 | 77.548 | −18.388 | 1.00 | 92.42 |
| ATOM | 1287 | NE | ARG | 93 | 39.647 | 76.158 | −18.521 | 1.00 | 86.05 |
| ATOM | 1288 | CZ | ARG | 93 | 38.374 | 75.770 | −18.603 | 1.00 | 96.18 |
| ATOM | 1289 | NH1 | ARG | 93 | 37.396 | 76.668 | −18.554 | 1.00 | 94.70 |
| ATOM | 1290 | NH2 | ARG | 93 | 38.070 | 74.482 | −18.725 | 1.00 | 84.26 |
| ATOM | 1291 | N | ALA | 94 | 38.517 | 76.204 | −13.558 | 1.00 | 39.54 |
| ATOM | 1292 | CA | ALA | 94 | 37.175 | 75.667 | −13.380 | 1.00 | 49.91 |

TABLE 10-continued

Three-Dimensional Coordinates of *Neisseria gonorrhoeae* GCYH-IB (SEQ. ID. No. 8)

| ATOM | 1293 | C   | ALA | 94  | 37.143 | 74.595 | −12.295 | 1.00 | 36.89 |
|------|------|-----|-----|-----|--------|--------|---------|------|-------|
| ATOM | 1294 | O   | ALA | 94  | 38.170 | 74.050 | −11.919 | 1.00 | 57.00 |
| ATOM | 1295 | CB  | ALA | 94  | 36.661 | 75.101 | −14.684 | 1.00 | 45.18 |
| ATOM | 1296 | N   | GLY | 95  | 35.950 | 74.288 | −11.804 | 1.00 | 48.07 |
| ATOM | 1297 | CA  | GLY | 95  | 35.800 | 73.287 | −10.765 | 1.00 | 43.22 |
| ATOM | 1298 | C   | GLY | 95  | 34.370 | 73.116 | −10.281 | 1.00 | 49.89 |
| ATOM | 1299 | O   | GLY | 95  | 33.492 | 73.863 | −10.670 | 1.00 | 43.58 |
| ATOM | 1300 | N   | ASP | 130 | 35.219 | 79.330 | −15.968 | 1.00 | 90.21 |
| ATOM | 1301 | CA  | ASP | 130 | 35.821 | 80.546 | −16.514 | 1.00 | 96.62 |
| ATOM | 1302 | C   | ASP | 130 | 35.339 | 81.803 | −15.804 | 1.00 | 88.70 |
| ATOM | 1303 | O   | ASP | 130 | 35.222 | 82.857 | −16.416 | 1.00 | 82.77 |
| ATOM | 1304 | CB  | ASP | 130 | 35.548 | 80.668 | −18.015 | 1.00 | 0.95  |
| ATOM | 1305 | CG  | ASP | 130 | 36.445 | 79.773 | −18.843 | 1.00 | 0.53  |
| ATOM | 1306 | OD1 | ASP | 130 | 35.915 | 79.058 | −19.724 | 1.00 | 0.60  |
| ATOM | 1307 | OD2 | ASP | 130 | 37.676 | 79.784 | −18.606 | 1.00 | 0.00  |
| ATOM | 1308 | N   | GLY | 131 | 35.073 | 81.693 | −14.509 | 1.00 | 89.33 |
| ATOM | 1309 | CA  | GLY | 131 | 34.571 | 82.821 | −13.752 | 1.00 | 78.51 |
| ATOM | 1310 | C   | GLY | 131 | 33.054 | 82.867 | −13.776 | 1.00 | 75.79 |
| ATOM | 1311 | O   | GLY | 131 | 32.443 | 83.619 | −13.016 | 1.00 | 71.46 |
| ATOM | 1312 | N   | LYS | 107 | 41.732 | 34.633 | −14.670 | 1.00 | 34.97 |
| ATOM | 1313 | CA  | LYS | 107 | 43.065 | 35.231 | −14.759 | 1.00 | 52.25 |
| ATOM | 1314 | C   | LYS | 107 | 44.181 | 34.257 | −14.370 | 1.00 | 51.78 |
| ATOM | 1315 | O   | LYS | 107 | 43.937 | 33.256 | −13.709 | 1.00 | 50.24 |
| ATOM | 1316 | CB  | LYS | 107 | 43.145 | 36.472 | −13.880 | 1.00 | 46.87 |
| ATOM | 1317 | CG  | LYS | 107 | 42.805 | 37.721 | −14.628 | 1.00 | 73.11 |
| ATOM | 1318 | CD  | LYS | 107 | 41.862 | 38.578 | −13.838 | 1.00 | 52.85 |
| ATOM | 1319 | CE  | LYS | 107 | 42.594 | 39.537 | −12.936 | 1.00 | 74.85 |
| ATOM | 1320 | NZ  | LYS | 107 | 43.478 | 40.475 | −13.679 | 1.00 | 60.74 |
| ATOM | 1321 | N   | THR | 108 | 45.406 | 34.585 | −14.768 | 1.00 | 39.92 |
| ATOM | 1322 | CA  | THR | 108 | 46.595 | 33.781 | −14.453 | 1.00 | 51.78 |
| ATOM | 1323 | C   | THR | 108 | 47.620 | 34.538 | −13.599 | 1.00 | 56.01 |
| ATOM | 1324 | O   | THR | 108 | 48.046 | 35.621 | −13.972 | 1.00 | 48.49 |
| ATOM | 1325 | CB  | THR | 108 | 47.265 | 33.329 | −15.743 | 1.00 | 58.98 |
| ATOM | 1326 | OG1 | THR | 108 | 46.367 | 32.471 | −16.453 | 1.00 | 76.08 |
| ATOM | 1327 | CG2 | THR | 108 | 48.565 | 32.578 | −15.439 | 1.00 | 63.78 |
| ATOM | 1328 | N   | ALA | 109 | 48.009 | 33.972 | −12.457 | 1.00 | 51.19 |
| ATOM | 1329 | CA  | ALA | 109 | 48.981 | 34.617 | −11.577 | 1.00 | 47.51 |
| ATOM | 1330 | C   | ALA | 109 | 50.292 | 34.835 | −12.332 | 1.00 | 56.59 |
| ATOM | 1331 | O   | ALA | 109 | 50.692 | 34.004 | −13.122 | 1.00 | 58.26 |
| ATOM | 1332 | CB  | ALA | 109 | 49.198 | 33.802 | −10.318 | 1.00 | 52.79 |
| ATOM | 1333 | N   | PRO | 110 | 50.940 | 35.985 | −12.120 | 1.00 | 60.88 |
| ATOM | 1334 | CA  | PRO | 110 | 52.063 | 36.434 | −12.954 | 1.00 | 54.80 |
| ATOM | 1335 | C   | PRO | 110 | 53.369 | 35.605 | −12.855 | 1.00 | 73.41 |
| ATOM | 1336 | O   | PRO | 110 | 54.163 | 35.648 | −13.794 | 1.00 | 94.80 |
| ATOM | 1337 | CB  | PRO | 110 | 52.284 | 37.871 | −12.469 | 1.00 | 59.86 |
| ATOM | 1338 | CG  | PRO | 110 | 51.694 | 37.885 | −11.099 | 1.00 | 62.30 |
| ATOM | 1339 | CD  | PRO | 110 | 50.486 | 37.051 | −11.220 | 1.00 | 65.45 |
| ATOM | 1340 | N   | VAL | 111 | 53.586 | 34.877 | −11.759 | 1.00 | 63.03 |
| ATOM | 1341 | CA  | VAL | 111 | 54.752 | 33.999 | −11.640 | 1.00 | 67.64 |
| ATOM | 1342 | C   | VAL | 111 | 54.375 | 32.511 | −11.620 | 1.00 | 74.71 |
| ATOM | 1343 | O   | VAL | 111 | 54.850 | 31.742 | −12.447 | 1.00 | 70.73 |
| ATOM | 1344 | CB  | VAL | 111 | 55.618 | 34.354 | −10.406 | 1.00 | 71.63 |
| ATOM | 1345 | CG1 | VAL | 111 | 56.663 | 33.285 | −10.150 | 1.00 | 85.60 |
| ATOM | 1346 | CG2 | VAL | 111 | 56.284 | 35.686 | −10.607 | 1.00 | 80.10 |
| ATOM | 1347 | N   | SER | 112 | 53.508 | 32.121 | −10.689 | 1.00 | 78.75 |
| ATOM | 1348 | CA  | SER | 112 | 53.131 | 30.724 | −10.506 | 1.00 | 75.70 |
| ATOM | 1349 | C   | SER | 112 | 52.215 | 30.186 | −11.605 | 1.00 | 69.51 |
| ATOM | 1350 | O   | SER | 112 | 52.104 | 28.964 | −11.801 | 1.00 | 49.35 |
| ATOM | 1351 | CB  | SER | 112 | 52.460 | 30.533 | −9.146  | 1.00 | 52.06 |
| ATOM | 1352 | OG  | SER | 112 | 51.115 | 30.965 | −9.190  | 1.00 | 56.21 |
| ATOM | 1353 | N   | GLY | 113 | 51.551 | 31.102 | −12.304 | 1.00 | 52.71 |
| ATOM | 1354 | CA  | GLY | 113 | 50.584 | 30.746 | −13.330 | 1.00 | 53.69 |
| ATOM | 1355 | C   | GLY | 113 | 49.263 | 30.170 | −12.828 | 1.00 | 57.78 |
| ATOM | 1356 | O   | GLY | 113 | 48.436 | 29.757 | −13.636 | 1.00 | 46.82 |
| ATOM | 1357 | N   | ILE | 114 | 49.067 | 30.126 | −11.509 | 1.00 | 48.95 |
| ATOM | 1358 | CA  | ILE | 114 | 47.827 | 29.602 | −10.954 | 1.00 | 62.98 |
| ATOM | 1359 | C   | ILE | 114 | 46.650 | 30.478 | −11.372 | 1.00 | 62.30 |
| ATOM | 1360 | O   | ILE | 114 | 46.718 | 31.709 | −11.321 | 1.00 | 62.97 |
| ATOM | 1361 | CB  | ILE | 114 | 47.875 | 29.465 | −9.417  | 1.00 | 74.53 |
| ATOM | 1362 | CG1 | ILE | 114 | 49.070 | 28.614 | −8.990  | 1.00 | 89.66 |
| ATOM | 1363 | CG2 | ILE | 114 | 46.597 | 28.818 | −8.904  | 1.00 | 60.35 |
| ATOM | 1364 | CD1 | ILE | 114 | 49.088 | 28.292 | −7.508  | 1.00 | 0.82  |
| ATOM | 1365 | N   | ARG | 115 | 45.581 | 29.830 | −11.809 | 1.00 | 58.21 |
| ATOM | 1366 | CA  | ARG | 115 | 44.416 | 30.526 | −12.333 | 1.00 | 66.68 |
| ATOM | 1367 | C   | ARG | 115 | 43.330 | 30.751 | −11.287 | 1.00 | 57.62 |
| ATOM | 1368 | O   | ARG | 115 | 43.135 | 29.941 | −10.377 | 1.00 | 46.10 |
| ATOM | 1369 | CB  | ARG | 115 | 43.858 | 29.777 | −13.536 | 1.00 | 68.26 |
| ATOM | 1370 | CG  | ARG | 115 | 44.883 | 29.623 | −14.648 | 1.00 | 96.72 |

TABLE 10-continued

Three-Dimensional Coordinates of *Neisseria gonorrhoeae* GCYH-IB (SEQ. ID. No. 8)

| ATOM | 1371 | CD | ARG | 115 | 44.398 | 28.685 | −15.733 | 1.00 | 0.68 |
|------|------|-----|-----|-----|--------|--------|---------|------|------|
| ATOM | 1372 | NE | ARG | 115 | 43.474 | 29.337 | −16.653 | 1.00 | 0.03 |
| ATOM | 1373 | CZ | ARG | 115 | 42.717 | 28.687 | −17.530 | 1.00 | 0.61 |
| ATOM | 1374 | NH1 | ARG | 115 | 42.768 | 27.364 | −17.601 | 1.00 | 0.15 |
| ATOM | 1375 | NH2 | ARG | 115 | 41.903 | 29.359 | −18.331 | 1.00 | 0.32 |
| ATOM | 1376 | N | SER | 116 | 42.647 | 31.884 | −11.413 | 1.00 | 42.68 |
| ATOM | 1377 | CA | SER | 116 | 41.529 | 32.215 | −10.535 | 1.00 | 43.53 |
| ATOM | 1378 | C | SER | 116 | 40.657 | 33.252 | −11.224 | 1.00 | 43.72 |
| ATOM | 1379 | O | SER | 116 | 41.096 | 33.941 | −12.142 | 1.00 | 45.98 |
| ATOM | 1380 | CB | SER | 116 | 42.026 | 32.729 | −9.184 | 1.00 | 62.92 |
| ATOM | 1381 | OG | SER | 116 | 42.807 | 33.901 | −9.331 | 1.00 | 72.92 |
| ATOM | 1382 | N | PRO | 142 | 38.424 | 46.871 | −10.783 | 1.00 | 23.25 |
| ATOM | 1383 | CA | PRO | 142 | 39.252 | 47.141 | −9.606 | 1.00 | 26.43 |
| ATOM | 1384 | C | PRO | 142 | 40.728 | 46.924 | −9.970 | 1.00 | 33.52 |
| ATOM | 1385 | O | PRO | 142 | 41.004 | 45.944 | −10.649 | 1.00 | 34.13 |
| ATOM | 1386 | CB | PRO | 142 | 38.856 | 46.034 | −8.632 | 1.00 | 33.09 |
| ATOM | 1387 | CG | PRO | 142 | 37.937 | 45.094 | −9.398 | 1.00 | 36.83 |
| ATOM | 1388 | CD | PRO | 142 | 37.951 | 45.482 | −10.830 | 1.00 | 33.30 |
| ATOM | 1389 | N | VAL | 143 | 41.629 | 47.802 | −9.535 | 1.00 | 29.80 |
| ATOM | 1390 | CA | VAL | 143 | 43.062 | 47.647 | −9.755 | 1.00 | 29.02 |
| ATOM | 1391 | C | VAL | 143 | 43.816 | 48.153 | −8.533 | 1.00 | 37.92 |
| ATOM | 1392 | O | VAL | 143 | 43.207 | 48.563 | −7.551 | 1.00 | 42.12 |
| ATOM | 1393 | CB | VAL | 143 | 43.547 | 48.424 | −10.977 | 1.00 | 45.56 |
| ATOM | 1394 | CG1 | VAL | 143 | 42.719 | 48.044 | −12.211 | 1.00 | 32.69 |
| ATOM | 1395 | CG2 | VAL | 143 | 43.500 | 49.926 | −10.696 | 1.00 | 46.28 |
| ATOM | 1396 | N | THR | 144 | 45.145 | 48.098 | −8.601 | 1.00 | 40.29 |
| ATOM | 1397 | CA | THR | 144 | 46.019 | 48.599 | −7.543 | 1.00 | 58.11 |
| ATOM | 1398 | C | THR | 144 | 46.639 | 49.889 | −8.022 | 1.00 | 45.82 |
| ATOM | 1399 | O | THR | 144 | 47.059 | 49.993 | −9.178 | 1.00 | 41.15 |
| ATOM | 1400 | CB | THR | 144 | 47.182 | 47.625 | −7.239 | 1.00 | 76.98 |
| ATOM | 1401 | OG1 | THR | 144 | 46.679 | 46.294 | −7.072 | 1.00 | 84.02 |
| ATOM | 1402 | CG2 | THR | 144 | 47.933 | 48.057 | −5.985 | 1.00 | 83.55 |
| ATOM | 1403 | N | SER | 145 | 46.701 | 50.876 | −7.145 | 1.00 | 36.24 |
| ATOM | 1404 | CA | SER | 145 | 47.395 | 52.108 | −7.473 | 1.00 | 52.43 |
| ATOM | 1405 | C | SER | 145 | 48.464 | 52.366 | −6.424 | 1.00 | 54.50 |
| ATOM | 1406 | O | SER | 145 | 48.248 | 52.133 | −5.250 | 1.00 | 43.53 |
| ATOM | 1407 | CB | SER | 145 | 46.416 | 53.282 | −7.539 | 1.00 | 64.86 |
| ATOM | 1408 | OG | SER | 145 | 45.730 | 53.440 | −6.309 | 1.00 | 68.39 |
| ATOM | 1409 | N | LEU | 146 | 49.621 | 52.839 | −6.852 | 1.00 | 56.00 |
| ATOM | 1410 | CA | LEU | 146 | 50.691 | 53.152 | −5.919 | 1.00 | 62.10 |
| ATOM | 1411 | C | LEU | 146 | 51.116 | 54.609 | −6.109 | 1.00 | 44.80 |
| ATOM | 1412 | O | LEU | 146 | 51.243 | 55.080 | −7.229 | 1.00 | 49.94 |
| ATOM | 1413 | CB | LEU | 146 | 51.872 | 52.188 | −6.111 | 1.00 | 66.77 |
| ATOM | 1414 | CG | LEU | 146 | 53.014 | 52.307 | −5.089 | 1.00 | 65.46 |
| ATOM | 1415 | CD1 | LEU | 146 | 53.480 | 50.945 | −4.611 | 1.00 | 57.34 |
| ATOM | 1416 | CD2 | LEU | 146 | 54.166 | 53.135 | −5.653 | 1.00 | 61.66 |
| ATOM | 1417 | N | CYS | 147 | 51.339 | 55.315 | −5.012 | 1.00 | 33.12 |
| ATOM | 1418 | CA | CYS | 147 | 51.537 | 56.760 | −5.062 | 1.00 | 53.22 |
| ATOM | 1419 | C | CYS | 147 | 52.978 | 57.186 | −5.361 | 1.00 | 49.05 |
| ATOM | 1420 | O | CYS | 147 | 53.874 | 56.937 | −4.568 | 1.00 | 43.23 |
| ATOM | 1421 | CB | CYS | 147 | 51.095 | 57.400 | −3.753 | 1.00 | 44.07 |
| ATOM | 1422 | SG | CYS | 147 | 51.253 | 59.215 | −3.766 | 1.00 | 43.71 |
| ATOM | 1423 | N | PRO | 148 | 53.185 | 57.880 | −6.485 | 1.00 | 76.53 |
| ATOM | 1424 | CA | PRO | 148 | 54.521 | 58.339 | −6.877 | 1.00 | 83.85 |
| ATOM | 1425 | C | PRO | 148 | 55.120 | 59.314 | −5.869 | 1.00 | 74.03 |
| ATOM | 1426 | O | PRO | 148 | 56.284 | 59.176 | −5.550 | 1.00 | 61.76 |
| ATOM | 1427 | CB | PRO | 148 | 54.274 | 59.035 | −8.215 | 1.00 | 84.26 |
| ATOM | 1428 | CG | PRO | 148 | 52.968 | 58.508 | −8.690 | 1.00 | 73.26 |
| ATOM | 1429 | CD | PRO | 148 | 52.165 | 58.287 | −7.458 | 1.00 | 71.33 |
| ATOM | 1430 | N | CYS | 149 | 54.340 | 60.266 | −5.369 | 1.00 | 75.80 |
| ATOM | 1431 | CA | CYS | 149 | 54.833 | 61.219 | −4.379 | 1.00 | 74.27 |
| ATOM | 1432 | C | CYS | 149 | 55.272 | 60.535 | −3.091 | 1.00 | 78.06 |
| ATOM | 1433 | O | CYS | 149 | 56.307 | 60.870 | −2.536 | 1.00 | 46.90 |
| ATOM | 1434 | CB | CYS | 149 | 53.772 | 62.281 | −4.067 | 1.00 | 95.66 |
| ATOM | 1435 | SG | CYS | 149 | 54.170 | 63.366 | −2.670 | 1.00 | 84.40 |
| ATOM | 1436 | N | SER | 150 | 54.470 | 59.585 | −2.625 | 1.00 | 80.75 |
| ATOM | 1437 | CA | SER | 150 | 54.775 | 58.811 | −1.431 | 1.00 | 64.38 |
| ATOM | 1438 | C | SER | 150 | 56.102 | 58.067 | −1.569 | 1.00 | 54.94 |
| ATOM | 1439 | O | SER | 150 | 56.914 | 58.067 | −0.646 | 1.00 | 38.94 |
| ATOM | 1440 | CB | SER | 150 | 53.651 | 57.807 | −1.173 | 1.00 | 69.77 |
| ATOM | 1441 | OG | SER | 150 | 53.899 | 57.028 | −0.023 | 1.00 | 33.31 |
| ATOM | 1442 | N | LYS | 151 | 56.300 | 57.406 | −2.708 | 1.00 | 33.12 |
| ATOM | 1443 | CA | LYS | 151 | 57.547 | 56.698 | −2.989 | 1.00 | 68.45 |
| ATOM | 1444 | C | LYS | 151 | 58.748 | 57.658 | −3.032 | 1.00 | 66.78 |
| ATOM | 1445 | O | LYS | 151 | 59.751 | 57.458 | −2.357 | 1.00 | 57.85 |
| ATOM | 1446 | CB | LYS | 151 | 57.428 | 55.963 | −4.320 | 1.00 | 71.24 |
| ATOM | 1447 | CG | LYS | 151 | 58.697 | 55.259 | −4.746 | 1.00 | 76.97 |
| ATOM | 1448 | CD | LYS | 151 | 58.592 | 54.692 | −6.148 | 1.00 | 68.20 |

TABLE 10-continued

Three-Dimensional Coordinates of *Neisseria gonorrhoeae* GCYH-IB (SEQ. ID. No. 8)

| ATOM | 1449 | CE | LYS | 151 | 59.889 | 54.020 | −6.539 | 1.00 | 58.17 |
|---|---|---|---|---|---|---|---|---|---|
| ATOM | 1450 | NZ | LYS | 151 | 59.812 | 53.468 | −7.902 | 1.00 | 59.77 |
| ATOM | 1451 | N | GLU | 152 | 58.613 | 58.706 | −3.829 | 1.00 | 78.41 |
| ATOM | 1452 | CA | GLU | 152 | 59.640 | 59.730 | −4.021 | 1.00 | 92.52 |
| ATOM | 1453 | C | GLU | 152 | 60.153 | 60.386 | −2.735 | 1.00 | 79.43 |
| ATOM | 1454 | O | GLU | 152 | 61.339 | 60.642 | −2.602 | 1.00 | 69.31 |
| ATOM | 1455 | CB | GLU | 152 | 59.091 | 60.802 | −4.962 | 1.00 | 0.08 |
| ATOM | 1456 | CG | GLU | 152 | 60.011 | 61.960 | −5.246 | 1.00 | 0.79 |
| ATOM | 1457 | CD | GLU | 152 | 59.323 | 63.033 | −6.072 | 1.00 | 0.24 |
| ATOM | 1458 | OE1 | GLU | 152 | 58.216 | 63.464 | −5.688 | 1.00 | 0.23 |
| ATOM | 1459 | OE2 | GLU | 152 | 59.884 | 63.443 | −7.108 | 1.00 | 0.86 |
| ATOM | 1460 | N | ILE | 153 | 59.262 | 60.657 | −1.790 | 1.00 | 89.96 |
| ATOM | 1461 | CA | ILE | 153 | 59.642 | 61.409 | −0.597 | 1.00 | 92.18 |
| ATOM | 1462 | C | ILE | 153 | 60.114 | 60.554 | 0.576 | 1.00 | 88.22 |
| ATOM | 1463 | O | ILE | 153 | 60.802 | 61.052 | 1.457 | 1.00 | 82.43 |
| ATOM | 1464 | CB | ILE | 153 | 58.513 | 62.359 | −0.108 | 1.00 | 86.38 |
| ATOM | 1465 | CG1 | ILE | 153 | 57.298 | 61.558 | 0.386 | 1.00 | 77.79 |
| ATOM | 1466 | CG2 | ILE | 153 | 58.133 | 63.347 | −1.202 | 1.00 | 83.92 |
| ATOM | 1467 | CD1 | ILE | 153 | 56.227 | 62.397 | 1.037 | 1.00 | 62.29 |
| ATOM | 1468 | N | SER | 154 | 59.745 | 59.278 | 0.609 | 1.00 | 88.01 |
| ATOM | 1469 | CA | SER | 154 | 60.133 | 58.438 | 1.742 | 1.00 | 86.91 |
| ATOM | 1470 | C | SER | 154 | 61.351 | 57.581 | 1.418 | 1.00 | 67.99 |
| ATOM | 1471 | O | SER | 154 | 61.612 | 57.274 | 0.263 | 1.00 | 52.76 |
| ATOM | 1472 | CB | SER | 154 | 58.960 | 57.590 | 2.253 | 1.00 | 78.98 |
| ATOM | 1473 | OG | SER | 154 | 58.304 | 56.928 | 1.197 | 1.00 | 77.89 |
| ATOM | 1474 | N | GLN | 155 | 62.102 | 57.212 | 2.448 | 1.00 | 68.23 |
| ATOM | 1475 | CA | GLN | 155 | 63.334 | 56.454 | 2.252 | 1.00 | 87.17 |
| ATOM | 1476 | C | GLN | 155 | 63.032 | 54.992 | 1.942 | 1.00 | 86.25 |
| ATOM | 1477 | O | GLN | 155 | 63.870 | 54.271 | 1.408 | 1.00 | 67.23 |
| ATOM | 1478 | CB | GLN | 155 | 64.269 | 56.587 | 3.460 | 1.00 | 96.47 |
| ATOM | 1479 | CG | GLN | 155 | 63.654 | 56.185 | 4.786 | 1.00 | 0.52 |
| ATOM | 1480 | CD | GLN | 155 | 64.638 | 56.285 | 5.936 | 1.00 | 0.43 |
| ATOM | 1481 | OE1 | GLN | 155 | 65.818 | 55.963 | 5.789 | 1.00 | 0.25 |
| ATOM | 1482 | NE2 | GLN | 155 | 64.156 | 56.732 | 7.090 | 1.00 | 0.08 |
| ATOM | 1483 | N | TYR | 156 | 61.822 | 54.568 | 2.284 | 1.00 | 82.97 |
| ATOM | 1484 | CA | TYR | 156 | 61.318 | 53.261 | 1.884 | 1.00 | 80.96 |
| ATOM | 1485 | C | TYR | 156 | 59.800 | 53.229 | 1.963 | 1.00 | 80.92 |
| ATOM | 1486 | O | TYR | 156 | 59.193 | 54.083 | 2.600 | 1.00 | 47.73 |
| ATOM | 1487 | CB | TYR | 156 | 61.929 | 52.133 | 2.723 | 1.00 | 65.47 |
| ATOM | 1488 | CG | TYR | 156 | 62.164 | 52.459 | 4.181 | 1.00 | 85.68 |
| ATOM | 1489 | CD1 | TYR | 156 | 61.111 | 52.765 | 5.027 | 1.00 | 77.03 |
| ATOM | 1490 | CD2 | TYR | 156 | 63.447 | 52.438 | 4.715 | 1.00 | 90.55 |
| ATOM | 1491 | CE1 | TYR | 156 | 61.328 | 53.053 | 6.361 | 1.00 | 99.10 |
| ATOM | 1492 | CE2 | TYR | 156 | 63.672 | 52.725 | 6.044 | 1.00 | 96.22 |
| ATOM | 1493 | CZ | TYR | 156 | 62.611 | 53.031 | 6.862 | 1.00 | 0.08 |
| ATOM | 1494 | OH | TYR | 156 | 62.837 | 53.315 | 8.186 | 1.00 | 90.79 |
| ATOM | 1495 | N | GLY | 157 | 59.196 | 52.247 | 1.304 | 1.00 | 72.73 |
| ATOM | 1496 | CA | GLY | 157 | 57.754 | 52.103 | 1.307 | 1.00 | 58.71 |
| ATOM | 1497 | C | GLY | 157 | 57.062 | 53.124 | 0.424 | 1.00 | 52.06 |
| ATOM | 1498 | O | GLY | 157 | 57.631 | 54.153 | 0.078 | 1.00 | 47.90 |
| ATOM | 1499 | N | ALA | 158 | 55.824 | 52.820 | 0.046 | 1.00 | 33.39 |
| ATOM | 1500 | CA | ALA | 158 | 54.953 | 53.755 | −0.669 | 1.00 | 56.02 |
| ATOM | 1501 | C | ALA | 158 | 53.518 | 53.340 | −0.406 | 1.00 | 62.89 |
| ATOM | 1502 | O | ALA | 158 | 53.168 | 52.178 | −0.567 | 1.00 | 42.34 |
| ATOM | 1503 | CB | ALA | 158 | 55.239 | 53.745 | −2.164 | 1.00 | 50.98 |
| ATOM | 1504 | N | HIS | 159 | 52.675 | 54.268 | 0.016 | 1.00 | 53.10 |
| ATOM | 1505 | CA | HIS | 159 | 51.307 | 53.870 | 0.280 | 1.00 | 50.36 |
| ATOM | 1506 | C | HIS | 159 | 50.642 | 53.486 | −1.043 | 1.00 | 46.60 |
| ATOM | 1507 | O | HIS | 159 | 50.840 | 54.135 | −2.077 | 1.00 | 42.85 |
| ATOM | 1508 | CB | HIS | 159 | 50.528 | 54.932 | 1.061 | 1.00 | 69.62 |
| ATOM | 1509 | CG | HIS | 159 | 50.007 | 56.049 | 0.218 | 1.00 | 64.17 |
| ATOM | 1510 | ND1 | HIS | 159 | 48.869 | 55.928 | −0.549 | 1.00 | 65.54 |
| ATOM | 1511 | CD2 | HIS | 159 | 50.456 | 57.306 | 0.031 | 1.00 | 51.87 |
| ATOM | 1512 | CE1 | HIS | 159 | 48.648 | 57.068 | −1.182 | 1.00 | 52.61 |
| ATOM | 1513 | NE2 | HIS | 159 | 49.595 | 57.918 | −0.846 | 1.00 | 61.55 |
| ATOM | 1514 | N | ASN | 160 | 49.913 | 52.376 | −1.011 | 1.00 | 39.47 |
| ATOM | 1515 | CA | ASN | 160 | 49.141 | 51.929 | −2.156 | 1.00 | 41.24 |
| ATOM | 1516 | C | ASN | 160 | 47.750 | 51.588 | −1.673 | 1.00 | 36.77 |
| ATOM | 1517 | O | ASN | 160 | 47.495 | 51.586 | −0.481 | 1.00 | 37.08 |
| ATOM | 1518 | CB | ASN | 160 | 49.819 | 50.746 | −2.865 | 1.00 | 40.95 |
| ATOM | 1519 | CG | ASN | 160 | 50.298 | 49.672 | −1.900 | 1.00 | 68.88 |
| ATOM | 1520 | OD1 | ASN | 160 | 51.460 | 49.673 | −1.484 | 1.00 | 66.81 |
| ATOM | 1521 | ND2 | ASN | 160 | 49.411 | 48.745 | −1.545 | 1.00 | 28.56 |
| ATOM | 1522 | N | GLN | 161 | 46.855 | 51.279 | −2.591 | 1.00 | 26.40 |
| ATOM | 1523 | CA | GLN | 161 | 45.458 | 51.039 | −2.236 | 1.00 | 43.83 |
| ATOM | 1524 | C | GLN | 161 | 44.713 | 50.497 | −3.417 | 1.00 | 49.46 |
| ATOM | 1525 | O | GLN | 161 | 45.198 | 50.553 | −4.542 | 1.00 | 43.92 |
| ATOM | 1526 | CB | GLN | 161 | 44.775 | 52.329 | −1.777 | 1.00 | 57.27 |

TABLE 10-continued

Three-Dimensional Coordinates of *Neisseria gonorrhoeae* GCYH-IB (SEQ. ID. No. 8)

| ATOM | 1527 | CG  | GLN | 161 | 44.857 | 53.439 | -2.784  | 1.00 | 60.87 |
|------|------|-----|-----|-----|--------|--------|---------|------|-------|
| ATOM | 1528 | CD  | GLN | 161 | 46.158 | 54.223 | -2.695  | 1.00 | 52.87 |
| ATOM | 1529 | OE1 | GLN | 161 | 46.634 | 54.553 | -1.601  | 1.00 | 41.97 |
| ATOM | 1530 | NE2 | GLN | 161 | 46.725 | 54.545 | -3.850  | 1.00 | 38.64 |
| ATOM | 1531 | N   | ARG | 162 | 43.522 | 49.979 | -3.158  | 1.00 | 52.54 |
| ATOM | 1532 | CA  | ARG | 162 | 42.648 | 49.553 | -4.232  | 1.00 | 46.71 |
| ATOM | 1533 | C   | ARG | 162 | 42.082 | 50.790 | -4.904  | 1.00 | 59.05 |
| ATOM | 1534 | O   | ARG | 162 | 41.814 | 51.795 | -4.270  | 1.00 | 42.45 |
| ATOM | 1535 | CB  | ARG | 162 | 41.524 | 48.647 | -3.711  | 1.00 | 54.51 |
| ATOM | 1536 | CG  | ARG | 162 | 41.034 | 47.627 | -4.718  | 1.00 | 71.10 |
| ATOM | 1537 | CD  | ARG | 162 | 39.975 | 46.712 | -4.129  | 1.00 | 86.06 |
| ATOM | 1538 | NE  | ARG | 162 | 40.524 | 45.743 | -3.190  | 1.00 | 68.39 |
| ATOM | 1539 | CZ  | ARG | 162 | 39.800 | 45.092 | -2.290  | 1.00 | 75.71 |
| ATOM | 1540 | NH1 | ARG | 162 | 38.499 | 45.318 | -2.206  | 1.00 | 62.22 |
| ATOM | 1541 | NH2 | ARG | 162 | 40.375 | 44.226 | -1.471  | 1.00 | 70.75 |
| ATOM | 1542 | N   | SER | 163 | 41.938 | 50.704 | -6.211  | 1.00 | 37.48 |
| ATOM | 1543 | CA  | SER | 163 | 41.365 | 51.764 | -7.016  | 1.00 | 34.90 |
| ATOM | 1544 | C   | SER | 163 | 40.248 | 51.166 | -7.885  | 1.00 | 42.81 |
| ATOM | 1545 | O   | SER | 163 | 40.317 | 50.026 | -8.350  | 1.00 | 29.13 |
| ATOM | 1546 | CB  | SER | 163 | 42.466 | 52.414 | -7.862  | 1.00 | 43.38 |
| ATOM | 1547 | OG  | SER | 163 | 41.956 | 53.287 | -8.840  | 1.00 | 73.12 |
| ATOM | 1548 | N   | HIS | 164 | 39.167 | 51.908 | -8.050  | 1.00 | 25.58 |
| ATOM | 1549 | CA  | HIS | 164 | 38.147 | 51.498 | -9.003  | 1.00 | 27.06 |
| ATOM | 1550 | C   | HIS | 164 | 38.230 | 52.398 | -10.208 | 1.00 | 36.62 |
| ATOM | 1551 | O   | HIS | 164 | 38.126 | 53.615 | -10.089 | 1.00 | 35.13 |
| ATOM | 1552 | CB  | HIS | 164 | 36.748 | 51.578 | -8.377  | 1.00 | 33.69 |
| ATOM | 1553 | CG  | HIS | 164 | 36.524 | 50.605 | -7.266  | 1.00 | 64.30 |
| ATOM | 1554 | ND1 | HIS | 164 | 35.667 | 50.848 | -6.221  | 1.00 | 73.91 |
| ATOM | 1555 | CD2 | HIS | 164 | 37.058 | 49.374 | -7.034  | 1.00 | 61.84 |
| ATOM | 1556 | CE1 | HIS | 164 | 35.671 | 49.816 | -5.393  | 1.00 | 72.47 |
| ATOM | 1557 | NE2 | HIS | 164 | 36.512 | 48.912 | -5.866  | 1.00 | 59.98 |
| ATOM | 1558 | N   | ILE | 181 | 38.345 | 45.784 | -20.306 | 1.00 | 27.44 |
| ATOM | 1559 | CA  | ILE | 181 | 39.097 | 45.407 | -19.126 | 1.00 | 29.36 |
| ATOM | 1560 | C   | ILE | 181 | 40.614 | 45.457 | -19.407 | 1.00 | 50.07 |
| ATOM | 1561 | O   | ILE | 181 | 41.397 | 45.908 | -18.564 | 1.00 | 40.42 |
| ATOM | 1562 | CB  | ILE | 181 | 38.699 | 44.026 | -18.613 | 1.00 | 30.81 |
| ATOM | 1563 | CG1 | ILE | 181 | 37.266 | 44.079 | -18.047 | 1.00 | 37.62 |
| ATOM | 1564 | CG2 | ILE | 181 | 39.754 | 43.517 | -17.599 | 1.00 | 29.95 |
| ATOM | 1565 | CD1 | ILE | 181 | 36.677 | 42.733 | -17.652 | 1.00 | 39.81 |
| ATOM | 1566 | N   | ASP | 182 | 41.004 | 45.009 | -20.598 | 1.00 | 29.14 |
| ATOM | 1567 | CA  | ASP | 182 | 42.401 | 44.978 | -21.019 | 1.00 | 37.82 |
| ATOM | 1568 | C   | ASP | 182 | 42.982 | 46.400 | -21.154 | 1.00 | 43.42 |
| ATOM | 1569 | O   | ASP | 182 | 44.074 | 46.681 | -20.662 | 1.00 | 47.73 |
| ATOM | 1570 | CB  | ASP | 182 | 42.558 | 44.199 | -22.331 | 1.00 | 36.01 |
| ATOM | 1571 | CG  | ASP | 182 | 42.444 | 42.677 | -22.149 | 1.00 | 52.83 |
| ATOM | 1572 | OD1 | ASP | 182 | 42.697 | 42.167 | -21.032 | 1.00 | 49.45 |
| ATOM | 1573 | OD2 | ASP | 182 | 42.108 | 41.985 | -23.144 | 1.00 | 54.83 |
| ATOM | 1574 | N   | TYR | 183 | 42.257 | 47.303 | -21.807 | 1.00 | 37.63 |
| ATOM | 1575 | CA  | TYR | 183 | 42.705 | 48.693 | -21.887 | 1.00 | 25.05 |
| ATOM | 1576 | C   | TYR | 183 | 43.036 | 49.232 | -20.493 | 1.00 | 47.61 |
| ATOM | 1577 | O   | TYR | 183 | 43.943 | 50.037 | -20.326 | 1.00 | 41.37 |
| ATOM | 1578 | CB  | TYR | 183 | 41.645 | 49.591 | -22.527 | 1.00 | 33.40 |
| ATOM | 1579 | CG  | TYR | 183 | 41.497 | 49.479 | -24.026 | 1.00 | 47.28 |
| ATOM | 1580 | CD1 | TYR | 183 | 42.600 | 49.293 | -24.836 | 1.00 | 56.26 |
| ATOM | 1581 | CD2 | TYR | 183 | 40.252 | 49.610 | -24.633 | 1.00 | 38.98 |
| ATOM | 1582 | CE1 | TYR | 183 | 42.477 | 49.216 | -26.207 | 1.00 | 67.80 |
| ATOM | 1583 | CE2 | TYR | 183 | 40.115 | 49.538 | -26.001 | 1.00 | 55.22 |
| ATOM | 1584 | CZ  | TYR | 183 | 41.233 | 49.336 | -26.789 | 1.00 | 67.84 |
| ATOM | 1585 | OH  | TYR | 183 | 41.117 | 49.255 | -28.160 | 1.00 | 69.73 |
| ATOM | 1586 | N   | VAL | 184 | 42.294 | 48.806 | -19.480 | 1.00 | 32.30 |
| ATOM | 1587 | CA  | VAL | 184 | 42.513 | 49.381 | -18.168 | 1.00 | 34.08 |
| ATOM | 1588 | C   | VAL | 184 | 43.614 | 48.674 | -17.387 | 1.00 | 36.57 |
| ATOM | 1589 | O   | VAL | 184 | 44.448 | 49.321 | -16.789 | 1.00 | 35.67 |
| ATOM | 1590 | CB  | VAL | 184 | 41.228 | 49.440 | -17.308 | 1.00 | 40.81 |
| ATOM | 1591 | CG1 | VAL | 184 | 41.578 | 49.791 | -15.876 | 1.00 | 41.01 |
| ATOM | 1592 | CG2 | VAL | 184 | 40.222 | 50.471 | -17.875 | 1.00 | 29.23 |
| ATOM | 1593 | N   | GLU | 185 | 43.610 | 47.350 | -17.391 | 1.00 | 40.28 |
| ATOM | 1594 | CA  | GLU | 185 | 44.548 | 46.602 | -16.562 | 1.00 | 39.88 |
| ATOM | 1595 | C   | GLU | 185 | 45.993 | 46.764 | -17.037 | 1.00 | 49.88 |
| ATOM | 1596 | O   | GLU | 185 | 46.913 | 46.795 | -16.236 | 1.00 | 56.83 |
| ATOM | 1597 | CB  | GLU | 185 | 44.119 | 45.137 | -16.470 | 1.00 | 28.85 |
| ATOM | 1598 | CG  | GLU | 185 | 42.883 | 44.926 | -15.585 | 1.00 | 48.56 |
| ATOM | 1599 | CD  | GLU | 185 | 42.538 | 43.458 | -15.405 | 1.00 | 52.66 |
| ATOM | 1600 | OE1 | GLU | 185 | 42.974 | 42.658 | -16.251 | 1.00 | 43.17 |
| ATOM | 1601 | OE2 | GLU | 185 | 41.836 | 43.100 | -14.430 | 1.00 | 39.75 |
| ATOM | 1602 | N   | THR | 186 | 46.158 | 46.875 | -18.348 | 1.00 | 56.19 |
| ATOM | 1603 | CA  | THR | 186 | 47.419 | 47.226 | -18.988 | 1.00 | 60.74 |
| ATOM | 1604 | C   | THR | 186 | 48.080 | 48.452 | -18.356 | 1.00 | 54.76 |

TABLE 10-continued

Three-Dimensional Coordinates of *Neisseria gonorrhoeae* GCYH-IB (SEQ. ID. No. 8)

| ATOM | 1605 | O | THR | 186 | 49.286 | 48.488 | −18.152 | 1.00 | 53.36 |
|---|---|---|---|---|---|---|---|---|---|
| ATOM | 1606 | CB | THR | 186 | 47.188 | 47.497 | −20.494 | 1.00 | 59.55 |
| ATOM | 1607 | OG1 | THR | 186 | 47.159 | 46.253 | −21.195 | 1.00 | 64.84 |
| ATOM | 1608 | CG2 | THR | 186 | 48.287 | 48.371 | −21.078 | 1.00 | 66.33 |
| ATOM | 1609 | N | GLN | 187 | 47.274 | 49.448 | −18.028 | 1.00 | 54.99 |
| ATOM | 1610 | CA | GLN | 187 | 47.774 | 50.730 | −17.551 | 1.00 | 53.27 |
| ATOM | 1611 | C | GLN | 187 | 47.868 | 50.860 | −16.034 | 1.00 | 47.18 |
| ATOM | 1612 | O | GLN | 187 | 48.309 | 51.880 | −15.541 | 1.00 | 56.60 |
| ATOM | 1613 | CB | GLN | 187 | 46.862 | 51.845 | −18.054 | 1.00 | 45.99 |
| ATOM | 1614 | CG | GLN | 187 | 46.659 | 51.847 | −19.536 | 1.00 | 53.53 |
| ATOM | 1615 | CD | GLN | 187 | 47.920 | 52.226 | −20.252 | 1.00 | 60.81 |
| ATOM | 1616 | OE1 | GLN | 187 | 48.807 | 52.856 | −19.670 | 1.00 | 55.31 |
| ATOM | 1617 | NE2 | GLN | 187 | 48.015 | 51.859 | −21.520 | 1.00 | 47.26 |
| ATOM | 1618 | N | ALA | 188 | 47.427 | 49.865 | −15.283 | 1.00 | 44.02 |
| ATOM | 1619 | CA | ALA | 188 | 47.445 | 50.001 | −13.834 | 1.00 | 52.84 |
| ATOM | 1620 | C | ALA | 188 | 48.853 | 49.795 | −13.242 | 1.00 | 61.50 |
| ATOM | 1621 | O | ALA | 188 | 49.666 | 49.088 | −13.820 | 1.00 | 45.67 |
| ATOM | 1622 | CB | ALA | 188 | 46.466 | 49.037 | −13.219 | 1.00 | 42.42 |
| ATOM | 1623 | N | SER | 189 | 49.135 | 50.431 | −12.103 | 1.00 | 36.67 |
| ATOM | 1624 | CA | SER | 189 | 50.352 | 50.161 | −11.336 | 1.00 | 49.39 |
| ATOM | 1625 | C | SER | 189 | 50.511 | 48.661 | −11.189 | 1.00 | 62.48 |
| ATOM | 1626 | O | SER | 189 | 51.589 | 48.122 | −11.411 | 1.00 | 51.33 |
| ATOM | 1627 | CB | SER | 189 | 50.289 | 50.808 | −9.953 | 1.00 | 35.57 |
| ATOM | 1628 | OG | SER | 189 | 50.524 | 52.200 | −10.040 | 1.00 | 49.82 |
| ATOM | 1629 | N | CYS | 190 | 49.420 | 48.006 | −10.796 | 1.00 | 43.06 |
| ATOM | 1630 | CA | CYS | 190 | 49.286 | 46.563 | −10.919 | 1.00 | 42.62 |
| ATOM | 1631 | C | CYS | 190 | 47.816 | 46.122 | −10.820 | 1.00 | 49.00 |
| ATOM | 1632 | O | CYS | 190 | 46.973 | 46.803 | −10.259 | 1.00 | 43.56 |
| ATOM | 1633 | CB | CYS | 190 | 50.158 | 45.805 | −9.912 | 1.00 | 80.65 |
| ATOM | 1634 | SG | CYS | 190 | 50.699 | 44.183 | −10.542 | 1.00 | 74.68 |
| ATOM | 1635 | N | GLN | 191 | 47.510 | 44.980 | −11.396 | 1.00 | 39.65 |
| ATOM | 1636 | CA | GLN | 191 | 46.148 | 44.494 | −11.388 | 1.00 | 60.24 |
| ATOM | 1637 | C | GLN | 191 | 45.908 | 43.561 | −10.210 | 1.00 | 52.12 |
| ATOM | 1638 | O | GLN | 191 | 46.837 | 43.189 | −9.515 | 1.00 | 49.03 |
| ATOM | 1639 | CB | GLN | 191 | 45.831 | 43.816 | −12.715 | 1.00 | 61.86 |
| ATOM | 1640 | CG | GLN | 191 | 46.995 | 43.093 | −13.327 | 1.00 | 60.94 |
| ATOM | 1641 | CD | GLN | 191 | 46.670 | 42.584 | −14.698 | 1.00 | 63.14 |
| ATOM | 1642 | OE1 | GLN | 191 | 45.933 | 41.617 | −14.849 | 1.00 | 54.80 |
| ATOM | 1643 | NE2 | GLN | 191 | 47.211 | 43.236 | −15.713 | 1.00 | 66.82 |
| ATOM | 1644 | N | LEU | 192 | 44.655 | 43.205 | −9.984 | 1.00 | 50.72 |
| ATOM | 1645 | CA | LEU | 192 | 44.289 | 42.365 | −8.860 | 1.00 | 41.55 |
| ATOM | 1646 | C | LEU | 192 | 44.159 | 40.920 | −9.315 | 1.00 | 50.00 |
| ATOM | 1647 | O | LEU | 192 | 43.876 | 40.670 | −10.475 | 1.00 | 36.32 |
| ATOM | 1648 | CB | LEU | 192 | 42.966 | 42.845 | −8.255 | 1.00 | 39.35 |
| ATOM | 1649 | CG | LEU | 192 | 42.940 | 44.272 | −7.727 | 1.00 | 46.42 |
| ATOM | 1650 | CD1 | LEU | 192 | 41.593 | 44.607 | −7.117 | 1.00 | 41.02 |
| ATOM | 1651 | CD2 | LEU | 192 | 44.044 | 44.455 | −6.701 | 1.00 | 49.16 |
| ATOM | 1652 | N | TYR | 193 | 44.386 | 39.984 | −8.394 | 1.00 | 41.05 |
| ATOM | 1653 | CA | TYR | 193 | 44.156 | 38.560 | −8.618 | 1.00 | 41.75 |
| ATOM | 1654 | C | TYR | 193 | 43.434 | 37.964 | −7.416 | 1.00 | 45.03 |
| ATOM | 1655 | O | TYR | 193 | 43.612 | 38.431 | −6.290 | 1.00 | 56.48 |
| ATOM | 1656 | CB | TYR | 193 | 45.482 | 37.820 | −8.851 | 1.00 | 46.33 |
| ATOM | 1657 | CG | TYR | 193 | 46.279 | 38.338 | −10.022 | 1.00 | 52.84 |
| ATOM | 1658 | CD1 | TYR | 193 | 46.090 | 37.808 | −11.290 | 1.00 | 47.66 |
| ATOM | 1659 | CD2 | TYR | 193 | 47.222 | 39.366 | −9.863 | 1.00 | 49.49 |
| ATOM | 1660 | CE1 | TYR | 193 | 46.804 | 38.273 | −12.366 | 1.00 | 57.04 |
| ATOM | 1661 | CE2 | TYR | 193 | 47.944 | 39.839 | −10.941 | 1.00 | 51.34 |
| ATOM | 1662 | CZ | TYR | 193 | 47.730 | 39.281 | −12.187 | 1.00 | 59.22 |
| ATOM | 1663 | OH | TYR | 193 | 48.427 | 39.722 | −13.273 | 1.00 | 45.64 |
| ATOM | 1664 | N | GLY | 194 | 42.625 | 36.934 | −7.649 | 1.00 | 47.68 |
| ATOM | 1665 | CA | GLY | 194 | 41.953 | 36.252 | −6.563 | 1.00 | 45.00 |
| ATOM | 1666 | C | GLY | 194 | 42.902 | 35.350 | −5.783 | 1.00 | 55.57 |
| ATOM | 1667 | O | GLY | 194 | 42.802 | 35.232 | −4.562 | 1.00 | 73.94 |
| ATOM | 1668 | N | LEU | 195 | 43.828 | 34.715 | −6.495 | 1.00 | 56.69 |
| ATOM | 1669 | CA | LEU | 195 | 44.748 | 33.746 | −5.903 | 1.00 | 68.95 |
| ATOM | 1670 | C | LEU | 195 | 46.190 | 34.088 | −6.238 | 1.00 | 68.24 |
| ATOM | 1671 | O | LEU | 195 | 46.552 | 34.129 | −7.408 | 1.00 | 53.14 |
| ATOM | 1672 | CB | LEU | 195 | 44.431 | 32.350 | −6.431 | 1.00 | 55.82 |
| ATOM | 1673 | CG | LEU | 195 | 44.860 | 31.147 | −5.603 | 1.00 | 63.65 |
| ATOM | 1674 | CD1 | LEU | 195 | 44.173 | 29.896 | −6.124 | 1.00 | 53.17 |
| ATOM | 1675 | CD2 | LEU | 195 | 46.371 | 30.988 | −5.634 | 1.00 | 83.63 |
| ATOM | 1676 | N | LEU | 196 | 47.000 | 34.331 | −5.208 | 1.00 | 49.64 |
| ATOM | 1677 | CA | LEU | 196 | 48.437 | 34.577 | −5.370 | 1.00 | 47.59 |
| ATOM | 1678 | C | LEU | 196 | 49.267 | 33.743 | −4.411 | 1.00 | 55.36 |
| ATOM | 1679 | O | LEU | 196 | 48.957 | 33.667 | −3.222 | 1.00 | 59.50 |
| ATOM | 1680 | CB | LEU | 196 | 48.768 | 36.045 | −5.111 | 1.00 | 47.54 |
| ATOM | 1681 | CG | LEU | 196 | 48.082 | 37.053 | −6.027 | 1.00 | 58.31 |
| ATOM | 1682 | CD1 | LEU | 196 | 48.266 | 38.450 | −5.517 | 1.00 | 54.87 |

TABLE 10-continued

Three-Dimensional Coordinates of *Neisseria gonorrhoeae* GCYH-IB (SEQ. ID. No. 8)

| ATOM | 1683 | CD2 | LEU | 196 | 48.630 | 36.905 | −7.419 | 1.00 | 37.88 |
|---|---|---|---|---|---|---|---|---|---|
| ATOM | 1684 | N | LYS | 197 | 50.338 | 33.145 | −4.923 | 1.00 | 48.39 |
| ATOM | 1685 | CA | LYS | 197 | 51.311 | 32.455 | −4.083 | 1.00 | 75.76 |
| ATOM | 1686 | C | LYS | 197 | 52.429 | 33.426 | −3.703 | 1.00 | 71.25 |
| ATOM | 1687 | O | LYS | 197 | 52.485 | 34.542 | −4.228 | 1.00 | 49.06 |
| ATOM | 1688 | CB | LYS | 197 | 51.880 | 31.231 | −4.807 | 1.00 | 81.92 |
| ATOM | 1689 | CG | LYS | 197 | 50.855 | 30.138 | −5.073 | 1.00 | 88.40 |
| ATOM | 1690 | CD | LYS | 197 | 49.784 | 30.130 | −3.999 | 1.00 | 0.78 |
| ATOM | 1691 | CE | LYS | 197 | 49.135 | 28.771 | −3.846 | 1.00 | 0.41 |
| ATOM | 1692 | NZ | LYS | 197 | 49.905 | 27.924 | −2.897 | 1.00 | 0.26 |
| ATOM | 1693 | N | ARG | 198 | 53.307 | 33.004 | −2.795 | 1.00 | 61.35 |
| ATOM | 1694 | CA | ARG | 198 | 54.429 | 33.836 | −2.340 | 1.00 | 78.19 |
| ATOM | 1695 | C | ARG | 198 | 55.195 | 34.547 | −3.462 | 1.00 | 75.65 |
| ATOM | 1696 | O | ARG | 198 | 55.372 | 35.758 | −3.408 | 1.00 | 52.93 |
| ATOM | 1697 | CB | ARG | 198 | 55.403 | 33.020 | −1.491 | 1.00 | 91.33 |
| ATOM | 1698 | CG | ARG | 198 | 55.218 | 33.165 | 0.001 | 1.00 | 0.83 |
| ATOM | 1699 | CD | ARG | 198 | 56.126 | 32.199 | 0.738 | 1.00 | 0.91 |
| ATOM | 1700 | NE | ARG | 198 | 56.610 | 32.758 | 1.995 | 1.00 | 0.29 |
| ATOM | 1701 | CZ | ARG | 198 | 57.805 | 33.318 | 2.152 | 1.00 | 0.90 |
| ATOM | 1702 | NH1 | ARG | 198 | 58.646 | 33.389 | 1.128 | 1.00 | 0.09 |
| ATOM | 1703 | NH2 | ARG | 198 | 58.162 | 33.803 | 3.334 | 1.00 | 0.42 |
| ATOM | 1704 | N | PRO | 199 | 55.669 | 33.797 | −4.471 | 1.00 | 70.03 |
| ATOM | 1705 | CA | PRO | 199 | 56.397 | 34.425 | −5.579 | 1.00 | 66.36 |
| ATOM | 1706 | C | PRO | 199 | 55.541 | 35.424 | −6.351 | 1.00 | 71.38 |
| ATOM | 1707 | O | PRO | 199 | 56.103 | 36.399 | −6.843 | 1.00 | 55.95 |
| ATOM | 1708 | CB | PRO | 199 | 56.757 | 33.232 | −6.482 | 1.00 | 64.71 |
| ATOM | 1709 | CG | PRO | 199 | 55.798 | 32.168 | −6.082 | 1.00 | 73.47 |
| ATOM | 1710 | CD | PRO | 199 | 55.666 | 32.334 | −4.609 | 1.00 | 77.02 |
| ATOM | 1711 | N | ASP | 200 | 54.227 | 35.176 | −6.456 | 1.00 | 60.82 |
| ATOM | 1712 | CA | ASP | 200 | 53.290 | 36.080 | −7.142 | 1.00 | 63.99 |
| ATOM | 1713 | C | ASP | 200 | 53.146 | 37.405 | −6.410 | 1.00 | 61.39 |
| ATOM | 1714 | O | ASP | 200 | 53.208 | 38.477 | −7.003 | 1.00 | 53.71 |
| ATOM | 1715 | CB | ASP | 200 | 51.899 | 35.453 | −7.228 | 1.00 | 50.68 |
| ATOM | 1716 | CG | ASP | 200 | 51.852 | 34.256 | −8.145 | 1.00 | 70.50 |
| ATOM | 1717 | OD1 | ASP | 200 | 52.439 | 34.336 | −9.241 | 1.00 | 53.74 |
| ATOM | 1718 | OD2 | ASP | 200 | 51.215 | 33.246 | −7.773 | 1.00 | 75.96 |
| ATOM | 1719 | N | GLU | 201 | 52.926 | 37.305 | −5.109 | 1.00 | 44.34 |
| ATOM | 1720 | CA | GLU | 201 | 52.811 | 38.464 | −4.255 | 1.00 | 68.64 |
| ATOM | 1721 | C | GLU | 201 | 54.094 | 39.288 | −4.267 | 1.00 | 64.75 |
| ATOM | 1722 | O | GLU | 201 | 54.046 | 40.504 | −4.319 | 1.00 | 40.48 |
| ATOM | 1723 | CB | GLU | 201 | 52.469 | 38.044 | −2.830 | 1.00 | 44.67 |
| ATOM | 1724 | CG | GLU | 201 | 52.608 | 39.169 | −1.836 | 1.00 | 71.92 |
| ATOM | 1725 | CD | GLU | 201 | 51.777 | 38.957 | −0.595 | 1.00 | 76.03 |
| ATOM | 1726 | OE1 | GLU | 201 | 51.495 | 37.797 | −0.255 | 1.00 | 87.45 |
| ATOM | 1727 | OE2 | GLU | 201 | 51.404 | 39.955 | 0.043 | 1.00 | 64.60 |
| ATOM | 1728 | N | LYS | 202 | 55.243 | 38.630 | −4.206 | 1.00 | 50.01 |
| ATOM | 1729 | CA | LYS | 202 | 56.513 | 39.334 | −4.314 | 1.00 | 53.02 |
| ATOM | 1730 | C | LYS | 202 | 56.564 | 40.134 | −5.628 | 1.00 | 42.78 |
| ATOM | 1731 | O | LYS | 202 | 56.876 | 41.318 | −5.640 | 1.00 | 43.49 |
| ATOM | 1732 | CB | LYS | 202 | 57.685 | 38.343 | −4.227 | 1.00 | 45.02 |
| ATOM | 1733 | CG | LYS | 202 | 59.008 | 38.947 | −4.615 | 1.00 | 59.66 |
| ATOM | 1734 | CD | LYS | 202 | 60.147 | 37.932 | −4.555 | 1.00 | 54.22 |
| ATOM | 1735 | CE | LYS | 202 | 61.395 | 38.559 | −5.112 | 1.00 | 46.69 |
| ATOM | 1736 | NZ | LYS | 202 | 62.492 | 37.561 | −5.135 | 1.00 | 0.21 |
| ATOM | 1737 | N | TYR | 203 | 56.261 | 39.464 | −6.729 | 1.00 | 53.09 |
| ATOM | 1738 | CA | TYR | 203 | 56.204 | 40.089 | −8.045 | 1.00 | 64.50 |
| ATOM | 1739 | C | TYR | 203 | 55.245 | 41.289 | −8.106 | 1.00 | 61.81 |
| ATOM | 1740 | O | TYR | 203 | 55.568 | 42.322 | −8.685 | 1.00 | 65.84 |
| ATOM | 1741 | CB | TYR | 203 | 55.783 | 39.046 | −9.075 | 1.00 | 67.81 |
| ATOM | 1742 | CG | TYR | 203 | 55.679 | 39.568 | −10.477 | 1.00 | 64.72 |
| ATOM | 1743 | CD1 | TYR | 203 | 56.748 | 39.472 | −11.345 | 1.00 | 52.12 |
| ATOM | 1744 | CD2 | TYR | 203 | 54.513 | 40.154 | −10.940 | 1.00 | 53.63 |
| ATOM | 1745 | CE1 | TYR | 203 | 56.664 | 39.935 | −12.633 | 1.00 | 60.02 |
| ATOM | 1746 | CE2 | TYR | 203 | 54.421 | 40.629 | −12.241 | 1.00 | 64.08 |
| ATOM | 1747 | CZ | TYR | 203 | 55.506 | 40.510 | −13.079 | 1.00 | 69.98 |
| ATOM | 1748 | OH | TYR | 203 | 55.444 | 40.975 | −14.365 | 1.00 | 69.48 |
| ATOM | 1749 | N | VAL | 204 | 54.068 | 41.150 | −7.506 | 1.00 | 60.20 |
| ATOM | 1750 | CA | VAL | 204 | 53.038 | 42.203 | −7.576 | 1.00 | 78.24 |
| ATOM | 1751 | C | VAL | 204 | 53.422 | 43.441 | −6.723 | 1.00 | 47.17 |
| ATOM | 1752 | O | VAL | 204 | 53.315 | 44.579 | −7.181 | 1.00 | 43.11 |
| ATOM | 1753 | CB | VAL | 204 | 51.612 | 41.622 | −7.250 | 1.00 | 43.63 |
| ATOM | 1754 | CG1 | VAL | 204 | 51.277 | 41.757 | −5.775 | 1.00 | 47.36 |
| ATOM | 1755 | CG2 | VAL | 204 | 50.563 | 42.242 | −8.102 | 1.00 | 71.25 |
| ATOM | 1756 | N | THR | 205 | 53.905 | 43.205 | −5.506 | 1.00 | 44.47 |
| ATOM | 1757 | CA | THR | 205 | 54.461 | 44.244 | −4.633 | 1.00 | 52.60 |
| ATOM | 1758 | C | THR | 205 | 55.540 | 45.083 | −5.338 | 1.00 | 57.12 |
| ATOM | 1759 | O | THR | 205 | 55.508 | 46.328 | −5.330 | 1.00 | 41.28 |
| ATOM | 1760 | CB | THR | 205 | 55.107 | 43.610 | −3.363 | 1.00 | 61.74 |

TABLE 10-continued

Three-Dimensional Coordinates of *Neisseria gonorrhoeae* GCYH-IB (SEQ. ID. No. 8)

| ATOM | 1761 | OG1 | THR | 205 | 54.153 | 42.798 | −2.669 | 1.00 | 49.23 |
|------|------|-----|-----|-----|--------|--------|--------|------|-------|
| ATOM | 1762 | CG2 | THR | 205 | 55.642 | 44.675 | −2.418 | 1.00 | 57.92 |
| ATOM | 1763 | N   | GLU | 206 | 56.501 | 44.386 | −5.939 | 1.00 | 51.43 |
| ATOM | 1764 | CA  | GLU | 206 | 57.652 | 45.021 | −6.587 | 1.00 | 49.67 |
| ATOM | 1765 | C   | GLU | 206 | 57.274 | 45.784 | −7.859 | 1.00 | 42.78 |
| ATOM | 1766 | O   | GLU | 206 | 57.708 | 46.911 | −8.056 | 1.00 | 46.60 |
| ATOM | 1767 | CB  | GLU | 206 | 58.753 | 43.979 | −6.872 | 1.00 | 32.43 |
| ATOM | 1768 | CG  | GLU | 206 | 59.406 | 43.451 | −5.608 | 1.00 | 67.25 |
| ATOM | 1769 | CD  | GLU | 206 | 60.333 | 42.277 | −5.874 | 1.00 | 94.44 |
| ATOM | 1770 | OE1 | GLU | 206 | 60.462 | 41.852 | −7.044 | 1.00 | 0.36  |
| ATOM | 1771 | OE2 | GLU | 206 | 60.933 | 41.777 | −4.904 | 1.00 | 89.69 |
| ATOM | 1772 | N   | LYS | 207 | 56.460 | 45.162 | −8.703 | 1.00 | 46.45 |
| ATOM | 1773 | CA  | LYS | 207 | 56.052 | 45.741 | −9.968 | 1.00 | 62.72 |
| ATOM | 1774 | C   | LYS | 207 | 55.270 | 47.029 | −9.746 | 1.00 | 63.15 |
| ATOM | 1775 | O   | LYS | 207 | 55.445 | 47.995 | −10.483| 1.00 | 51.88 |
| ATOM | 1776 | CB  | LYS | 207 | 55.237 | 44.720 | −10.776| 1.00 | 72.67 |
| ATOM | 1777 | CG  | LYS | 207 | 54.342 | 45.314 | −11.858| 1.00 | 0.74  |
| ATOM | 1778 | CD  | LYS | 207 | 55.121 | 45.667 | −13.113| 1.00 | 0.57  |
| ATOM | 1779 | CE  | LYS | 207 | 54.183 | 45.984 | −14.272| 1.00 | 0.12  |
| ATOM | 1780 | NZ  | LYS | 207 | 54.926 | 46.230 | −15.540| 1.00 | 0.37  |
| ATOM | 1781 | N   | ALA | 208 | 54.419 | 47.044 | −8.721 | 1.00 | 51.93 |
| ATOM | 1782 | CA  | ALA | 208 | 53.653 | 48.245 | −8.383 | 1.00 | 52.25 |
| ATOM | 1783 | C   | ALA | 208 | 54.595 | 49.340 | −7.896 | 1.00 | 57.98 |
| ATOM | 1784 | O   | ALA | 208 | 54.459 | 50.512 | −8.252 | 1.00 | 36.09 |
| ATOM | 1785 | CB  | ALA | 208 | 52.598 | 47.938 | −7.319 | 1.00 | 38.82 |
| ATOM | 1786 | N   | TYR | 209 | 55.565 | 48.948 | −7.077 | 1.00 | 52.31 |
| ATOM | 1787 | CA  | TYR | 209 | 56.567 | 49.884 | −6.594 | 1.00 | 56.68 |
| ATOM | 1788 | C   | TYR | 209 | 57.336 | 50.530 | −7.761 | 1.00 | 64.16 |
| ATOM | 1789 | O   | TYR | 209 | 57.634 | 51.710 | −7.726 | 1.00 | 52.26 |
| ATOM | 1790 | CB  | TYR | 209 | 57.510 | 49.192 | −5.615 | 1.00 | 51.72 |
| ATOM | 1791 | CG  | TYR | 209 | 58.410 | 50.129 | −4.833 | 1.00 | 63.67 |
| ATOM | 1792 | CD1 | TYR | 209 | 57.999 | 50.659 | −3.608 | 1.00 | 59.18 |
| ATOM | 1793 | CD2 | TYR | 209 | 59.667 | 50.478 | −5.309 | 1.00 | 67.39 |
| ATOM | 1794 | CE1 | TYR | 209 | 58.809 | 51.499 | −2.885 | 1.00 | 74.90 |
| ATOM | 1795 | CE2 | TYR | 209 | 60.490 | 51.325 | −4.586 | 1.00 | 55.98 |
| ATOM | 1796 | CZ  | TYR | 209 | 60.053 | 51.832 | −3.378 | 1.00 | 78.85 |
| ATOM | 1797 | OH  | TYR | 209 | 60.859 | 52.676 | −2.659 | 1.00 | 69.89 |
| ATOM | 1798 | N   | GLU | 210 | 57.623 | 49.764 | −8.806 | 1.00 | 59.87 |
| ATOM | 1799 | CA  | GLU | 210 | 58.365 | 50.287 | −9.952 | 1.00 | 55.94 |
| ATOM | 1800 | C   | GLU | 210 | 57.461 | 51.050 | −10.920| 1.00 | 69.29 |
| ATOM | 1801 | O   | GLU | 210 | 57.948 | 51.720 | −11.819| 1.00 | 56.02 |
| ATOM | 1802 | CB  | GLU | 210 | 59.066 | 49.155 | −10.702| 1.00 | 55.80 |
| ATOM | 1803 | CG  | GLU | 210 | 59.989 | 48.312 | −9.849 | 1.00 | 71.30 |
| ATOM | 1804 | CD  | GLU | 210 | 60.235 | 46.923 | −10.426| 1.00 | 87.58 |
| ATOM | 1805 | OE1 | GLU | 210 | 59.759 | 46.623 | −11.546| 1.00 | 73.11 |
| ATOM | 1806 | OE2 | GLU | 210 | 60.903 | 46.120 | −9.748 | 1.00 | 93.13 |
| ATOM | 1807 | N   | ASN | 211 | 56.144 | 50.943 | −10.751| 1.00 | 52.95 |
| ATOM | 1808 | CA  | ASN | 211 | 55.228 | 51.625 | −11.660| 1.00 | 72.66 |
| ATOM | 1809 | C   | ASN | 211 | 54.204 | 52.491 | −10.915| 1.00 | 72.42 |
| ATOM | 1810 | O   | ASN | 211 | 53.002 | 52.267 | −11.008| 1.00 | 55.20 |
| ATOM | 1811 | CB  | ASN | 211 | 54.537 | 50.614 | −12.586| 1.00 | 82.34 |
| ATOM | 1812 | CG  | ASN | 211 | 53.763 | 51.281 | −13.711| 1.00 | 96.40 |
| ATOM | 1813 | OD1 | ASN | 211 | 54.164 | 52.326 | −14.228| 1.00 | 0.40  |
| ATOM | 1814 | ND2 | ASN | 211 | 52.645 | 50.674 | −14.097| 1.00 | 93.22 |
| ATOM | 1815 | N   | PRO | 212 | 54.685 | 53.494 | −10.171| 1.00 | 55.52 |
| ATOM | 1816 | CA  | PRO | 212 | 53.771 | 54.353 | −9.417 | 1.00 | 50.78 |
| ATOM | 1817 | C   | PRO | 212 | 52.908 | 55.193 | −10.357| 1.00 | 62.47 |
| ATOM | 1818 | O   | PRO | 212 | 53.390 | 55.633 | −11.396| 1.00 | 43.99 |
| ATOM | 1819 | CB  | PRO | 212 | 54.717 | 55.271 | −8.633 | 1.00 | 44.67 |
| ATOM | 1820 | CG  | PRO | 212 | 56.099 | 54.674 | −8.786 | 1.00 | 53.75 |
| ATOM | 1821 | CD  | PRO | 212 | 56.078 | 53.969 | −10.087| 1.00 | 52.24 |
| ATOM | 1822 | N   | LYS | 213 | 51.647 | 55.402 | −10.000| 1.00 | 50.06 |
| ATOM | 1823 | CA  | LYS | 213 | 50.733 | 56.202 | −10.821| 1.00 | 60.06 |
| ATOM | 1824 | C   | LYS | 213 | 49.698 | 56.946 | −9.986 | 1.00 | 37.78 |
| ATOM | 1825 | O   | LYS | 213 | 48.985 | 56.351 | −9.184 | 1.00 | 49.66 |
| ATOM | 1826 | CB  | LYS | 213 | 50.019 | 55.344 | −11.877| 1.00 | 59.67 |
| ATOM | 1827 | CG  | LYS | 213 | 50.842 | 55.087 | −13.119| 1.00 | 67.39 |
| ATOM | 1828 | CD  | LYS | 213 | 50.009 | 54.535 | −14.255| 1.00 | 71.54 |
| ATOM | 1829 | CE  | LYS | 213 | 50.909 | 53.988 | −15.349| 1.00 | 66.53 |
| ATOM | 1830 | NZ  | LYS | 213 | 50.180 | 53.601 | −16.586| 1.00 | 54.59 |
| ATOM | 1831 | N   | PHE | 214 | 49.644 | 58.254 | −10.189| 1.00 | 44.37 |
| ATOM | 1832 | CA  | PHE | 214 | 48.577 | 59.094 | −9.666 | 1.00 | 57.67 |
| ATOM | 1833 | C   | PHE | 214 | 47.257 | 58.759 | −10.339| 1.00 | 50.58 |
| ATOM | 1834 | O   | PHE | 214 | 47.235 | 58.167 | −11.414| 1.00 | 52.80 |
| ATOM | 1835 | CB  | PHE | 214 | 48.882 | 60.570 | −9.950 | 1.00 | 53.34 |
| ATOM | 1836 | CG  | PHE | 214 | 49.983 | 61.143 | −9.112 | 1.00 | 60.66 |
| ATOM | 1837 | CD1 | PHE | 214 | 49.924 | 61.093 | −7.730 | 1.00 | 75.57 |
| ATOM | 1838 | CD2 | PHE | 214 | 51.063 | 61.763 | −9.708 | 1.00 | 74.87 |

TABLE 10-continued

Three-Dimensional Coordinates of *Neisseria gonorrhoeae* GCYH-IB (SEQ. ID. No. 8)

| ATOM | 1839 | CE1 | PHE | 214 | 50.932 | 61.631 | −6.959 | 1.00 | 68.54 |
|------|------|-----|-----|-----|--------|--------|--------|------|-------|
| ATOM | 1840 | CE2 | PHE | 214 | 52.075 | 62.307 | −8.943 | 1.00 | 73.49 |
| ATOM | 1841 | CZ | PHE | 214 | 52.009 | 62.240 | −7.565 | 1.00 | 65.16 |
| ATOM | 1842 | N | VAL | 215 | 46.161 | 59.189 | −9.721 | 1.00 | 50.21 |
| ATOM | 1843 | CA | VAL | 215 | 44.838 | 59.073 | −10.332 | 1.00 | 32.24 |
| ATOM | 1844 | C | VAL | 215 | 44.760 | 59.862 | −11.663 | 1.00 | 39.63 |
| ATOM | 1845 | O | VAL | 215 | 44.097 | 59.449 | −12.616 | 1.00 | 34.93 |
| ATOM | 1846 | CB | VAL | 215 | 43.736 | 59.462 | −9.328 | 1.00 | 49.44 |
| ATOM | 1847 | CG1 | VAL | 215 | 43.564 | 60.964 | −9.245 | 1.00 | 40.48 |
| ATOM | 1848 | CG2 | VAL | 215 | 42.442 | 58.814 | −9.698 | 1.00 | 43.26 |
| ATOM | 1849 | N | GLU | 216 | 45.483 | 60.976 | −11.741 | 1.00 | 31.87 |
| ATOM | 1850 | CA | GLU | 216 | 45.604 | 61.740 | −12.985 | 1.00 | 37.07 |
| ATOM | 1851 | C | GLU | 216 | 46.236 | 60.948 | −14.124 | 1.00 | 42.58 |
| ATOM | 1852 | O | GLU | 216 | 45.774 | 61.005 | −15.267 | 1.00 | 37.19 |
| ATOM | 1853 | CB | GLU | 216 | 46.392 | 63.038 | −12.760 | 1.00 | 37.27 |
| ATOM | 1854 | CG | GLU | 216 | 45.753 | 63.982 | −11.734 | 1.00 | 55.63 |
| ATOM | 1855 | CD | GLU | 216 | 46.293 | 63.800 | −10.315 | 1.00 | 64.24 |
| ATOM | 1856 | OE1 | GLU | 216 | 46.794 | 62.710 | −9.987 | 1.00 | 72.74 |
| ATOM | 1857 | OE2 | GLU | 216 | 46.212 | 64.750 | −9.514 | 1.00 | 72.11 |
| ATOM | 1858 | N | ASP | 217 | 47.297 | 60.209 | −13.821 | 1.00 | 42.79 |
| ATOM | 1859 | CA | ASP | 217 | 47.967 | 59.411 | −14.846 | 1.00 | 48.33 |
| ATOM | 1860 | C | ASP | 217 | 47.118 | 58.237 | −15.292 | 1.00 | 43.56 |
| ATOM | 1861 | O | ASP | 217 | 47.070 | 57.918 | −16.475 | 1.00 | 45.97 |
| ATOM | 1862 | CB | ASP | 217 | 49.316 | 58.927 | −14.338 | 1.00 | 53.19 |
| ATOM | 1863 | CG | ASP | 217 | 50.191 | 60.065 | −13.902 | 1.00 | 69.65 |
| ATOM | 1864 | OD1 | ASP | 217 | 50.265 | 61.060 | −14.662 | 1.00 | 73.54 |
| ATOM | 1865 | OD2 | ASP | 217 | 50.782 | 59.977 | −12.801 | 1.00 | 68.83 |
| ATOM | 1866 | N | MSE | 218 | 46.443 | 57.609 | −14.336 | 1.00 | 37.35 |
| ATOM | 1867 | CA | MSE | 218 | 45.542 | 56.503 | −14.634 | 1.00 | 39.78 |
| ATOM | 1868 | C | MSE | 218 | 44.546 | 56.896 | −15.734 | 1.00 | 24.72 |
| ATOM | 1869 | O | MSE | 218 | 44.499 | 56.279 | −16.796 | 1.00 | 29.59 |
| ATOM | 1870 | CB | MSE | 218 | 44.810 | 56.050 | −13.362 | 1.00 | 58.79 |
| ATOM | 1871 | CG | MSE | 218 | 44.073 | 54.718 | −13.480 | 1.00 | 77.38 |
| ATOM | 1872 | SE | MSE | 218 | 45.130 | 53.300 | −14.337 | 1.00 | 0.47 |
| ATOM | 1873 | CE | MSE | 218 | 44.023 | 51.745 | −13.914 | 1.00 | 0.92 |
| ATOM | 1874 | N | VAL | 219 | 43.774 | 57.954 | −15.494 | 1.00 | 29.59 |
| ATOM | 1875 | CA | VAL | 219 | 42.719 | 58.311 | −16.429 | 1.00 | 26.43 |
| ATOM | 1876 | C | VAL | 219 | 43.272 | 58.802 | −17.751 | 1.00 | 27.62 |
| ATOM | 1877 | O | VAL | 219 | 42.717 | 58.504 | −18.809 | 1.00 | 32.99 |
| ATOM | 1878 | CB | VAL | 219 | 41.705 | 59.336 | −15.837 | 1.00 | 36.95 |
| ATOM | 1879 | CG1 | VAL | 219 | 41.063 | 58.766 | −14.612 | 1.00 | 35.83 |
| ATOM | 1880 | CG2 | VAL | 219 | 42.391 | 60.634 | −15.492 | 1.00 | 30.34 |
| ATOM | 1881 | N | ARG | 220 | 44.362 | 59.557 | −17.691 | 1.00 | 30.45 |
| ATOM | 1882 | CA | ARG | 220 | 45.024 | 59.991 | −18.917 | 1.00 | 43.29 |
| ATOM | 1883 | C | ARG | 220 | 45.473 | 58.811 | −19.757 | 1.00 | 39.78 |
| ATOM | 1884 | O | ARG | 220 | 45.241 | 58.785 | −20.961 | 1.00 | 49.09 |
| ATOM | 1885 | CB | ARG | 220 | 46.204 | 60.899 | −18.606 | 1.00 | 37.68 |
| ATOM | 1886 | CG | ARG | 220 | 45.787 | 62.334 | −18.434 | 1.00 | 41.30 |
| ATOM | 1887 | CD | ARG | 220 | 46.922 | 63.184 | −17.877 | 1.00 | 37.85 |
| ATOM | 1888 | NE | ARG | 220 | 46.562 | 64.587 | −18.004 | 1.00 | 44.94 |
| ATOM | 1889 | CZ | ARG | 220 | 47.039 | 65.568 | −17.253 | 1.00 | 47.83 |
| ATOM | 1890 | NH1 | ARG | 220 | 47.911 | 65.315 | −16.293 | 1.00 | 39.44 |
| ATOM | 1891 | NH2 | ARG | 220 | 46.630 | 66.808 | −17.468 | 1.00 | 46.76 |
| ATOM | 1892 | N | ASP | 221 | 46.091 | 57.825 | −19.116 | 1.00 | 30.84 |
| ATOM | 1893 | CA | ASP | 221 | 46.593 | 56.663 | −19.863 | 1.00 | 39.37 |
| ATOM | 1894 | C | ASP | 221 | 45.487 | 55.785 | −20.456 | 1.00 | 39.67 |
| ATOM | 1895 | O | ASP | 221 | 45.582 | 55.333 | −21.584 | 1.00 | 44.32 |
| ATOM | 1896 | CB | ASP | 221 | 47.527 | 55.840 | −18.990 | 1.00 | 50.33 |
| ATOM | 1897 | CG | ASP | 221 | 48.803 | 56.596 | −18.628 | 1.00 | 76.67 |
| ATOM | 1898 | OD1 | ASP | 221 | 49.064 | 57.668 | −19.227 | 1.00 | 84.23 |
| ATOM | 1899 | OD2 | ASP | 221 | 49.549 | 56.121 | −17.741 | 1.00 | 61.34 |
| ATOM | 1900 | N | VAL | 222 | 44.411 | 55.570 | −19.707 | 1.00 | 35.67 |
| ATOM | 1901 | CA | VAL | 222 | 43.286 | 54.801 | −20.242 | 1.00 | 37.76 |
| ATOM | 1902 | C | VAL | 222 | 42.568 | 55.554 | −21.366 | 1.00 | 32.07 |
| ATOM | 1903 | O | VAL | 222 | 42.181 | 54.959 | −22.366 | 1.00 | 38.73 |
| ATOM | 1904 | CB | VAL | 222 | 42.265 | 54.474 | −19.163 | 1.00 | 30.54 |
| ATOM | 1905 | CG1 | VAL | 222 | 41.055 | 53.806 | −19.798 | 1.00 | 34.98 |
| ATOM | 1906 | CG2 | VAL | 222 | 42.880 | 53.609 | −18.116 | 1.00 | 31.33 |
| ATOM | 1907 | N | ALA | 223 | 42.408 | 56.867 | −21.189 | 1.00 | 27.50 |
| ATOM | 1908 | CA | ALA | 223 | 41.684 | 57.696 | −22.152 | 1.00 | 38.49 |
| ATOM | 1909 | C | ALA | 223 | 42.393 | 57.706 | −23.496 | 1.00 | 41.28 |
| ATOM | 1910 | O | ALA | 223 | 41.755 | 57.705 | −24.540 | 1.00 | 35.49 |
| ATOM | 1911 | CB | ALA | 223 | 41.531 | 59.102 | −21.634 | 1.00 | 32.48 |
| ATOM | 1912 | N | THR | 224 | 43.722 | 57.720 | −23.457 | 1.00 | 38.65 |
| ATOM | 1913 | CA | THR | 224 | 44.515 | 57.719 | −24.679 | 1.00 | 41.10 |
| ATOM | 1914 | C | THR | 224 | 44.251 | 56.444 | −25.487 | 1.00 | 40.22 |
| ATOM | 1915 | O | THR | 224 | 44.079 | 56.490 | −26.702 | 1.00 | 44.23 |
| ATOM | 1916 | CB | THR | 224 | 45.997 | 57.847 | −24.361 | 1.00 | 34.72 |

TABLE 10-continued

Three-Dimensional Coordinates of *Neisseria gonorrhoeae* GCYH-IB (SEQ. ID. No. 8)

| | | | | | | | | | |
|---|---|---|---|---|---|---|---|---|---|
| ATOM | 1917 | OG1 | THR | 224 | 46.230 | 59.095 | −23.701 | 1.00 | 47.19 |
| ATOM | 1918 | CG2 | THR | 224 | 46.809 | 57.787 | −25.634 | 1.00 | 51.18 |
| ATOM | 1919 | N | SER | 225 | 44.206 | 55.306 | −24.803 | 1.00 | 35.60 |
| ATOM | 1920 | CA | SER | 225 | 43.861 | 54.041 | −25.456 | 1.00 | 47.00 |
| ATOM | 1921 | C | SER | 225 | 42.478 | 54.062 | −26.070 | 1.00 | 45.84 |
| ATOM | 1922 | O | SER | 225 | 42.288 | 53.536 | −27.161 | 1.00 | 42.17 |
| ATOM | 1923 | CB | SER | 225 | 43.921 | 52.878 | −24.479 | 1.00 | 42.92 |
| ATOM | 1924 | OG | SER | 225 | 45.122 | 52.899 | −23.754 | 1.00 | 48.51 |
| ATOM | 1925 | N | LEU | 226 | 41.518 | 54.662 | −25.370 | 1.00 | 37.09 |
| ATOM | 1926 | CA | LEU | 226 | 40.133 | 54.686 | −25.853 | 1.00 | 36.24 |
| ATOM | 1927 | C | LEU | 226 | 40.008 | 55.632 | −27.036 | 1.00 | 37.89 |
| ATOM | 1928 | O | LEU | 226 | 39.325 | 55.318 | −28.006 | 1.00 | 43.78 |
| ATOM | 1929 | CB | LEU | 226 | 39.165 | 55.081 | −24.729 | 1.00 | 34.97 |
| ATOM | 1930 | CG | LEU | 226 | 39.134 | 54.201 | −23.479 | 1.00 | 33.84 |
| ATOM | 1931 | CD1 | LEU | 226 | 38.220 | 54.802 | −22.430 | 1.00 | 50.41 |
| ATOM | 1932 | CD2 | LEU | 226 | 38.715 | 52.749 | −23.789 | 1.00 | 39.51 |
| ATOM | 1933 | N | ILE | 227 | 40.697 | 56.774 | −26.953 | 1.00 | 36.57 |
| ATOM | 1934 | CA | ILE | 227 | 40.717 | 57.772 | −28.015 | 1.00 | 45.24 |
| ATOM | 1935 | C | ILE | 227 | 41.250 | 57.172 | −29.305 | 1.00 | 47.23 |
| ATOM | 1936 | O | ILE | 227 | 40.767 | 57.485 | −30.391 | 1.00 | 49.27 |
| ATOM | 1937 | CB | ILE | 227 | 41.584 | 58.982 | −27.644 | 1.00 | 47.34 |
| ATOM | 1938 | CG1 | ILE | 227 | 40.827 | 59.893 | −26.683 | 1.00 | 43.33 |
| ATOM | 1939 | CG2 | ILE | 227 | 42.004 | 59.759 | −28.913 | 1.00 | 38.95 |
| ATOM | 1940 | CD1 | ILE | 227 | 41.690 | 60.899 | −26.055 | 1.00 | 47.18 |
| ATOM | 1941 | N | ALA | 228 | 42.242 | 56.296 | −29.169 | 1.00 | 33.22 |
| ATOM | 1942 | CA | ALA | 228 | 42.793 | 55.595 | −30.316 | 1.00 | 51.83 |
| ATOM | 1943 | C | ALA | 228 | 41.791 | 54.642 | −30.994 | 1.00 | 62.10 |
| ATOM | 1944 | O | ALA | 228 | 41.712 | 54.585 | −32.215 | 1.00 | 60.35 |
| ATOM | 1945 | CB | ALA | 228 | 44.061 | 54.864 | −29.931 | 1.00 | 49.81 |
| ATOM | 1946 | N | ASP | 229 | 41.017 | 53.908 | −30.207 | 1.00 | 48.90 |
| ATOM | 1947 | CA | ASP | 229 | 40.031 | 52.979 | −30.765 | 1.00 | 44.21 |
| ATOM | 1948 | C | ASP | 229 | 38.912 | 53.684 | −31.570 | 1.00 | 52.96 |
| ATOM | 1949 | O | ASP | 229 | 38.167 | 54.496 | −31.024 | 1.00 | 56.32 |
| ATOM | 1950 | CB | ASP | 229 | 39.422 | 52.149 | −29.638 | 1.00 | 63.61 |
| ATOM | 1951 | CG | ASP | 229 | 38.777 | 50.880 | −30.137 | 1.00 | 71.21 |
| ATOM | 1952 | OD1 | ASP | 229 | 37.992 | 50.927 | −31.117 | 1.00 | 54.93 |
| ATOM | 1953 | OD2 | ASP | 229 | 39.065 | 49.829 | −29.541 | 1.00 | 59.40 |
| ATOM | 1954 | N | SER | 239 | 38.540 | 57.458 | −12.331 | 1.00 | 32.02 |
| ATOM | 1955 | CA | SER | 239 | 39.261 | 56.623 | −11.403 | 1.00 | 36.49 |
| ATOM | 1956 | C | SER | 239 | 39.027 | 57.122 | −9.984 | 1.00 | 38.44 |
| ATOM | 1957 | O | SER | 239 | 39.101 | 58.312 | −9.694 | 1.00 | 36.92 |
| ATOM | 1958 | CB | SER | 239 | 40.740 | 56.592 | −11.742 | 1.00 | 34.93 |
| ATOM | 1959 | OG | SER | 239 | 41.417 | 55.702 | −10.880 | 1.00 | 60.83 |
| ATOM | 1960 | N | GLU | 240 | 38.691 | 56.205 | −9.102 | 1.00 | 23.58 |
| ATOM | 1961 | CA | GLU | 240 | 38.605 | 56.532 | −7.698 | 1.00 | 29.00 |
| ATOM | 1962 | C | GLU | 240 | 39.659 | 55.781 | −6.871 | 1.00 | 42.70 |
| ATOM | 1963 | O | GLU | 240 | 39.693 | 54.562 | −6.885 | 1.00 | 34.93 |
| ATOM | 1964 | CB | GLU | 240 | 37.206 | 56.221 | −7.195 | 1.00 | 21.31 |
| ATOM | 1965 | CG | GLU | 240 | 37.038 | 56.469 | −5.723 | 1.00 | 44.72 |
| ATOM | 1966 | CD | GLU | 240 | 35.586 | 56.521 | −5.345 | 1.00 | 61.73 |
| ATOM | 1967 | OE1 | GLU | 240 | 34.730 | 56.323 | −6.244 | 1.00 | 55.18 |
| ATOM | 1968 | OE2 | GLU | 240 | 35.301 | 56.770 | −4.156 | 1.00 | 62.28 |
| ATOM | 1969 | N | ASN | 241 | 40.511 | 56.509 | −6.157 | 1.00 | 35.37 |
| ATOM | 1970 | CA | ASN | 241 | 41.557 | 55.895 | −5.336 | 1.00 | 35.84 |
| ATOM | 1971 | C | ASN | 241 | 41.181 | 55.931 | −3.868 | 1.00 | 44.30 |
| ATOM | 1972 | O | ASN | 241 | 41.131 | 57.006 | −3.277 | 1.00 | 35.87 |
| ATOM | 1973 | CB | ASN | 241 | 42.846 | 56.695 | −5.458 | 1.00 | 59.50 |
| ATOM | 1974 | CG | ASN | 241 | 43.834 | 56.080 | −6.385 | 1.00 | 74.07 |
| ATOM | 1975 | OD1 | ASN | 241 | 45.033 | 56.159 | −6.144 | 1.00 | 83.92 |
| ATOM | 1976 | ND2 | ASN | 241 | 43.353 | 55.474 | −7.461 | 1.00 | 73.43 |
| ATOM | 1977 | N | PHE | 242 | 40.947 | 54.779 | −3.261 | 1.00 | 34.18 |
| ATOM | 1978 | CA | PHE | 242 | 40.648 | 54.730 | −1.835 | 1.00 | 54.06 |
| ATOM | 1979 | C | PHE | 242 | 41.932 | 54.805 | −1.029 | 1.00 | 43.36 |
| ATOM | 1980 | O | PHE | 242 | 42.298 | 53.861 | −0.319 | 1.00 | 42.57 |
| ATOM | 1981 | CB | PHE | 242 | 39.837 | 53.479 | −1.491 | 1.00 | 49.71 |
| ATOM | 1982 | CG | PHE | 242 | 38.579 | 53.348 | −2.307 | 1.00 | 54.48 |
| ATOM | 1983 | CD1 | PHE | 242 | 37.400 | 53.964 | −1.899 | 1.00 | 48.92 |
| ATOM | 1984 | CD2 | PHE | 242 | 38.587 | 52.633 | −3.500 | 1.00 | 50.08 |
| ATOM | 1985 | CE1 | PHE | 242 | 36.249 | 53.865 | −2.662 | 1.00 | 44.33 |
| ATOM | 1986 | CE2 | PHE | 242 | 37.446 | 52.523 | −4.265 | 1.00 | 56.26 |
| ATOM | 1987 | CZ | PHE | 242 | 36.269 | 53.144 | −3.847 | 1.00 | 48.67 |
| ATOM | 1988 | N | GLU | 243 | 42.603 | 55.950 | −1.149 | 1.00 | 43.70 |
| ATOM | 1989 | CA | GLU | 243 | 43.938 | 56.145 | −0.598 | 1.00 | 53.80 |
| ATOM | 1990 | C | GLU | 243 | 44.041 | 55.657 | 0.836 | 1.00 | 54.72 |
| ATOM | 1991 | O | GLU | 243 | 43.155 | 55.892 | 1.662 | 1.00 | 36.12 |
| ATOM | 1992 | CB | GLU | 243 | 44.409 | 57.600 | −0.753 | 1.00 | 62.42 |
| ATOM | 1993 | CG | GLU | 243 | 43.409 | 58.632 | −0.338 | 1.00 | 98.18 |
| ATOM | 1994 | CD | GLU | 243 | 43.956 | 60.032 | −0.486 | 1.00 | 0.38 |

TABLE 10-continued

Three-Dimensional Coordinates of *Neisseria gonorrhoeae* GCYH-IB (SEQ. ID. No. 8)

| ATOM | 1995 | OE1 | GLU | 243 | 43.160 | 60.995 | −0.471 | 1.00 | 0.85 |
|---|---|---|---|---|---|---|---|---|---|
| ATOM | 1996 | OE2 | GLU | 243 | 45.189 | 60.168 | −0.625 | 1.00 | 0.45 |
| ATOM | 1997 | N | SER | 244 | 45.126 | 54.946 | 1.110 | 1.00 | 48.15 |
| ATOM | 1998 | CA | SER | 244 | 45.254 | 54.200 | 2.349 | 1.00 | 48.27 |
| ATOM | 1999 | C | SER | 244 | 45.764 | 55.075 | 3.487 | 1.00 | 43.29 |
| ATOM | 2000 | O | SER | 244 | 45.999 | 54.580 | 4.582 | 1.00 | 54.30 |
| ATOM | 2001 | CB | SER | 244 | 46.178 | 53.001 | 2.154 | 1.00 | 50.70 |
| ATOM | 2002 | OG | SER | 244 | 47.495 | 53.457 | 1.924 | 1.00 | 57.31 |
| ATOM | 2003 | N | ILE | 245 | 45.938 | 56.370 | 3.225 | 1.00 | 38.50 |
| ATOM | 2004 | CA | ILE | 245 | 46.367 | 57.306 | 4.273 | 1.00 | 54.46 |
| ATOM | 2005 | C | ILE | 245 | 45.290 | 58.330 | 4.654 | 1.00 | 49.60 |
| ATOM | 2006 | O | ILE | 245 | 45.474 | 59.101 | 5.595 | 1.00 | 39.53 |
| ATOM | 2007 | CB | ILE | 245 | 47.658 | 58.057 | 3.879 | 1.00 | 54.37 |
| ATOM | 2008 | CG1 | ILE | 245 | 47.401 | 58.957 | 2.669 | 1.00 | 54.44 |
| ATOM | 2009 | CG2 | ILE | 245 | 48.758 | 57.075 | 3.577 | 1.00 | 37.95 |
| ATOM | 2010 | CD1 | ILE | 245 | 48.629 | 59.708 | 2.192 | 1.00 | 73.40 |
| ATOM | 2011 | N | HIS | 246 | 44.188 | 58.351 | 3.908 | 1.00 | 43.91 |
| ATOM | 2012 | CA | HIS | 246 | 43.058 | 59.241 | 4.206 | 1.00 | 49.94 |
| ATOM | 2013 | C | HIS | 246 | 41.770 | 58.429 | 4.355 | 1.00 | 57.65 |
| ATOM | 2014 | O | HIS | 246 | 41.754 | 57.248 | 4.058 | 1.00 | 47.46 |
| ATOM | 2015 | CB | HIS | 246 | 42.893 | 60.286 | 3.104 | 1.00 | 40.63 |
| ATOM | 2016 | CG | HIS | 246 | 44.038 | 61.253 | 3.001 | 1.00 | 63.27 |
| ATOM | 2017 | ND1 | HIS | 246 | 44.749 | 61.446 | 1.831 | 1.00 | 58.15 |
| ATOM | 2018 | CD2 | HIS | 246 | 44.585 | 62.089 | 3.912 | 1.00 | 61.44 |
| ATOM | 2019 | CE1 | HIS | 246 | 45.683 | 62.358 | 2.032 | 1.00 | 69.99 |
| ATOM | 2020 | NE2 | HIS | 246 | 45.609 | 62.759 | 3.288 | 1.00 | 70.61 |
| ATOM | 2021 | N | ASN | 247 | 40.699 | 59.050 | 4.831 | 1.00 | 45.02 |
| ATOM | 2022 | CA | ASN | 247 | 39.407 | 58.387 | 4.820 | 1.00 | 41.42 |
| ATOM | 2023 | C | ASN | 247 | 38.445 | 58.933 | 3.747 | 1.00 | 46.46 |
| ATOM | 2024 | O | ASN | 247 | 37.230 | 58.936 | 3.930 | 1.00 | 59.35 |
| ATOM | 2025 | CB | ASN | 247 | 38.748 | 58.399 | 6.206 | 1.00 | 48.65 |
| ATOM | 2026 | CG | ASN | 247 | 37.673 | 57.326 | 6.343 | 1.00 | 49.46 |
| ATOM | 2027 | OD1 | ASN | 247 | 37.815 | 56.250 | 5.800 | 1.00 | 34.71 |
| ATOM | 2028 | ND2 | ASN | 247 | 36.602 | 57.621 | 7.065 | 1.00 | 32.52 |
| ATOM | 2029 | N | HIS | 248 | 39.003 | 59.394 | 2.636 | 1.00 | 43.29 |
| ATOM | 2030 | CA | HIS | 248 | 38.225 | 59.817 | 1.479 | 1.00 | 37.63 |
| ATOM | 2031 | C | HIS | 248 | 39.022 | 59.392 | 0.266 | 1.00 | 32.12 |
| ATOM | 2032 | O | HIS | 248 | 40.113 | 58.841 | 0.402 | 1.00 | 33.44 |
| ATOM | 2033 | CB | HIS | 248 | 38.002 | 61.334 | 1.461 | 1.00 | 24.97 |
| ATOM | 2034 | CG | HIS | 248 | 39.263 | 62.130 | 1.604 | 1.00 | 40.81 |
| ATOM | 2035 | ND1 | HIS | 248 | 39.979 | 62.602 | 0.523 | 1.00 | 37.83 |
| ATOM | 2036 | CD2 | HIS | 248 | 39.942 | 62.535 | 2.702 | 1.00 | 40.18 |
| ATOM | 2037 | CE1 | HIS | 248 | 41.038 | 63.258 | 0.949 | 1.00 | 38.94 |
| ATOM | 2038 | NE2 | HIS | 248 | 41.036 | 63.240 | 2.269 | 1.00 | 39.85 |
| ATOM | 2039 | N | SER | 249 | 38.501 | 59.662 | −0.921 | 1.00 | 31.92 |
| ATOM | 2040 | CA | SER | 249 | 39.118 | 59.158 | −2.132 | 1.00 | 28.87 |
| ATOM | 2041 | C | SER | 249 | 39.662 | 60.283 | −2.973 | 1.00 | 31.05 |
| ATOM | 2042 | O | SER | 249 | 39.077 | 61.355 | −3.026 | 1.00 | 37.57 |
| ATOM | 2043 | CB | SER | 249 | 38.081 | 58.383 | −2.967 | 1.00 | 34.29 |
| ATOM | 2044 | OG | SER | 249 | 37.538 | 57.285 | −2.250 | 1.00 | 37.64 |
| ATOM | 2045 | N | ALA | 250 | 40.762 | 60.012 | −3.661 | 1.00 | 28.85 |
| ATOM | 2046 | CA | ALA | 250 | 41.194 | 60.819 | −4.764 | 1.00 | 33.19 |
| ATOM | 2047 | C | ALA | 250 | 40.330 | 60.391 | −5.934 | 1.00 | 28.86 |
| ATOM | 2048 | O | ALA | 250 | 39.959 | 59.240 | −6.049 | 1.00 | 34.36 |
| ATOM | 2049 | CB | ALA | 250 | 42.673 | 60.554 | −5.065 | 1.00 | 31.23 |
| ATOM | 2050 | N | TYR | 251 | 40.036 | 61.321 | −6.826 | 1.00 | 33.24 |
| ATOM | 2051 | CA | TYR | 251 | 39.093 | 61.057 | −7.876 | 1.00 | 29.01 |
| ATOM | 2052 | C | TYR | 251 | 39.442 | 61.887 | −9.119 | 1.00 | 33.92 |
| ATOM | 2053 | O | TYR | 251 | 39.828 | 63.038 | −8.993 | 1.00 | 33.45 |
| ATOM | 2054 | CB | TYR | 251 | 37.699 | 61.414 | −7.347 | 1.00 | 32.19 |
| ATOM | 2055 | CG | TYR | 251 | 36.610 | 61.299 | −8.361 | 1.00 | 32.91 |
| ATOM | 2056 | CD1 | TYR | 251 | 36.196 | 60.054 | −8.816 | 1.00 | 29.52 |
| ATOM | 2057 | CD2 | TYR | 251 | 35.964 | 62.429 | −8.847 | 1.00 | 47.96 |
| ATOM | 2058 | CE1 | TYR | 251 | 35.180 | 59.933 | −9.755 | 1.00 | 39.22 |
| ATOM | 2059 | CE2 | TYR | 251 | 34.941 | 62.319 | −9.780 | 1.00 | 46.77 |
| ATOM | 2060 | CZ | TYR | 251 | 34.562 | 61.066 | −10.237 | 1.00 | 43.34 |
| ATOM | 2061 | OH | TYR | 251 | 33.557 | 60.940 | −11.171 | 1.00 | 54.07 |
| ATOM | 2062 | N | ALA | 252 | 39.310 | 61.309 | −10.310 | 1.00 | 30.32 |
| ATOM | 2063 | CA | ALA | 252 | 39.456 | 62.078 | −11.543 | 1.00 | 26.10 |
| ATOM | 2064 | C | ALA | 252 | 38.605 | 61.518 | −12.650 | 1.00 | 33.82 |
| ATOM | 2065 | O | ALA | 252 | 38.286 | 60.340 | −12.647 | 1.00 | 33.50 |
| ATOM | 2066 | CB | ALA | 252 | 40.884 | 62.096 | −11.983 | 1.00 | 24.77 |
| ATOM | 2067 | N | TYR | 253 | 38.232 | 62.365 | −13.604 | 1.00 | 23.03 |
| ATOM | 2068 | CA | TYR | 253 | 37.575 | 61.855 | −14.792 | 1.00 | 34.29 |
| ATOM | 2069 | C | TYR | 253 | 37.791 | 62.664 | −16.044 | 1.00 | 34.76 |
| ATOM | 2070 | O | TYR | 253 | 37.999 | 63.864 | −15.990 | 1.00 | 37.04 |
| ATOM | 2071 | CB | TYR | 253 | 36.078 | 61.662 | −14.551 | 1.00 | 39.33 |
| ATOM | 2072 | CG | TYR | 253 | 35.200 | 62.866 | −14.735 | 1.00 | 44.29 |

TABLE 10-continued

Three-Dimensional Coordinates of *Neisseria gonorrhoeae* GCYH-IB (SEQ. ID. No. 8)

| ATOM | 2073 | CD1 | TYR | 253 | 35.007 | 63.439 | −15.859 | 1.00 | 47.98 |
|---|---|---|---|---|---|---|---|---|---|
| ATOM | 2074 | CD2 | TYR | 253 | 34.487 | 63.346 | −13.801 | 1.00 | 71.67 |
| ATOM | 2075 | CE1 | TYR | 253 | 34.171 | 64.535 | −16.015 | 1.00 | 64.14 |
| ATOM | 2076 | CE2 | TYR | 253 | 33.654 | 64.444 | −13.979 | 1.00 | 82.86 |
| ATOM | 2077 | CZ | TYR | 253 | 33.494 | 65.031 | −15.080 | 1.00 | 89.73 |
| ATOM | 2078 | OH | TYR | 253 | 32.658 | 66.122 | −15.240 | 1.00 | 0.58 |
| TER | | | | | | | | | |
| ATOM | 2079 | ZN | ZN2 B | 258 | 50.203 | 59.884 | −1.793 | 1.00 | 35.76 |
| ATOM | 2080 | C | ACY B | 259 | 47.704 | 62.423 | −1.932 | 1.00 | 65.42 |
| ATOM | 2081 | O | ACY B | 259 | 47.758 | 62.761 | −3.162 | 1.00 | 54.29 |
| ATOM | 2082 | OXT | ACY B | 259 | 48.249 | 61.379 | −1.482 | 1.00 | 52.67 |
| ATOM | 2083 | CH3 | ACY B | 259 | 46.973 | 63.282 | −0.925 | 1.00 | 47.10 |
| TER | | | | | | | | | |
| ENDMDL | | | | | | | | | |
| MODEL | 2 | | | | | | | | |
| TER | | | | | | | | | |
| ATOM | 1 | N | ARG | 105 | 12.838 | 31.677 | −7.753 | 1.00 | 37.32 |
| ATOM | 2 | CA | ARG | 105 | 11.823 | 30.638 | −7.695 | 1.00 | 33.40 |
| ATOM | 3 | C | ARG | 105 | 10.667 | 30.993 | −8.623 | 1.00 | 41.58 |
| ATOM | 4 | O | ARG | 105 | 10.117 | 32.098 | −8.581 | 1.00 | 51.52 |
| ATOM | 5 | CB | ARG | 105 | 11.326 | 30.437 | −6.269 | 1.00 | 40.89 |
| ATOM | 6 | CG | ARG | 105 | 10.462 | 29.204 | −6.112 | 1.00 | 58.44 |
| ATOM | 7 | CD | ARG | 105 | 9.698 | 29.219 | −4.804 | 1.00 | 56.99 |
| ATOM | 8 | NE | ARG | 105 | 9.230 | 27.881 | −4.437 | 1.00 | 57.40 |
| ATOM | 9 | CZ | ARG | 105 | 8.424 | 27.637 | −3.416 | 1.00 | 59.07 |
| ATOM | 10 | NH1 | ARG | 105 | 7.994 | 28.656 | −2.684 | 1.00 | 44.70 |
| ATOM | 11 | NH2 | ARG | 105 | 8.046 | 26.390 | −3.134 | 1.00 | 57.95 |
| ATOM | 12 | N | LYS | 106 | 10.322 | 30.047 | −9.482 | 1.00 | 43.60 |
| ATOM | 13 | CA | LYS | 106 | 9.176 | 30.219 | −10.367 | 1.00 | 57.50 |
| ATOM | 14 | C | LYS | 106 | 7.853 | 30.213 | −9.582 | 1.00 | 51.91 |
| ATOM | 15 | O | LYS | 106 | 7.597 | 29.322 | −8.776 | 1.00 | 64.57 |
| ATOM | 16 | CB | LYS | 106 | 9.181 | 29.140 | −11.447 | 1.00 | 55.51 |
| ATOM | 17 | CG | LYS | 106 | 8.667 | 29.611 | −12.791 | 1.00 | 73.50 |
| ATOM | 18 | CD | LYS | 106 | 9.636 | 29.195 | −13.884 | 1.00 | 89.56 |
| ATOM | 19 | CE | LYS | 106 | 8.911 | 28.719 | −15.117 | 1.00 | 99.85 |
| ATOM | 20 | NZ | LYS | 106 | 7.842 | 29.667 | −15.491 | 1.00 | 0.62 |
| ATOM | 21 | N | LYS | 107 | 7.039 | 31.237 | −9.816 | 1.00 | 54.02 |
| ATOM | 22 | CA | LYS | 107 | 5.719 | 31.359 | −9.197 | 1.00 | 55.18 |
| ATOM | 23 | C | LYS | 107 | 4.623 | 31.427 | −10.238 | 1.00 | 64.44 |
| ATOM | 24 | O | LYS | 107 | 4.890 | 31.709 | −11.408 | 1.00 | 67.36 |
| ATOM | 25 | CB | LYS | 107 | 5.645 | 32.591 | −8.293 | 1.00 | 59.17 |
| ATOM | 26 | CG | LYS | 107 | 6.076 | 32.289 | −6.871 | 1.00 | 78.01 |
| ATOM | 27 | CD | LYS | 107 | 7.044 | 33.323 | −6.340 | 1.00 | 42.27 |
| ATOM | 28 | CE | LYS | 107 | 6.290 | 34.470 | −5.703 | 1.00 | 76.76 |
| ATOM | 29 | NZ | LYS | 107 | 5.410 | 34.007 | −4.585 | 1.00 | 63.95 |
| ATOM | 30 | N | THR | 108 | 3.391 | 31.175 | −9.794 | 1.00 | 52.40 |
| ATOM | 31 | CA | THR | 108 | 2.216 | 31.207 | −10.661 | 1.00 | 54.45 |
| ATOM | 32 | C | THR | 108 | 1.188 | 32.249 | −10.194 | 1.00 | 68.79 |
| ATOM | 33 | O | THR | 108 | 0.785 | 32.251 | −9.030 | 1.00 | 66.08 |
| ATOM | 34 | CB | THR | 108 | 1.551 | 29.818 | −10.712 | 1.00 | 69.12 |
| ATOM | 35 | OG1 | THR | 108 | 2.462 | 28.875 | −11.294 | 1.00 | 81.63 |
| ATOM | 36 | CG2 | THR | 108 | 0.254 | 29.851 | −11.508 | 1.00 | 60.33 |
| ATOM | 37 | N | ALA | 109 | 0.768 | 33.129 | −11.103 | 1.00 | 59.63 |
| ATOM | 38 | CA | ALA | 109 | −0.208 | 34.158 | −10.780 | 1.00 | 55.61 |
| ATOM | 39 | C | ALA | 109 | −1.539 | 33.521 | −10.335 | 1.00 | 71.15 |
| ATOM | 40 | O | ALA | 109 | −1.987 | 32.530 | −10.911 | 1.00 | 77.38 |
| ATOM | 41 | CB | ALA | 109 | −0.414 | 35.084 | −11.970 | 1.00 | 64.89 |
| ATOM | 42 | N | PRO | 110 | −2.167 | 34.088 | −9.292 | 1.00 | 77.07 |
| ATOM | 43 | CA | PRO | 110 | −3.301 | 33.451 | −8.607 | 1.00 | 60.99 |
| ATOM | 44 | C | PRO | 110 | −4.581 | 33.254 | −9.428 | 1.00 | 75.83 |
| ATOM | 45 | O | PRO | 110 | −5.376 | 32.386 | −9.075 | 1.00 | 0.83 |
| ATOM | 46 | CB | PRO | 110 | −3.554 | 34.398 | −7.428 | 1.00 | 69.05 |
| ATOM | 47 | CG | PRO | 110 | −2.920 | 35.694 | −7.844 | 1.00 | 73.14 |
| ATOM | 48 | CD | PRO | 110 | −1.683 | 35.259 | −8.540 | 1.00 | 70.35 |
| ATOM | 49 | N | VAL | 111 | −4.796 | 34.046 | −10.475 | 1.00 | 76.98 |
| ATOM | 50 | CA | VAL | 111 | −5.969 | 33.867 | −11.326 | 1.00 | 75.05 |
| ATOM | 51 | C | VAL | 111 | −5.617 | 33.407 | −12.751 | 1.00 | 83.25 |
| ATOM | 52 | O | VAL | 111 | −6.118 | 32.386 | −13.221 | 1.00 | 84.58 |
| ATOM | 53 | CB | VAL | 111 | −6.859 | 35.146 | −11.386 | 1.00 | 80.99 |
| ATOM | 54 | CG1 | VAL | 111 | −7.935 | 35.014 | −12.477 | 1.00 | 89.81 |
| ATOM | 55 | CG2 | VAL | 111 | −7.508 | 35.409 | −10.036 | 1.00 | 90.98 |
| ATOM | 56 | N | SER | 112 | −4.763 | 34.164 | −13.431 | 1.00 | 87.92 |
| ATOM | 57 | CA | SER | 112 | −4.384 | 33.866 | −14.813 | 1.00 | 84.89 |
| ATOM | 58 | C | SER | 112 | −3.470 | 32.637 | −14.961 | 1.00 | 80.23 |
| ATOM | 59 | O | SER | 112 | −3.417 | 32.026 | −16.035 | 1.00 | 72.07 |
| ATOM | 60 | CB | SER | 112 | −3.710 | 35.086 | −15.455 | 1.00 | 64.52 |
| ATOM | 61 | OG | SER | 112 | −2.361 | 35.214 | −15.020 | 1.00 | 67.63 |
| ATOM | 62 | N | GLY | 113 | −2.740 | 32.293 | −13.896 | 1.00 | 65.30 |

TABLE 10-continued

Three-Dimensional Coordinates of *Neisseria gonorrhoeae* GCYH-IB (SEQ. ID. No. 8)

| ATOM | 63 | CA | GLY | 113 | −1.815 | 31.176 | −13.934 | 1.00 | 57.14 |
|---|---|---|---|---|---|---|---|---|---|
| ATOM | 64 | C | GLY | 113 | −0.484 | 31.488 | −14.595 | 1.00 | 71.26 |
| ATOM | 65 | O | GLY | 113 | 0.410 | 30.631 | −14.638 | 1.00 | 69.71 |
| ATOM | 66 | N | ILE | 114 | −0.330 | 32.710 | −15.103 | 1.00 | 73.22 |
| ATOM | 67 | CA | ILE | 114 | 0.934 | 33.108 | −15.738 | 1.00 | 69.42 |
| ATOM | 68 | C | ILE | 114 | 2.125 | 33.020 | −14.779 | 1.00 | 68.09 |
| ATOM | 69 | O | ILE | 114 | 2.077 | 33.509 | −13.650 | 1.00 | 76.48 |
| ATOM | 70 | CB | ILE | 114 | 0.869 | 34.517 | −16.368 | 1.00 | 73.91 |
| ATOM | 71 | CG1 | ILE | 114 | −0.334 | 34.628 | −17.303 | 1.00 | 89.92 |
| ATOM | 72 | CG2 | ILE | 114 | 2.138 | 34.798 | −17.152 | 1.00 | 63.39 |
| ATOM | 73 | CD1 | ILE | 114 | −0.366 | 35.918 | −18.089 | 1.00 | 0.56 |
| ATOM | 74 | N | ARG | 115 | 3.193 | 32.389 | −15.248 | 1.00 | 61.46 |
| ATOM | 75 | CA | ARG | 115 | 4.354 | 32.117 | −14.415 | 1.00 | 70.33 |
| ATOM | 76 | C | ARG | 115 | 5.449 | 33.180 | −14.551 | 1.00 | 64.45 |
| ATOM | 77 | O | ARG | 115 | 5.670 | 33.747 | −15.625 | 1.00 | 63.87 |
| ATOM | 78 | CB | ARG | 115 | 4.903 | 30.716 | −14.718 | 1.00 | 74.16 |
| ATOM | 79 | CG | ARG | 115 | 3.876 | 29.607 | −14.512 | 1.00 | 97.70 |
| ATOM | 80 | CD | ARG | 115 | 4.378 | 28.283 | −15.043 | 1.00 | 0.22 |
| ATOM | 81 | NE | ARG | 115 | 5.317 | 27.638 | −14.130 | 1.00 | 0.87 |
| ATOM | 82 | CZ | ARG | 115 | 6.084 | 26.605 | −14.460 | 1.00 | 0.60 |
| ATOM | 83 | NH1 | ARG | 115 | 6.032 | 26.101 | −15.685 | 1.00 | 0.46 |
| ATOM | 84 | NH2 | ARG | 115 | 6.907 | 26.077 | −13.567 | 1.00 | 0.52 |
| ATOM | 85 | N | SER | 116 | 6.112 | 33.459 | −13.440 | 1.00 | 46.36 |
| ATOM | 86 | CA | SER | 116 | 7.241 | 34.376 | −13.437 | 1.00 | 58.82 |
| ATOM | 87 | C | SER | 116 | 8.116 | 34.069 | −12.239 | 1.00 | 52.50 |
| ATOM | 88 | O | SER | 116 | 7.667 | 33.429 | −11.292 | 1.00 | 69.05 |
| ATOM | 89 | CB | SER | 116 | 6.757 | 35.822 | −13.386 | 1.00 | 72.93 |
| ATOM | 90 | OG | SER | 116 | 6.002 | 36.061 | −12.213 | 1.00 | 83.93 |
| ATOM | 91 | N | LEU | 117 | 9.365 | 34.518 | −12.295 | 1.00 | 50.22 |
| ATOM | 92 | CA | LEU | 117 | 10.334 | 34.282 | −11.237 | 1.00 | 47.85 |
| ATOM | 93 | C | LEU | 117 | 10.235 | 35.354 | −10.178 | 1.00 | 44.22 |
| ATOM | 94 | O | LEU | 117 | 9.949 | 36.505 | −10.480 | 1.00 | 49.25 |
| ATOM | 95 | CB | LEU | 117 | 11.739 | 34.333 | −11.809 | 1.00 | 39.11 |
| ATOM | 96 | CG | LEU | 117 | 12.192 | 33.272 | −12.799 | 1.00 | 51.74 |
| ATOM | 97 | CD1 | LEU | 117 | 13.513 | 33.721 | −13.367 | 1.00 | 48.04 |
| ATOM | 98 | CD2 | LEU | 117 | 12.331 | 31.936 | −12.105 | 1.00 | 46.33 |
| ATOM | 99 | N | LEU | 118 | 10.475 | 34.980 | −8.930 | 1.00 | 47.30 |
| ATOM | 100 | CA | LEU | 118 | 10.672 | 35.969 | −7.891 | 1.00 | 38.20 |
| ATOM | 101 | C | LEU | 118 | 12.022 | 35.699 | −7.285 | 1.00 | 43.03 |
| ATOM | 102 | O | LEU | 118 | 12.460 | 34.561 | −7.267 | 1.00 | 38.94 |
| ATOM | 103 | CB | LEU | 118 | 9.584 | 35.909 | −6.813 | 1.00 | 48.88 |
| ATOM | 104 | CG | LEU | 118 | 9.555 | 37.141 | −5.883 | 1.00 | 59.07 |
| ATOM | 105 | CD1 | LEU | 118 | 8.998 | 38.351 | −6.609 | 1.00 | 50.36 |
| ATOM | 106 | CD2 | LEU | 118 | 8.775 | 36.905 | −4.595 | 1.00 | 64.70 |
| ATOM | 107 | N | PRO | 142 | 10.324 | 38.919 | 0.478 | 1.00 | 35.84 |
| ATOM | 108 | CA | PRO | 142 | 9.506 | 40.128 | 0.335 | 1.00 | 26.02 |
| ATOM | 109 | C | PRO | 142 | 8.056 | 39.748 | 0.236 | 1.00 | 44.44 |
| ATOM | 110 | O | PRO | 142 | 7.763 | 38.820 | −0.506 | 1.00 | 49.76 |
| ATOM | 111 | CB | PRO | 142 | 9.947 | 40.718 | −1.014 | 1.00 | 38.65 |
| ATOM | 112 | CG | PRO | 142 | 10.918 | 39.705 | −1.641 | 1.00 | 43.31 |
| ATOM | 113 | CD | PRO | 142 | 10.869 | 38.445 | −0.805 | 1.00 | 41.46 |
| ATOM | 114 | N | VAL | 143 | 7.177 | 40.433 | 0.968 | 1.00 | 38.87 |
| ATOM | 115 | CA | VAL | 143 | 5.740 | 40.182 | 0.923 | 1.00 | 40.60 |
| ATOM | 116 | C | VAL | 143 | 4.983 | 41.496 | 0.993 | 1.00 | 45.08 |
| ATOM | 117 | O | VAL | 143 | 5.574 | 42.567 | 1.073 | 1.00 | 57.65 |
| ATOM | 118 | CB | VAL | 143 | 5.270 | 39.281 | 2.083 | 1.00 | 54.37 |
| ATOM | 119 | CG1 | VAL | 143 | 6.160 | 38.046 | 2.195 | 1.00 | 39.31 |
| ATOM | 120 | CG2 | VAL | 143 | 5.283 | 40.049 | 3.384 | 1.00 | 52.85 |
| ATOM | 121 | N | THR | 144 | 3.670 | 41.401 | 0.931 | 1.00 | 46.10 |
| ATOM | 122 | CA | THR | 144 | 2.772 | 42.549 | 1.090 | 1.00 | 66.56 |
| ATOM | 123 | C | THR | 144 | 2.120 | 42.531 | 2.467 | 1.00 | 68.98 |
| ATOM | 124 | O | THR | 144 | 1.621 | 41.494 | 2.916 | 1.00 | 67.59 |
| ATOM | 125 | CB | THR | 144 | 1.608 | 42.519 | 0.073 | 1.00 | 79.38 |
| ATOM | 126 | OG1 | THR | 144 | 2.116 | 42.247 | −1.237 | 1.00 | 90.84 |
| ATOM | 127 | CG2 | THR | 144 | 0.848 | 43.849 | 0.073 | 1.00 | 84.80 |
| ATOM | 128 | N | SER | 145 | 2.112 | 43.673 | 3.138 | 1.00 | 92.35 |
| ATOM | 129 | CA | SER | 145 | 1.414 | 43.763 | 4.403 | 1.00 | 92.76 |
| ATOM | 130 | C | SER | 145 | 0.348 | 44.831 | 4.281 | 1.00 | 93.23 |
| ATOM | 131 | O | SER | 145 | 0.560 | 45.856 | 3.638 | 1.00 | 93.67 |
| ATOM | 132 | CB | SER | 145 | 2.387 | 44.082 | 5.536 | 1.00 | 93.44 |
| ATOM | 133 | OG | SER | 145 | 3.120 | 45.259 | 5.253 | 1.00 | 94.25 |
| ATOM | 134 | N | LEU | 146 | −0.811 | 44.578 | 4.875 | 1.00 | 93.12 |
| ATOM | 135 | CA | LEU | 146 | −1.886 | 45.558 | 4.883 | 1.00 | 93.52 |
| ATOM | 136 | C | LEU | 146 | −2.293 | 45.854 | 6.323 | 1.00 | 94.04 |
| ATOM | 137 | O | LEU | 146 | −2.412 | 44.943 | 7.135 | 1.00 | 93.70 |
| ATOM | 138 | CB | LEU | 146 | −3.069 | 45.066 | 4.048 | 1.00 | 92.85 |
| ATOM | 139 | CG | LEU | 146 | −4.193 | 46.079 | 3.829 | 1.00 | 93.13 |
| ATOM | 140 | CD1 | LEU | 146 | −4.655 | 46.067 | 2.381 | 1.00 | 92.61 |

TABLE 10-continued

Three-Dimensional Coordinates of *Neisseria gonorrhoeae* GCYH-IB (SEQ. ID. No. 8)

| ATOM | 141 | CD2 | LEU | 146 | −5.349 | 45.825 | 4.792 | 1.00 | 93.10 |
|---|---|---|---|---|---|---|---|---|---|
| ATOM | 142 | N | CYS | 147 | −2.491 | 47.129 | 6.639 | 1.00 | 94.85 |
| ATOM | 143 | CA | CYS | 147 | −2.704 | 47.545 | 8.023 | 1.00 | 95.44 |
| ATOM | 144 | C | CYS | 147 | −4.145 | 47.388 | 8.502 | 1.00 | 95.11 |
| ATOM | 145 | O | CYS | 147 | −5.049 | 48.015 | 7.955 | 1.00 | 95.12 |
| ATOM | 146 | CB | CYS | 147 | −2.269 | 49.000 | 8.216 | 1.00 | 96.58 |
| ATOM | 147 | SG | CYS | 147 | −2.408 | 49.540 | 9.928 | 1.00 | 97.39 |
| ATOM | 148 | N | PRO | 148 | −4.354 | 46.570 | 9.550 | 1.00 | 94.79 |
| ATOM | 149 | CA | PRO | 148 | −5.687 | 46.343 | 10.123 | 1.00 | 94.46 |
| ATOM | 150 | C | PRO | 148 | −6.311 | 47.616 | 10.712 | 1.00 | 95.13 |
| ATOM | 151 | O | PRO | 148 | −7.500 | 47.853 | 10.497 | 1.00 | 94.91 |
| ATOM | 152 | CB | PRO | 148 | −5.425 | 45.315 | 11.233 | 1.00 | 94.10 |
| ATOM | 153 | CG | PRO | 148 | −4.110 | 44.703 | 10.900 | 1.00 | 93.98 |
| ATOM | 154 | CD | PRO | 148 | −3.320 | 45.797 | 10.256 | 1.00 | 94.69 |
| ATOM | 155 | N | CYS | 149 | −5.524 | 48.414 | 11.438 | 1.00 | 95.97 |
| ATOM | 156 | CA | CYS | 149 | −6.015 | 49.657 | 12.031 | 1.00 | 96.73 |
| ATOM | 157 | C | CYS | 149 | −6.454 | 50.656 | 10.961 | 1.00 | 97.03 |
| ATOM | 158 | O | CYS | 149 | −7.487 | 51.309 | 11.100 | 1.00 | 97.11 |
| ATOM | 159 | CB | CYS | 149 | −4.953 | 50.289 | 12.937 | 1.00 | 0.39 |
| ATOM | 160 | SG | CYS | 149 | −5.365 | 51.972 | 13.513 | 1.00 | 98.92 |
| ATOM | 161 | N | SER | 150 | −5.661 | 50.766 | 9.897 | 1.00 | 97.14 |
| ATOM | 162 | CA | SER | 150 | −5.968 | 51.645 | 8.773 | 1.00 | 97.32 |
| ATOM | 163 | C | SER | 150 | −7.297 | 51.284 | 8.122 | 1.00 | 96.45 |
| ATOM | 164 | O | SER | 150 | −8.116 | 52.156 | 7.844 | 1.00 | 96.62 |
| ATOM | 165 | CB | SER | 150 | −4.853 | 51.566 | 7.731 | 1.00 | 97.36 |
| ATOM | 166 | OG | SER | 150 | −5.142 | 52.369 | 6.603 | 1.00 | 97.43 |
| ATOM | 167 | N | LYS | 151 | −7.494 | 49.991 | 7.874 | 1.00 | 95.57 |
| ATOM | 168 | CA | LYS | 151 | −8.742 | 49.474 | 7.308 | 1.00 | 94.80 |
| ATOM | 169 | C | LYS | 151 | −9.939 | 49.737 | 8.227 | 1.00 | 94.79 |
| ATOM | 170 | O | LYS | 151 | −10.957 | 50.290 | 7.802 | 1.00 | 94.68 |
| ATOM | 171 | CB | LYS | 151 | −8.611 | 47.970 | 7.039 | 1.00 | 94.03 |
| ATOM | 172 | CG | LYS | 151 | −9.884 | 47.324 | 6.534 | 1.00 | 93.37 |
| ATOM | 173 | CD | LYS | 151 | −9.763 | 45.813 | 6.462 | 1.00 | 92.78 |
| ATOM | 174 | CE | LYS | 151 | −11.067 | 45.208 | 5.973 | 1.00 | 92.30 |
| ATOM | 175 | NZ | LYS | 151 | −11.016 | 43.734 | 5.900 | 1.00 | 91.85 |
| ATOM | 176 | N | GLU | 152 | −9.789 | 49.335 | 9.486 | 1.00 | 94.88 |
| ATOM | 177 | CA | GLU | 152 | −10.808 | 49.477 | 10.524 | 1.00 | 99.88 |
| ATOM | 178 | C | GLU | 152 | −11.333 | 50.906 | 10.726 | 1.00 | 95.41 |
| ATOM | 179 | O | GLU | 152 | −12.530 | 51.111 | 10.933 | 1.00 | 95.13 |
| ATOM | 180 | CB | GLU | 152 | −10.246 | 48.940 | 11.842 | 1.00 | 0.77 |
| ATOM | 181 | CG | GLU | 152 | −11.165 | 49.055 | 13.038 | 1.00 | 0.86 |
| ATOM | 182 | CD | GLU | 152 | −10.473 | 48.628 | 14.318 | 1.00 | 0.48 |
| ATOM | 183 | OE1 | GLU | 152 | −9.369 | 49.144 | 14.596 | 1.00 | 0.36 |
| ATOM | 184 | OE2 | GLU | 152 | −11.028 | 47.776 | 15.043 | 1.00 | 0.55 |
| ATOM | 185 | N | ILE | 153 | −10.440 | 51.891 | 10.668 | 1.00 | 98.72 |
| ATOM | 186 | CA | ILE | 153 | −10.815 | 53.268 | 10.987 | 1.00 | 0.24 |
| ATOM | 187 | C | ILE | 153 | −11.296 | 54.104 | 9.797 | 1.00 | 97.15 |
| ATOM | 188 | O | ILE | 153 | −11.995 | 55.100 | 9.988 | 1.00 | 97.36 |
| ATOM | 189 | CB | ILE | 153 | −9.682 | 54.036 | 11.722 | 1.00 | 98.13 |
| ATOM | 190 | CG1 | ILE | 153 | −8.480 | 54.248 | 10.800 | 1.00 | 98.60 |
| ATOM | 191 | CG2 | ILE | 153 | −9.289 | 53.320 | 13.006 | 1.00 | 98.08 |
| ATOM | 192 | CD1 | ILE | 153 | −7.425 | 55.156 | 11.380 | 1.00 | 99.90 |
| ATOM | 193 | N | SER | 154 | −10.928 | 53.719 | 8.579 | 1.00 | 96.66 |
| ATOM | 194 | CA | SER | 154 | −11.331 | 54.502 | 7.411 | 1.00 | 96.63 |
| ATOM | 195 | C | SER | 154 | −12.547 | 53.901 | 6.712 | 1.00 | 95.64 |
| ATOM | 196 | O | SER | 154 | −12.783 | 52.693 | 6.793 | 1.00 | 94.99 |
| ATOM | 197 | CB | SER | 154 | −10.164 | 54.702 | 6.436 | 1.00 | 96.93 |
| ATOM | 198 | OG | SER | 154 | −9.523 | 53.481 | 6.138 | 1.00 | 96.38 |
| ATOM | 199 | N | GLN | 155 | −13.323 | 54.750 | 6.043 | 1.00 | 95.57 |
| ATOM | 200 | CA | GLN | 155 | −14.556 | 54.309 | 5.394 | 1.00 | 94.71 |
| ATOM | 201 | C | GLN | 155 | −14.265 | 53.543 | 4.110 | 1.00 | 94.12 |
| ATOM | 202 | O | GLN | 155 | −15.114 | 52.804 | 3.607 | 1.00 | 93.43 |
| ATOM | 203 | CB | GLN | 155 | −15.493 | 55.490 | 5.126 | 1.00 | 0.29 |
| ATOM | 204 | CG | GLN | 155 | −14.877 | 56.622 | 4.320 | 1.00 | 0.53 |
| ATOM | 205 | CD | GLN | 155 | −15.866 | 57.739 | 4.039 | 1.00 | 0.79 |
| ATOM | 206 | OE1 | GLN | 155 | −17.047 | 57.492 | 3.786 | 1.00 | 0.94 |
| ATOM | 207 | NE2 | GLN | 155 | −15.387 | 58.976 | 4.080 | 1.00 | 0.95 |
| ATOM | 208 | N | TYR | 156 | −13.058 | 53.733 | 3.586 | 1.00 | 94.45 |
| ATOM | 209 | CA | TYR | 156 | −12.548 | 52.923 | 2.483 | 1.00 | 93.90 |
| ATOM | 210 | C | TYR | 156 | −11.030 | 52.991 | 2.429 | 1.00 | 95.21 |
| ATOM | 211 | O | TYR | 156 | −10.417 | 53.882 | 3.023 | 1.00 | 95.22 |
| ATOM | 212 | CB | TYR | 156 | −13.154 | 53.337 | 1.136 | 1.00 | 93.42 |
| ATOM | 213 | CG | TYR | 156 | −13.397 | 54.821 | 0.969 | 1.00 | 96.29 |
| ATOM | 214 | CD1 | TYR | 156 | −12.340 | 55.724 | 0.952 | 1.00 | 94.61 |
| ATOM | 215 | CD2 | TYR | 156 | −14.688 | 55.316 | 0.804 | 1.00 | 93.79 |
| ATOM | 216 | CE1 | TYR | 156 | −12.565 | 57.086 | 0.793 | 1.00 | 0.99 |
| ATOM | 217 | CE2 | TYR | 156 | −14.923 | 56.671 | 0.643 | 1.00 | 0.56 |
| ATOM | 218 | CZ | TYR | 156 | −13.859 | 57.554 | 0.638 | 1.00 | 0.71 |

TABLE 10-continued

Three-Dimensional Coordinates of *Neisseria gonorrhoeae* GCYH-IB (SEQ. ID. No. 8)

| ATOM | 219 | OH | TYR | 156 | −14.088 | 58.902 | 0.475 | 1.00 | 0.86 |
|------|-----|-----|-----|-----|---------|--------|-------|------|-------|
| ATOM | 220 | N | GLY | 157 | −10.430 | 52.039 | 1.721 | 1.00 | 93.87 |
| ATOM | 221 | CA | GLY | 157 | −8.989 | 51.991 | 1.574 | 1.00 | 94.19 |
| ATOM | 222 | C | GLY | 157 | −8.289 | 51.501 | 2.826 | 1.00 | 94.61 |
| ATOM | 223 | O | GLY | 157 | −8.860 | 51.502 | 3.914 | 1.00 | 94.83 |
| ATOM | 224 | N | ALA | 158 | −7.044 | 51.068 | 2.658 | 1.00 | 94.67 |
| ATOM | 225 | CA | ALA | 158 | −6.180 | 50.692 | 3.770 | 1.00 | 95.10 |
| ATOM | 226 | C | ALA | 158 | −4.752 | 50.803 | 3.273 | 1.00 | 95.37 |
| ATOM | 227 | O | ALA | 158 | −4.422 | 50.276 | 2.213 | 1.00 | 94.74 |
| ATOM | 228 | CB | ALA | 158 | −6.473 | 49.274 | 4.229 | 1.00 | 94.43 |
| ATOM | 229 | N | HIS | 159 | −3.899 | 51.503 | 4.008 | 1.00 | 96.33 |
| ATOM | 230 | CA | HIS | 159 | −2.535 | 51.633 | 3.536 | 1.00 | 96.64 |
| ATOM | 231 | C | HIS | 159 | −1.857 | 50.268 | 3.619 | 1.00 | 95.96 |
| ATOM | 232 | O | HIS | 159 | −2.001 | 49.541 | 4.602 | 1.00 | 95.83 |
| ATOM | 233 | CB | HIS | 159 | −1.756 | 52.732 | 4.276 | 1.00 | 97.98 |
| ATOM | 234 | CG | HIS | 159 | −1.206 | 52.306 | 5.598 | 1.00 | 98.41 |
| ATOM | 235 | ND1 | HIS | 159 | −0.055 | 51.560 | 5.717 | 1.00 | 98.28 |
| ATOM | 236 | CD2 | HIS | 159 | −1.641 | 52.534 | 6.855 | 1.00 | 98.92 |
| ATOM | 237 | CE1 | HIS | 159 | 0.190 | 51.333 | 6.996 | 1.00 | 98.69 |
| ATOM | 238 | NE2 | HIS | 159 | −0.758 | 51.915 | 7.704 | 1.00 | 99.08 |
| ATOM | 239 | N | ASN | 160 | −1.173 | 49.911 | 2.541 | 1.00 | 95.46 |
| ATOM | 240 | CA | ASN | 160 | −0.370 | 48.706 | 2.495 | 1.00 | 94.85 |
| ATOM | 241 | C | ASN | 160 | 1.022 | 49.070 | 2.001 | 1.00 | 95.19 |
| ATOM | 242 | O | ASN | 160 | 1.264 | 50.211 | 1.603 | 1.00 | 95.86 |
| ATOM | 243 | CB | ASN | 160 | −1.025 | 47.634 | 1.613 | 1.00 | 93.70 |
| ATOM | 244 | CG | ASN | 160 | −1.510 | 48.175 | 0.286 | 1.00 | 93.37 |
| ATOM | 245 | OD1 | ASN | 160 | −2.673 | 48.552 | 0.146 | 1.00 | 93.31 |
| ATOM | 246 | ND2 | ASN | 160 | −0.626 | 48.206 | −0.699 | 1.00 | 93.09 |
| ATOM | 247 | N | GLN | 161 | 1.941 | 48.113 | 2.045 | 1.00 | 94.75 |
| ATOM | 248 | CA | GLN | 161 | 3.318 | 48.378 | 1.664 | 1.00 | 95.04 |
| ATOM | 249 | C | GLN | 161 | 4.075 | 47.079 | 1.518 | 1.00 | 94.19 |
| ATOM | 250 | O | GLN | 161 | 3.591 | 46.011 | 1.909 | 1.00 | 93.54 |
| ATOM | 251 | CB | GLN | 161 | 4.010 | 49.243 | 2.717 | 1.00 | 96.35 |
| ATOM | 252 | CG | GLN | 161 | 3.950 | 48.667 | 4.121 | 1.00 | 96.52 |
| ATOM | 253 | CD | GLN | 161 | 2.646 | 48.992 | 4.833 | 1.00 | 96.74 |
| ATOM | 254 | OE1 | GLN | 161 | 2.166 | 50.125 | 4.783 | 1.00 | 97.47 |
| ATOM | 255 | NE2 | GLN | 161 | 2.069 | 47.998 | 5.504 | 1.00 | 96.11 |
| ATOM | 256 | N | ARG | 162 | 5.267 | 47.176 | 0.948 | 1.00 | 94.19 |
| ATOM | 257 | CA | ARG | 162 | 6.137 | 46.029 | 0.884 | 1.00 | 93.45 |
| ATOM | 258 | C | ARG | 162 | 6.698 | 45.798 | 2.278 | 1.00 | 94.02 |
| ATOM | 259 | O | ARG | 162 | 6.983 | 46.742 | 3.020 | 1.00 | 95.15 |
| ATOM | 260 | CB | ARG | 162 | 7.251 | 46.234 | −0.145 | 1.00 | 93.25 |
| ATOM | 261 | CG | ARG | 162 | 7.743 | 44.935 | −0.778 | 1.00 | 92.02 |
| ATOM | 262 | CD | ARG | 162 | 8.796 | 45.188 | −1.840 | 1.00 | 0.01 |
| ATOM | 263 | NE | ARG | 162 | 8.231 | 45.757 | −3.059 | 1.00 | 91.42 |
| ATOM | 264 | CZ | ARG | 162 | 8.945 | 46.401 | −3.976 | 1.00 | 93.79 |
| ATOM | 265 | NH1 | ARG | 162 | 10.251 | 46.567 | −3.806 | 1.00 | 91.78 |
| ATOM | 266 | NH2 | ARG | 162 | 8.353 | 46.885 | −5.059 | 1.00 | 91.03 |
| ATOM | 267 | N | SER | 163 | 6.811 | 44.524 | 2.632 | 1.00 | 47.09 |
| ATOM | 268 | CA | SER | 163 | 7.414 | 44.106 | 3.886 | 1.00 | 43.85 |
| ATOM | 269 | C | SER | 163 | 8.524 | 43.090 | 3.595 | 1.00 | 48.09 |
| ATOM | 270 | O | SER | 163 | 8.397 | 42.276 | 2.694 | 1.00 | 43.99 |
| ATOM | 271 | CB | SER | 163 | 6.325 | 43.515 | 4.786 | 1.00 | 51.94 |
| ATOM | 272 | OG | SER | 163 | 6.868 | 42.925 | 5.949 | 1.00 | 81.97 |
| ATOM | 273 | N | HIS | 164 | 9.624 | 43.166 | 4.336 | 1.00 | 37.14 |
| ATOM | 274 | CA | HIS | 164 | 10.651 | 42.146 | 4.270 | 1.00 | 35.94 |
| ATOM | 275 | C | HIS | 164 | 10.540 | 41.311 | 5.529 | 1.00 | 43.89 |
| ATOM | 276 | O | HIS | 164 | 10.570 | 41.836 | 6.643 | 1.00 | 42.93 |
| ATOM | 277 | CB | HIS | 164 | 12.044 | 42.772 | 4.153 | 1.00 | 49.63 |
| ATOM | 278 | CG | HIS | 164 | 12.264 | 43.502 | 2.857 | 1.00 | 73.84 |
| ATOM | 279 | ND1 | HIS | 164 | 13.125 | 44.582 | 2.748 | 1.00 | 79.92 |
| ATOM | 280 | CD2 | HIS | 164 | 11.732 | 43.318 | 1.632 | 1.00 | 68.49 |
| ATOM | 281 | CE1 | HIS | 164 | 13.114 | 45.016 | 1.501 | 1.00 | 79.23 |
| ATOM | 282 | NE2 | HIS | 164 | 12.279 | 44.271 | 0.797 | 1.00 | 71.70 |
| ATOM | 283 | N | GLU | 178 | 13.020 | 26.531 | −0.097 | 1.00 | 46.89 |
| ATOM | 284 | CA | GLU | 178 | 11.633 | 26.683 | −0.524 | 1.00 | 46.96 |
| ATOM | 285 | C | GLU | 178 | 10.657 | 26.422 | 0.622 | 1.00 | 50.17 |
| ATOM | 286 | O | GLU | 178 | 9.596 | 27.029 | 0.679 | 1.00 | 54.75 |
| ATOM | 287 | CB | GLU | 178 | 11.331 | 25.803 | −1.744 | 1.00 | 44.87 |
| ATOM | 288 | CG | GLU | 178 | 11.198 | 24.305 | −1.443 | 1.00 | 70.11 |
| ATOM | 289 | CD | GLU | 178 | 12.503 | 23.640 | −1.010 | 1.00 | 73.32 |
| ATOM | 290 | OE1 | GLU | 178 | 13.597 | 24.158 | −1.347 | 1.00 | 65.34 |
| ATOM | 291 | OE2 | GLU | 178 | 12.423 | 22.588 | −0.339 | 1.00 | 68.91 |
| ATOM | 292 | N | GLU | 179 | 11.035 | 25.555 | 1.554 | 1.00 | 41.96 |
| ATOM | 293 | CA | GLU | 179 | 10.211 | 25.309 | 2.743 | 1.00 | 45.73 |
| ATOM | 294 | C | GLU | 179 | 10.130 | 26.536 | 3.642 | 1.00 | 38.32 |
| ATOM | 295 | O | GLU | 179 | 9.075 | 26.827 | 4.202 | 1.00 | 50.81 |
| ATOM | 296 | CB | GLU | 179 | 10.750 | 24.149 | 3.585 | 1.00 | 42.76 |

TABLE 10-continued

Three-Dimensional Coordinates of *Neisseria gonorrhoeae* GCYH-IB (SEQ. ID. No. 8)

| | | | | | | | | | |
|---|---|---|---|---|---|---|---|---|---|
| ATOM | 297 | CG | GLU | 179 | 10.771 | 22.791 | 2.920 | 1.00 | 64.32 |
| ATOM | 298 | CD | GLU | 179 | 11.114 | 21.682 | 3.911 | 1.00 | 77.87 |
| ATOM | 299 | OE1 | GLU | 179 | 10.229 | 21.300 | 4.717 | 1.00 | 65.15 |
| ATOM | 300 | OE2 | GLU | 179 | 12.270 | 21.195 | 3.887 | 1.00 | 62.58 |
| ATOM | 301 | N | VAL | 180 | 11.254 | 27.239 | 3.814 | 1.00 | 33.17 |
| ATOM | 302 | CA | VAL | 180 | 11.223 | 28.446 | 4.624 | 1.00 | 34.71 |
| ATOM | 303 | C | VAL | 180 | 10.415 | 29.555 | 3.927 | 1.00 | 41.23 |
| ATOM | 304 | O | VAL | 180 | 9.639 | 30.264 | 4.553 | 1.00 | 37.41 |
| ATOM | 305 | CB | VAL | 180 | 12.630 | 28.940 | 5.018 | 1.00 | 41.02 |
| ATOM | 306 | CG1 | VAL | 180 | 12.522 | 30.238 | 5.761 | 1.00 | 39.39 |
| ATOM | 307 | CG2 | VAL | 180 | 13.319 | 27.924 | 5.867 | 1.00 | 44.36 |
| ATOM | 308 | N | ILE | 181 | 10.571 | 29.676 | 2.622 | 1.00 | 38.53 |
| ATOM | 309 | CA | ILE | 181 | 9.757 | 30.616 | 1.864 | 1.00 | 36.63 |
| ATOM | 310 | C | ILE | 181 | 8.243 | 30.322 | 2.002 | 1.00 | 51.18 |
| ATOM | 311 | O | ILE | 181 | 7.433 | 31.246 | 2.155 | 1.00 | 44.19 |
| ATOM | 312 | CB | ILE | 181 | 10.171 | 30.637 | 0.377 | 1.00 | 35.04 |
| ATOM | 313 | CG1 | ILE | 181 | 11.587 | 31.220 | 0.239 | 1.00 | 31.82 |
| ATOM | 314 | CG2 | ILE | 181 | 9.132 | 31.388 | −0.457 | 1.00 | 30.75 |
| ATOM | 315 | CD1 | ILE | 181 | 12.198 | 31.128 | −1.161 | 1.00 | 38.43 |
| ATOM | 316 | N | ASP | 182 | 7.879 | 29.038 | 1.964 | 1.00 | 40.80 |
| ATOM | 317 | CA | ASP | 182 | 6.476 | 28.607 | 2.095 | 1.00 | 38.01 |
| ATOM | 318 | C | ASP | 182 | 5.902 | 28.943 | 3.478 | 1.00 | 44.33 |
| ATOM | 319 | O | ASP | 182 | 4.818 | 29.503 | 3.578 | 1.00 | 43.19 |
| ATOM | 320 | CB | ASP | 182 | 6.324 | 27.116 | 1.775 | 1.00 | 37.87 |
| ATOM | 321 | CG | ASP | 182 | 6.455 | 26.819 | 0.275 | 1.00 | 61.34 |
| ATOM | 322 | OD1 | ASP | 182 | 6.189 | 27.723 | −0.553 | 1.00 | 62.93 |
| ATOM | 323 | OD2 | ASP | 182 | 6.823 | 25.677 | −0.086 | 1.00 | 58.69 |
| ATOM | 324 | N | TYR | 183 | 6.643 | 28.636 | 4.539 | 1.00 | 37.99 |
| ATOM | 325 | CA | TYR | 183 | 6.211 | 29.031 | 5.878 | 1.00 | 39.70 |
| ATOM | 326 | C | TYR | 183 | 5.865 | 30.510 | 5.957 | 1.00 | 52.99 |
| ATOM | 327 | O | TYR | 183 | 4.984 | 30.910 | 6.708 | 1.00 | 53.89 |
| ATOM | 328 | CB | TYR | 183 | 7.279 | 28.739 | 6.934 | 1.00 | 39.65 |
| ATOM | 329 | CG | TYR | 183 | 7.415 | 27.289 | 7.330 | 1.00 | 55.07 |
| ATOM | 330 | CD1 | TYR | 183 | 6.300 | 26.457 | 7.413 | 1.00 | 60.10 |
| ATOM | 331 | CD2 | TYR | 183 | 8.655 | 26.756 | 7.651 | 1.00 | 44.43 |
| ATOM | 332 | CE1 | TYR | 183 | 6.421 | 25.130 | 7.783 | 1.00 | 73.20 |
| ATOM | 333 | CE2 | TYR | 183 | 8.787 | 25.438 | 8.028 | 1.00 | 60.20 |
| ATOM | 334 | CZ | TYR | 183 | 7.667 | 24.625 | 8.092 | 1.00 | 70.47 |
| ATOM | 335 | OH | TYR | 183 | 7.796 | 23.310 | 8.471 | 1.00 | 74.31 |
| ATOM | 336 | N | VAL | 184 | 6.571 | 31.335 | 5.201 | 1.00 | 40.52 |
| ATOM | 337 | CA | VAL | 184 | 6.324 | 32.765 | 5.295 | 1.00 | 41.20 |
| ATOM | 338 | C | VAL | 184 | 5.186 | 33.230 | 4.386 | 1.00 | 41.72 |
| ATOM | 339 | O | VAL | 184 | 4.304 | 33.957 | 4.826 | 1.00 | 46.40 |
| ATOM | 340 | CB | VAL | 184 | 7.604 | 33.624 | 5.056 | 1.00 | 39.23 |
| ATOM | 341 | CG1 | VAL | 184 | 7.230 | 35.090 | 4.946 | 1.00 | 44.52 |
| ATOM | 342 | CG2 | VAL | 184 | 8.605 | 33.419 | 6.185 | 1.00 | 37.38 |
| ATOM | 343 | N | GLU | 185 | 5.203 | 32.810 | 3.131 | 1.00 | 37.33 |
| ATOM | 344 | CA | GLU | 185 | 4.293 | 33.381 | 2.156 | 1.00 | 40.53 |
| ATOM | 345 | C | GLU | 185 | 2.849 | 32.980 | 2.472 | 1.00 | 58.15 |
| ATOM | 346 | O | GLU | 185 | 1.911 | 33.744 | 2.225 | 1.00 | 63.95 |
| ATOM | 347 | CB | GLU | 185 | 4.712 | 32.994 | 0.739 | 1.00 | 37.22 |
| ATOM | 348 | CG | GLU | 185 | 5.944 | 33.751 | 0.253 | 1.00 | 56.36 |
| ATOM | 349 | CD | GLU | 185 | 6.302 | 33.436 | −1.188 | 1.00 | 58.49 |
| ATOM | 350 | OE1 | GLU | 185 | 5.913 | 32.355 | −1.673 | 1.00 | 54.54 |
| ATOM | 351 | OE2 | GLU | 185 | 6.981 | 34.265 | −1.837 | 1.00 | 55.30 |
| ATOM | 352 | N | THR | 186 | 2.705 | 31.785 | 3.040 | 1.00 | 58.75 |
| ATOM | 353 | CA | THR | 186 | 1.442 | 31.267 | 3.556 | 1.00 | 61.49 |
| ATOM | 354 | C | THR | 186 | 0.776 | 32.254 | 4.505 | 1.00 | 55.72 |
| ATOM | 355 | O | THR | 186 | −0.429 | 32.446 | 4.459 | 1.00 | 61.05 |
| ATOM | 356 | CB | THR | 186 | 1.684 | 29.940 | 4.309 | 1.00 | 61.83 |
| ATOM | 357 | OG1 | THR | 186 | 1.715 | 28.860 | 3.369 | 1.00 | 68.11 |
| ATOM | 358 | CG2 | THR | 186 | 0.603 | 29.690 | 5.335 | 1.00 | 71.42 |
| ATOM | 359 | N | GLN | 187 | 1.581 | 32.898 | 5.339 | 1.00 | 77.31 |
| ATOM | 360 | CA | GLN | 187 | 1.078 | 33.768 | 6.393 | 1.00 | 77.26 |
| ATOM | 361 | C | GLN | 187 | 0.934 | 35.245 | 6.009 | 1.00 | 76.67 |
| ATOM | 362 | O | GLN | 187 | 0.447 | 36.044 | 6.804 | 1.00 | 76.96 |
| ATOM | 363 | CB | GLN | 187 | 2.001 | 33.671 | 7.606 | 1.00 | 76.96 |
| ATOM | 364 | CG | GLN | 187 | 2.215 | 32.274 | 8.095 | 1.00 | 77.69 |
| ATOM | 365 | CD | GLN | 187 | 0.969 | 31.712 | 8.695 | 1.00 | 79.02 |
| ATOM | 366 | OE1 | GLN | 187 | 0.067 | 32.456 | 9.079 | 1.00 | 79.37 |
| ATOM | 367 | NE2 | GLN | 187 | 0.901 | 30.393 | 8.786 | 1.00 | 80.11 |
| ATOM | 368 | N | ALA | 188 | 1.372 | 35.626 | 4.818 | 1.00 | 76.11 |
| ATOM | 369 | CA | ALA | 188 | 1.357 | 37.045 | 4.464 | 1.00 | 75.76 |
| ATOM | 370 | C | ALA | 188 | −0.046 | 37.533 | 4.083 | 1.00 | 76.42 |
| ATOM | 371 | O | ALA | 188 | −0.874 | 36.743 | 3.629 | 1.00 | 76.99 |
| ATOM | 372 | CB | ALA | 188 | 2.356 | 37.333 | 3.344 | 1.00 | 75.21 |
| ATOM | 373 | N | SER | 189 | −0.303 | 38.828 | 4.291 | 1.00 | 76.61 |
| ATOM | 374 | CA | SER | 189 | −1.531 | 39.468 | 3.819 | 1.00 | 77.40 |

TABLE 10-continued

Three-Dimensional Coordinates of *Neisseria gonorrhoeae* GCYH-IB (SEQ. ID. No. 8)

| ATOM | 375 | C | SER | 189 | −1.704 | 39.111 | 2.359 | 1.00 | 79.46 |
|---|---|---|---|---|---|---|---|---|---|
| ATOM | 376 | O | SER | 189 | −2.789 | 38.688 | 1.933 | 1.00 | 77.83 |
| ATOM | 377 | CB | SER | 189 | −1.461 | 40.989 | 3.965 | 1.00 | 77.73 |
| ATOM | 378 | OG | SER | 189 | −1.641 | 41.380 | 5.308 | 1.00 | 78.51 |
| ATOM | 379 | N | CYS | 190 | −0.625 | 39.300 | 1.602 | 1.00 | 76.27 |
| ATOM | 380 | CA | CYS | 190 | −0.481 | 38.684 | 0.291 | 1.00 | 76.02 |
| ATOM | 381 | C | CYS | 190 | 0.975 | 38.648 | −0.155 | 1.00 | 75.41 |
| ATOM | 382 | O | CYS | 190 | 1.801 | 39.427 | 0.313 | 1.00 | 75.21 |
| ATOM | 383 | CB | CYS | 190 | −1.348 | 39.366 | −0.766 | 1.00 | 91.77 |
| ATOM | 384 | SG | CYS | 190 | −1.875 | 38.213 | −2.080 | 1.00 | 98.91 |
| ATOM | 385 | N | GLN | 191 | 1.288 | 37.729 | −1.057 | 1.00 | 75.45 |
| ATOM | 386 | CA | GLN | 191 | 2.659 | 37.583 | −1.525 | 1.00 | 75.31 |
| ATOM | 387 | C | GLN | 191 | 2.889 | 38.390 | −2.799 | 1.00 | 75.40 |
| ATOM | 388 | O | GLN | 191 | 1.942 | 38.898 | −3.402 | 1.00 | 75.47 |
| ATOM | 389 | CB | GLN | 191 | 2.998 | 36.104 | −1.730 | 1.00 | 75.73 |
| ATOM | 390 | CG | GLN | 191 | 1.820 | 35.273 | −2.190 | 1.00 | 76.28 |
| ATOM | 391 | CD | GLN | 191 | 2.140 | 33.805 | −2.240 | 1.00 | 80.40 |
| ATOM | 392 | OE1 | GLN | 191 | 2.850 | 33.343 | −3.133 | 1.00 | 77.60 |
| ATOM | 393 | NE2 | GLN | 191 | 1.612 | 33.055 | −1.280 | 1.00 | 81.30 |
| ATOM | 394 | N | LEU | 192 | 4.153 | 38.514 | −3.192 | 1.00 | 75.60 |
| ATOM | 395 | CA | LEU | 192 | 4.528 | 39.279 | −4.379 | 1.00 | 75.98 |
| ATOM | 396 | C | LEU | 192 | 4.661 | 38.382 | −5.608 | 1.00 | 76.53 |
| ATOM | 397 | O | LEU | 192 | 4.959 | 37.193 | −5.494 | 1.00 | 76.85 |
| ATOM | 398 | CB | LEU | 192 | 5.842 | 40.025 | −4.138 | 1.00 | 76.39 |
| ATOM | 399 | CG | LEU | 192 | 5.866 | 40.989 | −2.956 | 1.00 | 76.19 |
| ATOM | 400 | CD1 | LEU | 192 | 7.208 | 41.684 | −2.866 | 1.00 | 76.97 |
| ATOM | 401 | CD2 | LEU | 192 | 4.755 | 42.001 | −3.089 | 1.00 | 76.14 |
| ATOM | 402 | N | TYR | 193 | 4.425 | 38.961 | −6.781 | 1.00 | 76.83 |
| ATOM | 403 | CA | TYR | 193 | 4.630 | 38.265 | −8.048 | 1.00 | 77.60 |
| ATOM | 404 | C | TYR | 193 | 5.343 | 39.205 | −9.011 | 1.00 | 78.30 |
| ATOM | 405 | O | TYR | 193 | 5.185 | 40.423 | −8.930 | 1.00 | 78.11 |
| ATOM | 406 | CB | TYR | 193 | 3.297 | 37.800 | −8.653 | 1.00 | 77.49 |
| ATOM | 407 | CG | TYR | 193 | 2.511 | 36.841 | −7.782 | 1.00 | 77.25 |
| ATOM | 408 | CD1 | TYR | 193 | 2.701 | 35.469 | −7.877 | 1.00 | 78.00 |
| ATOM | 409 | CD2 | TYR | 193 | 1.572 | 37.311 | −6.865 | 1.00 | 76.63 |
| ATOM | 410 | CE1 | TYR | 193 | 1.984 | 34.591 | −7.083 | 1.00 | 78.10 |
| ATOM | 411 | CE2 | TYR | 193 | 0.853 | 36.439 | −6.066 | 1.00 | 76.74 |
| ATOM | 412 | CZ | TYR | 193 | 1.064 | 35.081 | −6.183 | 1.00 | 77.46 |
| ATOM | 413 | OH | TYR | 193 | 0.356 | 34.211 | −5.395 | 1.00 | 77.87 |
| ATOM | 414 | N | GLY | 194 | 6.138 | 38.640 | −9.913 | 1.00 | 79.42 |
| ATOM | 415 | CA | GLY | 194 | 6.809 | 39.436 | −10.923 | 1.00 | 80.46 |
| ATOM | 416 | C | GLY | 194 | 5.856 | 39.875 | −12.024 | 1.00 | 80.39 |
| ATOM | 417 | O | GLY | 194 | 5.953 | 40.991 | −12.538 | 1.00 | 90.26 |
| ATOM | 418 | N | LEU | 195 | 4.923 | 38.992 | −12.375 | 1.00 | 80.09 |
| ATOM | 419 | CA | LEU | 195 | 3.999 | 39.222 | −13.483 | 1.00 | 80.50 |
| ATOM | 420 | C | LEU | 195 | 2.545 | 39.011 | −13.058 | 1.00 | 87.63 |
| ATOM | 421 | O | LEU | 195 | 2.166 | 37.913 | −12.639 | 1.00 | 79.12 |
| ATOM | 422 | CB | LEU | 195 | 4.334 | 38.281 | −14.641 | 1.00 | 81.47 |
| ATOM | 423 | CG | LEU | 195 | 3.877 | 38.671 | −16.046 | 1.00 | 82.08 |
| ATOM | 424 | CD1 | LEU | 195 | 4.554 | 37.777 | −17.068 | 1.00 | 83.80 |
| ATOM | 425 | CD2 | LEU | 195 | 2.368 | 38.595 | −16.186 | 1.00 | 91.32 |
| ATOM | 426 | N | LEU | 196 | 1.737 | 40.062 | −13.180 | 1.00 | 78.72 |
| ATOM | 427 | CA | LEU | 196 | 0.314 | 39.992 | −12.863 | 1.00 | 78.17 |
| ATOM | 428 | C | LEU | 196 | −0.524 | 40.617 | −13.969 | 1.00 | 78.46 |
| ATOM | 429 | O | LEU | 196 | −0.206 | 41.698 | −14.467 | 1.00 | 78.70 |
| ATOM | 430 | CB | LEU | 196 | 0.015 | 40.713 | −11.548 | 1.00 | 77.52 |
| ATOM | 431 | CG | LEU | 196 | 0.682 | 40.179 | −10.285 | 1.00 | 77.15 |
| ATOM | 432 | CD1 | LEU | 196 | 0.482 | 41.140 | −9.125 | 1.00 | 76.76 |
| ATOM | 433 | CD2 | LEU | 196 | 0.132 | 38.806 | −9.961 | 1.00 | 77.20 |
| ATOM | 434 | N | LYS | 197 | −1.600 | 39.937 | −14.347 | 1.00 | 78.62 |
| ATOM | 435 | CA | LYS | 197 | −2.579 | 40.508 | −15.265 | 1.00 | 86.92 |
| ATOM | 436 | C | LYS | 197 | −3.697 | 41.188 | −14.471 | 1.00 | 84.36 |
| ATOM | 437 | O | LYS | 197 | −3.750 | 41.064 | −13.250 | 1.00 | 78.30 |
| ATOM | 438 | CB | LYS | 197 | −3.149 | 39.426 | −16.187 | 1.00 | 87.85 |
| ATOM | 439 | CG | LYS | 197 | −2.125 | 38.825 | −17.140 | 1.00 | 97.73 |
| ATOM | 440 | CD | LYS | 197 | −1.043 | 39.843 | −17.481 | 1.00 | 0.65 |
| ATOM | 441 | CE | LYS | 197 | −0.395 | 39.561 | −18.825 | 1.00 | 0.58 |
| ATOM | 442 | NZ | LYS | 197 | −1.184 | 40.154 | −19.939 | 1.00 | 0.14 |
| ATOM | 443 | N | ARG | 198 | −4.582 | 41.901 | −15.165 | 1.00 | 79.02 |
| ATOM | 444 | CA | ARG | 198 | −5.703 | 42.597 | −14.523 | 1.00 | 88.62 |
| ATOM | 445 | C | ARG | 198 | −6.465 | 41.778 | −13.475 | 1.00 | 90.64 |
| ATOM | 446 | O | ARG | 198 | −6.648 | 42.239 | −12.349 | 1.00 | 79.37 |
| ATOM | 447 | CB | ARG | 198 | −6.685 | 43.120 | −15.572 | 1.00 | 95.76 |
| ATOM | 448 | CG | ARG | 198 | −6.523 | 44.581 | −15.908 | 1.00 | 0.91 |
| ATOM | 449 | CD | ARG | 198 | −7.421 | 44.960 | −17.070 | 1.00 | 0.94 |
| ATOM | 450 | NE | ARG | 198 | −7.901 | 46.332 | −16.953 | 1.00 | 0.52 |
| ATOM | 451 | CZ | ARG | 198 | −9.089 | 46.662 | −16.457 | 1.00 | 0.91 |
| ATOM | 452 | NH1 | ARG | 198 | −9.919 | 45.714 | −16.039 | 1.00 | 0.67 |

TABLE 10-continued

Three-Dimensional Coordinates of *Neisseria gonorrhoeae* GCYH-IB (SEQ. ID. No. 8)

| ATOM | 453 | NH2 | ARG | 198 | −9.448 | 47.938 | −16.381 | 1.00 | 0.24 |
|---|---|---|---|---|---|---|---|---|---|
| ATOM | 454 | N | PRO | 199 | −6.933 | 40.572 | −13.848 | 1.00 | 79.78 |
| ATOM | 455 | CA | PRO | 199 | −7.649 | 39.730 | −12.883 | 1.00 | 80.54 |
| ATOM | 456 | C | PRO | 199 | −6.782 | 39.325 | −11.684 | 1.00 | 83.44 |
| ATOM | 457 | O | PRO | 199 | −7.316 | 39.187 | −10.584 | 1.00 | 79.98 |
| ATOM | 458 | CB | PRO | 199 | −8.028 | 38.494 | −13.717 | 1.00 | 81.05 |
| ATOM | 459 | CG | PRO | 199 | −7.080 | 38.518 | −14.878 | 1.00 | 84.72 |
| ATOM | 460 | CD | PRO | 199 | −6.956 | 39.969 | −15.192 | 1.00 | 83.17 |
| ATOM | 461 | N | ASP | 200 | −5.479 | 39.139 | −11.899 | 1.00 | 78.96 |
| ATOM | 462 | CA | ASP | 200 | −4.541 | 38.786 | −10.831 | 1.00 | 78.42 |
| ATOM | 463 | C | ASP | 200 | −4.407 | 39.908 | −9.822 | 1.00 | 79.19 |
| ATOM | 464 | O | ASP | 200 | −4.465 | 39.688 | −8.611 | 1.00 | 77.91 |
| ATOM | 465 | CB | ASP | 200 | −3.155 | 38.515 | −11.407 | 1.00 | 78.13 |
| ATOM | 466 | CG | ASP | 200 | −3.103 | 37.261 | −12.223 | 1.00 | 82.28 |
| ATOM | 467 | OD1 | ASP | 200 | −3.716 | 36.265 | −11.799 | 1.00 | 79.46 |
| ATOM | 468 | OD2 | ASP | 200 | −2.441 | 37.268 | −13.280 | 1.00 | 87.15 |
| ATOM | 469 | N | GLU | 201 | −4.191 | 41.111 | −10.343 | 1.00 | 77.87 |
| ATOM | 470 | CA | GLU | 201 | −4.068 | 42.309 | −9.527 | 1.00 | 88.08 |
| ATOM | 471 | C | GLU | 201 | −5.343 | 42.577 | −8.731 | 1.00 | 82.38 |
| ATOM | 472 | O | GLU | 201 | −5.280 | 42.941 | −7.557 | 1.00 | 78.63 |
| ATOM | 473 | CB | GLU | 201 | −3.725 | 43.516 | −10.397 | 1.00 | 78.07 |
| ATOM | 474 | CG | GLU | 201 | −3.905 | 44.822 | −9.680 | 1.00 | 82.77 |
| ATOM | 475 | CD | GLU | 201 | −3.066 | 45.919 | −10.263 | 1.00 | 86.32 |
| ATOM | 476 | OE1 | GLU | 201 | −2.758 | 45.880 | −11.473 | 1.00 | 94.84 |
| ATOM | 477 | OE2 | GLU | 201 | −2.716 | 46.823 | −9.491 | 1.00 | 79.42 |
| ATOM | 478 | N | LYS | 202 | −6.497 | 42.401 | −9.370 | 1.00 | 79.23 |
| ATOM | 479 | CA | LYS | 202 | −7.769 | 42.529 | −8.673 | 1.00 | 80.32 |
| ATOM | 480 | C | LYS | 202 | −7.821 | 41.552 | −7.497 | 1.00 | 80.40 |
| ATOM | 481 | O | LYS | 202 | −8.153 | 41.932 | −6.374 | 1.00 | 80.99 |
| ATOM | 482 | CB | LYS | 202 | −8.931 | 42.277 | −9.630 | 1.00 | 81.23 |
| ATOM | 483 | CG | LYS | 202 | −10.249 | 42.104 | −8.921 | 1.00 | 82.74 |
| ATOM | 484 | CD | LYS | 202 | −11.374 | 41.804 | −9.885 | 1.00 | 83.85 |
| ATOM | 485 | CE | LYS | 202 | −12.645 | 41.477 | −9.126 | 1.00 | 85.72 |
| ATOM | 486 | NZ | LYS | 202 | −13.745 | 41.122 | −10.052 | 1.00 | 0.18 |
| ATOM | 487 | N | TYR | 203 | −7.468 | 40.299 | −7.767 | 1.00 | 80.02 |
| ATOM | 488 | CA | TYR | 203 | −7.406 | 39.253 | −6.751 | 1.00 | 80.20 |
| ATOM | 489 | C | TYR | 203 | −6.462 | 39.590 | −5.590 | 1.00 | 79.44 |
| ATOM | 490 | O | TYR | 203 | −6.804 | 39.384 | −4.429 | 1.00 | 79.97 |
| ATOM | 491 | CB | TYR | 203 | −6.983 | 37.931 | −7.399 | 1.00 | 80.10 |
| ATOM | 492 | CG | TYR | 203 | −6.890 | 36.768 | −6.439 | 1.00 | 80.53 |
| ATOM | 493 | CD1 | TYR | 203 | −7.977 | 35.925 | −6.231 | 1.00 | 82.06 |
| ATOM | 494 | CD2 | TYR | 203 | −5.717 | 36.512 | −5.740 | 1.00 | 79.65 |
| ATOM | 495 | CE1 | TYR | 203 | −7.900 | 34.862 | −5.356 | 1.00 | 82.73 |
| ATOM | 496 | CE2 | TYR | 203 | −5.629 | 35.449 | −4.858 | 1.00 | 80.16 |
| ATOM | 497 | CZ | TYR | 203 | −6.724 | 34.626 | −4.673 | 1.00 | 82.73 |
| ATOM | 498 | OH | TYR | 203 | −6.644 | 33.570 | −3.798 | 1.00 | 82.87 |
| ATOM | 499 | N | VAL | 204 | −5.276 | 40.101 | −5.909 | 1.00 | 78.40 |
| ATOM | 500 | CA | VAL | 204 | −4.255 | 40.392 | −4.897 | 1.00 | 87.71 |
| ATOM | 501 | C | VAL | 204 | −4.627 | 41.607 | −4.013 | 1.00 | 78.27 |
| ATOM | 502 | O | VAL | 204 | −4.436 | 41.585 | −2.795 | 1.00 | 78.34 |
| ATOM | 503 | CB | VAL | 204 | −2.831 | 40.525 | −5.553 | 1.00 | 76.92 |
| ATOM | 504 | CG1 | VAL | 204 | −2.497 | 41.967 | −5.901 | 1.00 | 76.96 |
| ATOM | 505 | CG2 | VAL | 204 | −1.766 | 39.942 | −4.663 | 1.00 | 76.41 |
| ATOM | 506 | N | THR | 205 | −5.180 | 42.647 | −4.639 | 1.00 | 78.84 |
| ATOM | 507 | CA | THR | 205 | −5.709 | 43.825 | −3.945 | 1.00 | 79.87 |
| ATOM | 508 | C | THR | 205 | −6.769 | 43.443 | −2.913 | 1.00 | 81.00 |
| ATOM | 509 | O | THR | 205 | −6.703 | 43.850 | −1.752 | 1.00 | 81.54 |
| ATOM | 510 | CB | THR | 205 | −6.358 | 44.817 | −4.951 | 1.00 | 80.67 |
| ATOM | 511 | OG1 | THR | 205 | −5.397 | 45.218 | −5.934 | 1.00 | 79.91 |
| ATOM | 512 | CG2 | THR | 205 | −6.887 | 46.051 | −4.241 | 1.00 | 82.14 |
| ATOM | 513 | N | GLU | 206 | −7.746 | 42.657 | −3.361 | 1.00 | 81.59 |
| ATOM | 514 | CA | GLU | 206 | −8.880 | 42.244 | −2.539 | 1.00 | 83.15 |
| ATOM | 515 | C | GLU | 206 | −8.497 | 41.283 | −1.417 | 1.00 | 82.92 |
| ATOM | 516 | O | GLU | 206 | −8.919 | 41.462 | −0.280 | 1.00 | 84.05 |
| ATOM | 517 | CB | GLU | 206 | −9.965 | 41.628 | −3.420 | 1.00 | 84.07 |
| ATOM | 518 | CG | GLU | 206 | −10.610 | 42.636 | −4.353 | 1.00 | 84.78 |
| ATOM | 519 | CD | GLU | 206 | −11.558 | 42.005 | −5.361 | 1.00 | 0.42 |
| ATOM | 520 | OE1 | GLU | 206 | −11.678 | 40.758 | −5.384 | 1.00 | 0.46 |
| ATOM | 521 | OE2 | GLU | 206 | −12.182 | 42.763 | −6.136 | 1.00 | 98.72 |
| ATOM | 522 | N | LYS | 207 | −7.699 | 40.269 | −1.744 | 1.00 | 81.67 |
| ATOM | 523 | CA | LYS | 207 | −7.228 | 39.284 | −0.769 | 1.00 | 81.45 |
| ATOM | 524 | C | LYS | 207 | −6.425 | 39.920 | 0.378 | 1.00 | 80.95 |
| ATOM | 525 | O | LYS | 207 | −6.573 | 39.531 | 1.535 | 1.00 | 81.57 |
| ATOM | 526 | CB | LYS | 207 | −6.403 | 38.194 | −1.471 | 1.00 | 82.62 |
| ATOM | 527 | CG | LYS | 207 | −5.506 | 37.363 | −0.558 | 1.00 | 0.81 |
| ATOM | 528 | CD | LYS | 207 | −6.286 | 36.288 | 0.185 | 1.00 | 0.19 |
| ATOM | 529 | CE | LYS | 207 | −5.345 | 35.303 | 0.866 | 1.00 | 0.78 |
| ATOM | 530 | NZ | LYS | 207 | −6.089 | 34.185 | 1.511 | 1.00 | 0.10 |

TABLE 10-continued

Three-Dimensional Coordinates of *Neisseria gonorrhoeae* GCYH-IB (SEQ. ID. No. 8)

| ATOM | 531 | N   | ALA | 208 | -5.577  | 40.893 | 0.054  | 1.00 | 80.02 |
|------|-----|-----|-----|-----|---------|--------|--------|------|-------|
| ATOM | 532 | CA  | ALA | 208 | -4.814  | 41.607 | 1.072  | 1.00 | 79.80 |
| ATOM | 533 | C   | ALA | 208 | -5.747  | 42.421 | 1.965  | 1.00 | 81.46 |
| ATOM | 534 | O   | ALA | 208 | -5.570  | 42.469 | 3.184  | 1.00 | 81.88 |
| ATOM | 535 | CB  | ALA | 208 | -3.767  | 42.508 | 0.420  | 1.00 | 78.93 |
| ATOM | 536 | N   | TYR | 209 | -6.740  | 43.056 | 1.344  | 1.00 | 82.59 |
| ATOM | 537 | CA  | TYR | 209 | -7.751  | 43.825 | 2.067  | 1.00 | 84.67 |
| ATOM | 538 | C   | TYR | 209 | -8.516  | 42.947 | 3.062  | 1.00 | 85.92 |
| ATOM | 539 | O   | TYR | 209 | -8.824  | 43.390 | 4.166  | 1.00 | 87.37 |
| ATOM | 540 | CB  | TYR | 209 | -8.716  | 44.510 | 1.090  | 1.00 | 85.82 |
| ATOM | 541 | CG  | TYR | 209 | -9.615  | 45.562 | 1.713  | 1.00 | 88.27 |
| ATOM | 542 | CD1 | TYR | 209 | -9.200  | 46.883 | 1.815  | 1.00 | 88.83 |
| ATOM | 543 | CD2 | TYR | 209 | -10.885 | 45.235 | 2.184  | 1.00 | 90.41 |
| ATOM | 544 | CE1 | TYR | 209 | -10.016 | 47.849 | 2.376  | 1.00 | 91.44 |
| ATOM | 545 | CE2 | TYR | 209 | -11.711 | 46.194 | 2.745  | 1.00 | 93.05 |
| ATOM | 546 | CZ  | TYR | 209 | -11.271 | 47.502 | 2.838  | 1.00 | 94.48 |
| ATOM | 547 | OH  | TYR | 209 | -12.080 | 48.472 | 3.394  | 1.00 | 96.54 |
| ATOM | 548 | N   | GLU | 210 | -8.805  | 41.705 | 2.677  | 1.00 | 85.61 |
| ATOM | 549 | CA  | GLU | 210 | -9.536  | 40.773 | 3.540  | 1.00 | 87.08 |
| ATOM | 550 | C   | GLU | 210 | -8.646  | 40.101 | 4.590  | 1.00 | 86.22 |
| ATOM | 551 | O   | GLU | 210 | -9.142  | 39.463 | 5.520  | 1.00 | 87.58 |
| ATOM | 552 | CB  | GLU | 210 | -10.225 | 39.692 | 2.704  | 1.00 | 87.52 |
| ATOM | 553 | CG  | GLU | 210 | -11.164 | 40.223 | 1.643  | 1.00 | 88.48 |
| ATOM | 554 | CD  | GLU | 210 | -11.399 | 39.226 | 0.522  | 1.00 | 0.19  |
| ATOM | 555 | OE1 | GLU | 210 | -10.915 | 38.075 | 0.625  | 1.00 | 87.54 |
| ATOM | 556 | OE2 | GLU | 210 | -12.070 | 39.599 | -0.467 | 1.00 | 0.58  |
| ATOM | 557 | N   | ASN | 211 | -7.332  | 40.238 | 4.440  | 1.00 | 84.16 |
| ATOM | 558 | CA  | ASN | 211 | -6.404  | 39.611 | 5.372  | 1.00 | 83.31 |
| ATOM | 559 | C   | ASN | 211 | -5.378  | 40.610 | 5.917  | 1.00 | 87.15 |
| ATOM | 560 | O   | ASN | 211 | -4.177  | 40.455 | 5.694  | 1.00 | 80.86 |
| ATOM | 561 | CB  | ASN | 211 | -5.707  | 38.415 | 4.705  | 1.00 | 89.00 |
| ATOM | 562 | CG  | ASN | 211 | -4.924  | 37.566 | 5.692  | 1.00 | 0.16  |
| ATOM | 563 | OD1 | ASN | 211 | -5.325  | 37.402 | 6.848  | 1.00 | 0.17  |
| ATOM | 564 | ND2 | ASN | 211 | -3.799  | 37.018 | 5.236  | 1.00 | 99.78 |
| ATOM | 565 | N   | PRO | 212 | -5.853  | 41.642 | 6.641  | 1.00 | 83.90 |
| ATOM | 566 | CA  | PRO | 212 | -4.944  | 42.647 | 7.205  | 1.00 | 83.57 |
| ATOM | 567 | C   | PRO | 212 | -4.058  | 42.036 | 8.296  | 1.00 | 82.85 |
| ATOM | 568 | O   | PRO | 212 | -4.523  | 41.194 | 9.062  | 1.00 | 83.56 |
| ATOM | 569 | CB  | PRO | 212 | -5.901  | 43.685 | 7.817  | 1.00 | 85.91 |
| ATOM | 570 | CG  | PRO | 212 | -7.256  | 43.349 | 7.287  | 1.00 | 87.27 |
| ATOM | 571 | CD  | PRO | 212 | -7.244  | 41.882 | 7.051  | 1.00 | 86.29 |
| ATOM | 572 | N   | LYS | 213 | -2.796  | 42.447 | 8.356  | 1.00 | 81.66 |
| ATOM | 573 | CA  | LYS | 213 | -1.879  | 41.932 | 9.368  | 1.00 | 81.02 |
| ATOM | 574 | C   | LYS | 213 | -0.847  | 42.956 | 9.811  | 1.00 | 80.90 |
| ATOM | 575 | O   | LYS | 213 | -0.140  | 43.545 | 8.996  | 1.00 | 80.25 |
| ATOM | 576 | CB  | LYS | 213 | -1.174  | 40.659 | 8.888  | 1.00 | 79.48 |
| ATOM | 577 | CG  | LYS | 213 | -1.990  | 39.393 | 9.075  | 1.00 | 80.00 |
| ATOM | 578 | CD  | LYS | 213 | -1.147  | 38.133 | 8.942  | 1.00 | 80.38 |
| ATOM | 579 | CE  | LYS | 213 | -2.048  | 36.915 | 8.819  | 1.00 | 79.77 |
| ATOM | 580 | NZ  | LYS | 213 | -1.310  | 35.630 | 8.798  | 1.00 | 79.21 |
| ATOM | 581 | N   | PHE | 214 | -0.777  | 43.159 | 11.117 | 1.00 | 81.78 |
| ATOM | 582 | CA  | PHE | 214 | 0.279   | 43.940 | 11.712 | 1.00 | 81.81 |
| ATOM | 583 | C   | PHE | 214 | 1.610   | 43.197 | 11.578 | 1.00 | 80.07 |
| ATOM | 584 | O   | PHE | 214 | 1.666   | 41.997 | 11.322 | 1.00 | 79.06 |
| ATOM | 585 | CB  | PHE | 214 | -0.011  | 44.168 | 13.199 | 1.00 | 83.28 |
| ATOM | 586 | CG  | PHE | 214 | -1.127  | 45.146 | 13.477 | 1.00 | 85.59 |
| ATOM | 587 | CD1 | PHE | 214 | -1.079  | 46.442 | 12.980 | 1.00 | 88.35 |
| ATOM | 588 | CD2 | PHE | 214 | -2.205  | 44.780 | 14.265 | 1.00 | 87.15 |
| ATOM | 589 | CE1 | PHE | 214 | -2.096  | 47.345 | 13.248 | 1.00 | 89.02 |
| ATOM | 590 | CE2 | PHE | 214 | -3.217  | 45.680 | 14.536 | 1.00 | 89.66 |
| ATOM | 591 | CZ  | PHE | 214 | -3.163  | 46.962 | 14.027 | 1.00 | 90.59 |
| ATOM | 592 | N   | VAL | 215 | 2.690   | 43.924 | 11.777 | 1.00 | 50.17 |
| ATOM | 593 | CA  | VAL | 215 | 4.001   | 43.320 | 11.876 | 1.00 | 41.74 |
| ATOM | 594 | C   | VAL | 215 | 4.075   | 42.335 | 13.059 | 1.00 | 47.63 |
| ATOM | 595 | O   | VAL | 215 | 4.762   | 41.314 | 12.985 | 1.00 | 45.88 |
| ATOM | 596 | CB  | VAL | 215 | 5.105   | 44.420 | 11.916 | 1.00 | 50.90 |
| ATOM | 597 | CG1 | VAL | 215 | 5.318   | 44.942 | 13.325 | 1.00 | 44.79 |
| ATOM | 598 | CG2 | VAL | 215 | 6.377   | 43.890 | 11.342 | 1.00 | 44.27 |
| ATOM | 599 | N   | GLU | 216 | 3.350   | 42.626 | 14.133 | 1.00 | 38.86 |
| ATOM | 600 | CA  | GLU | 216 | 3.280   | 41.716 | 15.267 | 1.00 | 45.56 |
| ATOM | 601 | C   | GLU | 216 | 2.645   | 40.375 | 14.884 | 1.00 | 44.87 |
| ATOM | 602 | O   | GLU | 216 | 3.128   | 39.318 | 15.290 | 1.00 | 42.87 |
| ATOM | 603 | CB  | GLU | 216 | 2.519   | 42.347 | 16.431 | 1.00 | 49.41 |
| ATOM | 604 | CG  | GLU | 216 | 3.149   | 43.630 | 16.979 | 1.00 | 63.76 |
| ATOM | 605 | CD  | GLU | 216 | 2.569   | 44.897 | 16.362 | 1.00 | 68.55 |
| ATOM | 606 | OE1 | GLU | 216 | 2.046   | 44.833 | 15.233 | 1.00 | 69.32 |
| ATOM | 607 | OE2 | GLU | 216 | 2.638   | 45.966 | 17.008 | 1.00 | 75.24 |
| ATOM | 608 | N   | ASP | 217 | 1.582   | 40.416 | 14.088 | 1.00 | 45.69 |

TABLE 10-continued

Three-Dimensional Coordinates of *Neisseria gonorrhoeae* GCYH-IB (SEQ. ID. No. 8)

| ATOM | 609 | CA | ASP | 217 | 0.909 | 39.184 | 13.681 | 1.00 | 47.86 |
|---|---|---|---|---|---|---|---|---|---|
| ATOM | 610 | C | ASP | 217 | 1.749 | 38.388 | 12.716 | 1.00 | 53.47 |
| ATOM | 611 | O | ASP | 217 | 1.778 | 37.164 | 12.780 | 1.00 | 61.34 |
| ATOM | 612 | CB | ASP | 217 | −0.454 | 39.468 | 13.071 | 1.00 | 56.10 |
| ATOM | 613 | CG | ASP | 217 | −1.341 | 40.215 | 14.015 | 1.00 | 74.86 |
| ATOM | 614 | OD1 | ASP | 217 | −1.385 | 39.803 | 15.200 | 1.00 | 74.32 |
| ATOM | 615 | OD2 | ASP | 217 | −1.963 | 41.218 | 13.578 | 1.00 | 80.99 |
| ATOM | 616 | N | MSE | 218 | 2.447 | 39.088 | 11.828 | 1.00 | 48.18 |
| ATOM | 617 | CA | MSE | 218 | 3.335 | 38.430 | 10.876 | 1.00 | 48.13 |
| ATOM | 618 | C | MSE | 218 | 4.367 | 37.519 | 11.572 | 1.00 | 44.35 |
| ATOM | 619 | O | MSE | 218 | 4.451 | 36.316 | 11.295 | 1.00 | 44.73 |
| ATOM | 620 | CB | MSE | 218 | 4.043 | 39.482 | 10.013 | 1.00 | 67.17 |
| ATOM | 621 | CG | MSE | 218 | 4.792 | 38.920 | 8.792 | 1.00 | 78.71 |
| ATOM | 622 | SE | MSE | 218 | 3.762 | 37.588 | 7.728 | 1.00 | 0.04 |
| ATOM | 623 | CE | MSE | 218 | 4.841 | 37.553 | 6.111 | 1.00 | 0.62 |
| ATOM | 624 | N | VAL | 219 | 5.153 | 38.090 | 12.479 | 1.00 | 38.53 |
| ATOM | 625 | CA | VAL | 219 | 6.170 | 37.311 | 13.154 | 1.00 | 34.39 |
| ATOM | 626 | C | VAL | 219 | 5.567 | 36.223 | 14.048 | 1.00 | 37.70 |
| ATOM | 627 | O | VAL | 219 | 6.082 | 35.110 | 14.104 | 1.00 | 41.68 |
| ATOM | 628 | CB | VAL | 219 | 7.162 | 38.186 | 13.952 | 1.00 | 44.91 |
| ATOM | 629 | CG1 | VAL | 219 | 7.886 | 39.169 | 13.008 | 1.00 | 51.70 |
| ATOM | 630 | CG2 | VAL | 219 | 6.458 | 38.927 | 15.067 | 1.00 | 34.05 |
| ATOM | 631 | N | ARG | 220 | 4.485 | 36.532 | 14.750 | 1.00 | 38.89 |
| ATOM | 632 | CA | ARG | 220 | 3.850 | 35.506 | 15.578 | 1.00 | 45.03 |
| ATOM | 633 | C | ARG | 220 | 3.434 | 34.298 | 14.742 | 1.00 | 49.38 |
| ATOM | 634 | O | ARG | 220 | 3.726 | 33.158 | 15.099 | 1.00 | 54.21 |
| ATOM | 635 | CB | ARG | 220 | 2.675 | 36.066 | 16.369 | 1.00 | 44.05 |
| ATOM | 636 | CG | ARG | 220 | 3.115 | 36.735 | 17.641 | 1.00 | 46.49 |
| ATOM | 637 | CD | ARG | 220 | 2.038 | 37.571 | 18.249 | 1.00 | 46.91 |
| ATOM | 638 | NE | ARG | 220 | 2.410 | 37.910 | 19.605 | 1.00 | 48.02 |
| ATOM | 639 | CZ | ARG | 220 | 1.898 | 38.925 | 20.279 | 1.00 | 55.99 |
| ATOM | 640 | NH1 | ARG | 220 | 0.979 | 39.703 | 19.716 | 1.00 | 44.26 |
| ATOM | 641 | NH2 | ARG | 220 | 2.305 | 39.152 | 21.519 | 1.00 | 53.88 |
| ATOM | 642 | N | ASP | 221 | 2.795 | 34.555 | 13.607 | 1.00 | 43.66 |
| ATOM | 643 | CA | ASP | 221 | 2.279 | 33.478 | 12.760 | 1.00 | 41.62 |
| ATOM | 644 | C | ASP | 221 | 3.400 | 32.639 | 12.130 | 1.00 | 50.60 |
| ATOM | 645 | O | ASP | 221 | 3.305 | 31.413 | 12.090 | 1.00 | 44.79 |
| ATOM | 646 | CB | ASP | 221 | 1.350 | 34.039 | 11.691 | 1.00 | 46.23 |
| ATOM | 647 | CG | ASP | 221 | 0.080 | 34.656 | 12.287 | 1.00 | 78.89 |
| ATOM | 648 | OD1 | ASP | 221 | −0.171 | 34.471 | 13.503 | 1.00 | 87.03 |
| ATOM | 649 | OD2 | ASP | 221 | −0.667 | 35.328 | 11.545 | 1.00 | 63.65 |
| ATOM | 650 | N | VAL | 222 | 4.471 | 33.289 | 11.658 | 1.00 | 40.55 |
| ATOM | 651 | CA | VAL | 222 | 5.611 | 32.547 | 11.110 | 1.00 | 39.97 |
| ATOM | 652 | C | VAL | 222 | 6.353 | 31.754 | 12.189 | 1.00 | 40.25 |
| ATOM | 653 | O | VAL | 222 | 6.749 | 30.618 | 11.969 | 1.00 | 43.37 |
| ATOM | 654 | CB | VAL | 222 | 6.641 | 33.466 | 10.424 | 1.00 | 40.52 |
| ATOM | 655 | CG1 | VAL | 222 | 7.854 | 32.663 | 10.029 | 1.00 | 40.76 |
| ATOM | 656 | CG2 | VAL | 222 | 6.044 | 34.136 | 9.216 | 1.00 | 39.98 |
| ATOM | 657 | N | ALA | 223 | 6.558 | 32.365 | 13.350 | 1.00 | 42.74 |
| ATOM | 658 | CA | ALA | 223 | 7.248 | 31.712 | 14.462 | 1.00 | 38.34 |
| ATOM | 659 | C | ALA | 223 | 6.516 | 30.454 | 14.951 | 1.00 | 48.36 |
| ATOM | 660 | O | ALA | 223 | 7.137 | 29.450 | 15.296 | 1.00 | 53.21 |
| ATOM | 661 | CB | ALA | 223 | 7.427 | 32.680 | 15.606 | 1.00 | 45.59 |
| ATOM | 662 | N | THR | 224 | 5.193 | 30.509 | 14.972 | 1.00 | 44.31 |
| ATOM | 663 | CA | THR | 224 | 4.393 | 29.338 | 15.339 | 1.00 | 43.02 |
| ATOM | 664 | C | THR | 224 | 4.677 | 28.152 | 14.414 | 1.00 | 45.58 |
| ATOM | 665 | O | THR | 224 | 4.851 | 27.031 | 14.871 | 1.00 | 49.95 |
| ATOM | 666 | CB | THR | 224 | 2.905 | 29.682 | 15.329 | 1.00 | 42.71 |
| ATOM | 667 | OG1 | THR | 224 | 2.659 | 30.725 | 16.279 | 1.00 | 53.74 |
| ATOM | 668 | CG2 | THR | 224 | 2.085 | 28.478 | 15.691 | 1.00 | 50.78 |
| ATOM | 669 | N | SER | 225 | 4.746 | 28.420 | 13.115 | 1.00 | 41.80 |
| ATOM | 670 | CA | SER | 225 | 5.075 | 27.389 | 12.142 | 1.00 | 51.93 |
| ATOM | 671 | C | SER | 225 | 6.481 | 26.839 | 12.386 | 1.00 | 52.55 |
| ATOM | 672 | O | SER | 225 | 6.711 | 25.633 | 12.275 | 1.00 | 52.97 |
| ATOM | 673 | CB | SER | 225 | 4.988 | 27.922 | 10.707 | 1.00 | 50.08 |
| ATOM | 674 | OG | SER | 225 | 3.762 | 28.589 | 10.467 | 1.00 | 64.07 |
| ATOM | 675 | N | LEU | 226 | 7.430 | 27.715 | 12.708 | 1.00 | 43.70 |
| ATOM | 676 | CA | LEU | 226 | 8.819 | 27.270 | 12.875 | 1.00 | 41.18 |
| ATOM | 677 | C | LEU | 226 | 9.005 | 26.498 | 14.182 | 1.00 | 49.52 |
| ATOM | 678 | O | LEU | 226 | 9.774 | 25.549 | 14.249 | 1.00 | 48.99 |
| ATOM | 679 | CB | LEU | 226 | 9.817 | 28.440 | 12.812 | 1.00 | 35.26 |
| ATOM | 680 | CG | LEU | 226 | 9.817 | 29.332 | 11.577 | 1.00 | 41.80 |
| ATOM | 681 | CD1 | LEU | 226 | 10.725 | 30.527 | 11.814 | 1.00 | 43.92 |
| ATOM | 682 | CD2 | LEU | 226 | 10.225 | 28.566 | 10.330 | 1.00 | 38.82 |
| ATOM | 683 | N | ILE | 227 | 8.308 | 26.932 | 15.221 | 1.00 | 44.77 |
| ATOM | 684 | CA | ILE | 227 | 8.303 | 26.231 | 16.499 | 1.00 | 46.88 |
| ATOM | 685 | C | ILE | 227 | 7.765 | 24.810 | 16.353 | 1.00 | 51.88 |
| ATOM | 686 | O | ILE | 227 | 8.255 | 23.893 | 17.004 | 1.00 | 54.76 |

TABLE 10-continued

Three-Dimensional Coordinates of *Neisseria gonorrhoeae* GCYH-IB (SEQ. ID. No. 8)

| ATOM | 687 | CB | ILE | 227 | 7.422 | 26.966 | 17.508 | 1.00 | 52.15 |
|---|---|---|---|---|---|---|---|---|---|
| ATOM | 688 | CG1 | ILE | 227 | 8.152 | 28.188 | 18.052 | 1.00 | 53.45 |
| ATOM | 689 | CG2 | ILE | 227 | 7.072 | 26.084 | 18.664 | 1.00 | 38.00 |
| ATOM | 690 | CD1 | ILE | 227 | 7.233 | 29.100 | 18.818 | 1.00 | 47.15 |
| ATOM | 691 | N | ALA | 228 | 6.764 | 24.635 | 15.496 | 1.00 | 47.59 |
| ATOM | 692 | CA | ALA | 228 | 6.186 | 23.315 | 15.236 | 1.00 | 54.10 |
| ATOM | 693 | C | ALA | 228 | 7.189 | 22.370 | 14.557 | 1.00 | 63.76 |
| ATOM | 694 | O | ALA | 228 | 7.263 | 21.200 | 14.912 | 1.00 | 56.69 |
| ATOM | 695 | CB | ALA | 228 | 4.914 | 23.441 | 14.405 | 1.00 | 50.72 |
| ATOM | 696 | N | ASP | 229 | 7.973 | 22.882 | 13.605 | 1.00 | 57.62 |
| ATOM | 697 | CA | ASP | 229 | 8.941 | 22.062 | 12.867 | 1.00 | 50.20 |
| ATOM | 698 | C | ASP | 229 | 10.052 | 21.540 | 13.783 | 1.00 | 53.28 |
| ATOM | 699 | O | ASP | 229 | 10.788 | 22.315 | 14.380 | 1.00 | 55.26 |
| ATOM | 700 | CB | ASP | 229 | 9.523 | 22.857 | 11.694 | 1.00 | 62.28 |
| ATOM | 701 | CG | ASP | 229 | 10.189 | 21.974 | 10.660 | 1.00 | 69.82 |
| ATOM | 702 | OD1 | ASP | 229 | 11.076 | 21.183 | 11.048 | 1.00 | 51.12 |
| ATOM | 703 | OD2 | ASP | 229 | 9.837 | 22.081 | 9.460 | 1.00 | 58.63 |
| ATOM | 704 | N | LYS | 230 | 10.175 | 20.222 | 13.888 | 1.00 | 58.48 |
| ATOM | 705 | CA | LYS | 230 | 11.084 | 19.605 | 14.857 | 1.00 | 53.49 |
| ATOM | 706 | C | LYS | 230 | 12.558 | 19.649 | 14.425 | 1.00 | 56.06 |
| ATOM | 707 | O | LYS | 230 | 13.456 | 19.411 | 15.234 | 1.00 | 48.87 |
| ATOM | 708 | CB | LYS | 230 | 10.668 | 18.153 | 15.141 | 1.00 | 68.41 |
| ATOM | 709 | CG | LYS | 230 | 9.187 | 17.952 | 15.488 | 1.00 | 89.06 |
| ATOM | 710 | CD | LYS | 230 | 8.784 | 18.696 | 16.761 | 1.00 | 95.42 |
| ATOM | 711 | CE | LYS | 230 | 7.366 | 18.329 | 17.220 | 1.00 | 92.94 |
| ATOM | 712 | NZ | LYS | 230 | 6.250 | 18.989 | 16.461 | 1.00 | 71.70 |
| ATOM | 713 | N | ASN | 241 | 8.276 | 46.463 | 8.105 | 1.00 | 42.17 |
| ATOM | 714 | CA | ASN | 241 | 7.235 | 47.043 | 7.269 | 1.00 | 43.83 |
| ATOM | 715 | C | ASN | 241 | 7.582 | 48.432 | 6.808 | 1.00 | 51.54 |
| ATOM | 716 | O | ASN | 241 | 7.578 | 49.346 | 7.620 | 1.00 | 52.46 |
| ATOM | 717 | CB | ASN | 241 | 5.955 | 47.182 | 8.075 | 1.00 | 60.29 |
| ATOM | 718 | CG | ASN | 241 | 4.965 | 46.097 | 7.784 | 1.00 | 76.81 |
| ATOM | 719 | OD1 | ASN | 241 | 3.765 | 46.346 | 7.766 | 1.00 | 80.52 |
| ATOM | 720 | ND2 | ASN | 241 | 5.451 | 44.883 | 7.553 | 1.00 | 79.98 |
| ATOM | 721 | N | PHE | 242 | 7.845 | 48.615 | 5.517 | 1.00 | 50.46 |
| ATOM | 722 | CA | PHE | 242 | 8.149 | 49.962 | 5.009 | 1.00 | 66.54 |
| ATOM | 723 | C | PHE | 242 | 6.862 | 50.760 | 4.825 | 1.00 | 56.00 |
| ATOM | 724 | O | PHE | 242 | 6.502 | 51.144 | 3.714 | 1.00 | 54.94 |
| ATOM | 725 | CB | PHE | 242 | 8.972 | 49.901 | 3.719 | 1.00 | 55.87 |
| ATOM | 726 | CG | PHE | 242 | 10.225 | 49.076 | 3.851 | 1.00 | 58.67 |
| ATOM | 727 | CD1 | PHE | 242 | 11.398 | 49.654 | 4.299 | 1.00 | 54.65 |
| ATOM | 728 | CD2 | PHE | 242 | 10.218 | 47.717 | 3.547 | 1.00 | 54.51 |
| ATOM | 729 | CE1 | PHE | 242 | 12.546 | 48.899 | 4.432 | 1.00 | 56.56 |
| ATOM | 730 | CE2 | PHE | 242 | 11.360 | 46.955 | 3.670 | 1.00 | 56.59 |
| ATOM | 731 | CZ | PHE | 242 | 12.526 | 47.542 | 4.116 | 1.00 | 56.20 |
| ATOM | 732 | N | GLU | 243 | 6.186 | 50.995 | 5.946 | 1.00 | 52.01 |
| ATOM | 733 | CA | GLU | 243 | 4.849 | 51.565 | 5.946 | 1.00 | 59.99 |
| ATOM | 734 | C | GLU | 243 | 4.747 | 52.767 | 5.025 | 1.00 | 64.49 |
| ATOM | 735 | O | GLU | 243 | 5.620 | 53.648 | 5.016 | 1.00 | 57.32 |
| ATOM | 736 | CB | GLU | 243 | 4.390 | 51.905 | 7.366 | 1.00 | 67.73 |
| ATOM | 737 | CG | GLU | 243 | 5.399 | 52.658 | 8.197 | 1.00 | 99.15 |
| ATOM | 738 | CD | GLU | 243 | 4.861 | 52.972 | 9.575 | 1.00 | 0.05 |
| ATOM | 739 | OE1 | GLU | 243 | 5.665 | 53.302 | 10.472 | 1.00 | 0.86 |
| ATOM | 740 | OE2 | GLU | 243 | 3.627 | 52.882 | 9.758 | 1.00 | 0.90 |
| ATOM | 741 | N | SER | 244 | 3.672 | 52.779 | 4.243 | 1.00 | 53.45 |
| ATOM | 742 | CA | SER | 244 | 3.523 | 53.732 | 3.154 | 1.00 | 53.27 |
| ATOM | 743 | C | SER | 244 | 3.021 | 55.097 | 3.625 | 1.00 | 55.37 |
| ATOM | 744 | O | SER | 244 | 2.754 | 55.969 | 2.800 | 1.00 | 62.63 |
| ATOM | 745 | CB | SER | 244 | 2.589 | 53.174 | 2.074 | 1.00 | 58.33 |
| ATOM | 746 | OG | SER | 244 | 1.267 | 53.101 | 2.564 | 1.00 | 72.38 |
| ATOM | 747 | N | ILE | 245 | 2.887 | 55.278 | 4.936 | 1.00 | 45.75 |
| ATOM | 748 | CA | ILE | 245 | 2.430 | 56.553 | 5.482 | 1.00 | 59.96 |
| ATOM | 749 | C | ILE | 245 | 3.505 | 57.255 | 6.314 | 1.00 | 53.42 |
| ATOM | 750 | O | ILE | 245 | 3.319 | 58.398 | 6.741 | 1.00 | 58.48 |
| ATOM | 751 | CB | ILE | 245 | 1.131 | 56.400 | 6.323 | 1.00 | 61.54 |
| ATOM | 752 | CG1 | ILE | 245 | 1.395 | 55.530 | 7.550 | 1.00 | 63.07 |
| ATOM | 753 | CG2 | ILE | 245 | −0.003 | 55.821 | 5.479 | 1.00 | 53.03 |
| ATOM | 754 | CD1 | ILE | 245 | 0.187 | 55.356 | 8.429 | 1.00 | 78.07 |
| ATOM | 755 | N | HIS | 246 | 4.619 | 56.564 | 6.557 | 1.00 | 50.73 |
| ATOM | 756 | CA | HIS | 246 | 5.736 | 57.142 | 7.299 | 1.00 | 53.43 |
| ATOM | 757 | C | HIS | 246 | 7.027 | 57.010 | 6.499 | 1.00 | 64.72 |
| ATOM | 758 | O | HIS | 246 | 7.071 | 56.289 | 5.509 | 1.00 | 62.83 |
| ATOM | 759 | CB | HIS | 246 | 5.905 | 56.448 | 8.646 | 1.00 | 49.66 |
| ATOM | 760 | CG | HIS | 246 | 4.773 | 56.673 | 9.600 | 1.00 | 65.04 |
| ATOM | 761 | ND1 | HIS | 246 | 4.062 | 55.635 | 10.162 | 1.00 | 65.95 |
| ATOM | 762 | CD2 | HIS | 246 | 4.238 | 57.812 | 10.101 | 1.00 | 64.99 |
| ATOM | 763 | CE1 | HIS | 246 | 3.137 | 56.124 | 10.969 | 1.00 | 77.08 |
| ATOM | 764 | NE2 | HIS | 246 | 3.219 | 57.443 | 10.948 | 1.00 | 73.91 |

TABLE 10-continued

Three-Dimensional Coordinates of *Neisseria gonorrhoeae* GCYH-IB (SEQ. ID. No. 8)

| ATOM | 765 | N | ASN | 247 | 8.085 | 57.698 | 6.923 | 1.00 | 56.86 |
|---|---|---|---|---|---|---|---|---|---|
| ATOM | 766 | CA | ASN | 247 | 9.385 | 57.471 | 6.291 | 1.00 | 52.91 |
| ATOM | 767 | C | ASN | 247 | 10.353 | 56.631 | 7.152 | 1.00 | 50.50 |
| ATOM | 768 | O | ASN | 247 | 11.566 | 56.789 | 7.087 | 1.00 | 66.31 |
| ATOM | 769 | CB | ASN | 247 | 10.035 | 58.774 | 5.808 | 1.00 | 55.98 |
| ATOM | 770 | CG | ASN | 247 | 11.118 | 58.521 | 4.744 | 1.00 | 59.98 |
| ATOM | 771 | OD1 | ASN | 247 | 10.980 | 57.614 | 3.910 | 1.00 | 49.10 |
| ATOM | 772 | ND2 | ASN | 247 | 12.199 | 59.309 | 4.779 | 1.00 | 48.52 |
| ATOM | 773 | N | ASN | 15 | 0.218 | 32.086 | 22.240 | 1.00 | 0.61 |
| ATOM | 774 | CA | ASN | 15 | 0.186 | 33.528 | 22.018 | 1.00 | 0.98 |
| ATOM | 775 | C | ASN | 15 | 1.535 | 34.235 | 21.874 | 1.00 | 0.70 |
| ATOM | 776 | O | ASN | 15 | 1.568 | 35.421 | 21.554 | 1.00 | 0.18 |
| ATOM | 777 | CB | ASN | 15 | −0.630 | 34.213 | 23.111 | 1.00 | 0.60 |
| ATOM | 778 | CG | ASN | 15 | −1.982 | 34.679 | 22.621 | 1.00 | 0.45 |
| ATOM | 779 | OD1 | ASN | 15 | −2.111 | 35.186 | 21.513 | 1.00 | 0.18 |
| ATOM | 780 | ND2 | ASN | 15 | −2.995 | 34.526 | 23.454 | 1.00 | 0.78 |
| ATOM | 781 | N | LEU | 16 | 2.627 | 33.518 | 22.133 | 1.00 | 94.87 |
| ATOM | 782 | CA | LEU | 16 | 4.002 | 34.005 | 21.882 | 1.00 | 68.59 |
| ATOM | 783 | C | LEU | 16 | 4.304 | 35.483 | 22.181 | 1.00 | 62.20 |
| ATOM | 784 | O | LEU | 16 | 3.765 | 36.386 | 21.537 | 1.00 | 47.59 |
| ATOM | 785 | CB | LEU | 16 | 4.440 | 33.654 | 20.458 | 1.00 | 58.51 |
| ATOM | 786 | CG | LEU | 16 | 5.071 | 32.271 | 20.284 | 1.00 | 71.98 |
| ATOM | 787 | CD1 | LEU | 16 | 4.166 | 31.193 | 20.815 | 1.00 | 95.09 |
| ATOM | 788 | CD2 | LEU | 16 | 5.387 | 32.009 | 18.826 | 1.00 | 66.90 |
| ATOM | 789 | N | PRO | 17 | 5.172 | 35.727 | 23.174 | 1.00 | 59.11 |
| ATOM | 790 | CA | PRO | 17 | 5.692 | 37.076 | 23.383 | 1.00 | 56.32 |
| ATOM | 791 | C | PRO | 17 | 6.546 | 37.470 | 22.172 | 1.00 | 53.83 |
| ATOM | 792 | O | PRO | 17 | 7.090 | 36.599 | 21.490 | 1.00 | 55.40 |
| ATOM | 793 | CB | PRO | 17 | 6.593 | 36.929 | 24.615 | 1.00 | 49.67 |
| ATOM | 794 | CG | PRO | 17 | 6.313 | 35.601 | 25.173 | 1.00 | 57.25 |
| ATOM | 795 | CD | PRO | 17 | 5.780 | 34.751 | 24.087 | 1.00 | 51.52 |
| ATOM | 796 | N | ILE | 18 | 6.635 | 38.764 | 21.898 | 1.00 | 44.93 |
| ATOM | 797 | CA | ILE | 18 | 7.572 | 39.262 | 20.914 | 1.00 | 40.29 |
| ATOM | 798 | C | ILE | 18 | 8.729 | 39.970 | 21.625 | 1.00 | 42.04 |
| ATOM | 799 | O | ILE | 18 | 8.521 | 40.914 | 22.379 | 1.00 | 43.41 |
| ATOM | 800 | CB | ILE | 18 | 6.889 | 40.190 | 19.902 | 1.00 | 38.13 |
| ATOM | 801 | CG1 | ILE | 18 | 5.875 | 39.414 | 19.075 | 1.00 | 45.13 |
| ATOM | 802 | CG2 | ILE | 18 | 7.929 | 40.830 | 18.976 | 1.00 | 48.42 |
| ATOM | 803 | CD1 | ILE | 18 | 4.852 | 40.278 | 18.363 | 1.00 | 47.95 |
| ATOM | 804 | N | TYR | 50 | 9.472 | 45.033 | 24.568 | 1.00 | 48.54 |
| ATOM | 805 | CA | TYR | 50 | 8.939 | 43.690 | 24.720 | 1.00 | 42.54 |
| ATOM | 806 | C | TYR | 50 | 7.415 | 43.706 | 24.665 | 1.00 | 38.18 |
| ATOM | 807 | O | TYR | 50 | 6.765 | 44.559 | 25.274 | 1.00 | 59.47 |
| ATOM | 808 | CB | TYR | 50 | 9.421 | 43.125 | 26.063 | 1.00 | 48.65 |
| ATOM | 809 | CG | TYR | 50 | 8.877 | 41.770 | 26.439 | 1.00 | 46.41 |
| ATOM | 810 | CD1 | TYR | 50 | 9.495 | 40.601 | 26.002 | 1.00 | 48.12 |
| ATOM | 811 | CD2 | TYR | 50 | 7.780 | 41.656 | 27.288 | 1.00 | 45.63 |
| ATOM | 812 | CE1 | TYR | 50 | 9.005 | 39.351 | 26.369 | 1.00 | 49.82 |
| ATOM | 813 | CE2 | TYR | 50 | 7.282 | 40.418 | 27.658 | 1.00 | 64.78 |
| ATOM | 814 | CZ | TYR | 50 | 7.891 | 39.267 | 27.200 | 1.00 | 66.95 |
| ATOM | 815 | OH | TYR | 50 | 7.378 | 38.038 | 27.576 | 1.00 | 63.72 |
| ATOM | 816 | N | LEU | 51 | 6.845 | 42.762 | 23.925 | 1.00 | 41.19 |
| ATOM | 817 | CA | LEU | 51 | 5.392 | 42.650 | 23.852 | 1.00 | 45.35 |
| ATOM | 818 | C | LEU | 51 | 4.944 | 41.327 | 24.477 | 1.00 | 59.79 |
| ATOM | 819 | O | LEU | 51 | 5.234 | 40.259 | 23.953 | 1.00 | 57.86 |
| ATOM | 820 | CB | LEU | 51 | 4.903 | 42.786 | 22.407 | 1.00 | 41.63 |
| ATOM | 821 | CG | LEU | 51 | 3.390 | 42.955 | 22.268 | 1.00 | 57.45 |
| ATOM | 822 | CD1 | LEU | 51 | 3.024 | 44.309 | 22.804 | 1.00 | 53.37 |
| ATOM | 823 | CD2 | LEU | 51 | 2.896 | 42.786 | 20.817 | 1.00 | 46.74 |
| ATOM | 824 | N | PRO | 52 | 4.252 | 41.404 | 25.620 | 1.00 | 50.41 |
| ATOM | 825 | CA | PRO | 52 | 3.698 | 40.238 | 26.327 | 1.00 | 60.78 |
| ATOM | 826 | C | PRO | 52 | 2.845 | 39.355 | 25.412 | 1.00 | 55.59 |
| ATOM | 827 | O | PRO | 52 | 2.252 | 39.850 | 24.464 | 1.00 | 45.38 |
| ATOM | 828 | CB | PRO | 52 | 2.799 | 40.873 | 27.398 | 1.00 | 51.53 |
| ATOM | 829 | CG | PRO | 52 | 3.307 | 42.272 | 27.560 | 1.00 | 54.38 |
| ATOM | 830 | CD | PRO | 52 | 3.795 | 42.675 | 26.204 | 1.00 | 47.05 |
| ATOM | 831 | N | ALA | 53 | 2.787 | 38.061 | 25.706 | 1.00 | 65.72 |
| ATOM | 832 | CA | ALA | 53 | 2.046 | 37.103 | 24.882 | 1.00 | 66.94 |
| ATOM | 833 | C | ALA | 53 | 0.629 | 37.544 | 24.490 | 1.00 | 71.17 |
| ATOM | 834 | O | ALA | 53 | 0.223 | 37.378 | 23.341 | 1.00 | 71.46 |
| ATOM | 835 | CB | ALA | 53 | 1.998 | 35.748 | 25.564 | 1.00 | 66.90 |
| ATOM | 836 | N | GLU | 54 | −0.130 | 38.108 | 25.424 | 1.00 | 75.20 |
| ATOM | 837 | CA | GLU | 54 | −1.535 | 38.373 | 25.120 | 1.00 | 0.50 |
| ATOM | 838 | C | GLU | 54 | −1.871 | 39.834 | 24.827 | 1.00 | 90.42 |
| ATOM | 839 | O | GLU | 54 | −3.039 | 40.201 | 24.744 | 1.00 | 95.12 |
| ATOM | 840 | CB | GLU | 54 | −2.466 | 37.767 | 26.176 | 1.00 | 0.71 |
| ATOM | 841 | CG | GLU | 54 | −2.722 | 38.621 | 27.397 | 1.00 | 0.20 |
| ATOM | 842 | CD | GLU | 54 | −3.621 | 37.920 | 28.398 | 1.00 | 0.17 |

TABLE 10-continued

Three-Dimensional Coordinates of *Neisseria gonorrhoeae* GCYH-IB (SEQ. ID. No. 8)

| ATOM | 843 | OE1 | GLU | 54 | −3.217 | 36.856 | 28.908 | 1.00 | 0.84 |
|---|---|---|---|---|---|---|---|---|---|
| ATOM | 844 | OE2 | GLU | 54 | −4.728 | 38.427 | 28.672 | 1.00 | 0.50 |
| ATOM | 845 | N | GLN | 55 | −0.845 | 40.659 | 24.656 | 1.00 | 78.83 |
| ATOM | 846 | CA | GLN | 55 | −1.035 | 41.995 | 24.104 | 1.00 | 68.58 |
| ATOM | 847 | C | GLN | 55 | −0.918 | 41.857 | 22.589 | 1.00 | 58.44 |
| ATOM | 848 | O | GLN | 55 | 0.009 | 41.221 | 22.092 | 1.00 | 65.77 |
| ATOM | 849 | CB | GLN | 55 | 0.011 | 42.970 | 24.658 | 1.00 | 58.13 |
| ATOM | 850 | CG | GLN | 55 | −0.321 | 44.447 | 24.474 | 1.00 | 67.08 |
| ATOM | 851 | CD | GLN | 55 | 0.672 | 45.362 | 25.189 | 1.00 | 79.71 |
| ATOM | 852 | OE1 | GLN | 55 | 1.214 | 45.006 | 26.235 | 1.00 | 88.70 |
| ATOM | 853 | NE2 | GLN | 55 | 0.912 | 46.547 | 24.625 | 1.00 | 63.58 |
| ATOM | 854 | N | LYS | 56 | −1.859 | 42.436 | 21.852 | 1.00 | 61.67 |
| ATOM | 855 | CA | LYS | 56 | −1.921 | 42.230 | 20.410 | 1.00 | 65.88 |
| ATOM | 856 | C | LYS | 56 | −0.919 | 43.095 | 19.648 | 1.00 | 73.54 |
| ATOM | 857 | O | LYS | 56 | −0.438 | 42.707 | 18.578 | 1.00 | 73.26 |
| ATOM | 858 | CB | LYS | 56 | −3.326 | 42.503 | 19.872 | 1.00 | 88.06 |
| ATOM | 859 | CG | LYS | 56 | −3.413 | 42.433 | 18.349 | 1.00 | 0.53 |
| ATOM | 860 | CD | LYS | 56 | −4.837 | 42.642 | 17.847 | 1.00 | 0.29 |
| ATOM | 861 | CE | LYS | 56 | −5.261 | 44.101 | 17.948 | 1.00 | 0.17 |
| ATOM | 862 | NZ | LYS | 56 | −6.636 | 44.318 | 17.419 | 1.00 | 0.56 |
| ATOM | 863 | N | GLY | 57 | −0.613 | 44.266 | 20.205 | 1.00 | 63.39 |
| ATOM | 864 | CA | GLY | 57 | 0.166 | 45.280 | 19.520 | 1.00 | 60.23 |
| ATOM | 865 | C | GLY | 57 | 0.775 | 46.299 | 20.465 | 1.00 | 67.31 |
| ATOM | 866 | O | GLY | 57 | 0.404 | 46.397 | 21.628 | 1.00 | 65.95 |
| ATOM | 867 | N | THR | 58 | 1.747 | 47.048 | 19.964 | 1.00 | 71.54 |
| ATOM | 868 | CA | THR | 58 | 2.338 | 48.127 | 20.736 | 1.00 | 72.16 |
| ATOM | 869 | C | THR | 58 | 1.743 | 49.429 | 20.216 | 1.00 | 61.69 |
| ATOM | 870 | O | THR | 58 | 0.837 | 49.406 | 19.387 | 1.00 | 61.90 |
| ATOM | 871 | CB | THR | 58 | 3.879 | 48.132 | 20.619 | 1.00 | 69.56 |
| ATOM | 872 | OG1 | THR | 58 | 4.439 | 48.979 | 21.629 | 1.00 | 79.35 |
| ATOM | 873 | CG2 | THR | 58 | 4.316 | 48.611 | 19.244 | 1.00 | 68.68 |
| ATOM | 874 | N | HIS | 59 | 2.246 | 50.562 | 20.695 | 1.00 | 71.58 |
| ATOM | 875 | CA | HIS | 59 | 1.724 | 51.852 | 20.259 | 1.00 | 69.19 |
| ATOM | 876 | C | HIS | 59 | 2.798 | 52.593 | 19.487 | 1.00 | 62.91 |
| ATOM | 877 | O | HIS | 59 | 3.641 | 53.268 | 20.075 | 1.00 | 74.03 |
| ATOM | 878 | CB | HIS | 59 | 1.246 | 52.655 | 21.466 | 1.00 | 67.89 |
| ATOM | 879 | CG | HIS | 59 | 0.355 | 51.877 | 22.386 | 1.00 | 73.78 |
| ATOM | 880 | ND1 | HIS | 59 | 0.848 | 51.082 | 23.406 | 1.00 | 79.21 |
| ATOM | 881 | CD2 | HIS | 59 | −0.988 | 51.758 | 22.440 | 1.00 | 74.77 |
| ATOM | 882 | CE1 | HIS | 59 | −0.155 | 50.522 | 24.049 | 1.00 | 81.43 |
| ATOM | 883 | NE2 | HIS | 59 | −1.283 | 50.913 | 23.482 | 1.00 | 82.11 |
| ATOM | 884 | N | MSE | 60 | 2.754 | 52.467 | 18.164 | 1.00 | 69.20 |
| ATOM | 885 | CA | MSE | 60 | 3.889 | 52.836 | 17.308 | 1.00 | 64.49 |
| ATOM | 886 | C | MSE | 60 | 4.271 | 54.314 | 17.333 | 1.00 | 57.44 |
| ATOM | 887 | O | MSE | 60 | 5.453 | 54.663 | 17.259 | 1.00 | 55.33 |
| ATOM | 888 | CB | MSE | 60 | 3.626 | 52.396 | 15.866 | 1.00 | 68.93 |
| ATOM | 889 | CG | MSE | 60 | 3.645 | 50.886 | 15.670 | 1.00 | 88.07 |
| ATOM | 890 | SE | MSE | 60 | 5.452 | 50.082 | 15.726 | 1.00 | 90.92 |
| ATOM | 891 | CE | MSE | 60 | 4.956 | 48.218 | 15.352 | 1.00 | 91.55 |
| ATOM | 892 | N | SER | 61 | 3.265 | 55.177 | 17.436 | 1.00 | 49.65 |
| ATOM | 893 | CA | SER | 61 | 3.490 | 56.624 | 17.384 | 1.00 | 52.54 |
| ATOM | 894 | C | SER | 61 | 4.202 | 57.193 | 18.627 | 1.00 | 57.67 |
| ATOM | 895 | O | SER | 61 | 4.824 | 58.251 | 18.555 | 1.00 | 63.02 |
| ATOM | 896 | CB | SER | 61 | 2.158 | 57.360 | 17.127 | 1.00 | 60.89 |
| ATOM | 897 | OG | SER | 61 | 1.418 | 57.470 | 18.313 | 1.00 | 63.53 |
| ATOM | 898 | N | ARG | 62 | 4.112 | 56.495 | 19.757 | 1.00 | 58.58 |
| ATOM | 899 | CA | ARG | 62 | 4.804 | 56.928 | 20.970 | 1.00 | 54.99 |
| ATOM | 900 | C | ARG | 62 | 6.330 | 56.959 | 20.816 | 1.00 | 47.98 |
| ATOM | 901 | O | ARG | 62 | 6.992 | 57.829 | 21.385 | 1.00 | 58.75 |
| ATOM | 902 | CB | ARG | 62 | 4.407 | 56.069 | 22.169 | 1.00 | 48.24 |
| ATOM | 903 | CG | ARG | 62 | 2.980 | 56.278 | 22.584 | 1.00 | 54.45 |
| ATOM | 904 | CD | ARG | 62 | 2.567 | 55.281 | 23.663 | 1.00 | 53.24 |
| ATOM | 905 | NE | ARG | 62 | 1.122 | 55.256 | 23.836 | 1.00 | 68.95 |
| ATOM | 906 | CZ | ARG | 62 | 0.492 | 54.612 | 24.808 | 1.00 | 67.76 |
| ATOM | 907 | NH1 | ARG | 62 | 1.186 | 53.948 | 25.719 | 1.00 | 58.36 |
| ATOM | 908 | NH2 | ARG | 62 | −0.838 | 54.642 | 24.869 | 1.00 | 72.93 |
| ATOM | 909 | N | PHE | 63 | 6.879 | 56.017 | 20.049 | 1.00 | 45.59 |
| ATOM | 910 | CA | PHE | 63 | 8.317 | 55.990 | 19.800 | 1.00 | 51.33 |
| ATOM | 911 | C | PHE | 63 | 8.788 | 57.305 | 19.200 | 1.00 | 57.30 |
| ATOM | 912 | O | PHE | 63 | 9.781 | 57.895 | 19.641 | 1.00 | 55.44 |
| ATOM | 913 | CB | PHE | 63 | 8.688 | 54.840 | 18.866 | 1.00 | 49.40 |
| ATOM | 914 | CG | PHE | 63 | 8.439 | 53.498 | 19.449 | 1.00 | 44.13 |
| ATOM | 915 | CD1 | PHE | 63 | 9.233 | 53.021 | 20.474 | 1.00 | 41.09 |
| ATOM | 916 | CD2 | PHE | 63 | 7.394 | 52.718 | 18.995 | 1.00 | 50.77 |
| ATOM | 917 | CE1 | PHE | 63 | 9.008 | 51.782 | 21.018 | 1.00 | 39.25 |
| ATOM | 918 | CE2 | PHE | 63 | 7.161 | 51.471 | 19.543 | 1.00 | 57.73 |
| ATOM | 919 | CZ | PHE | 63 | 7.977 | 50.996 | 20.546 | 1.00 | 41.41 |
| ATOM | 920 | N | VAL | 64 | 8.065 | 57.751 | 18.180 | 1.00 | 47.97 |

TABLE 10-continued

Three-Dimensional Coordinates of *Neisseria gonorrhoeae* GCYH-IB (SEQ. ID. No. 8)

| ATOM | 921 | CA | VAL | 64 | 8.375 | 59.013 | 17.524 | 1.00 | 55.02 |
|------|-----|-----|-----|-----|--------|--------|--------|------|-------|
| ATOM | 922 | C | VAL | 64 | 8.125 | 60.197 | 18.472 | 1.00 | 53.37 |
| ATOM | 923 | O | VAL | 64 | 9.000 | 61.047 | 18.648 | 1.00 | 45.07 |
| ATOM | 924 | CB | VAL | 64 | 7.537 | 59.188 | 16.238 | 1.00 | 69.71 |
| ATOM | 925 | CG1 | VAL | 64 | 7.874 | 60.505 | 15.564 | 1.00 | 71.34 |
| ATOM | 926 | CG2 | VAL | 64 | 7.770 | 58.025 | 15.293 | 1.00 | 71.51 |
| ATOM | 927 | N | ALA | 65 | 6.935 | 60.248 | 19.081 | 1.00 | 43.65 |
| ATOM | 928 | CA | ALA | 65 | 6.603 | 61.331 | 20.017 | 1.00 | 45.85 |
| ATOM | 929 | C | ALA | 65 | 7.693 | 61.470 | 21.074 | 1.00 | 55.77 |
| ATOM | 930 | O | ALA | 65 | 8.040 | 62.575 | 21.480 | 1.00 | 62.71 |
| ATOM | 931 | CB | ALA | 65 | 5.251 | 61.081 | 20.673 | 1.00 | 51.78 |
| ATOM | 932 | N | ALA | 88 | 8.534 | 53.005 | 30.061 | 1.00 | 37.50 |
| ATOM | 933 | CA | ALA | 88 | 7.456 | 53.494 | 30.916 | 1.00 | 51.61 |
| ATOM | 934 | C | ALA | 88 | 6.339 | 54.012 | 30.058 | 1.00 | 56.02 |
| ATOM | 935 | O | ALA | 88 | 5.185 | 53.700 | 30.295 | 1.00 | 63.47 |
| ATOM | 936 | CB | ALA | 88 | 7.943 | 54.591 | 31.853 | 1.00 | 50.46 |
| ATOM | 937 | N | LEU | 89 | 6.697 | 54.794 | 29.047 | 1.00 | 57.64 |
| ATOM | 938 | CA | LEU | 89 | 5.730 | 55.400 | 28.124 | 1.00 | 59.78 |
| ATOM | 939 | C | LEU | 89 | 4.942 | 54.357 | 27.315 | 1.00 | 53.97 |
| ATOM | 940 | O | LEU | 89 | 3.743 | 54.487 | 27.119 | 1.00 | 56.91 |
| ATOM | 941 | CB | LEU | 89 | 6.451 | 56.368 | 27.181 | 1.00 | 57.63 |
| ATOM | 942 | CG | LEU | 89 | 5.628 | 57.042 | 26.094 | 1.00 | 56.32 |
| ATOM | 943 | CD1 | LEU | 89 | 4.718 | 58.084 | 26.716 | 1.00 | 42.44 |
| ATOM | 944 | CD2 | LEU | 89 | 6.536 | 57.676 | 25.055 | 1.00 | 61.18 |
| ATOM | 945 | N | LEU | 90 | 5.612 | 53.321 | 26.837 | 1.00 | 54.16 |
| ATOM | 946 | CA | LEU | 90 | 4.924 | 52.266 | 26.111 | 1.00 | 63.18 |
| ATOM | 947 | C | LEU | 90 | 4.361 | 51.189 | 27.032 | 1.00 | 67.68 |
| ATOM | 948 | O | LEU | 90 | 3.870 | 50.160 | 26.575 | 1.00 | 65.17 |
| ATOM | 949 | CB | LEU | 90 | 5.844 | 51.657 | 25.065 | 1.00 | 54.20 |
| ATOM | 950 | CG | LEU | 90 | 5.801 | 52.540 | 23.824 | 1.00 | 61.73 |
| ATOM | 951 | CD1 | LEU | 90 | 7.055 | 53.389 | 23.699 | 1.00 | 41.72 |
| ATOM | 952 | CD2 | LEU | 90 | 5.595 | 51.690 | 22.601 | 1.00 | 75.98 |
| ATOM | 953 | N | ASP | 91 | 4.432 | 51.443 | 28.332 | 1.00 | 62.55 |
| ATOM | 954 | CA | ASP | 91 | 3.870 | 50.543 | 29.329 | 1.00 | 74.29 |
| ATOM | 955 | C | ASP | 91 | 4.407 | 49.124 | 29.159 | 1.00 | 64.93 |
| ATOM | 956 | O | ASP | 91 | 3.634 | 48.184 | 29.035 | 1.00 | 56.16 |
| ATOM | 957 | CB | ASP | 91 | 2.333 | 50.539 | 29.242 | 1.00 | 84.05 |
| ATOM | 958 | CG | ASP | 91 | 1.698 | 51.810 | 29.813 | 1.00 | 0.91 |
| ATOM | 959 | OD1 | ASP | 91 | 2.435 | 52.672 | 30.332 | 1.00 | 0.11 |
| ATOM | 960 | OD2 | ASP | 91 | 0.456 | 51.944 | 29.753 | 1.00 | 98.46 |
| ATOM | 961 | N | SER | 92 | 5.730 | 48.970 | 29.156 | 1.00 | 57.68 |
| ATOM | 962 | CA | SER | 92 | 6.349 | 47.662 | 28.929 | 1.00 | 40.55 |
| ATOM | 963 | C | SER | 92 | 7.432 | 47.291 | 29.952 | 1.00 | 52.93 |
| ATOM | 964 | O | SER | 92 | 7.981 | 48.149 | 30.636 | 1.00 | 58.12 |
| ATOM | 965 | CB | SER | 92 | 6.909 | 47.602 | 27.509 | 1.00 | 47.88 |
| ATOM | 966 | OG | SER | 92 | 7.480 | 46.339 | 27.226 | 1.00 | 53.37 |
| ATOM | 967 | N | ARG | 93 | 7.744 | 46.001 | 30.016 | 1.00 | 53.73 |
| ATOM | 968 | CA | ARG | 93 | 8.714 | 45.427 | 30.946 | 1.00 | 47.19 |
| ATOM | 969 | C | ARG | 93 | 10.185 | 45.602 | 30.507 | 1.00 | 61.56 |
| ATOM | 970 | O | ARG | 93 | 11.110 | 45.546 | 31.327 | 1.00 | 57.47 |
| ATOM | 971 | CB | ARG | 93 | 8.417 | 43.934 | 31.073 | 1.00 | 57.38 |
| ATOM | 972 | CG | ARG | 93 | 9.157 | 43.215 | 32.169 | 1.00 | 80.07 |
| ATOM | 973 | CD | ARG | 93 | 8.893 | 41.714 | 32.098 | 1.00 | 91.35 |
| ATOM | 974 | NE | ARG | 93 | 9.315 | 41.137 | 30.822 | 1.00 | 84.96 |
| ATOM | 975 | CZ | ARG | 93 | 10.584 | 40.930 | 30.474 | 1.00 | 95.02 |
| ATOM | 976 | NH1 | ARG | 93 | 11.571 | 41.262 | 31.296 | 1.00 | 95.51 |
| ATOM | 977 | NH2 | ARG | 93 | 10.872 | 40.398 | 29.297 | 1.00 | 81.77 |
| ATOM | 978 | ZN | ZN2 | 258 | −1.421 | 51.727 | 9.888 | 1.00 | 71.07 |
| ATOM | 979 | N | LYS | 107 | 7.039 | 69.054 | 9.816 | 1.00 | 54.02 |
| ATOM | 980 | CA | LYS | 107 | 5.719 | 68.932 | 9.197 | 1.00 | 55.18 |
| ATOM | 981 | C | LYS | 107 | 4.623 | 68.864 | 10.238 | 1.00 | 64.44 |
| ATOM | 982 | O | LYS | 107 | 4.890 | 68.582 | 11.408 | 1.00 | 67.36 |
| ATOM | 983 | CB | LYS | 107 | 5.645 | 67.700 | 8.293 | 1.00 | 59.17 |
| ATOM | 984 | CG | LYS | 107 | 6.076 | 68.002 | 6.871 | 1.00 | 78.01 |
| ATOM | 985 | CD | LYS | 107 | 7.044 | 66.968 | 6.340 | 1.00 | 42.27 |
| ATOM | 986 | CE | LYS | 107 | 6.290 | 65.821 | 5.703 | 1.00 | 76.76 |
| ATOM | 987 | NZ | LYS | 107 | 5.410 | 66.284 | 4.585 | 1.00 | 63.95 |
| ATOM | 988 | N | THR | 108 | 3.391 | 69.116 | 9.794 | 1.00 | 52.40 |
| ATOM | 989 | CA | THR | 108 | 2.216 | 69.084 | 10.661 | 1.00 | 54.45 |
| ATOM | 990 | C | THR | 108 | 1.188 | 68.042 | 10.194 | 1.00 | 68.79 |
| ATOM | 991 | O | THR | 108 | 0.785 | 68.040 | 9.030 | 1.00 | 66.08 |
| ATOM | 992 | CB | THR | 108 | 1.551 | 70.473 | 10.712 | 1.00 | 69.12 |
| ATOM | 993 | OG1 | THR | 108 | 2.462 | 71.416 | 11.294 | 1.00 | 81.63 |
| ATOM | 994 | CG2 | THR | 108 | 0.254 | 70.440 | 11.508 | 1.00 | 60.33 |
| ATOM | 995 | N | ALA | 109 | 0.768 | 67.162 | 11.103 | 1.00 | 59.63 |
| ATOM | 996 | CA | ALA | 109 | −0.208 | 66.133 | 10.780 | 1.00 | 55.61 |
| ATOM | 997 | C | ALA | 109 | −1.539 | 66.770 | 10.335 | 1.00 | 71.15 |
| ATOM | 998 | O | ALA | 109 | −1.987 | 67.761 | 10.911 | 1.00 | 77.38 |

TABLE 10-continued

Three-Dimensional Coordinates of *Neisseria gonorrhoeae* GCYH-IB (SEQ. ID. No. 8)

| ATOM | 999 | CB | ALA | 109 | −0.414 | 65.207 | 11.970 | 1.00 | 64.89 |
|---|---|---|---|---|---|---|---|---|---|
| ATOM | 1000 | N | PRO | 110 | −2.167 | 66.203 | 9.292 | 1.00 | 77.07 |
| ATOM | 1001 | CA | PRO | 110 | −3.301 | 66.840 | 8.607 | 1.00 | 60.99 |
| ATOM | 1002 | C | PRO | 110 | −4.581 | 67.037 | 9.428 | 1.00 | 75.83 |
| ATOM | 1003 | O | PRO | 110 | −5.376 | 67.905 | 9.075 | 1.00 | 0.83 |
| ATOM | 1004 | CB | PRO | 110 | −3.554 | 65.893 | 7.428 | 1.00 | 69.05 |
| ATOM | 1005 | CG | PRO | 110 | −2.920 | 64.597 | 7.844 | 1.00 | 73.14 |
| ATOM | 1006 | CD | PRO | 110 | −1.683 | 65.032 | 8.540 | 1.00 | 70.35 |
| ATOM | 1007 | N | VAL | 111 | −4.796 | 66.245 | 10.475 | 1.00 | 76.98 |
| ATOM | 1008 | CA | VAL | 111 | −5.969 | 66.424 | 11.326 | 1.00 | 75.05 |
| ATOM | 1009 | C | VAL | 111 | −5.617 | 66.884 | 12.751 | 1.00 | 83.25 |
| ATOM | 1010 | O | VAL | 111 | −6.118 | 67.905 | 13.221 | 1.00 | 84.58 |
| ATOM | 1011 | CB | VAL | 111 | −6.859 | 65.145 | 11.386 | 1.00 | 80.99 |
| ATOM | 1012 | CG1 | VAL | 111 | −7.935 | 65.277 | 12.477 | 1.00 | 89.81 |
| ATOM | 1013 | CG2 | VAL | 111 | −7.508 | 64.882 | 10.036 | 1.00 | 90.98 |
| ATOM | 1014 | N | SER | 112 | −4.763 | 66.127 | 13.431 | 1.00 | 87.92 |
| ATOM | 1015 | CA | SER | 112 | −4.384 | 66.425 | 14.813 | 1.00 | 84.89 |
| ATOM | 1016 | C | SER | 112 | −3.470 | 67.654 | 14.961 | 1.00 | 80.23 |
| ATOM | 1017 | O | SER | 112 | −3.417 | 68.265 | 16.035 | 1.00 | 72.07 |
| ATOM | 1018 | CB | SER | 112 | −3.710 | 65.205 | 15.455 | 1.00 | 64.52 |
| ATOM | 1019 | OG | SER | 112 | −2.361 | 65.077 | 15.020 | 1.00 | 67.63 |
| ATOM | 1020 | N | GLY | 113 | −2.740 | 67.998 | 13.896 | 1.00 | 65.30 |
| ATOM | 1021 | CA | GLY | 113 | −1.815 | 69.115 | 13.934 | 1.00 | 57.14 |
| ATOM | 1022 | C | GLY | 113 | −0.484 | 68.803 | 14.595 | 1.00 | 71.26 |
| ATOM | 1023 | O | GLY | 113 | 0.410 | 69.660 | 14.638 | 1.00 | 69.71 |
| ATOM | 1024 | N | ILE | 114 | −0.330 | 67.581 | 15.103 | 1.00 | 73.22 |
| ATOM | 1025 | CA | ILE | 114 | 0.934 | 67.183 | 15.738 | 1.00 | 69.42 |
| ATOM | 1026 | C | ILE | 114 | 2.125 | 67.271 | 14.779 | 1.00 | 68.09 |
| ATOM | 1027 | O | ILE | 114 | 2.077 | 66.782 | 13.650 | 1.00 | 76.48 |
| ATOM | 1028 | CB | ILE | 114 | 0.869 | 65.774 | 16.368 | 1.00 | 73.91 |
| ATOM | 1029 | CG1 | ILE | 114 | −0.334 | 65.663 | 17.303 | 1.00 | 89.92 |
| ATOM | 1030 | CG2 | ILE | 114 | 2.138 | 65.493 | 17.152 | 1.00 | 63.39 |
| ATOM | 1031 | CD1 | ILE | 114 | −0.366 | 64.373 | 18.089 | 1.00 | 0.56 |
| ATOM | 1032 | N | ARG | 115 | 3.193 | 67.902 | 15.248 | 1.00 | 61.46 |
| ATOM | 1033 | CA | ARG | 115 | 4.354 | 68.174 | 14.415 | 1.00 | 70.33 |
| ATOM | 1034 | C | ARG | 115 | 5.449 | 67.111 | 14.551 | 1.00 | 64.45 |
| ATOM | 1035 | O | ARG | 115 | 5.670 | 66.544 | 15.625 | 1.00 | 63.87 |
| ATOM | 1036 | CB | ARG | 115 | 4.903 | 69.575 | 14.718 | 1.00 | 74.16 |
| ATOM | 1037 | CG | ARG | 115 | 3.876 | 70.684 | 14.512 | 1.00 | 97.70 |
| ATOM | 1038 | CD | ARG | 115 | 4.378 | 72.008 | 15.043 | 1.00 | 0.22 |
| ATOM | 1039 | NE | ARG | 115 | 5.317 | 72.653 | 14.130 | 1.00 | 0.87 |
| ATOM | 1040 | CZ | ARG | 115 | 6.084 | 73.686 | 14.460 | 1.00 | 0.60 |
| ATOM | 1041 | NH1 | ARG | 115 | 6.032 | 74.190 | 15.685 | 1.00 | 0.46 |
| ATOM | 1042 | NH2 | ARG | 115 | 6.907 | 74.214 | 13.567 | 1.00 | 0.52 |
| ATOM | 1043 | N | SER | 116 | 6.112 | 66.832 | 13.440 | 1.00 | 46.36 |
| ATOM | 1044 | CA | SER | 116 | 7.241 | 65.915 | 13.437 | 1.00 | 58.82 |
| ATOM | 1045 | C | SER | 116 | 8.116 | 66.222 | 12.239 | 1.00 | 52.50 |
| ATOM | 1046 | O | SER | 116 | 7.667 | 66.862 | 11.292 | 1.00 | 69.05 |
| ATOM | 1047 | CB | SER | 116 | 6.757 | 64.469 | 13.386 | 1.00 | 72.93 |
| ATOM | 1048 | OG | SER | 116 | 6.002 | 64.230 | 12.213 | 1.00 | 83.93 |
| ATOM | 1049 | N | PRO | 142 | 10.324 | 61.372 | −0.478 | 1.00 | 35.84 |
| ATOM | 1050 | CA | PRO | 142 | 9.506 | 60.163 | −0.335 | 1.00 | 26.02 |
| ATOM | 1051 | C | PRO | 142 | 8.056 | 60.543 | −0.236 | 1.00 | 44.44 |
| ATOM | 1052 | O | PRO | 142 | 7.763 | 61.471 | 0.506 | 1.00 | 49.76 |
| ATOM | 1053 | CB | PRO | 142 | 9.947 | 59.573 | 1.014 | 1.00 | 38.65 |
| ATOM | 1054 | CG | PRO | 142 | 10.918 | 60.586 | 1.641 | 1.00 | 43.31 |
| ATOM | 1055 | CD | PRO | 142 | 10.869 | 61.846 | 0.805 | 1.00 | 41.46 |
| ATOM | 1056 | N | VAL | 143 | 7.177 | 59.858 | −0.968 | 1.00 | 38.87 |
| ATOM | 1057 | CA | VAL | 143 | 5.740 | 60.109 | −0.923 | 1.00 | 40.60 |
| ATOM | 1058 | C | VAL | 143 | 4.983 | 58.795 | −0.993 | 1.00 | 45.08 |
| ATOM | 1059 | O | VAL | 143 | 5.574 | 57.724 | −1.073 | 1.00 | 57.65 |
| ATOM | 1060 | CB | VAL | 143 | 5.270 | 61.010 | −2.083 | 1.00 | 54.37 |
| ATOM | 1061 | CG1 | VAL | 143 | 6.160 | 62.245 | −2.195 | 1.00 | 39.31 |
| ATOM | 1062 | CG2 | VAL | 143 | 5.283 | 60.242 | −3.384 | 1.00 | 52.85 |
| ATOM | 1063 | N | THR | 144 | 3.670 | 58.890 | −0.931 | 1.00 | 46.10 |
| ATOM | 1064 | CA | THR | 144 | 2.772 | 57.742 | −1.090 | 1.00 | 66.56 |
| ATOM | 1065 | C | THR | 144 | 2.120 | 57.760 | −2.467 | 1.00 | 68.98 |
| ATOM | 1066 | O | THR | 144 | 1.621 | 58.797 | −2.916 | 1.00 | 67.59 |
| ATOM | 1067 | CB | THR | 144 | 1.608 | 57.772 | −0.073 | 1.00 | 79.38 |
| ATOM | 1068 | OG1 | THR | 144 | 2.116 | 58.044 | 1.237 | 1.00 | 90.84 |
| ATOM | 1069 | CG2 | THR | 144 | 0.848 | 56.442 | −0.073 | 1.00 | 84.80 |
| ATOM | 1070 | N | SER | 145 | 2.112 | 56.618 | −3.138 | 1.00 | 92.35 |
| ATOM | 1071 | CA | SER | 145 | 1.414 | 56.528 | −4.403 | 1.00 | 92.76 |
| ATOM | 1072 | C | SER | 145 | 0.348 | 55.460 | −4.281 | 1.00 | 93.23 |
| ATOM | 1073 | O | SER | 145 | 0.560 | 54.435 | −3.638 | 1.00 | 93.67 |
| ATOM | 1074 | CB | SER | 145 | 2.387 | 56.209 | −5.536 | 1.00 | 93.44 |
| ATOM | 1075 | OG | SER | 145 | 3.120 | 55.032 | −5.253 | 1.00 | 94.25 |
| ATOM | 1076 | N | LEU | 146 | −0.811 | 55.713 | −4.875 | 1.00 | 93.12 |

TABLE 10-continued

Three-Dimensional Coordinates of *Neisseria gonorrhoeae* GCYH-IB (SEQ. ID. No. 8)

| ATOM | 1077 | CA  | LEU | 146 | -1.886  | 54.733 | -4.883  | 1.00 | 93.52 |
|------|------|-----|-----|-----|---------|--------|---------|------|-------|
| ATOM | 1078 | C   | LEU | 146 | -2.293  | 54.437 | -6.323  | 1.00 | 94.04 |
| ATOM | 1079 | O   | LEU | 146 | -2.412  | 55.348 | -7.135  | 1.00 | 93.70 |
| ATOM | 1080 | CB  | LEU | 146 | -3.069  | 55.225 | -4.048  | 1.00 | 92.85 |
| ATOM | 1081 | CG  | LEU | 146 | -4.193  | 54.212 | -3.829  | 1.00 | 93.13 |
| ATOM | 1082 | CD1 | LEU | 146 | -4.655  | 54.224 | -2.381  | 1.00 | 92.61 |
| ATOM | 1083 | CD2 | LEU | 146 | -5.349  | 54.466 | -4.792  | 1.00 | 93.10 |
| ATOM | 1084 | N   | CYS | 147 | -2.491  | 53.162 | -6.639  | 1.00 | 94.85 |
| ATOM | 1085 | CA  | CYS | 147 | -2.704  | 52.746 | -8.023  | 1.00 | 95.44 |
| ATOM | 1086 | C   | CYS | 147 | -4.145  | 52.903 | -8.502  | 1.00 | 95.11 |
| ATOM | 1087 | O   | CYS | 147 | -5.049  | 52.276 | -7.955  | 1.00 | 95.12 |
| ATOM | 1088 | CB  | CYS | 147 | -2.269  | 51.291 | -8.216  | 1.00 | 96.58 |
| ATOM | 1089 | SG  | CYS | 147 | -2.408  | 50.751 | -9.928  | 1.00 | 97.39 |
| ATOM | 1090 | N   | PRO | 148 | -4.354  | 53.721 | -9.550  | 1.00 | 94.79 |
| ATOM | 1091 | CA  | PRO | 148 | -5.687  | 53.948 | -10.123 | 1.00 | 94.46 |
| ATOM | 1092 | C   | PRO | 148 | -6.311  | 52.675 | -10.712 | 1.00 | 95.13 |
| ATOM | 1093 | O   | PRO | 148 | -7.500  | 52.438 | -10.497 | 1.00 | 94.91 |
| ATOM | 1094 | CB  | PRO | 148 | -5.425  | 54.976 | -11.233 | 1.00 | 94.10 |
| ATOM | 1095 | CG  | PRO | 148 | -4.110  | 55.588 | -10.900 | 1.00 | 93.98 |
| ATOM | 1096 | CD  | PRO | 148 | -3.320  | 54.494 | -10.256 | 1.00 | 94.69 |
| ATOM | 1097 | N   | CYS | 149 | -5.524  | 51.877 | -11.438 | 1.00 | 95.97 |
| ATOM | 1098 | CA  | CYS | 149 | -6.015  | 50.634 | -12.031 | 1.00 | 96.73 |
| ATOM | 1099 | C   | CYS | 149 | -6.454  | 49.635 | -10.961 | 1.00 | 97.03 |
| ATOM | 1100 | O   | CYS | 149 | -7.487  | 48.982 | -11.100 | 1.00 | 97.11 |
| ATOM | 1101 | CB  | CYS | 149 | -4.953  | 50.002 | -12.937 | 1.00 | 0.39  |
| ATOM | 1102 | SG  | CYS | 149 | -5.365  | 48.319 | -13.513 | 1.00 | 98.92 |
| ATOM | 1103 | N   | SER | 150 | -5.661  | 49.525 | -9.897  | 1.00 | 97.14 |
| ATOM | 1104 | CA  | SER | 150 | -5.968  | 48.646 | -8.773  | 1.00 | 97.32 |
| ATOM | 1105 | C   | SER | 150 | -7.297  | 49.007 | -8.122  | 1.00 | 96.45 |
| ATOM | 1106 | O   | SER | 150 | -8.116  | 48.135 | -7.844  | 1.00 | 96.62 |
| ATOM | 1107 | CB  | SER | 150 | -4.853  | 48.725 | -7.731  | 1.00 | 97.36 |
| ATOM | 1108 | OG  | SER | 150 | -5.142  | 47.922 | -6.603  | 1.00 | 97.43 |
| ATOM | 1109 | N   | LYS | 151 | -7.494  | 50.300 | -7.874  | 1.00 | 95.57 |
| ATOM | 1110 | CA  | LYS | 151 | -8.742  | 50.817 | -7.308  | 1.00 | 94.80 |
| ATOM | 1111 | C   | LYS | 151 | -9.939  | 50.554 | -8.227  | 1.00 | 94.79 |
| ATOM | 1112 | O   | LYS | 151 | -10.957 | 50.001 | -7.802  | 1.00 | 94.68 |
| ATOM | 1113 | CB  | LYS | 151 | -8.611  | 52.321 | -7.039  | 1.00 | 94.03 |
| ATOM | 1114 | CG  | LYS | 151 | -9.884  | 52.967 | -6.534  | 1.00 | 93.37 |
| ATOM | 1115 | CD  | LYS | 151 | -9.763  | 54.478 | -6.462  | 1.00 | 92.78 |
| ATOM | 1116 | CE  | LYS | 151 | -11.067 | 55.083 | -5.973  | 1.00 | 92.30 |
| ATOM | 1117 | NZ  | LYS | 151 | -11.016 | 56.557 | -5.900  | 1.00 | 91.85 |
| ATOM | 1118 | N   | GLU | 152 | -9.789  | 50.956 | -9.486  | 1.00 | 94.88 |
| ATOM | 1119 | CA  | GLU | 152 | -10.808 | 50.814 | -10.524 | 1.00 | 99.88 |
| ATOM | 1120 | C   | GLU | 152 | -11.333 | 49.385 | -10.726 | 1.00 | 95.41 |
| ATOM | 1121 | O   | GLU | 152 | -12.530 | 49.180 | -10.933 | 1.00 | 95.13 |
| ATOM | 1122 | CB  | GLU | 152 | -10.246 | 51.351 | -11.842 | 1.00 | 0.77  |
| ATOM | 1123 | CG  | GLU | 152 | -11.165 | 51.236 | -13.038 | 1.00 | 0.86  |
| ATOM | 1124 | CD  | GLU | 152 | -10.473 | 51.663 | -14.318 | 1.00 | 0.48  |
| ATOM | 1125 | OE1 | GLU | 152 | -9.369  | 51.147 | -14.596 | 1.00 | 0.36  |
| ATOM | 1126 | OE2 | GLU | 152 | -11.028 | 52.515 | -15.043 | 1.00 | 0.55  |
| ATOM | 1127 | N   | ILE | 153 | -10.440 | 48.400 | -10.668 | 1.00 | 98.72 |
| ATOM | 1128 | CA  | ILE | 153 | -10.815 | 47.023 | -10.987 | 1.00 | 0.24  |
| ATOM | 1129 | C   | ILE | 153 | -11.296 | 46.187 | -9.797  | 1.00 | 97.15 |
| ATOM | 1130 | O   | ILE | 153 | -11.995 | 45.191 | -9.988  | 1.00 | 97.36 |
| ATOM | 1131 | CB  | ILE | 153 | -9.682  | 46.255 | -11.722 | 1.00 | 98.13 |
| ATOM | 1132 | CG1 | ILE | 153 | -8.480  | 46.043 | -10.800 | 1.00 | 98.60 |
| ATOM | 1133 | CG2 | ILE | 153 | -9.289  | 46.971 | -13.006 | 1.00 | 98.08 |
| ATOM | 1134 | CD1 | ILE | 153 | -7.425  | 45.135 | -11.380 | 1.00 | 99.90 |
| ATOM | 1135 | N   | SER | 154 | -10.928 | 46.572 | -8.579  | 1.00 | 96.66 |
| ATOM | 1136 | CA  | SER | 154 | -11.331 | 45.789 | -7.411  | 1.00 | 96.63 |
| ATOM | 1137 | C   | SER | 154 | -12.547 | 46.390 | -6.712  | 1.00 | 95.64 |
| ATOM | 1138 | O   | SER | 154 | -12.783 | 47.598 | -6.793  | 1.00 | 94.99 |
| ATOM | 1139 | CB  | SER | 154 | -10.164 | 45.589 | -6.436  | 1.00 | 96.93 |
| ATOM | 1140 | OG  | SER | 154 | -9.523  | 46.810 | -6.138  | 1.00 | 96.38 |
| ATOM | 1141 | N   | GLN | 155 | -13.323 | 45.541 | -6.043  | 1.00 | 95.57 |
| ATOM | 1142 | CA  | GLN | 155 | -14.556 | 45.982 | -5.394  | 1.00 | 94.71 |
| ATOM | 1143 | C   | GLN | 155 | -14.265 | 46.748 | -4.110  | 1.00 | 94.12 |
| ATOM | 1144 | O   | GLN | 155 | -15.114 | 47.487 | -3.607  | 1.00 | 93.43 |
| ATOM | 1145 | CB  | GLN | 155 | -15.493 | 44.801 | -5.126  | 1.00 | 0.29  |
| ATOM | 1146 | CG  | GLN | 155 | -14.877 | 43.669 | -4.320  | 1.00 | 0.53  |
| ATOM | 1147 | CD  | GLN | 155 | -15.866 | 42.552 | -4.039  | 1.00 | 0.79  |
| ATOM | 1148 | OE1 | GLN | 155 | -17.047 | 42.799 | -3.786  | 1.00 | 0.94  |
| ATOM | 1149 | NE2 | GLN | 155 | -15.387 | 41.315 | -4.080  | 1.00 | 0.95  |
| ATOM | 1150 | N   | TYR | 156 | -13.058 | 46.558 | -3.586  | 1.00 | 94.45 |
| ATOM | 1151 | CA  | TYR | 156 | -12.548 | 47.368 | -2.483  | 1.00 | 93.90 |
| ATOM | 1152 | C   | TYR | 156 | -11.030 | 47.300 | -2.429  | 1.00 | 95.21 |
| ATOM | 1153 | O   | TYR | 156 | -10.417 | 46.409 | -3.023  | 1.00 | 95.22 |
| ATOM | 1154 | CB  | TYR | 156 | -13.154 | 46.954 | -1.136  | 1.00 | 93.42 |

TABLE 10-continued

Three-Dimensional Coordinates of *Neisseria gonorrhoeae* GCYH-IB (SEQ. ID. No. 8)

| ATOM | 1155 | CG | TYR | 156 | −13.397 | 45.470 | −0.969 | 1.00 | 96.29 |
|---|---|---|---|---|---|---|---|---|---|
| ATOM | 1156 | CD1 | TYR | 156 | −12.340 | 44.567 | −0.952 | 1.00 | 94.61 |
| ATOM | 1157 | CD2 | TYR | 156 | −14.688 | 44.975 | −0.804 | 1.00 | 93.79 |
| ATOM | 1158 | CE1 | TYR | 156 | −12.565 | 43.205 | −0.793 | 1.00 | 0.99 |
| ATOM | 1159 | CE2 | TYR | 156 | −14.923 | 43.620 | −0.643 | 1.00 | 0.56 |
| ATOM | 1160 | CZ | TYR | 156 | −13.859 | 42.737 | −0.638 | 1.00 | 0.71 |
| ATOM | 1161 | OH | TYR | 156 | −14.088 | 41.389 | −0.475 | 1.00 | 0.86 |
| ATOM | 1162 | N | GLY | 157 | −10.430 | 48.252 | −1.721 | 1.00 | 93.87 |
| ATOM | 1163 | CA | GLY | 157 | −8.989 | 48.300 | −1.574 | 1.00 | 94.19 |
| ATOM | 1164 | C | GLY | 157 | −8.289 | 48.790 | −2.826 | 1.00 | 94.61 |
| ATOM | 1165 | O | GLY | 157 | −8.860 | 48.789 | −3.914 | 1.00 | 94.83 |
| ATOM | 1166 | N | ALA | 158 | −7.044 | 49.223 | −2.658 | 1.00 | 94.67 |
| ATOM | 1167 | CA | ALA | 158 | −6.180 | 49.599 | −3.770 | 1.00 | 95.10 |
| ATOM | 1168 | C | ALA | 158 | −4.752 | 49.488 | −3.273 | 1.00 | 95.37 |
| ATOM | 1169 | O | ALA | 158 | −4.422 | 50.015 | −2.213 | 1.00 | 94.74 |
| ATOM | 1170 | CB | ALA | 158 | −6.473 | 51.017 | −4.229 | 1.00 | 94.43 |
| ATOM | 1171 | N | HIS | 159 | −3.899 | 48.788 | −4.008 | 1.00 | 96.33 |
| ATOM | 1172 | CA | HIS | 159 | −2.535 | 48.658 | −3.536 | 1.00 | 96.64 |
| ATOM | 1173 | C | HIS | 159 | −1.857 | 50.023 | −3.619 | 1.00 | 95.96 |
| ATOM | 1174 | O | HIS | 159 | −2.001 | 50.750 | −4.602 | 1.00 | 95.83 |
| ATOM | 1175 | CB | HIS | 159 | −1.756 | 47.559 | −4.276 | 1.00 | 97.98 |
| ATOM | 1176 | CG | HIS | 159 | −1.206 | 47.985 | −5.598 | 1.00 | 98.41 |
| ATOM | 1177 | ND1 | HIS | 159 | −0.055 | 48.731 | −5.717 | 1.00 | 98.28 |
| ATOM | 1178 | CD2 | HIS | 159 | −1.641 | 47.757 | −6.855 | 1.00 | 98.92 |
| ATOM | 1179 | CE1 | HIS | 159 | 0.190 | 48.958 | −6.996 | 1.00 | 98.69 |
| ATOM | 1180 | NE2 | HIS | 159 | −0.758 | 48.376 | −7.704 | 1.00 | 99.08 |
| ATOM | 1181 | N | ASN | 160 | −1.173 | 50.380 | −2.541 | 1.00 | 95.46 |
| ATOM | 1182 | CA | ASN | 160 | −0.370 | 51.585 | −2.495 | 1.00 | 94.85 |
| ATOM | 1183 | C | ASN | 160 | 1.022 | 51.221 | −2.001 | 1.00 | 95.19 |
| ATOM | 1184 | O | ASN | 160 | 1.264 | 50.080 | −1.603 | 1.00 | 95.86 |
| ATOM | 1185 | CB | ASN | 160 | −1.025 | 52.657 | −1.613 | 1.00 | 93.70 |
| ATOM | 1186 | CG | ASN | 160 | −1.510 | 52.116 | −0.286 | 1.00 | 93.37 |
| ATOM | 1187 | OD1 | ASN | 160 | −2.673 | 51.739 | −0.146 | 1.00 | 93.31 |
| ATOM | 1188 | ND2 | ASN | 160 | −0.626 | 52.085 | 0.699 | 1.00 | 93.09 |
| ATOM | 1189 | N | GLN | 161 | 1.941 | 52.178 | −2.045 | 1.00 | 94.75 |
| ATOM | 1190 | CA | GLN | 161 | 3.318 | 51.913 | −1.664 | 1.00 | 95.04 |
| ATOM | 1191 | C | GLN | 161 | 4.075 | 53.212 | −1.518 | 1.00 | 94.19 |
| ATOM | 1192 | O | GLN | 161 | 3.591 | 54.280 | −1.909 | 1.00 | 93.54 |
| ATOM | 1193 | CB | GLN | 161 | 4.010 | 51.048 | −2.717 | 1.00 | 96.35 |
| ATOM | 1194 | CG | GLN | 161 | 3.950 | 51.624 | −4.121 | 1.00 | 96.52 |
| ATOM | 1195 | CD | GLN | 161 | 2.646 | 51.299 | −4.833 | 1.00 | 96.74 |
| ATOM | 1196 | OE1 | GLN | 161 | 2.166 | 50.166 | −4.783 | 1.00 | 97.47 |
| ATOM | 1197 | NE2 | GLN | 161 | 2.069 | 52.293 | −5.504 | 1.00 | 96.11 |
| ATOM | 1198 | N | ARG | 162 | 5.267 | 53.115 | −0.948 | 1.00 | 94.19 |
| ATOM | 1199 | CA | ARG | 162 | 6.137 | 54.262 | −0.884 | 1.00 | 93.45 |
| ATOM | 1200 | C | ARG | 162 | 6.698 | 54.493 | −2.278 | 1.00 | 94.02 |
| ATOM | 1201 | O | ARG | 162 | 6.983 | 53.549 | −3.020 | 1.00 | 95.15 |
| ATOM | 1202 | CB | ARG | 162 | 7.251 | 54.057 | 0.145 | 1.00 | 93.25 |
| ATOM | 1203 | CG | ARG | 162 | 7.743 | 55.356 | 0.778 | 1.00 | 92.02 |
| ATOM | 1204 | CD | ARG | 162 | 8.796 | 55.103 | 1.840 | 1.00 | 0.01 |
| ATOM | 1205 | NE | ARG | 162 | 8.231 | 54.534 | 3.059 | 1.00 | 91.42 |
| ATOM | 1206 | CZ | ARG | 162 | 8.945 | 53.890 | 3.976 | 1.00 | 93.79 |
| ATOM | 1207 | NH1 | ARG | 162 | 10.251 | 53.724 | 3.806 | 1.00 | 91.78 |
| ATOM | 1208 | NH2 | ARG | 162 | 8.353 | 53.406 | 5.059 | 1.00 | 91.03 |
| ATOM | 1209 | N | SER | 163 | 6.811 | 55.767 | −2.632 | 1.00 | 47.09 |
| ATOM | 1210 | CA | SER | 163 | 7.414 | 56.185 | −3.886 | 1.00 | 43.85 |
| ATOM | 1211 | C | SER | 163 | 8.524 | 57.201 | −3.595 | 1.00 | 48.09 |
| ATOM | 1212 | O | SER | 163 | 8.397 | 58.015 | −2.694 | 1.00 | 43.99 |
| ATOM | 1213 | CB | SER | 163 | 6.325 | 56.776 | −4.786 | 1.00 | 51.94 |
| ATOM | 1214 | OG | SER | 163 | 6.868 | 57.366 | −5.949 | 1.00 | 81.97 |
| ATOM | 1215 | N | HIS | 164 | 9.624 | 57.125 | −4.336 | 1.00 | 37.14 |
| ATOM | 1216 | CA | HIS | 164 | 10.651 | 58.145 | −4.270 | 1.00 | 35.94 |
| ATOM | 1217 | C | HIS | 164 | 10.540 | 58.980 | −5.529 | 1.00 | 43.89 |
| ATOM | 1218 | O | HIS | 164 | 10.570 | 58.455 | −6.643 | 1.00 | 42.93 |
| ATOM | 1219 | CB | HIS | 164 | 12.044 | 57.519 | −4.153 | 1.00 | 49.63 |
| ATOM | 1220 | CG | HIS | 164 | 12.264 | 56.789 | −2.857 | 1.00 | 73.84 |
| ATOM | 1221 | ND1 | HIS | 164 | 13.125 | 55.709 | −2.748 | 1.00 | 79.92 |
| ATOM | 1222 | CD2 | HIS | 164 | 11.732 | 56.973 | −1.632 | 1.00 | 68.49 |
| ATOM | 1223 | CE1 | HIS | 164 | 13.114 | 55.275 | −1.501 | 1.00 | 79.23 |
| ATOM | 1224 | NE2 | HIS | 164 | 12.279 | 56.020 | −0.797 | 1.00 | 71.70 |
| ATOM | 1225 | N | ILE | 181 | 10.571 | 70.615 | −2.622 | 1.00 | 38.53 |
| ATOM | 1226 | CA | ILE | 181 | 9.757 | 69.675 | −1.864 | 1.00 | 36.63 |
| ATOM | 1227 | C | ILE | 181 | 8.243 | 69.969 | −2.002 | 1.00 | 51.18 |
| ATOM | 1228 | O | ILE | 181 | 7.433 | 69.045 | −2.155 | 1.00 | 44.19 |
| ATOM | 1229 | CB | ILE | 181 | 10.171 | 69.654 | −0.377 | 1.00 | 35.04 |
| ATOM | 1230 | CG1 | ILE | 181 | 11.587 | 69.071 | −0.239 | 1.00 | 31.82 |
| ATOM | 1231 | CG2 | ILE | 181 | 9.132 | 68.903 | 0.457 | 1.00 | 30.75 |
| ATOM | 1232 | CD1 | ILE | 181 | 12.198 | 69.163 | 1.161 | 1.00 | 38.43 |

TABLE 10-continued

Three-Dimensional Coordinates of *Neisseria gonorrhoeae* GCYH-IB (SEQ. ID. No. 8)

| ATOM | 1233 | N   | ASP | 182 | 7.879  | 71.253 | -1.964 | 1.00 | 40.80 |
|------|------|-----|-----|-----|--------|--------|--------|------|-------|
| ATOM | 1234 | CA  | ASP | 182 | 6.476  | 71.684 | -2.095 | 1.00 | 38.01 |
| ATOM | 1235 | C   | ASP | 182 | 5.902  | 71.348 | -3.478 | 1.00 | 44.33 |
| ATOM | 1236 | O   | ASP | 182 | 4.818  | 70.788 | -3.578 | 1.00 | 43.19 |
| ATOM | 1237 | CB  | ASP | 182 | 6.324  | 73.175 | -1.775 | 1.00 | 37.87 |
| ATOM | 1238 | CG  | ASP | 182 | 6.455  | 73.472 | -0.275 | 1.00 | 61.34 |
| ATOM | 1239 | OD1 | ASP | 182 | 6.189  | 72.568 | 0.553  | 1.00 | 62.93 |
| ATOM | 1240 | OD2 | ASP | 182 | 6.823  | 74.614 | 0.086  | 1.00 | 58.69 |
| ATOM | 1241 | N   | TYR | 183 | 6.643  | 71.655 | -4.539 | 1.00 | 37.99 |
| ATOM | 1242 | CA  | TYR | 183 | 6.211  | 71.260 | -5.878 | 1.00 | 39.70 |
| ATOM | 1243 | C   | TYR | 183 | 5.865  | 69.781 | -5.957 | 1.00 | 52.99 |
| ATOM | 1244 | O   | TYR | 183 | 4.984  | 69.381 | -6.708 | 1.00 | 53.89 |
| ATOM | 1245 | CB  | TYR | 183 | 7.279  | 71.552 | -6.934 | 1.00 | 39.65 |
| ATOM | 1246 | CG  | TYR | 183 | 7.415  | 73.002 | -7.330 | 1.00 | 55.07 |
| ATOM | 1247 | CD1 | TYR | 183 | 6.300  | 73.834 | -7.413 | 1.00 | 60.10 |
| ATOM | 1248 | CD2 | TYR | 183 | 8.655  | 73.535 | -7.651 | 1.00 | 44.43 |
| ATOM | 1249 | CE1 | TYR | 183 | 6.421  | 75.161 | -7.783 | 1.00 | 73.20 |
| ATOM | 1250 | CE2 | TYR | 183 | 8.787  | 74.853 | -8.028 | 1.00 | 60.20 |
| ATOM | 1251 | CZ  | TYR | 183 | 7.667  | 75.666 | -8.092 | 1.00 | 70.47 |
| ATOM | 1252 | OH  | TYR | 183 | 7.796  | 76.981 | -8.471 | 1.00 | 74.31 |
| ATOM | 1253 | N   | VAL | 184 | 6.571  | 68.956 | -5.201 | 1.00 | 40.52 |
| ATOM | 1254 | CA  | VAL | 184 | 6.324  | 67.526 | -5.295 | 1.00 | 41.20 |
| ATOM | 1255 | C   | VAL | 184 | 5.186  | 67.061 | -4.386 | 1.00 | 41.72 |
| ATOM | 1256 | O   | VAL | 184 | 4.304  | 66.334 | -4.826 | 1.00 | 46.40 |
| ATOM | 1257 | CB  | VAL | 184 | 7.604  | 66.667 | -5.056 | 1.00 | 39.23 |
| ATOM | 1258 | CG1 | VAL | 184 | 7.230  | 65.201 | -4.946 | 1.00 | 44.52 |
| ATOM | 1259 | CG2 | VAL | 184 | 8.605  | 66.872 | -6.185 | 1.00 | 37.38 |
| ATOM | 1260 | N   | GLU | 185 | 5.203  | 67.481 | -3.131 | 1.00 | 37.33 |
| ATOM | 1261 | CA  | GLU | 185 | 4.293  | 66.910 | -2.156 | 1.00 | 40.53 |
| ATOM | 1262 | C   | GLU | 185 | 2.849  | 67.311 | -2.472 | 1.00 | 58.15 |
| ATOM | 1263 | O   | GLU | 185 | 1.911  | 66.547 | -2.225 | 1.00 | 63.95 |
| ATOM | 1264 | CB  | GLU | 185 | 4.712  | 67.297 | -0.739 | 1.00 | 37.22 |
| ATOM | 1265 | CG  | GLU | 185 | 5.944  | 66.540 | -0.253 | 1.00 | 56.36 |
| ATOM | 1266 | CD  | GLU | 185 | 6.302  | 66.855 | 1.188  | 1.00 | 58.49 |
| ATOM | 1267 | OE1 | GLU | 185 | 5.913  | 67.936 | 1.673  | 1.00 | 54.54 |
| ATOM | 1268 | OE2 | GLU | 185 | 6.981  | 66.026 | 1.837  | 1.00 | 55.30 |
| ATOM | 1269 | N   | THR | 186 | 2.705  | 68.506 | -3.040 | 1.00 | 58.75 |
| ATOM | 1270 | CA  | THR | 186 | 1.442  | 69.024 | -3.556 | 1.00 | 61.49 |
| ATOM | 1271 | C   | THR | 186 | 0.776  | 68.037 | -4.505 | 1.00 | 55.72 |
| ATOM | 1272 | O   | THR | 186 | -0.429 | 67.845 | -4.459 | 1.00 | 61.05 |
| ATOM | 1273 | CB  | THR | 186 | 1.684  | 70.351 | -4.309 | 1.00 | 61.83 |
| ATOM | 1274 | OG1 | THR | 186 | 1.715  | 71.431 | -3.369 | 1.00 | 68.11 |
| ATOM | 1275 | CG2 | THR | 186 | 0.603  | 70.601 | -5.335 | 1.00 | 71.42 |
| ATOM | 1276 | N   | GLN | 187 | 1.581  | 67.393 | -5.339 | 1.00 | 77.31 |
| ATOM | 1277 | CA  | GLN | 187 | 1.078  | 66.523 | -6.393 | 1.00 | 77.26 |
| ATOM | 1278 | C   | GLN | 187 | 0.934  | 65.046 | -6.009 | 1.00 | 76.67 |
| ATOM | 1279 | O   | GLN | 187 | 0.447  | 64.247 | -6.804 | 1.00 | 76.96 |
| ATOM | 1280 | CB  | GLN | 187 | 2.001  | 66.620 | -7.606 | 1.00 | 76.96 |
| ATOM | 1281 | CG  | GLN | 187 | 2.215  | 68.017 | -8.095 | 1.00 | 77.69 |
| ATOM | 1282 | CD  | GLN | 187 | 0.969  | 68.579 | -8.695 | 1.00 | 79.02 |
| ATOM | 1283 | OE1 | GLN | 187 | 0.067  | 67.835 | -9.079 | 1.00 | 79.37 |
| ATOM | 1284 | NE2 | GLN | 187 | 0.901  | 69.898 | -8.786 | 1.00 | 80.11 |
| ATOM | 1285 | N   | ALA | 188 | 1.372  | 64.665 | -4.818 | 1.00 | 76.11 |
| ATOM | 1286 | CA  | ALA | 188 | 1.357  | 63.246 | -4.464 | 1.00 | 75.76 |
| ATOM | 1287 | C   | ALA | 188 | -0.046 | 62.758 | -4.083 | 1.00 | 76.42 |
| ATOM | 1288 | O   | ALA | 188 | -0.874 | 63.548 | -3.629 | 1.00 | 76.99 |
| ATOM | 1289 | CB  | ALA | 188 | 2.356  | 62.958 | -3.344 | 1.00 | 75.21 |
| ATOM | 1290 | N   | SER | 189 | -0.303 | 61.463 | -4.291 | 1.00 | 76.61 |
| ATOM | 1291 | CA  | SER | 189 | -1.531 | 60.823 | -3.819 | 1.00 | 77.40 |
| ATOM | 1292 | C   | SER | 189 | -1.704 | 61.180 | -2.359 | 1.00 | 79.46 |
| ATOM | 1293 | O   | SER | 189 | -2.789 | 61.603 | -1.933 | 1.00 | 77.83 |
| ATOM | 1294 | CB  | SER | 189 | -1.461 | 59.302 | -3.965 | 1.00 | 77.73 |
| ATOM | 1295 | OG  | SER | 189 | -1.641 | 58.911 | -5.308 | 1.00 | 78.51 |
| ATOM | 1296 | N   | CYS | 190 | -0.625 | 60.991 | -1.602 | 1.00 | 76.27 |
| ATOM | 1297 | CA  | CYS | 190 | -0.481 | 61.607 | -0.291 | 1.00 | 76.02 |
| ATOM | 1298 | C   | CYS | 190 | 0.975  | 61.643 | 0.155  | 1.00 | 75.41 |
| ATOM | 1299 | O   | CYS | 190 | 1.801  | 60.864 | -0.313 | 1.00 | 75.21 |
| ATOM | 1300 | CB  | CYS | 190 | -1.348 | 60.925 | 0.766  | 1.00 | 91.77 |
| ATOM | 1301 | SG  | CYS | 190 | -1.875 | 62.078 | 2.080  | 1.00 | 98.91 |
| ATOM | 1302 | N   | GLN | 191 | 1.288  | 62.562 | 1.057  | 1.00 | 75.45 |
| ATOM | 1303 | CA  | GLN | 191 | 2.659  | 62.708 | 1.525  | 1.00 | 75.31 |
| ATOM | 1304 | C   | GLN | 191 | 2.889  | 61.901 | 2.799  | 1.00 | 75.40 |
| ATOM | 1305 | O   | GLN | 191 | 1.942  | 61.393 | 3.402  | 1.00 | 75.47 |
| ATOM | 1306 | CB  | GLN | 191 | 2.998  | 64.187 | 1.730  | 1.00 | 75.73 |
| ATOM | 1307 | CG  | GLN | 191 | 1.820  | 65.018 | 2.190  | 1.00 | 76.28 |
| ATOM | 1308 | CD  | GLN | 191 | 2.140  | 66.486 | 2.240  | 1.00 | 80.40 |
| ATOM | 1309 | OE1 | GLN | 191 | 2.850  | 66.948 | 3.133  | 1.00 | 77.60 |
| ATOM | 1310 | NE2 | GLN | 191 | 1.612  | 67.236 | 1.280  | 1.00 | 81.30 |

TABLE 10-continued

Three-Dimensional Coordinates of *Neisseria gonorrhoeae* GCYH-IB (SEQ. ID. No. 8)

| ATOM | 1311 | N | LEU | 192 | 4.153 | 61.777 | 3.192 | 1.00 | 75.60 |
|------|------|-----|-----|-----|-------|--------|-------|------|-------|
| ATOM | 1312 | CA | LEU | 192 | 4.528 | 61.012 | 4.379 | 1.00 | 75.98 |
| ATOM | 1313 | C | LEU | 192 | 4.661 | 61.909 | 5.608 | 1.00 | 76.53 |
| ATOM | 1314 | O | LEU | 192 | 4.959 | 63.098 | 5.494 | 1.00 | 76.85 |
| ATOM | 1315 | CB | LEU | 192 | 5.842 | 60.266 | 4.138 | 1.00 | 76.39 |
| ATOM | 1316 | CG | LEU | 192 | 5.866 | 59.302 | 2.956 | 1.00 | 76.19 |
| ATOM | 1317 | CD1 | LEU | 192 | 7.208 | 58.607 | 2.866 | 1.00 | 76.97 |
| ATOM | 1318 | CD2 | LEU | 192 | 4.755 | 58.290 | 3.089 | 1.00 | 76.14 |
| ATOM | 1319 | N | TYR | 193 | 4.425 | 61.330 | 6.781 | 1.00 | 76.83 |
| ATOM | 1320 | CA | TYR | 193 | 4.630 | 62.026 | 8.048 | 1.00 | 77.60 |
| ATOM | 1321 | C | TYR | 193 | 5.343 | 61.086 | 9.011 | 1.00 | 78.30 |
| ATOM | 1322 | O | TYR | 193 | 5.185 | 59.868 | 8.930 | 1.00 | 78.11 |
| ATOM | 1323 | CB | TYR | 193 | 3.297 | 62.491 | 8.653 | 1.00 | 77.49 |
| ATOM | 1324 | CG | TYR | 193 | 2.511 | 63.450 | 7.782 | 1.00 | 77.25 |
| ATOM | 1325 | CD1 | TYR | 193 | 2.701 | 64.822 | 7.877 | 1.00 | 78.00 |
| ATOM | 1326 | CD2 | TYR | 193 | 1.572 | 62.980 | 6.865 | 1.00 | 76.63 |
| ATOM | 1327 | CE1 | TYR | 193 | 1.984 | 65.700 | 7.083 | 1.00 | 78.10 |
| ATOM | 1328 | CE2 | TYR | 193 | 0.853 | 63.852 | 6.066 | 1.00 | 76.74 |
| ATOM | 1329 | CZ | TYR | 193 | 1.064 | 65.210 | 6.183 | 1.00 | 77.46 |
| ATOM | 1330 | OH | TYR | 193 | 0.356 | 66.080 | 5.395 | 1.00 | 77.87 |
| ATOM | 1331 | N | GLY | 194 | 6.138 | 61.651 | 9.913 | 1.00 | 79.42 |
| ATOM | 1332 | CA | GLY | 194 | 6.809 | 60.855 | 10.923 | 1.00 | 80.46 |
| ATOM | 1333 | C | GLY | 194 | 5.856 | 60.416 | 12.024 | 1.00 | 80.39 |
| ATOM | 1334 | O | GLY | 194 | 5.953 | 59.300 | 12.538 | 1.00 | 90.26 |
| ATOM | 1335 | N | LEU | 195 | 4.923 | 61.299 | 12.375 | 1.00 | 80.09 |
| ATOM | 1336 | CA | LEU | 195 | 3.999 | 61.069 | 13.483 | 1.00 | 80.50 |
| ATOM | 1337 | C | LEU | 195 | 2.545 | 61.280 | 13.058 | 1.00 | 87.63 |
| ATOM | 1338 | O | LEU | 195 | 2.166 | 62.378 | 12.639 | 1.00 | 79.12 |
| ATOM | 1339 | CB | LEU | 195 | 4.334 | 62.010 | 14.641 | 1.00 | 81.47 |
| ATOM | 1340 | CG | LEU | 195 | 3.877 | 61.620 | 16.046 | 1.00 | 82.08 |
| ATOM | 1341 | CD1 | LEU | 195 | 4.554 | 62.514 | 17.068 | 1.00 | 83.80 |
| ATOM | 1342 | CD2 | LEU | 195 | 2.368 | 61.696 | 16.186 | 1.00 | 91.32 |
| ATOM | 1343 | N | LEU | 196 | 1.737 | 60.229 | 13.180 | 1.00 | 78.72 |
| ATOM | 1344 | CA | LEU | 196 | 0.314 | 60.299 | 12.863 | 1.00 | 78.17 |
| ATOM | 1345 | C | LEU | 196 | −0.524 | 59.674 | 13.969 | 1.00 | 78.46 |
| ATOM | 1346 | O | LEU | 196 | −0.206 | 58.593 | 14.467 | 1.00 | 78.70 |
| ATOM | 1347 | CB | LEU | 196 | 0.015 | 59.578 | 11.548 | 1.00 | 77.52 |
| ATOM | 1348 | CG | LEU | 196 | 0.682 | 60.112 | 10.285 | 1.00 | 77.15 |
| ATOM | 1349 | CD1 | LEU | 196 | 0.482 | 59.151 | 9.125 | 1.00 | 76.76 |
| ATOM | 1350 | CD2 | LEU | 196 | 0.132 | 61.485 | 9.961 | 1.00 | 77.20 |
| ATOM | 1351 | N | LYS | 197 | −1.600 | 60.354 | 14.347 | 1.00 | 78.62 |
| ATOM | 1352 | CA | LYS | 197 | −2.579 | 59.783 | 15.265 | 1.00 | 86.92 |
| ATOM | 1353 | C | LYS | 197 | −3.697 | 59.103 | 14.471 | 1.00 | 84.36 |
| ATOM | 1354 | O | LYS | 197 | −3.750 | 59.227 | 13.250 | 1.00 | 78.30 |
| ATOM | 1355 | CB | LYS | 197 | −3.149 | 60.865 | 16.187 | 1.00 | 87.85 |
| ATOM | 1356 | CG | LYS | 197 | −2.125 | 61.466 | 17.140 | 1.00 | 97.73 |
| ATOM | 1357 | CD | LYS | 197 | −1.043 | 60.448 | 17.481 | 1.00 | 0.65 |
| ATOM | 1358 | CE | LYS | 197 | −0.395 | 60.730 | 18.825 | 1.00 | 0.58 |
| ATOM | 1359 | NZ | LYS | 197 | −1.184 | 60.137 | 19.939 | 1.00 | 0.14 |
| ATOM | 1360 | N | ARG | 198 | −4.582 | 58.390 | 15.165 | 1.00 | 79.02 |
| ATOM | 1361 | CA | ARG | 198 | −5.703 | 57.694 | 14.523 | 1.00 | 88.62 |
| ATOM | 1362 | C | ARG | 198 | −6.465 | 58.513 | 13.475 | 1.00 | 90.64 |
| ATOM | 1363 | O | ARG | 198 | −6.648 | 58.052 | 12.349 | 1.00 | 79.37 |
| ATOM | 1364 | CB | ARG | 198 | −6.685 | 57.171 | 15.572 | 1.00 | 95.76 |
| ATOM | 1365 | CG | ARG | 198 | −6.523 | 55.710 | 15.908 | 1.00 | 0.91 |
| ATOM | 1366 | CD | ARG | 198 | −7.421 | 55.331 | 17.070 | 1.00 | 0.94 |
| ATOM | 1367 | NE | ARG | 198 | −7.901 | 53.959 | 16.953 | 1.00 | 0.52 |
| ATOM | 1368 | CZ | ARG | 198 | −9.089 | 53.629 | 16.457 | 1.00 | 0.91 |
| ATOM | 1369 | NH1 | ARG | 198 | −9.919 | 54.577 | 16.039 | 1.00 | 0.67 |
| ATOM | 1370 | NH2 | ARG | 198 | −9.448 | 52.353 | 16.381 | 1.00 | 0.24 |
| ATOM | 1371 | N | PRO | 199 | −6.933 | 59.719 | 13.848 | 1.00 | 79.78 |
| ATOM | 1372 | CA | PRO | 199 | −7.649 | 60.561 | 12.883 | 1.00 | 80.54 |
| ATOM | 1373 | C | PRO | 199 | −6.782 | 60.966 | 11.684 | 1.00 | 83.44 |
| ATOM | 1374 | O | PRO | 199 | −7.316 | 61.104 | 10.584 | 1.00 | 79.98 |
| ATOM | 1375 | CB | PRO | 199 | −8.028 | 61.797 | 13.717 | 1.00 | 81.05 |
| ATOM | 1376 | CG | PRO | 199 | −7.080 | 61.773 | 14.878 | 1.00 | 84.72 |
| ATOM | 1377 | CD | PRO | 199 | −6.956 | 60.322 | 15.192 | 1.00 | 83.17 |
| ATOM | 1378 | N | ASP | 200 | −5.479 | 61.152 | 11.899 | 1.00 | 78.96 |
| ATOM | 1379 | CA | ASP | 200 | −4.541 | 61.505 | 10.831 | 1.00 | 78.42 |
| ATOM | 1380 | C | ASP | 200 | −4.407 | 60.383 | 9.822 | 1.00 | 79.19 |
| ATOM | 1381 | O | ASP | 200 | −4.465 | 60.603 | 8.611 | 1.00 | 77.91 |
| ATOM | 1382 | CB | ASP | 200 | −3.155 | 61.776 | 11.407 | 1.00 | 78.13 |
| ATOM | 1383 | CG | ASP | 200 | −3.103 | 63.030 | 12.223 | 1.00 | 82.28 |
| ATOM | 1384 | OD1 | ASP | 200 | −3.716 | 64.026 | 11.799 | 1.00 | 79.46 |
| ATOM | 1385 | OD2 | ASP | 200 | −2.441 | 63.023 | 13.280 | 1.00 | 87.15 |
| ATOM | 1386 | N | GLU | 201 | −4.191 | 59.180 | 10.343 | 1.00 | 77.87 |
| ATOM | 1387 | CA | GLU | 201 | −4.068 | 57.982 | 9.527 | 1.00 | 88.08 |
| ATOM | 1388 | C | GLU | 201 | −5.343 | 57.714 | 8.731 | 1.00 | 82.38 |

TABLE 10-continued

Three-Dimensional Coordinates of *Neisseria gonorrhoeae* GCYH-IB (SEQ. ID. No. 8)

| ATOM | 1389 | O | GLU | 201 | −5.280 | 57.350 | 7.557 | 1.00 | 78.63 |
|------|------|-----|-----|-----|--------|--------|--------|------|-------|
| ATOM | 1390 | CB | GLU | 201 | −3.725 | 56.775 | 10.397 | 1.00 | 78.07 |
| ATOM | 1391 | CG | GLU | 201 | −3.905 | 55.469 | 9.680 | 1.00 | 82.77 |
| ATOM | 1392 | CD | GLU | 201 | −3.066 | 54.372 | 10.263 | 1.00 | 86.32 |
| ATOM | 1393 | OE1 | GLU | 201 | −2.758 | 54.411 | 11.473 | 1.00 | 94.84 |
| ATOM | 1394 | OE2 | GLU | 201 | −2.716 | 53.468 | 9.491 | 1.00 | 79.42 |
| ATOM | 1395 | N | LYS | 202 | −6.497 | 57.890 | 9.370 | 1.00 | 79.23 |
| ATOM | 1396 | CA | LYS | 202 | −7.769 | 57.762 | 8.673 | 1.00 | 80.32 |
| ATOM | 1397 | C | LYS | 202 | −7.821 | 58.739 | 7.497 | 1.00 | 80.40 |
| ATOM | 1398 | O | LYS | 202 | −8.153 | 58.359 | 6.374 | 1.00 | 80.99 |
| ATOM | 1399 | CB | LYS | 202 | −8.931 | 58.014 | 9.630 | 1.00 | 81.23 |
| ATOM | 1400 | CG | LYS | 202 | −10.249 | 58.187 | 8.921 | 1.00 | 82.74 |
| ATOM | 1401 | CD | LYS | 202 | −11.374 | 58.487 | 9.885 | 1.00 | 83.85 |
| ATOM | 1402 | CE | LYS | 202 | −12.645 | 58.814 | 9.126 | 1.00 | 85.72 |
| ATOM | 1403 | NZ | LYS | 202 | −13.745 | 59.169 | 10.052 | 1.00 | 0.18 |
| ATOM | 1404 | N | TYR | 203 | −7.468 | 59.992 | 7.767 | 1.00 | 80.02 |
| ATOM | 1405 | CA | TYR | 203 | −7.406 | 61.038 | 6.751 | 1.00 | 80.20 |
| ATOM | 1406 | C | TYR | 203 | −6.462 | 60.701 | 5.590 | 1.00 | 79.44 |
| ATOM | 1407 | O | TYR | 203 | −6.804 | 60.907 | 4.429 | 1.00 | 79.97 |
| ATOM | 1408 | CB | TYR | 203 | −6.983 | 62.360 | 7.399 | 1.00 | 80.10 |
| ATOM | 1409 | CG | TYR | 203 | −6.890 | 63.523 | 6.439 | 1.00 | 80.53 |
| ATOM | 1410 | CD1 | TYR | 203 | −7.977 | 64.366 | 6.231 | 1.00 | 82.06 |
| ATOM | 1411 | CD2 | TYR | 203 | −5.717 | 63.779 | 5.740 | 1.00 | 79.65 |
| ATOM | 1412 | CE1 | TYR | 203 | −7.900 | 65.429 | 5.356 | 1.00 | 82.73 |
| ATOM | 1413 | CE2 | TYR | 203 | −5.629 | 64.842 | 4.858 | 1.00 | 80.16 |
| ATOM | 1414 | CZ | TYR | 203 | −6.724 | 65.665 | 4.673 | 1.00 | 82.73 |
| ATOM | 1415 | OH | TYR | 203 | −6.644 | 66.721 | 3.798 | 1.00 | 82.87 |
| ATOM | 1416 | N | VAL | 204 | −5.276 | 60.190 | 5.909 | 1.00 | 78.40 |
| ATOM | 1417 | CA | VAL | 204 | −4.255 | 59.899 | 4.897 | 1.00 | 87.71 |
| ATOM | 1418 | C | VAL | 204 | −4.627 | 58.684 | 4.013 | 1.00 | 78.27 |
| ATOM | 1419 | O | VAL | 204 | −4.436 | 58.706 | 2.795 | 1.00 | 78.34 |
| ATOM | 1420 | CB | VAL | 204 | −2.831 | 59.766 | 5.553 | 1.00 | 76.92 |
| ATOM | 1421 | CG1 | VAL | 204 | −2.497 | 58.324 | 5.901 | 1.00 | 76.96 |
| ATOM | 1422 | CG2 | VAL | 204 | −1.766 | 60.349 | 4.663 | 1.00 | 76.41 |
| ATOM | 1423 | N | THR | 205 | −5.180 | 57.644 | 4.639 | 1.00 | 78.84 |
| ATOM | 1424 | CA | THR | 205 | −5.709 | 56.466 | 3.945 | 1.00 | 79.87 |
| ATOM | 1425 | C | THR | 205 | −6.769 | 56.848 | 2.913 | 1.00 | 81.00 |
| ATOM | 1426 | O | THR | 205 | −6.703 | 56.441 | 1.752 | 1.00 | 81.54 |
| ATOM | 1427 | CB | THR | 205 | −6.358 | 55.474 | 4.951 | 1.00 | 80.67 |
| ATOM | 1428 | OG1 | THR | 205 | −5.397 | 55.073 | 5.934 | 1.00 | 79.91 |
| ATOM | 1429 | CG2 | THR | 205 | −6.887 | 54.240 | 4.241 | 1.00 | 82.14 |
| ATOM | 1430 | N | GLU | 206 | −7.746 | 57.634 | 3.361 | 1.00 | 81.59 |
| ATOM | 1431 | CA | GLU | 206 | −8.880 | 58.047 | 2.539 | 1.00 | 83.15 |
| ATOM | 1432 | C | GLU | 206 | −8.497 | 59.008 | 1.417 | 1.00 | 82.92 |
| ATOM | 1433 | O | GLU | 206 | −8.919 | 58.829 | 0.280 | 1.00 | 84.05 |
| ATOM | 1434 | CB | GLU | 206 | −9.965 | 58.663 | 3.420 | 1.00 | 84.07 |
| ATOM | 1435 | CG | GLU | 206 | −10.610 | 57.655 | 4.353 | 1.00 | 84.78 |
| ATOM | 1436 | CD | GLU | 206 | −11.558 | 58.286 | 5.361 | 1.00 | 0.42 |
| ATOM | 1437 | OE1 | GLU | 206 | −11.678 | 59.533 | 5.384 | 1.00 | 0.46 |
| ATOM | 1438 | OE2 | GLU | 206 | −12.182 | 57.528 | 6.136 | 1.00 | 98.72 |
| ATOM | 1439 | N | LYS | 207 | −7.699 | 60.022 | 1.744 | 1.00 | 81.67 |
| ATOM | 1440 | CA | LYS | 207 | −7.228 | 61.007 | 0.769 | 1.00 | 81.45 |
| ATOM | 1441 | C | LYS | 207 | −6.425 | 60.371 | −0.378 | 1.00 | 80.95 |
| ATOM | 1442 | O | LYS | 207 | −6.573 | 60.760 | −1.535 | 1.00 | 81.57 |
| ATOM | 1443 | CB | LYS | 207 | −6.403 | 62.097 | 1.471 | 1.00 | 82.62 |
| ATOM | 1444 | CG | LYS | 207 | −5.506 | 62.928 | 0.558 | 1.00 | 0.81 |
| ATOM | 1445 | CD | LYS | 207 | −6.286 | 64.003 | −0.185 | 1.00 | 0.19 |
| ATOM | 1446 | CE | LYS | 207 | −5.345 | 64.988 | −0.866 | 1.00 | 0.78 |
| ATOM | 1447 | NZ | LYS | 207 | −6.089 | 66.106 | −1.511 | 1.00 | 0.10 |
| ATOM | 1448 | N | ALA | 208 | −5.577 | 59.398 | −0.054 | 1.00 | 80.02 |
| ATOM | 1449 | CA | ALA | 208 | −4.814 | 58.684 | −1.072 | 1.00 | 79.80 |
| ATOM | 1450 | C | ALA | 208 | −5.747 | 57.870 | −1.965 | 1.00 | 81.46 |
| ATOM | 1451 | O | ALA | 208 | −5.570 | 57.822 | −3.184 | 1.00 | 81.88 |
| ATOM | 1452 | CB | ALA | 208 | −3.767 | 57.783 | −0.420 | 1.00 | 78.93 |
| ATOM | 1453 | N | TYR | 209 | −6.740 | 57.235 | −1.344 | 1.00 | 82.59 |
| ATOM | 1454 | CA | TYR | 209 | −7.751 | 56.466 | −2.067 | 1.00 | 84.67 |
| ATOM | 1455 | C | TYR | 209 | −8.516 | 57.344 | −3.062 | 1.00 | 85.92 |
| ATOM | 1456 | O | TYR | 209 | −8.824 | 56.901 | −4.166 | 1.00 | 87.37 |
| ATOM | 1457 | CB | TYR | 209 | −8.716 | 55.781 | −1.090 | 1.00 | 85.82 |
| ATOM | 1458 | CG | TYR | 209 | −9.615 | 54.729 | −1.713 | 1.00 | 88.27 |
| ATOM | 1459 | CD1 | TYR | 209 | −9.200 | 53.408 | −1.815 | 1.00 | 88.83 |
| ATOM | 1460 | CD2 | TYR | 209 | −10.885 | 55.056 | −2.184 | 1.00 | 90.41 |
| ATOM | 1461 | CE1 | TYR | 209 | −10.016 | 52.442 | −2.376 | 1.00 | 91.44 |
| ATOM | 1462 | CE2 | TYR | 209 | −11.711 | 54.097 | −2.745 | 1.00 | 93.05 |
| ATOM | 1463 | CZ | TYR | 209 | −11.271 | 52.789 | −2.838 | 1.00 | 94.48 |
| ATOM | 1464 | OH | TYR | 209 | −12.080 | 51.819 | −3.394 | 1.00 | 96.54 |
| ATOM | 1465 | N | GLU | 210 | −8.805 | 58.586 | −2.677 | 1.00 | 85.61 |
| ATOM | 1466 | CA | GLU | 210 | −9.536 | 59.518 | −3.540 | 1.00 | 87.08 |

TABLE 10-continued

Three-Dimensional Coordinates of *Neisseria gonorrhoeae* GCYH-IB (SEQ. ID. No. 8)

| ATOM | 1467 | C   | GLU | 210 | -8.646  | 60.190 | -4.590  | 1.00 | 86.22 |
|------|------|-----|-----|-----|---------|--------|---------|------|-------|
| ATOM | 1468 | O   | GLU | 210 | -9.142  | 60.828 | -5.520  | 1.00 | 87.58 |
| ATOM | 1469 | CB  | GLU | 210 | -10.225 | 60.599 | -2.704  | 1.00 | 87.52 |
| ATOM | 1470 | CG  | GLU | 210 | -11.164 | 60.068 | -1.643  | 1.00 | 88.48 |
| ATOM | 1471 | CD  | GLU | 210 | -11.399 | 61.065 | -0.522  | 1.00 | 0.19  |
| ATOM | 1472 | OE1 | GLU | 210 | -10.915 | 62.216 | -0.625  | 1.00 | 87.54 |
| ATOM | 1473 | OE2 | GLU | 210 | -12.070 | 60.692 | 0.467   | 1.00 | 0.58  |
| ATOM | 1474 | N   | ASN | 211 | -7.332  | 60.053 | -4.440  | 1.00 | 84.16 |
| ATOM | 1475 | CA  | ASN | 211 | -6.404  | 60.680 | -5.372  | 1.00 | 83.31 |
| ATOM | 1476 | C   | ASN | 211 | -5.378  | 59.681 | -5.917  | 1.00 | 87.15 |
| ATOM | 1477 | O   | ASN | 211 | -4.177  | 59.836 | -5.694  | 1.00 | 80.86 |
| ATOM | 1478 | CB  | ASN | 211 | -5.707  | 61.876 | -4.705  | 1.00 | 89.00 |
| ATOM | 1479 | CG  | ASN | 211 | -4.924  | 62.725 | -5.692  | 1.00 | 0.16  |
| ATOM | 1480 | OD1 | ASN | 211 | -5.325  | 62.889 | -6.848  | 1.00 | 0.17  |
| ATOM | 1481 | ND2 | ASN | 211 | -3.799  | 63.273 | -5.236  | 1.00 | 99.78 |
| ATOM | 1482 | N   | PRO | 212 | -5.853  | 58.649 | -6.641  | 1.00 | 83.90 |
| ATOM | 1483 | CA  | PRO | 212 | -4.944  | 57.644 | -7.205  | 1.00 | 83.57 |
| ATOM | 1484 | C   | PRO | 212 | -4.058  | 58.255 | -8.296  | 1.00 | 82.85 |
| ATOM | 1485 | O   | PRO | 212 | -4.523  | 59.097 | -9.062  | 1.00 | 83.56 |
| ATOM | 1486 | CB  | PRO | 212 | -5.901  | 56.606 | -7.817  | 1.00 | 85.91 |
| ATOM | 1487 | CG  | PRO | 212 | -7.256  | 56.942 | -7.287  | 1.00 | 87.27 |
| ATOM | 1488 | CD  | PRO | 212 | -7.244  | 58.409 | -7.051  | 1.00 | 86.29 |
| ATOM | 1489 | N   | LYS | 213 | -2.796  | 57.844 | -8.356  | 1.00 | 81.66 |
| ATOM | 1490 | CA  | LYS | 213 | -1.879  | 58.359 | -9.368  | 1.00 | 81.02 |
| ATOM | 1491 | C   | LYS | 213 | -0.847  | 57.335 | -9.811  | 1.00 | 80.90 |
| ATOM | 1492 | O   | LYS | 213 | -0.140  | 56.746 | -8.996  | 1.00 | 80.25 |
| ATOM | 1493 | CB  | LYS | 213 | -1.174  | 59.632 | -8.888  | 1.00 | 79.48 |
| ATOM | 1494 | CG  | LYS | 213 | -1.990  | 60.898 | -9.075  | 1.00 | 80.00 |
| ATOM | 1495 | CD  | LYS | 213 | -1.147  | 62.158 | -8.942  | 1.00 | 80.38 |
| ATOM | 1496 | CE  | LYS | 213 | -2.048  | 63.376 | -8.819  | 1.00 | 79.77 |
| ATOM | 1497 | NZ  | LYS | 213 | -1.310  | 64.661 | -8.798  | 1.00 | 79.21 |
| ATOM | 1498 | N   | PHE | 214 | -0.777  | 57.132 | -11.117 | 1.00 | 81.78 |
| ATOM | 1499 | CA  | PHE | 214 | 0.279   | 56.351 | -11.712 | 1.00 | 81.81 |
| ATOM | 1500 | C   | PHE | 214 | 1.610   | 57.094 | -11.578 | 1.00 | 80.07 |
| ATOM | 1501 | O   | PHE | 214 | 1.666   | 58.294 | -11.322 | 1.00 | 79.06 |
| ATOM | 1502 | CB  | PHE | 214 | -0.011  | 56.123 | -13.199 | 1.00 | 83.28 |
| ATOM | 1503 | CG  | PHE | 214 | -1.127  | 55.145 | -13.477 | 1.00 | 85.59 |
| ATOM | 1504 | CD1 | PHE | 214 | -1.079  | 53.849 | -12.980 | 1.00 | 88.35 |
| ATOM | 1505 | CD2 | PHE | 214 | -2.205  | 55.511 | -14.265 | 1.00 | 87.15 |
| ATOM | 1506 | CE1 | PHE | 214 | -2.096  | 52.946 | -13.248 | 1.00 | 89.02 |
| ATOM | 1507 | CE2 | PHE | 214 | -3.217  | 54.611 | -14.536 | 1.00 | 89.66 |
| ATOM | 1508 | CZ  | PHE | 214 | -3.163  | 53.329 | -14.027 | 1.00 | 90.59 |
| ATOM | 1509 | N   | VAL | 215 | 2.690   | 56.367 | -11.777 | 1.00 | 50.17 |
| ATOM | 1510 | CA  | VAL | 215 | 4.001   | 56.971 | -11.876 | 1.00 | 41.74 |
| ATOM | 1511 | C   | VAL | 215 | 4.075   | 57.956 | -13.059 | 1.00 | 47.63 |
| ATOM | 1512 | O   | VAL | 215 | 4.762   | 58.977 | -12.985 | 1.00 | 45.88 |
| ATOM | 1513 | CB  | VAL | 215 | 5.105   | 55.871 | -11.916 | 1.00 | 50.90 |
| ATOM | 1514 | CG1 | VAL | 215 | 5.318   | 55.349 | -13.325 | 1.00 | 44.79 |
| ATOM | 1515 | CG2 | VAL | 215 | 6.377   | 56.401 | -11.342 | 1.00 | 44.27 |
| ATOM | 1516 | N   | GLU | 216 | 3.350   | 57.665 | -14.133 | 1.00 | 38.86 |
| ATOM | 1517 | CA  | GLU | 216 | 3.280   | 58.575 | -15.267 | 1.00 | 45.56 |
| ATOM | 1518 | C   | GLU | 216 | 2.645   | 59.916 | -14.884 | 1.00 | 44.87 |
| ATOM | 1519 | O   | GLU | 216 | 3.128   | 60.973 | -15.290 | 1.00 | 42.87 |
| ATOM | 1520 | CB  | GLU | 216 | 2.519   | 57.944 | -16.431 | 1.00 | 49.41 |
| ATOM | 1521 | CG  | GLU | 216 | 3.149   | 56.661 | -16.979 | 1.00 | 63.76 |
| ATOM | 1522 | CD  | GLU | 216 | 2.569   | 55.394 | -16.362 | 1.00 | 68.55 |
| ATOM | 1523 | OE1 | GLU | 216 | 2.046   | 55.458 | -15.233 | 1.00 | 69.32 |
| ATOM | 1524 | OE2 | GLU | 216 | 2.638   | 54.325 | -17.008 | 1.00 | 75.24 |
| ATOM | 1525 | N   | ASP | 217 | 1.582   | 59.875 | -14.088 | 1.00 | 45.69 |
| ATOM | 1526 | CA  | ASP | 217 | 0.909   | 61.107 | -13.681 | 1.00 | 47.86 |
| ATOM | 1527 | C   | ASP | 217 | 1.749   | 61.903 | -12.716 | 1.00 | 53.47 |
| ATOM | 1528 | O   | ASP | 217 | 1.778   | 63.127 | -12.780 | 1.00 | 61.34 |
| ATOM | 1529 | CB  | ASP | 217 | -0.454  | 60.823 | -13.071 | 1.00 | 56.10 |
| ATOM | 1530 | CG  | ASP | 217 | -1.341  | 60.076 | -14.015 | 1.00 | 74.86 |
| ATOM | 1531 | OD1 | ASP | 217 | -1.385  | 60.488 | -15.200 | 1.00 | 74.32 |
| ATOM | 1532 | OD2 | ASP | 217 | -1.963  | 59.073 | -13.578 | 1.00 | 80.99 |
| ATOM | 1533 | N   | MSE | 218 | 2.447   | 61.203 | -11.828 | 1.00 | 48.18 |
| ATOM | 1534 | CA  | MSE | 218 | 3.335   | 61.861 | -10.876 | 1.00 | 48.13 |
| ATOM | 1535 | C   | MSE | 218 | 4.367   | 62.772 | -11.572 | 1.00 | 44.35 |
| ATOM | 1536 | O   | MSE | 218 | 4.451   | 63.975 | -11.295 | 1.00 | 44.73 |
| ATOM | 1537 | CB  | MSE | 218 | 4.043   | 60.809 | -10.013 | 1.00 | 67.17 |
| ATOM | 1538 | CG  | MSE | 218 | 4.792   | 61.371 | -8.792  | 1.00 | 78.71 |
| ATOM | 1539 | SE  | MSE | 218 | 3.762   | 62.703 | -7.728  | 1.00 | 0.04  |
| ATOM | 1540 | CE  | MSE | 218 | 4.841   | 62.738 | -6.111  | 1.00 | 0.62  |
| ATOM | 1541 | N   | VAL | 219 | 5.153   | 62.201 | -12.479 | 1.00 | 38.53 |
| ATOM | 1542 | CA  | VAL | 219 | 6.170   | 62.980 | -13.154 | 1.00 | 34.39 |
| ATOM | 1543 | C   | VAL | 219 | 5.567   | 64.068 | -14.048 | 1.00 | 37.70 |
| ATOM | 1544 | O   | VAL | 219 | 6.082   | 65.181 | -14.104 | 1.00 | 41.68 |

TABLE 10-continued

Three-Dimensional Coordinates of *Neisseria gonorrhoeae* GCYH-IB (SEQ. ID. No. 8)

| ATOM | 1545 | CB | VAL | 219 | 7.162 | 62.105 | −13.952 | 1.00 | 44.91 |
|---|---|---|---|---|---|---|---|---|---|
| ATOM | 1546 | CG1 | VAL | 219 | 7.886 | 61.122 | −13.008 | 1.00 | 51.70 |
| ATOM | 1547 | CG2 | VAL | 219 | 6.458 | 61.364 | −15.067 | 1.00 | 34.05 |
| ATOM | 1548 | N | ARG | 220 | 4.485 | 63.759 | −14.750 | 1.00 | 38.89 |
| ATOM | 1549 | CA | ARG | 220 | 3.850 | 64.785 | −15.578 | 1.00 | 45.03 |
| ATOM | 1550 | C | ARG | 220 | 3.434 | 65.993 | −14.742 | 1.00 | 49.38 |
| ATOM | 1551 | O | ARG | 220 | 3.726 | 67.133 | −15.099 | 1.00 | 54.21 |
| ATOM | 1552 | CB | ARG | 220 | 2.675 | 64.225 | −16.369 | 1.00 | 44.05 |
| ATOM | 1553 | CG | ARG | 220 | 3.115 | 63.556 | −17.641 | 1.00 | 46.49 |
| ATOM | 1554 | CD | ARG | 220 | 2.038 | 62.720 | −18.249 | 1.00 | 46.91 |
| ATOM | 1555 | NE | ARG | 220 | 2.410 | 62.381 | −19.605 | 1.00 | 48.02 |
| ATOM | 1556 | CZ | ARG | 220 | 1.898 | 61.366 | −20.279 | 1.00 | 55.99 |
| ATOM | 1557 | NH1 | ARG | 220 | 0.979 | 60.588 | −19.716 | 1.00 | 44.26 |
| ATOM | 1558 | NH2 | ARG | 220 | 2.305 | 61.139 | −21.519 | 1.00 | 53.88 |
| ATOM | 1559 | N | ASP | 221 | 2.795 | 65.736 | −13.607 | 1.00 | 43.66 |
| ATOM | 1560 | CA | ASP | 221 | 2.279 | 66.813 | −12.760 | 1.00 | 41.62 |
| ATOM | 1561 | C | ASP | 221 | 3.400 | 67.652 | −12.130 | 1.00 | 50.60 |
| ATOM | 1562 | O | ASP | 221 | 3.305 | 68.878 | −12.090 | 1.00 | 44.79 |
| ATOM | 1563 | CB | ASP | 221 | 1.350 | 66.252 | −11.691 | 1.00 | 46.23 |
| ATOM | 1564 | CG | ASP | 221 | 0.080 | 65.635 | −12.287 | 1.00 | 78.89 |
| ATOM | 1565 | OD1 | ASP | 221 | −0.171 | 65.820 | −13.503 | 1.00 | 87.03 |
| ATOM | 1566 | OD2 | ASP | 221 | −0.667 | 64.963 | −11.545 | 1.00 | 63.65 |
| ATOM | 1567 | N | VAL | 222 | 4.471 | 67.002 | −11.658 | 1.00 | 40.55 |
| ATOM | 1568 | CA | VAL | 222 | 5.611 | 67.744 | −11.110 | 1.00 | 39.97 |
| ATOM | 1569 | C | VAL | 222 | 6.353 | 68.537 | −12.189 | 1.00 | 40.25 |
| ATOM | 1570 | O | VAL | 222 | 6.749 | 69.673 | −11.969 | 1.00 | 43.37 |
| ATOM | 1571 | CB | VAL | 222 | 6.641 | 66.825 | −10.424 | 1.00 | 40.52 |
| ATOM | 1572 | CG1 | VAL | 222 | 7.854 | 67.628 | −10.029 | 1.00 | 40.76 |
| ATOM | 1573 | CG2 | VAL | 222 | 6.044 | 66.155 | −9.216 | 1.00 | 39.98 |
| ATOM | 1574 | N | ALA | 223 | 6.558 | 67.926 | −13.350 | 1.00 | 42.74 |
| ATOM | 1575 | CA | ALA | 223 | 7.248 | 68.579 | −14.462 | 1.00 | 38.34 |
| ATOM | 1576 | C | ALA | 223 | 6.516 | 69.837 | −14.951 | 1.00 | 48.36 |
| ATOM | 1577 | O | ALA | 223 | 7.137 | 70.841 | −15.296 | 1.00 | 53.21 |
| ATOM | 1578 | CB | ALA | 223 | 7.427 | 67.611 | −15.606 | 1.00 | 45.59 |
| ATOM | 1579 | N | THR | 224 | 5.193 | 69.782 | −14.972 | 1.00 | 44.31 |
| ATOM | 1580 | CA | THR | 224 | 4.393 | 70.953 | −15.339 | 1.00 | 43.02 |
| ATOM | 1581 | C | THR | 224 | 4.677 | 72.139 | −14.414 | 1.00 | 45.58 |
| ATOM | 1582 | O | THR | 224 | 4.851 | 73.260 | −14.871 | 1.00 | 49.95 |
| ATOM | 1583 | CB | THR | 224 | 2.905 | 70.609 | −15.329 | 1.00 | 42.71 |
| ATOM | 1584 | OG1 | THR | 224 | 2.659 | 69.566 | −16.279 | 1.00 | 53.74 |
| ATOM | 1585 | CG2 | THR | 224 | 2.085 | 71.813 | −15.691 | 1.00 | 50.78 |
| ATOM | 1586 | N | SER | 225 | 4.746 | 71.871 | −13.115 | 1.00 | 41.80 |
| ATOM | 1587 | CA | SER | 225 | 5.075 | 72.902 | −12.142 | 1.00 | 51.93 |
| ATOM | 1588 | C | SER | 225 | 6.481 | 73.452 | −12.386 | 1.00 | 52.55 |
| ATOM | 1589 | O | SER | 225 | 6.711 | 74.658 | −12.275 | 1.00 | 52.97 |
| ATOM | 1590 | CB | SER | 225 | 4.988 | 72.369 | −10.707 | 1.00 | 50.08 |
| ATOM | 1591 | OG | SER | 225 | 3.762 | 71.702 | −10.467 | 1.00 | 64.07 |
| ATOM | 1592 | N | LEU | 226 | 7.430 | 72.576 | −12.708 | 1.00 | 43.70 |
| ATOM | 1593 | CA | LEU | 226 | 8.819 | 73.021 | −12.875 | 1.00 | 41.18 |
| ATOM | 1594 | C | LEU | 226 | 9.005 | 73.793 | −14.182 | 1.00 | 49.52 |
| ATOM | 1595 | O | LEU | 226 | 9.774 | 74.742 | −14.249 | 1.00 | 48.99 |
| ATOM | 1596 | CB | LEU | 226 | 9.817 | 71.851 | −12.812 | 1.00 | 35.26 |
| ATOM | 1597 | CG | LEU | 226 | 9.817 | 70.959 | −11.577 | 1.00 | 41.80 |
| ATOM | 1598 | CD1 | LEU | 226 | 10.725 | 69.764 | −11.814 | 1.00 | 43.92 |
| ATOM | 1599 | CD2 | LEU | 226 | 10.225 | 71.725 | −10.330 | 1.00 | 38.82 |
| ATOM | 1600 | N | ILE | 227 | 8.308 | 73.359 | −15.221 | 1.00 | 44.77 |
| ATOM | 1601 | CA | ILE | 227 | 8.303 | 74.060 | −16.499 | 1.00 | 46.88 |
| ATOM | 1602 | C | ILE | 227 | 7.765 | 75.481 | −16.353 | 1.00 | 51.88 |
| ATOM | 1603 | O | ILE | 227 | 8.255 | 76.398 | −17.004 | 1.00 | 54.76 |
| ATOM | 1604 | CB | ILE | 227 | 7.422 | 73.325 | −17.508 | 1.00 | 52.15 |
| ATOM | 1605 | CG1 | ILE | 227 | 8.152 | 72.103 | −18.052 | 1.00 | 53.45 |
| ATOM | 1606 | CG2 | ILE | 227 | 7.072 | 74.207 | −18.664 | 1.00 | 38.00 |
| ATOM | 1607 | CD1 | ILE | 227 | 7.233 | 71.191 | −18.818 | 1.00 | 47.15 |
| ATOM | 1608 | N | ALA | 228 | 6.764 | 75.656 | −15.496 | 1.00 | 47.59 |
| ATOM | 1609 | CA | ALA | 228 | 6.186 | 76.976 | −15.236 | 1.00 | 54.10 |
| ATOM | 1610 | C | ALA | 228 | 7.189 | 77.921 | −14.557 | 1.00 | 63.76 |
| ATOM | 1611 | O | ALA | 228 | 7.263 | 79.091 | −14.912 | 1.00 | 56.69 |
| ATOM | 1612 | CB | ALA | 228 | 4.914 | 76.850 | −14.405 | 1.00 | 50.72 |
| ATOM | 1613 | N | ASP | 229 | 7.973 | 77.409 | −13.605 | 1.00 | 57.62 |
| ATOM | 1614 | CA | ASP | 229 | 8.941 | 78.229 | −12.867 | 1.00 | 50.20 |
| ATOM | 1615 | C | ASP | 229 | 10.052 | 78.751 | −13.783 | 1.00 | 53.28 |
| ATOM | 1616 | O | ASP | 229 | 10.788 | 77.976 | −14.380 | 1.00 | 55.26 |
| ATOM | 1617 | CB | ASP | 229 | 9.523 | 77.434 | −11.694 | 1.00 | 62.28 |
| ATOM | 1618 | CG | ASP | 229 | 10.189 | 78.317 | −10.660 | 1.00 | 69.82 |
| ATOM | 1619 | OD1 | ASP | 229 | 11.076 | 79.108 | −11.048 | 1.00 | 51.12 |
| ATOM | 1620 | OD2 | ASP | 229 | 9.837 | 78.210 | −9.460 | 1.00 | 58.63 |
| ATOM | 1621 | N | SER | 239 | 10.316 | 59.328 | −11.007 | 1.00 | 33.39 |
| ATOM | 1622 | CA | SER | 239 | 9.562 | 58.739 | −9.923 | 1.00 | 37.64 |

TABLE 10-continued

Three-Dimensional Coordinates of *Neisseria gonorrhoeae* GCYH-IB (SEQ. ID. No. 8)

| ATOM | 1623 | C | SER | 239 | 9.770 | 57.242 | −9.947 | 1.00 | 41.56 |
|---|---|---|---|---|---|---|---|---|---|
| ATOM | 1624 | O | SER | 239 | 9.717 | 56.603 | −10.999 | 1.00 | 40.74 |
| ATOM | 1625 | CB | SER | 239 | 8.066 | 59.088 | −10.029 | 1.00 | 39.51 |
| ATOM | 1626 | OG | SER | 239 | 7.366 | 58.601 | −8.908 | 1.00 | 58.13 |
| ATOM | 1627 | N | GLU | 240 | 10.028 | 56.688 | −8.776 | 1.00 | 36.90 |
| ATOM | 1628 | CA | GLU | 240 | 10.164 | 55.253 | −8.629 | 1.00 | 41.05 |
| ATOM | 1629 | C | GLU | 240 | 9.111 | 54.745 | −7.646 | 1.00 | 48.68 |
| ATOM | 1630 | O | GLU | 240 | 9.046 | 55.178 | −6.505 | 1.00 | 44.51 |
| ATOM | 1631 | CB | GLU | 240 | 11.576 | 54.886 | −8.176 | 1.00 | 33.98 |
| ATOM | 1632 | CG | GLU | 240 | 11.769 | 53.430 | −7.885 | 1.00 | 52.95 |
| ATOM | 1633 | CD | GLU | 240 | 13.243 | 53.043 | −7.821 | 1.00 | 68.35 |
| ATOM | 1634 | OE1 | GLU | 240 | 14.102 | 53.961 | −7.886 | 1.00 | 66.40 |
| ATOM | 1635 | OE2 | GLU | 240 | 13.531 | 51.822 | −7.709 | 1.00 | 63.55 |
| ATOM | 1636 | N | ASN | 241 | 8.276 | 53.828 | −8.105 | 1.00 | 42.17 |
| ATOM | 1637 | CA | ASN | 241 | 7.235 | 53.248 | −7.269 | 1.00 | 43.83 |
| ATOM | 1638 | C | ASN | 241 | 7.582 | 51.859 | −6.808 | 1.00 | 51.54 |
| ATOM | 1639 | O | ASN | 241 | 7.578 | 50.945 | −7.620 | 1.00 | 52.46 |
| ATOM | 1640 | CB | ASN | 241 | 5.955 | 53.109 | −8.075 | 1.00 | 60.29 |
| ATOM | 1641 | CG | ASN | 241 | 4.965 | 54.194 | −7.784 | 1.00 | 76.81 |
| ATOM | 1642 | OD1 | ASN | 241 | 3.765 | 53.945 | −7.766 | 1.00 | 80.52 |
| ATOM | 1643 | ND2 | ASN | 241 | 5.451 | 55.408 | −7.553 | 1.00 | 79.98 |
| ATOM | 1644 | N | PHE | 242 | 7.845 | 51.676 | −5.517 | 1.00 | 50.46 |
| ATOM | 1645 | CA | PHE | 242 | 8.149 | 50.329 | −5.009 | 1.00 | 66.54 |
| ATOM | 1646 | C | PHE | 242 | 6.862 | 49.531 | −4.825 | 1.00 | 56.00 |
| ATOM | 1647 | O | PHE | 242 | 6.502 | 49.147 | −3.714 | 1.00 | 54.94 |
| ATOM | 1648 | CB | PHE | 242 | 8.972 | 50.390 | −3.719 | 1.00 | 55.87 |
| ATOM | 1649 | CG | PHE | 242 | 10.225 | 51.215 | −3.851 | 1.00 | 58.67 |
| ATOM | 1650 | CD1 | PHE | 242 | 11.398 | 50.637 | −4.299 | 1.00 | 54.65 |
| ATOM | 1651 | CD2 | PHE | 242 | 10.218 | 52.574 | −3.547 | 1.00 | 54.51 |
| ATOM | 1652 | CE1 | PHE | 242 | 12.546 | 51.392 | −4.432 | 1.00 | 56.56 |
| ATOM | 1653 | CE2 | PHE | 242 | 11.360 | 53.336 | −3.670 | 1.00 | 56.59 |
| ATOM | 1654 | CZ | PHE | 242 | 12.526 | 52.749 | −4.116 | 1.00 | 56.20 |
| ATOM | 1655 | N | GLU | 243 | 6.186 | 49.296 | −5.946 | 1.00 | 52.01 |
| ATOM | 1656 | CA | GLU | 243 | 4.849 | 48.726 | −5.946 | 1.00 | 59.99 |
| ATOM | 1657 | C | GLU | 243 | 4.747 | 47.524 | −5.025 | 1.00 | 64.49 |
| ATOM | 1658 | O | GLU | 243 | 5.620 | 46.643 | −5.016 | 1.00 | 57.32 |
| ATOM | 1659 | CB | GLU | 243 | 4.390 | 48.386 | −7.366 | 1.00 | 67.73 |
| ATOM | 1660 | CG | GLU | 243 | 5.399 | 47.633 | −8.197 | 1.00 | 99.15 |
| ATOM | 1661 | CD | GLU | 243 | 4.861 | 47.319 | −9.575 | 1.00 | 0.05 |
| ATOM | 1662 | OE1 | GLU | 243 | 5.665 | 46.989 | −10.472 | 1.00 | 0.86 |
| ATOM | 1663 | OE2 | GLU | 243 | 3.627 | 47.409 | −9.758 | 1.00 | 0.90 |
| ATOM | 1664 | N | SER | 244 | 3.672 | 47.512 | −4.243 | 1.00 | 53.45 |
| ATOM | 1665 | CA | SER | 244 | 3.523 | 46.559 | −3.154 | 1.00 | 53.27 |
| ATOM | 1666 | C | SER | 244 | 3.021 | 45.194 | −3.625 | 1.00 | 55.37 |
| ATOM | 1667 | O | SER | 244 | 2.754 | 44.322 | −2.800 | 1.00 | 62.63 |
| ATOM | 1668 | CB | SER | 244 | 2.589 | 47.117 | −2.074 | 1.00 | 58.33 |
| ATOM | 1669 | OG | SER | 244 | 1.267 | 47.190 | −2.564 | 1.00 | 72.38 |
| ATOM | 1670 | N | ILE | 245 | 2.887 | 45.013 | −4.936 | 1.00 | 45.75 |
| ATOM | 1671 | CA | ILE | 245 | 2.430 | 43.738 | −5.482 | 1.00 | 59.96 |
| ATOM | 1672 | C | ILE | 245 | 3.505 | 43.036 | −6.314 | 1.00 | 53.42 |
| ATOM | 1673 | O | ILE | 245 | 3.319 | 41.893 | −6.741 | 1.00 | 58.48 |
| ATOM | 1674 | CB | ILE | 245 | 1.131 | 43.891 | −6.323 | 1.00 | 61.54 |
| ATOM | 1675 | CG1 | ILE | 245 | 1.395 | 44.761 | −7.550 | 1.00 | 63.07 |
| ATOM | 1676 | CG2 | ILE | 245 | −0.003 | 44.470 | −5.479 | 1.00 | 53.03 |
| ATOM | 1677 | CD1 | ILE | 245 | 0.187 | 44.935 | −8.429 | 1.00 | 78.07 |
| ATOM | 1678 | N | HIS | 246 | 4.619 | 43.727 | −6.557 | 1.00 | 50.73 |
| ATOM | 1679 | CA | HIS | 246 | 5.736 | 43.149 | −7.299 | 1.00 | 53.43 |
| ATOM | 1680 | C | HIS | 246 | 7.027 | 43.281 | −6.499 | 1.00 | 64.72 |
| ATOM | 1681 | O | HIS | 246 | 7.071 | 44.002 | −5.509 | 1.00 | 62.83 |
| ATOM | 1682 | CB | HIS | 246 | 5.905 | 43.843 | −8.646 | 1.00 | 49.66 |
| ATOM | 1683 | CG | HIS | 246 | 4.773 | 43.618 | −9.600 | 1.00 | 65.04 |
| ATOM | 1684 | ND1 | HIS | 246 | 4.062 | 44.656 | −10.162 | 1.00 | 65.95 |
| ATOM | 1685 | CD2 | HIS | 246 | 4.238 | 42.479 | −10.101 | 1.00 | 64.99 |
| ATOM | 1686 | CE1 | HIS | 246 | 3.137 | 44.167 | −10.969 | 1.00 | 77.08 |
| ATOM | 1687 | NE2 | HIS | 246 | 3.219 | 42.848 | −10.948 | 1.00 | 73.91 |
| ATOM | 1688 | N | ASN | 247 | 8.085 | 42.593 | −6.923 | 1.00 | 56.86 |
| ATOM | 1689 | CA | ASN | 247 | 9.385 | 42.820 | −6.291 | 1.00 | 52.91 |
| ATOM | 1690 | C | ASN | 247 | 10.353 | 43.660 | −7.152 | 1.00 | 50.50 |
| ATOM | 1691 | O | ASN | 247 | 11.566 | 43.502 | −7.087 | 1.00 | 66.31 |
| ATOM | 1692 | CB | ASN | 247 | 10.035 | 41.517 | −5.808 | 1.00 | 55.98 |
| ATOM | 1693 | CG | ASN | 247 | 11.118 | 41.770 | −4.744 | 1.00 | 59.98 |
| ATOM | 1694 | OD1 | ASN | 247 | 10.980 | 42.677 | −3.910 | 1.00 | 49.10 |
| ATOM | 1695 | ND2 | ASN | 247 | 12.199 | 40.982 | −4.779 | 1.00 | 48.52 |
| ATOM | 1696 | N | HIS | 248 | 9.792 | 44.549 | −7.958 | 1.00 | 46.70 |
| ATOM | 1697 | CA | HIS | 248 | 10.564 | 45.518 | −8.725 | 1.00 | 45.58 |
| ATOM | 1698 | C | HIS | 248 | 9.778 | 46.828 | −8.712 | 1.00 | 43.64 |
| ATOM | 1699 | O | HIS | 248 | 8.694 | 46.904 | −8.130 | 1.00 | 49.26 |
| ATOM | 1700 | CB | HIS | 248 | 10.789 | 45.045 | −10.163 | 1.00 | 35.45 |

TABLE 10-continued

Three-Dimensional Coordinates of *Neisseria gonorrhoeae* GCYH-IB (SEQ. ID. No. 8)

| | | | | | | | | | |
|---|---|---|---|---|---|---|---|---|---|
| ATOM | 1701 | CG | HIS | 248 | 9.529 | 44.638 | −10.863 | 1.00 | 47.99 |
| ATOM | 1702 | ND1 | HIS | 248 | 8.828 | 45.493 | −11.689 | 1.00 | 54.22 |
| ATOM | 1703 | CD2 | HIS | 248 | 8.830 | 43.477 | −10.842 | 1.00 | 46.59 |
| ATOM | 1704 | CE1 | HIS | 248 | 7.758 | 44.875 | −12.150 | 1.00 | 51.61 |
| ATOM | 1705 | NE2 | HIS | 248 | 7.735 | 43.649 | −11.659 | 1.00 | 55.20 |
| ATOM | 1706 | N | SER | 249 | 10.318 | 47.849 | −9.351 | 1.00 | 39.68 |
| ATOM | 1707 | CA | SER | 249 | 9.715 | 49.166 | −9.284 | 1.00 | 46.54 |
| ATOM | 1708 | C | SER | 249 | 9.181 | 49.632 | −10.625 | 1.00 | 37.56 |
| ATOM | 1709 | O | SER | 249 | 9.766 | 49.357 | −11.653 | 1.00 | 43.92 |
| ATOM | 1710 | CB | SER | 249 | 10.740 | 50.194 | −8.784 | 1.00 | 43.78 |
| ATOM | 1711 | OG | SER | 249 | 11.184 | 49.896 | −7.473 | 1.00 | 57.17 |
| ATOM | 1712 | N | ALA | 250 | 8.075 | 50.357 | −10.598 | 1.00 | 36.21 |
| ATOM | 1713 | CA | ALA | 250 | 7.637 | 51.113 | −11.743 | 1.00 | 34.75 |
| ATOM | 1714 | C | ALA | 250 | 8.476 | 52.369 | −11.719 | 1.00 | 36.51 |
| ATOM | 1715 | O | ALA | 250 | 8.838 | 52.865 | −10.661 | 1.00 | 45.60 |
| ATOM | 1716 | CB | ALA | 250 | 6.182 | 51.465 | −11.612 | 1.00 | 37.23 |
| ATOM | 1717 | N | TYR | 251 | 8.773 | 52.909 | −12.886 | 1.00 | 35.78 |
| ATOM | 1718 | CA | TYR | 251 | 9.763 | 53.968 | −12.989 | 1.00 | 31.65 |
| ATOM | 1719 | C | TYR | 251 | 9.449 | 54.882 | −14.175 | 1.00 | 34.60 |
| ATOM | 1720 | O | TYR | 251 | 9.086 | 54.400 | −15.231 | 1.00 | 39.05 |
| ATOM | 1721 | CB | TYR | 251 | 11.155 | 53.318 | −13.140 | 1.00 | 33.30 |
| ATOM | 1722 | CG | TYR | 251 | 12.262 | 54.313 | −13.345 | 1.00 | 33.98 |
| ATOM | 1723 | CD1 | TYR | 251 | 12.662 | 55.157 | −12.309 | 1.00 | 37.10 |
| ATOM | 1724 | CD2 | TYR | 251 | 12.910 | 54.414 | −14.566 | 1.00 | 39.17 |
| ATOM | 1725 | CE1 | TYR | 251 | 13.679 | 56.080 | −12.486 | 1.00 | 38.91 |
| ATOM | 1726 | CE2 | TYR | 251 | 13.936 | 55.326 | −14.754 | 1.00 | 46.69 |
| ATOM | 1727 | CZ | TYR | 251 | 14.314 | 56.152 | −13.715 | 1.00 | 46.28 |
| ATOM | 1728 | OH | TYR | 251 | 15.317 | 57.062 | −13.900 | 1.00 | 60.47 |
| ATOM | 1729 | N | ALA | 252 | 9.569 | 56.196 | −14.002 | 1.00 | 37.22 |
| ATOM | 1730 | CA | ALA | 252 | 9.398 | 57.099 | −15.124 | 1.00 | 31.12 |
| ATOM | 1731 | C | ALA | 252 | 10.255 | 58.324 | −14.985 | 1.00 | 37.45 |
| ATOM | 1732 | O | ALA | 252 | 10.575 | 58.740 | −13.878 | 1.00 | 37.06 |
| ATOM | 1733 | CB | ALA | 252 | 7.956 | 57.501 | −15.300 | 1.00 | 32.57 |
| ATOM | 1734 | N | TYR | 253 | 10.622 | 58.943 | −16.098 | 1.00 | 29.71 |
| ATOM | 1735 | CA | TYR | 253 | 11.326 | 60.221 | −15.963 | 1.00 | 39.30 |
| ATOM | 1736 | C | TYR | 253 | 11.165 | 61.127 | −17.156 | 1.00 | 36.10 |
| ATOM | 1737 | O | TYR | 253 | 10.963 | 60.680 | −18.277 | 1.00 | 40.44 |
| ATOM | 1738 | CB | TYR | 253 | 12.824 | 59.989 | −15.661 | 1.00 | 46.73 |
| ATOM | 1739 | CG | TYR | 253 | 13.734 | 59.833 | −16.858 | 1.00 | 49.56 |
| ATOM | 1740 | CD1 | TYR | 253 | 13.812 | 58.756 | −17.504 | 1.00 | 56.37 |
| ATOM | 1741 | CD2 | TYR | 253 | 14.537 | 60.749 | −17.280 | 1.00 | 65.68 |
| ATOM | 1742 | CE1 | TYR | 253 | 14.640 | 58.593 | −18.575 | 1.00 | 75.03 |
| ATOM | 1743 | CE2 | TYR | 253 | 15.363 | 60.567 | −18.365 | 1.00 | 78.78 |
| ATOM | 1744 | CZ | TYR | 253 | 15.421 | 59.488 | −19.013 | 1.00 | 93.20 |
| ATOM | 1745 | OH | TYR | 253 | 16.262 | 59.296 | −20.105 | 1.00 | 0.44 |
| ATOM | 1746 | ZN | ZN2 | 258 | −1.421 | 48.564 | −9.888 | 1.00 | 71.07 |
| ATOM | 1747 | N | ASN | 15 | 0.218 | 68.205 | −22.240 | 1.00 | 0.61 |
| ATOM | 1748 | CA | ASN | 15 | 0.186 | 66.763 | −22.018 | 1.00 | 0.98 |
| ATOM | 1749 | C | ASN | 15 | 1.535 | 66.056 | −21.874 | 1.00 | 0.70 |
| ATOM | 1750 | O | ASN | 15 | 1.568 | 64.870 | −21.554 | 1.00 | 0.18 |
| ATOM | 1751 | CB | ASN | 15 | −0.630 | 66.078 | −23.111 | 1.00 | 0.60 |
| ATOM | 1752 | CG | ASN | 15 | −1.982 | 65.612 | −22.621 | 1.00 | 0.45 |
| ATOM | 1753 | OD1 | ASN | 15 | −2.111 | 65.105 | −21.513 | 1.00 | 0.18 |
| ATOM | 1754 | ND2 | ASN | 15 | −2.995 | 65.765 | −23.454 | 1.00 | 0.78 |
| ATOM | 1755 | N | LEU | 16 | 2.627 | 66.773 | −22.133 | 1.00 | 94.87 |
| ATOM | 1756 | CA | LEU | 16 | 4.002 | 66.286 | −21.882 | 1.00 | 68.59 |
| ATOM | 1757 | C | LEU | 16 | 4.304 | 64.808 | −22.181 | 1.00 | 62.20 |
| ATOM | 1758 | O | LEU | 16 | 3.765 | 63.905 | −21.537 | 1.00 | 47.59 |
| ATOM | 1759 | CB | LEU | 16 | 4.440 | 66.637 | −20.458 | 1.00 | 58.51 |
| ATOM | 1760 | CG | LEU | 16 | 5.071 | 68.020 | −20.284 | 1.00 | 71.98 |
| ATOM | 1761 | CD1 | LEU | 16 | 4.166 | 69.098 | −20.815 | 1.00 | 95.09 |
| ATOM | 1762 | CD2 | LEU | 16 | 5.387 | 68.282 | −18.826 | 1.00 | 66.90 |
| ATOM | 1763 | N | PRO | 17 | 5.172 | 64.564 | −23.174 | 1.00 | 59.11 |
| ATOM | 1764 | CA | PRO | 17 | 5.692 | 63.215 | −23.383 | 1.00 | 56.32 |
| ATOM | 1765 | C | PRO | 17 | 6.546 | 62.821 | −22.172 | 1.00 | 53.83 |
| ATOM | 1766 | O | PRO | 17 | 7.090 | 63.692 | −21.490 | 1.00 | 55.40 |
| ATOM | 1767 | CB | PRO | 17 | 6.593 | 63.362 | −24.615 | 1.00 | 49.67 |
| ATOM | 1768 | CG | PRO | 17 | 6.313 | 64.690 | −25.173 | 1.00 | 57.25 |
| ATOM | 1769 | CD | PRO | 17 | 5.780 | 65.540 | −24.087 | 1.00 | 51.52 |
| ATOM | 1770 | N | ILE | 18 | 6.635 | 61.527 | −21.898 | 1.00 | 44.93 |
| ATOM | 1771 | CA | ILE | 18 | 7.572 | 61.029 | −20.914 | 1.00 | 40.29 |
| ATOM | 1772 | C | ILE | 18 | 8.729 | 60.321 | −21.625 | 1.00 | 42.04 |
| ATOM | 1773 | O | ILE | 18 | 8.521 | 59.377 | −22.379 | 1.00 | 43.41 |
| ATOM | 1774 | CB | ILE | 18 | 6.889 | 60.101 | −19.902 | 1.00 | 38.13 |
| ATOM | 1775 | CG1 | ILE | 18 | 5.875 | 60.877 | −19.075 | 1.00 | 45.13 |
| ATOM | 1776 | CG2 | ILE | 18 | 7.929 | 59.461 | −18.976 | 1.00 | 48.42 |
| ATOM | 1777 | CD1 | ILE | 18 | 4.852 | 60.013 | −18.363 | 1.00 | 47.95 |
| ATOM | 1778 | N | ASN | 19 | 9.946 | 60.803 | −21.377 | 1.00 | 38.56 |

TABLE 10-continued

Three-Dimensional Coordinates of *Neisseria gonorrhoeae* GCYH-IB (SEQ. ID. No. 8)

| ATOM | 1779 | CA  | ASN | 19 | 11.151 | 60.265 | −22.005 | 1.00 | 45.65 |
|------|------|-----|-----|----|--------|--------|---------|------|-------|
| ATOM | 1780 | C   | ASN | 19 | 11.296 | 58.752 | −21.879 | 1.00 | 49.75 |
| ATOM | 1781 | O   | ASN | 19 | 11.592 | 58.067 | −22.855 | 1.00 | 53.42 |
| ATOM | 1782 | CB  | ASN | 19 | 12.407 | 60.935 | −21.440 | 1.00 | 48.95 |
| ATOM | 1783 | CG  | ASN | 19 | 12.450 | 62.410 | −21.714 | 1.00 | 54.49 |
| ATOM | 1784 | OD1 | ASN | 19 | 13.260 | 62.892 | −22.513 | 1.00 | 68.59 |
| ATOM | 1785 | ND2 | ASN | 19 | 11.586 | 63.141 | −21.048 | 1.00 | 35.74 |
| ATOM | 1786 | N   | GLN | 20 | 11.101 | 58.241 | −20.671 | 1.00 | 46.80 |
| ATOM | 1787 | CA  | GLN | 20 | 11.192 | 56.807 | −20.435 | 1.00 | 38.04 |
| ATOM | 1788 | C   | GLN | 20 | 10.243 | 56.403 | −19.325 | 1.00 | 38.60 |
| ATOM | 1789 | O   | GLN | 20 | 10.218 | 57.007 | −18.259 | 1.00 | 41.07 |
| ATOM | 1790 | CB  | GLN | 20 | 12.635 | 56.383 | −20.038 | 1.00 | 33.85 |
| ATOM | 1791 | CG  | GLN | 20 | 13.749 | 56.734 | −21.029 | 1.00 | 34.91 |
| ATOM | 1792 | CD  | GLN | 20 | 13.680 | 55.963 | −22.344 | 1.00 | 56.22 |
| ATOM | 1793 | OE1 | GLN | 20 | 13.058 | 54.904 | −22.429 | 1.00 | 49.36 |
| ATOM | 1794 | NE2 | GLN | 20 | 14.322 | 56.501 | −23.380 | 1.00 | 56.75 |
| ATOM | 1795 | N   | VAL | 21 | 9.461  | 55.371 | −19.574 | 1.00 | 37.98 |
| ATOM | 1796 | CA  | VAL | 21 | 8.625  | 54.813 | −18.532 | 1.00 | 36.09 |
| ATOM | 1797 | C   | VAL | 21 | 8.640  | 53.314 | −18.683 | 1.00 | 49.71 |
| ATOM | 1798 | O   | VAL | 21 | 8.605  | 52.800 | −19.800 | 1.00 | 43.59 |
| ATOM | 1799 | CB  | VAL | 21 | 7.176  | 55.332 | −18.615 | 1.00 | 47.00 |
| ATOM | 1800 | CG1 | VAL | 21 | 6.612  | 55.089 | −19.972 | 1.00 | 42.94 |
| ATOM | 1801 | CG2 | VAL | 21 | 6.292  | 54.635 | −17.580 | 1.00 | 46.40 |
| ATOM | 1802 | N   | GLY | 22 | 8.703  | 52.616 | −17.556 | 1.00 | 43.61 |
| ATOM | 1803 | CA  | GLY | 22 | 8.784  | 51.173 | −17.557 | 1.00 | 35.97 |
| ATOM | 1804 | C   | GLY | 22 | 9.120  | 50.661 | −16.173 | 1.00 | 42.16 |
| ATOM | 1805 | O   | GLY | 22 | 8.507  | 51.064 | −15.177 | 1.00 | 41.03 |
| ATOM | 1806 | N   | ILE | 23 | 10.092 | 49.757 | −16.107 | 1.00 | 27.58 |
| ATOM | 1807 | CA  | ILE | 23 | 10.433 | 49.117 | −14.851 | 1.00 | 28.73 |
| ATOM | 1808 | C   | ILE | 23 | 11.926 | 49.234 | −14.573 | 1.00 | 34.99 |
| ATOM | 1809 | O   | ILE | 23 | 12.750 | 49.357 | −15.484 | 1.00 | 36.46 |
| ATOM | 1810 | CB  | ILE | 23 | 10.049 | 47.609 | −14.835 | 1.00 | 37.25 |
| ATOM | 1811 | CG1 | ILE | 23 | 10.915 | 46.827 | −15.823 | 1.00 | 43.10 |
| ATOM | 1812 | CG2 | ILE | 23 | 8.530  | 47.392 | −15.108 | 1.00 | 33.88 |
| ATOM | 1813 | CD1 | ILE | 23 | 10.871 | 45.338 | −15.634 | 1.00 | 54.70 |
| ATOM | 1814 | N   | THR | 48 | 12.474 | 50.488 | −20.323 | 1.00 | 29.81 |
| ATOM | 1815 | CA  | THR | 48 | 11.604 | 51.653 | −20.402 | 1.00 | 30.70 |
| ATOM | 1816 | C   | THR | 48 | 11.352 | 51.979 | −21.873 | 1.00 | 42.96 |
| ATOM | 1817 | O   | THR | 48 | 12.134 | 51.579 | −22.746 | 1.00 | 36.92 |
| ATOM | 1818 | CB  | THR | 48 | 12.283 | 52.868 | −19.734 | 1.00 | 49.92 |
| ATOM | 1819 | OG1 | THR | 48 | 13.497 | 53.165 | −20.433 | 1.00 | 50.87 |
| ATOM | 1820 | CG2 | THR | 48 | 12.627 | 52.597 | −18.233 | 1.00 | 36.60 |
| ATOM | 1821 | N   | VAL | 49 | 10.263 | 52.695 | −22.139 | 1.00 | 39.32 |
| ATOM | 1822 | CA  | VAL | 49 | 9.940  | 53.162 | −23.485 | 1.00 | 40.47 |
| ATOM | 1823 | C   | VAL | 49 | 9.428  | 54.590 | −23.429 | 1.00 | 47.31 |
| ATOM | 1824 | O   | VAL | 49 | 8.994  | 55.065 | −22.393 | 1.00 | 39.62 |
| ATOM | 1825 | CB  | VAL | 49 | 8.827  | 52.307 | −24.190 | 1.00 | 39.46 |
| ATOM | 1826 | CG1 | VAL | 49 | 9.252  | 50.874 | −24.353 | 1.00 | 38.61 |
| ATOM | 1827 | CG2 | VAL | 49 | 7.464  | 52.427 | −23.453 | 1.00 | 32.61 |
| ATOM | 1828 | N   | TYR | 50 | 9.472  | 55.258 | −24.568 | 1.00 | 48.54 |
| ATOM | 1829 | CA  | TYR | 50 | 8.939  | 56.601 | −24.720 | 1.00 | 42.54 |
| ATOM | 1830 | C   | TYR | 50 | 7.415  | 56.585 | −24.665 | 1.00 | 38.18 |
| ATOM | 1831 | O   | TYR | 50 | 6.765  | 55.732 | −25.274 | 1.00 | 59.47 |
| ATOM | 1832 | CB  | TYR | 50 | 9.421  | 57.166 | −26.063 | 1.00 | 48.65 |
| ATOM | 1833 | CG  | TYR | 50 | 8.877  | 58.521 | −26.439 | 1.00 | 46.41 |
| ATOM | 1834 | CD1 | TYR | 50 | 9.495  | 59.690 | −26.002 | 1.00 | 48.12 |
| ATOM | 1835 | CD2 | TYR | 50 | 7.780  | 58.635 | −27.288 | 1.00 | 45.63 |
| ATOM | 1836 | CE1 | TYR | 50 | 9.005  | 60.940 | −26.369 | 1.00 | 49.82 |
| ATOM | 1837 | CE2 | TYR | 50 | 7.282  | 59.873 | −27.658 | 1.00 | 64.78 |
| ATOM | 1838 | CZ  | TYR | 50 | 7.891  | 61.024 | −27.200 | 1.00 | 66.95 |
| ATOM | 1839 | OH  | TYR | 50 | 7.378  | 62.253 | −27.576 | 1.00 | 63.72 |
| ATOM | 1840 | N   | LEU | 51 | 6.845  | 57.529 | −23.925 | 1.00 | 41.19 |
| ATOM | 1841 | CA  | LEU | 51 | 5.392  | 57.641 | −23.852 | 1.00 | 45.35 |
| ATOM | 1842 | C   | LEU | 51 | 4.944  | 58.964 | −24.477 | 1.00 | 59.79 |
| ATOM | 1843 | O   | LEU | 51 | 5.234  | 60.032 | −23.953 | 1.00 | 57.86 |
| ATOM | 1844 | CB  | LEU | 51 | 4.903  | 57.505 | −22.407 | 1.00 | 41.63 |
| ATOM | 1845 | CG  | LEU | 51 | 3.390  | 57.336 | −22.268 | 1.00 | 57.45 |
| ATOM | 1846 | CD1 | LEU | 51 | 3.024  | 55.982 | −22.804 | 1.00 | 53.37 |
| ATOM | 1847 | CD2 | LEU | 51 | 2.896  | 57.505 | −20.817 | 1.00 | 46.74 |
| ATOM | 1848 | N   | PRO | 52 | 4.252  | 58.887 | −25.620 | 1.00 | 50.41 |
| ATOM | 1849 | CA  | PRO | 52 | 3.698  | 60.053 | −26.327 | 1.00 | 60.78 |
| ATOM | 1850 | C   | PRO | 52 | 2.845  | 60.936 | −25.412 | 1.00 | 55.59 |
| ATOM | 1851 | O   | PRO | 52 | 2.252  | 60.441 | −24.464 | 1.00 | 45.38 |
| ATOM | 1852 | CB  | PRO | 52 | 2.799  | 59.418 | −27.398 | 1.00 | 51.53 |
| ATOM | 1853 | CG  | PRO | 52 | 3.307  | 58.019 | −27.560 | 1.00 | 54.38 |
| ATOM | 1854 | CD  | PRO | 52 | 3.795  | 57.616 | −26.204 | 1.00 | 47.05 |
| ATOM | 1855 | N   | ALA | 53 | 2.787  | 62.230 | −25.706 | 1.00 | 65.72 |
| ATOM | 1856 | CA  | ALA | 53 | 2.046  | 63.188 | −24.882 | 1.00 | 66.94 |

TABLE 10-continued

Three-Dimensional Coordinates of *Neisseria gonorrhoeae* GCYH-IB (SEQ. ID. No. 8)

| ATOM | 1857 | C | ALA | 53 | 0.629 | 62.747 | −24.490 | 1.00 | 71.17 |
|---|---|---|---|---|---|---|---|---|---|
| ATOM | 1858 | O | ALA | 53 | 0.223 | 62.913 | −23.341 | 1.00 | 71.46 |
| ATOM | 1859 | CB | ALA | 53 | 1.998 | 64.543 | −25.564 | 1.00 | 66.90 |
| ATOM | 1860 | N | GLU | 54 | −0.130 | 62.183 | −25.424 | 1.00 | 75.20 |
| ATOM | 1861 | CA | GLU | 54 | −1.535 | 61.918 | −25.120 | 1.00 | 0.50 |
| ATOM | 1862 | C | GLU | 54 | −1.871 | 60.457 | −24.827 | 1.00 | 90.42 |
| ATOM | 1863 | O | GLU | 54 | −3.039 | 60.090 | −24.744 | 1.00 | 95.12 |
| ATOM | 1864 | CB | GLU | 54 | −2.466 | 62.524 | −26.176 | 1.00 | 0.71 |
| ATOM | 1865 | CG | GLU | 54 | −2.722 | 61.670 | −27.397 | 1.00 | 0.20 |
| ATOM | 1866 | CD | GLU | 54 | −3.621 | 62.371 | −28.398 | 1.00 | 0.17 |
| ATOM | 1867 | OE1 | GLU | 54 | −3.217 | 63.435 | −28.908 | 1.00 | 0.84 |
| ATOM | 1868 | OE2 | GLU | 54 | −4.728 | 61.864 | −28.672 | 1.00 | 0.50 |
| ATOM | 1869 | N | GLN | 55 | −0.845 | 59.632 | −24.656 | 1.00 | 78.83 |
| ATOM | 1870 | CA | GLN | 55 | −1.035 | 58.296 | −24.104 | 1.00 | 68.58 |
| ATOM | 1871 | C | GLN | 55 | −0.918 | 58.434 | −22.589 | 1.00 | 58.44 |
| ATOM | 1872 | O | GLN | 55 | 0.009 | 59.070 | −22.092 | 1.00 | 65.77 |
| ATOM | 1873 | CB | GLN | 55 | 0.011 | 57.321 | −24.658 | 1.00 | 58.13 |
| ATOM | 1874 | CG | GLN | 55 | −0.321 | 55.844 | −24.474 | 1.00 | 67.08 |
| ATOM | 1875 | CD | GLN | 55 | 0.672 | 54.929 | −25.189 | 1.00 | 79.71 |
| ATOM | 1876 | OE1 | GLN | 55 | 1.214 | 55.285 | −26.235 | 1.00 | 88.70 |
| ATOM | 1877 | NE2 | GLN | 55 | 0.912 | 53.744 | −24.625 | 1.00 | 63.58 |
| ATOM | 1878 | N | LYS | 56 | −1.859 | 57.855 | −21.852 | 1.00 | 61.67 |
| ATOM | 1879 | CA | LYS | 56 | −1.921 | 58.061 | −20.410 | 1.00 | 65.88 |
| ATOM | 1880 | C | LYS | 56 | −0.919 | 57.196 | −19.648 | 1.00 | 73.54 |
| ATOM | 1881 | O | LYS | 56 | −0.438 | 57.584 | −18.578 | 1.00 | 73.26 |
| ATOM | 1882 | CB | LYS | 56 | −3.326 | 57.788 | −19.872 | 1.00 | 88.06 |
| ATOM | 1883 | CG | LYS | 56 | −3.413 | 57.858 | −18.349 | 1.00 | 0.53 |
| ATOM | 1884 | CD | LYS | 56 | −4.837 | 57.649 | −17.847 | 1.00 | 0.29 |
| ATOM | 1885 | CE | LYS | 56 | −5.261 | 56.190 | −17.948 | 1.00 | 0.17 |
| ATOM | 1886 | NZ | LYS | 56 | −6.636 | 55.973 | −17.419 | 1.00 | 0.56 |
| ATOM | 1887 | N | GLY | 57 | −0.613 | 56.025 | −20.205 | 1.00 | 63.39 |
| ATOM | 1888 | CA | GLY | 57 | 0.166 | 55.011 | −19.520 | 1.00 | 60.23 |
| ATOM | 1889 | C | GLY | 57 | 0.775 | 53.992 | −20.465 | 1.00 | 67.31 |
| ATOM | 1890 | O | GLY | 57 | 0.404 | 53.894 | −21.628 | 1.00 | 65.95 |
| ATOM | 1891 | N | THR | 58 | 1.747 | 53.243 | −19.964 | 1.00 | 71.54 |
| ATOM | 1892 | CA | THR | 58 | 2.338 | 52.164 | −20.736 | 1.00 | 72.16 |
| ATOM | 1893 | C | THR | 58 | 1.743 | 50.862 | −20.216 | 1.00 | 61.69 |
| ATOM | 1894 | O | THR | 58 | 0.837 | 50.885 | −19.387 | 1.00 | 61.90 |
| ATOM | 1895 | CB | THR | 58 | 3.879 | 52.159 | −20.619 | 1.00 | 69.56 |
| ATOM | 1896 | OG1 | THR | 58 | 4.439 | 51.312 | −21.629 | 1.00 | 79.35 |
| ATOM | 1897 | CG2 | THR | 58 | 4.316 | 51.680 | −19.244 | 1.00 | 68.68 |
| ATOM | 1898 | N | HIS | 59 | 2.246 | 49.729 | −20.695 | 1.00 | 71.58 |
| ATOM | 1899 | CA | HIS | 59 | 1.724 | 48.439 | −20.259 | 1.00 | 69.19 |
| ATOM | 1900 | C | HIS | 59 | 2.798 | 47.698 | −19.487 | 1.00 | 62.91 |
| ATOM | 1901 | O | HIS | 59 | 3.641 | 47.023 | −20.075 | 1.00 | 74.03 |
| ATOM | 1902 | CB | HIS | 59 | 1.246 | 47.636 | −21.466 | 1.00 | 67.89 |
| ATOM | 1903 | CG | HIS | 59 | 0.355 | 48.414 | −22.386 | 1.00 | 73.78 |
| ATOM | 1904 | ND1 | HIS | 59 | 0.848 | 49.209 | −23.406 | 1.00 | 79.21 |
| ATOM | 1905 | CD2 | HIS | 59 | −0.988 | 48.533 | −22.440 | 1.00 | 74.77 |
| ATOM | 1906 | CE1 | HIS | 59 | −0.155 | 49.769 | −24.049 | 1.00 | 81.43 |
| ATOM | 1907 | NE2 | HIS | 59 | −1.283 | 49.378 | −23.482 | 1.00 | 82.11 |
| ATOM | 1908 | N | MSE | 60 | 2.754 | 47.824 | −18.164 | 1.00 | 69.20 |
| ATOM | 1909 | CA | MSE | 60 | 3.889 | 47.455 | −17.308 | 1.00 | 64.49 |
| ATOM | 1910 | C | MSE | 60 | 4.271 | 45.977 | −17.333 | 1.00 | 57.44 |
| ATOM | 1911 | O | MSE | 60 | 5.453 | 45.628 | −17.259 | 1.00 | 55.33 |
| ATOM | 1912 | CB | MSE | 60 | 3.626 | 47.895 | −15.866 | 1.00 | 68.93 |
| ATOM | 1913 | CG | MSE | 60 | 3.645 | 49.405 | −15.670 | 1.00 | 88.07 |
| ATOM | 1914 | SE | MSE | 60 | 5.452 | 50.209 | −15.726 | 1.00 | 90.92 |
| ATOM | 1915 | CE | MSE | 60 | 4.956 | 52.073 | −15.352 | 1.00 | 91.55 |
| ATOM | 1916 | N | SER | 61 | 3.265 | 45.114 | −17.436 | 1.00 | 49.65 |
| ATOM | 1917 | CA | SER | 61 | 3.490 | 43.667 | −17.384 | 1.00 | 52.54 |
| ATOM | 1918 | C | SER | 61 | 4.202 | 43.098 | −18.627 | 1.00 | 57.67 |
| ATOM | 1919 | O | SER | 61 | 4.824 | 42.040 | −18.555 | 1.00 | 63.02 |
| ATOM | 1920 | CB | SER | 61 | 2.158 | 42.931 | −17.127 | 1.00 | 60.89 |
| ATOM | 1921 | OG | SER | 61 | 1.418 | 42.821 | −18.313 | 1.00 | 63.53 |
| ATOM | 1922 | N | ARG | 62 | 4.112 | 43.796 | −19.757 | 1.00 | 58.58 |
| ATOM | 1923 | CA | ARG | 62 | 4.804 | 43.363 | −20.970 | 1.00 | 54.99 |
| ATOM | 1924 | C | ARG | 62 | 6.330 | 43.332 | −20.816 | 1.00 | 47.98 |
| ATOM | 1925 | O | ARG | 62 | 6.992 | 42.462 | −21.385 | 1.00 | 58.75 |
| ATOM | 1926 | CB | ARG | 62 | 4.407 | 44.222 | −22.169 | 1.00 | 48.24 |
| ATOM | 1927 | CG | ARG | 62 | 2.980 | 44.013 | −22.584 | 1.00 | 54.45 |
| ATOM | 1928 | CD | ARG | 62 | 2.567 | 45.010 | −23.663 | 1.00 | 53.24 |
| ATOM | 1929 | NE | ARG | 62 | 1.122 | 45.035 | −23.836 | 1.00 | 68.95 |
| ATOM | 1930 | CZ | ARG | 62 | 0.492 | 45.679 | −24.808 | 1.00 | 67.76 |
| ATOM | 1931 | NH1 | ARG | 62 | 1.186 | 46.343 | −25.719 | 1.00 | 58.36 |
| ATOM | 1932 | NH2 | ARG | 62 | −0.838 | 45.649 | −24.869 | 1.00 | 72.93 |
| ATOM | 1933 | N | PHE | 63 | 6.879 | 44.274 | −20.049 | 1.00 | 45.59 |
| ATOM | 1934 | CA | PHE | 63 | 8.317 | 44.301 | −19.800 | 1.00 | 51.33 |

TABLE 10-continued

Three-Dimensional Coordinates of *Neisseria gonorrhoeae* GCYH-IB (SEQ. ID. No. 8)

| ATOM | 1935 | C   | PHE | 63 | 8.788  | 42.986 | −19.200 | 1.00 | 57.30 |
|------|------|-----|-----|----|--------|--------|---------|------|-------|
| ATOM | 1936 | O   | PHE | 63 | 9.781  | 42.396 | −19.641 | 1.00 | 55.44 |
| ATOM | 1937 | CB  | PHE | 63 | 8.688  | 45.451 | −18.866 | 1.00 | 49.40 |
| ATOM | 1938 | CG  | PHE | 63 | 8.439  | 46.793 | −19.449 | 1.00 | 44.13 |
| ATOM | 1939 | CD1 | PHE | 63 | 9.233  | 47.270 | −20.474 | 1.00 | 41.09 |
| ATOM | 1940 | CD2 | PHE | 63 | 7.394  | 47.573 | −18.995 | 1.00 | 50.77 |
| ATOM | 1941 | CE1 | PHE | 63 | 9.008  | 48.509 | −21.018 | 1.00 | 39.25 |
| ATOM | 1942 | CE2 | PHE | 63 | 7.161  | 48.820 | −19.543 | 1.00 | 57.73 |
| ATOM | 1943 | CZ  | PHE | 63 | 7.977  | 49.295 | −20.546 | 1.00 | 41.41 |
| ATOM | 1944 | N   | VAL | 64 | 8.065  | 42.540 | −18.180 | 1.00 | 47.97 |
| ATOM | 1945 | CA  | VAL | 64 | 8.375  | 41.278 | −17.524 | 1.00 | 55.02 |
| ATOM | 1946 | C   | VAL | 64 | 8.125  | 40.094 | −18.472 | 1.00 | 53.37 |
| ATOM | 1947 | O   | VAL | 64 | 9.000  | 39.244 | −18.648 | 1.00 | 45.07 |
| ATOM | 1948 | CB  | VAL | 64 | 7.537  | 41.103 | −16.238 | 1.00 | 69.71 |
| ATOM | 1949 | CG1 | VAL | 64 | 7.874  | 39.786 | −15.564 | 1.00 | 71.34 |
| ATOM | 1950 | CG2 | VAL | 64 | 7.770  | 42.266 | −15.293 | 1.00 | 71.51 |
| ATOM | 1951 | N   | ALA | 65 | 6.935  | 40.043 | −19.081 | 1.00 | 43.65 |
| ATOM | 1952 | CA  | ALA | 65 | 6.603  | 38.960 | −20.017 | 1.00 | 45.85 |
| ATOM | 1953 | C   | ALA | 65 | 7.693  | 38.821 | −21.074 | 1.00 | 55.77 |
| ATOM | 1954 | O   | ALA | 65 | 8.040  | 37.716 | −21.480 | 1.00 | 62.71 |
| ATOM | 1955 | CB  | ALA | 65 | 5.251  | 39.210 | −20.673 | 1.00 | 51.78 |
| ATOM | 1956 | N   | LEU | 66 | 8.246  | 39.951 | −21.498 | 1.00 | 48.51 |
| ATOM | 1957 | CA  | LEU | 66 | 9.263  | 39.949 | −22.523 | 1.00 | 43.71 |
| ATOM | 1958 | C   | LEU | 66 | 10.473 | 39.169 | −22.012 | 1.00 | 59.09 |
| ATOM | 1959 | O   | LEU | 66 | 11.024 | 38.322 | −22.717 | 1.00 | 63.51 |
| ATOM | 1960 | CB  | LEU | 66 | 9.645  | 41.382 | −22.900 | 1.00 | 57.57 |
| ATOM | 1961 | CG  | LEU | 66 | 10.720 | 41.475 | −23.984 | 1.00 | 65.50 |
| ATOM | 1962 | CD1 | LEU | 66 | 10.131 | 41.113 | −25.331 | 1.00 | 62.26 |
| ATOM | 1963 | CD2 | LEU | 66 | 11.344 | 42.854 | −24.030 | 1.00 | 66.51 |
| ATOM | 1964 | N   | MSE | 67 | 10.863 | 39.435 | −20.768 | 1.00 | 56.08 |
| ATOM | 1965 | CA  | MSE | 67 | 11.995 | 38.730 | −20.156 | 1.00 | 50.31 |
| ATOM | 1966 | C   | MSE | 67 | 11.739 | 37.245 | −19.931 | 1.00 | 57.07 |
| ATOM | 1967 | O   | MSE | 67 | 12.615 | 36.424 | −20.190 | 1.00 | 56.89 |
| ATOM | 1968 | CB  | MSE | 67 | 12.389 | 39.382 | −18.829 | 1.00 | 60.46 |
| ATOM | 1969 | CG  | MSE | 67 | 13.175 | 40.665 | −19.002 | 1.00 | 70.04 |
| ATOM | 1970 | SE  | MSE | 67 | 14.532 | 40.440 | −20.393 | 1.00 | 0.01  |
| ATOM | 1971 | CE  | MSE | 67 | 15.381 | 42.197 | −20.260 | 1.00 | 0.53  |
| ATOM | 1972 | N   | GLU | 68 | 10.548 | 36.900 | −19.437 | 1.00 | 43.15 |
| ATOM | 1973 | CA  | GLU | 68 | 10.235 | 35.514 | −19.126 | 1.00 | 52.89 |
| ATOM | 1974 | C   | GLU | 68 | 10.264 | 34.643 | −20.374 | 1.00 | 66.07 |
| ATOM | 1975 | O   | GLU | 68 | 10.597 | 33.455 | −20.312 | 1.00 | 65.29 |
| ATOM | 1976 | CB  | GLU | 68 | 8.854  | 35.414 | −18.459 | 1.00 | 60.06 |
| ATOM | 1977 | CG  | GLU | 68 | 8.743  | 36.180 | −17.138 | 1.00 | 77.68 |
| ATOM | 1978 | CD  | GLU | 68 | 9.549  | 35.547 | −16.007 | 1.00 | 95.66 |
| ATOM | 1979 | OE1 | GLU | 68 | 10.258 | 34.545 | −16.254 | 1.00 | 95.42 |
| ATOM | 1980 | OE2 | GLU | 68 | 9.472  | 36.052 | −14.866 | 1.00 | 0.24  |
| ATOM | 1981 | N   | GLN | 69 | 9.916  | 35.245 | −21.507 | 1.00 | 80.73 |
| ATOM | 1982 | CA  | GLN | 69 | 9.751  | 34.495 | −22.744 | 1.00 | 93.63 |
| ATOM | 1983 | C   | GLN | 69 | 11.061 | 34.321 | −23.493 | 1.00 | 89.35 |
| ATOM | 1984 | O   | GLN | 69 | 11.165 | 33.485 | −24.386 | 1.00 | 94.28 |
| ATOM | 1985 | CB  | GLN | 69 | 8.735  | 35.176 | −23.655 | 1.00 | 0.97  |
| ATOM | 1986 | CG  | GLN | 69 | 8.083  | 34.221 | −24.639 | 1.00 | 0.88  |
| ATOM | 1987 | CD  | GLN | 69 | 7.454  | 34.936 | −25.812 | 1.00 | 0.36  |
| ATOM | 1988 | OE1 | GLN | 69 | 7.850  | 36.048 | −26.162 | 1.00 | 0.96  |
| ATOM | 1989 | NE2 | GLN | 69 | 6.471  | 34.297 | −26.433 | 1.00 | 0.47  |
| ATOM | 1990 | N   | HIS | 70 | 12.059 | 35.114 | −23.128 | 1.00 | 87.50 |
| ATOM | 1991 | CA  | HIS | 70 | 13.355 | 35.066 | −23.793 | 1.00 | 91.35 |
| ATOM | 1992 | C   | HIS | 70 | 14.373 | 34.251 | −22.988 | 1.00 | 93.16 |
| ATOM | 1993 | O   | HIS | 70 | 14.977 | 34.751 | −22.039 | 1.00 | 0.23  |
| ATOM | 1994 | CB  | HIS | 70 | 13.849 | 36.491 | −24.045 | 1.00 | 0.10  |
| ATOM | 1995 | CG  | HIS | 70 | 15.339 | 36.630 | −24.061 | 1.00 | 0.47  |
| ATOM | 1996 | ND1 | HIS | 70 | 16.086 | 36.773 | −22.911 | 1.00 | 0.14  |
| ATOM | 1997 | CD2 | HIS | 70 | 16.218 | 36.673 | −25.089 | 1.00 | 0.88  |
| ATOM | 1998 | CE1 | HIS | 70 | 17.365 | 36.882 | −23.229 | 1.00 | 0.10  |
| ATOM | 1999 | NE2 | HIS | 70 | 17.471 | 36.829 | −24.544 | 1.00 | 0.29  |
| ATOM | 2000 | N   | ALA | 84 | 14.585 | 45.967 | −29.802 | 1.00 | 39.91 |
| ATOM | 2001 | CA  | ALA | 84 | 13.671 | 46.186 | −30.913 | 1.00 | 51.43 |
| ATOM | 2002 | C   | ALA | 84 | 12.362 | 45.463 | −30.642 | 1.00 | 49.14 |
| ATOM | 2003 | O   | ALA | 84 | 11.285 | 46.009 | −30.853 | 1.00 | 53.26 |
| ATOM | 2004 | CB  | ALA | 84 | 14.281 | 45.707 | −32.223 | 1.00 | 36.81 |
| ATOM | 2005 | N   | GLU | 85 | 12.470 | 44.232 | −30.156 | 1.00 | 43.56 |
| ATOM | 2006 | CA  | GLU | 85 | 11.296 | 43.422 | −29.859 | 1.00 | 48.49 |
| ATOM | 2007 | C   | GLU | 85 | 10.448 | 44.096 | −28.778 | 1.00 | 46.67 |
| ATOM | 2008 | O   | GLU | 85 | 9.222  | 44.003 | −28.785 | 1.00 | 56.68 |
| ATOM | 2009 | CB  | GLU | 85 | 11.724 | 42.022 | −29.434 | 1.00 | 49.28 |
| ATOM | 2010 | CG  | GLU | 85 | 10.587 | 41.034 | −29.353 | 1.00 | 80.44 |
| ATOM | 2011 | CD  | GLU | 85 | 11.069 | 39.600 | −29.385 | 1.00 | 0.75  |
| ATOM | 2012 | OE1 | GLU | 85 | 12.298 | 39.399 | −29.519 | 1.00 | 0.01  |

TABLE 10-continued

Three-Dimensional Coordinates of *Neisseria gonorrhoeae* GCYH-IB (SEQ. ID. No. 8)

| | | | | | | | | |
|---|---|---|---|---|---|---|---|---|
| ATOM | 2013 | OE2 | GLU | 85 | 10.223 | 38.680 | −29.283 | 1.00 | 0.82 |
| ATOM | 2014 | N | MSE | 86 | 11.110 | 44.803 | −27.866 | 1.00 | 40.52 |
| ATOM | 2015 | CA | MSE | 86 | 10.417 | 45.484 | −26.786 | 1.00 | 39.51 |
| ATOM | 2016 | C | MSE | 86 | 9.631 | 46.703 | −27.235 | 1.00 | 44.35 |
| ATOM | 2017 | O | MSE | 86 | 8.460 | 46.850 | −26.896 | 1.00 | 50.93 |
| ATOM | 2018 | CB | MSE | 86 | 11.365 | 45.906 | −25.682 | 1.00 | 40.42 |
| ATOM | 2019 | CG | MSE | 86 | 10.708 | 46.867 | −24.705 | 1.00 | 48.85 |
| ATOM | 2020 | SE | MSE | 86 | 11.954 | 47.555 | −23.380 | 1.00 | 71.76 |
| ATOM | 2021 | CE | MSE | 86 | 12.844 | 48.922 | −24.467 | 1.00 | 36.65 |
| ATOM | 2022 | N | VAL | 87 | 10.277 | 47.597 | −27.972 | 1.00 | 44.35 |
| ATOM | 2023 | CA | VAL | 87 | 9.589 | 48.791 | −28.442 | 1.00 | 45.24 |
| ATOM | 2024 | C | VAL | 87 | 8.398 | 48.392 | −29.329 | 1.00 | 44.79 |
| ATOM | 2025 | O | VAL | 87 | 7.382 | 49.081 | −29.339 | 1.00 | 48.45 |
| ATOM | 2026 | CB | VAL | 87 | 10.508 | 49.762 | −29.222 | 1.00 | 49.52 |
| ATOM | 2027 | CG1 | VAL | 87 | 11.666 | 50.235 | −28.352 | 1.00 | 37.17 |
| ATOM | 2028 | CG2 | VAL | 87 | 11.008 | 49.119 | −30.499 | 1.00 | 53.31 |
| ATOM | 2029 | N | ALA | 88 | 8.534 | 47.286 | −30.061 | 1.00 | 37.50 |
| ATOM | 2030 | CA | ALA | 88 | 7.456 | 46.797 | −30.916 | 1.00 | 51.61 |
| ATOM | 2031 | C | ALA | 88 | 6.339 | 46.279 | −30.058 | 1.00 | 56.02 |
| ATOM | 2032 | O | ALA | 88 | 5.185 | 46.591 | −30.295 | 1.00 | 63.47 |
| ATOM | 2033 | CB | ALA | 88 | 7.943 | 45.700 | −31.853 | 1.00 | 50.46 |
| ATOM | 2034 | N | LEU | 89 | 6.697 | 45.497 | −29.047 | 1.00 | 57.64 |
| ATOM | 2035 | CA | LEU | 89 | 5.730 | 44.891 | −28.124 | 1.00 | 59.78 |
| ATOM | 2036 | C | LEU | 89 | 4.942 | 45.934 | −27.315 | 1.00 | 53.97 |
| ATOM | 2037 | O | LEU | 89 | 3.743 | 45.804 | −27.119 | 1.00 | 56.91 |
| ATOM | 2038 | CB | LEU | 89 | 6.451 | 43.923 | −27.181 | 1.00 | 57.63 |
| ATOM | 2039 | CG | LEU | 89 | 5.628 | 43.249 | −26.094 | 1.00 | 56.32 |
| ATOM | 2040 | CD1 | LEU | 89 | 4.718 | 42.207 | −26.716 | 1.00 | 42.44 |
| ATOM | 2041 | CD2 | LEU | 89 | 6.536 | 42.615 | −25.055 | 1.00 | 61.18 |
| ATOM | 2042 | N | LEU | 90 | 5.612 | 46.970 | −26.837 | 1.00 | 54.16 |
| ATOM | 2043 | CA | LEU | 90 | 4.924 | 48.025 | −26.111 | 1.00 | 63.18 |
| ATOM | 2044 | C | LEU | 90 | 4.361 | 49.102 | −27.032 | 1.00 | 67.68 |
| ATOM | 2045 | O | LEU | 90 | 3.870 | 50.131 | −26.575 | 1.00 | 65.17 |
| ATOM | 2046 | CB | LEU | 90 | 5.844 | 48.634 | −25.065 | 1.00 | 54.20 |
| ATOM | 2047 | CG | LEU | 90 | 5.801 | 47.751 | −23.824 | 1.00 | 61.73 |
| ATOM | 2048 | CD1 | LEU | 90 | 7.055 | 46.902 | −23.699 | 1.00 | 41.72 |
| ATOM | 2049 | CD2 | LEU | 90 | 5.595 | 48.601 | −22.601 | 1.00 | 75.98 |
| ATOM | 2050 | N | ASP | 91 | 4.432 | 48.848 | −28.332 | 1.00 | 62.55 |
| ATOM | 2051 | CA | ASP | 91 | 3.870 | 49.748 | −29.329 | 1.00 | 74.29 |
| ATOM | 2052 | C | ASP | 91 | 4.407 | 51.167 | −29.159 | 1.00 | 64.93 |
| ATOM | 2053 | O | ASP | 91 | 3.634 | 52.107 | −29.035 | 1.00 | 56.16 |
| ATOM | 2054 | CB | ASP | 91 | 2.333 | 49.752 | −29.242 | 1.00 | 84.05 |
| ATOM | 2055 | CG | ASP | 91 | 1.698 | 48.481 | −29.813 | 1.00 | 0.91 |
| ATOM | 2056 | OD1 | ASP | 91 | 2.435 | 47.619 | −30.332 | 1.00 | 0.11 |
| ATOM | 2057 | OD2 | ASP | 91 | 0.456 | 48.347 | −29.753 | 1.00 | 98.46 |
| ATOM | 2058 | N | SER | 92 | 5.730 | 51.321 | −29.156 | 1.00 | 57.68 |
| ATOM | 2059 | CA | SER | 92 | 6.349 | 52.629 | −28.929 | 1.00 | 40.55 |
| ATOM | 2060 | C | SER | 92 | 7.432 | 53.000 | −29.952 | 1.00 | 52.93 |
| ATOM | 2061 | O | SER | 92 | 7.981 | 52.142 | −30.636 | 1.00 | 58.12 |
| ATOM | 2062 | CB | SER | 92 | 6.909 | 52.689 | −27.509 | 1.00 | 47.88 |
| ATOM | 2063 | OG | SER | 92 | 7.480 | 53.952 | −27.226 | 1.00 | 53.37 |
| ATOM | 2064 | N | ARG | 93 | 7.744 | 54.290 | −30.016 | 1.00 | 53.73 |
| ATOM | 2065 | CA | ARG | 93 | 8.714 | 54.864 | −30.946 | 1.00 | 47.19 |
| ATOM | 2066 | C | ARG | 93 | 10.185 | 54.689 | −30.507 | 1.00 | 61.56 |
| ATOM | 2067 | O | ARG | 93 | 11.110 | 54.745 | −31.327 | 1.00 | 57.47 |
| ATOM | 2068 | CB | ARG | 93 | 8.417 | 56.357 | −31.073 | 1.00 | 57.38 |
| ATOM | 2069 | CG | ARG | 93 | 9.157 | 57.076 | −32.169 | 1.00 | 80.07 |
| ATOM | 2070 | CD | ARG | 93 | 8.893 | 58.577 | −32.098 | 1.00 | 91.35 |
| ATOM | 2071 | NE | ARG | 93 | 9.315 | 59.154 | −30.822 | 1.00 | 84.96 |
| ATOM | 2072 | CZ | ARG | 93 | 10.584 | 59.361 | −30.474 | 1.00 | 95.02 |
| ATOM | 2073 | NH1 | ARG | 93 | 11.571 | 59.029 | −31.296 | 1.00 | 95.51 |
| ATOM | 2074 | NH2 | ARG | 93 | 10.872 | 59.893 | −29.297 | 1.00 | 81.77 |
| ATOM | 2075 | N | ALA | 94 | 10.396 | 54.497 | −29.210 | 1.00 | 48.21 |
| ATOM | 2076 | CA | ALA | 94 | 11.749 | 54.469 | −28.642 | 1.00 | 54.64 |
| ATOM | 2077 | C | ALA | 94 | 11.768 | 53.778 | −27.293 | 1.00 | 43.02 |
| ATOM | 2078 | O | ALA | 94 | 10.722 | 53.561 | −26.681 | 1.00 | 51.06 |
| ATOM | 2079 | CB | ALA | 94 | 12.297 | 55.883 | −28.505 | 1.00 | 43.30 |
| ATOM | 2080 | N | GLY | 95 | 12.966 | 53.446 | −26.817 | 1.00 | 49.26 |
| ATOM | 2081 | CA | GLY | 95 | 13.115 | 52.824 | −25.518 | 1.00 | 35.71 |
| ATOM | 2082 | C | GLY | 95 | 14.522 | 52.335 | −25.225 | 1.00 | 55.15 |
| ATOM | 2083 | O | GLY | 95 | 15.394 | 52.348 | −26.092 | 1.00 | 48.14 |
| TER | | | | | | | | | |
| ENDMDL | | | | | | | | | |

TABLE 11

Three-Dimensional Coordinates of *Neisseria gonorrhoeae* GCYH-IB·Mn$^{2+}$
(SEQ. ID. No. 8)

| | | | | | | | | | |
|---|---|---|---|---|---|---|---|---|---|
| ATOM | 1 | N | LYS | 106 | 10.392 | 70.600 | 9.408 | 1.00 | 39.71 |
| ATOM | 2 | CA | LYS | 106 | 9.306 | 70.423 | 10.391 | 1.00 | 42.95 |
| ATOM | 3 | C | LYS | 106 | 7.939 | 70.297 | 9.736 | 1.00 | 43.79 |
| ATOM | 4 | O | LYS | 106 | 7.463 | 71.233 | 9.099 | 1.00 | 44.80 |
| ATOM | 5 | CB | LYS | 106 | 9.305 | 71.577 | 11.392 | 1.00 | 43.80 |
| ATOM | 6 | CG | LYS | 106 | 8.686 | 71.208 | 12.748 | 1.00 | 48.36 |
| ATOM | 7 | CD | LYS | 106 | 9.747 | 71.087 | 13.838 | 1.00 | 53.64 |
| ATOM | 8 | CE | LYS | 106 | 9.171 | 70.635 | 15.168 | 1.00 | 55.97 |
| ATOM | 9 | NZ | LYS | 106 | 8.461 | 69.303 | 15.127 | 1.00 | 59.34 |
| ATOM | 10 | N | LYS | 107 | 7.304 | 69.138 | 9.880 | 1.00 | 44.36 |
| ATOM | 11 | CA | LYS | 107 | 5.973 | 68.949 | 9.312 | 1.00 | 44.70 |
| ATOM | 12 | C | LYS | 107 | 4.898 | 68.958 | 10.414 | 1.00 | 45.13 |
| ATOM | 13 | O | LYS | 107 | 5.213 | 68.843 | 11.615 | 1.00 | 44.87 |
| ATOM | 14 | CB | LYS | 107 | 5.919 | 67.670 | 8.473 | 1.00 | 44.28 |
| ATOM | 15 | CG | LYS | 107 | 7.016 | 67.604 | 7.384 | 1.00 | 43.47 |
| ATOM | 16 | CD | LYS | 107 | 6.748 | 66.456 | 6.423 | 1.00 | 41.18 |
| ATOM | 17 | CE | LYS | 107 | 5.476 | 66.755 | 5.604 | 1.00 | 42.21 |
| ATOM | 18 | NZ | LYS | 107 | 5.334 | 65.886 | 4.400 | 1.00 | 40.46 |
| ATOM | 19 | N | THR | 108 | 3.641 | 69.114 | 9.996 | 1.00 | 45.84 |
| ATOM | 20 | CA | THR | 108 | 2.494 | 69.116 | 10.901 | 1.00 | 46.81 |
| ATOM | 21 | C | THR | 108 | 1.453 | 68.111 | 10.397 | 1.00 | 47.68 |
| ATOM | 22 | O | THR | 108 | 1.123 | 68.099 | 9.198 | 1.00 | 47.71 |
| ATOM | 23 | CB | THR | 108 | 1.900 | 70.564 | 11.037 | 1.00 | 47.35 |
| ATOM | 24 | OG1 | THR | 108 | 2.963 | 71.502 | 11.302 | 1.00 | 47.19 |
| ATOM | 25 | CG2 | THR | 108 | 0.851 | 70.649 | 12.172 | 1.00 | 47.03 |
| ATOM | 26 | N | ALA | 109 | 0.950 | 67.260 | 11.299 | 1.00 | 48.80 |
| ATOM | 27 | CA | ALA | 109 | −0.043 | 66.235 | 10.948 | 1.00 | 50.14 |
| ATOM | 28 | C | ALA | 109 | −1.364 | 66.869 | 10.468 | 1.00 | 51.03 |
| ATOM | 29 | O | ALA | 109 | −1.770 | 67.916 | 11.004 | 1.00 | 51.15 |
| ATOM | 30 | CB | ALA | 109 | −0.284 | 65.278 | 12.127 | 1.00 | 50.35 |
| ATOM | 31 | N | PRO | 110 | −2.009 | 66.268 | 9.427 | 1.00 | 51.43 |
| ATOM | 32 | CA | PRO | 110 | −3.180 | 66.907 | 8.859 | 1.00 | 51.94 |
| ATOM | 33 | C | PRO | 110 | −4.394 | 67.037 | 9.798 | 1.00 | 52.99 |
| ATOM | 34 | O | PRO | 110 | −5.175 | 67.962 | 9.609 | 1.00 | 52.84 |
| ATOM | 35 | CB | PRO | 110 | −3.517 | 66.029 | 7.639 | 1.00 | 51.48 |
| ATOM | 36 | CG | PRO | 110 | −2.880 | 64.767 | 7.863 | 1.00 | 51.48 |
| ATOM | 37 | CD | PRO | 110 | −1.654 | 65.036 | 8.684 | 1.00 | 51.45 |
| ATOM | 38 | N | VAL | 111 | −4.578 | 66.145 | 10.780 | 1.00 | 53.92 |
| ATOM | 39 | CA | VAL | 111 | −5.756 | 66.302 | 11.660 | 1.00 | 55.03 |
| ATOM | 40 | C | VAL | 111 | −5.429 | 66.827 | 13.057 | 1.00 | 55.25 |
| ATOM | 41 | O | VAL | 111 | −5.957 | 67.878 | 13.469 | 1.00 | 55.19 |
| ATOM | 42 | CB | VAL | 111 | −6.709 | 65.062 | 11.692 | 1.00 | 55.46 |
| ATOM | 43 | CG1 | VAL | 111 | −7.959 | 65.351 | 12.557 | 1.00 | 54.84 |
| ATOM | 44 | CG2 | VAL | 111 | −7.125 | 64.682 | 10.262 | 1.00 | 55.47 |
| ATOM | 45 | N | SER | 112 | −4.559 | 66.102 | 13.764 | 1.00 | 55.19 |
| ATOM | 46 | CA | SER | 112 | −4.113 | 66.499 | 15.099 | 1.00 | 55.31 |
| ATOM | 47 | C | SER | 112 | −3.377 | 67.852 | 15.158 | 1.00 | 54.97 |
| ATOM | 48 | O | SER | 112 | −3.518 | 68.577 | 16.147 | 1.00 | 54.91 |
| ATOM | 49 | CB | SER | 112 | −3.256 | 65.399 | 15.742 | 1.00 | 55.47 |
| ATOM | 50 | OG | SER | 112 | −2.087 | 65.121 | 14.963 | 1.00 | 56.21 |
| ATOM | 51 | N | GLY | 113 | −2.614 | 68.189 | 14.106 | 1.00 | 54.62 |
| ATOM | 52 | CA | GLY | 113 | −1.646 | 69.315 | 14.149 | 1.00 | 53.64 |
| ATOM | 53 | C | GLY | 113 | −0.355 | 69.022 | 14.943 | 1.00 | 53.03 |
| ATOM | 54 | O | GLY | 113 | 0.471 | 69.929 | 15.166 | 1.00 | 52.84 |
| ATOM | 55 | N | ILE | 114 | −0.174 | 67.772 | 15.384 | 1.00 | 52.24 |
| ATOM | 56 | CA | ILE | 114 | 1.092 | 67.361 | 16.020 | 1.00 | 52.01 |
| ATOM | 57 | C | ILE | 114 | 2.254 | 67.467 | 14.992 | 1.00 | 51.48 |
| ATOM | 58 | O | ILE | 114 | 2.100 | 67.114 | 13.808 | 1.00 | 50.80 |
| ATOM | 59 | CB | ILE | 114 | 1.024 | 65.935 | 16.667 | 1.00 | 52.23 |
| ATOM | 60 | CG1 | ILE | 114 | −0.088 | 65.851 | 17.722 | 1.00 | 53.68 |
| ATOM | 61 | CG2 | ILE | 114 | 2.337 | 65.584 | 17.370 | 1.00 | 51.30 |
| ATOM | 62 | CD1 | ILE | 114 | −0.418 | 64.414 | 18.174 | 1.00 | 53.39 |
| ATOM | 63 | N | ARG | 115 | 3.393 | 67.989 | 15.450 | 1.00 | 50.22 |
| ATOM | 64 | CA | ARG | 115 | 4.520 | 68.263 | 14.576 | 1.00 | 49.39 |
| ATOM | 65 | C | ARG | 115 | 5.561 | 67.156 | 14.723 | 1.00 | 47.82 |
| ATOM | 66 | O | ARG | 115 | 5.733 | 66.586 | 15.820 | 1.00 | 46.47 |
| ATOM | 67 | CB | ARG | 115 | 5.159 | 69.625 | 14.893 | 1.00 | 50.41 |
| ATOM | 68 | CG | ARG | 115 | 4.234 | 70.839 | 14.773 | 1.00 | 53.80 |
| ATOM | 69 | CD | ARG | 115 | 4.782 | 71.939 | 15.657 | 1.00 | 58.84 |
| ATOM | 70 | NE | ARG | 115 | 5.550 | 72.917 | 14.885 | 1.00 | 64.83 |
| ATOM | 71 | CZ | ARG | 115 | 6.714 | 73.450 | 15.257 | 1.00 | 61.10 |
| ATOM | 72 | NH1 | ARG | 115 | 7.313 | 73.074 | 16.394 | 1.00 | 65.93 |
| ATOM | 73 | NH2 | ARG | 115 | 7.300 | 74.341 | 14.454 | 1.00 | 66.59 |
| ATOM | 74 | N | SER | 116 | 6.238 | 66.869 | 13.609 | 1.00 | 45.50 |
| ATOM | 75 | CA | SER | 116 | 7.398 | 65.999 | 13.565 | 1.00 | 44.28 |
| ATOM | 76 | C | SER | 116 | 8.251 | 66.377 | 12.346 | 1.00 | 43.63 |
| ATOM | 77 | O | SER | 116 | 7.748 | 67.050 | 11.418 | 1.00 | 43.82 |

TABLE 11-continued

Three-Dimensional Coordinates of *Neisseria gonorrhoeae* GCYH-IB·Mn$^{2+}$
(SEQ. ID. No. 8)

| ATOM | 78 | CB | SER | 116 | 6.977 | 64.524 | 13.499 | 1.00 | 44.12 |
|------|-----|------|-----|-----|--------|--------|---------|------|-------|
| ATOM | 79 | OG | SER | 116 | 6.181 | 64.263 | 12.365 | 1.00 | 44.28 |
| ATOM | 80 | N | LEU | 117 | 9.513 | 65.929 | 12.343 | 1.00 | 41.18 |
| ATOM | 81 | CA | LEU | 117 | 10.420 | 66.162 | 11.222 | 1.00 | 39.32 |
| ATOM | 82 | C | LEU | 117 | 10.214 | 65.130 | 10.135 | 1.00 | 38.39 |
| ATOM | 83 | O | LEU | 117 | 9.828 | 64.006 | 10.421 | 1.00 | 37.25 |
| ATOM | 84 | CB | LEU | 117 | 11.869 | 66.098 | 11.684 | 1.00 | 38.72 |
| ATOM | 85 | CG | LEU | 117 | 12.234 | 67.020 | 12.841 | 1.00 | 38.20 |
| ATOM | 86 | CD1 | LEU | 117 | 13.674 | 66.792 | 13.245 | 1.00 | 37.30 |
| ATOM | 87 | CD2 | LEU | 117 | 11.986 | 68.492 | 12.494 | 1.00 | 37.50 |
| ATOM | 88 | N | PRO | 142 | 10.478 | 61.583 | −0.479 | 1.00 | 31.78 |
| ATOM | 89 | CA | PRO | 142 | 9.695 | 60.360 | −0.363 | 1.00 | 32.72 |
| ATOM | 90 | C | PRO | 142 | 8.237 | 60.743 | −0.204 | 1.00 | 34.76 |
| ATOM | 91 | O | PRO | 142 | 7.899 | 61.618 | 0.638 | 1.00 | 35.43 |
| ATOM | 92 | CB | PRO | 142 | 10.240 | 59.663 | 0.917 | 1.00 | 32.41 |
| ATOM | 93 | CG | PRO | 142 | 10.949 | 60.785 | 1.722 | 1.00 | 32.83 |
| ATOM | 94 | CD | PRO | 142 | 11.041 | 62.043 | 0.817 | 1.00 | 31.61 |
| ATOM | 95 | N | VAL | 143 | 7.390 | 60.112 | −1.006 | 1.00 | 34.49 |
| ATOM | 96 | CA | VAL | 143 | 5.966 | 60.332 | −0.977 | 1.00 | 36.54 |
| ATOM | 97 | C | VAL | 143 | 5.257 | 58.987 | −0.907 | 1.00 | 37.50 |
| ATOM | 98 | O | VAL | 143 | 5.873 | 57.931 | −1.010 | 1.00 | 37.31 |
| ATOM | 99 | CB | VAL | 143 | 5.435 | 61.127 | −2.220 | 1.00 | 36.15 |
| ATOM | 100 | CG1 | VAL | 143 | 6.186 | 62.446 | −2.420 | 1.00 | 36.77 |
| ATOM | 101 | CG2 | VAL | 143 | 5.542 | 60.303 | −3.443 | 1.00 | 35.72 |
| ATOM | 102 | N | THR | 144 | 3.957 | 59.043 | −0.692 | 1.00 | 40.85 |
| ATOM | 103 | CA | THR | 144 | 3.070 | 57.890 | −0.876 | 1.00 | 43.22 |
| ATOM | 104 | C | THR | 144 | 2.496 | 57.940 | −2.296 | 1.00 | 45.07 |
| ATOM | 105 | O | THR | 144 | 2.017 | 59.013 | −2.764 | 1.00 | 44.61 |
| ATOM | 106 | CB | THR | 144 | 1.904 | 57.920 | 0.137 | 1.00 | 43.97 |
| ATOM | 107 | OG1 | THR | 144 | 2.430 | 58.174 | 1.451 | 1.00 | 45.02 |
| ATOM | 108 | CG2 | THR | 144 | 1.090 | 56.604 | 0.134 | 1.00 | 43.92 |
| ATOM | 109 | N | SER | 145 | 2.564 | 56.789 | −2.974 | 1.00 | 46.62 |
| ATOM | 110 | CA | SER | 145 | 1.899 | 56.587 | −4.274 | 1.00 | 48.13 |
| ATOM | 111 | C | SER | 145 | 0.841 | 55.504 | −4.119 | 1.00 | 48.74 |
| ATOM | 112 | O | SER | 145 | 1.058 | 54.516 | −3.417 | 1.00 | 48.82 |
| ATOM | 113 | CB | SER | 145 | 2.886 | 56.201 | −5.384 | 1.00 | 48.45 |
| ATOM | 114 | OG | SER | 145 | 3.671 | 55.067 | −5.036 | 1.00 | 50.19 |
| ATOM | 115 | N | LEU | 146 | −0.314 | 55.720 | −4.746 | 1.00 | 49.98 |
| ATOM | 116 | CA | LEU | 146 | −1.427 | 54.755 | −4.705 | 1.00 | 50.76 |
| ATOM | 117 | C | LEU | 146 | −1.915 | 54.476 | −6.134 | 1.00 | 51.52 |
| ATOM | 118 | O | LEU | 146 | −2.141 | 55.419 | −6.927 | 1.00 | 51.71 |
| ATOM | 119 | CB | LEU | 146 | −2.560 | 55.248 | −3.800 | 1.00 | 50.62 |
| ATOM | 120 | CG | LEU | 146 | −3.742 | 54.279 | −3.605 | 1.00 | 50.27 |
| ATOM | 121 | CD1 | LEU | 146 | −4.266 | 54.208 | −2.164 | 1.00 | 49.21 |
| ATOM | 122 | CD2 | LEU | 146 | −4.852 | 54.635 | −4.576 | 1.00 | 50.20 |
| ATOM | 123 | N | CYS | 147 | −2.050 | 53.195 | −6.469 | 1.00 | 51.52 |
| ATOM | 124 | CA | CYS | 147 | −2.304 | 52.802 | −7.849 | 1.00 | 52.46 |
| ATOM | 125 | C | CYS | 147 | −3.773 | 52.944 | −8.331 | 1.00 | 53.73 |
| ATOM | 126 | O | CYS | 147 | −4.690 | 52.294 | −7.788 | 1.00 | 53.40 |
| ATOM | 127 | CB | CYS | 147 | −1.804 | 51.375 | −8.098 | 1.00 | 52.50 |
| ATOM | 128 | SG | CYS | 147 | −2.131 | 50.800 | −9.803 | 1.00 | 51.33 |
| ATOM | 129 | N | PRO | 148 | −3.988 | 53.744 | −9.400 | 1.00 | 54.93 |
| ATOM | 130 | CA | PRO | 148 | −5.373 | 53.975 | −9.860 | 1.00 | 55.87 |
| ATOM | 131 | C | PRO | 148 | −6.026 | 52.699 | −10.446 | 1.00 | 56.77 |
| ATOM | 132 | O | PRO | 148 | −7.222 | 52.445 | −10.198 | 1.00 | 56.68 |
| ATOM | 133 | CB | PRO | 148 | −5.243 | 55.099 | −10.909 | 1.00 | 55.91 |
| ATOM | 134 | CG | PRO | 148 | −3.778 | 55.216 | −11.232 | 1.00 | 55.66 |
| ATOM | 135 | CD | PRO | 148 | −2.970 | 54.424 | −10.237 | 1.00 | 55.10 |
| ATOM | 136 | N | CYS | 149 | −5.232 | 51.900 | −11.172 | 1.00 | 57.41 |
| ATOM | 137 | CA | CYS | 149 | −5.692 | 50.637 | −11.765 | 1.00 | 57.40 |
| ATOM | 138 | C | CYS | 149 | −6.185 | 49.651 | −10.685 | 1.00 | 57.29 |
| ATOM | 139 | O | CYS | 149 | −7.265 | 49.043 | −10.819 | 1.00 | 56.51 |
| ATOM | 140 | CB | CYS | 149 | −4.577 | 50.006 | −12.613 | 1.00 | 57.61 |
| ATOM | 141 | SG | CYS | 149 | −5.106 | 48.508 | −13.511 | 1.00 | 59.83 |
| ATOM | 142 | N | SER | 150 | −5.389 | 49.517 | −9.621 | 1.00 | 57.10 |
| ATOM | 143 | CA | SER | 150 | −5.755 | 48.730 | −8.438 | 1.00 | 57.37 |
| ATOM | 144 | C | SER | 150 | −7.159 | 49.087 | −7.927 | 1.00 | 57.54 |
| ATOM | 145 | O | SER | 150 | −8.069 | 48.243 | −7.942 | 1.00 | 56.90 |
| ATOM | 146 | CB | SER | 150 | −4.699 | 48.908 | −7.315 | 1.00 | 57.56 |
| ATOM | 147 | OG | SER | 150 | −4.960 | 48.056 | −6.196 | 1.00 | 56.24 |
| ATOM | 148 | N | LYS | 151 | −7.325 | 50.335 | −7.480 | 1.00 | 58.20 |
| ATOM | 149 | CA | LYS | 151 | −8.614 | 50.826 | −6.980 | 1.00 | 58.78 |
| ATOM | 150 | C | LYS | 151 | −9.768 | 50.518 | −7.953 | 1.00 | 59.60 |
| ATOM | 151 | O | LYS | 151 | −10.820 | 49.980 | −7.548 | 1.00 | 59.74 |
| ATOM | 152 | CB | LYS | 151 | −8.530 | 52.335 | −6.737 | 1.00 | 58.67 |
| ATOM | 153 | CG | LYS | 151 | −9.859 | 52.996 | −6.372 | 1.00 | 57.80 |
| ATOM | 154 | CD | LYS | 151 | −9.711 | 54.513 | −6.375 | 1.00 | 57.00 |

TABLE 11-continued

Three-Dimensional Coordinates of *Neisseria gonorrhoeae* GCYH-IB·Mn$^{2+}$
(SEQ. ID. No. 8)

| ATOM | 155 | CE | LYS | 151 | −10.975 | 55.191 | −5.868 | 1.00 | 56.13 |
|---|---|---|---|---|---|---|---|---|---|
| ATOM | 156 | NZ | LYS | 151 | −10.706 | 56.603 | −5.487 | 1.00 | 54.37 |
| ATOM | 157 | N | GLU | 152 | −9.526 | 50.867 | −9.222 | 1.00 | 60.08 |
| ATOM | 158 | CA | GLU | 152 | −10.491 | 50.858 | −10.326 | 1.00 | 60.84 |
| ATOM | 159 | C | GLU | 152 | −11.066 | 49.467 | −10.619 | 1.00 | 60.69 |
| ATOM | 160 | O | GLU | 152 | −12.257 | 49.323 | −10.912 | 1.00 | 60.54 |
| ATOM | 161 | CB | GLU | 152 | −9.782 | 51.379 | −11.572 | 1.00 | 61.06 |
| ATOM | 162 | CG | GLU | 152 | −10.668 | 51.860 | −12.727 | 1.00 | 64.00 |
| ATOM | 163 | CD | GLU | 152 | −9.947 | 52.910 | −13.573 | 1.00 | 65.38 |
| ATOM | 164 | OE1 | GLU | 152 | −8.784 | 52.679 | −13.986 | 1.00 | 65.59 |
| ATOM | 165 | OE2 | GLU | 152 | −10.537 | 53.987 | −13.794 | 1.00 | 67.79 |
| ATOM | 166 | N | ILE | 153 | −10.199 | 48.459 | −10.551 | 1.00 | 60.40 |
| ATOM | 167 | CA | ILE | 153 | −10.560 | 47.088 | −10.885 | 1.00 | 59.97 |
| ATOM | 168 | C | ILE | 153 | −11.005 | 46.287 | −9.649 | 1.00 | 59.93 |
| ATOM | 169 | O | ILE | 153 | −11.676 | 45.255 | −9.806 | 1.00 | 59.92 |
| ATOM | 170 | CB | ILE | 153 | −9.396 | 46.345 | −11.633 | 1.00 | 60.11 |
| ATOM | 171 | CG1 | ILE | 153 | −8.231 | 46.011 | −10.666 | 1.00 | 59.91 |
| ATOM | 172 | CG2 | ILE | 153 | −8.954 | 47.141 | −12.886 | 1.00 | 59.57 |
| ATOM | 173 | CD1 | ILE | 153 | −7.180 | 45.087 | −11.244 | 1.00 | 59.73 |
| ATOM | 174 | N | SER | 154 | −10.639 | 46.762 | −8.442 | 1.00 | 59.44 |
| ATOM | 175 | CA | SER | 154 | −10.934 | 46.046 | −7.191 | 1.00 | 59.16 |
| ATOM | 176 | C | SER | 154 | −12.228 | 46.524 | −6.536 | 1.00 | 59.11 |
| ATOM | 177 | O | SER | 154 | −12.506 | 47.729 | −6.506 | 1.00 | 58.66 |
| ATOM | 178 | CB | SER | 154 | −9.777 | 46.159 | −6.179 | 1.00 | 59.05 |
| ATOM | 179 | OG | SER | 154 | −8.528 | 45.889 | −6.786 | 1.00 | 58.46 |
| ATOM | 180 | N | GLN | 155 | −12.998 | 45.574 | −5.992 | 1.00 | 59.19 |
| ATOM | 181 | CA | GLN | 155 | −14.252 | 45.887 | −5.279 | 1.00 | 59.20 |
| ATOM | 182 | C | GLN | 155 | −13.990 | 46.642 | −3.969 | 1.00 | 58.56 |
| ATOM | 183 | O | GLN | 155 | −14.872 | 47.344 | −3.441 | 1.00 | 58.43 |
| ATOM | 184 | CB | GLN | 155 | −15.103 | 44.620 | −5.037 | 1.00 | 59.42 |
| ATOM | 185 | CG | GLN | 155 | −14.478 | 43.547 | −4.109 | 1.00 | 59.96 |
| ATOM | 186 | CD | GLN | 155 | −15.294 | 42.235 | −4.047 | 1.00 | 60.84 |
| ATOM | 187 | OE1 | GLN | 155 | −16.514 | 42.259 | −3.833 | 1.00 | 63.53 |
| ATOM | 188 | NE2 | GLN | 155 | −14.613 | 41.090 | −4.221 | 1.00 | 61.62 |
| ATOM | 189 | N | TYR | 156 | −12.775 | 46.479 | −3.447 | 1.00 | 57.89 |
| ATOM | 190 | CA | TYR | 156 | −12.301 | 47.244 | −2.290 | 1.00 | 57.36 |
| ATOM | 191 | C | TYR | 156 | −10.756 | 47.310 | −2.288 | 1.00 | 56.68 |
| ATOM | 192 | O | TYR | 156 | −10.080 | 46.428 | −2.857 | 1.00 | 55.91 |
| ATOM | 193 | CB | TYR | 156 | −12.874 | 46.699 | −0.957 | 1.00 | 57.64 |
| ATOM | 194 | CG | TYR | 156 | −13.016 | 45.174 | −0.860 | 1.00 | 59.03 |
| ATOM | 195 | CD1 | TYR | 156 | −11.895 | 44.325 | −0.994 | 1.00 | 59.96 |
| ATOM | 196 | CD2 | TYR | 156 | −14.268 | 44.578 | −0.624 | 1.00 | 60.16 |
| ATOM | 197 | CE1 | TYR | 156 | −12.014 | 42.918 | −0.915 | 1.00 | 59.50 |
| ATOM | 198 | CE2 | TYR | 156 | −14.399 | 43.161 | −0.535 | 1.00 | 60.74 |
| ATOM | 199 | CZ | TYR | 156 | −13.260 | 42.346 | −0.684 | 1.00 | 59.41 |
| ATOM | 200 | OH | TYR | 156 | −13.355 | 40.974 | −0.586 | 1.00 | 58.74 |
| ATOM | 201 | N | GLY | 157 | −10.224 | 48.381 | −1.686 | 1.00 | 55.88 |
| ATOM | 202 | CA | GLY | 157 | −8.782 | 48.552 | −1.486 | 1.00 | 54.70 |
| ATOM | 203 | C | GLY | 157 | −8.046 | 48.941 | −2.750 | 1.00 | 53.87 |
| ATOM | 204 | O | GLY | 157 | −8.628 | 48.988 | −3.838 | 1.00 | 53.85 |
| ATOM | 205 | N | ALA | 158 | −6.753 | 49.211 | −2.600 | 1.00 | 53.06 |
| ATOM | 206 | CA | ALA | 158 | −5.889 | 49.638 | −3.704 | 1.00 | 52.34 |
| ATOM | 207 | C | ALA | 158 | −4.458 | 49.573 | −3.233 | 1.00 | 51.79 |
| ATOM | 208 | O | ALA | 158 | −4.116 | 50.133 | −2.176 | 1.00 | 51.74 |
| ATOM | 209 | CB | ALA | 158 | −6.210 | 51.065 | −4.162 | 1.00 | 52.30 |
| ATOM | 210 | N | HIS | 159 | −3.601 | 48.919 | −4.006 | 1.00 | 50.50 |
| ATOM | 211 | CA | HIS | 159 | −2.245 | 48.777 | −3.514 | 1.00 | 49.70 |
| ATOM | 212 | C | HIS | 159 | −1.569 | 50.148 | −3.570 | 1.00 | 49.57 |
| ATOM | 213 | O | HIS | 159 | −1.826 | 50.969 | −4.477 | 1.00 | 49.86 |
| ATOM | 214 | CB | HIS | 159 | −1.439 | 47.699 | −4.251 | 1.00 | 48.45 |
| ATOM | 215 | CG | HIS | 159 | −0.801 | 48.164 | −5.524 | 1.00 | 45.98 |
| ATOM | 216 | ND1 | HIS | 159 | 0.410 | 48.828 | −5.551 | 1.00 | 43.16 |
| ATOM | 217 | CD2 | HIS | 159 | −1.178 | 48.011 | −6.819 | 1.00 | 42.93 |
| ATOM | 218 | CE1 | HIS | 159 | 0.738 | 49.088 | −6.808 | 1.00 | 42.42 |
| ATOM | 219 | NE2 | HIS | 159 | −0.194 | 48.579 | −7.595 | 1.00 | 39.71 |
| ATOM | 220 | N | ASN | 160 | −0.746 | 50.384 | −2.560 | 1.00 | 49.49 |
| ATOM | 221 | CA | ASN | 160 | 0.054 | 51.594 | −2.464 | 1.00 | 48.81 |
| ATOM | 222 | C | ASN | 160 | 1.412 | 51.224 | −1.879 | 1.00 | 48.38 |
| ATOM | 223 | O | ASN | 160 | 1.642 | 50.069 | −1.462 | 1.00 | 47.84 |
| ATOM | 224 | CB | ASN | 160 | −0.673 | 52.701 | −1.658 | 1.00 | 48.67 |
| ATOM | 225 | CG | ASN | 160 | −1.276 | 52.196 | −0.336 | 1.00 | 48.57 |
| ATOM | 226 | OD1 | ASN | 160 | −2.384 | 51.659 | −0.308 | 1.00 | 49.39 |
| ATOM | 227 | ND2 | ASN | 160 | −0.557 | 52.409 | 0.762 | 1.00 | 47.12 |
| ATOM | 228 | N | GLN | 161 | 2.316 | 52.203 | −1.878 | 1.00 | 47.92 |
| ATOM | 229 | CA | GLN | 161 | 3.710 | 51.989 | −1.502 | 1.00 | 47.53 |
| ATOM | 230 | C | GLN | 161 | 4.428 | 53.326 | −1.401 | 1.00 | 47.31 |
| ATOM | 231 | O | GLN | 161 | 3.974 | 54.353 | −1.960 | 1.00 | 47.48 |

TABLE 11-continued

Three-Dimensional Coordinates of *Neisseria gonorrhoeae* GCYH-IB·Mn$^{2+}$
(SEQ. ID. No. 8)

| | | | | | | | | |
|---|---|---|---|---|---|---|---|---|
| ATOM | 232 | CB | GLN | 161 | 4.425 | 51.114 | −2.542 | 1.00 | 47.08 |
| ATOM | 233 | CG | GLN | 161 | 4.320 | 51.651 | −3.982 | 1.00 | 47.63 |
| ATOM | 234 | CD | GLN | 161 | 3.004 | 51.296 | −4.648 | 1.00 | 48.13 |
| ATOM | 235 | OE1 | GLN | 161 | 2.504 | 50.166 | −4.487 | 1.00 | 47.49 |
| ATOM | 236 | NE2 | GLN | 161 | 2.426 | 52.249 | −5.397 | 1.00 | 48.31 |
| ATOM | 237 | N | ARG | 162 | 5.536 | 53.313 | −0.668 | 1.00 | 46.28 |
| ATOM | 238 | CA | ARG | 162 | 6.427 | 54.435 | −0.704 | 1.00 | 45.81 |
| ATOM | 239 | C | ARG | 162 | 7.032 | 54.593 | −2.125 | 1.00 | 45.47 |
| ATOM | 240 | O | ARG | 162 | 7.245 | 53.605 | −2.901 | 1.00 | 44.60 |
| ATOM | 241 | CB | ARG | 162 | 7.495 | 54.348 | 0.389 | 1.00 | 45.64 |
| ATOM | 242 | CG | ARG | 162 | 7.999 | 55.693 | 0.859 | 1.00 | 45.77 |
| ATOM | 243 | CD | ARG | 162 | 9.102 | 55.488 | 1.931 | 1.00 | 46.20 |
| ATOM | 244 | NE | ARG | 162 | 8.617 | 54.789 | 3.121 | 1.00 | 43.09 |
| ATOM | 245 | CZ | ARG | 162 | 9.405 | 54.167 | 4.011 | 1.00 | 45.13 |
| ATOM | 246 | NH1 | ARG | 162 | 10.739 | 54.160 | 3.862 | 1.00 | 43.75 |
| ATOM | 247 | NH2 | ARG | 162 | 8.864 | 53.570 | 5.077 | 1.00 | 44.59 |
| ATOM | 248 | N | SER | 163 | 7.246 | 55.858 | −2.479 | 1.00 | 44.43 |
| ATOM | 249 | CA | SER | 163 | 7.914 | 56.146 | −3.716 | 1.00 | 43.91 |
| ATOM | 250 | C | SER | 163 | 8.854 | 57.331 | −3.548 | 1.00 | 42.32 |
| ATOM | 251 | O | SER | 163 | 8.597 | 58.236 | −2.760 | 1.00 | 43.00 |
| ATOM | 252 | CB | SER | 163 | 6.887 | 56.300 | −4.856 | 1.00 | 44.01 |
| ATOM | 253 | OG | SER | 163 | 6.306 | 57.569 | −4.855 | 1.00 | 47.10 |
| ATOM | 254 | N | ILE | 181 | 10.703 | 70.756 | −2.585 | 1.00 | 27.65 |
| ATOM | 255 | CA | ILE | 181 | 9.879 | 69.847 | −1.798 | 1.00 | 28.15 |
| ATOM | 256 | C | ILE | 181 | 8.375 | 70.134 | −1.999 | 1.00 | 29.61 |
| ATOM | 257 | O | ILE | 181 | 7.584 | 69.196 | −2.237 | 1.00 | 30.26 |
| ATOM | 258 | CB | ILE | 181 | 10.259 | 69.876 | −0.283 | 1.00 | 28.11 |
| ATOM | 259 | CG1 | ILE | 181 | 11.633 | 69.233 | −0.105 | 1.00 | 25.88 |
| ATOM | 260 | CG2 | ILE | 181 | 9.239 | 69.090 | 0.517 | 1.00 | 26.16 |
| ATOM | 261 | CD1 | ILE | 181 | 12.443 | 69.751 | 1.114 | 1.00 | 27.81 |
| ATOM | 262 | N | ASP | 182 | 7.974 | 71.413 | −1.900 | 1.00 | 30.08 |
| ATOM | 263 | CA | ASP | 182 | 6.555 | 71.756 | −2.064 | 1.00 | 31.00 |
| ATOM | 264 | C | ASP | 182 | 6.038 | 71.466 | −3.464 | 1.00 | 31.45 |
| ATOM | 265 | O | ASP | 182 | 4.964 | 70.923 | −3.592 | 1.00 | 32.21 |
| ATOM | 266 | CB | ASP | 182 | 6.253 | 73.205 | −1.669 | 1.00 | 31.45 |
| ATOM | 267 | CG | ASP | 182 | 6.358 | 73.420 | −0.194 | 1.00 | 33.00 |
| ATOM | 268 | OD1 | ASP | 182 | 6.060 | 72.499 | 0.589 | 1.00 | 38.70 |
| ATOM | 269 | OD2 | ASP | 182 | 6.807 | 74.473 | 0.202 | 1.00 | 33.35 |
| ATOM | 270 | N | TYR | 183 | 6.801 | 71.776 | −4.512 | 1.00 | 31.67 |
| ATOM | 271 | CA | TYR | 183 | 6.346 | 71.379 | −5.878 | 1.00 | 31.88 |
| ATOM | 272 | C | TYR | 183 | 5.996 | 69.892 | −6.001 | 1.00 | 31.33 |
| ATOM | 273 | O | TYR | 183 | 5.079 | 69.513 | −6.769 | 1.00 | 31.50 |
| ATOM | 274 | CB | TYR | 183 | 7.407 | 71.695 | −6.959 | 1.00 | 32.44 |
| ATOM | 275 | CG | TYR | 183 | 7.509 | 73.139 | −7.389 | 1.00 | 32.80 |
| ATOM | 276 | CD1 | TYR | 183 | 6.354 | 73.909 | −7.666 | 1.00 | 34.47 |
| ATOM | 277 | CD2 | TYR | 183 | 8.759 | 73.729 | −7.578 | 1.00 | 32.37 |
| ATOM | 278 | CE1 | TYR | 183 | 6.468 | 75.247 | −8.101 | 1.00 | 33.02 |
| ATOM | 279 | CE2 | TYR | 183 | 8.889 | 75.045 | −7.983 | 1.00 | 31.79 |
| ATOM | 280 | CZ | TYR | 183 | 7.731 | 75.807 | −8.253 | 1.00 | 33.92 |
| ATOM | 281 | OH | TYR | 183 | 7.879 | 77.117 | −8.689 | 1.00 | 34.75 |
| ATOM | 282 | N | VAL | 184 | 6.739 | 69.036 | −5.299 | 1.00 | 31.13 |
| ATOM | 283 | CA | VAL | 184 | 6.472 | 67.566 | −5.349 | 1.00 | 30.51 |
| ATOM | 284 | C | VAL | 184 | 5.338 | 67.145 | −4.441 | 1.00 | 31.17 |
| ATOM | 285 | O | VAL | 184 | 4.415 | 66.457 | −4.858 | 1.00 | 31.57 |
| ATOM | 286 | CB | VAL | 184 | 7.746 | 66.711 | −4.997 | 1.00 | 30.57 |
| ATOM | 287 | CG1 | VAL | 184 | 7.398 | 65.190 | −5.041 | 1.00 | 29.99 |
| ATOM | 288 | CG2 | VAL | 184 | 8.844 | 67.002 | −5.995 | 1.00 | 31.45 |
| ATOM | 289 | N | GLU | 185 | 5.420 | 67.543 | −3.173 | 1.00 | 31.99 |
| ATOM | 290 | CA | GLU | 185 | 4.476 | 67.096 | −2.159 | 1.00 | 33.75 |
| ATOM | 291 | C | GLU | 185 | 3.061 | 67.540 | −2.469 | 1.00 | 35.59 |
| ATOM | 292 | O | GLU | 185 | 2.087 | 66.813 | −2.163 | 1.00 | 34.88 |
| ATOM | 293 | CB | GLU | 185 | 4.923 | 67.550 | −0.764 | 1.00 | 33.52 |
| ATOM | 294 | CG | GLU | 185 | 6.124 | 66.727 | −0.249 | 1.00 | 34.66 |
| ATOM | 295 | CD | GLU | 185 | 6.472 | 67.088 | 1.180 | 1.00 | 37.62 |
| ATOM | 296 | OE1 | GLU | 185 | 6.132 | 68.250 | 1.552 | 1.00 | 34.07 |
| ATOM | 297 | OE2 | GLU | 185 | 7.071 | 66.223 | 1.905 | 1.00 | 39.40 |
| ATOM | 298 | N | THR | 186 | 2.962 | 68.703 | −3.113 | 1.00 | 37.29 |
| ATOM | 299 | CA | THR | 186 | 1.671 | 69.219 | −3.581 | 1.00 | 39.44 |
| ATOM | 300 | C | THR | 186 | 0.997 | 68.210 | −4.470 | 1.00 | 39.55 |
| ATOM | 301 | O | THR | 186 | −0.216 | 68.035 | −4.416 | 1.00 | 39.96 |
| ATOM | 302 | CB | THR | 186 | 1.831 | 70.510 | −4.351 | 1.00 | 39.43 |
| ATOM | 303 | OG1 | THR | 186 | 1.926 | 71.571 | −3.413 | 1.00 | 41.26 |
| ATOM | 304 | CG2 | THR | 186 | 0.608 | 70.760 | −5.263 | 1.00 | 42.27 |
| ATOM | 305 | N | GLN | 187 | 1.809 | 67.527 | −5.263 | 1.00 | 40.30 |
| ATOM | 306 | CA | GLN | 187 | 1.310 | 66.644 | −6.305 | 1.00 | 40.35 |
| ATOM | 307 | C | GLN | 187 | 1.120 | 65.204 | −5.847 | 1.00 | 40.86 |
| ATOM | 308 | O | GLN | 187 | 0.467 | 64.414 | −6.546 | 1.00 | 40.53 |

TABLE 11-continued

Three-Dimensional Coordinates of *Neisseria gonorrhoeae* GCYH-IB·Mn$^{2+}$
(SEQ. ID. No. 8)

| ATOM | 309 | CB | GLN | 187 | 2.233 | 66.690 | −7.547 | 1.00 | 40.36 |
|---|---|---|---|---|---|---|---|---|---|
| ATOM | 310 | CG | GLN | 187 | 2.314 | 68.075 | −8.228 | 1.00 | 39.80 |
| ATOM | 311 | CD | GLN | 187 | 0.947 | 68.577 | −8.653 | 1.00 | 39.36 |
| ATOM | 312 | OE1 | GLN | 187 | 0.005 | 67.783 | −8.777 | 1.00 | 39.91 |
| ATOM | 313 | NE2 | GLN | 187 | 0.828 | 69.887 | −8.887 | 1.00 | 35.15 |
| ATOM | 314 | N | ALA | 188 | 1.671 | 64.843 | −4.691 | 1.00 | 41.85 |
| ATOM | 315 | CA | ALA | 188 | 1.614 | 63.438 | −4.252 | 1.00 | 43.17 |
| ATOM | 316 | C | ALA | 188 | 0.192 | 62.942 | −4.004 | 1.00 | 43.55 |
| ATOM | 317 | O | ALA | 188 | −0.660 | 63.715 | −3.577 | 1.00 | 43.98 |
| ATOM | 318 | CB | ALA | 188 | 2.520 | 63.199 | −2.984 | 1.00 | 43.74 |
| ATOM | 319 | N | SER | 189 | −0.068 | 61.656 | −4.297 | 1.00 | 44.60 |
| ATOM | 320 | CA | SER | 189 | −1.298 | 60.977 | −3.803 | 1.00 | 45.06 |
| ATOM | 321 | C | SER | 189 | −1.502 | 61.373 | −2.327 | 1.00 | 45.29 |
| ATOM | 322 | O | SER | 189 | −2.600 | 61.760 | −1.911 | 1.00 | 45.23 |
| ATOM | 323 | CB | SER | 189 | −1.173 | 59.435 | −3.887 | 1.00 | 45.28 |
| ATOM | 324 | OG | SER | 189 | −1.596 | 58.905 | −5.133 | 1.00 | 44.89 |
| ATOM | 325 | N | CYS | 190 | −0.429 | 61.225 | −1.550 | 1.00 | 45.95 |
| ATOM | 326 | CA | CYS | 190 | −0.330 | 61.796 | −0.189 | 1.00 | 46.60 |
| ATOM | 327 | C | CYS | 190 | 1.148 | 61.866 | 0.259 | 1.00 | 46.70 |
| ATOM | 328 | O | CYS | 190 | 1.985 | 61.031 | −0.126 | 1.00 | 46.76 |
| ATOM | 329 | CB | CYS | 190 | −1.153 | 61.017 | 0.841 | 1.00 | 46.68 |
| ATOM | 330 | SG | CYS | 190 | −1.465 | 61.939 | 2.425 | 1.00 | 48.51 |
| ATOM | 331 | N | GLN | 191 | 1.450 | 62.873 | 1.064 | 1.00 | 46.03 |
| ATOM | 332 | CA | GLN | 191 | 2.796 | 63.026 | 1.622 | 1.00 | 46.34 |
| ATOM | 333 | C | GLN | 191 | 2.995 | 62.247 | 2.921 | 1.00 | 45.74 |
| ATOM | 334 | O | GLN | 191 | 2.041 | 61.751 | 3.533 | 1.00 | 45.80 |
| ATOM | 335 | CB | GLN | 191 | 3.115 | 64.501 | 1.856 | 1.00 | 46.24 |
| ATOM | 336 | CG | GLN | 191 | 1.986 | 65.240 | 2.522 | 1.00 | 46.12 |
| ATOM | 337 | CD | GLN | 191 | 2.257 | 66.708 | 2.616 | 1.00 | 45.71 |
| ATOM | 338 | OE1 | GLN | 191 | 3.128 | 67.120 | 3.362 | 1.00 | 42.50 |
| ATOM | 339 | NE2 | GLN | 191 | 1.513 | 67.518 | 1.839 | 1.00 | 47.50 |
| ATOM | 340 | N | LEU | 192 | 4.251 | 62.176 | 3.341 | 1.00 | 45.93 |
| ATOM | 341 | CA | LEU | 192 | 4.634 | 61.393 | 4.508 | 1.00 | 45.42 |
| ATOM | 342 | C | LEU | 192 | 4.759 | 62.259 | 5.762 | 1.00 | 45.84 |
| ATOM | 343 | O | LEU | 192 | 5.036 | 63.474 | 5.694 | 1.00 | 45.09 |
| ATOM | 344 | CB | LEU | 192 | 5.940 | 60.636 | 4.234 | 1.00 | 45.16 |
| ATOM | 345 | CG | LEU | 192 | 5.993 | 59.679 | 3.044 | 1.00 | 43.78 |
| ATOM | 346 | CD1 | LEU | 192 | 7.329 | 58.955 | 3.016 | 1.00 | 43.93 |
| ATOM | 347 | CD2 | LEU | 192 | 4.893 | 58.657 | 3.093 | 1.00 | 43.70 |
| ATOM | 348 | N | TYR | 193 | 4.520 | 61.615 | 6.906 | 1.00 | 45.73 |
| ATOM | 349 | CA | TYR | 193 | 4.756 | 62.218 | 8.203 | 1.00 | 45.73 |
| ATOM | 350 | C | TYR | 193 | 5.404 | 61.167 | 9.120 | 1.00 | 46.31 |
| ATOM | 351 | O | TYR | 193 | 5.035 | 59.967 | 9.095 | 1.00 | 45.28 |
| ATOM | 352 | CB | TYR | 193 | 3.445 | 62.738 | 8.812 | 1.00 | 45.20 |
| ATOM | 353 | CG | TYR | 193 | 2.638 | 63.691 | 7.907 | 1.00 | 44.11 |
| ATOM | 354 | CD1 | TYR | 193 | 2.823 | 65.078 | 7.964 | 1.00 | 43.87 |
| ATOM | 355 | CD2 | TYR | 193 | 1.683 | 63.186 | 6.998 | 1.00 | 44.60 |
| ATOM | 356 | CE1 | TYR | 193 | 2.068 | 65.944 | 7.143 | 1.00 | 43.56 |
| ATOM | 357 | CE2 | TYR | 193 | 0.930 | 64.029 | 6.190 | 1.00 | 42.74 |
| ATOM | 358 | CZ | TYR | 193 | 1.133 | 65.409 | 6.273 | 1.00 | 42.90 |
| ATOM | 359 | OH | TYR | 193 | 0.401 | 66.227 | 5.474 | 1.00 | 44.37 |
| ATOM | 360 | N | GLY | 194 | 6.385 | 61.623 | 9.896 | 1.00 | 47.12 |
| ATOM | 361 | CA | GLY | 194 | 6.981 | 60.801 | 10.936 | 1.00 | 48.68 |
| ATOM | 362 | C | GLY | 194 | 5.913 | 60.387 | 11.934 | 1.00 | 49.53 |
| ATOM | 363 | O | GLY | 194 | 5.722 | 59.183 | 12.171 | 1.00 | 49.81 |
| ATOM | 364 | N | LEU | 195 | 5.188 | 61.368 | 12.482 | 1.00 | 50.33 |
| ATOM | 365 | CA | LEU | 195 | 4.240 | 61.095 | 13.579 | 1.00 | 51.06 |
| ATOM | 366 | C | LEU | 195 | 2.784 | 61.345 | 13.193 | 1.00 | 52.16 |
| ATOM | 367 | O | LEU | 195 | 2.389 | 62.489 | 12.837 | 1.00 | 51.75 |
| ATOM | 368 | CB | LEU | 195 | 4.612 | 61.889 | 14.840 | 1.00 | 50.86 |
| ATOM | 369 | CG | LEU | 195 | 3.940 | 61.618 | 16.195 | 1.00 | 50.48 |
| ATOM | 370 | CD1 | LEU | 195 | 4.719 | 62.355 | 17.275 | 1.00 | 49.39 |
| ATOM | 371 | CD2 | LEU | 195 | 2.516 | 62.141 | 16.207 | 1.00 | 51.52 |
| ATOM | 372 | N | LEU | 196 | 1.990 | 60.277 | 13.290 | 1.00 | 53.08 |
| ATOM | 373 | CA | LEU | 196 | 0.583 | 60.340 | 12.936 | 1.00 | 55.19 |
| ATOM | 374 | C | LEU | 196 | −0.282 | 59.778 | 14.069 | 1.00 | 56.77 |
| ATOM | 375 | O | LEU | 196 | 0.000 | 58.705 | 14.604 | 1.00 | 56.95 |
| ATOM | 376 | CB | LEU | 196 | 0.326 | 59.604 | 11.612 | 1.00 | 54.79 |
| ATOM | 377 | CG | LEU | 196 | 0.949 | 60.235 | 10.346 | 1.00 | 55.32 |
| ATOM | 378 | CD1 | LEU | 196 | 0.931 | 59.273 | 9.136 | 1.00 | 54.75 |
| ATOM | 379 | CD2 | LEU | 196 | 0.317 | 61.613 | 9.990 | 1.00 | 54.04 |
| ATOM | 380 | N | LYS | 197 | −1.314 | 60.519 | 14.463 | 1.00 | 58.59 |
| ATOM | 381 | CA | LYS | 197 | −2.334 | 59.933 | 15.353 | 1.00 | 60.40 |
| ATOM | 382 | C | LYS | 197 | −3.393 | 59.174 | 14.545 | 1.00 | 60.81 |
| ATOM | 383 | O | LYS | 197 | −3.364 | 59.195 | 13.294 | 1.00 | 60.59 |
| ATOM | 384 | CB | LYS | 197 | −2.941 | 60.970 | 16.316 | 1.00 | 60.82 |
| ATOM | 385 | CG | LYS | 197 | −2.344 | 60.884 | 17.753 | 1.00 | 63.00 |

TABLE 11-continued

Three-Dimensional Coordinates of *Neisseria gonorrhoeae* GCYH-IB·Mn$^{2+}$
(SEQ. ID. No. 8)

| ATOM | 386 | CD | LYS | 197 | −0.793 | 60.988 | 17.781 | 1.00 | 64.23 |
|------|-----|-----|-----|-----|--------|--------|--------|------|-------|
| ATOM | 387 | CE | LYS | 197 | −0.195 | 60.868 | 19.202 | 1.00 | 64.55 |
| ATOM | 388 | NZ | LYS | 197 | −0.184 | 59.471 | 19.739 | 1.00 | 64.56 |
| ATOM | 389 | N | ARG | 198 | −4.289 | 58.479 | 15.256 | 1.00 | 61.03 |
| ATOM | 390 | CA | ARG | 198 | −5.388 | 57.746 | 14.631 | 1.00 | 61.98 |
| ATOM | 391 | C | ARG | 198 | −6.168 | 58.558 | 13.574 | 1.00 | 61.01 |
| ATOM | 392 | O | ARG | 198 | −6.279 | 58.122 | 12.435 | 1.00 | 60.94 |
| ATOM | 393 | CB | ARG | 198 | −6.332 | 57.144 | 15.690 | 1.00 | 62.12 |
| ATOM | 394 | CG | ARG | 198 | −6.388 | 55.616 | 15.679 | 1.00 | 64.00 |
| ATOM | 395 | CD | ARG | 198 | −6.848 | 54.991 | 17.028 | 1.00 | 64.71 |
| ATOM | 396 | NE | ARG | 198 | −7.001 | 53.536 | 16.895 | 1.00 | 70.51 |
| ATOM | 397 | CZ | ARG | 198 | −8.173 | 52.893 | 16.895 | 1.00 | 71.39 |
| ATOM | 398 | NH1 | ARG | 198 | −9.309 | 53.569 | 17.049 | 1.00 | 74.34 |
| ATOM | 399 | NH2 | ARG | 198 | −8.216 | 51.570 | 16.745 | 1.00 | 73.50 |
| ATOM | 400 | N | PRO | 199 | −6.712 | 59.735 | 13.949 | 1.00 | 60.31 |
| ATOM | 401 | CA | PRO | 199 | −7.394 | 60.542 | 12.926 | 1.00 | 59.80 |
| ATOM | 402 | C | PRO | 199 | −6.506 | 60.946 | 11.725 | 1.00 | 59.02 |
| ATOM | 403 | O | PRO | 199 | −6.975 | 60.893 | 10.582 | 1.00 | 58.60 |
| ATOM | 404 | CB | PRO | 199 | −7.891 | 61.778 | 13.706 | 1.00 | 60.10 |
| ATOM | 405 | CG | PRO | 199 | −7.149 | 61.780 | 15.009 | 1.00 | 60.56 |
| ATOM | 406 | CD | PRO | 199 | −6.771 | 60.356 | 15.291 | 1.00 | 60.60 |
| ATOM | 407 | N | ASP | 200 | −5.247 | 61.316 | 11.978 | 1.00 | 58.37 |
| ATOM | 408 | CA | ASP | 200 | −4.289 | 61.627 | 10.889 | 1.00 | 58.09 |
| ATOM | 409 | C | ASP | 200 | −4.123 | 60.454 | 9.932 | 1.00 | 57.97 |
| ATOM | 410 | O | ASP | 200 | −4.210 | 60.623 | 8.707 | 1.00 | 58.11 |
| ATOM | 411 | CB | ASP | 200 | −2.916 | 62.014 | 11.440 | 1.00 | 57.41 |
| ATOM | 412 | CG | ASP | 200 | −2.987 | 63.149 | 12.416 | 1.00 | 56.87 |
| ATOM | 413 | OD1 | ASP | 200 | −3.551 | 64.204 | 12.044 | 1.00 | 56.53 |
| ATOM | 414 | OD2 | ASP | 200 | −2.471 | 62.986 | 13.545 | 1.00 | 54.07 |
| ATOM | 415 | N | GLU | 201 | −3.876 | 59.271 | 10.498 | 1.00 | 57.96 |
| ATOM | 416 | CA | GLU | 201 | −3.801 | 58.036 | 9.707 | 1.00 | 58.04 |
| ATOM | 417 | C | GLU | 201 | −5.089 | 57.778 | 8.868 | 1.00 | 57.99 |
| ATOM | 418 | O | GLU | 201 | −5.010 | 57.296 | 7.717 | 1.00 | 57.08 |
| ATOM | 419 | CB | GLU | 201 | −3.411 | 56.822 | 10.577 | 1.00 | 58.12 |
| ATOM | 420 | CG | GLU | 201 | −3.762 | 55.479 | 9.910 | 1.00 | 59.81 |
| ATOM | 421 | CD | GLU | 201 | −2.850 | 54.339 | 10.275 | 1.00 | 59.25 |
| ATOM | 422 | OE1 | GLU | 201 | −2.353 | 54.293 | 11.424 | 1.00 | 61.24 |
| ATOM | 423 | OE2 | GLU | 201 | −2.653 | 53.472 | 9.394 | 1.00 | 61.33 |
| ATOM | 424 | N | LYS | 202 | −6.258 | 58.106 | 9.444 | 1.00 | 58.11 |
| ATOM | 425 | CA | LYS | 202 | −7.538 | 58.002 | 8.733 | 1.00 | 58.01 |
| ATOM | 426 | C | LYS | 202 | −7.538 | 58.940 | 7.519 | 1.00 | 57.58 |
| ATOM | 427 | O | LYS | 202 | −7.884 | 58.514 | 6.416 | 1.00 | 57.11 |
| ATOM | 428 | CB | LYS | 202 | −8.729 | 58.282 | 9.670 | 1.00 | 58.00 |
| ATOM | 429 | CG | LYS | 202 | −10.094 | 58.289 | 8.991 | 1.00 | 58.29 |
| ATOM | 430 | CD | LYS | 202 | −11.235 | 58.423 | 10.025 | 1.00 | 58.66 |
| ATOM | 431 | CE | LYS | 202 | −12.517 | 59.076 | 9.442 | 1.00 | 58.41 |
| ATOM | 432 | NZ | LYS | 202 | −12.846 | 58.760 | 8.009 | 1.00 | 59.05 |
| ATOM | 433 | N | TYR | 203 | −7.132 | 60.198 | 7.752 | 1.00 | 57.29 |
| ATOM | 434 | CA | TYR | 203 | −7.027 | 61.255 | 6.731 | 1.00 | 56.76 |
| ATOM | 435 | C | TYR | 203 | −6.051 | 60.847 | 5.622 | 1.00 | 55.73 |
| ATOM | 436 | O | TYR | 203 | −6.365 | 60.900 | 4.439 | 1.00 | 55.19 |
| ATOM | 437 | CB | TYR | 203 | −6.594 | 62.584 | 7.391 | 1.00 | 57.82 |
| ATOM | 438 | CG | TYR | 203 | −6.403 | 63.759 | 6.431 | 1.00 | 57.69 |
| ATOM | 439 | CD1 | TYR | 203 | −7.378 | 64.778 | 6.304 | 1.00 | 59.41 |
| ATOM | 440 | CD2 | TYR | 203 | −5.257 | 63.838 | 5.633 | 1.00 | 59.00 |
| ATOM | 441 | CE1 | TYR | 203 | −7.192 | 65.857 | 5.410 | 1.00 | 59.51 |
| ATOM | 442 | CE2 | TYR | 203 | −5.065 | 64.889 | 4.745 | 1.00 | 60.75 |
| ATOM | 443 | CZ | TYR | 203 | −6.017 | 65.900 | 4.636 | 1.00 | 58.13 |
| ATOM | 444 | OH | TYR | 203 | −5.754 | 66.922 | 3.740 | 1.00 | 60.67 |
| ATOM | 445 | N | VAL | 204 | −4.866 | 60.422 | 6.026 | 1.00 | 54.95 |
| ATOM | 446 | CA | VAL | 204 | −3.835 | 60.017 | 5.072 | 1.00 | 54.58 |
| ATOM | 447 | C | VAL | 204 | −4.290 | 58.782 | 4.213 | 1.00 | 53.79 |
| ATOM | 448 | O | VAL | 204 | −4.091 | 58.758 | 2.986 | 1.00 | 52.60 |
| ATOM | 449 | CB | VAL | 204 | −2.469 | 59.851 | 5.822 | 1.00 | 54.92 |
| ATOM | 450 | CG1 | VAL | 204 | −1.523 | 58.898 | 5.116 | 1.00 | 56.19 |
| ATOM | 451 | CG2 | VAL | 204 | −1.820 | 61.233 | 6.087 | 1.00 | 53.61 |
| ATOM | 452 | N | THR | 205 | −4.949 | 57.801 | 4.851 | 1.00 | 53.09 |
| ATOM | 453 | CA | THR | 205 | −5.456 | 56.626 | 4.132 | 1.00 | 52.58 |
| ATOM | 454 | C | THR | 205 | −6.437 | 57.018 | 3.017 | 1.00 | 53.09 |
| ATOM | 455 | O | THR | 205 | −6.340 | 56.514 | 1.878 | 1.00 | 52.50 |
| ATOM | 456 | CB | THR | 205 | −6.109 | 55.579 | 5.091 | 1.00 | 52.24 |
| ATOM | 457 | OG1 | THR | 205 | −5.109 | 55.049 | 5.976 | 1.00 | 50.47 |
| ATOM | 458 | CG2 | THR | 205 | −6.716 | 54.420 | 4.305 | 1.00 | 51.46 |
| ATOM | 459 | N | GLU | 206 | −7.352 | 57.929 | 3.365 | 1.00 | 53.01 |
| ATOM | 460 | CA | GLU | 206 | −8.444 | 58.355 | 2.489 | 1.00 | 53.57 |
| ATOM | 461 | C | GLU | 206 | −7.956 | 59.243 | 1.363 | 1.00 | 53.60 |
| ATOM | 462 | O | GLU | 206 | −8.280 | 58.979 | 0.203 | 1.00 | 53.68 |

TABLE 11-continued

Three-Dimensional Coordinates of *Neisseria gonorrhoeae* GCYH-IB·Mn$^{2+}$
(SEQ. ID. No. 8)

| ATOM | 463 | CB  | GLU | 206 | −9.563  | 59.021 | 3.295   | 1.00 | 53.31 |
|------|-----|-----|-----|-----|---------|--------|---------|------|-------|
| ATOM | 464 | CG  | GLU | 206 | −10.150 | 58.061 | 4.283   | 1.00 | 54.66 |
| ATOM | 465 | CD  | GLU | 206 | −11.279 | 58.627 | 5.124   | 1.00 | 55.83 |
| ATOM | 466 | OE1 | GLU | 206 | −11.449 | 59.865 | 5.199   | 1.00 | 58.27 |
| ATOM | 467 | OE2 | GLU | 206 | −11.993 | 57.802 | 5.731   | 1.00 | 57.86 |
| ATOM | 468 | N   | LYS | 207 | −7.171  | 60.270 | 1.714   | 1.00 | 53.98 |
| ATOM | 469 | CA  | LYS | 207 | −6.504  | 61.175 | 0.746   | 1.00 | 54.40 |
| ATOM | 470 | C   | LYS | 207 | −5.834  | 60.360 | −0.379  | 1.00 | 54.04 |
| ATOM | 471 | O   | LYS | 207 | −6.116  | 60.553 | −1.572  | 1.00 | 53.03 |
| ATOM | 472 | CB  | LYS | 207 | −5.463  | 62.044 | 1.481   | 1.00 | 54.50 |
| ATOM | 473 | CG  | LYS | 207 | −4.727  | 63.081 | 0.646   | 1.00 | 56.04 |
| ATOM | 474 | CD  | LYS | 207 | −3.784  | 63.911 | 1.522   | 1.00 | 58.59 |
| ATOM | 475 | CE  | LYS | 207 | −3.018  | 64.957 | 0.713   | 1.00 | 59.46 |
| ATOM | 476 | NZ  | LYS | 207 | −2.119  | 65.730 | 1.635   | 1.00 | 58.18 |
| ATOM | 477 | N   | ALA | 208 | −4.973  | 59.429 | 0.029   | 1.00 | 54.31 |
| ATOM | 478 | CA  | ALA | 208 | −4.238  | 58.613 | −0.900  | 1.00 | 55.01 |
| ATOM | 479 | C   | ALA | 208 | −5.226  | 57.838 | −1.799  | 1.00 | 55.58 |
| ATOM | 480 | O   | ALA | 208 | −5.072  | 57.834 | −3.021  | 1.00 | 55.47 |
| ATOM | 481 | CB  | ALA | 208 | −3.292  | 57.663 | −0.130  | 1.00 | 55.20 |
| ATOM | 482 | N   | TYR | 209 | −6.243  | 57.217 | −1.183  | 1.00 | 57.15 |
| ATOM | 483 | CA  | TYR | 209 | −7.312  | 56.466 | −1.915  | 1.00 | 56.96 |
| ATOM | 484 | C   | TYR | 209 | −8.039  | 57.342 | −2.964  | 1.00 | 56.61 |
| ATOM | 485 | O   | TYR | 209 | −8.230  | 56.916 | −4.130  | 1.00 | 56.39 |
| ATOM | 486 | CB  | TYR | 209 | −8.321  | 55.842 | −0.925  | 1.00 | 57.07 |
| ATOM | 487 | CG  | TYR | 209 | −9.265  | 54.766 | −1.483  | 1.00 | 57.70 |
| ATOM | 488 | CD1 | TYR | 209 | −8.809  | 53.454 | −1.731  | 1.00 | 58.72 |
| ATOM | 489 | CD2 | TYR | 209 | −10.631 | 55.048 | −1.719  | 1.00 | 58.01 |
| ATOM | 490 | CE1 | TYR | 209 | −9.689  | 52.458 | −2.216  | 1.00 | 59.35 |
| ATOM | 491 | CE2 | TYR | 209 | −11.506 | 54.068 | −2.208  | 1.00 | 57.42 |
| ATOM | 492 | CZ  | TYR | 209 | −11.026 | 52.777 | −2.451  | 1.00 | 55.90 |
| ATOM | 493 | OH  | TYR | 209 | −11.881 | 51.806 | −2.917  | 1.00 | 58.74 |
| ATOM | 494 | N   | GLU | 210 | −8.389  | 58.570 | −2.558  | 1.00 | 56.26 |
| ATOM | 495 | CA  | GLU | 210 | −9.155  | 59.505 | −3.411  | 1.00 | 56.42 |
| ATOM | 496 | C   | GLU | 210 | −8.343  | 60.109 | −4.566  | 1.00 | 56.04 |
| ATOM | 497 | O   | GLU | 210 | −8.907  | 60.607 | −5.553  | 1.00 | 56.04 |
| ATOM | 498 | CB  | GLU | 210 | −9.743  | 60.642 | −2.566  | 1.00 | 56.91 |
| ATOM | 499 | CG  | GLU | 210 | −10.701 | 60.175 | −1.446  | 1.00 | 58.24 |
| ATOM | 500 | CD  | GLU | 210 | −10.842 | 61.207 | −0.337  | 1.00 | 61.03 |
| ATOM | 501 | OE1 | GLU | 210 | −10.317 | 62.342 | −0.514  | 1.00 | 63.30 |
| ATOM | 502 | OE2 | GLU | 210 | −11.480 | 60.889 | 0.700   | 1.00 | 60.60 |
| ATOM | 503 | N   | ASN | 211 | −7.021  | 60.028 | −4.434  | 1.00 | 54.85 |
| ATOM | 504 | CA  | ASN | 211 | −6.079  | 60.747 | −5.277  | 1.00 | 54.55 |
| ATOM | 505 | C   | ASN | 211 | −5.033  | 59.735 | −5.879  | 1.00 | 53.11 |
| ATOM | 506 | O   | ASN | 211 | −3.831  | 59.980 | −5.806  | 1.00 | 52.60 |
| ATOM | 507 | CB  | ASN | 211 | −5.479  | 61.894 | −4.393  | 1.00 | 55.22 |
| ATOM | 508 | CG  | ASN | 211 | −4.332  | 62.682 | −5.055  | 1.00 | 58.06 |
| ATOM | 509 | OD1 | ASN | 211 | −4.018  | 62.510 | −6.243  | 1.00 | 60.91 |
| ATOM | 510 | ND2 | ASN | 211 | −3.692  | 63.565 | −4.261  | 1.00 | 59.82 |
| ATOM | 511 | N   | PRO | 212 | −5.496  | 58.597 | −6.491  | 1.00 | 51.64 |
| ATOM | 512 | CA  | PRO | 212 | −4.515  | 57.628 | −6.998  | 1.00 | 50.32 |
| ATOM | 513 | C   | PRO | 212 | −3.784  | 58.231 | −8.212  | 1.00 | 49.35 |
| ATOM | 514 | O   | PRO | 212 | −4.417  | 58.916 | −9.022  | 1.00 | 48.96 |
| ATOM | 515 | CB  | PRO | 212 | −5.386  | 56.455 | −7.461  | 1.00 | 50.49 |
| ATOM | 516 | CG  | PRO | 212 | −6.674  | 57.098 | −7.891  | 1.00 | 51.04 |
| ATOM | 517 | CD  | PRO | 212 | −6.876  | 58.180 | −6.826  | 1.00 | 51.68 |
| ATOM | 518 | N   | LYS | 213 | −2.479  | 57.973 | −8.318  | 1.00 | 47.51 |
| ATOM | 519 | CA  | LYS | 213 | −1.648  | 58.498 | −9.375  | 1.00 | 46.52 |
| ATOM | 520 | C   | LYS | 213 | −0.638  | 57.445 | −9.769  | 1.00 | 46.02 |
| ATOM | 521 | O   | LYS | 213 | 0.019   | 56.851 | −8.906  | 1.00 | 46.15 |
| ATOM | 522 | CB  | LYS | 213 | −0.893  | 59.737 | −8.909  | 1.00 | 46.06 |
| ATOM | 523 | CG  | LYS | 213 | −1.769  | 60.976 | −8.686  | 1.00 | 45.94 |
| ATOM | 524 | CD  | LYS | 213 | −1.021  | 62.289 | −9.006  | 1.00 | 42.30 |
| ATOM | 525 | CE  | LYS | 213 | −1.946  | 63.481 | −8.706  | 1.00 | 42.12 |
| ATOM | 526 | NZ  | LYS | 213 | −1.223  | 64.796 | −8.755  | 1.00 | 41.19 |
| ATOM | 527 | N   | PHE | 214 | −0.534  | 57.201 | −11.073 | 1.00 | 45.52 |
| ATOM | 528 | CA  | PHE | 214 | 0.540   | 56.384 | −11.634 | 1.00 | 45.58 |
| ATOM | 529 | C   | PHE | 214 | 1.875   | 57.134 | −11.471 | 1.00 | 43.76 |
| ATOM | 530 | O   | PHE | 214 | 1.897   | 58.364 | −11.285 | 1.00 | 43.89 |
| ATOM | 531 | CB  | PHE | 214 | 0.299   | 56.150 | −13.141 | 1.00 | 46.89 |
| ATOM | 532 | CG  | PHE | 214 | −0.840  | 55.212 | −13.471 | 1.00 | 48.64 |
| ATOM | 533 | CD1 | PHE | 214 | −0.830  | 53.881 | −13.033 | 1.00 | 51.01 |
| ATOM | 534 | CD2 | PHE | 214 | −1.890  | 55.646 | −14.309 | 1.00 | 50.55 |
| ATOM | 535 | CE1 | PHE | 214 | −1.876  | 52.991 | −13.378 | 1.00 | 52.20 |
| ATOM | 536 | CE2 | PHE | 214 | −2.938  | 54.788 | −14.672 | 1.00 | 50.78 |
| ATOM | 537 | CZ  | PHE | 214 | −2.938  | 53.451 | −14.199 | 1.00 | 51.48 |
| ATOM | 538 | N   | VAL | 215 | 2.986   | 56.408 | −11.572 | 1.00 | 41.22 |
| ATOM | 539 | CA  | VAL | 215 | 4.268   | 57.060 | −11.753 | 1.00 | 39.38 |

TABLE 11-continued

Three-Dimensional Coordinates of *Neisseria gonorrhoeae* GCYH-IB·Mn$^{2+}$
(SEQ. ID. No. 8)

| ATOM | 540 | C   | VAL | 215 | 4.255  | 58.075 | −12.936 | 1.00 | 38.44 |
|------|-----|-----|-----|-----|--------|--------|---------|------|-------|
| ATOM | 541 | O   | VAL | 215 | 4.831  | 59.167 | −12.830 | 1.00 | 37.18 |
| ATOM | 542 | CB  | VAL | 215 | 5.451  | 56.045 | −11.859 | 1.00 | 39.18 |
| ATOM | 543 | CG1 | VAL | 215 | 5.390  | 55.182 | −13.135 | 1.00 | 37.11 |
| ATOM | 544 | CG2 | VAL | 215 | 6.681  | 56.782 | −11.833 | 1.00 | 39.54 |
| ATOM | 545 | N   | GLU | 216 | 3.578  | 57.712 | −14.035 | 1.00 | 37.54 |
| ATOM | 546 | CA  | GLU | 216 | 3.430  | 58.603 | −15.200 | 1.00 | 36.83 |
| ATOM | 547 | C   | GLU | 216 | 2.775  | 59.953 | −14.819 | 1.00 | 36.37 |
| ATOM | 548 | O   | GLU | 216 | 3.271  | 61.013 | −15.164 | 1.00 | 35.59 |
| ATOM | 549 | CB  | GLU | 216 | 2.592  | 57.931 | −16.287 | 1.00 | 36.59 |
| ATOM | 550 | CG  | GLU | 216 | 3.269  | 56.750 | −17.002 | 1.00 | 36.95 |
| ATOM | 551 | CD  | GLU | 216 | 2.843  | 55.395 | −16.448 | 1.00 | 36.23 |
| ATOM | 552 | OE1 | GLU | 216 | 2.424  | 55.387 | −15.285 | 1.00 | 35.17 |
| ATOM | 553 | OE2 | GLU | 216 | 2.953  | 54.341 | −17.152 | 1.00 | 36.48 |
| ATOM | 554 | N   | ASP | 217 | 1.666  | 59.879 | −14.096 | 1.00 | 37.46 |
| ATOM | 555 | CA  | ASP | 217 | 0.924  | 61.055 | −13.575 | 1.00 | 37.41 |
| ATOM | 556 | C   | ASP | 217 | 1.763  | 61.917 | −12.679 | 1.00 | 36.40 |
| ATOM | 557 | O   | ASP | 217 | 1.733  | 63.152 | −12.781 | 1.00 | 35.80 |
| ATOM | 558 | CB  | ASP | 217 | −0.305 | 60.587 | −12.782 | 1.00 | 39.17 |
| ATOM | 559 | CG  | ASP | 217 | −1.379 | 59.979 | −13.689 | 1.00 | 42.59 |
| ATOM | 560 | OD1 | ASP | 217 | −1.611 | 60.541 | −14.803 | 1.00 | 44.14 |
| ATOM | 561 | OD2 | ASP | 217 | −1.972 | 58.946 | −13.294 | 1.00 | 45.24 |
| ATOM | 562 | N   | MET | 218 | 2.523  | 61.279 | −11.793 | 1.00 | 36.11 |
| ATOM | 563 | CA  | MET | 218 | 3.384  | 62.025 | −10.895 | 1.00 | 35.43 |
| ATOM | 564 | C   | MET | 218 | 4.516  | 62.729 | −11.624 | 1.00 | 33.47 |
| ATOM | 565 | O   | MET | 218 | 4.761  | 63.892 | −11.387 | 1.00 | 32.57 |
| ATOM | 566 | CB  | MET | 218 | 3.919  | 61.129 | −9.744  | 1.00 | 36.86 |
| ATOM | 567 | CG  | MET | 218 | 4.835  | 61.863 | −8.686  | 1.00 | 39.05 |
| ATOM | 568 | SD  | MET | 218 | 4.098  | 63.050 | −7.489  | 1.00 | 48.15 |
| ATOM | 569 | CE  | MET | 218 | 2.385  | 62.882 | −7.908  | 1.00 | 47.14 |
| ATOM | 570 | N   | VAL | 219 | 5.233  | 62.058 | −12.507 | 1.00 | 32.53 |
| ATOM | 571 | CA  | VAL | 219 | 6.310  | 62.816 | −13.169 | 1.00 | 32.64 |
| ATOM | 572 | C   | VAL | 219 | 5.758  | 64.016 | −13.970 | 1.00 | 32.02 |
| ATOM | 573 | O   | VAL | 219 | 6.383  | 65.105 | −13.996 | 1.00 | 30.73 |
| ATOM | 574 | CB  | VAL | 219 | 7.290  | 61.951 | −14.026 | 1.00 | 32.81 |
| ATOM | 575 | CG1 | VAL | 219 | 8.108  | 61.031 | −13.124 | 1.00 | 33.18 |
| ATOM | 576 | CG2 | VAL | 219 | 6.570  | 61.164 | −15.095 | 1.00 | 33.07 |
| ATOM | 577 | N   | ARG | 220 | 4.613  | 63.799 | −14.631 | 1.00 | 32.42 |
| ATOM | 578 | CA  | ARG | 220 | 3.940  | 64.851 | −15.425 | 1.00 | 32.49 |
| ATOM | 579 | C   | ARG | 220 | 3.445  | 66.069 | −14.650 | 1.00 | 33.39 |
| ATOM | 580 | O   | ARG | 220 | 3.745  | 67.221 | −15.037 | 1.00 | 34.66 |
| ATOM | 581 | CB  | ARG | 220 | 2.814  | 64.264 | −16.220 | 1.00 | 32.42 |
| ATOM | 582 | CG  | ARG | 220 | 3.309  | 63.496 | −17.434 | 1.00 | 31.64 |
| ATOM | 583 | CD  | ARG | 220 | 2.123  | 62.782 | −18.065 | 1.00 | 32.29 |
| ATOM | 584 | NE  | ARG | 220 | 2.428  | 62.444 | −19.436 | 1.00 | 34.95 |
| ATOM | 585 | CZ  | ARG | 220 | 1.932  | 61.391 | −20.059 | 1.00 | 35.09 |
| ATOM | 586 | NH1 | ARG | 220 | 1.120  | 60.547 | −19.417 | 1.00 | 33.56 |
| ATOM | 587 | NH2 | ARG | 220 | 2.268  | 61.180 | −21.319 | 1.00 | 36.65 |
| ATOM | 588 | N   | ASP | 221 | 2.717  | 65.830 | −13.566 | 1.00 | 34.07 |
| ATOM | 589 | CA  | ASP | 221 | 2.290  | 66.894 | −12.636 | 1.00 | 33.76 |
| ATOM | 590 | C   | ASP | 221 | 3.446  | 67.711 | −12.069 | 1.00 | 33.51 |
| ATOM | 591 | O   | ASP | 221 | 3.342  | 68.931 | −11.968 | 1.00 | 33.79 |
| ATOM | 592 | CB  | ASP | 221 | 1.453  | 66.265 | −11.505 | 1.00 | 34.70 |
| ATOM | 593 | CG  | ASP | 221 | 0.124  | 65.715 | −12.009 | 1.00 | 36.94 |
| ATOM | 594 | OD1 | ASP | 221 | −0.162 | 65.982 | −13.197 | 1.00 | 40.28 |
| ATOM | 595 | OD2 | ASP | 221 | −0.626 | 65.034 | −11.263 | 1.00 | 36.36 |
| ATOM | 596 | N   | VAL | 222 | 4.559  | 67.058 | −11.697 | 1.00 | 32.83 |
| ATOM | 597 | CA  | VAL | 222 | 5.737  | 67.797 | −11.232 | 1.00 | 31.91 |
| ATOM | 598 | C   | VAL | 222 | 6.418  | 68.561 | −12.389 | 1.00 | 32.92 |
| ATOM | 599 | O   | VAL | 222 | 6.823  | 69.731 | −12.243 | 1.00 | 32.48 |
| ATOM | 600 | CB  | VAL | 222 | 6.756  | 66.875 | −10.431 | 1.00 | 31.86 |
| ATOM | 601 | CG1 | VAL | 222 | 8.053  | 67.588 | −10.118 | 1.00 | 29.78 |
| ATOM | 602 | CG2 | VAL | 222 | 6.119  | 66.313 | −9.133  | 1.00 | 28.77 |
| ATOM | 603 | N   | ALA | 223 | 6.553  | 67.923 | −13.549 | 1.00 | 32.41 |
| ATOM | 604 | CA  | ALA | 223 | 7.218  | 68.622 | −14.660 | 1.00 | 32.79 |
| ATOM | 605 | C   | ALA | 223 | 6.469  | 69.921 | −15.061 | 1.00 | 32.87 |
| ATOM | 606 | O   | ALA | 223 | 7.092  | 70.971 | −15.365 | 1.00 | 32.40 |
| ATOM | 607 | CB  | ALA | 223 | 7.311  | 67.714 | −15.851 | 1.00 | 33.64 |
| ATOM | 608 | N   | THR | 224 | 5.138  | 69.838 | −15.076 | 1.00 | 33.30 |
| ATOM | 609 | CA  | THR | 224 | 4.311  | 71.039 | −15.348 | 1.00 | 34.28 |
| ATOM | 610 | C   | THR | 224 | 4.709  | 72.191 | −14.426 | 1.00 | 33.80 |
| ATOM | 611 | O   | THR | 224 | 4.883  | 73.312 | −14.896 | 1.00 | 32.18 |
| ATOM | 612 | CB  | THR | 224 | 2.834  | 70.753 | −15.250 | 1.00 | 34.79 |
| ATOM | 613 | OG1 | THR | 224 | 2.527  | 69.657 | −16.107 | 1.00 | 34.54 |
| ATOM | 614 | CG2 | THR | 224 | 2.009  | 71.981 | −15.738 | 1.00 | 38.37 |
| ATOM | 615 | N   | SER | 225 | 4.876  | 71.926 | −13.115 | 1.00 | 34.23 |
| ATOM | 616 | CA  | SER | 225 | 5.217  | 73.008 | −12.194 | 1.00 | 34.27 |

TABLE 11-continued

Three-Dimensional Coordinates of *Neisseria gonorrhoeae* GCYH-IB·Mn$^{2+}$
(SEQ. ID. No. 8)

| ATOM | 617 | C   | SER | 225 | 6.582  | 73.547 | −12.546 | 1.00 | 34.88 |
|------|-----|-----|-----|-----|--------|--------|---------|------|-------|
| ATOM | 618 | O   | SER | 225 | 6.833  | 74.788 | −12.517 | 1.00 | 34.49 |
| ATOM | 619 | CB  | SER | 225 | 5.208  | 72.552 | −10.736 | 1.00 | 34.83 |
| ATOM | 620 | OG  | SER | 225 | 3.879  | 72.289 | −10.317 | 1.00 | 36.16 |
| ATOM | 621 | N   | LEU | 226 | 7.499  | 72.638 | −12.887 | 1.00 | 34.32 |
| ATOM | 622 | CA  | LEU | 226 | 8.863  | 73.093 | −13.123 | 1.00 | 34.58 |
| ATOM | 623 | C   | LEU | 226 | 9.034  | 73.818 | −14.480 | 1.00 | 35.09 |
| ATOM | 624 | O   | LEU | 226 | 9.871  | 74.718 | −14.624 | 1.00 | 35.39 |
| ATOM | 625 | CB  | LEU | 226 | 9.867  | 71.920 | −12.956 | 1.00 | 34.96 |
| ATOM | 626 | CG  | LEU | 226 | 9.770  | 71.026 | −11.699 | 1.00 | 33.32 |
| ATOM | 627 | CD1 | LEU | 226 | 10.737 | 69.840 | −11.796 | 1.00 | 29.72 |
| ATOM | 628 | CD2 | LEU | 226 | 10.017 | 71.850 | −10.444 | 1.00 | 31.90 |
| ATOM | 629 | N   | ILE | 227 | 8.285  | 73.410 | −15.499 | 1.00 | 35.24 |
| ATOM | 630 | CA  | ILE | 227 | 8.359  | 74.134 | −16.791 | 1.00 | 34.80 |
| ATOM | 631 | C   | ILE | 227 | 7.912  | 75.610 | −16.620 | 1.00 | 35.08 |
| ATOM | 632 | O   | ILE | 227 | 8.456  | 76.548 | −17.253 | 1.00 | 34.52 |
| ATOM | 633 | CB  | ILE | 227 | 7.486  | 73.438 | −17.862 | 1.00 | 35.35 |
| ATOM | 634 | CG1 | ILE | 227 | 8.228  | 72.188 | −18.401 | 1.00 | 35.35 |
| ATOM | 635 | CG2 | ILE | 227 | 7.131  | 74.418 | −18.992 | 1.00 | 35.51 |
| ATOM | 636 | CD1 | ILE | 227 | 7.329  | 71.149 | −19.011 | 1.00 | 35.08 |
| ATOM | 637 | N   | ALA | 228 | 6.950  | 75.792 | −15.727 | 1.00 | 35.42 |
| ATOM | 638 | CA  | ALA | 228 | 6.324  | 77.073 | −15.459 | 1.00 | 36.53 |
| ATOM | 639 | C   | ALA | 228 | 7.183  | 78.037 | −14.640 | 1.00 | 36.58 |
| ATOM | 640 | O   | ALA | 228 | 7.024  | 79.270 | −14.741 | 1.00 | 37.14 |
| ATOM | 641 | CB  | ALA | 228 | 4.984  | 76.835 | −14.774 | 1.00 | 36.82 |
| ATOM | 642 | N   | ASP | 229 | 8.109  | 77.505 | −13.850 | 1.00 | 36.37 |
| ATOM | 643 | CA  | ASP | 229 | 8.973  | 78.352 | −13.018 | 1.00 | 36.10 |
| ATOM | 644 | C   | ASP | 229 | 10.034 | 78.994 | −13.915 | 1.00 | 37.32 |
| ATOM | 645 | O   | ASP | 229 | 10.792 | 78.279 | −14.572 | 1.00 | 37.73 |
| ATOM | 646 | CB  | ASP | 229 | 9.585  | 77.499 | −11.897 | 1.00 | 35.82 |
| ATOM | 647 | CG  | ASP | 229 | 10.310 | 78.324 | −10.861 | 1.00 | 35.00 |
| ATOM | 648 | OD1 | ASP | 229 | 11.209 | 79.106 | −11.240 | 1.00 | 32.09 |
| ATOM | 649 | OD2 | ASP | 229 | 9.966  | 78.202 | −9.653  | 1.00 | 34.51 |
| ATOM | 650 | N   | PHE | 242 | 7.931  | 51.871 | −5.327  | 1.00 | 42.06 |
| ATOM | 651 | CA  | PHE | 242 | 8.328  | 50.538 | −4.849  | 1.00 | 43.01 |
| ATOM | 652 | C   | PHE | 242 | 7.099  | 49.620 | −4.761  | 1.00 | 43.06 |
| ATOM | 653 | O   | PHE | 242 | 6.628  | 49.305 | −3.649  | 1.00 | 41.83 |
| ATOM | 654 | CB  | PHE | 242 | 9.160  | 50.645 | −3.539  | 1.00 | 42.80 |
| ATOM | 655 | CG  | PHE | 242 | 10.470 | 51.378 | −3.748  | 1.00 | 43.34 |
| ATOM | 656 | CD1 | PHE | 242 | 11.578 | 50.701 | −4.232  | 1.00 | 43.78 |
| ATOM | 657 | CD2 | PHE | 242 | 10.565 | 52.770 | −3.542  | 1.00 | 43.59 |
| ATOM | 658 | CE1 | PHE | 242 | 12.781 | 51.376 | −4.457  | 1.00 | 45.11 |
| ATOM | 659 | CE2 | PHE | 242 | 11.767 | 53.451 | −3.755  | 1.00 | 42.03 |
| ATOM | 660 | CZ  | PHE | 242 | 12.872 | 52.752 | −4.214  | 1.00 | 43.33 |
| ATOM | 661 | N   | GLU | 243 | 6.591  | 49.235 | −5.947  | 1.00 | 42.20 |
| ATOM | 662 | CA  | GLU | 243 | 5.313  | 48.530 | −6.091  | 1.00 | 43.24 |
| ATOM | 663 | C   | GLU | 243 | 5.193  | 47.503 | −4.975  | 1.00 | 42.95 |
| ATOM | 664 | O   | GLU | 243 | 6.100  | 46.664 | −4.795  | 1.00 | 41.58 |
| ATOM | 665 | CB  | GLU | 243 | 5.176  | 47.817 | −7.456  | 1.00 | 43.53 |
| ATOM | 666 | CG  | GLU | 243 | 5.166  | 48.729 | −8.686  | 1.00 | 47.74 |
| ATOM | 667 | CD  | GLU | 243 | 4.045  | 49.790 | −8.672  | 1.00 | 53.02 |
| ATOM | 668 | OE1 | GLU | 243 | 2.909  | 49.485 | −9.111  | 1.00 | 56.85 |
| ATOM | 669 | OE2 | GLU | 243 | 4.313  | 50.950 | −8.262  | 1.00 | 54.32 |
| ATOM | 670 | N   | SER | 244 | 4.109  | 47.621 | −4.205  | 1.00 | 42.95 |
| ATOM | 671 | CA  | SER | 244 | 3.917  | 46.786 | −3.017  | 1.00 | 43.67 |
| ATOM | 672 | C   | SER | 244 | 3.492  | 45.363 | −3.422  | 1.00 | 44.11 |
| ATOM | 673 | O   | SER | 244 | 3.430  | 44.503 | −2.559  | 1.00 | 43.54 |
| ATOM | 674 | CB  | SER | 244 | 2.872  | 47.385 | −2.062  | 1.00 | 43.70 |
| ATOM | 675 | OG  | SER | 244 | 1.608  | 47.538 | −2.714  | 1.00 | 43.76 |
| ATOM | 676 | N   | ILE | 245 | 3.247  | 45.151 | −4.732  | 1.00 | 44.53 |
| ATOM | 677 | CA  | ILE | 245 | 2.762  | 43.878 | −5.305  | 1.00 | 44.90 |
| ATOM | 678 | C   | ILE | 245 | 3.796  | 43.050 | −6.114  | 1.00 | 44.98 |
| ATOM | 679 | O   | ILE | 245 | 3.579  | 41.858 | −6.399  | 1.00 | 45.25 |
| ATOM | 680 | CB  | ILE | 245 | 1.446  | 44.092 | −6.131  | 1.00 | 45.08 |
| ATOM | 681 | CG1 | ILE | 245 | 1.678  | 45.000 | −7.340  | 1.00 | 45.82 |
| ATOM | 682 | CG2 | ILE | 245 | 0.327  | 44.676 | −5.234  | 1.00 | 45.11 |
| ATOM | 683 | CD1 | ILE | 245 | 0.563  | 44.940 | −8.372  | 1.00 | 45.19 |
| ATOM | 684 | N   | HIS | 246 | 4.912  | 43.691 | −6.467  | 1.00 | 44.82 |
| ATOM | 685 | CA  | HIS | 246 | 6.046  | 43.056 | −7.170  | 1.00 | 44.40 |
| ATOM | 686 | C   | HIS | 246 | 7.299  | 43.248 | −6.337  | 1.00 | 43.85 |
| ATOM | 687 | O   | HIS | 246 | 7.274  | 43.929 | −5.290  | 1.00 | 43.92 |
| ATOM | 688 | CB  | HIS | 246 | 6.306  | 43.733 | −8.529  | 1.00 | 45.24 |
| ATOM | 689 | CG  | HIS | 246 | 5.125  | 43.746 | −9.448  | 1.00 | 45.19 |
| ATOM | 690 | ND1 | HIS | 246 | 4.574  | 44.916 | −9.935  | 1.00 | 47.43 |
| ATOM | 691 | CD2 | HIS | 246 | 4.390  | 42.735 | −9.968  | 1.00 | 44.55 |
| ATOM | 692 | CE1 | HIS | 246 | 3.557  | 44.616 | −10.729 | 1.00 | 47.01 |
| ATOM | 693 | NE2 | HIS | 246 | 3.423  | 43.299 | −10.761 | 1.00 | 45.51 |

TABLE 11-continued

Three-Dimensional Coordinates of *Neisseria gonorrhoeae* GCYH-IB·Mn$^{2+}$
(SEQ. ID. No. 8)

TER
| ATOM | 694 | MN | MN2 A | 258 | −0.987 | 48.653 | −9.777 | 1.00 | 49.60 |
|---|---|---|---|---|---|---|---|---|---|

TER
| ATOM | 695 | N | ASN | 15 | −0.055 | 68.475 | −21.743 | 1.00 | 57.77 |
|---|---|---|---|---|---|---|---|---|---|
| ATOM | 696 | CA | ASN | 15 | 0.077 | 66.987 | −21.573 | 1.00 | 57.60 |
| ATOM | 697 | C | ASN | 15 | 1.474 | 66.516 | −21.106 | 1.00 | 56.17 |
| ATOM | 698 | O | ASN | 15 | 1.638 | 66.048 | −19.944 | 1.00 | 57.59 |
| ATOM | 699 | CB | ASN | 15 | −0.349 | 66.258 | −22.857 | 1.00 | 58.61 |
| ATOM | 700 | CG | ASN | 15 | −1.826 | 65.843 | −22.840 | 1.00 | 61.05 |
| ATOM | 701 | OD1 | ASN | 15 | −2.439 | 65.713 | −21.763 | 1.00 | 62.70 |
| ATOM | 702 | ND2 | ASN | 15 | −2.407 | 65.626 | −24.045 | 1.00 | 62.68 |
| ATOM | 703 | N | LEU | 16 | 2.466 | 66.657 | −21.989 | 1.00 | 53.16 |
| ATOM | 704 | CA | LEU | 16 | 3.873 | 66.273 | −21.715 | 1.00 | 49.45 |
| ATOM | 705 | C | LEU | 16 | 4.265 | 64.821 | −22.049 | 1.00 | 46.26 |
| ATOM | 706 | O | LEU | 16 | 3.774 | 63.857 | −21.428 | 1.00 | 45.34 |
| ATOM | 707 | CB | LEU | 16 | 4.286 | 66.643 | −20.281 | 1.00 | 50.00 |
| ATOM | 708 | CG | LEU | 16 | 5.106 | 67.898 | −20.015 | 1.00 | 50.00 |
| ATOM | 709 | CD1 | LEU | 16 | 4.760 | 69.101 | −20.907 | 1.00 | 49.39 |
| ATOM | 710 | CD2 | LEU | 16 | 5.019 | 68.235 | −18.515 | 1.00 | 49.75 |
| ATOM | 711 | N | PRO | 17 | 5.144 | 64.662 | −23.051 | 1.00 | 43.37 |
| ATOM | 712 | CA | PRO | 17 | 5.673 | 63.318 | −23.272 | 1.00 | 42.01 |
| ATOM | 713 | C | PRO | 17 | 6.630 | 62.898 | −22.123 | 1.00 | 39.49 |
| ATOM | 714 | O | PRO | 17 | 7.206 | 63.762 | −21.457 | 1.00 | 38.46 |
| ATOM | 715 | CB | PRO | 17 | 6.387 | 63.410 | −24.638 | 1.00 | 41.94 |
| ATOM | 716 | CG | PRO | 17 | 6.625 | 64.921 | −24.889 | 1.00 | 42.78 |
| ATOM | 717 | CD | PRO | 17 | 5.660 | 65.673 | −24.004 | 1.00 | 43.71 |
| ATOM | 718 | N | ILE | 18 | 6.757 | 61.587 | −21.888 | 1.00 | 37.20 |
| ATOM | 719 | CA | ILE | 18 | 7.707 | 61.060 | −20.889 | 1.00 | 34.81 |
| ATOM | 720 | C | ILE | 18 | 8.860 | 60.366 | −21.617 | 1.00 | 34.48 |
| ATOM | 721 | O | ILE | 18 | 8.658 | 59.400 | −22.359 | 1.00 | 33.94 |
| ATOM | 722 | CB | ILE | 18 | 7.007 | 60.115 | −19.844 | 1.00 | 35.33 |
| ATOM | 723 | CG1 | ILE | 18 | 5.742 | 60.779 | −19.284 | 1.00 | 34.34 |
| ATOM | 724 | CG2 | ILE | 18 | 7.994 | 59.691 | −18.733 | 1.00 | 34.30 |
| ATOM | 725 | CD1 | ILE | 18 | 4.965 | 60.057 | −18.195 | 1.00 | 33.50 |
| ATOM | 726 | N | TYR | 50 | 9.592 | 55.233 | −24.510 | 1.00 | 32.49 |
| ATOM | 727 | CA | TYR | 50 | 9.011 | 56.572 | −24.698 | 1.00 | 33.92 |
| ATOM | 728 | C | TYR | 50 | 7.472 | 56.559 | −24.508 | 1.00 | 34.74 |
| ATOM | 729 | O | TYR | 50 | 6.795 | 55.620 | −24.894 | 1.00 | 34.44 |
| ATOM | 730 | CB | TYR | 50 | 9.391 | 57.083 | −26.100 | 1.00 | 34.27 |
| ATOM | 731 | CG | TYR | 50 | 8.732 | 58.354 | −26.497 | 1.00 | 34.16 |
| ATOM | 732 | CD1 | TYR | 50 | 9.239 | 59.573 | −26.086 | 1.00 | 34.55 |
| ATOM | 733 | CD2 | TYR | 50 | 7.621 | 58.344 | −27.334 | 1.00 | 34.69 |
| ATOM | 734 | CE1 | TYR | 50 | 8.612 | 60.776 | −26.451 | 1.00 | 34.91 |
| ATOM | 735 | CE2 | TYR | 50 | 7.008 | 59.513 | −27.724 | 1.00 | 34.31 |
| ATOM | 736 | CZ | TYR | 50 | 7.497 | 60.717 | −27.280 | 1.00 | 34.93 |
| ATOM | 737 | OH | TYR | 50 | 6.858 | 61.883 | −27.670 | 1.00 | 37.56 |
| ATOM | 738 | N | LEU | 51 | 6.920 | 57.574 | −23.856 | 1.00 | 36.01 |
| ATOM | 739 | CA | LEU | 51 | 5.459 | 57.628 | −23.743 | 1.00 | 38.06 |
| ATOM | 740 | C | LEU | 51 | 4.970 | 58.946 | −24.359 | 1.00 | 38.71 |
| ATOM | 741 | O | LEU | 51 | 5.357 | 60.033 | −23.891 | 1.00 | 38.72 |
| ATOM | 742 | CB | LEU | 51 | 4.966 | 57.508 | −22.293 | 1.00 | 38.26 |
| ATOM | 743 | CG | LEU | 51 | 3.483 | 57.129 | −22.071 | 1.00 | 39.97 |
| ATOM | 744 | CD1 | LEU | 51 | 3.196 | 55.722 | −22.569 | 1.00 | 41.59 |
| ATOM | 745 | CD2 | LEU | 51 | 3.106 | 57.206 | −20.601 | 1.00 | 39.18 |
| ATOM | 746 | N | PRO | 52 | 4.132 | 58.851 | −25.410 | 1.00 | 39.27 |
| ATOM | 747 | CA | PRO | 52 | 3.607 | 60.049 | −26.084 | 1.00 | 40.56 |
| ATOM | 748 | C | PRO | 52 | 2.762 | 60.931 | −25.170 | 1.00 | 40.53 |
| ATOM | 749 | O | PRO | 52 | 2.094 | 60.428 | −24.289 | 1.00 | 39.33 |
| ATOM | 750 | CB | PRO | 52 | 2.720 | 59.470 | −27.209 | 1.00 | 40.48 |
| ATOM | 751 | CG | PRO | 52 | 3.168 | 58.035 | −27.390 | 1.00 | 40.75 |
| ATOM | 752 | CD | PRO | 52 | 3.626 | 57.600 | −26.013 | 1.00 | 39.83 |
| ATOM | 753 | N | ALA | 53 | 2.808 | 62.240 | −25.420 | 1.00 | 42.43 |
| ATOM | 754 | CA | ALA | 53 | 2.081 | 63.263 | −24.663 | 1.00 | 44.05 |
| ATOM | 755 | C | ALA | 53 | 0.632 | 62.937 | −24.238 | 1.00 | 46.03 |
| ATOM | 756 | O | ALA | 53 | 0.269 | 63.114 | −23.079 | 1.00 | 45.37 |
| ATOM | 757 | CB | ALA | 53 | 2.158 | 64.611 | −25.400 | 1.00 | 44.31 |
| ATOM | 758 | N | GLU | 54 | −0.201 | 62.432 | −25.147 | 1.00 | 48.17 |
| ATOM | 759 | CA | GLU | 54 | −1.588 | 62.156 | −24.742 | 1.00 | 50.27 |
| ATOM | 760 | C | GLU | 54 | −1.866 | 60.696 | −24.298 | 1.00 | 50.27 |
| ATOM | 761 | O | GLU | 54 | −3.005 | 60.374 | −23.975 | 1.00 | 50.60 |
| ATOM | 762 | CB | GLU | 54 | −2.627 | 62.696 | −25.771 | 1.00 | 50.47 |
| ATOM | 763 | CG | GLU | 54 | −2.726 | 61.898 | −27.079 | 1.00 | 52.14 |
| ATOM | 764 | CD | GLU | 54 | −3.853 | 62.381 | −28.041 | 1.00 | 52.30 |
| ATOM | 765 | OE1 | GLU | 54 | −3.510 | 63.067 | −29.047 | 1.00 | 53.98 |
| ATOM | 766 | OE2 | GLU | 54 | −5.059 | 62.074 | −27.795 | 1.00 | 52.76 |
| ATOM | 767 | N | GLN | 55 | −0.842 | 59.833 | −24.264 | 1.00 | 49.80 |
| ATOM | 768 | CA | GLN | 55 | −1.008 | 58.463 | −23.723 | 1.00 | 49.67 |

TABLE 11-continued

Three-Dimensional Coordinates of *Neisseria gonorrhoeae* GCYH-IB·Mn$^{2+}$
(SEQ. ID. No. 8)

| ATOM | 769 | C | GLN | 55 | −0.821 | 58.421 | −22.204 | 1.00 | 49.52 |
|------|-----|-----|-----|----|--------|--------|---------|------|-------|
| ATOM | 770 | O | GLN | 55 | 0.162 | 58.960 | −21.673 | 1.00 | 48.68 |
| ATOM | 771 | CB | GLN | 55 | −0.060 | 57.476 | −24.415 | 1.00 | 49.73 |
| ATOM | 772 | CG | GLN | 55 | −0.274 | 55.997 | −24.053 | 1.00 | 49.02 |
| ATOM | 773 | CD | GLN | 55 | 0.539 | 55.065 | −24.963 | 1.00 | 50.64 |
| ATOM | 774 | OE1 | GLN | 55 | 0.798 | 55.402 | −26.127 | 1.00 | 50.76 |
| ATOM | 775 | NE2 | GLN | 55 | 0.928 | 53.872 | −24.442 | 1.00 | 50.99 |
| ATOM | 776 | N | LYS | 56 | −1.761 | 57.772 | −21.514 | 1.00 | 49.80 |
| ATOM | 777 | CA | LYS | 56 | −1.878 | 57.919 | −20.046 | 1.00 | 50.35 |
| ATOM | 778 | C | LYS | 56 | −0.832 | 57.125 | −19.269 | 1.00 | 48.93 |
| ATOM | 779 | O | LYS | 56 | −0.302 | 57.610 | −18.259 | 1.00 | 48.73 |
| ATOM | 780 | CB | LYS | 56 | −3.292 | 57.572 | −19.523 | 1.00 | 50.57 |
| ATOM | 781 | CG | LYS | 56 | −3.464 | 57.835 | −18.019 | 1.00 | 51.80 |
| ATOM | 782 | CD | LYS | 56 | −4.918 | 57.915 | −17.578 | 1.00 | 53.30 |
| ATOM | 783 | CE | LYS | 56 | −5.380 | 56.598 | −16.954 | 1.00 | 55.68 |
| ATOM | 784 | NZ | LYS | 56 | −6.597 | 56.015 | −17.633 | 1.00 | 59.22 |
| ATOM | 785 | N | GLY | 57 | −0.585 | 55.903 | −19.747 | 1.00 | 47.49 |
| ATOM | 786 | CA | GLY | 57 | 0.319 | 54.958 | −19.131 | 1.00 | 45.82 |
| ATOM | 787 | C | GLY | 57 | 0.834 | 53.928 | −20.127 | 1.00 | 45.53 |
| ATOM | 788 | O | GLY | 57 | 0.337 | 53.804 | −21.261 | 1.00 | 44.75 |
| ATOM | 789 | N | THR | 58 | 1.867 | 53.202 | −19.715 | 1.00 | 44.32 |
| ATOM | 790 | CA | THR | 58 | 2.451 | 52.188 | −20.551 | 1.00 | 43.57 |
| ATOM | 791 | C | THR | 58 | 1.880 | 50.881 | −20.016 | 1.00 | 44.18 |
| ATOM | 792 | O | THR | 58 | 0.915 | 50.906 | −19.236 | 1.00 | 43.92 |
| ATOM | 793 | CB | THR | 58 | 4.020 | 52.240 | −20.514 | 1.00 | 43.34 |
| ATOM | 794 | OG1 | THR | 58 | 4.567 | 51.259 | −21.411 | 1.00 | 42.06 |
| ATOM | 795 | CG2 | THR | 58 | 4.552 | 51.995 | −19.087 | 1.00 | 41.24 |
| ATOM | 796 | N | HIS | 59 | 2.484 | 49.759 | −20.416 | 1.00 | 44.36 |
| ATOM | 797 | CA | HIS | 59 | 1.990 | 48.432 | −20.089 | 1.00 | 44.59 |
| ATOM | 798 | C | HIS | 59 | 3.042 | 47.682 | −19.315 | 1.00 | 43.83 |
| ATOM | 799 | O | HIS | 59 | 3.780 | 46.885 | −19.885 | 1.00 | 42.81 |
| ATOM | 800 | CB | HIS | 59 | 1.636 | 47.699 | −21.380 | 1.00 | 45.60 |
| ATOM | 801 | CG | HIS | 59 | 0.703 | 48.482 | −22.252 | 1.00 | 48.60 |
| ATOM | 802 | ND1 | HIS | 59 | 1.144 | 49.285 | −23.288 | 1.00 | 51.29 |
| ATOM | 803 | CD2 | HIS | 59 | −0.637 | 48.661 | −22.180 | 1.00 | 50.27 |
| ATOM | 804 | CE1 | HIS | 59 | 0.109 | 49.887 | −23.847 | 1.00 | 51.31 |
| ATOM | 805 | NE2 | HIS | 59 | −0.984 | 49.521 | −23.198 | 1.00 | 52.01 |
| ATOM | 806 | N | MET | 60 | 3.060 | 47.922 | −18.003 | 1.00 | 43.45 |
| ATOM | 807 | CA | MET | 60 | 4.118 | 47.452 | −17.111 | 1.00 | 43.58 |
| ATOM | 808 | C | MET | 60 | 4.408 | 45.950 | −17.126 | 1.00 | 42.81 |
| ATOM | 809 | O | MET | 60 | 5.568 | 45.558 | −17.000 | 1.00 | 43.78 |
| ATOM | 810 | CB | MET | 60 | 3.826 | 47.903 | −15.662 | 1.00 | 44.75 |
| ATOM | 811 | CG | MET | 60 | 3.874 | 49.424 | −15.481 | 1.00 | 45.80 |
| ATOM | 812 | SD | MET | 60 | 5.554 | 50.030 | −15.559 | 1.00 | 47.38 |
| ATOM | 813 | CE | MET | 60 | 5.341 | 51.725 | −15.015 | 1.00 | 46.89 |
| ATOM | 814 | N | SER | 61 | 3.378 | 45.104 | −17.240 | 1.00 | 41.77 |
| ATOM | 815 | CA | SER | 61 | 3.580 | 43.646 | −17.190 | 1.00 | 40.55 |
| ATOM | 816 | C | SER | 61 | 4.316 | 43.095 | −18.401 | 1.00 | 40.20 |
| ATOM | 817 | O | SER | 61 | 4.872 | 41.980 | −18.354 | 1.00 | 39.73 |
| ATOM | 818 | CB | SER | 61 | 2.253 | 42.915 | −17.058 | 1.00 | 40.87 |
| ATOM | 819 | OG | SER | 61 | 1.535 | 42.951 | −18.286 | 1.00 | 42.74 |
| ATOM | 820 | N | ARG | 62 | 4.306 | 43.848 | −19.502 | 1.00 | 38.76 |
| ATOM | 821 | CA | ARG | 62 | 4.907 | 43.356 | −20.760 | 1.00 | 37.81 |
| ATOM | 822 | C | ARG | 62 | 6.430 | 43.334 | −20.708 | 1.00 | 36.60 |
| ATOM | 823 | O | ARG | 62 | 7.053 | 42.553 | −21.407 | 1.00 | 35.27 |
| ATOM | 824 | CB | ARG | 62 | 4.471 | 44.223 | −21.946 | 1.00 | 38.07 |
| ATOM | 825 | CG | ARG | 62 | 2.986 | 44.333 | −22.103 | 1.00 | 37.78 |
| ATOM | 826 | CD | ARG | 62 | 2.650 | 44.941 | −23.453 | 1.00 | 37.88 |
| ATOM | 827 | NE | ARG | 62 | 1.202 | 45.064 | −23.598 | 1.00 | 37.07 |
| ATOM | 828 | CZ | ARG | 62 | 0.569 | 45.715 | −24.579 | 1.00 | 37.18 |
| ATOM | 829 | NH1 | ARG | 62 | 1.229 | 46.323 | −25.571 | 1.00 | 37.21 |
| ATOM | 830 | NH2 | ARG | 62 | −0.745 | 45.735 | −24.564 | 1.00 | 35.43 |
| ATOM | 831 | N | PHE | 63 | 7.029 | 44.222 | −19.900 | 1.00 | 36.09 |
| ATOM | 832 | CA | PHE | 63 | 8.464 | 44.216 | −19.720 | 1.00 | 35.73 |
| ATOM | 833 | C | PHE | 63 | 8.893 | 42.871 | −19.109 | 1.00 | 36.45 |
| ATOM | 834 | O | PHE | 63 | 9.793 | 42.213 | −19.617 | 1.00 | 36.12 |
| ATOM | 835 | CB | PHE | 63 | 8.934 | 45.382 | −18.850 | 1.00 | 35.41 |
| ATOM | 836 | CG | PHE | 63 | 8.621 | 46.727 | −19.413 | 1.00 | 34.78 |
| ATOM | 837 | CD1 | PHE | 63 | 9.340 | 47.217 | −20.503 | 1.00 | 32.25 |
| ATOM | 838 | CD2 | PHE | 63 | 7.598 | 47.499 | −18.852 | 1.00 | 33.93 |
| ATOM | 839 | CE1 | PHE | 63 | 9.074 | 48.487 | −21.031 | 1.00 | 32.28 |
| ATOM | 840 | CE2 | PHE | 63 | 7.303 | 48.777 | −19.376 | 1.00 | 34.29 |
| ATOM | 841 | CZ | PHE | 63 | 8.050 | 49.274 | −20.464 | 1.00 | 33.57 |
| ATOM | 842 | N | VAL | 64 | 8.236 | 42.472 | −18.020 | 1.00 | 37.27 |
| ATOM | 843 | CA | VAL | 64 | 8.517 | 41.190 | −17.375 | 1.00 | 37.13 |
| ATOM | 844 | C | VAL | 64 | 8.161 | 40.006 | −18.267 | 1.00 | 38.00 |
| ATOM | 845 | O | VAL | 64 | 8.928 | 39.046 | −18.346 | 1.00 | 38.05 |

TABLE 11-continued

Three-Dimensional Coordinates of *Neisseria gonorrhoeae* GCYH-IB·Mn$^{2+}$
(SEQ. ID. No. 8)

| ATOM | 846 | CB | VAL | 64 | 7.771 | 41.072 | −15.995 | 1.00 | 37.68 |
|------|-----|-----|-----|-----|--------|--------|---------|------|-------|
| ATOM | 847 | CG1 | VAL | 64 | 7.969 | 39.680 | −15.348 | 1.00 | 35.90 |
| ATOM | 848 | CG2 | VAL | 64 | 8.246 | 42.118 | −15.051 | 1.00 | 35.99 |
| ATOM | 849 | N | ALA | 65 | 6.995 | 40.064 | −18.920 | 1.00 | 39.07 |
| ATOM | 850 | CA | ALA | 65 | 6.604 | 39.084 | −19.959 | 1.00 | 39.65 |
| ATOM | 851 | C | ALA | 65 | 7.709 | 38.860 | −20.985 | 1.00 | 39.89 |
| ATOM | 852 | O | ALA | 65 | 8.040 | 37.714 | −21.288 | 1.00 | 40.81 |
| ATOM | 853 | CB | ALA | 65 | 5.314 | 39.527 | −20.661 | 1.00 | 39.83 |
| ATOM | 854 | N | ALA | 88 | 8.500 | 47.251 | −29.983 | 1.00 | 37.69 |
| ATOM | 855 | CA | ALA | 88 | 7.412 | 46.662 | −30.793 | 1.00 | 39.22 |
| ATOM | 856 | C | ALA | 88 | 6.275 | 46.238 | −29.879 | 1.00 | 39.76 |
| ATOM | 857 | O | ALA | 88 | 5.118 | 46.646 | −30.063 | 1.00 | 40.54 |
| ATOM | 858 | CB | ALA | 88 | 7.930 | 45.445 | −31.529 | 1.00 | 39.27 |
| ATOM | 859 | N | LEU | 89 | 6.607 | 45.422 | −28.880 | 1.00 | 39.88 |
| ATOM | 860 | CA | LEU | 89 | 5.615 | 44.873 | −27.936 | 1.00 | 40.55 |
| ATOM | 861 | C | LEU | 89 | 4.903 | 45.956 | −27.096 | 1.00 | 39.98 |
| ATOM | 862 | O | LEU | 89 | 3.701 | 45.889 | −26.799 | 1.00 | 40.50 |
| ATOM | 863 | CB | LEU | 89 | 6.293 | 43.838 | −27.020 | 1.00 | 40.81 |
| ATOM | 864 | CG | LEU | 89 | 5.482 | 43.171 | −25.912 | 1.00 | 41.42 |
| ATOM | 865 | CD1 | LEU | 89 | 4.311 | 42.388 | −26.507 | 1.00 | 43.86 |
| ATOM | 866 | CD2 | LEU | 89 | 6.373 | 42.242 | −25.071 | 1.00 | 41.85 |
| ATOM | 867 | N | LEU | 90 | 5.634 | 46.969 | −26.699 | 1.00 | 39.63 |
| ATOM | 868 | CA | LEU | 90 | 4.988 | 48.003 | −25.934 | 1.00 | 39.66 |
| ATOM | 869 | C | LEU | 90 | 4.345 | 49.029 | −26.854 | 1.00 | 39.64 |
| ATOM | 870 | O | LEU | 90 | 3.830 | 50.045 | −26.394 | 1.00 | 40.47 |
| ATOM | 871 | CB | LEU | 90 | 5.975 | 48.630 | −24.943 | 1.00 | 38.91 |
| ATOM | 872 | CG | LEU | 90 | 5.850 | 47.641 | −23.753 | 1.00 | 40.39 |
| ATOM | 873 | CD1 | LEU | 90 | 7.044 | 46.740 | −23.526 | 1.00 | 36.51 |
| ATOM | 874 | CD2 | LEU | 90 | 5.400 | 48.294 | −22.503 | 1.00 | 38.67 |
| ATOM | 875 | N | ASP | 91 | 4.389 | 48.771 | −28.159 | 1.00 | 40.21 |
| ATOM | 876 | CA | ASP | 91 | 3.915 | 49.746 | −29.157 | 1.00 | 39.95 |
| ATOM | 877 | C | ASP | 91 | 4.453 | 51.174 | −28.929 | 1.00 | 38.80 |
| ATOM | 878 | O | ASP | 91 | 3.678 | 52.138 | −28.926 | 1.00 | 38.19 |
| ATOM | 879 | CB | ASP | 91 | 2.355 | 49.735 | −29.285 | 1.00 | 40.89 |
| ATOM | 880 | CG | ASP | 91 | 1.796 | 48.482 | −30.023 | 1.00 | 43.50 |
| ATOM | 881 | OD1 | ASP | 91 | 2.494 | 47.945 | −30.931 | 1.00 | 46.25 |
| ATOM | 882 | OD2 | ASP | 91 | 0.645 | 48.039 | −29.723 | 1.00 | 42.88 |
| ATOM | 883 | N | SER | 92 | 5.775 | 51.327 | −28.785 | 1.00 | 38.12 |
| ATOM | 884 | CA | SER | 92 | 6.384 | 52.673 | −28.609 | 1.00 | 37.45 |
| ATOM | 885 | C | SER | 92 | 7.380 | 53.024 | −29.694 | 1.00 | 38.08 |
| ATOM | 886 | O | SER | 92 | 7.959 | 52.116 | −30.317 | 1.00 | 38.79 |
| ATOM | 887 | CB | SER | 92 | 7.087 | 52.787 | −27.263 | 1.00 | 37.32 |
| ATOM | 888 | OG | SER | 92 | 7.773 | 54.032 | −27.125 | 1.00 | 36.68 |
| ATOM | 889 | N | LYS | 107 | 7.304 | 31.282 | −9.880 | 1.00 | 44.36 |
| ATOM | 890 | CA | LYS | 107 | 5.973 | 31.471 | −9.312 | 1.00 | 44.70 |
| ATOM | 891 | C | LYS | 107 | 4.898 | 31.462 | −10.414 | 1.00 | 45.13 |
| ATOM | 892 | O | LYS | 107 | 5.213 | 31.577 | −11.615 | 1.00 | 44.87 |
| ATOM | 893 | CB | LYS | 107 | 5.919 | 32.750 | −8.473 | 1.00 | 44.28 |
| ATOM | 894 | CG | LYS | 107 | 7.016 | 32.816 | −7.384 | 1.00 | 43.47 |
| ATOM | 895 | CD | LYS | 107 | 6.748 | 33.964 | −6.423 | 1.00 | 41.18 |
| ATOM | 896 | CE | LYS | 107 | 5.476 | 33.665 | −5.604 | 1.00 | 42.21 |
| ATOM | 897 | NZ | LYS | 107 | 5.334 | 34.534 | −4.400 | 1.00 | 40.46 |
| ATOM | 898 | N | THR | 108 | 3.641 | 31.306 | −9.996 | 1.00 | 45.84 |
| ATOM | 899 | CA | THR | 108 | 2.494 | 31.304 | −10.901 | 1.00 | 46.81 |
| ATOM | 900 | C | THR | 108 | 1.453 | 32.309 | −10.397 | 1.00 | 47.68 |
| ATOM | 901 | O | THR | 108 | 1.123 | 32.321 | −9.198 | 1.00 | 47.71 |
| ATOM | 902 | CB | THR | 108 | 1.900 | 29.856 | −11.037 | 1.00 | 47.35 |
| ATOM | 903 | OG1 | THR | 108 | 2.963 | 28.918 | −11.302 | 1.00 | 47.19 |
| ATOM | 904 | CG2 | THR | 108 | 0.851 | 29.771 | −12.172 | 1.00 | 47.03 |
| ATOM | 905 | N | ALA | 109 | 0.950 | 33.160 | −11.299 | 1.00 | 48.80 |
| ATOM | 906 | CA | ALA | 109 | −0.043 | 34.185 | −10.948 | 1.00 | 50.14 |
| ATOM | 907 | C | ALA | 109 | −1.364 | 33.551 | −10.468 | 1.00 | 51.03 |
| ATOM | 908 | O | ALA | 109 | −1.770 | 32.504 | −11.004 | 1.00 | 51.15 |
| ATOM | 909 | CB | ALA | 109 | −0.284 | 35.142 | −12.127 | 1.00 | 50.35 |
| ATOM | 910 | N | PRO | 110 | −2.009 | 34.152 | −9.427 | 1.00 | 51.43 |
| ATOM | 911 | CA | PRO | 110 | −3.180 | 33.513 | −8.859 | 1.00 | 51.94 |
| ATOM | 912 | C | PRO | 110 | −4.394 | 33.383 | −9.798 | 1.00 | 52.99 |
| ATOM | 913 | O | PRO | 110 | −5.175 | 32.458 | −9.609 | 1.00 | 52.84 |
| ATOM | 914 | CB | PRO | 110 | −3.517 | 34.391 | −7.639 | 1.00 | 51.48 |
| ATOM | 915 | CG | PRO | 110 | −2.880 | 35.653 | −7.863 | 1.00 | 51.48 |
| ATOM | 916 | CD | PRO | 110 | −1.654 | 35.384 | −8.684 | 1.00 | 51.45 |
| ATOM | 917 | N | VAL | 111 | −4.578 | 34.275 | −10.780 | 1.00 | 53.92 |
| ATOM | 918 | CA | VAL | 111 | −5.756 | 34.118 | −11.660 | 1.00 | 55.03 |
| ATOM | 919 | C | VAL | 111 | −5.429 | 33.593 | −13.057 | 1.00 | 55.25 |
| ATOM | 920 | O | VAL | 111 | −5.957 | 32.542 | −13.469 | 1.00 | 55.19 |
| ATOM | 921 | CB | VAL | 111 | −6.709 | 35.358 | −11.692 | 1.00 | 55.46 |
| ATOM | 922 | CG1 | VAL | 111 | −7.959 | 35.069 | −12.557 | 1.00 | 54.84 |

TABLE 11-continued

Three-Dimensional Coordinates of *Neisseria gonorrhoeae* GCYH-IB·Mn$^{2+}$
(SEQ. ID. No. 8)

| ATOM | 923 | CG2 | VAL | 111 | −7.125 | 35.738 | −10.262 | 1.00 | 55.47 |
|------|-----|-----|-----|-----|--------|--------|---------|------|-------|
| ATOM | 924 | N   | SER | 112 | −4.559 | 34.318 | −13.764 | 1.00 | 55.19 |
| ATOM | 925 | CA  | SER | 112 | −4.113 | 33.921 | −15.099 | 1.00 | 55.31 |
| ATOM | 926 | C   | SER | 112 | −3.377 | 32.568 | −15.158 | 1.00 | 54.97 |
| ATOM | 927 | O   | SER | 112 | −3.518 | 31.843 | −16.147 | 1.00 | 54.91 |
| ATOM | 928 | CB  | SER | 112 | −3.256 | 35.021 | −15.742 | 1.00 | 55.47 |
| ATOM | 929 | OG  | SER | 112 | −2.087 | 35.299 | −14.963 | 1.00 | 56.21 |
| ATOM | 930 | N   | GLY | 113 | −2.614 | 32.231 | −14.106 | 1.00 | 54.62 |
| ATOM | 931 | CA  | GLY | 113 | −1.646 | 31.105 | −14.149 | 1.00 | 53.64 |
| ATOM | 932 | C   | GLY | 113 | −0.355 | 31.398 | −14.943 | 1.00 | 53.03 |
| ATOM | 933 | O   | GLY | 113 | 0.471  | 30.491 | −15.166 | 1.00 | 52.84 |
| ATOM | 934 | N   | ILE | 114 | −0.174 | 32.648 | −15.384 | 1.00 | 52.24 |
| ATOM | 935 | CA  | ILE | 114 | 1.092  | 33.059 | −16.020 | 1.00 | 52.01 |
| ATOM | 936 | C   | ILE | 114 | 2.254  | 32.953 | −14.992 | 1.00 | 51.48 |
| ATOM | 937 | O   | ILE | 114 | 2.100  | 33.306 | −13.808 | 1.00 | 50.80 |
| ATOM | 938 | CB  | ILE | 114 | 1.024  | 34.485 | −16.667 | 1.00 | 52.23 |
| ATOM | 939 | CG1 | ILE | 114 | −0.088 | 34.569 | −17.722 | 1.00 | 53.68 |
| ATOM | 940 | CG2 | ILE | 114 | 2.337  | 34.836 | −17.370 | 1.00 | 51.30 |
| ATOM | 941 | CD1 | ILE | 114 | −0.418 | 36.006 | −18.174 | 1.00 | 53.39 |
| ATOM | 942 | N   | ARG | 115 | 3.393  | 32.431 | −15.450 | 1.00 | 50.22 |
| ATOM | 943 | CA  | ARG | 115 | 4.520  | 32.157 | −14.576 | 1.00 | 49.39 |
| ATOM | 944 | C   | ARG | 115 | 5.561  | 33.264 | −14.723 | 1.00 | 47.82 |
| ATOM | 945 | O   | ARG | 115 | 5.733  | 33.834 | −15.820 | 1.00 | 46.47 |
| ATOM | 946 | CB  | ARG | 115 | 5.159  | 30.795 | −14.893 | 1.00 | 50.41 |
| ATOM | 947 | CG  | ARG | 115 | 4.234  | 29.581 | −14.773 | 1.00 | 53.80 |
| ATOM | 948 | CD  | ARG | 115 | 4.782  | 28.481 | −15.657 | 1.00 | 58.84 |
| ATOM | 949 | NE  | ARG | 115 | 5.550  | 27.503 | −14.885 | 1.00 | 64.83 |
| ATOM | 950 | CZ  | ARG | 115 | 6.714  | 26.970 | −15.257 | 1.00 | 61.10 |
| ATOM | 951 | NH1 | ARG | 115 | 7.313  | 27.346 | −16.394 | 1.00 | 65.93 |
| ATOM | 952 | NH2 | ARG | 115 | 7.300  | 26.079 | −14.454 | 1.00 | 66.59 |
| ATOM | 953 | N   | SER | 116 | 6.238  | 33.551 | −13.609 | 1.00 | 45.50 |
| ATOM | 954 | CA  | SER | 116 | 7.398  | 34.421 | −13.565 | 1.00 | 44.28 |
| ATOM | 955 | C   | SER | 116 | 8.251  | 34.043 | −12.346 | 1.00 | 43.63 |
| ATOM | 956 | O   | SER | 116 | 7.748  | 33.370 | −11.418 | 1.00 | 43.82 |
| ATOM | 957 | CB  | SER | 116 | 6.977  | 35.896 | −13.499 | 1.00 | 44.12 |
| ATOM | 958 | OG  | SER | 116 | 6.181  | 36.157 | −12.365 | 1.00 | 44.28 |
| ATOM | 959 | N   | VAL | 143 | 7.390  | 40.308 | 1.006   | 1.00 | 34.49 |
| ATOM | 960 | CA  | VAL | 143 | 5.966  | 40.088 | 0.977   | 1.00 | 36.54 |
| ATOM | 961 | C   | VAL | 143 | 5.257  | 41.433 | 0.907   | 1.00 | 37.50 |
| ATOM | 962 | O   | VAL | 143 | 5.873  | 42.489 | 1.010   | 1.00 | 37.31 |
| ATOM | 963 | CB  | VAL | 143 | 5.435  | 39.293 | 2.220   | 1.00 | 36.15 |
| ATOM | 964 | CG1 | VAL | 143 | 6.186  | 37.974 | 2.420   | 1.00 | 36.77 |
| ATOM | 965 | CG2 | VAL | 143 | 5.542  | 40.117 | 3.443   | 1.00 | 35.72 |
| ATOM | 966 | N   | THR | 144 | 3.957  | 41.377 | 0.692   | 1.00 | 40.85 |
| ATOM | 967 | CA  | THR | 144 | 3.070  | 42.530 | 0.876   | 1.00 | 43.22 |
| ATOM | 968 | C   | THR | 144 | 2.496  | 42.480 | 2.296   | 1.00 | 45.07 |
| ATOM | 969 | O   | THR | 144 | 2.017  | 41.407 | 2.764   | 1.00 | 44.61 |
| ATOM | 970 | CB  | THR | 144 | 1.904  | 42.500 | −0.137  | 1.00 | 43.97 |
| ATOM | 971 | OG1 | THR | 144 | 2.430  | 42.246 | −1.451  | 1.00 | 45.02 |
| ATOM | 972 | CG2 | THR | 144 | 1.090  | 43.816 | −0.134  | 1.00 | 43.92 |
| ATOM | 973 | N   | SER | 145 | 2.564  | 43.631 | 2.974   | 1.00 | 46.62 |
| ATOM | 974 | CA  | SER | 145 | 1.899  | 43.833 | 4.274   | 1.00 | 48.13 |
| ATOM | 975 | C   | SER | 145 | 0.841  | 44.916 | 4.119   | 1.00 | 48.74 |
| ATOM | 976 | O   | SER | 145 | 1.058  | 45.904 | 3.417   | 1.00 | 48.82 |
| ATOM | 977 | CB  | SER | 145 | 2.886  | 44.219 | 5.384   | 1.00 | 48.45 |
| ATOM | 978 | OG  | SER | 145 | 3.671  | 45.353 | 5.036   | 1.00 | 50.19 |
| ATOM | 979 | N   | LEU | 146 | −0.314 | 44.700 | 4.746   | 1.00 | 49.98 |
| ATOM | 980 | CA  | LEU | 146 | −1.427 | 45.665 | 4.705   | 1.00 | 50.76 |
| ATOM | 981 | C   | LEU | 146 | −1.915 | 45.944 | 6.134   | 1.00 | 51.52 |
| ATOM | 982 | O   | LEU | 146 | −2.141 | 45.001 | 6.927   | 1.00 | 51.71 |
| ATOM | 983 | CB  | LEU | 146 | −2.560 | 45.172 | 3.800   | 1.00 | 50.62 |
| ATOM | 984 | CG  | LEU | 146 | −3.742 | 46.141 | 3.605   | 1.00 | 50.27 |
| ATOM | 985 | CD1 | LEU | 146 | −4.266 | 46.212 | 2.164   | 1.00 | 49.21 |
| ATOM | 986 | CD2 | LEU | 146 | −4.852 | 45.785 | 4.576   | 1.00 | 50.20 |
| ATOM | 987 | N   | CYS | 147 | −2.050 | 47.225 | 6.469   | 1.00 | 51.52 |
| ATOM | 988 | CA  | CYS | 147 | −2.304 | 47.618 | 7.849   | 1.00 | 52.46 |
| ATOM | 989 | C   | CYS | 147 | −3.773 | 47.476 | 8.331   | 1.00 | 53.73 |
| ATOM | 990 | O   | CYS | 147 | −4.690 | 48.126 | 7.788   | 1.00 | 53.40 |
| ATOM | 991 | CB  | CYS | 147 | −1.804 | 49.045 | 8.098   | 1.00 | 52.50 |
| ATOM | 992 | SG  | CYS | 147 | −2.131 | 49.620 | 9.803   | 1.00 | 51.33 |
| ATOM | 993 | N   | PRO | 148 | −3.988 | 46.676 | 9.400   | 1.00 | 54.93 |
| ATOM | 994 | CA  | PRO | 148 | −5.373 | 46.445 | 9.860   | 1.00 | 55.87 |
| ATOM | 995 | C   | PRO | 148 | −6.026 | 47.721 | 10.446  | 1.00 | 56.77 |
| ATOM | 996 | O   | PRO | 148 | −7.222 | 47.975 | 10.198  | 1.00 | 56.68 |
| ATOM | 997 | CB  | PRO | 148 | −5.243 | 45.321 | 10.909  | 1.00 | 55.91 |
| ATOM | 998 | CG  | PRO | 148 | −3.778 | 45.204 | 11.232  | 1.00 | 55.66 |
| ATOM | 999 | CD  | PRO | 148 | −2.970 | 45.996 | 10.237  | 1.00 | 55.10 |

TABLE 11-continued

Three-Dimensional Coordinates of *Neisseria gonorrhoeae* GCYH-IB·Mn$^{2+}$
(SEQ. ID. No. 8)

| ATOM | 1000 | N | CYS | 149 | −5.232 | 48.520 | 11.172 | 1.00 | 57.41 |
|---|---|---|---|---|---|---|---|---|---|
| ATOM | 1001 | CA | CYS | 149 | −5.692 | 49.783 | 11.765 | 1.00 | 57.40 |
| ATOM | 1002 | C | CYS | 149 | −6.185 | 50.769 | 10.685 | 1.00 | 57.29 |
| ATOM | 1003 | O | CYS | 149 | −7.265 | 51.377 | 10.819 | 1.00 | 56.51 |
| ATOM | 1004 | CB | CYS | 149 | −4.577 | 50.414 | 12.613 | 1.00 | 57.61 |
| ATOM | 1005 | SG | CYS | 149 | −5.106 | 51.912 | 13.511 | 1.00 | 59.83 |
| ATOM | 1006 | N | SER | 150 | −5.389 | 50.903 | 9.621 | 1.00 | 57.10 |
| ATOM | 1007 | CA | SER | 150 | −5.755 | 51.690 | 8.438 | 1.00 | 57.37 |
| ATOM | 1008 | C | SER | 150 | −7.159 | 51.333 | 7.927 | 1.00 | 57.54 |
| ATOM | 1009 | O | SER | 150 | −8.069 | 52.177 | 7.942 | 1.00 | 56.90 |
| ATOM | 1010 | CB | SER | 150 | −4.699 | 51.512 | 7.315 | 1.00 | 57.56 |
| ATOM | 1011 | OG | SER | 150 | −4.960 | 52.364 | 6.196 | 1.00 | 56.24 |
| ATOM | 1012 | N | LYS | 151 | −7.325 | 50.085 | 7.480 | 1.00 | 58.20 |
| ATOM | 1013 | CA | LYS | 151 | −8.614 | 49.594 | 6.980 | 1.00 | 58.78 |
| ATOM | 1014 | C | LYS | 151 | −9.768 | 49.902 | 7.953 | 1.00 | 59.60 |
| ATOM | 1015 | O | LYS | 151 | −10.820 | 50.440 | 7.548 | 1.00 | 59.74 |
| ATOM | 1016 | CB | LYS | 151 | −8.530 | 48.085 | 6.737 | 1.00 | 58.67 |
| ATOM | 1017 | CG | LYS | 151 | −9.859 | 47.424 | 6.372 | 1.00 | 57.80 |
| ATOM | 1018 | CD | LYS | 151 | −9.711 | 45.907 | 6.375 | 1.00 | 57.00 |
| ATOM | 1019 | CE | LYS | 151 | −10.975 | 45.229 | 5.868 | 1.00 | 56.13 |
| ATOM | 1020 | NZ | LYS | 151 | −10.706 | 43.817 | 5.487 | 1.00 | 54.37 |
| ATOM | 1021 | N | GLU | 152 | −9.526 | 49.553 | 9.222 | 1.00 | 60.08 |
| ATOM | 1022 | CA | GLU | 152 | −10.491 | 49.562 | 10.326 | 1.00 | 60.84 |
| ATOM | 1023 | C | GLU | 152 | −11.066 | 50.953 | 10.619 | 1.00 | 60.69 |
| ATOM | 1024 | O | GLU | 152 | −12.257 | 51.097 | 10.912 | 1.00 | 60.54 |
| ATOM | 1025 | CB | GLU | 152 | −9.782 | 49.041 | 11.572 | 1.00 | 61.06 |
| ATOM | 1026 | CG | GLU | 152 | −10.668 | 48.560 | 12.727 | 1.00 | 64.00 |
| ATOM | 1027 | CD | GLU | 152 | −9.947 | 47.510 | 13.573 | 1.00 | 65.38 |
| ATOM | 1028 | OE1 | GLU | 152 | −8.784 | 47.741 | 13.986 | 1.00 | 65.59 |
| ATOM | 1029 | OE2 | GLU | 152 | −10.537 | 46.433 | 13.794 | 1.00 | 67.79 |
| ATOM | 1030 | N | ILE | 153 | −10.199 | 51.961 | 10.551 | 1.00 | 60.40 |
| ATOM | 1031 | CA | ILE | 153 | −10.560 | 53.332 | 10.885 | 1.00 | 59.97 |
| ATOM | 1032 | C | ILE | 153 | −11.005 | 54.133 | 9.649 | 1.00 | 59.93 |
| ATOM | 1033 | O | ILE | 153 | −11.676 | 55.165 | 9.806 | 1.00 | 59.92 |
| ATOM | 1034 | CB | ILE | 153 | −9.396 | 54.075 | 11.633 | 1.00 | 60.11 |
| ATOM | 1035 | CG1 | ILE | 153 | −8.231 | 54.409 | 10.666 | 1.00 | 59.91 |
| ATOM | 1036 | CG2 | ILE | 153 | −8.954 | 53.279 | 12.886 | 1.00 | 59.57 |
| ATOM | 1037 | CD1 | ILE | 153 | −7.180 | 55.333 | 11.244 | 1.00 | 59.73 |
| ATOM | 1038 | N | SER | 154 | −10.639 | 53.658 | 8.442 | 1.00 | 59.44 |
| ATOM | 1039 | CA | SER | 154 | −10.934 | 54.374 | 7.191 | 1.00 | 59.16 |
| ATOM | 1040 | C | SER | 154 | −12.228 | 53.896 | 6.536 | 1.00 | 59.11 |
| ATOM | 1041 | O | SER | 154 | −12.506 | 52.691 | 6.506 | 1.00 | 58.66 |
| ATOM | 1042 | CB | SER | 154 | −9.777 | 54.261 | 6.179 | 1.00 | 59.05 |
| ATOM | 1043 | OG | SER | 154 | −8.528 | 54.531 | 6.786 | 1.00 | 58.46 |
| ATOM | 1044 | N | GLN | 155 | −12.998 | 54.846 | 5.992 | 1.00 | 59.19 |
| ATOM | 1045 | CA | GLN | 155 | −14.252 | 54.533 | 5.279 | 1.00 | 59.20 |
| ATOM | 1046 | C | GLN | 155 | −13.990 | 53.778 | 3.969 | 1.00 | 58.56 |
| ATOM | 1047 | O | GLN | 155 | −14.872 | 53.076 | 3.441 | 1.00 | 58.43 |
| ATOM | 1048 | CB | GLN | 155 | −15.103 | 55.800 | 5.037 | 1.00 | 59.42 |
| ATOM | 1049 | CG | GLN | 155 | −14.478 | 56.873 | 4.109 | 1.00 | 59.96 |
| ATOM | 1050 | CD | GLN | 155 | −15.294 | 58.185 | 4.047 | 1.00 | 60.84 |
| ATOM | 1051 | OE1 | GLN | 155 | −16.514 | 58.161 | 3.833 | 1.00 | 63.53 |
| ATOM | 1052 | NE2 | GLN | 155 | −14.613 | 59.330 | 4.221 | 1.00 | 61.62 |
| ATOM | 1053 | N | TYR | 156 | −12.775 | 53.941 | 3.447 | 1.00 | 57.89 |
| ATOM | 1054 | CA | TYR | 156 | −12.301 | 53.176 | 2.290 | 1.00 | 57.36 |
| ATOM | 1055 | C | TYR | 156 | −10.756 | 53.110 | 2.288 | 1.00 | 56.68 |
| ATOM | 1056 | O | TYR | 156 | −10.080 | 53.992 | 2.857 | 1.00 | 55.91 |
| ATOM | 1057 | CB | TYR | 156 | −12.874 | 53.721 | 0.957 | 1.00 | 57.64 |
| ATOM | 1058 | CG | TYR | 156 | −13.016 | 55.246 | 0.860 | 1.00 | 59.03 |
| ATOM | 1059 | CD1 | TYR | 156 | −11.895 | 56.095 | 0.994 | 1.00 | 59.96 |
| ATOM | 1060 | CD2 | TYR | 156 | −14.268 | 55.842 | 0.624 | 1.00 | 60.16 |
| ATOM | 1061 | CE1 | TYR | 156 | −12.014 | 57.502 | 0.915 | 1.00 | 59.50 |
| ATOM | 1062 | CE2 | TYR | 156 | −14.399 | 57.259 | 0.535 | 1.00 | 60.74 |
| ATOM | 1063 | CZ | TYR | 156 | −13.260 | 58.074 | 0.684 | 1.00 | 59.41 |
| ATOM | 1064 | OH | TYR | 156 | −13.355 | 59.446 | 0.586 | 1.00 | 58.74 |
| ATOM | 1065 | N | GLY | 157 | −10.224 | 52.039 | 1.686 | 1.00 | 55.88 |
| ATOM | 1066 | CA | GLY | 157 | −8.782 | 51.868 | 1.486 | 1.00 | 54.70 |
| ATOM | 1067 | C | GLY | 157 | −8.046 | 51.479 | 2.750 | 1.00 | 53.87 |
| ATOM | 1068 | O | GLY | 157 | −8.628 | 51.432 | 3.838 | 1.00 | 53.85 |
| ATOM | 1069 | N | ALA | 158 | −6.753 | 51.209 | 2.600 | 1.00 | 53.06 |
| ATOM | 1070 | CA | ALA | 158 | −5.889 | 50.782 | 3.704 | 1.00 | 52.34 |
| ATOM | 1071 | C | ALA | 158 | −4.458 | 50.847 | 3.233 | 1.00 | 51.79 |
| ATOM | 1072 | O | ALA | 158 | −4.116 | 50.287 | 2.176 | 1.00 | 51.74 |
| ATOM | 1073 | CB | ALA | 158 | −6.210 | 49.355 | 4.162 | 1.00 | 52.30 |
| ATOM | 1074 | N | HIS | 159 | −3.601 | 51.501 | 4.006 | 1.00 | 50.50 |
| ATOM | 1075 | CA | HIS | 159 | −2.245 | 51.643 | 3.514 | 1.00 | 49.70 |
| ATOM | 1076 | C | HIS | 159 | −1.569 | 50.272 | 3.570 | 1.00 | 49.57 |

TABLE 11-continued

Three-Dimensional Coordinates of *Neisseria gonorrhoeae* GCYH-IB·Mn$^{2+}$
(SEQ. ID. No. 8)

| ATOM | 1077 | O | HIS | 159 | −1.826 | 49.451 | 4.477 | 1.00 | 49.86 |
|---|---|---|---|---|---|---|---|---|---|
| ATOM | 1078 | CB | HIS | 159 | −1.439 | 52.721 | 4.251 | 1.00 | 48.45 |
| ATOM | 1079 | CG | HIS | 159 | −0.801 | 52.256 | 5.524 | 1.00 | 45.98 |
| ATOM | 1080 | ND1 | HIS | 159 | 0.410 | 51.592 | 5.551 | 1.00 | 43.16 |
| ATOM | 1081 | CD2 | HIS | 159 | −1.178 | 52.409 | 6.819 | 1.00 | 42.93 |
| ATOM | 1082 | CE1 | HIS | 159 | 0.738 | 51.332 | 6.808 | 1.00 | 42.42 |
| ATOM | 1083 | NE2 | HIS | 159 | −0.194 | 51.841 | 7.595 | 1.00 | 39.71 |
| ATOM | 1084 | N | ASN | 160 | −0.746 | 50.036 | 2.560 | 1.00 | 49.49 |
| ATOM | 1085 | CA | ASN | 160 | 0.054 | 48.826 | 2.464 | 1.00 | 48.81 |
| ATOM | 1086 | C | ASN | 160 | 1.412 | 49.196 | 1.879 | 1.00 | 48.38 |
| ATOM | 1087 | O | ASN | 160 | 1.642 | 50.351 | 1.462 | 1.00 | 47.84 |
| ATOM | 1088 | CB | ASN | 160 | −0.673 | 47.719 | 1.658 | 1.00 | 48.67 |
| ATOM | 1089 | CG | ASN | 160 | −1.276 | 48.224 | 0.336 | 1.00 | 48.57 |
| ATOM | 1090 | OD1 | ASN | 160 | −2.384 | 48.761 | 0.308 | 1.00 | 49.39 |
| ATOM | 1091 | ND2 | ASN | 160 | −0.557 | 48.011 | −0.762 | 1.00 | 47.12 |
| ATOM | 1092 | N | GLN | 161 | 2.316 | 48.217 | 1.878 | 1.00 | 47.92 |
| ATOM | 1093 | CA | GLN | 161 | 3.710 | 48.431 | 1.502 | 1.00 | 47.53 |
| ATOM | 1094 | C | GLN | 161 | 4.428 | 47.094 | 1.401 | 1.00 | 47.31 |
| ATOM | 1095 | O | GLN | 161 | 3.974 | 46.067 | 1.960 | 1.00 | 47.48 |
| ATOM | 1096 | CB | GLN | 161 | 4.425 | 49.306 | 2.542 | 1.00 | 47.08 |
| ATOM | 1097 | CG | GLN | 161 | 4.320 | 48.769 | 3.982 | 1.00 | 47.63 |
| ATOM | 1098 | CD | GLN | 161 | 3.004 | 49.124 | 4.648 | 1.00 | 48.13 |
| ATOM | 1099 | OE1 | GLN | 161 | 2.504 | 50.254 | 4.487 | 1.00 | 47.49 |
| ATOM | 1100 | NE2 | GLN | 161 | 2.426 | 48.171 | 5.397 | 1.00 | 48.31 |
| ATOM | 1101 | N | ARG | 162 | 5.536 | 47.107 | 0.668 | 1.00 | 46.28 |
| ATOM | 1102 | CA | ARG | 162 | 6.427 | 45.985 | 0.704 | 1.00 | 45.81 |
| ATOM | 1103 | C | ARG | 162 | 7.032 | 45.827 | 2.125 | 1.00 | 45.47 |
| ATOM | 1104 | O | ARG | 162 | 7.245 | 46.815 | 2.901 | 1.00 | 44.60 |
| ATOM | 1105 | CB | ARG | 162 | 7.495 | 46.072 | −0.389 | 1.00 | 45.64 |
| ATOM | 1106 | CG | ARG | 162 | 7.999 | 44.727 | −0.859 | 1.00 | 45.77 |
| ATOM | 1107 | CD | ARG | 162 | 9.102 | 44.932 | −1.931 | 1.00 | 46.20 |
| ATOM | 1108 | NE | ARG | 162 | 8.617 | 45.631 | −3.121 | 1.00 | 43.09 |
| ATOM | 1109 | CZ | ARG | 162 | 9.405 | 46.253 | −4.011 | 1.00 | 45.13 |
| ATOM | 1110 | NH1 | ARG | 162 | 10.739 | 46.260 | −3.862 | 1.00 | 43.75 |
| ATOM | 1111 | NH2 | ARG | 162 | 8.864 | 46.850 | −5.077 | 1.00 | 44.59 |
| ATOM | 1112 | N | SER | 163 | 7.246 | 44.562 | 2.479 | 1.00 | 44.43 |
| ATOM | 1113 | CA | SER | 163 | 7.914 | 44.274 | 3.716 | 1.00 | 43.91 |
| ATOM | 1114 | C | SER | 163 | 8.854 | 43.089 | 3.548 | 1.00 | 42.32 |
| ATOM | 1115 | O | SER | 163 | 8.597 | 42.184 | 2.760 | 1.00 | 43.00 |
| ATOM | 1116 | CB | SER | 163 | 6.887 | 44.120 | 4.856 | 1.00 | 44.01 |
| ATOM | 1117 | OG | SER | 163 | 6.306 | 42.851 | 4.855 | 1.00 | 47.10 |
| ATOM | 1118 | N | ASP | 182 | 7.974 | 29.007 | 1.900 | 1.00 | 30.08 |
| ATOM | 1119 | CA | ASP | 182 | 6.555 | 28.664 | 2.064 | 1.00 | 31.00 |
| ATOM | 1120 | C | ASP | 182 | 6.038 | 28.954 | 3.464 | 1.00 | 31.45 |
| ATOM | 1121 | O | ASP | 182 | 4.964 | 29.497 | 3.592 | 1.00 | 32.21 |
| ATOM | 1122 | CB | ASP | 182 | 6.253 | 27.215 | 1.669 | 1.00 | 31.45 |
| ATOM | 1123 | CG | ASP | 182 | 6.358 | 27.000 | 0.194 | 1.00 | 33.00 |
| ATOM | 1124 | OD1 | ASP | 182 | 6.060 | 27.921 | −0.589 | 1.00 | 38.70 |
| ATOM | 1125 | OD2 | ASP | 182 | 6.807 | 25.947 | −0.202 | 1.00 | 33.35 |
| ATOM | 1126 | N | TYR | 183 | 6.801 | 28.644 | 4.512 | 1.00 | 31.67 |
| ATOM | 1127 | CA | TYR | 183 | 6.346 | 29.041 | 5.878 | 1.00 | 31.88 |
| ATOM | 1128 | C | TYR | 183 | 5.996 | 30.528 | 6.001 | 1.00 | 31.33 |
| ATOM | 1129 | O | TYR | 183 | 5.079 | 30.907 | 6.769 | 1.00 | 31.50 |
| ATOM | 1130 | CB | TYR | 183 | 7.407 | 28.725 | 6.959 | 1.00 | 32.44 |
| ATOM | 1131 | CG | TYR | 183 | 7.509 | 27.281 | 7.389 | 1.00 | 32.80 |
| ATOM | 1132 | CD1 | TYR | 183 | 6.354 | 26.511 | 7.666 | 1.00 | 34.47 |
| ATOM | 1133 | CD2 | TYR | 183 | 8.759 | 26.691 | 7.578 | 1.00 | 32.37 |
| ATOM | 1134 | CE1 | TYR | 183 | 6.468 | 25.173 | 8.101 | 1.00 | 33.02 |
| ATOM | 1135 | CE2 | TYR | 183 | 8.889 | 25.375 | 7.983 | 1.00 | 31.79 |
| ATOM | 1136 | CZ | TYR | 183 | 7.731 | 24.613 | 8.253 | 1.00 | 33.92 |
| ATOM | 1137 | OH | TYR | 183 | 7.879 | 23.303 | 8.689 | 1.00 | 34.75 |
| ATOM | 1138 | N | VAL | 184 | 6.739 | 31.384 | 5.299 | 1.00 | 31.13 |
| ATOM | 1139 | CA | VAL | 184 | 6.472 | 32.854 | 5.349 | 1.00 | 30.51 |
| ATOM | 1140 | C | VAL | 184 | 5.338 | 33.275 | 4.441 | 1.00 | 31.17 |
| ATOM | 1141 | O | VAL | 184 | 4.415 | 33.963 | 4.858 | 1.00 | 31.57 |
| ATOM | 1142 | CB | VAL | 184 | 7.746 | 33.709 | 4.997 | 1.00 | 30.57 |
| ATOM | 1143 | CG1 | VAL | 184 | 7.398 | 35.230 | 5.041 | 1.00 | 29.99 |
| ATOM | 1144 | CG2 | VAL | 184 | 8.844 | 33.418 | 5.995 | 1.00 | 31.45 |
| ATOM | 1145 | N | GLU | 185 | 5.420 | 32.877 | 3.173 | 1.00 | 31.99 |
| ATOM | 1146 | CA | GLU | 185 | 4.476 | 33.324 | 2.159 | 1.00 | 33.75 |
| ATOM | 1147 | C | GLU | 185 | 3.061 | 32.880 | 2.469 | 1.00 | 35.59 |
| ATOM | 1148 | O | GLU | 185 | 2.087 | 33.607 | 2.163 | 1.00 | 34.88 |
| ATOM | 1149 | CB | GLU | 185 | 4.923 | 32.870 | 0.764 | 1.00 | 33.52 |
| ATOM | 1150 | CG | GLU | 185 | 6.124 | 33.693 | 0.249 | 1.00 | 34.66 |
| ATOM | 1151 | CD | GLU | 185 | 6.472 | 33.332 | −1.180 | 1.00 | 37.62 |
| ATOM | 1152 | OE1 | GLU | 185 | 6.132 | 32.170 | −1.552 | 1.00 | 34.07 |
| ATOM | 1153 | OE2 | GLU | 185 | 7.071 | 34.197 | −1.905 | 1.00 | 39.40 |

TABLE 11-continued

Three-Dimensional Coordinates of *Neisseria gonorrhoeae* GCYH-IB·Mn$^{2+}$
(SEQ. ID. No. 8)

| ATOM | 1154 | N | THR | 186 | 2.962 | 31.717 | 3.113 | 1.00 | 37.29 |
|---|---|---|---|---|---|---|---|---|---|
| ATOM | 1155 | CA | THR | 186 | 1.671 | 31.201 | 3.581 | 1.00 | 39.44 |
| ATOM | 1156 | C | THR | 186 | 0.997 | 32.210 | 4.470 | 1.00 | 39.55 |
| ATOM | 1157 | O | THR | 186 | −0.216 | 32.385 | 4.416 | 1.00 | 39.96 |
| ATOM | 1158 | CB | THR | 186 | 1.831 | 29.910 | 4.351 | 1.00 | 39.43 |
| ATOM | 1159 | OG1 | THR | 186 | 1.926 | 28.849 | 3.413 | 1.00 | 41.26 |
| ATOM | 1160 | CG2 | THR | 186 | 0.608 | 29.660 | 5.263 | 1.00 | 42.27 |
| ATOM | 1161 | N | GLN | 187 | 1.809 | 32.893 | 5.263 | 1.00 | 40.30 |
| ATOM | 1162 | CA | GLN | 187 | 1.310 | 33.776 | 6.305 | 1.00 | 40.35 |
| ATOM | 1163 | C | GLN | 187 | 1.120 | 35.216 | 5.847 | 1.00 | 40.86 |
| ATOM | 1164 | O | GLN | 187 | 0.467 | 36.006 | 6.546 | 1.00 | 40.53 |
| ATOM | 1165 | CB | GLN | 187 | 2.233 | 33.730 | 7.547 | 1.00 | 40.36 |
| ATOM | 1166 | CG | GLN | 187 | 2.314 | 32.345 | 8.228 | 1.00 | 39.80 |
| ATOM | 1167 | CD | GLN | 187 | 0.947 | 31.843 | 8.653 | 1.00 | 39.36 |
| ATOM | 1168 | OE1 | GLN | 187 | 0.005 | 32.637 | 8.777 | 1.00 | 39.91 |
| ATOM | 1169 | NE2 | GLN | 187 | 0.828 | 30.533 | 8.887 | 1.00 | 35.15 |
| ATOM | 1170 | N | ALA | 188 | 1.671 | 35.577 | 4.691 | 1.00 | 41.85 |
| ATOM | 1171 | CA | ALA | 188 | 1.614 | 36.982 | 4.252 | 1.00 | 43.17 |
| ATOM | 1172 | C | ALA | 188 | 0.192 | 37.478 | 4.004 | 1.00 | 43.55 |
| ATOM | 1173 | O | ALA | 188 | −0.660 | 36.705 | 3.577 | 1.00 | 43.98 |
| ATOM | 1174 | CB | ALA | 188 | 2.520 | 37.221 | 2.984 | 1.00 | 43.74 |
| ATOM | 1175 | N | SER | 189 | −0.068 | 38.764 | 4.297 | 1.00 | 44.60 |
| ATOM | 1176 | CA | SER | 189 | −1.298 | 39.443 | 3.803 | 1.00 | 45.06 |
| ATOM | 1177 | C | SER | 189 | −1.502 | 39.047 | 2.327 | 1.00 | 45.29 |
| ATOM | 1178 | O | SER | 189 | −2.600 | 38.660 | 1.911 | 1.00 | 45.23 |
| ATOM | 1179 | CB | SER | 189 | −1.173 | 40.985 | 3.887 | 1.00 | 45.28 |
| ATOM | 1180 | OG | SER | 189 | −1.596 | 41.515 | 5.133 | 1.00 | 44.89 |
| ATOM | 1181 | N | CYS | 190 | −0.429 | 39.195 | 1.550 | 1.00 | 45.95 |
| ATOM | 1182 | CA | CYS | 190 | −0.320 | 38.624 | 0.189 | 1.00 | 46.60 |
| ATOM | 1183 | C | CYS | 190 | 1.148 | 38.554 | −0.259 | 1.00 | 46.70 |
| ATOM | 1184 | O | CYS | 190 | 1.985 | 39.389 | 0.126 | 1.00 | 46.76 |
| ATOM | 1185 | CB | CYS | 190 | −1.153 | 39.403 | −0.841 | 1.00 | 46.68 |
| ATOM | 1186 | SG | CYS | 190 | −1.465 | 38.481 | −2.425 | 1.00 | 48.51 |
| ATOM | 1187 | N | GLN | 191 | 1.450 | 37.547 | −1.064 | 1.00 | 46.03 |
| ATOM | 1188 | CA | GLN | 191 | 2.796 | 37.394 | −1.622 | 1.00 | 46.34 |
| ATOM | 1189 | C | GLN | 191 | 2.995 | 38.173 | −2.921 | 1.00 | 45.74 |
| ATOM | 1190 | O | GLN | 191 | 2.041 | 38.669 | −3.533 | 1.00 | 45.80 |
| ATOM | 1191 | CB | GLN | 191 | 3.115 | 35.919 | −1.856 | 1.00 | 46.24 |
| ATOM | 1192 | CG | GLN | 191 | 1.986 | 35.180 | −2.522 | 1.00 | 46.12 |
| ATOM | 1193 | CD | GLN | 191 | 2.257 | 33.712 | −2.616 | 1.00 | 45.71 |
| ATOM | 1194 | OE1 | GLN | 191 | 3.128 | 33.300 | −3.362 | 1.00 | 42.50 |
| ATOM | 1195 | NE2 | GLN | 191 | 1.513 | 32.902 | −1.839 | 1.00 | 47.50 |
| ATOM | 1196 | N | LEU | 192 | 4.251 | 38.244 | −3.341 | 1.00 | 45.93 |
| ATOM | 1197 | CA | LEU | 192 | 4.634 | 39.027 | −4.508 | 1.00 | 45.42 |
| ATOM | 1198 | C | LEU | 192 | 4.759 | 38.161 | −5.762 | 1.00 | 45.84 |
| ATOM | 1199 | O | LEU | 192 | 5.036 | 36.946 | −5.694 | 1.00 | 45.09 |
| ATOM | 1200 | CB | LEU | 192 | 5.940 | 39.784 | −4.234 | 1.00 | 45.16 |
| ATOM | 1201 | CG | LEU | 192 | 5.993 | 40.741 | −3.044 | 1.00 | 43.78 |
| ATOM | 1202 | CD1 | LEU | 192 | 7.329 | 41.465 | −3.016 | 1.00 | 43.93 |
| ATOM | 1203 | CD2 | LEU | 192 | 4.893 | 41.763 | −3.093 | 1.00 | 43.70 |
| ATOM | 1204 | N | TYR | 193 | 4.520 | 38.805 | −6.906 | 1.00 | 45.73 |
| ATOM | 1205 | CA | TYR | 193 | 4.756 | 38.202 | −8.203 | 1.00 | 45.73 |
| ATOM | 1206 | C | TYR | 193 | 5.404 | 39.253 | −9.120 | 1.00 | 46.31 |
| ATOM | 1207 | O | TYR | 193 | 5.035 | 40.453 | −9.095 | 1.00 | 45.28 |
| ATOM | 1208 | CB | TYR | 193 | 3.445 | 37.682 | −8.812 | 1.00 | 45.20 |
| ATOM | 1209 | CG | TYR | 193 | 2.638 | 36.729 | −7.907 | 1.00 | 44.11 |
| ATOM | 1210 | CD1 | TYR | 193 | 2.823 | 35.342 | −7.964 | 1.00 | 43.87 |
| ATOM | 1211 | CD2 | TYR | 193 | 1.683 | 37.234 | −6.998 | 1.00 | 44.60 |
| ATOM | 1212 | CE1 | TYR | 193 | 2.068 | 34.476 | −7.143 | 1.00 | 43.56 |
| ATOM | 1213 | CE2 | TYR | 193 | 0.930 | 36.391 | −6.190 | 1.00 | 42.74 |
| ATOM | 1214 | CZ | TYR | 193 | 1.133 | 35.011 | −6.273 | 1.00 | 42.90 |
| ATOM | 1215 | OH | TYR | 193 | 0.401 | 34.193 | −5.474 | 1.00 | 44.37 |
| ATOM | 1216 | N | GLY | 194 | 6.385 | 38.797 | −9.896 | 1.00 | 47.12 |
| ATOM | 1217 | CA | GLY | 194 | 6.981 | 39.619 | −10.936 | 1.00 | 48.68 |
| ATOM | 1218 | C | GLY | 194 | 5.913 | 40.033 | −11.934 | 1.00 | 49.53 |
| ATOM | 1219 | O | GLY | 194 | 5.722 | 41.237 | −12.171 | 1.00 | 49.81 |
| ATOM | 1220 | N | LEU | 195 | 5.188 | 39.052 | −12.482 | 1.00 | 50.33 |
| ATOM | 1221 | CA | LEU | 195 | 4.240 | 39.325 | −13.579 | 1.00 | 51.06 |
| ATOM | 1222 | C | LEU | 195 | 2.784 | 39.075 | −13.193 | 1.00 | 52.16 |
| ATOM | 1223 | O | LEU | 195 | 2.389 | 37.931 | −12.837 | 1.00 | 51.75 |
| ATOM | 1224 | CB | LEU | 195 | 4.612 | 38.531 | −14.840 | 1.00 | 50.86 |
| ATOM | 1225 | CG | LEU | 195 | 3.940 | 38.802 | −16.195 | 1.00 | 50.48 |
| ATOM | 1226 | CD1 | LEU | 195 | 4.719 | 38.065 | −17.275 | 1.00 | 49.39 |
| ATOM | 1227 | CD2 | LEU | 195 | 2.516 | 38.279 | −16.207 | 1.00 | 51.52 |
| ATOM | 1228 | N | LEU | 196 | 1.990 | 40.143 | −13.290 | 1.00 | 53.08 |
| ATOM | 1229 | CA | LEU | 196 | 0.583 | 40.080 | −12.936 | 1.00 | 55.19 |
| ATOM | 1230 | C | LEU | 196 | −0.282 | 40.642 | −14.069 | 1.00 | 56.77 |

TABLE 11-continued

Three-Dimensional Coordinates of *Neisseria gonorrhoeae* GCYH-IB·Mn$^{2+}$
(SEQ. ID. No. 8)

| ATOM | 1231 | O | LEU | 196 | 0.000 | 41.715 | −14.604 | 1.00 | 56.95 |
|---|---|---|---|---|---|---|---|---|---|
| ATOM | 1232 | CB | LEU | 196 | 0.326 | 40.816 | −11.612 | 1.00 | 54.79 |
| ATOM | 1233 | CG | LEU | 196 | 0.949 | 40.185 | −10.346 | 1.00 | 55.32 |
| ATOM | 1234 | CD1 | LEU | 196 | 0.931 | 41.147 | −9.136 | 1.00 | 54.75 |
| ATOM | 1235 | CD2 | LEU | 196 | 0.317 | 38.807 | −9.990 | 1.00 | 54.04 |
| ATOM | 1236 | N | LYS | 197 | −1.314 | 39.901 | −14.463 | 1.00 | 58.59 |
| ATOM | 1237 | CA | LYS | 197 | −2.334 | 40.487 | −15.353 | 1.00 | 60.40 |
| ATOM | 1238 | C | LYS | 197 | −3.393 | 41.246 | −14.545 | 1.00 | 60.81 |
| ATOM | 1239 | O | LYS | 197 | −3.364 | 41.225 | −13.294 | 1.00 | 60.59 |
| ATOM | 1240 | CB | LYS | 197 | −2.941 | 39.450 | −16.316 | 1.00 | 60.82 |
| ATOM | 1241 | CG | LYS | 197 | −2.344 | 39.536 | −17.753 | 1.00 | 63.00 |
| ATOM | 1242 | CD | LYS | 197 | −0.793 | 39.432 | −17.781 | 1.00 | 64.23 |
| ATOM | 1243 | CE | LYS | 197 | −0.195 | 39.552 | −19.202 | 1.00 | 64.55 |
| ATOM | 1244 | NZ | LYS | 197 | −0.184 | 40.949 | −19.739 | 1.00 | 64.56 |
| ATOM | 1245 | N | ARG | 198 | −4.289 | 41.941 | −15.256 | 1.00 | 61.03 |
| ATOM | 1246 | CA | ARG | 198 | −5.388 | 42.674 | −14.631 | 1.00 | 61.98 |
| ATOM | 1247 | C | ARG | 198 | −6.168 | 41.862 | −13.574 | 1.00 | 61.01 |
| ATOM | 1248 | O | ARG | 198 | −6.279 | 42.298 | −12.435 | 1.00 | 60.94 |
| ATOM | 1249 | CB | ARG | 198 | −6.332 | 43.276 | −15.690 | 1.00 | 62.12 |
| ATOM | 1250 | CG | ARG | 198 | −6.388 | 44.804 | −15.679 | 1.00 | 64.00 |
| ATOM | 1251 | CD | ARG | 198 | −6.848 | 45.429 | −17.028 | 1.00 | 64.71 |
| ATOM | 1252 | NE | ARG | 198 | −7.001 | 46.884 | −16.895 | 1.00 | 70.51 |
| ATOM | 1253 | CZ | ARG | 198 | −8.173 | 47.527 | −16.895 | 1.00 | 71.39 |
| ATOM | 1254 | NH1 | ARG | 198 | −9.309 | 46.851 | −17.049 | 1.00 | 74.34 |
| ATOM | 1255 | NH2 | ARG | 198 | −8.216 | 48.850 | −16.745 | 1.00 | 73.50 |
| ATOM | 1256 | N | PRO | 199 | −6.712 | 40.685 | −13.949 | 1.00 | 60.31 |
| ATOM | 1257 | CA | PRO | 199 | −7.394 | 39.878 | −12.926 | 1.00 | 59.80 |
| ATOM | 1258 | C | PRO | 199 | −6.506 | 39.474 | −11.725 | 1.00 | 59.02 |
| ATOM | 1259 | O | PRO | 199 | −6.975 | 39.527 | −10.582 | 1.00 | 58.60 |
| ATOM | 1260 | CB | PRO | 199 | −7.891 | 38.642 | −13.706 | 1.00 | 60.10 |
| ATOM | 1261 | CG | PRO | 199 | −7.149 | 38.640 | −15.009 | 1.00 | 60.56 |
| ATOM | 1262 | CD | PRO | 199 | −6.771 | 40.064 | −15.291 | 1.00 | 60.60 |
| ATOM | 1263 | N | ASP | 200 | −5.247 | 39.104 | −11.978 | 1.00 | 58.37 |
| ATOM | 1264 | CA | ASP | 200 | −4.289 | 38.793 | −10.889 | 1.00 | 58.09 |
| ATOM | 1265 | C | ASP | 200 | −4.123 | 39.966 | −9.932 | 1.00 | 57.97 |
| ATOM | 1266 | O | ASP | 200 | −4.210 | 39.797 | −8.707 | 1.00 | 58.11 |
| ATOM | 1267 | CB | ASP | 200 | −2.916 | 38.406 | −11.440 | 1.00 | 57.41 |
| ATOM | 1268 | CG | ASP | 200 | −2.987 | 37.271 | −12.416 | 1.00 | 56.87 |
| ATOM | 1269 | OD1 | ASP | 200 | −3.551 | 36.216 | −12.044 | 1.00 | 56.53 |
| ATOM | 1270 | OD2 | ASP | 200 | −2.471 | 37.434 | −13.545 | 1.00 | 54.07 |
| ATOM | 1271 | N | GLU | 201 | −3.876 | 41.149 | −10.498 | 1.00 | 57.96 |
| ATOM | 1272 | CA | GLU | 201 | −3.801 | 42.384 | −9.707 | 1.00 | 58.04 |
| ATOM | 1273 | C | GLU | 201 | −5.089 | 42.642 | −8.868 | 1.00 | 57.99 |
| ATOM | 1274 | O | GLU | 201 | −5.010 | 43.124 | −7.717 | 1.00 | 57.08 |
| ATOM | 1275 | CB | GLU | 201 | −3.411 | 43.598 | −10.577 | 1.00 | 58.12 |
| ATOM | 1276 | CG | GLU | 201 | −3.762 | 44.941 | −9.910 | 1.00 | 59.81 |
| ATOM | 1277 | CD | GLU | 201 | −2.850 | 46.081 | −10.275 | 1.00 | 59.25 |
| ATOM | 1278 | OE1 | GLU | 201 | −2.353 | 46.127 | −11.424 | 1.00 | 61.24 |
| ATOM | 1279 | OE2 | GLU | 201 | −2.653 | 46.948 | −9.394 | 1.00 | 61.33 |
| ATOM | 1280 | N | LYS | 202 | −6.258 | 42.314 | −9.444 | 1.00 | 58.11 |
| ATOM | 1281 | CA | LYS | 202 | −7.538 | 42.418 | −8.733 | 1.00 | 58.01 |
| ATOM | 1282 | C | LYS | 202 | −7.538 | 41.480 | −7.519 | 1.00 | 57.58 |
| ATOM | 1283 | O | LYS | 202 | −7.884 | 41.906 | −6.416 | 1.00 | 57.11 |
| ATOM | 1284 | CB | LYS | 202 | −8.729 | 42.138 | −9.670 | 1.00 | 58.00 |
| ATOM | 1285 | CG | LYS | 202 | −10.094 | 42.131 | −8.991 | 1.00 | 58.29 |
| ATOM | 1286 | CD | LYS | 202 | −11.235 | 41.997 | −10.025 | 1.00 | 58.66 |
| ATOM | 1287 | CE | LYS | 202 | −12.517 | 41.344 | −9.442 | 1.00 | 58.41 |
| ATOM | 1288 | NZ | LYS | 202 | −12.846 | 41.660 | −8.009 | 1.00 | 59.05 |
| ATOM | 1289 | N | TYR | 203 | −7.132 | 40.222 | −7.752 | 1.00 | 57.29 |
| ATOM | 1290 | CA | TYR | 203 | −7.027 | 39.165 | −6.731 | 1.00 | 56.76 |
| ATOM | 1291 | C | TYR | 203 | −6.051 | 39.573 | −5.622 | 1.00 | 55.73 |
| ATOM | 1292 | O | TYR | 203 | −6.365 | 39.520 | −4.439 | 1.00 | 55.19 |
| ATOM | 1293 | CB | TYR | 203 | −6.594 | 37.836 | −7.391 | 1.00 | 57.82 |
| ATOM | 1294 | CG | TYR | 203 | −6.403 | 36.661 | −6.431 | 1.00 | 57.69 |
| ATOM | 1295 | CD1 | TYR | 203 | −7.378 | 35.642 | −6.304 | 1.00 | 59.41 |
| ATOM | 1296 | CD2 | TYR | 203 | −5.257 | 36.582 | −5.633 | 1.00 | 59.00 |
| ATOM | 1297 | CE1 | TYR | 203 | −7.192 | 34.563 | −5.410 | 1.00 | 59.51 |
| ATOM | 1298 | CE2 | TYR | 203 | −5.065 | 35.531 | −4.745 | 1.00 | 60.75 |
| ATOM | 1299 | CZ | TYR | 203 | −6.017 | 34.520 | −4.636 | 1.00 | 58.13 |
| ATOM | 1300 | OH | TYR | 203 | −5.754 | 33.498 | −3.740 | 1.00 | 60.67 |
| ATOM | 1301 | N | VAL | 204 | −4.866 | 39.998 | −6.026 | 1.00 | 54.95 |
| ATOM | 1302 | CA | VAL | 204 | −3.835 | 40.403 | −5.072 | 1.00 | 54.58 |
| ATOM | 1303 | C | VAL | 204 | −4.290 | 41.638 | −4.213 | 1.00 | 53.79 |
| ATOM | 1304 | O | VAL | 204 | −4.091 | 41.662 | −2.986 | 1.00 | 52.60 |
| ATOM | 1305 | CB | VAL | 204 | −2.469 | 40.569 | −5.822 | 1.00 | 54.92 |
| ATOM | 1306 | CG1 | VAL | 204 | −1.523 | 41.522 | −5.116 | 1.00 | 56.19 |
| ATOM | 1307 | CG2 | VAL | 204 | −1.820 | 39.187 | −6.087 | 1.00 | 53.61 |

TABLE 11-continued

Three-Dimensional Coordinates of *Neisseria gonorrhoeae* GCYH-IB·Mn$^{2+}$
(SEQ. ID. No. 8)

| ATOM | 1308 | N   | THR | 205 | -4.949  | 42.619 | -4.851 | 1.00 | 53.09 |
|------|------|-----|-----|-----|---------|--------|--------|------|-------|
| ATOM | 1309 | CA  | THR | 205 | -5.456  | 43.794 | -4.132 | 1.00 | 52.58 |
| ATOM | 1310 | C   | THR | 205 | -6.437  | 43.402 | -3.017 | 1.00 | 53.09 |
| ATOM | 1311 | O   | THR | 205 | -6.340  | 43.906 | -1.878 | 1.00 | 52.50 |
| ATOM | 1312 | CB  | THR | 205 | -6.109  | 44.841 | -5.091 | 1.00 | 52.24 |
| ATOM | 1313 | OG1 | THR | 205 | -5.109  | 45.371 | -5.976 | 1.00 | 50.47 |
| ATOM | 1314 | CG2 | THR | 205 | -6.716  | 46.000 | -4.305 | 1.00 | 51.46 |
| ATOM | 1315 | N   | GLU | 206 | -7.352  | 42.491 | -3.365 | 1.00 | 53.01 |
| ATOM | 1316 | CA  | GLU | 206 | -8.444  | 42.065 | -2.489 | 1.00 | 53.57 |
| ATOM | 1317 | C   | GLU | 206 | -7.956  | 41.177 | -1.363 | 1.00 | 53.60 |
| ATOM | 1318 | O   | GLU | 206 | -8.280  | 41.441 | -0.203 | 1.00 | 53.68 |
| ATOM | 1319 | CB  | GLU | 206 | -9.563  | 41.399 | -3.295 | 1.00 | 53.31 |
| ATOM | 1320 | CG  | GLU | 206 | -10.150 | 42.359 | -4.283 | 1.00 | 54.66 |
| ATOM | 1321 | CD  | GLU | 206 | -11.279 | 41.793 | -5.124 | 1.00 | 55.83 |
| ATOM | 1322 | OE1 | GLU | 206 | -11.449 | 40.555 | -5.199 | 1.00 | 58.27 |
| ATOM | 1323 | OE2 | GLU | 206 | -11.993 | 42.618 | -5.731 | 1.00 | 57.86 |
| ATOM | 1324 | N   | LYS | 207 | -7.171  | 40.150 | -1.714 | 1.00 | 53.98 |
| ATOM | 1325 | CA  | LYS | 207 | -6.504  | 39.245 | -0.746 | 1.00 | 54.40 |
| ATOM | 1326 | C   | LYS | 207 | -5.834  | 40.060 | 0.379  | 1.00 | 54.04 |
| ATOM | 1327 | O   | LYS | 207 | -6.116  | 39.867 | 1.572  | 1.00 | 53.03 |
| ATOM | 1328 | CB  | LYS | 207 | -5.463  | 38.376 | -1.481 | 1.00 | 54.50 |
| ATOM | 1329 | CG  | LYS | 207 | -4.727  | 37.339 | -0.646 | 1.00 | 56.04 |
| ATOM | 1330 | CD  | LYS | 207 | -3.784  | 36.509 | -1.522 | 1.00 | 58.59 |
| ATOM | 1331 | CE  | LYS | 207 | -3.018  | 35.463 | -0.713 | 1.00 | 59.46 |
| ATOM | 1332 | NZ  | LYS | 207 | -2.119  | 34.690 | -1.635 | 1.00 | 58.18 |
| ATOM | 1333 | N   | ALA | 208 | -4.973  | 40.991 | -0.029 | 1.00 | 54.31 |
| ATOM | 1334 | CA  | ALA | 208 | -4.238  | 41.807 | 0.900  | 1.00 | 55.01 |
| ATOM | 1335 | C   | ALA | 208 | -5.226  | 42.582 | 1.799  | 1.00 | 55.58 |
| ATOM | 1336 | O   | ALA | 208 | -5.072  | 42.586 | 3.021  | 1.00 | 55.47 |
| ATOM | 1337 | CB  | ALA | 208 | -3.292  | 42.757 | 0.130  | 1.00 | 55.20 |
| ATOM | 1338 | N   | TYR | 209 | -6.243  | 43.203 | 1.183  | 1.00 | 57.15 |
| ATOM | 1339 | CA  | TYR | 209 | -7.312  | 43.954 | 1.915  | 1.00 | 56.96 |
| ATOM | 1340 | C   | TYR | 209 | -8.039  | 43.078 | 2.964  | 1.00 | 56.61 |
| ATOM | 1341 | O   | TYR | 209 | -8.230  | 43.504 | 4.130  | 1.00 | 56.39 |
| ATOM | 1342 | CB  | TYR | 209 | -8.321  | 44.578 | 0.925  | 1.00 | 57.07 |
| ATOM | 1343 | CG  | TYR | 209 | -9.265  | 45.654 | 1.483  | 1.00 | 57.70 |
| ATOM | 1344 | CD1 | TYR | 209 | -8.809  | 46.966 | 1.731  | 1.00 | 58.72 |
| ATOM | 1345 | CD2 | TYR | 209 | -10.631 | 45.372 | 1.719  | 1.00 | 58.01 |
| ATOM | 1346 | CE1 | TYR | 209 | -9.689  | 47.962 | 2.216  | 1.00 | 59.35 |
| ATOM | 1347 | CE2 | TYR | 209 | -11.506 | 46.352 | 2.208  | 1.00 | 57.42 |
| ATOM | 1348 | CZ  | TYR | 209 | -11.026 | 47.643 | 2.451  | 1.00 | 55.90 |
| ATOM | 1349 | OH  | TYR | 209 | -11.881 | 48.614 | 2.917  | 1.00 | 58.74 |
| ATOM | 1350 | N   | GLU | 210 | -8.389  | 41.850 | 2.558  | 1.00 | 56.26 |
| ATOM | 1351 | CA  | GLU | 210 | -9.155  | 40.915 | 3.411  | 1.00 | 56.42 |
| ATOM | 1352 | C   | GLU | 210 | -8.343  | 40.311 | 4.566  | 1.00 | 56.04 |
| ATOM | 1353 | O   | GLU | 210 | -8.907  | 39.813 | 5.553  | 1.00 | 56.04 |
| ATOM | 1354 | CB  | GLU | 210 | -9.743  | 39.778 | 2.566  | 1.00 | 56.91 |
| ATOM | 1355 | CG  | GLU | 210 | -10.701 | 40.245 | 1.446  | 1.00 | 58.24 |
| ATOM | 1356 | CD  | GLU | 210 | -10.842 | 39.213 | 0.337  | 1.00 | 61.03 |
| ATOM | 1357 | OE1 | GLU | 210 | -10.317 | 38.078 | 0.514  | 1.00 | 63.30 |
| ATOM | 1358 | OE2 | GLU | 210 | -11.480 | 39.531 | -0.700 | 1.00 | 60.60 |
| ATOM | 1359 | N   | ASN | 211 | -7.021  | 40.392 | 4.434  | 1.00 | 54.85 |
| ATOM | 1360 | CA  | ASN | 211 | -6.079  | 39.673 | 5.277  | 1.00 | 54.55 |
| ATOM | 1361 | C   | ASN | 211 | -5.033  | 40.685 | 5.879  | 1.00 | 53.11 |
| ATOM | 1362 | O   | ASN | 211 | -3.831  | 40.440 | 5.806  | 1.00 | 52.60 |
| ATOM | 1363 | CB  | ASN | 211 | -5.479  | 38.526 | 4.393  | 1.00 | 55.22 |
| ATOM | 1364 | CG  | ASN | 211 | -4.332  | 37.738 | 5.055  | 1.00 | 58.06 |
| ATOM | 1365 | OD1 | ASN | 211 | -4.018  | 37.910 | 6.243  | 1.00 | 60.91 |
| ATOM | 1366 | ND2 | ASN | 211 | -3.692  | 36.855 | 4.261  | 1.00 | 59.82 |
| ATOM | 1367 | N   | PRO | 212 | -5.496  | 41.823 | 6.491  | 1.00 | 51.64 |
| ATOM | 1368 | CA  | PRO | 212 | -4.515  | 42.792 | 6.998  | 1.00 | 50.32 |
| ATOM | 1369 | C   | PRO | 212 | -3.784  | 42.189 | 8.212  | 1.00 | 49.35 |
| ATOM | 1370 | O   | PRO | 212 | -4.417  | 41.504 | 9.022  | 1.00 | 48.96 |
| ATOM | 1371 | CB  | PRO | 212 | -5.386  | 43.965 | 7.461  | 1.00 | 50.49 |
| ATOM | 1372 | CG  | PRO | 212 | -6.674  | 43.322 | 7.891  | 1.00 | 51.04 |
| ATOM | 1373 | CD  | PRO | 212 | -6.876  | 42.240 | 6.826  | 1.00 | 51.68 |
| ATOM | 1374 | N   | LYS | 213 | -2.479  | 42.447 | 8.318  | 1.00 | 47.51 |
| ATOM | 1375 | CA  | LYS | 213 | -1.648  | 41.922 | 9.375  | 1.00 | 46.52 |
| ATOM | 1376 | C   | LYS | 213 | -0.638  | 42.975 | 9.769  | 1.00 | 46.02 |
| ATOM | 1377 | O   | LYS | 213 | 0.019   | 43.569 | 8.906  | 1.00 | 46.15 |
| ATOM | 1378 | CB  | LYS | 213 | -0.893  | 40.683 | 8.909  | 1.00 | 46.06 |
| ATOM | 1379 | CG  | LYS | 213 | -1.769  | 39.444 | 8.686  | 1.00 | 45.94 |
| ATOM | 1380 | CD  | LYS | 213 | -1.021  | 38.131 | 9.006  | 1.00 | 42.30 |
| ATOM | 1381 | CE  | LYS | 213 | -1.946  | 36.939 | 8.706  | 1.00 | 42.12 |
| ATOM | 1382 | NZ  | LYS | 213 | -1.223  | 35.624 | 8.755  | 1.00 | 41.19 |
| ATOM | 1383 | N   | PHE | 214 | -0.534  | 43.219 | 11.073 | 1.00 | 45.52 |
| ATOM | 1384 | CA  | PHE | 214 | 0.540   | 44.036 | 11.634 | 1.00 | 45.58 |

TABLE 11-continued

Three-Dimensional Coordinates of *Neisseria gonorrhoeae* GCYH-IB·Mn$^{2+}$
(SEQ. ID. No. 8)

| ATOM | 1385 | C   | PHE | 214 | 1.875  | 43.286 | 11.471 | 1.00 | 43.76 |
|------|------|-----|-----|-----|--------|--------|--------|------|-------|
| ATOM | 1386 | O   | PHE | 214 | 1.897  | 42.056 | 11.285 | 1.00 | 43.89 |
| ATOM | 1387 | CB  | PHE | 214 | 0.299  | 44.270 | 13.141 | 1.00 | 46.89 |
| ATOM | 1388 | CG  | PHE | 214 | −0.840 | 45.208 | 13.471 | 1.00 | 48.64 |
| ATOM | 1389 | CD1 | PHE | 214 | −0.830 | 46.539 | 13.033 | 1.00 | 51.01 |
| ATOM | 1390 | CD2 | PHE | 214 | −1.890 | 44.774 | 14.309 | 1.00 | 50.55 |
| ATOM | 1391 | CE1 | PHE | 214 | −1.876 | 47.429 | 13.378 | 1.00 | 52.20 |
| ATOM | 1392 | CE2 | PHE | 214 | −2.938 | 45.632 | 14.672 | 1.00 | 50.78 |
| ATOM | 1393 | CZ  | PHE | 214 | −2.938 | 46.969 | 14.199 | 1.00 | 51.48 |
| ATOM | 1394 | N   | VAL | 215 | 2.986  | 44.012 | 11.572 | 1.00 | 41.22 |
| ATOM | 1395 | CA  | VAL | 215 | 4.268  | 43.360 | 11.753 | 1.00 | 39.38 |
| ATOM | 1396 | C   | VAL | 215 | 4.255  | 42.345 | 12.936 | 1.00 | 38.44 |
| ATOM | 1397 | O   | VAL | 215 | 4.831  | 41.253 | 12.830 | 1.00 | 37.18 |
| ATOM | 1398 | CB  | VAL | 215 | 5.451  | 44.375 | 11.859 | 1.00 | 39.18 |
| ATOM | 1399 | CG1 | VAL | 215 | 5.390  | 45.238 | 13.135 | 1.00 | 37.11 |
| ATOM | 1400 | CG2 | VAL | 215 | 6.681  | 43.638 | 11.833 | 1.00 | 39.54 |
| ATOM | 1401 | N   | GLU | 216 | 3.578  | 42.708 | 14.035 | 1.00 | 37.54 |
| ATOM | 1402 | CA  | GLU | 216 | 3.430  | 41.817 | 15.200 | 1.00 | 36.83 |
| ATOM | 1403 | C   | GLU | 216 | 2.775  | 40.467 | 14.819 | 1.00 | 36.37 |
| ATOM | 1404 | O   | GLU | 216 | 3.271  | 39.407 | 15.164 | 1.00 | 35.59 |
| ATOM | 1405 | CB  | GLU | 216 | 2.592  | 42.489 | 16.287 | 1.00 | 36.59 |
| ATOM | 1406 | CG  | GLU | 216 | 3.269  | 43.670 | 17.002 | 1.00 | 36.95 |
| ATOM | 1407 | CD  | GLU | 216 | 2.843  | 45.025 | 16.448 | 1.00 | 36.23 |
| ATOM | 1408 | OE1 | GLU | 216 | 2.424  | 45.033 | 15.285 | 1.00 | 35.17 |
| ATOM | 1409 | OE2 | GLU | 216 | 2.953  | 46.079 | 17.152 | 1.00 | 36.48 |
| ATOM | 1410 | N   | ASP | 217 | 1.666  | 40.541 | 14.096 | 1.00 | 37.46 |
| ATOM | 1411 | CA  | ASP | 217 | 0.924  | 39.365 | 13.575 | 1.00 | 37.41 |
| ATOM | 1412 | C   | ASP | 217 | 1.763  | 38.503 | 12.679 | 1.00 | 36.40 |
| ATOM | 1413 | O   | ASP | 217 | 1.733  | 37.268 | 12.781 | 1.00 | 35.80 |
| ATOM | 1414 | CB  | ASP | 217 | −0.305 | 39.833 | 12.782 | 1.00 | 39.17 |
| ATOM | 1415 | CG  | ASP | 217 | −1.379 | 40.441 | 13.689 | 1.00 | 42.59 |
| ATOM | 1416 | OD1 | ASP | 217 | −1.611 | 39.879 | 14.803 | 1.00 | 44.14 |
| ATOM | 1417 | OD2 | ASP | 217 | −1.972 | 41.474 | 13.294 | 1.00 | 45.24 |
| ATOM | 1418 | N   | MET | 218 | 2.523  | 39.141 | 11.793 | 1.00 | 36.11 |
| ATOM | 1419 | CA  | MET | 218 | 3.384  | 38.395 | 10.895 | 1.00 | 35.43 |
| ATOM | 1420 | C   | MET | 218 | 4.516  | 37.691 | 11.624 | 1.00 | 33.47 |
| ATOM | 1421 | O   | MET | 218 | 4.761  | 36.528 | 11.387 | 1.00 | 32.57 |
| ATOM | 1422 | CB  | MET | 218 | 3.919  | 39.291 | 9.744  | 1.00 | 36.86 |
| ATOM | 1423 | CG  | MET | 218 | 4.835  | 38.557 | 8.686  | 1.00 | 39.05 |
| ATOM | 1424 | SD  | MET | 218 | 4.098  | 37.370 | 7.489  | 1.00 | 48.15 |
| ATOM | 1425 | CE  | MET | 218 | 2.385  | 37.538 | 7.908  | 1.00 | 47.14 |
| ATOM | 1426 | N   | VAL | 219 | 5.233  | 38.362 | 12.507 | 1.00 | 32.53 |
| ATOM | 1427 | CA  | VAL | 219 | 6.310  | 37.604 | 13.169 | 1.00 | 32.64 |
| ATOM | 1428 | C   | VAL | 219 | 5.758  | 36.404 | 13.970 | 1.00 | 32.02 |
| ATOM | 1429 | O   | VAL | 219 | 6.383  | 35.315 | 13.996 | 1.00 | 30.73 |
| ATOM | 1430 | CB  | VAL | 219 | 7.290  | 38.469 | 14.026 | 1.00 | 32.81 |
| ATOM | 1431 | CG1 | VAL | 219 | 8.108  | 39.389 | 13.124 | 1.00 | 33.18 |
| ATOM | 1432 | CG2 | VAL | 219 | 6.570  | 39.256 | 15.095 | 1.00 | 33.07 |
| ATOM | 1433 | N   | ARG | 220 | 4.613  | 36.621 | 14.631 | 1.00 | 32.42 |
| ATOM | 1434 | CA  | ARG | 220 | 3.940  | 35.569 | 15.425 | 1.00 | 32.49 |
| ATOM | 1435 | C   | ARG | 220 | 3.445  | 34.351 | 14.650 | 1.00 | 33.39 |
| ATOM | 1436 | O   | ARG | 220 | 3.745  | 33.199 | 15.037 | 1.00 | 34.66 |
| ATOM | 1437 | CB  | ARG | 220 | 2.814  | 36.156 | 16.220 | 1.00 | 32.42 |
| ATOM | 1438 | CG  | ARG | 220 | 3.309  | 36.924 | 17.434 | 1.00 | 31.64 |
| ATOM | 1439 | CD  | ARG | 220 | 2.123  | 37.638 | 18.065 | 1.00 | 32.29 |
| ATOM | 1440 | NE  | ARG | 220 | 2.428  | 37.976 | 19.436 | 1.00 | 34.95 |
| ATOM | 1441 | CZ  | ARG | 220 | 1.932  | 39.029 | 20.059 | 1.00 | 35.09 |
| ATOM | 1442 | NH1 | ARG | 220 | 1.120  | 39.873 | 19.417 | 1.00 | 33.56 |
| ATOM | 1443 | NH2 | ARG | 220 | 2.268  | 39.240 | 21.319 | 1.00 | 36.65 |
| ATOM | 1444 | N   | ASP | 221 | 2.717  | 34.590 | 13.566 | 1.00 | 34.07 |
| ATOM | 1445 | CA  | ASP | 221 | 2.290  | 33.526 | 12.636 | 1.00 | 33.76 |
| ATOM | 1446 | C   | ASP | 221 | 3.446  | 32.709 | 12.069 | 1.00 | 33.51 |
| ATOM | 1447 | O   | ASP | 221 | 3.342  | 31.489 | 11.968 | 1.00 | 33.79 |
| ATOM | 1448 | CB  | ASP | 221 | 1.453  | 34.155 | 11.505 | 1.00 | 34.70 |
| ATOM | 1449 | CG  | ASP | 221 | 0.124  | 34.705 | 12.009 | 1.00 | 36.94 |
| ATOM | 1450 | OD1 | ASP | 221 | −0.162 | 34.438 | 13.197 | 1.00 | 40.28 |
| ATOM | 1451 | OD2 | ASP | 221 | −0.626 | 35.386 | 11.263 | 1.00 | 36.36 |
| ATOM | 1452 | N   | VAL | 222 | 4.559  | 33.362 | 11.697 | 1.00 | 32.83 |
| ATOM | 1453 | CA  | VAL | 222 | 5.737  | 32.623 | 11.232 | 1.00 | 31.91 |
| ATOM | 1454 | C   | VAL | 222 | 6.418  | 31.859 | 12.389 | 1.00 | 32.92 |
| ATOM | 1455 | O   | VAL | 222 | 6.823  | 30.689 | 12.243 | 1.00 | 32.48 |
| ATOM | 1456 | CB  | VAL | 222 | 6.756  | 33.545 | 10.431 | 1.00 | 31.86 |
| ATOM | 1457 | CG1 | VAL | 222 | 8.053  | 32.832 | 10.118 | 1.00 | 29.78 |
| ATOM | 1458 | CG2 | VAL | 222 | 6.119  | 34.107 | 9.133  | 1.00 | 28.77 |
| ATOM | 1459 | N   | ALA | 223 | 6.553  | 32.497 | 13.549 | 1.00 | 32.41 |
| ATOM | 1460 | CA  | ALA | 223 | 7.218  | 31.798 | 14.660 | 1.00 | 32.79 |
| ATOM | 1461 | C   | ALA | 223 | 6.469  | 30.499 | 15.061 | 1.00 | 32.87 |

TABLE 11-continued

Three-Dimensional Coordinates of *Neisseria gonorrhoeae* GCYH-IB·Mn$^{2+}$
(SEQ. ID. No. 8)

| ATOM | 1462 | O   | ALA | 223 | 7.092  | 29.449 | 15.365 | 1.00 | 32.40 |
|------|------|-----|-----|-----|--------|--------|--------|------|-------|
| ATOM | 1463 | CB  | ALA | 223 | 7.311  | 32.706 | 15.851 | 1.00 | 33.64 |
| ATOM | 1464 | N   | THR | 224 | 5.138  | 30.582 | 15.076 | 1.00 | 33.30 |
| ATOM | 1465 | CA  | THR | 224 | 4.311  | 29.381 | 15.348 | 1.00 | 34.28 |
| ATOM | 1466 | C   | THR | 224 | 4.709  | 28.229 | 14.426 | 1.00 | 33.80 |
| ATOM | 1467 | O   | THR | 224 | 4.883  | 27.108 | 14.896 | 1.00 | 32.18 |
| ATOM | 1468 | CB  | THR | 224 | 2.834  | 29.667 | 15.250 | 1.00 | 34.79 |
| ATOM | 1469 | OG1 | THR | 224 | 2.527  | 30.763 | 16.107 | 1.00 | 34.54 |
| ATOM | 1470 | CG2 | THR | 224 | 2.009  | 28.439 | 15.738 | 1.00 | 38.37 |
| ATOM | 1471 | N   | SER | 225 | 4.876  | 28.494 | 13.115 | 1.00 | 34.23 |
| ATOM | 1472 | CA  | SER | 225 | 5.217  | 27.412 | 12.194 | 1.00 | 34.27 |
| ATOM | 1473 | C   | SER | 225 | 6.582  | 26.873 | 12.546 | 1.00 | 34.88 |
| ATOM | 1474 | O   | SER | 225 | 6.833  | 25.632 | 12.517 | 1.00 | 34.49 |
| ATOM | 1475 | CB  | SER | 225 | 5.208  | 27.868 | 10.736 | 1.00 | 34.83 |
| ATOM | 1476 | OG  | SER | 225 | 3.879  | 28.131 | 10.317 | 1.00 | 36.16 |
| ATOM | 1477 | N   | LEU | 226 | 7.499  | 27.782 | 12.887 | 1.00 | 34.32 |
| ATOM | 1478 | CA  | LEU | 226 | 8.863  | 27.327 | 13.123 | 1.00 | 34.58 |
| ATOM | 1479 | C   | LEU | 226 | 9.034  | 26.602 | 14.480 | 1.00 | 35.09 |
| ATOM | 1480 | O   | LEU | 226 | 9.871  | 25.702 | 14.624 | 1.00 | 35.39 |
| ATOM | 1481 | CB  | LEU | 226 | 9.867  | 28.500 | 12.956 | 1.00 | 34.96 |
| ATOM | 1482 | CG  | LEU | 226 | 9.770  | 29.394 | 11.699 | 1.00 | 33.32 |
| ATOM | 1483 | CD1 | LEU | 226 | 10.737 | 30.580 | 11.796 | 1.00 | 29.72 |
| ATOM | 1484 | CD2 | LEU | 226 | 10.017 | 28.570 | 10.444 | 1.00 | 31.90 |
| ATOM | 1485 | N   | ILE | 227 | 8.285  | 27.010 | 15.499 | 1.00 | 35.24 |
| ATOM | 1486 | CA  | ILE | 227 | 8.359  | 26.286 | 16.791 | 1.00 | 34.80 |
| ATOM | 1487 | C   | ILE | 227 | 7.912  | 24.810 | 16.620 | 1.00 | 35.08 |
| ATOM | 1488 | O   | ILE | 227 | 8.456  | 23.872 | 17.253 | 1.00 | 34.52 |
| ATOM | 1489 | CB  | ILE | 227 | 7.486  | 26.982 | 17.862 | 1.00 | 35.35 |
| ATOM | 1490 | CG1 | ILE | 227 | 8.228  | 28.232 | 18.401 | 1.00 | 35.35 |
| ATOM | 1491 | CG2 | ILE | 227 | 7.131  | 26.002 | 18.992 | 1.00 | 35.51 |
| ATOM | 1492 | CD1 | ILE | 227 | 7.329  | 29.271 | 19.011 | 1.00 | 35.08 |
| ATOM | 1493 | N   | ALA | 228 | 6.950  | 24.628 | 15.727 | 1.00 | 35.42 |
| ATOM | 1494 | CA  | ALA | 228 | 6.324  | 23.347 | 15.459 | 1.00 | 36.53 |
| ATOM | 1495 | C   | ALA | 228 | 7.183  | 22.383 | 14.640 | 1.00 | 36.58 |
| ATOM | 1496 | O   | ALA | 228 | 7.024  | 21.150 | 14.741 | 1.00 | 37.14 |
| ATOM | 1497 | CB  | ALA | 228 | 4.984  | 23.585 | 14.774 | 1.00 | 36.82 |
| ATOM | 1498 | N   | ASP | 229 | 8.109  | 22.915 | 13.850 | 1.00 | 36.37 |
| ATOM | 1499 | CA  | ASP | 229 | 8.973  | 22.068 | 13.018 | 1.00 | 36.10 |
| ATOM | 1500 | C   | ASP | 229 | 10.034 | 21.426 | 13.915 | 1.00 | 37.32 |
| ATOM | 1501 | O   | ASP | 229 | 10.792 | 22.141 | 14.572 | 1.00 | 37.73 |
| ATOM | 1502 | CB  | ASP | 229 | 9.585  | 22.921 | 11.897 | 1.00 | 35.82 |
| ATOM | 1503 | CG  | ASP | 229 | 10.310 | 22.096 | 10.861 | 1.00 | 35.00 |
| ATOM | 1504 | OD1 | ASP | 229 | 11.209 | 21.314 | 11.240 | 1.00 | 32.09 |
| ATOM | 1505 | OD2 | ASP | 229 | 9.966  | 22.218 | 9.653  | 1.00 | 34.51 |
| ATOM | 1506 | N   | ASN | 241 | 8.407  | 46.451 | 7.910  | 1.00 | 38.75 |
| ATOM | 1507 | CA  | ASN | 241 | 7.350  | 46.945 | 7.062  | 1.00 | 40.86 |
| ATOM | 1508 | C   | ASN | 241 | 7.685  | 48.355 | 6.625  | 1.00 | 41.84 |
| ATOM | 1509 | O   | ASN | 241 | 7.708  | 49.260 | 7.459  | 1.00 | 41.53 |
| ATOM | 1510 | CB  | ASN | 241 | 6.035  | 47.019 | 7.831  | 1.00 | 41.45 |
| ATOM | 1511 | CG  | ASN | 241 | 5.404  | 45.673 | 8.066  | 1.00 | 45.01 |
| ATOM | 1512 | OD1 | ASN | 241 | 4.426  | 45.578 | 8.807  | 1.00 | 50.80 |
| ATOM | 1513 | ND2 | ASN | 241 | 5.938  | 44.623 | 7.443  | 1.00 | 47.80 |
| ATOM | 1514 | N   | PHE | 242 | 7.931  | 48.549 | 5.327  | 1.00 | 42.06 |
| ATOM | 1515 | CA  | PHE | 242 | 8.328  | 49.882 | 4.849  | 1.00 | 43.01 |
| ATOM | 1516 | C   | PHE | 242 | 7.099  | 50.800 | 4.761  | 1.00 | 43.06 |
| ATOM | 1517 | O   | PHE | 242 | 6.628  | 51.115 | 3.649  | 1.00 | 41.83 |
| ATOM | 1518 | CB  | PHE | 242 | 9.160  | 49.775 | 3.539  | 1.00 | 42.80 |
| ATOM | 1519 | CG  | PHE | 242 | 10.470 | 49.042 | 3.748  | 1.00 | 43.34 |
| ATOM | 1520 | CD1 | PHE | 242 | 11.578 | 49.719 | 4.232  | 1.00 | 43.78 |
| ATOM | 1521 | CD2 | PHE | 242 | 10.565 | 47.650 | 3.542  | 1.00 | 43.59 |
| ATOM | 1522 | CE1 | PHE | 242 | 12.781 | 49.044 | 4.457  | 1.00 | 45.11 |
| ATOM | 1523 | CE2 | PHE | 242 | 11.767 | 46.969 | 3.755  | 1.00 | 42.03 |
| ATOM | 1524 | CZ  | PHE | 242 | 12.872 | 47.668 | 4.214  | 1.00 | 43.33 |
| ATOM | 1525 | N   | GLU | 243 | 6.591  | 51.185 | 5.947  | 1.00 | 42.20 |
| ATOM | 1526 | CA  | GLU | 243 | 5.313  | 51.890 | 6.091  | 1.00 | 43.24 |
| ATOM | 1527 | C   | GLU | 243 | 5.193  | 52.917 | 4.975  | 1.00 | 42.95 |
| ATOM | 1528 | O   | GLU | 243 | 6.100  | 53.756 | 4.795  | 1.00 | 41.58 |
| ATOM | 1529 | CB  | GLU | 243 | 5.176  | 52.603 | 7.456  | 1.00 | 43.53 |
| ATOM | 1530 | CG  | GLU | 243 | 5.166  | 51.691 | 8.686  | 1.00 | 47.74 |
| ATOM | 1531 | CD  | GLU | 243 | 4.045  | 50.630 | 8.672  | 1.00 | 53.02 |
| ATOM | 1532 | OE1 | GLU | 243 | 2.909  | 50.935 | 9.111  | 1.00 | 56.85 |
| ATOM | 1533 | OE2 | GLU | 243 | 4.313  | 49.470 | 8.262  | 1.00 | 54.32 |
| ATOM | 1534 | N   | SER | 244 | 4.109  | 52.799 | 4.205  | 1.00 | 42.95 |
| ATOM | 1535 | CA  | SER | 244 | 3.917  | 53.634 | 3.017  | 1.00 | 43.67 |
| ATOM | 1536 | C   | SER | 244 | 3.492  | 55.057 | 3.422  | 1.00 | 44.11 |
| ATOM | 1537 | O   | SER | 244 | 3.430  | 55.917 | 2.559  | 1.00 | 43.54 |
| ATOM | 1538 | CB  | SER | 244 | 2.872  | 53.035 | 2.062  | 1.00 | 43.70 |

TABLE 11-continued

Three-Dimensional Coordinates of *Neisseria gonorrhoeae* GCYH-IB·Mn$^{2+}$
(SEQ. ID. No. 8)

| | | | | | | | | |
|---|---|---|---|---|---|---|---|---|
| ATOM | 1539 | OG | SER | 244 | 1.608 | 52.882 | 2.714 | 1.00 | 43.76 |
| ATOM | 1540 | N | ILE | 245 | 3.247 | 55.269 | 4.732 | 1.00 | 44.53 |
| ATOM | 1541 | CA | ILE | 245 | 2.762 | 56.542 | 5.305 | 1.00 | 44.90 |
| ATOM | 1542 | C | ILE | 245 | 3.796 | 57.370 | 6.114 | 1.00 | 44.98 |
| ATOM | 1543 | O | ILE | 245 | 3.579 | 58.562 | 6.399 | 1.00 | 45.25 |
| ATOM | 1544 | CB | ILE | 245 | 1.446 | 56.328 | 6.131 | 1.00 | 45.08 |
| ATOM | 1545 | CG1 | ILE | 245 | 1.678 | 55.420 | 7.340 | 1.00 | 45.82 |
| ATOM | 1546 | CG2 | ILE | 245 | 0.327 | 55.744 | 5.234 | 1.00 | 45.11 |
| ATOM | 1547 | CD1 | ILE | 245 | 0.563 | 55.480 | 8.372 | 1.00 | 45.19 |
| ATOM | 1548 | N | HIS | 246 | 4.912 | 56.729 | 6.467 | 1.00 | 44.82 |
| ATOM | 1549 | CA | HIS | 246 | 6.046 | 57.364 | 7.170 | 1.00 | 44.40 |
| ATOM | 1550 | C | HIS | 246 | 7.299 | 57.172 | 6.337 | 1.00 | 43.85 |
| ATOM | 1551 | O | HIS | 246 | 7.274 | 56.491 | 5.290 | 1.00 | 43.92 |
| ATOM | 1552 | CB | HIS | 246 | 6.306 | 56.687 | 8.529 | 1.00 | 45.24 |
| ATOM | 1553 | CG | HIS | 246 | 5.125 | 56.674 | 9.448 | 1.00 | 45.19 |
| ATOM | 1554 | ND1 | HIS | 246 | 4.574 | 55.504 | 9.935 | 1.00 | 47.43 |
| ATOM | 1555 | CD2 | HIS | 246 | 4.390 | 57.685 | 9.968 | 1.00 | 44.55 |
| ATOM | 1556 | CE1 | HIS | 246 | 3.557 | 55.804 | 10.729 | 1.00 | 47.01 |
| ATOM | 1557 | NE2 | HIS | 246 | 3.423 | 57.121 | 10.761 | 1.00 | 45.51 |
| ATOM | 1558 | N | ASN | 247 | 8.409 | 57.740 | 6.798 | 1.00 | 42.26 |
| ATOM | 1559 | CA | ASN | 247 | 9.689 | 57.458 | 6.151 | 1.00 | 40.75 |
| ATOM | 1560 | C | ASN | 247 | 10.617 | 56.602 | 7.022 | 1.00 | 39.27 |
| ATOM | 1561 | O | ASN | 247 | 11.858 | 56.641 | 6.871 | 1.00 | 39.39 |
| ATOM | 1562 | CB | ASN | 247 | 10.388 | 58.753 | 5.655 | 1.00 | 41.37 |
| ATOM | 1563 | CG | ASN | 247 | 11.418 | 58.491 | 4.526 | 1.00 | 41.38 |
| ATOM | 1564 | OD1 | ASN | 247 | 11.262 | 57.564 | 3.727 | 1.00 | 42.55 |
| ATOM | 1565 | ND2 | ASN | 247 | 12.482 | 59.322 | 4.475 | 1.00 | 40.83 |
| ATOM | 1566 | N | TYR | 251 | 8.983 | 47.503 | 12.864 | 1.00 | 31.14 |
| ATOM | 1567 | CA | TYR | 251 | 9.911 | 46.418 | 12.972 | 1.00 | 31.17 |
| ATOM | 1568 | C | TYR | 251 | 9.549 | 45.501 | 14.174 | 1.00 | 31.66 |
| ATOM | 1569 | O | TYR | 251 | 9.072 | 45.965 | 15.166 | 1.00 | 31.06 |
| ATOM | 1570 | CB | TYR | 251 | 11.325 | 46.995 | 13.106 | 1.00 | 30.79 |
| ATOM | 1571 | CG | TYR | 251 | 12.393 | 45.981 | 13.307 | 1.00 | 30.68 |
| ATOM | 1572 | CD1 | TYR | 251 | 12.814 | 45.139 | 12.251 | 1.00 | 29.05 |
| ATOM | 1573 | CD2 | TYR | 251 | 12.998 | 45.830 | 14.566 | 1.00 | 30.94 |
| ATOM | 1574 | CE1 | TYR | 251 | 13.793 | 44.182 | 12.450 | 1.00 | 30.88 |
| ATOM | 1575 | CE2 | TYR | 251 | 13.994 | 44.862 | 14.766 | 1.00 | 33.74 |
| ATOM | 1576 | CZ | TYR | 251 | 14.389 | 44.058 | 13.702 | 1.00 | 31.97 |
| ATOM | 1577 | OH | TYR | 251 | 15.362 | 43.101 | 13.900 | 1.00 | 35.58 |
| TER | | | | | | | | | |
| ATOM | 1578 | MN | MN2 C | 258 | −0.987 | 51.767 | 9.777 | 1.00 | 49.60 |
| TER | | | | | | | | | |
| ATOM | 1579 | N | ASN | 15 | −0.055 | 31.945 | 21.743 | 1.00 | 57.77 |
| ATOM | 1580 | CA | ASN | 15 | 0.077 | 33.433 | 21.573 | 1.00 | 57.60 |
| ATOM | 1581 | C | ASN | 15 | 1.474 | 33.904 | 21.106 | 1.00 | 56.17 |
| ATOM | 1582 | O | ASN | 15 | 1.638 | 34.372 | 19.944 | 1.00 | 57.59 |
| ATOM | 1583 | CB | ASN | 15 | −0.349 | 34.162 | 22.857 | 1.00 | 58.61 |
| ATOM | 1584 | CG | ASN | 15 | −1.826 | 34.577 | 22.840 | 1.00 | 61.05 |
| ATOM | 1585 | OD1 | ASN | 15 | −2.439 | 34.707 | 21.763 | 1.00 | 62.70 |
| ATOM | 1586 | ND2 | ASN | 15 | −2.407 | 34.794 | 24.045 | 1.00 | 62.68 |
| ATOM | 1587 | N | LEU | 16 | 2.466 | 33.763 | 21.989 | 1.00 | 53.16 |
| ATOM | 1588 | CA | LEU | 16 | 3.873 | 34.147 | 21.715 | 1.00 | 49.45 |
| ATOM | 1589 | C | LEU | 16 | 4.265 | 35.599 | 22.049 | 1.00 | 46.26 |
| ATOM | 1590 | O | LEU | 16 | 3.774 | 36.563 | 21.428 | 1.00 | 45.34 |
| ATOM | 1591 | CB | LEU | 16 | 4.286 | 33.777 | 20.281 | 1.00 | 50.00 |
| ATOM | 1592 | CG | LEU | 16 | 5.106 | 32.522 | 20.015 | 1.00 | 50.00 |
| ATOM | 1593 | CD1 | LEU | 16 | 4.760 | 31.319 | 20.907 | 1.00 | 49.39 |
| ATOM | 1594 | CD2 | LEU | 16 | 5.019 | 32.185 | 18.515 | 1.00 | 49.75 |
| ATOM | 1595 | N | PRO | 17 | 5.144 | 35.758 | 23.051 | 1.00 | 43.37 |
| ATOM | 1596 | CA | PRO | 17 | 5.673 | 37.102 | 23.272 | 1.00 | 42.01 |
| ATOM | 1597 | C | PRO | 17 | 6.630 | 37.522 | 22.123 | 1.00 | 39.49 |
| ATOM | 1598 | O | PRO | 17 | 7.206 | 36.658 | 2.1.457 | 1.00 | 38.46 |
| ATOM | 1599 | CB | PRO | 17 | 6.387 | 37.010 | 24.638 | 1.00 | 41.94 |
| ATOM | 1600 | CG | PRO | 17 | 6.625 | 35.499 | 24.889 | 1.00 | 42.78 |
| ATOM | 1601 | CD | PRO | 17 | 5.660 | 34.747 | 24.004 | 1.00 | 43.71 |
| ATOM | 1602 | N | ILE | 18 | 6.757 | 38.833 | 21.888 | 1.00 | 37.20 |
| ATOM | 1603 | CA | ILE | 18 | 7.707 | 39.360 | 20.889 | 1.00 | 34.81 |
| ATOM | 1604 | C | ILE | 18 | 8.860 | 40.054 | 21.617 | 1.00 | 34.48 |
| ATOM | 1605 | O | ILE | 18 | 8.658 | 41.020 | 22.359 | 1.00 | 33.94 |
| ATOM | 1606 | CB | ILE | 18 | 7.007 | 40.305 | 19.844 | 1.00 | 35.33 |
| ATOM | 1607 | CG1 | ILE | 18 | 5.742 | 39.641 | 19.284 | 1.00 | 34.34 |
| ATOM | 1608 | CG2 | ILE | 18 | 7.994 | 40.729 | 18.733 | 1.00 | 34.30 |
| ATOM | 1609 | CD1 | ILE | 18 | 4.965 | 40.363 | 18.195 | 1.00 | 33.50 |
| ATOM | 1610 | N | ASN | 19 | 10.077 | 39.554 | 21.388 | 1.00 | 34.14 |
| ATOM | 1611 | CA | ASN | 19 | 11.282 | 40.096 | 22.001 | 1.00 | 33.65 |
| ATOM | 1612 | C | ASN | 19 | 11.389 | 41.597 | 21.857 | 1.00 | 33.26 |
| ATOM | 1613 | O | ASN | 19 | 11.644 | 42.306 | 22.834 | 1.00 | 32.04 |

TABLE 11-continued

Three-Dimensional Coordinates of *Neisseria gonorrhoeae* GCYH-IB·Mn$^{2+}$
(SEQ. ID. No. 8)

| ATOM | 1614 | CB  | ASN | 19 | 12.539 | 39.407 | 21.443 | 1.00 | 34.52 |
|------|------|-----|-----|----|--------|--------|--------|------|-------|
| ATOM | 1615 | CG  | ASN | 19 | 12.552 | 37.950 | 21.744 | 1.00 | 36.27 |
| ATOM | 1616 | OD1 | ASN | 19 | 13.318 | 37.480 | 22.582 | 1.00 | 42.25 |
| ATOM | 1617 | ND2 | ASN | 19 | 11.678 | 37.229 | 21.114 | 1.00 | 35.29 |
| ATOM | 1618 | N   | GLY | 22 | 8.798  | 47.783 | 17.427 | 1.00 | 30.37 |
| ATOM | 1619 | CA  | GLY | 22 | 8.928  | 49.238 | 17.433 | 1.00 | 29.76 |
| ATOM | 1620 | C   | GLY | 22 | 9.283  | 49.783 | 16.066 | 1.00 | 30.75 |
| ATOM | 1621 | O   | GLY | 22 | 8.767  | 49.302 | 15.054 | 1.00 | 31.28 |
| ATOM | 1622 | N   | VAL | 49 | 10.256 | 47.847 | 22.103 | 1.00 | 29.99 |
| ATOM | 1623 | CA  | VAL | 49 | 9.882  | 47.350 | 23.439 | 1.00 | 30.64 |
| ATOM | 1624 | C   | VAL | 49 | 9.500  | 45.862 | 23.366 | 1.00 | 31.81 |
| ATOM | 1625 | O   | VAL | 49 | 9.173  | 45.339 | 22.282 | 1.00 | 31.69 |
| ATOM | 1626 | CB  | VAL | 49 | 8.711  | 48.165 | 24.139 | 1.00 | 30.27 |
| ATOM | 1627 | CG1 | VAL | 49 | 9.066  | 49.625 | 24.338 | 1.00 | 27.05 |
| ATOM | 1628 | CG2 | VAL | 49 | 7.386  | 48.097 | 23.369 | 1.00 | 28.65 |
| ATOM | 1629 | N   | TYR | 50 | 9.592  | 45.187 | 24.510 | 1.00 | 32.49 |
| ATOM | 1630 | CA  | TYR | 50 | 9.011  | 43.848 | 24.698 | 1.00 | 33.92 |
| ATOM | 1631 | C   | TYR | 50 | 7.472  | 43.861 | 24.508 | 1.00 | 34.74 |
| ATOM | 1632 | O   | TYR | 50 | 6.795  | 44.800 | 24.894 | 1.00 | 34.44 |
| ATOM | 1633 | CB  | TYR | 50 | 9.391  | 43.337 | 26.100 | 1.00 | 34.27 |
| ATOM | 1634 | CG  | TYR | 50 | 8.732  | 42.066 | 26.497 | 1.00 | 34.16 |
| ATOM | 1635 | CD1 | TYR | 50 | 9.239  | 40.847 | 26.086 | 1.00 | 34.55 |
| ATOM | 1636 | CD2 | TYR | 50 | 7.621  | 42.076 | 27.334 | 1.00 | 34.69 |
| ATOM | 1637 | CE1 | TYR | 50 | 8.612  | 39.644 | 26.451 | 1.00 | 34.91 |
| ATOM | 1638 | CE2 | TYR | 50 | 7.008  | 40.907 | 27.724 | 1.00 | 34.31 |
| ATOM | 1639 | CZ  | TYR | 50 | 7.497  | 39.703 | 27.280 | 1.00 | 34.93 |
| ATOM | 1640 | OH  | TYR | 50 | 6.858  | 38.537 | 27.670 | 1.00 | 37.56 |
| ATOM | 1641 | N   | LEU | 51 | 6.920  | 42.846 | 23.856 | 1.00 | 36.01 |
| ATOM | 1642 | CA  | LEU | 51 | 5.459  | 42.792 | 23.743 | 1.00 | 38.06 |
| ATOM | 1643 | C   | LEU | 51 | 4.970  | 41.474 | 24.359 | 1.00 | 38.71 |
| ATOM | 1644 | O   | LEU | 51 | 5.357  | 40.387 | 23.891 | 1.00 | 38.72 |
| ATOM | 1645 | CB  | LEU | 51 | 4.966  | 42.912 | 22.293 | 1.00 | 38.26 |
| ATOM | 1646 | CG  | LEU | 51 | 3.483  | 43.291 | 22.071 | 1.00 | 39.97 |
| ATOM | 1647 | CD1 | LEU | 51 | 3.196  | 44.698 | 22.569 | 1.00 | 41.59 |
| ATOM | 1648 | CD2 | LEU | 51 | 3.106  | 43.214 | 20.601 | 1.00 | 39.18 |
| ATOM | 1649 | N   | PRO | 52 | 4.132  | 41.569 | 25.410 | 1.00 | 39.27 |
| ATOM | 1650 | CA  | PRO | 52 | 3.607  | 40.371 | 26.084 | 1.00 | 40.56 |
| ATOM | 1651 | C   | PRO | 52 | 2.762  | 39.489 | 25.170 | 1.00 | 40.53 |
| ATOM | 1652 | O   | PRO | 52 | 2.094  | 39.992 | 24.289 | 1.00 | 39.33 |
| ATOM | 1653 | CB  | PRO | 52 | 2.720  | 40.950 | 27.209 | 1.00 | 40.48 |
| ATOM | 1654 | CG  | PRO | 52 | 3.168  | 42.385 | 27.390 | 1.00 | 40.75 |
| ATOM | 1655 | CD  | PRO | 52 | 3.626  | 42.820 | 26.013 | 1.00 | 39.83 |
| ATOM | 1656 | N   | ALA | 53 | 2.808  | 38.180 | 25.420 | 1.00 | 42.43 |
| ATOM | 1657 | CA  | ALA | 53 | 2.081  | 37.157 | 24.663 | 1.00 | 44.05 |
| ATOM | 1658 | C   | ALA | 53 | 0.632  | 37.483 | 24.238 | 1.00 | 46.03 |
| ATOM | 1659 | O   | ALA | 53 | 0.269  | 37.306 | 23.079 | 1.00 | 45.37 |
| ATOM | 1660 | CB  | ALA | 53 | 2.158  | 35.809 | 25.400 | 1.00 | 44.31 |
| ATOM | 1661 | N   | GLU | 54 | -0.201 | 37.988 | 25.147 | 1.00 | 48.17 |
| ATOM | 1662 | CA  | GLU | 54 | -1.588 | 38.264 | 24.742 | 1.00 | 50.27 |
| ATOM | 1663 | C   | GLU | 54 | -1.866 | 39.724 | 24.298 | 1.00 | 50.27 |
| ATOM | 1664 | O   | GLU | 54 | -3.005 | 40.046 | 23.975 | 1.00 | 50.60 |
| ATOM | 1665 | CB  | GLU | 54 | -2.627 | 37.724 | 25.771 | 1.00 | 50.47 |
| ATOM | 1666 | CG  | GLU | 54 | -2.726 | 38.522 | 27.079 | 1.00 | 52.14 |
| ATOM | 1667 | CD  | GLU | 54 | -3.853 | 38.039 | 28.041 | 1.00 | 52.30 |
| ATOM | 1668 | OE1 | GLU | 54 | -3.510 | 37.353 | 29.047 | 1.00 | 53.98 |
| ATOM | 1669 | OE2 | GLU | 54 | -5.059 | 38.346 | 27.795 | 1.00 | 52.76 |
| ATOM | 1670 | N   | GLN | 55 | -0.842 | 40.587 | 24.264 | 1.00 | 49.80 |
| ATOM | 1671 | CA  | GLN | 55 | -1.008 | 41.957 | 23.723 | 1.00 | 49.67 |
| ATOM | 1672 | C   | GLN | 55 | -0.821 | 41.999 | 22.204 | 1.00 | 49.52 |
| ATOM | 1673 | O   | GLN | 55 | 0.162  | 41.460 | 21.673 | 1.00 | 48.68 |
| ATOM | 1674 | CB  | GLN | 55 | -0.060 | 42.944 | 24.415 | 1.00 | 49.73 |
| ATOM | 1675 | CG  | GLN | 55 | -0.274 | 44.423 | 24.053 | 1.00 | 49.02 |
| ATOM | 1676 | CD  | GLN | 55 | 0.539  | 45.355 | 24.963 | 1.00 | 50.64 |
| ATOM | 1677 | OE1 | GLN | 55 | 0.798  | 45.018 | 26.127 | 1.00 | 50.76 |
| ATOM | 1678 | NE2 | GLN | 55 | 0.928  | 46.548 | 24.442 | 1.00 | 50.99 |
| ATOM | 1679 | N   | LYS | 56 | -1.761 | 42.648 | 21.514 | 1.00 | 49.80 |
| ATOM | 1680 | CA  | LYS | 56 | -1.878 | 42.501 | 20.046 | 1.00 | 50.35 |
| ATOM | 1681 | C   | LYS | 56 | -0.832 | 43.295 | 19.269 | 1.00 | 48.93 |
| ATOM | 1682 | O   | LYS | 56 | -0.302 | 42.810 | 18.259 | 1.00 | 48.73 |
| ATOM | 1683 | CB  | LYS | 56 | -3.292 | 42.848 | 19.523 | 1.00 | 50.57 |
| ATOM | 1684 | CG  | LYS | 56 | -3.464 | 42.585 | 18.019 | 1.00 | 51.80 |
| ATOM | 1685 | CD  | LYS | 56 | -4.918 | 42.505 | 17.578 | 1.00 | 53.30 |
| ATOM | 1686 | CE  | LYS | 56 | -5.380 | 43.822 | 16.954 | 1.00 | 55.68 |
| ATOM | 1687 | NZ  | LYS | 56 | -6.597 | 44.405 | 17.633 | 1.00 | 59.22 |
| ATOM | 1688 | N   | GLY | 57 | -0.585 | 44.517 | 19.747 | 1.00 | 47.49 |
| ATOM | 1689 | CA  | GLY | 57 | 0.319  | 45.462 | 19.131 | 1.00 | 45.82 |
| ATOM | 1690 | C   | GLY | 57 | 0.834  | 46.492 | 20.127 | 1.00 | 45.53 |

TABLE 11-continued

Three-Dimensional Coordinates of *Neisseria gonorrhoeae* GCYH-IB·Mn$^{2+}$
(SEQ. ID. No. 8)

| ATOM | 1691 | O   | GLY | 57 | 0.337  | 46.616 | 21.261 | 1.00 | 44.75 |
|------|------|-----|-----|----|--------|--------|--------|------|-------|
| ATOM | 1692 | N   | THR | 58 | 1.867  | 47.218 | 19.715 | 1.00 | 44.32 |
| ATOM | 1693 | CA  | THR | 58 | 2.451  | 48.232 | 20.551 | 1.00 | 43.57 |
| ATOM | 1694 | C   | THR | 58 | 1.880  | 49.539 | 20.016 | 1.00 | 44.18 |
| ATOM | 1695 | O   | THR | 58 | 0.915  | 49.514 | 19.236 | 1.00 | 43.92 |
| ATOM | 1696 | CB  | THR | 58 | 4.020  | 48.180 | 20.514 | 1.00 | 43.34 |
| ATOM | 1697 | OG1 | THR | 58 | 4.567  | 49.161 | 21.411 | 1.00 | 42.06 |
| ATOM | 1698 | CG2 | THR | 58 | 4.552  | 48.425 | 19.087 | 1.00 | 41.24 |
| ATOM | 1699 | N   | HIS | 59 | 2.484  | 50.661 | 20.416 | 1.00 | 44.36 |
| ATOM | 1700 | CA  | HIS | 59 | 1.990  | 51.988 | 20.089 | 1.00 | 44.59 |
| ATOM | 1701 | C   | HIS | 59 | 3.042  | 52.738 | 19.315 | 1.00 | 43.83 |
| ATOM | 1702 | O   | HIS | 59 | 3.780  | 53.535 | 19.885 | 1.00 | 42.81 |
| ATOM | 1703 | CB  | HIS | 59 | 1.636  | 52.721 | 21.380 | 1.00 | 45.60 |
| ATOM | 1704 | CG  | HIS | 59 | 0.703  | 51.938 | 22.252 | 1.00 | 48.60 |
| ATOM | 1705 | ND1 | HIS | 59 | 1.144  | 51.135 | 23.288 | 1.00 | 51.29 |
| ATOM | 1706 | CD2 | HIS | 59 | −0.637 | 51.759 | 22.180 | 1.00 | 50.27 |
| ATOM | 1707 | CE1 | HIS | 59 | 0.109  | 50.533 | 23.847 | 1.00 | 51.31 |
| ATOM | 1708 | NE2 | HIS | 59 | −0.984 | 50.899 | 23.198 | 1.00 | 52.01 |
| ATOM | 1709 | N   | MET | 60 | 3.060  | 52.498 | 18.003 | 1.00 | 43.45 |
| ATOM | 1710 | CA  | MET | 60 | 4.118  | 52.968 | 17.111 | 1.00 | 43.58 |
| ATOM | 1711 | C   | MET | 60 | 4.408  | 54.470 | 17.126 | 1.00 | 42.81 |
| ATOM | 1712 | O   | MET | 60 | 5.568  | 54.862 | 17.000 | 1.00 | 43.78 |
| ATOM | 1713 | CB  | MET | 60 | 3.826  | 52.517 | 15.662 | 1.00 | 44.75 |
| ATOM | 1714 | CG  | MET | 60 | 3.874  | 50.996 | 15.481 | 1.00 | 45.80 |
| ATOM | 1715 | SD  | MET | 60 | 5.554  | 50.390 | 15.559 | 1.00 | 47.38 |
| ATOM | 1716 | CE  | MET | 60 | 5.341  | 48.695 | 15.015 | 1.00 | 46.89 |
| ATOM | 1717 | N   | SER | 61 | 3.378  | 55.316 | 17.240 | 1.00 | 41.77 |
| ATOM | 1718 | CA  | SER | 61 | 3.580  | 56.774 | 17.190 | 1.00 | 40.55 |
| ATOM | 1719 | C   | SER | 61 | 4.316  | 57.325 | 18.401 | 1.00 | 40.20 |
| ATOM | 1720 | O   | SER | 61 | 4.872  | 58.440 | 18.354 | 1.00 | 39.73 |
| ATOM | 1721 | CB  | SER | 61 | 2.253  | 57.505 | 17.058 | 1.00 | 40.87 |
| ATOM | 1722 | OG  | SER | 61 | 1.535  | 57.469 | 18.286 | 1.00 | 42.74 |
| ATOM | 1723 | N   | ARG | 62 | 4.306  | 56.572 | 19.502 | 1.00 | 38.76 |
| ATOM | 1724 | CA  | ARG | 62 | 4.907  | 57.064 | 20.760 | 1.00 | 37.81 |
| ATOM | 1725 | C   | ARG | 62 | 6.430  | 57.086 | 20.708 | 1.00 | 36.60 |
| ATOM | 1726 | O   | ARG | 62 | 7.053  | 57.867 | 21.407 | 1.00 | 35.27 |
| ATOM | 1727 | CB  | ARG | 62 | 4.471  | 56.197 | 21.946 | 1.00 | 38.07 |
| ATOM | 1728 | CG  | ARG | 62 | 2.986  | 56.087 | 22.103 | 1.00 | 37.78 |
| ATOM | 1729 | CD  | ARG | 62 | 2.650  | 55.479 | 23.453 | 1.00 | 37.88 |
| ATOM | 1730 | NE  | ARG | 62 | 1.202  | 55.356 | 23.598 | 1.00 | 37.07 |
| ATOM | 1731 | CZ  | ARG | 62 | 0.569  | 54.705 | 24.579 | 1.00 | 37.18 |
| ATOM | 1732 | NH1 | ARG | 62 | 1.229  | 54.097 | 25.571 | 1.00 | 37.21 |
| ATOM | 1733 | NH2 | ARG | 62 | −0.745 | 54.685 | 24.564 | 1.00 | 35.43 |
| ATOM | 1734 | N   | PHE | 63 | 7.029  | 56.198 | 19.900 | 1.00 | 36.09 |
| ATOM | 1735 | CA  | PHE | 63 | 8.464  | 56.204 | 19.720 | 1.00 | 35.73 |
| ATOM | 1736 | C   | PHE | 63 | 8.893  | 57.549 | 19.109 | 1.00 | 36.45 |
| ATOM | 1737 | O   | PHE | 63 | 9.793  | 58.207 | 19.617 | 1.00 | 36.12 |
| ATOM | 1738 | CB  | PHE | 63 | 8.934  | 55.038 | 18.850 | 1.00 | 35.41 |
| ATOM | 1739 | CG  | PHE | 63 | 8.621  | 53.693 | 19.413 | 1.00 | 34.78 |
| ATOM | 1740 | CD1 | PHE | 63 | 9.340  | 53.203 | 20.503 | 1.00 | 32.25 |
| ATOM | 1741 | CD2 | PHE | 63 | 7.598  | 52.921 | 18.852 | 1.00 | 33.93 |
| ATOM | 1742 | CE1 | PHE | 63 | 9.074  | 51.933 | 21.031 | 1.00 | 32.28 |
| ATOM | 1743 | CE2 | PHE | 63 | 7.303  | 51.643 | 19.376 | 1.00 | 34.29 |
| ATOM | 1744 | CZ  | PHE | 63 | 8.050  | 51.146 | 20.464 | 1.00 | 33.57 |
| ATOM | 1745 | N   | VAL | 64 | 8.236  | 57.948 | 18.020 | 1.00 | 37.27 |
| ATOM | 1746 | CA  | VAL | 64 | 8.517  | 59.230 | 17.375 | 1.00 | 37.13 |
| ATOM | 1747 | C   | VAL | 64 | 8.161  | 60.414 | 18.267 | 1.00 | 38.00 |
| ATOM | 1748 | O   | VAL | 64 | 8.928  | 61.374 | 18.346 | 1.00 | 38.05 |
| ATOM | 1749 | CB  | VAL | 64 | 7.771  | 59.348 | 15.995 | 1.00 | 37.68 |
| ATOM | 1750 | CG1 | VAL | 64 | 7.969  | 60.740 | 15.348 | 1.00 | 35.90 |
| ATOM | 1751 | CG2 | VAL | 64 | 8.246  | 58.302 | 15.051 | 1.00 | 35.99 |
| ATOM | 1752 | N   | ALA | 65 | 6.995  | 60.356 | 18.920 | 1.00 | 39.07 |
| ATOM | 1753 | CA  | ALA | 65 | 6.604  | 61.336 | 19.959 | 1.00 | 39.65 |
| ATOM | 1754 | C   | ALA | 65 | 7.709  | 61.560 | 20.985 | 1.00 | 39.89 |
| ATOM | 1755 | O   | ALA | 65 | 8.040  | 62.706 | 21.288 | 1.00 | 40.81 |
| ATOM | 1756 | CB  | ALA | 65 | 5.314  | 60.893 | 20.661 | 1.00 | 39.83 |
| ATOM | 1757 | N   | LEU | 66 | 8.289  | 60.476 | 21.511 | 1.00 | 39.65 |
| ATOM | 1758 | CA  | LEU | 66 | 9.366  | 60.572 | 22.481 | 1.00 | 39.87 |
| ATOM | 1759 | C   | LEU | 66 | 10.574 | 61.353 | 21.914 | 1.00 | 41.30 |
| ATOM | 1760 | O   | LEU | 66 | 11.115 | 62.244 | 22.594 | 1.00 | 40.47 |
| ATOM | 1761 | CB  | LEU | 66 | 9.791  | 59.179 | 22.920 | 1.00 | 40.26 |
| ATOM | 1762 | CG  | LEU | 66 | 10.824 | 59.054 | 24.047 | 1.00 | 40.85 |
| ATOM | 1763 | CD1 | LEU | 66 | 10.177 | 59.321 | 25.386 | 1.00 | 40.55 |
| ATOM | 1764 | CD2 | LEU | 66 | 11.503 | 57.695 | 24.065 | 1.00 | 39.84 |
| ATOM | 1765 | N   | GLU | 68 | 10.766 | 63.558 | 19.363 | 1.00 | 46.22 |
| ATOM | 1766 | CA  | GLU | 68 | 10.381 | 64.976 | 19.114 | 1.00 | 48.69 |
| ATOM | 1767 | C   | GLU | 68 | 10.315 | 65.841 | 20.391 | 1.00 | 50.90 |

TABLE 11-continued

Three-Dimensional Coordinates of *Neisseria gonorrhoeae* GCYH-IB·Mn$^{2+}$
(SEQ. ID. No. 8)

| ATOM | 1768 | O | GLU | 68 | 10.662 | 67.033 | 20.349 | 1.00 | 51.17 |
|------|------|-----|-----|----|--------|--------|--------|------|-------|
| ATOM | 1769 | CB | GLU | 68 | 9.037 | 65.069 | 18.353 | 1.00 | 48.22 |
| ATOM | 1770 | CG | GLU | 68 | 8.992 | 64.362 | 16.978 | 1.00 | 46.41 |
| ATOM | 1771 | CD | GLU | 68 | 9.820 | 65.064 | 15.886 | 1.00 | 47.69 |
| ATOM | 1772 | OE1 | GLU | 68 | 10.263 | 66.237 | 16.080 | 1.00 | 45.80 |
| ATOM | 1773 | OE2 | GLU | 68 | 10.032 | 64.419 | 14.824 | 1.00 | 47.66 |
| ATOM | 1774 | N | GLN | 69 | 9.878 | 65.225 | 21.502 | 1.00 | 53.44 |
| ATOM | 1775 | CA | GLN | 69 | 9.737 | 65.894 | 22.821 | 1.00 | 55.64 |
| ATOM | 1776 | C | GLN | 69 | 11.066 | 66.234 | 23.455 | 1.00 | 56.51 |
| ATOM | 1777 | O | GLN | 69 | 11.205 | 67.300 | 24.052 | 1.00 | 56.81 |
| ATOM | 1778 | CB | GLN | 69 | 8.960 | 65.033 | 23.819 | 1.00 | 56.03 |
| ATOM | 1779 | CG | GLN | 69 | 7.481 | 65.390 | 23.982 | 1.00 | 59.13 |
| ATOM | 1780 | CD | GLN | 69 | 6.553 | 64.171 | 23.830 | 1.00 | 61.60 |
| ATOM | 1781 | OE1 | GLN | 69 | 6.731 | 63.130 | 24.489 | 1.00 | 63.56 |
| ATOM | 1782 | NE2 | GLN | 69 | 5.565 | 64.296 | 22.941 | 1.00 | 62.80 |
| ATOM | 1783 | N | GLU | 85 | 12.285 | 56.401 | 29.960 | 1.00 | 35.51 |
| ATOM | 1784 | CA | GLU | 85 | 11.043 | 57.106 | 29.645 | 1.00 | 36.75 |
| ATOM | 1785 | C | GLU | 85 | 10.286 | 56.367 | 28.558 | 1.00 | 36.10 |
| ATOM | 1786 | O | GLU | 85 | 9.063 | 56.381 | 28.509 | 1.00 | 35.56 |
| ATOM | 1787 | CB | GLU | 85 | 11.345 | 58.521 | 29.186 | 1.00 | 37.91 |
| ATOM | 1788 | CG | GLU | 85 | 10.511 | 59.561 | 29.872 | 1.00 | 45.60 |
| ATOM | 1789 | CD | GLU | 85 | 10.938 | 60.971 | 29.494 | 1.00 | 51.33 |
| ATOM | 1790 | OE1 | GLU | 85 | 11.946 | 61.450 | 30.082 | 1.00 | 56.31 |
| ATOM | 1791 | OE2 | GLU | 85 | 10.262 | 61.599 | 28.612 | 1.00 | 57.98 |
| ATOM | 1792 | N | MET | 86 | 11.027 | 55.701 | 27.682 | 1.00 | 34.68 |
| ATOM | 1793 | CA | MET | 86 | 10.396 | 54.953 | 26.610 | 1.00 | 33.27 |
| ATOM | 1794 | C | MET | 86 | 9.602 | 53.755 | 27.109 | 1.00 | 32.94 |
| ATOM | 1795 | O | MET | 86 | 8.444 | 53.580 | 26.743 | 1.00 | 31.87 |
| ATOM | 1796 | CB | MET | 86 | 11.438 | 54.437 | 25.623 | 1.00 | 31.72 |
| ATOM | 1797 | CG | MET | 86 | 10.773 | 53.653 | 24.513 | 1.00 | 29.97 |
| ATOM | 1798 | SD | MET | 86 | 11.938 | 52.947 | 23.321 | 1.00 | 32.42 |
| ATOM | 1799 | CE | MET | 86 | 12.806 | 51.729 | 24.284 | 1.00 | 23.54 |
| ATOM | 1800 | N | VAL | 87 | 10.244 | 52.890 | 27.888 | 1.00 | 34.25 |
| ATOM | 1801 | CA | VAL | 87 | 9.560 | 51.671 | 28.364 | 1.00 | 35.93 |
| ATOM | 1802 | C | VAL | 87 | 8.348 | 52.052 | 29.271 | 1.00 | 36.89 |
| ATOM | 1803 | O | VAL | 87 | 7.303 | 51.369 | 29.273 | 1.00 | 36.38 |
| ATOM | 1804 | CB | VAL | 87 | 10.512 | 50.648 | 29.024 | 1.00 | 36.17 |
| ATOM | 1805 | CG1 | VAL | 87 | 11.577 | 50.146 | 28.033 | 1.00 | 36.15 |
| ATOM | 1806 | CG2 | VAL | 87 | 11.181 | 51.186 | 30.300 | 1.00 | 37.44 |
| ATOM | 1807 | N | ALA | 88 | 8.500 | 53.169 | 29.983 | 1.00 | 37.69 |
| ATOM | 1808 | CA | ALA | 88 | 7.412 | 53.758 | 30.793 | 1.00 | 39.22 |
| ATOM | 1809 | C | ALA | 88 | 6.275 | 54.182 | 29.879 | 1.00 | 39.76 |
| ATOM | 1810 | O | ALA | 88 | 5.118 | 53.774 | 30.063 | 1.00 | 40.54 |
| ATOM | 1811 | CB | ALA | 88 | 7.930 | 54.975 | 31.529 | 1.00 | 39.27 |
| ATOM | 1812 | N | LEU | 89 | 6.607 | 54.998 | 28.880 | 1.00 | 39.88 |
| ATOM | 1813 | CA | LEU | 89 | 5.615 | 55.547 | 27.936 | 1.00 | 40.55 |
| ATOM | 1814 | C | LEU | 89 | 4.903 | 54.464 | 27.096 | 1.00 | 39.98 |
| ATOM | 1815 | O | LEU | 89 | 3.701 | 54.531 | 26.799 | 1.00 | 40.50 |
| ATOM | 1816 | CB | LEU | 89 | 6.293 | 56.582 | 27.020 | 1.00 | 40.81 |
| ATOM | 1817 | CG | LEU | 89 | 5.482 | 57.249 | 25.912 | 1.00 | 41.42 |
| ATOM | 1818 | CD1 | LEU | 89 | 4.311 | 58.032 | 26.507 | 1.00 | 43.86 |
| ATOM | 1819 | CD2 | LEU | 89 | 6.373 | 58.178 | 25.071 | 1.00 | 41.85 |
| ATOM | 1820 | N | LEU | 90 | 5.634 | 53.451 | 26.699 | 1.00 | 39.63 |
| ATOM | 1821 | CA | LEU | 90 | 4.988 | 52.417 | 25.934 | 1.00 | 39.66 |
| ATOM | 1822 | C | LEU | 90 | 4.345 | 51.391 | 26.854 | 1.00 | 39.64 |
| ATOM | 1823 | O | LEU | 90 | 3.830 | 50.375 | 26.394 | 1.00 | 40.47 |
| ATOM | 1824 | CB | LEU | 90 | 5.975 | 51.790 | 24.943 | 1.00 | 38.91 |
| ATOM | 1825 | CG | LEU | 90 | 5.850 | 52.779 | 23.753 | 1.00 | 40.39 |
| ATOM | 1826 | CD1 | LEU | 90 | 7.044 | 53.680 | 23.526 | 1.00 | 36.51 |
| ATOM | 1827 | CD2 | LEU | 90 | 5.400 | 52.126 | 22.503 | 1.00 | 38.67 |
| ATOM | 1828 | N | ASP | 91 | 4.389 | 51.649 | 28.159 | 1.00 | 40.21 |
| ATOM | 1829 | CA | ASP | 91 | 3.915 | 50.674 | 29.157 | 1.00 | 39.95 |
| ATOM | 1830 | C | ASP | 91 | 4.453 | 49.246 | 28.929 | 1.00 | 38.80 |
| ATOM | 1831 | O | ASP | 91 | 3.678 | 48.282 | 28.926 | 1.00 | 38.19 |
| ATOM | 1832 | CB | ASP | 91 | 2.355 | 50.685 | 29.285 | 1.00 | 40.89 |
| ATOM | 1833 | CG | ASP | 91 | 1.796 | 51.938 | 30.023 | 1.00 | 43.50 |
| ATOM | 1834 | OD1 | ASP | 91 | 2.494 | 52.475 | 30.931 | 1.00 | 46.25 |
| ATOM | 1835 | OD2 | ASP | 91 | 0.645 | 52.381 | 29.723 | 1.00 | 42.88 |
| ATOM | 1836 | N | SER | 92 | 5.775 | 49.093 | 28.785 | 1.00 | 38.12 |
| ATOM | 1837 | CA | SER | 92 | 6.384 | 47.747 | 28.609 | 1.00 | 37.45 |
| ATOM | 1838 | C | SER | 92 | 7.380 | 47.396 | 29.694 | 1.00 | 38.08 |
| ATOM | 1839 | O | SER | 92 | 7.959 | 48.304 | 30.317 | 1.00 | 38.79 |
| ATOM | 1840 | CB | SER | 92 | 7.087 | 47.633 | 27.263 | 1.00 | 37.32 |
| ATOM | 1841 | OG | SER | 92 | 7.773 | 46.388 | 27.125 | 1.00 | 36.68 |
| ATOM | 1842 | N | ARG | 93 | 7.604 | 46.097 | 29.905 | 1.00 | 38.34 |
| ATOM | 1843 | CA | ARG | 93 | 8.632 | 45.629 | 30.871 | 1.00 | 39.41 |
| ATOM | 1844 | C | ARG | 93 | 10.085 | 45.856 | 30.407 | 1.00 | 38.10 |

TABLE 11-continued

Three-Dimensional Coordinates of *Neisseria gonorrhoeae* GCYH-IB·Mn$^{2+}$
(SEQ. ID. No. 8)

| ATOM | 1845 | O | ARG | 93 | 11.001 | 45.895 | 31.225 | 1.00 | 35.83 |
|---|---|---|---|---|---|---|---|---|---|
| ATOM | 1846 | CB | ARG | 93 | 8.453 | 44.139 | 31.247 | 1.00 | 41.31 |
| ATOM | 1847 | CG | ARG | 93 | 8.978 | 43.121 | 30.205 | 1.00 | 44.67 |
| ATOM | 1848 | CD | ARG | 93 | 9.790 | 41.938 | 30.865 | 1.00 | 50.90 |
| ATOM | 1849 | NE | ARG | 93 | 10.206 | 40.824 | 29.954 | 1.00 | 51.36 |
| ATOM | 1850 | CZ | ARG | 93 | 11.437 | 40.590 | 29.478 | 1.00 | 51.92 |
| ATOM | 1851 | NH1 | ARG | 93 | 12.467 | 41.370 | 29.790 | 1.00 | 54.64 |
| ATOM | 1852 | NH2 | ARG | 93 | 11.641 | 39.537 | 28.689 | 1.00 | 53.40 |
| ATOM | 1853 | N | ALA | 94 | 10.292 | 45.964 | 29.082 | 1.00 | 36.95 |
| ATOM | 1854 | CA | ALA | 94 | 11.653 | 46.011 | 28.533 | 1.00 | 35.38 |
| ATOM | 1855 | C | ALA | 94 | 11.703 | 46.705 | 27.171 | 1.00 | 35.03 |
| ATOM | 1856 | O | ALA | 94 | 10.680 | 46.841 | 26.484 | 1.00 | 33.23 |
| ATOM | 1857 | CB | ALA | 94 | 12.245 | 44.572 | 28.431 | 1.00 | 34.91 |
| TER | | | | | | | | | |
| ENDMDL | | | | | | | | | |
| MODEL | 2 | | | | | | | | |
| TER | | | | | | | | | |
| ATOM | 1 | N | ARG | 14 | 51.699 | 63.155 | −25.990 | 1.00 | 59.94 |
| ATOM | 2 | CA | ARG | 14 | 50.569 | 64.101 | −25.839 | 1.00 | 60.10 |
| ATOM | 3 | C | ARG | 14 | 49.765 | 63.744 | −24.590 | 1.00 | 59.52 |
| ATOM | 4 | O | ARG | 14 | 49.543 | 62.552 | −24.283 | 1.00 | 59.50 |
| ATOM | 5 | CB | ARG | 14 | 49.727 | 64.169 | −27.117 | 1.00 | 60.86 |
| ATOM | 6 | CG | ARG | 14 | 50.102 | 65.332 | −28.041 | 1.00 | 62.47 |
| ATOM | 7 | CD | ARG | 14 | 51.596 | 65.658 | −28.056 | 1.00 | 66.68 |
| ATOM | 8 | NE | ARG | 14 | 52.030 | 66.690 | −27.094 | 1.00 | 66.83 |
| ATOM | 9 | CZ | ARG | 14 | 52.974 | 66.531 | −26.153 | 1.00 | 74.89 |
| ATOM | 10 | NH1 | ARG | 14 | 53.616 | 65.358 | −25.985 | 1.00 | 70.24 |
| ATOM | 11 | NH2 | ARG | 14 | 53.281 | 67.559 | −25.359 | 1.00 | 70.54 |
| ATOM | 12 | N | ASN | 15 | 49.332 | 64.800 | −23.892 | 1.00 | 58.31 |
| ATOM | 13 | CA | ASN | 15 | 49.230 | 64.790 | −22.425 | 1.00 | 56.79 |
| ATOM | 14 | C | ASN | 15 | 47.825 | 64.669 | −21.839 | 1.00 | 54.53 |
| ATOM | 15 | O | ASN | 15 | 47.622 | 63.943 | −20.862 | 1.00 | 55.84 |
| ATOM | 16 | CB | ASN | 15 | 49.946 | 66.021 | −21.842 | 1.00 | 57.64 |
| ATOM | 17 | CG | ASN | 15 | 51.363 | 65.720 | −21.380 | 1.00 | 58.56 |
| ATOM | 18 | OD1 | ASN | 15 | 51.644 | 64.656 | −20.812 | 1.00 | 59.64 |
| ATOM | 19 | ND2 | ASN | 15 | 52.266 | 66.681 | −21.597 | 1.00 | 59.50 |
| ATOM | 20 | N | LEU | 16 | 46.876 | 65.374 | −22.445 | 1.00 | 50.71 |
| ATOM | 21 | CA | LEU | 16 | 45.451 | 65.266 | −22.128 | 1.00 | 45.72 |
| ATOM | 22 | C | LEU | 16 | 45.008 | 66.059 | −20.897 | 1.00 | 42.62 |
| ATOM | 23 | O | LEU | 16 | 45.480 | 65.849 | −19.781 | 1.00 | 41.21 |
| ATOM | 24 | CB | LEU | 16 | 44.990 | 63.823 | −22.066 | 1.00 | 46.03 |
| ATOM | 25 | CG | LEU | 16 | 44.014 | 63.129 | −23.024 | 1.00 | 45.53 |
| ATOM | 26 | CD1 | LEU | 16 | 44.094 | 63.555 | −24.479 | 1.00 | 46.94 |
| ATOM | 27 | CD2 | LEU | 16 | 44.289 | 61.658 | −22.907 | 1.00 | 42.24 |
| ATOM | 28 | N | PRO | 17 | 44.091 | 66.999 | −21.118 | 1.00 | 39.73 |
| ATOM | 29 | CA | PRO | 17 | 43.589 | 67.732 | −19.976 | 1.00 | 37.59 |
| ATOM | 30 | C | PRO | 17 | 42.594 | 66.792 | −19.285 | 1.00 | 35.06 |
| ATOM | 31 | O | PRO | 17 | 41.991 | 65.908 | −19.928 | 1.00 | 34.66 |
| ATOM | 32 | CB | PRO | 17 | 42.862 | 68.914 | −20.612 | 1.00 | 37.49 |
| ATOM | 33 | CG | PRO | 17 | 42.391 | 68.361 | −21.904 | 1.00 | 38.46 |
| ATOM | 34 | CD | PRO | 17 | 43.431 | 67.395 | −22.375 | 1.00 | 39.21 |
| ATOM | 35 | N | ILE | 18 | 42.450 | 66.965 | −17.988 | 1.00 | 32.48 |
| ATOM | 36 | CA | ILE | 18 | 41.485 | 66.174 | −17.234 | 1.00 | 29.75 |
| ATOM | 37 | C | ILE | 18 | 40.315 | 67.048 | −16.866 | 1.00 | 28.71 |
| ATOM | 38 | O | ILE | 18 | 40.492 | 68.138 | −16.313 | 1.00 | 29.46 |
| ATOM | 39 | CB | ILE | 18 | 42.172 | 65.505 | −16.010 | 1.00 | 29.27 |
| ATOM | 40 | CG1 | ILE | 18 | 43.186 | 64.487 | −16.555 | 1.00 | 28.75 |
| ATOM | 41 | CG2 | ILE | 18 | 41.139 | 64.819 | −15.144 | 1.00 | 26.93 |
| ATOM | 42 | CD1 | ILE | 18 | 44.188 | 64.021 | −15.568 | 1.00 | 29.65 |
| ATOM | 43 | N | ASN | 19 | 39.124 | 66.588 | −17.218 | 1.00 | 27.84 |
| ATOM | 44 | CA | ASN | 19 | 37.917 | 67.332 | −17.011 | 1.00 | 28.72 |
| ATOM | 45 | C | ASN | 19 | 37.791 | 67.749 | −15.535 | 1.00 | 29.30 |
| ATOM | 46 | O | ASN | 19 | 37.556 | 68.901 | −15.230 | 1.00 | 29.67 |
| ATOM | 47 | CB | ASN | 19 | 36.692 | 66.523 | −17.443 | 1.00 | 27.56 |
| ATOM | 48 | CG | ASN | 19 | 36.566 | 66.383 | −18.934 | 1.00 | 30.11 |
| ATOM | 49 | OD1 | ASN | 19 | 35.628 | 66.910 | −19.537 | 1.00 | 35.03 |
| ATOM | 50 | ND2 | ASN | 19 | 37.457 | 65.617 | −19.541 | 1.00 | 26.59 |
| ATOM | 51 | N | GLY | 22 | 40.265 | 65.648 | −8.214 | 1.00 | 25.74 |
| ATOM | 52 | CA | GLY | 22 | 40.312 | 66.105 | −6.847 | 1.00 | 25.43 |
| ATOM | 53 | C | GLY | 22 | 39.912 | 65.005 | −5.893 | 1.00 | 25.13 |
| ATOM | 54 | O | GLY | 22 | 40.462 | 63.857 | −5.962 | 1.00 | 24.40 |
| ATOM | 55 | N | TYR | 50 | 39.658 | 71.451 | −12.980 | 1.00 | 30.77 |
| ATOM | 56 | CA | TYR | 50 | 40.097 | 71.065 | −14.333 | 1.00 | 31.30 |
| ATOM | 57 | C | TYR | 50 | 41.584 | 71.055 | −14.291 | 1.00 | 31.89 |
| ATOM | 58 | O | TYR | 50 | 42.174 | 71.917 | −13.663 | 1.00 | 31.71 |
| ATOM | 59 | CB | TYR | 50 | 39.619 | 72.128 | −15.301 | 1.00 | 32.58 |
| ATOM | 60 | CG | TYR | 50 | 40.188 | 72.091 | −16.695 | 1.00 | 33.26 |

TABLE 11-continued

Three-Dimensional Coordinates of *Neisseria gonorrhoeae* GCYH-IB·Mn$^{2+}$
(SEQ. ID. No. 8)

| ATOM | 61 | CD1 | TYR | 50 | 39.629 | 71.282 | −17.651 | 1.00 | 32.16 |
|---|---|---|---|---|---|---|---|---|---|
| ATOM | 62 | CD2 | TYR | 50 | 41.235 | 72.942 | −17.067 | 1.00 | 34.15 |
| ATOM | 63 | CE1 | TYR | 50 | 40.135 | 71.254 | −18.975 | 1.00 | 35.06 |
| ATOM | 64 | CE2 | TYR | 50 | 41.748 | 72.932 | −18.387 | 1.00 | 34.47 |
| ATOM | 65 | CZ | TYR | 50 | 41.182 | 72.084 | −19.318 | 1.00 | 34.05 |
| ATOM | 66 | OH | TYR | 50 | 41.636 | 72.058 | −20.629 | 1.00 | 36.34 |
| ATOM | 67 | N | LEU | 51 | 42.199 | 70.064 | −14.925 | 1.00 | 32.43 |
| ATOM | 68 | CA | LEU | 51 | 43.649 | 69.995 | −15.047 | 1.00 | 33.24 |
| ATOM | 69 | C | LEU | 51 | 44.061 | 70.148 | −16.526 | 1.00 | 33.57 |
| ATOM | 70 | O | LEU | 51 | 43.695 | 69.305 | −17.330 | 1.00 | 31.07 |
| ATOM | 71 | CB | LEU | 51 | 44.161 | 68.642 | −14.528 | 1.00 | 32.42 |
| ATOM | 72 | CG | LEU | 51 | 45.656 | 68.642 | −14.277 | 1.00 | 33.30 |
| ATOM | 73 | CD1 | LEU | 51 | 46.001 | 69.646 | −13.207 | 1.00 | 32.77 |
| ATOM | 74 | CD2 | LEU | 51 | 46.156 | 67.251 | −13.840 | 1.00 | 33.73 |
| ATOM | 75 | N | PRO | 52 | 44.803 | 71.240 | −16.884 | 1.00 | 35.48 |
| ATOM | 76 | CA | PRO | 52 | 45.196 | 71.393 | −18.303 | 1.00 | 36.24 |
| ATOM | 77 | C | PRO | 52 | 46.242 | 70.341 | −18.713 | 1.00 | 37.08 |
| ATOM | 78 | O | PRO | 52 | 46.981 | 69.804 | −17.867 | 1.00 | 35.03 |
| ATOM | 79 | CB | PRO | 52 | 45.803 | 72.800 | −18.378 | 1.00 | 36.44 |
| ATOM | 80 | CG | PRO | 52 | 46.191 | 73.152 | −16.968 | 1.00 | 37.84 |
| ATOM | 81 | CD | PRO | 52 | 45.255 | 72.361 | −16.042 | 1.00 | 35.65 |
| ATOM | 82 | N | ALA | 53 | 46.312 | 70.068 | −20.008 | 1.00 | 39.26 |
| ATOM | 83 | CA | ALA | 53 | 47.259 | 69.078 | −20.509 | 1.00 | 41.52 |
| ATOM | 84 | C | ALA | 53 | 48.632 | 69.158 | −19.902 | 1.00 | 43.70 |
| ATOM | 85 | O | ALA | 53 | 49.213 | 68.120 | −19.542 | 1.00 | 44.05 |
| ATOM | 86 | CB | ALA | 53 | 47.343 | 69.125 | −22.028 | 1.00 | 41.87 |
| ATOM | 87 | N | GLU | 54 | 49.176 | 70.369 | −19.770 | 1.00 | 46.18 |
| ATOM | 88 | CA | GLU | 54 | 50.595 | 70.473 | −19.416 | 1.00 | 48.84 |
| ATOM | 89 | C | GLU | 54 | 50.950 | 70.231 | −17.960 | 1.00 | 48.48 |
| ATOM | 90 | O | GLU | 54 | 52.143 | 70.110 | −17.626 | 1.00 | 48.68 |
| ATOM | 91 | CB | GLU | 54 | 51.290 | 71.741 | −19.988 | 1.00 | 49.42 |
| ATOM | 92 | CG | GLU | 54 | 50.930 | 73.116 | −19.376 | 1.00 | 51.16 |
| ATOM | 93 | CD | GLU | 54 | 51.905 | 74.263 | −19.853 | 1.00 | 52.55 |
| ATOM | 94 | OE1 | GLU | 54 | 51.600 | 75.467 | −19.611 | 1.00 | 55.01 |
| ATOM | 95 | OE2 | GLU | 54 | 52.984 | 73.964 | −20.462 | 1.00 | 56.97 |
| ATOM | 96 | N | GLN | 55 | 49.943 | 70.156 | −17.098 | 1.00 | 47.97 |
| ATOM | 97 | CA | GLN | 55 | 50.192 | 70.024 | −15.657 | 1.00 | 48.24 |
| ATOM | 98 | C | GLN | 55 | 50.070 | 68.560 | −15.229 | 1.00 | 47.26 |
| ATOM | 99 | O | GLN | 55 | 49.114 | 67.887 | −15.588 | 1.00 | 46.59 |
| ATOM | 100 | CB | GLN | 55 | 49.222 | 70.920 | −14.877 | 1.00 | 48.23 |
| ATOM | 101 | CG | GLN | 55 | 49.460 | 70.937 | −13.359 | 1.00 | 49.79 |
| ATOM | 102 | CD | GLN | 55 | 48.669 | 72.024 | −12.661 | 1.00 | 49.97 |
| ATOM | 103 | OE1 | GLN | 55 | 48.367 | 73.045 | −13.266 | 1.00 | 53.57 |
| ATOM | 104 | NE2 | GLN | 55 | 48.337 | 71.819 | −11.382 | 1.00 | 50.86 |
| ATOM | 105 | N | LYS | 56 | 51.043 | 68.068 | −14.471 | 1.00 | 47.46 |
| ATOM | 106 | CA | LYS | 56 | 51.091 | 66.651 | −14.130 | 1.00 | 48.23 |
| ATOM | 107 | C | LYS | 56 | 49.978 | 66.288 | −13.149 | 1.00 | 47.43 |
| ATOM | 108 | O | LYS | 56 | 49.311 | 65.270 | −13.323 | 1.00 | 47.38 |
| ATOM | 109 | CB | LYS | 56 | 52.461 | 66.246 | −13.542 | 1.00 | 48.49 |
| ATOM | 110 | CG | LYS | 56 | 52.559 | 64.719 | −13.239 | 1.00 | 50.23 |
| ATOM | 111 | CD | LYS | 56 | 53.838 | 64.316 | −12.483 | 1.00 | 51.07 |
| ATOM | 112 | CE | LYS | 56 | 54.040 | 65.144 | −11.199 | 1.00 | 54.39 |
| ATOM | 113 | NZ | LYS | 56 | 55.448 | 65.054 | −10.676 | 1.00 | 56.64 |
| ATOM | 114 | N | GLY | 57 | 49.801 | 67.120 | −12.124 | 1.00 | 46.67 |
| ATOM | 115 | CA | GLY | 57 | 48.811 | 66.866 | −11.099 | 1.00 | 46.24 |
| ATOM | 116 | C | GLY | 57 | 48.282 | 68.107 | −10.412 | 1.00 | 46.03 |
| ATOM | 117 | O | GLY | 57 | 48.843 | 69.212 | −10.570 | 1.00 | 46.27 |
| ATOM | 118 | N | THR | 58 | 47.195 | 67.911 | −9.654 | 1.00 | 45.17 |
| ATOM | 119 | CA | THR | 58 | 46.597 | 68.937 | −8.810 | 1.00 | 43.95 |
| ATOM | 120 | C | THR | 58 | 47.170 | 68.864 | −7.387 | 1.00 | 43.93 |
| ATOM | 121 | O | THR | 58 | 48.149 | 68.150 | −7.156 | 1.00 | 43.84 |
| ATOM | 122 | CB | THR | 58 | 45.031 | 68.866 | −8.784 | 1.00 | 43.76 |
| ATOM | 123 | OG1 | THR | 58 | 44.529 | 70.079 | −8.239 | 1.00 | 42.58 |
| ATOM | 124 | CG2 | THR | 58 | 44.481 | 67.663 | −7.957 | 1.00 | 41.26 |
| ATOM | 125 | N | HIS | 59 | 46.542 | 69.590 | −6.456 | 1.00 | 42.61 |
| ATOM | 126 | CA | HIS | 59 | 47.038 | 69.729 | −5.097 | 1.00 | 42.55 |
| ATOM | 127 | C | HIS | 59 | 46.006 | 69.244 | −4.075 | 1.00 | 41.58 |
| ATOM | 128 | O | HIS | 59 | 45.185 | 70.018 | −3.565 | 1.00 | 40.93 |
| ATOM | 129 | CB | HIS | 59 | 47.431 | 71.174 | −4.868 | 1.00 | 43.03 |
| ATOM | 130 | CG | HIS | 59 | 48.369 | 71.688 | −5.915 | 1.00 | 46.13 |
| ATOM | 131 | ND1 | HIS | 59 | 47.926 | 72.295 | −7.076 | 1.00 | 48.89 |
| ATOM | 132 | CD2 | HIS | 59 | 49.716 | 71.610 | −6.019 | 1.00 | 48.32 |
| ATOM | 133 | CE1 | HIS | 59 | 48.966 | 72.593 | −7.840 | 1.00 | 48.82 |
| ATOM | 134 | NE2 | HIS | 59 | 50.063 | 72.187 | −7.222 | 1.00 | 50.35 |
| ATOM | 135 | N | MET | 60 | 46.054 | 67.949 | −3.790 | 1.00 | 40.23 |
| ATOM | 136 | CA | MET | 60 | 44.936 | 67.253 | −3.145 | 1.00 | 38.85 |
| ATOM | 137 | C | MET | 60 | 44.631 | 67.691 | −1.718 | 1.00 | 37.25 |

TABLE 11-continued

Three-Dimensional Coordinates of *Neisseria gonorrhoeae* GCYH-IB·Mn$^{2+}$
(SEQ. ID. No. 8)

| ATOM | 138 | O | MET | 60 | 43.465 | 67.703 | −1.303 | 1.00 | 37.16 |
|---|---|---|---|---|---|---|---|---|---|
| ATOM | 139 | CB | MET | 60 | 45.147 | 65.734 | −3.231 | 1.00 | 40.07 |
| ATOM | 140 | CG | MET | 60 | 45.182 | 65.202 | −4.688 | 1.00 | 40.71 |
| ATOM | 141 | SD | MET | 60 | 43.511 | 64.820 | −5.252 | 1.00 | 45.21 |
| ATOM | 142 | CE | MET | 60 | 43.801 | 63.999 | −6.813 | 1.00 | 42.50 |
| ATOM | 143 | N | SER | 61 | 45.652 | 68.067 | −0.956 | 1.00 | 36.21 |
| ATOM | 144 | CA | SER | 61 | 45.423 | 68.452 | 0.429 | 1.00 | 35.39 |
| ATOM | 145 | C | SER | 61 | 44.706 | 69.789 | 0.540 | 1.00 | 35.50 |
| ATOM | 146 | O | SER | 61 | 44.116 | 70.095 | 1.581 | 1.00 | 35.82 |
| ATOM | 147 | CB | SER | 61 | 46.719 | 68.519 | 1.204 | 1.00 | 36.22 |
| ATOM | 148 | OG | SER | 61 | 47.456 | 69.699 | 0.911 | 1.00 | 36.27 |
| ATOM | 149 | N | ARG | 62 | 44.724 | 70.576 | −0.533 | 1.00 | 34.65 |
| ATOM | 150 | CA | ARG | 62 | 44.188 | 71.946 | −0.507 | 1.00 | 34.67 |
| ATOM | 151 | C | ARG | 62 | 42.670 | 71.915 | −0.519 | 1.00 | 33.66 |
| ATOM | 152 | O | ARG | 62 | 42.029 | 72.852 | −0.064 | 1.00 | 33.93 |
| ATOM | 153 | CB | ARG | 62 | 44.700 | 72.765 | −1.718 | 1.00 | 35.39 |
| ATOM | 154 | CG | ARG | 62 | 46.213 | 73.028 | −1.757 | 1.00 | 35.71 |
| ATOM | 155 | CD | ARG | 62 | 46.596 | 73.881 | −2.992 | 1.00 | 36.59 |
| ATOM | 156 | NE | ARG | 62 | 48.060 | 73.991 | −3.152 | 1.00 | 40.81 |
| ATOM | 157 | CZ | ARG | 62 | 48.673 | 74.793 | −4.030 | 1.00 | 42.85 |
| ATOM | 158 | NH1 | ARG | 62 | 47.947 | 75.568 | −4.833 | 1.00 | 42.89 |
| ATOM | 159 | NH2 | ARG | 62 | 50.010 | 74.829 | −4.101 | 1.00 | 39.58 |
| ATOM | 160 | N | PHE | 63 | 42.080 | 70.851 | −1.073 | 1.00 | 31.76 |
| ATOM | 161 | CA | PHE | 63 | 40.621 | 70.685 | −1.039 | 1.00 | 29.77 |
| ATOM | 162 | C | PHE | 63 | 40.169 | 70.511 | 0.413 | 1.00 | 29.97 |
| ATOM | 163 | O | PHE | 63 | 39.205 | 71.121 | 0.833 | 1.00 | 29.60 |
| ATOM | 164 | CB | PHE | 63 | 40.155 | 69.450 | −1.815 | 1.00 | 29.04 |
| ATOM | 165 | CG | PHE | 63 | 40.440 | 69.502 | −3.280 | 1.00 | 24.94 |
| ATOM | 166 | CD1 | PHE | 63 | 39.661 | 70.280 | −4.105 | 1.00 | 25.06 |
| ATOM | 167 | CD2 | PHE | 63 | 41.475 | 68.758 | −3.828 | 1.00 | 25.62 |
| ATOM | 168 | CE1 | PHE | 63 | 39.904 | 70.352 | −5.464 | 1.00 | 25.26 |
| ATOM | 169 | CE2 | PHE | 63 | 41.738 | 68.810 | −5.202 | 1.00 | 27.19 |
| ATOM | 170 | CZ | PHE | 63 | 40.938 | 69.618 | −6.022 | 1.00 | 26.37 |
| ATOM | 171 | N | VAL | 64 | 40.880 | 69.691 | 1.178 | 1.00 | 29.57 |
| ATOM | 172 | CA | VAL | 64 | 40.513 | 69.476 | 2.578 | 1.00 | 29.55 |
| ATOM | 173 | C | VAL | 64 | 40.837 | 70.749 | 3.361 | 1.00 | 30.87 |
| ATOM | 174 | O | VAL | 64 | 40.065 | 71.110 | 4.227 | 1.00 | 30.92 |
| ATOM | 175 | CB | VAL | 64 | 41.256 | 68.306 | 3.207 | 1.00 | 29.58 |
| ATOM | 176 | CG1 | VAL | 64 | 40.690 | 68.037 | 4.582 | 1.00 | 30.02 |
| ATOM | 177 | CG2 | VAL | 64 | 41.126 | 67.008 | 2.311 | 1.00 | 27.42 |
| ATOM | 178 | N | ALA | 65 | 41.967 | 71.415 | 3.068 | 1.00 | 31.39 |
| ATOM | 179 | CA | ALA | 65 | 42.338 | 72.696 | 3.733 | 1.00 | 32.56 |
| ATOM | 180 | C | ALA | 65 | 41.193 | 73.717 | 3.642 | 1.00 | 33.22 |
| ATOM | 181 | O | ALA | 65 | 40.842 | 74.399 | 4.620 | 1.00 | 33.73 |
| ATOM | 182 | CB | ALA | 65 | 43.688 | 73.301 | 3.097 | 1.00 | 32.21 |
| ATOM | 183 | N | LEU | 66 | 40.610 | 73.829 | 2.448 | 1.00 | 33.30 |
| ATOM | 184 | CA | LEU | 66 | 39.528 | 74.760 | 2.226 | 1.00 | 32.82 |
| ATOM | 185 | C | LEU | 66 | 38.364 | 74.505 | 3.196 | 1.00 | 33.60 |
| ATOM | 186 | O | LEU | 66 | 37.849 | 75.424 | 3.856 | 1.00 | 32.31 |
| ATOM | 187 | CB | LEU | 66 | 39.061 | 74.662 | 0.775 | 1.00 | 31.90 |
| ATOM | 188 | CG | LEU | 66 | 37.995 | 75.668 | 0.377 | 1.00 | 32.41 |
| ATOM | 189 | CD1 | LEU | 66 | 38.590 | 77.115 | 0.361 | 1.00 | 35.12 |
| ATOM | 190 | CD2 | LEU | 66 | 37.421 | 75.285 | −0.955 | 1.00 | 31.49 |
| ATOM | 191 | N | VAL | 87 | 38.796 | 77.246 | −6.771 | 1.00 | 36.21 |
| ATOM | 192 | CA | VAL | 87 | 39.569 | 77.287 | −8.040 | 1.00 | 37.84 |
| ATOM | 193 | C | VAL | 87 | 40.803 | 78.166 | −7.905 | 1.00 | 39.36 |
| ATOM | 194 | O | VAL | 87 | 41.838 | 77.892 | −8.531 | 1.00 | 40.24 |
| ATOM | 195 | CB | VAL | 87 | 38.730 | 77.746 | −9.245 | 1.00 | 38.61 |
| ATOM | 196 | CG1 | VAL | 87 | 37.639 | 76.748 | −9.519 | 1.00 | 37.63 |
| ATOM | 197 | CG2 | VAL | 87 | 38.122 | 79.147 | −9.011 | 1.00 | 37.58 |
| ATOM | 198 | N | ALA | 88 | 40.699 | 79.210 | −7.071 | 1.00 | 39.92 |
| ATOM | 199 | CA | ALA | 88 | 41.823 | 80.128 | −6.824 | 1.00 | 40.37 |
| ATOM | 200 | C | ALA | 88 | 42.893 | 79.477 | −5.987 | 1.00 | 40.95 |
| ATOM | 201 | O | ALA | 88 | 44.082 | 79.564 | −6.326 | 1.00 | 41.91 |
| ATOM | 202 | CB | ALA | 88 | 41.339 | 81.398 | −6.156 | 1.00 | 40.29 |
| ATOM | 203 | N | LEU | 89 | 42.467 | 78.793 | −4.917 | 1.00 | 40.06 |
| ATOM | 204 | CA | LEU | 89 | 43.380 | 78.086 | −4.017 | 1.00 | 40.50 |
| ATOM | 205 | C | LEU | 89 | 44.174 | 76.985 | −4.745 | 1.00 | 39.98 |
| ATOM | 206 | O | LEU | 89 | 45.363 | 76.752 | −4.462 | 1.00 | 38.44 |
| ATOM | 207 | CB | LEU | 89 | 42.588 | 77.469 | −2.848 | 1.00 | 40.68 |
| ATOM | 208 | CG | LEU | 89 | 43.370 | 76.638 | −1.820 | 1.00 | 41.74 |
| ATOM | 209 | CD1 | LEU | 89 | 44.363 | 77.552 | −1.059 | 1.00 | 44.04 |
| ATOM | 210 | CD2 | LEU | 89 | 42.426 | 75.936 | −0.818 | 1.00 | 40.51 |
| ATOM | 211 | N | LEU | 90 | 43.494 | 76.319 | −5.678 | 1.00 | 40.31 |
| ATOM | 212 | CA | LEU | 90 | 44.053 | 75.180 | −6.402 | 1.00 | 40.41 |
| ATOM | 213 | C | LEU | 90 | 44.739 | 75.607 | −7.709 | 1.00 | 41.69 |
| ATOM | 214 | O | LEU | 90 | 45.256 | 74.765 | −8.483 | 1.00 | 40.27 |

TABLE 11-continued

Three-Dimensional Coordinates of *Neisseria gonorrhoeae* GCYH-IB·Mn$^{2+}$
(SEQ. ID. No. 8)

| ATOM | 215 | CB | LEU | 90 | 42.955 | 74.186 | −6.699 | 1.00 | 39.60 |
|---|---|---|---|---|---|---|---|---|---|
| ATOM | 216 | CG | LEU | 90 | 43.070 | 73.338 | −5.455 | 1.00 | 38.10 |
| ATOM | 217 | CD1 | LEU | 90 | 41.936 | 73.564 | −4.502 | 1.00 | 33.65 |
| ATOM | 218 | CD2 | LEU | 90 | 43.272 | 71.963 | −5.834 | 1.00 | 34.46 |
| ATOM | 219 | N | ASP | 91 | 44.738 | 76.926 | −7.925 | 1.00 | 41.99 |
| ATOM | 220 | CA | ASP | 91 | 45.381 | 77.552 | −9.110 | 1.00 | 42.31 |
| ATOM | 221 | C | ASP | 91 | 44.863 | 76.971 | −10.409 | 1.00 | 41.35 |
| ATOM | 222 | O | ASP | 91 | 45.669 | 76.497 | −11.225 | 1.00 | 42.00 |
| ATOM | 223 | CB | ASP | 91 | 46.900 | 77.345 | −9.073 | 1.00 | 42.72 |
| ATOM | 224 | CG | ASP | 91 | 47.545 | 77.948 | −7.880 | 1.00 | 46.18 |
| ATOM | 225 | OD1 | ASP | 91 | 47.169 | 79.083 | −7.503 | 1.00 | 52.04 |
| ATOM | 226 | OD2 | ASP | 91 | 48.439 | 77.296 | −7.313 | 1.00 | 48.88 |
| ATOM | 227 | N | SER | 92 | 43.543 | 76.994 | −10.605 | 1.00 | 40.27 |
| ATOM | 228 | CA | SER | 92 | 42.920 | 76.417 | −11.793 | 1.00 | 39.39 |
| ATOM | 229 | C | SER | 92 | 41.864 | 77.332 | −12.372 | 1.00 | 40.36 |
| ATOM | 230 | O | SER | 92 | 41.378 | 78.237 | −11.699 | 1.00 | 42.15 |
| ATOM | 231 | CB | SER | 92 | 42.236 | 75.078 | −11.488 | 1.00 | 39.41 |
| ATOM | 232 | OG | SER | 92 | 41.483 | 74.625 | −12.630 | 1.00 | 34.46 |
| ATOM | 233 | N | ARG | 93 | 41.454 | 77.042 | −13.594 | 1.00 | 40.29 |
| ATOM | 234 | CA | ARG | 93 | 40.521 | 77.885 | −14.309 | 1.00 | 42.05 |
| ATOM | 235 | C | ARG | 93 | 39.068 | 77.472 | −14.088 | 1.00 | 40.68 |
| ATOM | 236 | O | ARG | 93 | 38.152 | 78.227 | −14.428 | 1.00 | 41.97 |
| ATOM | 237 | CB | ARG | 93 | 40.847 | 77.844 | −15.799 | 1.00 | 42.19 |
| ATOM | 238 | CG | ARG | 93 | 39.854 | 77.034 | −16.613 | 1.00 | 45.63 |
| ATOM | 239 | CD | ARG | 93 | 40.382 | 76.504 | −17.978 | 1.00 | 46.18 |
| ATOM | 240 | NE | ARG | 93 | 39.617 | 75.295 | −18.363 | 1.00 | 54.20 |
| ATOM | 241 | CZ | ARG | 93 | 38.309 | 75.266 | −18.680 | 1.00 | 54.69 |
| ATOM | 242 | NH1 | ARG | 93 | 37.576 | 76.384 | −18.686 | 1.00 | 58.29 |
| ATOM | 243 | NH2 | ARG | 93 | 37.720 | 74.113 | −18.984 | 1.00 | 56.33 |
| ATOM | 244 | N | ARG | 105 | 36.120 | 36.645 | −15.040 | 1.00 | 26.77 |
| ATOM | 245 | CA | ARG | 105 | 37.159 | 36.313 | −15.992 | 1.00 | 29.12 |
| ATOM | 246 | C | ARG | 105 | 38.248 | 35.521 | −15.275 | 1.00 | 30.18 |
| ATOM | 247 | O | ARG | 105 | 38.650 | 35.872 | −14.149 | 1.00 | 30.90 |
| ATOM | 248 | CB | ARG | 105 | 37.726 | 37.566 | −16.629 | 1.00 | 28.06 |
| ATOM | 249 | CG | ARG | 105 | 38.582 | 37.254 | −17.864 | 1.00 | 30.28 |
| ATOM | 250 | CD | ARG | 105 | 39.194 | 38.513 | −18.372 | 1.00 | 32.89 |
| ATOM | 251 | NE | ARG | 105 | 39.735 | 38.397 | −19.720 | 1.00 | 34.73 |
| ATOM | 252 | CZ | ARG | 105 | 40.665 | 39.201 | −20.218 | 1.00 | 33.07 |
| ATOM | 253 | NH1 | ARG | 105 | 41.174 | 40.185 | −19.454 | 1.00 | 33.32 |
| ATOM | 254 | NH2 | ARG | 105 | 41.061 | 39.029 | −21.482 | 1.00 | 31.76 |
| ATOM | 255 | N | LYS | 106 | 38.708 | 34.443 | −15.909 | 1.00 | 31.12 |
| ATOM | 256 | CA | LYS | 106 | 39.798 | 33.620 | −15.380 | 1.00 | 32.80 |
| ATOM | 257 | C | LYS | 106 | 41.145 | 34.298 | −15.628 | 1.00 | 32.96 |
| ATOM | 258 | O | LYS | 106 | 41.449 | 34.697 | −16.783 | 1.00 | 33.18 |
| ATOM | 259 | CB | LYS | 106 | 39.757 | 32.229 | −16.041 | 1.00 | 34.65 |
| ATOM | 260 | CG | LYS | 106 | 40.696 | 31.185 | −15.401 | 1.00 | 39.55 |
| ATOM | 261 | CD | LYS | 106 | 40.008 | 30.232 | −14.406 | 1.00 | 47.35 |
| ATOM | 262 | CE | LYS | 106 | 38.963 | 29.324 | −15.070 | 1.00 | 49.33 |
| ATOM | 263 | NZ | LYS | 106 | 39.461 | 28.601 | −16.300 | 1.00 | 54.56 |
| ATOM | 264 | N | LYS | 107 | 41.930 | 34.484 | −14.557 | 1.00 | 31.08 |
| ATOM | 265 | CA | LYS | 107 | 43.263 | 35.059 | −14.676 | 1.00 | 30.55 |
| ATOM | 266 | C | LYS | 107 | 44.327 | 34.034 | −14.279 | 1.00 | 30.89 |
| ATOM | 267 | O | LYS | 107 | 44.023 | 33.035 | −13.627 | 1.00 | 31.02 |
| ATOM | 268 | CB | LYS | 107 | 43.437 | 36.302 | −13.789 | 1.00 | 30.30 |
| ATOM | 269 | CG | LYS | 107 | 42.291 | 37.283 | −13.910 | 1.00 | 30.97 |
| ATOM | 270 | CD | LYS | 107 | 42.610 | 38.648 | −13.245 | 1.00 | 29.55 |
| ATOM | 271 | CE | LYS | 107 | 43.721 | 39.346 | −13.925 | 1.00 | 27.26 |
| ATOM | 272 | NZ | LYS | 107 | 43.937 | 40.678 | −13.259 | 1.00 | 25.91 |
| ATOM | 273 | N | THR | 108 | 45.561 | 34.339 | −14.645 | 1.00 | 31.14 |
| ATOM | 274 | CA | THR | 108 | 46.746 | 33.518 | −14.404 | 1.00 | 32.51 |
| ATOM | 275 | C | THR | 108 | 47.714 | 34.323 | −13.548 | 1.00 | 32.54 |
| ATOM | 276 | O | THR | 108 | 48.188 | 35.392 | −13.983 | 1.00 | 33.24 |
| ATOM | 277 | CB | THR | 108 | 47.397 | 33.254 | −15.779 | 1.00 | 32.61 |
| ATOM | 278 | OG1 | THR | 108 | 46.422 | 32.634 | −16.589 | 1.00 | 35.34 |
| ATOM | 279 | CG2 | THR | 108 | 48.586 | 32.351 | −15.699 | 1.00 | 33.31 |
| ATOM | 280 | N | ALA | 109 | 48.002 | 33.854 | −12.335 | 1.00 | 33.07 |
| ATOM | 281 | CA | ALA | 109 | 49.018 | 34.514 | −11.498 | 1.00 | 33.80 |
| ATOM | 282 | C | ALA | 109 | 50.355 | 34.702 | −12.250 | 1.00 | 34.89 |
| ATOM | 283 | O | ALA | 109 | 50.734 | 33.856 | −13.083 | 1.00 | 34.88 |
| ATOM | 284 | CB | ALA | 109 | 49.209 | 33.734 | −10.195 | 1.00 | 34.10 |
| ATOM | 285 | N | PRO | 110 | 51.057 | 35.844 | −11.991 | 1.00 | 35.11 |
| ATOM | 286 | CA | PRO | 110 | 52.171 | 36.240 | −12.837 | 1.00 | 35.19 |
| ATOM | 287 | C | PRO | 110 | 53.463 | 35.436 | −12.693 | 1.00 | 35.83 |
| ATOM | 288 | O | PRO | 110 | 54.287 | 35.522 | −13.615 | 1.00 | 36.44 |
| ATOM | 289 | CB | PRO | 110 | 52.426 | 37.698 | −12.426 | 1.00 | 35.24 |
| ATOM | 290 | CG | PRO | 110 | 51.888 | 37.802 | −11.047 | 1.00 | 35.53 |
| ATOM | 291 | CD | PRO | 110 | 50.757 | 36.844 | −10.945 | 1.00 | 33.91 |

TABLE 11-continued

Three-Dimensional Coordinates of *Neisseria gonorrhoeae* GCYH-IB·$Mn^{2+}$
(SEQ. ID. No. 8)

| ATOM | 292 | N | VAL | 111 | 53.642 | 34.688 | −11.579 | 1.00 | 34.87 |
|---|---|---|---|---|---|---|---|---|---|
| ATOM | 293 | CA | VAL | 111 | 54.845 | 33.859 | −11.401 | 1.00 | 34.55 |
| ATOM | 294 | C | VAL | 111 | 54.480 | 32.371 | −11.361 | 1.00 | 34.44 |
| ATOM | 295 | O | VAL | 111 | 54.889 | 31.613 | −12.217 | 1.00 | 34.73 |
| ATOM | 296 | CB | VAL | 111 | 55.721 | 34.316 | −10.201 | 1.00 | 35.20 |
| ATOM | 297 | CG1 | VAL | 111 | 56.926 | 33.367 | −10.018 | 1.00 | 35.13 |
| ATOM | 298 | CG2 | VAL | 111 | 56.258 | 35.758 | −10.458 | 1.00 | 33.36 |
| ATOM | 299 | N | SER | 112 | 53.644 | 31.975 | −10.411 | 1.00 | 34.36 |
| ATOM | 300 | CA | SER | 112 | 53.171 | 30.591 | −10.301 | 1.00 | 33.65 |
| ATOM | 301 | C | SER | 112 | 52.276 | 30.124 | −11.430 | 1.00 | 34.37 |
| ATOM | 302 | O | SER | 112 | 52.205 | 28.898 | −11.716 | 1.00 | 34.40 |
| ATOM | 303 | CB | SER | 112 | 52.457 | 30.385 | −8.980 | 1.00 | 33.85 |
| ATOM | 304 | OG | SER | 112 | 51.195 | 31.061 | −8.954 | 1.00 | 32.93 |
| ATOM | 305 | N | GLY | 113 | 51.573 | 31.072 | −12.067 | 1.00 | 33.94 |
| ATOM | 306 | CA | GLY | 113 | 50.585 | 30.736 | −13.125 | 1.00 | 32.54 |
| ATOM | 307 | C | GLY | 113 | 49.345 | 30.023 | −12.624 | 1.00 | 33.41 |
| ATOM | 308 | O | GLY | 113 | 48.569 | 29.470 | −13.442 | 1.00 | 32.86 |
| ATOM | 309 | N | ILE | 114 | 49.131 | 30.036 | −11.289 | 1.00 | 33.45 |
| ATOM | 310 | CA | ILE | 114 | 47.931 | 29.430 | −10.697 | 1.00 | 34.24 |
| ATOM | 311 | C | ILE | 114 | 46.768 | 30.282 | −11.217 | 1.00 | 34.53 |
| ATOM | 312 | O | ILE | 114 | 46.890 | 31.519 | −11.331 | 1.00 | 33.15 |
| ATOM | 313 | CB | ILE | 114 | 47.910 | 29.455 | −9.134 | 1.00 | 35.17 |
| ATOM | 314 | CG1 | ILE | 114 | 49.151 | 28.779 | −8.519 | 1.00 | 38.77 |
| ATOM | 315 | CG2 | ILE | 114 | 46.701 | 28.738 | −8.582 | 1.00 | 33.39 |
| ATOM | 316 | CD1 | ILE | 114 | 49.226 | 27.332 | −8.731 | 1.00 | 42.74 |
| ATOM | 317 | N | ARG | 115 | 45.664 | 29.624 | −11.562 | 1.00 | 34.61 |
| ATOM | 318 | CA | ARG | 115 | 44.558 | 30.341 | −12.189 | 1.00 | 35.62 |
| ATOM | 319 | C | ARG | 115 | 43.499 | 30.661 | −11.134 | 1.00 | 33.87 |
| ATOM | 320 | O | ARG | 115 | 43.329 | 29.908 | −10.171 | 1.00 | 32.92 |
| ATOM | 321 | CB | ARG | 115 | 43.976 | 29.576 | −13.399 | 1.00 | 35.86 |
| ATOM | 322 | CG | ARG | 115 | 45.049 | 29.195 | −14.495 | 1.00 | 39.50 |
| ATOM | 323 | CD | ARG | 115 | 44.457 | 29.202 | −15.918 | 1.00 | 41.37 |
| ATOM | 324 | NE | ARG | 115 | 44.156 | 30.581 | −16.349 | 1.00 | 49.17 |
| ATOM | 325 | CZ | ARG | 115 | 43.421 | 30.934 | −17.420 | 1.00 | 50.07 |
| ATOM | 326 | NH1 | ARG | 115 | 42.877 | 30.002 | −18.205 | 1.00 | 52.25 |
| ATOM | 327 | NH2 | ARG | 115 | 43.228 | 32.238 | −17.705 | 1.00 | 50.44 |
| ATOM | 328 | N | SER | 116 | 42.829 | 31.808 | −11.305 | 1.00 | 32.49 |
| ATOM | 329 | CA | SER | 116 | 41.712 | 32.164 | −10.444 | 1.00 | 31.24 |
| ATOM | 330 | C | SER | 116 | 40.804 | 33.216 | −11.123 | 1.00 | 30.84 |
| ATOM | 331 | O | SER | 116 | 41.201 | 33.934 | −12.080 | 1.00 | 31.63 |
| ATOM | 332 | CB | SER | 116 | 42.218 | 32.585 | −9.021 | 1.00 | 31.35 |
| ATOM | 333 | OG | SER | 116 | 42.970 | 33.795 | −9.062 | 1.00 | 29.62 |
| ATOM | 334 | N | LEU | 117 | 39.573 | 33.282 | −10.665 | 1.00 | 29.03 |
| ATOM | 335 | CA | LEU | 117 | 38.620 | 34.242 | −11.222 | 1.00 | 28.26 |
| ATOM | 336 | C | LEU | 117 | 38.876 | 35.615 | −10.633 | 1.00 | 27.66 |
| ATOM | 337 | O | LEU | 117 | 39.382 | 35.753 | −9.495 | 1.00 | 27.40 |
| ATOM | 338 | CB | LEU | 117 | 37.170 | 33.830 | −10.922 | 1.00 | 27.18 |
| ATOM | 339 | CG | LEU | 117 | 36.731 | 32.487 | −11.525 | 1.00 | 27.76 |
| ATOM | 340 | CD1 | LEU | 117 | 35.345 | 32.155 | −11.063 | 1.00 | 26.57 |
| ATOM | 341 | CD2 | LEU | 117 | 36.831 | 32.452 | −13.070 | 1.00 | 28.10 |
| ATOM | 342 | N | LEU | 118 | 38.495 | 36.637 | −11.388 | 1.00 | 26.69 |
| ATOM | 343 | CA | LEU | 118 | 38.297 | 37.963 | −10.773 | 1.00 | 25.88 |
| ATOM | 344 | C | LEU | 118 | 36.918 | 38.468 | −11.237 | 1.00 | 24.69 |
| ATOM | 345 | O | LEU | 118 | 36.471 | 38.091 | −12.322 | 1.00 | 22.82 |
| ATOM | 346 | CB | LEU | 118 | 39.392 | 38.921 | −11.221 | 1.00 | 26.05 |
| ATOM | 347 | CG | LEU | 118 | 39.524 | 40.162 | −10.290 | 1.00 | 27.63 |
| ATOM | 348 | CD1 | LEU | 118 | 40.096 | 39.788 | −8.861 | 1.00 | 29.00 |
| ATOM | 349 | CD2 | LEU | 118 | 40.387 | 41.128 | −10.945 | 1.00 | 27.18 |
| ATOM | 350 | N | PRO | 142 | 38.636 | 46.847 | −10.939 | 1.00 | 23.23 |
| ATOM | 351 | CA | PRO | 142 | 39.398 | 47.173 | −9.753 | 1.00 | 23.79 |
| ATOM | 352 | C | PRO | 142 | 40.866 | 46.809 | −9.963 | 1.00 | 24.65 |
| ATOM | 353 | O | PRO | 142 | 41.162 | 45.753 | −10.563 | 1.00 | 25.09 |
| ATOM | 354 | CB | PRO | 142 | 38.715 | 46.295 | −8.699 | 1.00 | 24.09 |
| ATOM | 355 | CG | PRO | 142 | 38.391 | 44.964 | −9.539 | 1.00 | 23.27 |
| ATOM | 356 | CD | PRO | 142 | 37.978 | 45.519 | −10.870 | 1.00 | 23.22 |
| ATOM | 357 | N | VAL | 143 | 41.771 | 47.687 | −9.512 | 1.00 | 24.51 |
| ATOM | 358 | CA | VAL | 143 | 43.210 | 47.555 | −9.769 | 1.00 | 25.26 |
| ATOM | 359 | C | VAL | 143 | 43.912 | 48.079 | −8.527 | 1.00 | 26.54 |
| ATOM | 360 | O | VAL | 143 | 43.270 | 48.615 | −7.611 | 1.00 | 25.34 |
| ATOM | 361 | CB | VAL | 143 | 43.698 | 48.366 | −11.032 | 1.00 | 24.57 |
| ATOM | 362 | CG1 | VAL | 143 | 42.985 | 47.887 | −12.322 | 1.00 | 25.48 |
| ATOM | 363 | CG2 | VAL | 143 | 43.463 | 49.910 | −10.826 | 1.00 | 23.63 |
| ATOM | 364 | N | THR | 144 | 45.225 | 47.878 | −8.503 | 1.00 | 27.67 |
| ATOM | 365 | CA | THR | 144 | 46.106 | 48.449 | −7.510 | 1.00 | 27.19 |
| ATOM | 366 | C | THR | 144 | 46.653 | 49.802 | −8.005 | 1.00 | 27.74 |
| ATOM | 367 | O | THR | 144 | 47.110 | 49.884 | −9.150 | 1.00 | 27.09 |
| ATOM | 368 | CB | THR | 144 | 47.302 | 47.525 | −7.281 | 1.00 | 27.10 |

TABLE 11-continued

Three-Dimensional Coordinates of *Neisseria gonorrhoeae* GCYH-IB·Mn$^{2+}$
(SEQ. ID. No. 8)

| ATOM | 369 | OG1 | THR | 144 | 46.827 | 46.219 | −6.909 | 1.00 | 24.38 |
|------|-----|-----|-----|-----|--------|--------|--------|------|-------|
| ATOM | 370 | CG2 | THR | 144 | 48.174 | 48.091 | −6.162 | 1.00 | 28.95 |
| ATOM | 371 | N   | SER | 145 | 46.572 | 50.851 | −7.157 | 1.00 | 26.89 |
| ATOM | 372 | CA  | SER | 145 | 47.241 | 52.127 | −7.442 | 1.00 | 27.89 |
| ATOM | 373 | C   | SER | 145 | 48.318 | 52.371 | −6.381 | 1.00 | 28.66 |
| ATOM | 374 | O   | SER | 145 | 48.130 | 52.002 | −5.237 | 1.00 | 28.16 |
| ATOM | 375 | CB  | SER | 145 | 46.217 | 53.288 | −7.504 | 1.00 | 28.02 |
| ATOM | 376 | OG  | SER | 145 | 45.570 | 53.460 | −6.232 | 1.00 | 26.68 |
| ATOM | 377 | N   | LEU | 146 | 49.460 | 52.952 | −6.756 | 1.00 | 29.89 |
| ATOM | 378 | CA  | LEU | 146 | 50.545 | 53.212 | −5.789 | 1.00 | 29.68 |
| ATOM | 379 | C   | LEU | 146 | 51.070 | 54.633 | −5.993 | 1.00 | 30.59 |
| ATOM | 380 | O   | LEU | 146 | 51.229 | 55.058 | −7.132 | 1.00 | 28.81 |
| ATOM | 381 | CB  | LEU | 146 | 51.662 | 52.183 | −5.962 | 1.00 | 29.41 |
| ATOM | 382 | CG  | LEU | 146 | 52.892 | 52.265 | −5.020 | 1.00 | 29.93 |
| ATOM | 383 | CD1 | LEU | 146 | 53.407 | 50.894 | −4.667 | 1.00 | 27.71 |
| ATOM | 384 | CD2 | LEU | 146 | 54.018 | 53.136 | −5.659 | 1.00 | 28.67 |
| ATOM | 385 | N   | CYS | 147 | 51.337 | 55.375 | −4.903 | 1.00 | 31.66 |
| ATOM | 386 | CA  | CYS | 147 | 51.527 | 56.839 | −5.043 | 1.00 | 31.98 |
| ATOM | 387 | C   | CYS | 147 | 52.968 | 57.271 | −5.421 | 1.00 | 31.99 |
| ATOM | 388 | O   | CYS | 147 | 53.908 | 57.022 | −4.649 | 1.00 | 31.52 |
| ATOM | 389 | CB  | CYS | 147 | 51.081 | 57.556 | −3.767 | 1.00 | 31.07 |
| ATOM | 390 | SG  | CYS | 147 | 51.160 | 59.374 | −3.962 | 1.00 | 34.30 |
| ATOM | 391 | N   | PRO | 148 | 53.160 | 57.932 | −6.599 | 1.00 | 32.55 |
| ATOM | 392 | CA  | PRO | 148 | 54.563 | 58.342 | −6.962 | 1.00 | 33.44 |
| ATOM | 393 | C   | PRO | 148 | 55.189 | 59.356 | −5.986 | 1.00 | 34.23 |
| ATOM | 394 | O   | PRO | 148 | 56.410 | 59.363 | −5.794 | 1.00 | 34.47 |
| ATOM | 395 | CB  | PRO | 148 | 54.420 | 58.991 | −8.350 | 1.00 | 33.47 |
| ATOM | 396 | CG  | PRO | 148 | 53.058 | 58.526 | −8.878 | 1.00 | 33.36 |
| ATOM | 397 | CD  | PRO | 148 | 52.191 | 58.286 | −7.641 | 1.00 | 32.15 |
| ATOM | 398 | N   | CYS | 149 | 54.353 | 60.186 | −5.358 | 1.00 | 35.48 |
| ATOM | 399 | CA  | CYS | 149 | 54.815 | 61.208 | −4.420 | 1.00 | 34.64 |
| ATOM | 400 | C   | CYS | 149 | 55.291 | 60.533 | −3.120 | 1.00 | 33.98 |
| ATOM | 401 | O   | CYS | 149 | 56.400 | 60.836 | −2.588 | 1.00 | 33.37 |
| ATOM | 402 | CB  | CYS | 149 | 53.683 | 62.215 | −4.164 | 1.00 | 34.81 |
| ATOM | 403 | SG  | CYS | 149 | 54.068 | 63.434 | −2.863 | 1.00 | 41.23 |
| ATOM | 404 | N   | SER | 150 | 54.474 | 59.586 | −2.636 | 1.00 | 32.17 |
| ATOM | 405 | CA  | SER | 150 | 54.840 | 58.743 | −1.498 | 1.00 | 31.42 |
| ATOM | 406 | C   | SER | 150 | 56.187 | 57.998 | −1.673 | 1.00 | 31.54 |
| ATOM | 407 | O   | SER | 150 | 57.066 | 58.051 | −0.783 | 1.00 | 31.16 |
| ATOM | 408 | CB  | SER | 150 | 53.698 | 57.728 | −1.218 | 1.00 | 31.09 |
| ATOM | 409 | OG  | SER | 150 | 54.012 | 56.905 | −0.114 | 1.00 | 28.82 |
| ATOM | 410 | N   | LYS | 151 | 56.340 | 57.283 | −2.787 | 1.00 | 30.89 |
| ATOM | 411 | CA  | LYS | 151 | 57.609 | 56.647 | −3.108 | 1.00 | 32.75 |
| ATOM | 412 | C   | LYS | 151 | 58.783 | 57.685 | −3.082 | 1.00 | 34.08 |
| ATOM | 413 | O   | LYS | 151 | 59.806 | 57.498 | −2.380 | 1.00 | 35.64 |
| ATOM | 414 | CB  | LYS | 151 | 57.521 | 55.977 | −4.506 | 1.00 | 31.90 |
| ATOM | 415 | CG  | LYS | 151 | 58.790 | 55.268 | −4.942 | 1.00 | 31.20 |
| ATOM | 416 | CD  | LYS | 151 | 58.619 | 54.627 | −6.326 | 1.00 | 31.30 |
| ATOM | 417 | CE  | LYS | 151 | 59.952 | 54.049 | −6.776 | 1.00 | 33.03 |
| ATOM | 418 | NZ  | LYS | 151 | 59.848 | 53.308 | −8.026 | 1.00 | 30.24 |
| ATOM | 419 | N   | GLU | 152 | 58.639 | 58.749 | −3.850 | 1.00 | 35.50 |
| ATOM | 420 | CA  | GLU | 152 | 59.707 | 59.745 | −4.032 | 1.00 | 38.06 |
| ATOM | 421 | C   | GLU | 152 | 60.216 | 60.387 | −2.718 | 1.00 | 38.25 |
| ATOM | 422 | O   | GLU | 152 | 61.426 | 60.523 | −2.526 | 1.00 | 39.41 |
| ATOM | 423 | CB  | GLU | 152 | 59.253 | 60.823 | −5.017 | 1.00 | 39.11 |
| ATOM | 424 | CG  | GLU | 152 | 60.091 | 62.096 | −4.985 | 1.00 | 45.31 |
| ATOM | 425 | CD  | GLU | 152 | 59.694 | 63.051 | −6.069 | 1.00 | 52.84 |
| ATOM | 426 | OE1 | GLU | 152 | 58.956 | 64.019 | −5.769 | 1.00 | 57.04 |
| ATOM | 427 | OE2 | GLU | 152 | 60.086 | 62.806 | −7.237 | 1.00 | 57.07 |
| ATOM | 428 | N   | ILE | 153 | 59.302 | 60.775 | −1.824 | 1.00 | 37.49 |
| ATOM | 429 | CA  | ILE | 153 | 59.688 | 61.492 | −0.608 | 1.00 | 37.01 |
| ATOM | 430 | C   | ILE | 153 | 60.152 | 60.522 | 0.517  | 1.00 | 37.61 |
| ATOM | 431 | O   | ILE | 153 | 60.871 | 60.943 | 1.429  | 1.00 | 37.14 |
| ATOM | 432 | CB  | ILE | 153 | 58.543 | 62.463 | −0.113 | 1.00 | 37.48 |
| ATOM | 433 | CG1 | ILE | 153 | 57.332 | 61.670 | 0.436  | 1.00 | 37.02 |
| ATOM | 434 | CG2 | ILE | 153 | 58.110 | 63.473 | −1.257 | 1.00 | 35.87 |
| ATOM | 435 | CD1 | ILE | 153 | 56.064 | 62.465 | 0.708  | 1.00 | 36.43 |
| ATOM | 436 | N   | SER | 154 | 59.742 | 59.236 | 0.451  | 1.00 | 36.39 |
| ATOM | 437 | CA  | SER | 154 | 59.982 | 58.295 | 1.561  | 1.00 | 36.06 |
| ATOM | 438 | C   | SER | 154 | 61.247 | 57.527 | 1.398  | 1.00 | 36.42 |
| ATOM | 439 | O   | SER | 154 | 61.594 | 57.143 | 0.288  | 1.00 | 36.52 |
| ATOM | 440 | CB  | SER | 154 | 58.810 | 57.316 | 1.733  | 1.00 | 34.92 |
| ATOM | 441 | OG  | SER | 154 | 57.623 | 58.073 | 1.874  | 1.00 | 34.60 |
| ATOM | 442 | N   | GLN | 155 | 61.952 | 57.274 | 2.491  | 1.00 | 37.31 |
| ATOM | 443 | CA  | GLN | 155 | 63.209 | 56.510 | 2.338  | 1.00 | 39.20 |
| ATOM | 444 | C   | GLN | 155 | 62.959 | 55.059 | 2.004  | 1.00 | 38.30 |
| ATOM | 445 | O   | GLN | 155 | 63.840 | 54.363 | 1.475  | 1.00 | 37.74 |

TABLE 11-continued

Three-Dimensional Coordinates of *Neisseria gonorrhoeae* GCYH-IB·Mn$^{2+}$
(SEQ. ID. No. 8)

| ATOM | 446 | CB | GLN | 155 | 64.129 | 56.635 | 3.565 | 1.00 | 40.45 |
|---|---|---|---|---|---|---|---|---|---|
| ATOM | 447 | CG | GLN | 155 | 63.556 | 56.180 | 4.895 | 1.00 | 42.35 |
| ATOM | 448 | CD | GLN | 155 | 64.560 | 56.373 | 6.021 | 1.00 | 42.99 |
| ATOM | 449 | OE1 | GLN | 155 | 65.753 | 56.075 | 5.856 | 1.00 | 45.28 |
| ATOM | 450 | NE2 | GLN | 155 | 64.086 | 56.879 | 7.171 | 1.00 | 46.69 |
| ATOM | 451 | N | TYR | 156 | 61.739 | 54.610 | 2.305 | 1.00 | 37.89 |
| ATOM | 452 | CA | TYR | 156 | 61.285 | 53.248 | 1.997 | 1.00 | 36.80 |
| ATOM | 453 | C | TYR | 156 | 59.761 | 53.190 | 2.042 | 1.00 | 36.04 |
| ATOM | 454 | O | TYR | 156 | 59.130 | 54.076 | 2.647 | 1.00 | 36.63 |
| ATOM | 455 | CB | TYR | 156 | 61.934 | 52.218 | 2.936 | 1.00 | 36.72 |
| ATOM | 456 | CG | TYR | 156 | 62.101 | 52.631 | 4.392 | 1.00 | 36.70 |
| ATOM | 457 | CD1 | TYR | 156 | 61.034 | 53.108 | 5.141 | 1.00 | 37.81 |
| ATOM | 458 | CD2 | TYR | 156 | 63.346 | 52.526 | 5.026 | 1.00 | 38.83 |
| ATOM | 459 | CE1 | TYR | 156 | 61.201 | 53.472 | 6.492 | 1.00 | 37.24 |
| ATOM | 460 | CE2 | TYR | 156 | 63.520 | 52.874 | 6.405 | 1.00 | 38.26 |
| ATOM | 461 | CZ | TYR | 156 | 62.456 | 53.334 | 7.110 | 1.00 | 37.10 |
| ATOM | 462 | OH | TYR | 156 | 62.629 | 53.656 | 8.447 | 1.00 | 37.14 |
| ATOM | 463 | N | GLY | 157 | 59.159 | 52.204 | 1.365 | 1.00 | 34.75 |
| ATOM | 464 | CA | GLY | 157 | 57.687 | 52.157 | 1.303 | 1.00 | 33.03 |
| ATOM | 465 | C | GLY | 157 | 57.048 | 53.125 | 0.316 | 1.00 | 31.76 |
| ATOM | 466 | O | GLY | 157 | 57.700 | 54.071 | −0.178 | 1.00 | 30.74 |
| ATOM | 467 | N | ALA | 158 | 55.778 | 52.870 | 0.010 | 1.00 | 30.83 |
| ATOM | 468 | CA | ALA | 158 | 54.967 | 53.774 | −0.799 | 1.00 | 31.12 |
| ATOM | 469 | C | ALA | 158 | 53.511 | 53.422 | −0.556 | 1.00 | 30.73 |
| ATOM | 470 | O | ALA | 158 | 53.158 | 52.234 | −0.675 | 1.00 | 31.76 |
| ATOM | 471 | CB | ALA | 158 | 55.327 | 53.625 | −2.295 | 1.00 | 30.85 |
| ATOM | 472 | N | HIS | 159 | 52.661 | 54.390 | −0.177 | 1.00 | 28.96 |
| ATOM | 473 | CA | HIS | 159 | 51.271 | 54.002 | 0.084 | 1.00 | 27.54 |
| ATOM | 474 | C | HIS | 159 | 50.593 | 53.588 | −1.198 | 1.00 | 26.90 |
| ATOM | 475 | O | HIS | 159 | 50.909 | 54.116 | −2.264 | 1.00 | 27.11 |
| ATOM | 476 | CB | HIS | 159 | 50.445 | 55.046 | 0.843 | 1.00 | 27.56 |
| ATOM | 477 | CG | HIS | 159 | 49.942 | 56.201 | 0.023 | 1.00 | 27.53 |
| ATOM | 478 | ND1 | HIS | 159 | 48.771 | 56.137 | −0.707 | 1.00 | 28.80 |
| ATOM | 479 | CD2 | HIS | 159 | 50.386 | 57.483 | −0.080 | 1.00 | 25.15 |
| ATOM | 480 | CE1 | HIS | 159 | 48.537 | 57.311 | −1.261 | 1.00 | 26.96 |
| ATOM | 481 | NE2 | HIS | 159 | 49.509 | 58.145 | −0.905 | 1.00 | 27.80 |
| ATOM | 482 | N | ASN | 160 | 49.683 | 52.626 | −1.076 | 1.00 | 25.77 |
| ATOM | 483 | CA | ASN | 160 | 49.021 | 52.005 | −2.233 | 1.00 | 24.99 |
| ATOM | 484 | C | ASN | 160 | 47.670 | 51.560 | −1.744 | 1.00 | 25.23 |
| ATOM | 485 | O | ASN | 160 | 47.413 | 51.549 | −0.501 | 1.00 | 25.07 |
| ATOM | 486 | CB | ASN | 160 | 49.886 | 50.887 | −2.882 | 1.00 | 24.72 |
| ATOM | 487 | CG | ASN | 160 | 50.412 | 49.837 | −1.905 | 1.00 | 26.68 |
| ATOM | 488 | OD1 | ASN | 160 | 51.537 | 49.971 | −1.397 | 1.00 | 31.21 |
| ATOM | 489 | ND2 | ASN | 160 | 49.665 | 48.741 | −1.721 | 1.00 | 22.78 |
| ATOM | 490 | N | GLN | 161 | 46.763 | 51.287 | −2.659 | 1.00 | 24.62 |
| ATOM | 491 | CA | GLN | 161 | 45.373 | 51.074 | −2.282 | 1.00 | 25.62 |
| ATOM | 492 | C | GLN | 161 | 44.660 | 50.437 | −3.461 | 1.00 | 25.75 |
| ATOM | 493 | O | GLN | 161 | 45.160 | 50.509 | −4.567 | 1.00 | 25.66 |
| ATOM | 494 | CB | GLN | 161 | 44.663 | 52.390 | −1.948 | 1.00 | 24.86 |
| ATOM | 495 | CG | GLN | 161 | 44.856 | 53.512 | −3.004 | 1.00 | 25.88 |
| ATOM | 496 | CD | GLN | 161 | 46.155 | 54.290 | −2.795 | 1.00 | 26.01 |
| ATOM | 497 | OE1 | GLN | 161 | 46.542 | 54.608 | −1.652 | 1.00 | 25.80 |
| ATOM | 498 | NE2 | GLN | 161 | 46.835 | 54.609 | −3.899 | 1.00 | 24.43 |
| ATOM | 499 | N | ARG | 162 | 43.511 | 49.814 | −3.202 | 1.00 | 25.37 |
| ATOM | 500 | CA | ARG | 162 | 42.654 | 49.399 | −4.265 | 1.00 | 26.23 |
| ATOM | 501 | C | ARG | 162 | 42.032 | 50.654 | −4.913 | 1.00 | 26.60 |
| ATOM | 502 | O | ARG | 162 | 41.775 | 51.671 | −4.252 | 1.00 | 25.80 |
| ATOM | 503 | CB | ARG | 162 | 41.556 | 48.495 | −3.741 | 1.00 | 26.40 |
| ATOM | 504 | CG | ARG | 162 | 40.992 | 47.552 | −4.879 | 1.00 | 29.11 |
| ATOM | 505 | CD | ARG | 162 | 39.866 | 46.616 | −4.360 | 1.00 | 27.52 |
| ATOM | 506 | NE | ARG | 162 | 40.374 | 45.658 | −3.381 | 1.00 | 26.18 |
| ATOM | 507 | CZ | ARG | 162 | 39.603 | 45.119 | −2.453 | 1.00 | 19.53 |
| ATOM | 508 | NH1 | ARG | 162 | 38.283 | 45.457 | −2.374 | 1.00 | 23.76 |
| ATOM | 509 | NH2 | ARG | 162 | 40.179 | 44.253 | −1.612 | 1.00 | 23.47 |
| ATOM | 510 | N | SER | 163 | 41.787 | 50.544 | −6.208 | 1.00 | 26.65 |
| ATOM | 511 | CA | SER | 163 | 41.244 | 51.627 | −6.987 | 1.00 | 27.57 |
| ATOM | 512 | C | SER | 163 | 40.155 | 51.052 | −7.909 | 1.00 | 26.82 |
| ATOM | 513 | O | SER | 163 | 40.152 | 49.843 | −8.235 | 1.00 | 26.70 |
| ATOM | 514 | CB | SER | 163 | 42.423 | 52.376 | −7.657 | 1.00 | 27.35 |
| ATOM | 515 | OG | SER | 163 | 42.151 | 52.643 | −9.023 | 1.00 | 35.69 |
| ATOM | 516 | N | HIS | 164 | 39.122 | 51.841 | −8.156 | 1.00 | 24.51 |
| ATOM | 517 | CA | HIS | 164 | 38.004 | 51.427 | −9.015 | 1.00 | 24.40 |
| ATOM | 518 | C | HIS | 164 | 38.080 | 52.287 | −10.243 | 1.00 | 23.64 |
| ATOM | 519 | O | HIS | 164 | 37.868 | 53.506 | −10.154 | 1.00 | 23.83 |
| ATOM | 520 | CB | HIS | 164 | 36.623 | 51.581 | −8.342 | 1.00 | 22.54 |
| ATOM | 521 | CG | HIS | 164 | 36.351 | 50.532 | −7.265 | 1.00 | 26.02 |
| ATOM | 522 | ND1 | HIS | 164 | 35.215 | 50.544 | −6.470 | 1.00 | 26.46 |

TABLE 11-continued

Three-Dimensional Coordinates of *Neisseria gonorrhoeae* GCYH-IB·Mn$^{2+}$
(SEQ. ID. No. 8)

| ATOM | 523 | CD2 | HIS | 164 | 37.072 | 49.449 | −6.864 | 1.00 | 24.91 |
|---|---|---|---|---|---|---|---|---|---|
| ATOM | 524 | CE1 | HIS | 164 | 35.273 | 49.536 | −5.602 | 1.00 | 27.18 |
| ATOM | 525 | NE2 | HIS | 164 | 36.379 | 48.844 | −5.837 | 1.00 | 23.87 |
| ATOM | 526 | N | GLU | 178 | 36.025 | 42.070 | −22.347 | 1.00 | 27.67 |
| ATOM | 527 | CA | GLU | 178 | 37.377 | 41.730 | −21.959 | 1.00 | 27.98 |
| ATOM | 528 | C | GLU | 178 | 38.387 | 42.678 | −22.559 | 1.00 | 27.24 |
| ATOM | 529 | O | GLU | 178 | 39.453 | 42.873 | −21.988 | 1.00 | 25.70 |
| ATOM | 530 | CB | GLU | 178 | 37.685 | 40.262 | −22.280 | 1.00 | 28.97 |
| ATOM | 531 | CG | GLU | 178 | 37.779 | 39.941 | −23.817 | 1.00 | 32.86 |
| ATOM | 532 | CD | GLU | 178 | 36.465 | 40.133 | −24.630 | 1.00 | 33.62 |
| ATOM | 533 | OE1 | GLU | 178 | 35.328 | 39.936 | −24.092 | 1.00 | 34.70 |
| ATOM | 534 | OE2 | GLU | 178 | 36.596 | 40.482 | −25.829 | 1.00 | 31.93 |
| ATOM | 535 | N | GLU | 179 | 38.056 | 43.272 | −23.720 | 1.00 | 26.74 |
| ATOM | 536 | CA | GLU | 179 | 38.884 | 44.273 | −24.302 | 1.00 | 26.64 |
| ATOM | 537 | C | GLU | 179 | 39.000 | 45.480 | −23.395 | 1.00 | 25.61 |
| ATOM | 538 | O | GLU | 179 | 40.060 | 46.034 | −23.237 | 1.00 | 26.26 |
| ATOM | 539 | CB | GLU | 179 | 38.303 | 44.699 | −25.661 | 1.00 | 27.63 |
| ATOM | 540 | CG | GLU | 179 | 38.361 | 43.565 | −26.687 | 1.00 | 30.31 |
| ATOM | 541 | CD | GLU | 179 | 38.099 | 44.069 | −28.094 | 1.00 | 32.92 |
| ATOM | 542 | OE1 | GLU | 179 | 39.042 | 44.622 | −28.702 | 1.00 | 33.44 |
| ATOM | 543 | OE2 | GLU | 179 | 36.964 | 43.925 | −28.543 | 1.00 | 32.90 |
| ATOM | 544 | N | VAL | 180 | 37.883 | 45.905 | −22.809 | 1.00 | 25.11 |
| ATOM | 545 | CA | VAL | 180 | 37.896 | 47.086 | −21.946 | 1.00 | 23.45 |
| ATOM | 546 | C | VAL | 180 | 38.719 | 46.745 | −20.705 | 1.00 | 23.67 |
| ATOM | 547 | O | VAL | 180 | 39.508 | 47.555 | −20.236 | 1.00 | 23.44 |
| ATOM | 548 | CB | VAL | 180 | 36.480 | 47.466 | −21.502 | 1.00 | 24.00 |
| ATOM | 549 | CG1 | VAL | 180 | 36.479 | 48.682 | −20.487 | 1.00 | 21.69 |
| ATOM | 550 | CG2 | VAL | 180 | 35.579 | 47.700 | −22.690 | 1.00 | 21.64 |
| ATOM | 551 | N | ILE | 181 | 38.506 | 45.553 | −20.151 | 1.00 | 22.91 |
| ATOM | 552 | CA | ILE | 181 | 39.317 | 45.101 | −18.995 | 1.00 | 23.75 |
| ATOM | 553 | C | ILE | 181 | 40.825 | 45.159 | −19.310 | 1.00 | 26.04 |
| ATOM | 554 | O | ILE | 181 | 41.638 | 45.674 | −18.478 | 1.00 | 27.11 |
| ATOM | 555 | CB | ILE | 181 | 38.911 | 43.630 | −18.555 | 1.00 | 23.88 |
| ATOM | 556 | CG1 | ILE | 181 | 37.430 | 43.577 | −18.071 | 1.00 | 21.17 |
| ATOM | 557 | CG2 | ILE | 181 | 39.925 | 43.030 | −17.477 | 1.00 | 21.79 |
| ATOM | 558 | CD1 | ILE | 181 | 36.943 | 42.131 | −17.780 | 1.00 | 20.98 |
| ATOM | 559 | N | ASP | 182 | 41.225 | 44.643 | −20.488 | 1.00 | 26.54 |
| ATOM | 560 | CA | ASP | 182 | 42.657 | 44.616 | −20.814 | 1.00 | 26.69 |
| ATOM | 561 | C | ASP | 182 | 43.199 | 46.024 | −20.957 | 1.00 | 25.88 |
| ATOM | 562 | O | ASP | 182 | 44.296 | 46.286 | −20.514 | 1.00 | 26.00 |
| ATOM | 563 | CB | ASP | 182 | 42.995 | 43.772 | −22.070 | 1.00 | 27.60 |
| ATOM | 564 | CG | ASP | 182 | 42.783 | 42.263 | −21.860 | 1.00 | 30.47 |
| ATOM | 565 | OD1 | ASP | 182 | 42.991 | 41.759 | −20.746 | 1.00 | 31.48 |
| ATOM | 566 | OD2 | ASP | 182 | 42.373 | 41.576 | −22.814 | 1.00 | 33.73 |
| ATOM | 567 | N | TYR | 183 | 42.452 | 46.930 | −21.589 | 1.00 | 26.54 |
| ATOM | 568 | CA | TYR | 183 | 42.882 | 48.337 | −21.703 | 1.00 | 26.51 |
| ATOM | 569 | C | TYR | 183 | 43.281 | 48.920 | −20.323 | 1.00 | 27.37 |
| ATOM | 570 | O | TYR | 183 | 44.284 | 49.646 | −20.180 | 1.00 | 28.29 |
| ATOM | 571 | CB | TYR | 183 | 41.761 | 49.172 | −22.358 | 1.00 | 27.89 |
| ATOM | 572 | CG | TYR | 183 | 41.688 | 49.124 | −23.877 | 1.00 | 27.72 |
| ATOM | 573 | CD1 | TYR | 183 | 42.832 | 49.062 | −24.634 | 1.00 | 31.11 |
| ATOM | 574 | CD2 | TYR | 183 | 40.457 | 49.185 | −24.546 | 1.00 | 27.18 |
| ATOM | 575 | CE1 | TYR | 183 | 42.777 | 49.054 | −26.075 | 1.00 | 32.80 |
| ATOM | 576 | CE2 | TYR | 183 | 40.377 | 49.157 | −25.943 | 1.00 | 31.64 |
| ATOM | 577 | CZ | TYR | 183 | 41.555 | 49.102 | −26.706 | 1.00 | 31.01 |
| ATOM | 578 | OH | TYR | 183 | 41.507 | 49.115 | −28.099 | 1.00 | 33.34 |
| ATOM | 579 | N | VAL | 184 | 42.476 | 48.626 | −19.307 | 1.00 | 26.40 |
| ATOM | 580 | CA | VAL | 184 | 42.668 | 49.212 | −17.997 | 1.00 | 24.57 |
| ATOM | 581 | C | VAL | 184 | 43.796 | 48.478 | −17.240 | 1.00 | 25.20 |
| ATOM | 582 | O | VAL | 184 | 44.694 | 49.099 | −16.708 | 1.00 | 25.99 |
| ATOM | 583 | CB | VAL | 184 | 41.309 | 49.197 | −17.190 | 1.00 | 23.34 |
| ATOM | 584 | CG1 | VAL | 184 | 41.538 | 49.434 | −15.671 | 1.00 | 24.07 |
| ATOM | 585 | CG2 | VAL | 184 | 40.331 | 50.295 | −17.729 | 1.00 | 21.77 |
| ATOM | 586 | N | GLU | 185 | 43.711 | 47.159 | −17.177 | 1.00 | 25.17 |
| ATOM | 587 | CA | GLU | 185 | 44.647 | 46.338 | −16.391 | 1.00 | 25.55 |
| ATOM | 588 | C | GLU | 185 | 46.078 | 46.559 | −16.857 | 1.00 | 27.14 |
| ATOM | 589 | O | GLU | 185 | 47.019 | 46.547 | −16.027 | 1.00 | 26.38 |
| ATOM | 590 | CB | GLU | 185 | 44.185 | 44.872 | −16.421 | 1.00 | 25.17 |
| ATOM | 591 | CG | GLU | 185 | 42.920 | 44.621 | −15.549 | 1.00 | 23.68 |
| ATOM | 592 | CD | GLU | 185 | 42.609 | 43.139 | −15.318 | 1.00 | 26.50 |
| ATOM | 593 | OE1 | GLU | 185 | 42.984 | 42.320 | −16.171 | 1.00 | 24.21 |
| ATOM | 594 | OE2 | GLU | 185 | 41.987 | 42.784 | −14.288 | 1.00 | 26.85 |
| ATOM | 595 | N | THR | 186 | 46.230 | 46.823 | −18.172 | 1.00 | 27.44 |
| ATOM | 596 | CA | THR | 186 | 47.548 | 47.060 | −18.780 | 1.00 | 29.10 |
| ATOM | 597 | C | THR | 186 | 48.130 | 48.338 | −18.223 | 1.00 | 28.82 |
| ATOM | 598 | O | THR | 186 | 49.335 | 48.470 | −18.137 | 1.00 | 29.57 |
| ATOM | 599 | CB | THR | 186 | 47.488 | 47.249 | −20.331 | 1.00 | 28.74 |

TABLE 11-continued

Three-Dimensional Coordinates of *Neisseria gonorrhoeae* GCYH-IB·Mn$^{2+}$
(SEQ. ID. No. 8)

| ATOM | 600 | OG1 | THR | 186 | 46.989 | 46.059 | −20.926 | 1.00 | 31.76 |
|---|---|---|---|---|---|---|---|---|---|
| ATOM | 601 | CG2 | THR | 186 | 48.900 | 47.440 | −20.950 | 1.00 | 31.01 |
| ATOM | 602 | N | GLN | 187 | 47.266 | 49.282 | −17.880 | 1.00 | 27.63 |
| ATOM | 603 | CA | GLN | 187 | 47.734 | 50.582 | −17.463 | 1.00 | 27.72 |
| ATOM | 604 | C | GLN | 187 | 47.895 | 50.719 | −15.963 | 1.00 | 27.83 |
| ATOM | 605 | O | GLN | 187 | 48.495 | 51.676 | −15.524 | 1.00 | 29.63 |
| ATOM | 606 | CB | GLN | 187 | 46.797 | 51.676 | −17.974 | 1.00 | 27.75 |
| ATOM | 607 | CG | GLN | 187 | 46.783 | 51.841 | −19.519 | 1.00 | 26.73 |
| ATOM | 608 | CD | GLN | 187 | 48.157 | 52.026 | −20.097 | 1.00 | 27.76 |
| ATOM | 609 | OE1 | GLN | 187 | 49.015 | 52.720 | −19.533 | 1.00 | 30.15 |
| ATOM | 610 | NE2 | GLN | 187 | 48.378 | 51.441 | −21.239 | 1.00 | 28.32 |
| ATOM | 611 | N | ALA | 188 | 47.356 | 49.795 | −15.176 | 1.00 | 27.23 |
| ATOM | 612 | CA | ALA | 188 | 47.369 | 49.946 | −13.725 | 1.00 | 27.88 |
| ATOM | 613 | C | ALA | 188 | 48.791 | 49.798 | −13.135 | 1.00 | 28.74 |
| ATOM | 614 | O | ALA | 188 | 49.614 | 49.086 | −13.715 | 1.00 | 28.55 |
| ATOM | 615 | CB | ALA | 188 | 46.445 | 48.903 | −13.118 | 1.00 | 27.58 |
| ATOM | 616 | N | SER | 189 | 49.102 | 50.485 | −12.010 | 1.00 | 28.35 |
| ATOM | 617 | CA | SER | 189 | 50.358 | 50.203 | −11.299 | 1.00 | 28.39 |
| ATOM | 618 | C | SER | 189 | 50.551 | 48.679 | −11.159 | 1.00 | 28.75 |
| ATOM | 619 | O | SER | 189 | 51.626 | 48.161 | −11.474 | 1.00 | 29.75 |
| ATOM | 620 | CB | SER | 189 | 50.435 | 50.919 | −9.947 | 1.00 | 28.00 |
| ATOM | 621 | OG | SER | 189 | 50.545 | 52.349 | −10.203 | 1.00 | 31.33 |
| ATOM | 622 | N | CYS | 190 | 49.503 | 47.986 | −10.730 | 1.00 | 28.89 |
| ATOM | 623 | CA | CYS | 190 | 49.416 | 46.536 | −10.865 | 1.00 | 29.72 |
| ATOM | 624 | C | CYS | 190 | 47.958 | 46.096 | −10.868 | 1.00 | 29.12 |
| ATOM | 625 | O | CYS | 190 | 47.134 | 46.656 | −10.176 | 1.00 | 29.39 |
| ATOM | 626 | CB | CYS | 190 | 50.183 | 45.813 | −9.738 | 1.00 | 29.28 |
| ATOM | 627 | SG | CYS | 190 | 50.602 | 44.059 | −10.127 | 1.00 | 31.60 |
| ATOM | 628 | N | GLN | 191 | 47.637 | 45.079 | −11.649 | 1.00 | 28.56 |
| ATOM | 629 | CA | GLN | 191 | 46.306 | 44.513 | −11.624 | 1.00 | 28.62 |
| ATOM | 630 | C | GLN | 191 | 46.093 | 43.539 | −10.431 | 1.00 | 28.18 |
| ATOM | 631 | O | GLN | 191 | 47.055 | 43.115 | −9.816 | 1.00 | 30.09 |
| ATOM | 632 | CB | GLN | 191 | 46.007 | 43.833 | −12.982 | 1.00 | 27.91 |
| ATOM | 633 | CG | GLN | 191 | 46.917 | 42.657 | −13.269 | 1.00 | 29.69 |
| ATOM | 634 | CD | GLN | 191 | 46.745 | 42.128 | −14.681 | 1.00 | 28.05 |
| ATOM | 635 | OE1 | GLN | 191 | 45.815 | 41.379 | −14.953 | 1.00 | 26.08 |
| ATOM | 636 | NE2 | GLN | 191 | 47.663 | 42.480 | −15.563 | 1.00 | 27.88 |
| ATOM | 637 | N | LEU | 192 | 44.838 | 43.159 | −10.165 | 1.00 | 27.13 |
| ATOM | 638 | CA | LEU | 192 | 44.458 | 42.247 | −9.084 | 1.00 | 26.58 |
| ATOM | 639 | C | LEU | 192 | 44.288 | 40.777 | −9.519 | 1.00 | 26.86 |
| ATOM | 640 | O | LEU | 192 | 43.984 | 40.493 | −10.665 | 1.00 | 26.33 |
| ATOM | 641 | CB | LEU | 192 | 43.123 | 42.692 | −8.459 | 1.00 | 25.94 |
| ATOM | 642 | CG | LEU | 192 | 42.975 | 44.148 | −8.007 | 1.00 | 25.68 |
| ATOM | 643 | CD1 | LEU | 192 | 41.595 | 44.361 | −7.442 | 1.00 | 24.34 |
| ATOM | 644 | CD2 | LEU | 192 | 44.038 | 44.511 | −6.967 | 1.00 | 25.68 |
| ATOM | 645 | N | TYR | 193 | 44.460 | 39.880 | −8.550 | 1.00 | 26.29 |
| ATOM | 646 | CA | TYR | 193 | 44.264 | 38.410 | −8.677 | 1.00 | 27.06 |
| ATOM | 647 | C | TYR | 193 | 43.652 | 37.912 | −7.373 | 1.00 | 27.76 |
| ATOM | 648 | O | TYR | 193 | 43.991 | 38.458 | −6.293 | 1.00 | 28.41 |
| ATOM | 649 | CB | TYR | 193 | 45.624 | 37.737 | −8.820 | 1.00 | 26.43 |
| ATOM | 650 | CG | TYR | 193 | 46.409 | 38.226 | −10.009 | 1.00 | 26.85 |
| ATOM | 651 | CD1 | TYR | 193 | 46.305 | 37.586 | −11.260 | 1.00 | 26.58 |
| ATOM | 652 | CD2 | TYR | 193 | 47.243 | 39.344 | −9.887 | 1.00 | 28.66 |
| ATOM | 653 | CE1 | TYR | 193 | 47.035 | 38.045 | −12.367 | 1.00 | 24.85 |
| ATOM | 654 | CE2 | TYR | 193 | 47.967 | 39.818 | −10.959 | 1.00 | 26.95 |
| ATOM | 655 | CZ | TYR | 193 | 47.841 | 39.172 | −12.187 | 1.00 | 26.61 |
| ATOM | 656 | OH | TYR | 193 | 48.580 | 39.668 | −13.189 | 1.00 | 26.01 |
| ATOM | 657 | N | GLY | 194 | 42.805 | 36.879 | −7.430 | 1.00 | 27.45 |
| ATOM | 658 | CA | GLY | 194 | 42.219 | 36.368 | −6.211 | 1.00 | 28.39 |
| ATOM | 659 | C | GLY | 194 | 43.250 | 35.477 | −5.558 | 1.00 | 29.37 |
| ATOM | 660 | O | GLY | 194 | 43.404 | 35.433 | −4.351 | 1.00 | 29.71 |
| ATOM | 661 | N | LEU | 195 | 43.997 | 34.760 | −6.377 | 1.00 | 30.72 |
| ATOM | 662 | CA | LEU | 195 | 44.913 | 33.749 | −5.828 | 1.00 | 30.71 |
| ATOM | 663 | C | LEU | 195 | 46.347 | 34.064 | −6.172 | 1.00 | 29.77 |
| ATOM | 664 | O | LEU | 195 | 46.736 | 34.103 | −7.330 | 1.00 | 28.47 |
| ATOM | 665 | CB | LEU | 195 | 44.495 | 32.356 | −6.282 | 1.00 | 30.93 |
| ATOM | 666 | CG | LEU | 195 | 44.897 | 31.120 | −5.459 | 1.00 | 33.19 |
| ATOM | 667 | CD1 | LEU | 195 | 44.301 | 29.867 | −6.174 | 1.00 | 33.40 |
| ATOM | 668 | CD2 | LEU | 195 | 46.381 | 31.012 | −5.430 | 1.00 | 35.11 |
| ATOM | 669 | N | LEU | 196 | 47.125 | 34.301 | −5.120 | 1.00 | 29.88 |
| ATOM | 670 | CA | LEU | 196 | 48.509 | 34.678 | −5.234 | 1.00 | 31.16 |
| ATOM | 671 | C | LEU | 196 | 49.300 | 33.837 | −4.255 | 1.00 | 32.87 |
| ATOM | 672 | O | LEU | 196 | 48.981 | 33.824 | −3.049 | 1.00 | 31.79 |
| ATOM | 673 | CB | LEU | 196 | 48.716 | 36.158 | −4.891 | 1.00 | 30.65 |
| ATOM | 674 | CG | LEU | 196 | 48.111 | 37.202 | −5.856 | 1.00 | 31.74 |
| ATOM | 675 | CD1 | LEU | 196 | 48.363 | 38.544 | −5.281 | 1.00 | 32.71 |
| ATOM | 676 | CD2 | LEU | 196 | 48.735 | 37.132 | −7.252 | 1.00 | 32.09 |

TABLE 11-continued

Three-Dimensional Coordinates of *Neisseria gonorrhoeae* GCYH-IB·Mn$^{2+}$
(SEQ. ID. No. 8)

| | | | | | | | | | |
|---|---|---|---|---|---|---|---|---|---|
| ATOM | 677 | N | LYS | 197 | 50.312 | 33.151 | −4.790 | 1.00 | 33.78 |
| ATOM | 678 | CA | LYS | 197 | 51.318 | 32.493 | −3.980 | 1.00 | 36.74 |
| ATOM | 679 | C | LYS | 197 | 52.431 | 33.510 | −3.573 | 1.00 | 36.95 |
| ATOM | 680 | O | LYS | 197 | 52.487 | 34.658 | −4.085 | 1.00 | 37.20 |
| ATOM | 681 | CB | LYS | 197 | 51.883 | 31.254 | −4.722 | 1.00 | 37.53 |
| ATOM | 682 | CG | LYS | 197 | 50.885 | 30.079 | −4.822 | 1.00 | 39.92 |
| ATOM | 683 | CD | LYS | 197 | 50.542 | 29.675 | −3.378 | 1.00 | 44.49 |
| ATOM | 684 | CE | LYS | 197 | 49.503 | 28.600 | −3.289 | 1.00 | 49.11 |
| ATOM | 685 | NZ | LYS | 197 | 50.033 | 27.283 | −3.746 | 1.00 | 51.33 |
| ATOM | 686 | N | ARG | 198 | 53.316 | 33.087 | −2.673 | 1.00 | 36.70 |
| ATOM | 687 | CA | ARG | 198 | 54.337 | 33.976 | −2.112 | 1.00 | 37.70 |
| ATOM | 688 | C | ARG | 198 | 55.200 | 34.587 | −3.247 | 1.00 | 36.39 |
| ATOM | 689 | O | ARG | 198 | 55.469 | 35.791 | −3.250 | 1.00 | 35.97 |
| ATOM | 690 | CB | ARG | 198 | 55.148 | 33.225 | −1.021 | 1.00 | 37.77 |
| ATOM | 691 | CG | ARG | 198 | 56.366 | 33.946 | −0.404 | 1.00 | 40.32 |
| ATOM | 692 | CD | ARG | 198 | 57.175 | 32.979 | 0.517 | 1.00 | 41.88 |
| ATOM | 693 | NE | ARG | 198 | 58.574 | 33.393 | 0.649 | 1.00 | 49.67 |
| ATOM | 694 | CZ | ARG | 198 | 59.170 | 33.718 | 1.802 | 1.00 | 51.87 |
| ATOM | 695 | NH1 | ARG | 198 | 58.489 | 33.677 | 2.947 | 1.00 | 53.30 |
| ATOM | 696 | NH2 | ARG | 198 | 60.453 | 34.087 | 1.808 | 1.00 | 51.58 |
| ATOM | 697 | N | PRO | 199 | 55.623 | 33.776 | −4.241 | 1.00 | 35.71 |
| ATOM | 698 | CA | PRO | 199 | 56.383 | 34.445 | −5.318 | 1.00 | 34.81 |
| ATOM | 699 | C | PRO | 199 | 55.516 | 35.443 | −6.110 | 1.00 | 35.08 |
| ATOM | 700 | O | PRO | 199 | 56.055 | 36.446 | −6.651 | 1.00 | 34.43 |
| ATOM | 701 | CB | PRO | 199 | 56.823 | 33.291 | −6.208 | 1.00 | 34.84 |
| ATOM | 702 | CG | PRO | 199 | 55.836 | 32.170 | −5.874 | 1.00 | 35.30 |
| ATOM | 703 | CD | PRO | 199 | 55.517 | 32.321 | −4.440 | 1.00 | 35.36 |
| ATOM | 704 | N | ASP | 200 | 54.201 | 35.173 | −6.175 | 1.00 | 34.66 |
| ATOM | 705 | CA | ASP | 200 | 53.252 | 36.049 | −6.906 | 1.00 | 35.25 |
| ATOM | 706 | C | ASP | 200 | 53.062 | 37.348 | −6.146 | 1.00 | 35.17 |
| ATOM | 707 | O | ASP | 200 | 53.055 | 38.437 | −6.722 | 1.00 | 35.34 |
| ATOM | 708 | CB | ASP | 200 | 51.908 | 35.366 | −7.035 | 1.00 | 35.09 |
| ATOM | 709 | CG | ASP | 200 | 51.976 | 34.109 | −7.874 | 1.00 | 35.57 |
| ATOM | 710 | OD1 | ASP | 200 | 52.551 | 34.160 | −8.989 | 1.00 | 33.86 |
| ATOM | 711 | OD2 | ASP | 200 | 51.410 | 33.089 | −7.420 | 1.00 | 35.70 |
| ATOM | 712 | N | GLU | 201 | 52.943 | 37.224 | −4.831 | 1.00 | 35.17 |
| ATOM | 713 | CA | GLU | 201 | 52.823 | 38.397 | −3.976 | 1.00 | 34.49 |
| ATOM | 714 | C | GLU | 201 | 54.086 | 39.284 | −4.066 | 1.00 | 34.61 |
| ATOM | 715 | O | GLU | 201 | 53.997 | 40.507 | −4.171 | 1.00 | 32.47 |
| ATOM | 716 | CB | GLU | 201 | 52.492 | 38.022 | −2.523 | 1.00 | 34.51 |
| ATOM | 717 | CG | GLU | 201 | 52.407 | 39.289 | −1.648 | 1.00 | 34.40 |
| ATOM | 718 | CD | GLU | 201 | 51.698 | 39.072 | −0.353 | 1.00 | 36.89 |
| ATOM | 719 | OE1 | GLU | 201 | 51.475 | 37.926 | 0.017 | 1.00 | 40.24 |
| ATOM | 720 | OE2 | GLU | 201 | 51.344 | 40.059 | 0.298 | 1.00 | 36.83 |
| ATOM | 721 | N | LYS | 202 | 55.260 | 38.656 | −4.042 | 1.00 | 34.91 |
| ATOM | 722 | CA | LYS | 202 | 56.499 | 39.369 | −4.256 | 1.00 | 35.18 |
| ATOM | 723 | C | LYS | 202 | 56.511 | 40.155 | −5.589 | 1.00 | 34.53 |
| ATOM | 724 | O | LYS | 202 | 56.870 | 41.335 | −5.584 | 1.00 | 33.52 |
| ATOM | 725 | CB | LYS | 202 | 57.704 | 38.404 | −4.144 | 1.00 | 36.19 |
| ATOM | 726 | CG | LYS | 202 | 58.953 | 38.888 | −4.837 | 1.00 | 36.45 |
| ATOM | 727 | CD | LYS | 202 | 60.187 | 37.956 | −4.538 | 1.00 | 36.73 |
| ATOM | 728 | CE | LYS | 202 | 61.352 | 38.334 | −5.420 | 1.00 | 38.08 |
| ATOM | 729 | NZ | LYS | 202 | 62.094 | 39.558 | −5.001 | 1.00 | 38.27 |
| ATOM | 730 | N | TYR | 203 | 56.132 | 39.496 | −6.695 | 1.00 | 34.14 |
| ATOM | 731 | CA | TYR | 203 | 56.081 | 40.077 | −8.049 | 1.00 | 34.26 |
| ATOM | 732 | C | TYR | 203 | 55.182 | 41.362 | −8.081 | 1.00 | 33.41 |
| ATOM | 733 | O | TYR | 203 | 55.545 | 42.408 | −8.591 | 1.00 | 32.66 |
| ATOM | 734 | CB | TYR | 203 | 55.507 | 39.040 | −9.034 | 1.00 | 34.85 |
| ATOM | 735 | CG | TYR | 203 | 55.420 | 39.550 | −10.446 | 1.00 | 36.49 |
| ATOM | 736 | CD1 | TYR | 203 | 56.444 | 39.292 | −11.371 | 1.00 | 37.59 |
| ATOM | 737 | CD2 | TYR | 203 | 54.323 | 40.333 | −10.869 | 1.00 | 36.73 |
| ATOM | 738 | CE1 | TYR | 203 | 56.386 | 39.791 | −12.694 | 1.00 | 38.56 |
| ATOM | 739 | CE2 | TYR | 203 | 54.267 | 40.841 | −12.195 | 1.00 | 38.63 |
| ATOM | 740 | CZ | TYR | 203 | 55.309 | 40.546 | −13.091 | 1.00 | 37.44 |
| ATOM | 741 | OH | TYR | 203 | 55.280 | 41.022 | −14.372 | 1.00 | 40.73 |
| ATOM | 742 | N | VAL | 204 | 54.002 | 41.216 | −7.518 | 1.00 | 32.56 |
| ATOM | 743 | CA | VAL | 204 | 52.952 | 42.234 | −7.520 | 1.00 | 32.86 |
| ATOM | 744 | C | VAL | 204 | 53.349 | 43.472 | −6.664 | 1.00 | 32.32 |
| ATOM | 745 | O | VAL | 204 | 53.162 | 44.628 | −7.075 | 1.00 | 32.22 |
| ATOM | 746 | CB | VAL | 204 | 51.675 | 41.454 | −7.117 | 1.00 | 33.17 |
| ATOM | 747 | CG1 | VAL | 204 | 50.933 | 41.971 | −5.882 | 1.00 | 33.70 |
| ATOM | 748 | CG2 | VAL | 204 | 50.855 | 40.953 | −8.375 | 1.00 | 31.96 |
| ATOM | 749 | N | THR | 205 | 53.936 | 43.214 | −5.498 | 1.00 | 32.24 |
| ATOM | 750 | CA | THR | 205 | 54.428 | 44.259 | −4.608 | 1.00 | 31.51 |
| ATOM | 751 | C | THR | 205 | 55.481 | 45.129 | −5.321 | 1.00 | 31.55 |
| ATOM | 752 | O | THR | 205 | 55.359 | 46.388 | −5.363 | 1.00 | 30.90 |
| ATOM | 753 | CB | THR | 205 | 54.970 | 43.608 | −3.295 | 1.00 | 31.73 |

TABLE 11-continued

Three-Dimensional Coordinates of *Neisseria gonorrhoeae* GCYH-IB·Mn$^{2+}$
(SEQ. ID. No. 8)

| ATOM | 754 | OG1 | THR | 205 | 53.875 | 42.946 | −2.591 | 1.00 | 30.86 |
|---|---|---|---|---|---|---|---|---|---|
| ATOM | 755 | CG2 | THR | 205 | 55.646 | 44.659 | −2.411 | 1.00 | 31.29 |
| ATOM | 756 | N | GLU | 206 | 56.491 | 44.454 | −5.892 | 1.00 | 31.37 |
| ATOM | 757 | CA | GLU | 206 | 57.593 | 45.095 | −6.652 | 1.00 | 32.61 |
| ATOM | 758 | C | GLU | 206 | 57.142 | 45.761 | −7.949 | 1.00 | 32.07 |
| ATOM | 759 | O | GLU | 206 | 57.573 | 46.855 | −8.226 | 1.00 | 31.97 |
| ATOM | 760 | CB | GLU | 206 | 58.753 | 44.123 | −6.930 | 1.00 | 32.31 |
| ATOM | 761 | CG | GLU | 206 | 59.419 | 43.619 | −5.654 | 1.00 | 33.50 |
| ATOM | 762 | CD | GLU | 206 | 60.435 | 42.484 | −5.897 | 1.00 | 34.50 |
| ATOM | 763 | OE1 | GLU | 206 | 60.604 | 42.040 | −7.066 | 1.00 | 38.19 |
| ATOM | 764 | OE2 | GLU | 206 | 61.035 | 42.032 | −4.917 | 1.00 | 31.10 |
| ATOM | 765 | N | LYS | 207 | 56.281 | 45.110 | −8.721 | 1.00 | 31.90 |
| ATOM | 766 | CA | LYS | 207 | 55.750 | 45.712 | −9.952 | 1.00 | 32.07 |
| ATOM | 767 | C | LYS | 207 | 55.029 | 47.049 | −9.645 | 1.00 | 32.17 |
| ATOM | 768 | O | LYS | 207 | 55.321 | 48.081 | −10.253 | 1.00 | 32.06 |
| ATOM | 769 | CB | LYS | 207 | 54.804 | 44.732 | −10.670 | 1.00 | 32.80 |
| ATOM | 770 | CG | LYS | 207 | 54.356 | 45.155 | −12.090 | 1.00 | 36.71 |
| ATOM | 771 | CD | LYS | 207 | 55.577 | 45.529 | −12.935 | 1.00 | 43.40 |
| ATOM | 772 | CE | LYS | 207 | 55.461 | 45.108 | −14.453 | 1.00 | 46.89 |
| ATOM | 773 | NZ | LYS | 207 | 56.763 | 45.323 | −15.135 | 1.00 | 47.00 |
| ATOM | 774 | N | ALA | 208 | 54.094 | 47.030 | −8.690 | 1.00 | 30.86 |
| ATOM | 775 | CA | ALA | 208 | 53.376 | 48.257 | −8.340 | 1.00 | 30.32 |
| ATOM | 776 | C | ALA | 208 | 54.366 | 49.365 | −7.984 | 1.00 | 30.56 |
| ATOM | 777 | O | ALA | 208 | 54.272 | 50.500 | −8.483 | 1.00 | 29.36 |
| ATOM | 778 | CB | ALA | 208 | 52.364 | 48.005 | −7.163 | 1.00 | 28.98 |
| ATOM | 779 | N | TYR | 209 | 55.321 | 49.017 | −7.116 | 1.00 | 31.34 |
| ATOM | 780 | CA | TYR | 209 | 56.333 | 49.945 | −6.618 | 1.00 | 32.07 |
| ATOM | 781 | C | TYR | 209 | 57.240 | 50.482 | −7.739 | 1.00 | 32.83 |
| ATOM | 782 | O | TYR | 209 | 57.700 | 51.637 | −7.691 | 1.00 | 32.54 |
| ATOM | 783 | CB | TYR | 209 | 57.154 | 49.253 | −5.554 | 1.00 | 32.73 |
| ATOM | 784 | CG | TYR | 209 | 58.158 | 50.135 | −4.853 | 1.00 | 33.75 |
| ATOM | 785 | CD1 | TYR | 209 | 57.787 | 50.864 | −3.703 | 1.00 | 34.84 |
| ATOM | 786 | CD2 | TYR | 209 | 59.483 | 50.223 | −5.299 | 1.00 | 33.51 |
| ATOM | 787 | CE1 | TYR | 209 | 58.718 | 51.662 | −3.031 | 1.00 | 34.86 |
| ATOM | 788 | CE2 | TYR | 209 | 60.438 | 51.049 | −4.623 | 1.00 | 34.90 |
| ATOM | 789 | CZ | TYR | 209 | 60.032 | 51.759 | −3.486 | 1.00 | 33.05 |
| ATOM | 790 | OH | TYR | 209 | 60.932 | 52.575 | −2.791 | 1.00 | 35.66 |
| ATOM | 791 | N | GLU | 210 | 57.463 | 49.666 | −8.762 | 1.00 | 34.05 |
| ATOM | 792 | CA | GLU | 210 | 58.206 | 50.124 | −9.956 | 1.00 | 34.62 |
| ATOM | 793 | C | GLU | 210 | 57.331 | 50.963 | −10.902 | 1.00 | 35.41 |
| ATOM | 794 | O | GLU | 210 | 57.848 | 51.629 | −11.824 | 1.00 | 34.97 |
| ATOM | 795 | CB | GLU | 210 | 58.758 | 48.924 | −10.696 | 1.00 | 35.86 |
| ATOM | 796 | CG | GLU | 210 | 59.770 | 48.085 | −9.883 | 1.00 | 36.13 |
| ATOM | 797 | CD | GLU | 210 | 59.917 | 46.646 | −10.388 | 1.00 | 38.52 |
| ATOM | 798 | OE1 | GLU | 210 | 59.209 | 46.222 | −11.326 | 1.00 | 38.33 |
| ATOM | 799 | OE2 | GLU | 210 | 60.761 | 45.923 | −9.805 | 1.00 | 40.89 |
| ATOM | 800 | N | ASN | 211 | 56.010 | 50.925 | −10.701 | 1.00 | 34.65 |
| ATOM | 801 | CA | ASN | 211 | 55.071 | 51.615 | −11.625 | 1.00 | 35.17 |
| ATOM | 802 | C | ASN | 211 | 54.033 | 52.471 | −10.929 | 1.00 | 33.23 |
| ATOM | 803 | O | ASN | 211 | 52.844 | 52.319 | −11.179 | 1.00 | 34.24 |
| ATOM | 804 | CB | ASN | 211 | 54.387 | 50.656 | −12.597 | 1.00 | 35.24 |
| ATOM | 805 | CG | ASN | 211 | 55.388 | 49.871 | −13.414 | 1.00 | 38.14 |
| ATOM | 806 | OD1 | ASN | 211 | 55.927 | 48.833 | −12.954 | 1.00 | 41.46 |
| ATOM | 807 | ND2 | ASN | 211 | 55.681 | 50.367 | −14.617 | 1.00 | 36.20 |
| ATOM | 808 | N | PRO | 212 | 54.503 | 53.427 | −10.110 | 1.00 | 32.10 |
| ATOM | 809 | CA | PRO | 212 | 53.583 | 54.274 | −9.385 | 1.00 | 31.76 |
| ATOM | 810 | C | PRO | 212 | 52.823 | 55.163 | −10.356 | 1.00 | 31.38 |
| ATOM | 811 | O | PRO | 212 | 53.380 | 55.633 | −11.353 | 1.00 | 30.16 |
| ATOM | 812 | CB | PRO | 212 | 54.490 | 55.103 | −8.486 | 1.00 | 30.78 |
| ATOM | 813 | CG | PRO | 212 | 55.845 | 55.134 | −9.224 | 1.00 | 31.04 |
| ATOM | 814 | CD | PRO | 212 | 55.922 | 53.801 | −9.893 | 1.00 | 31.09 |
| ATOM | 815 | N | LYS | 213 | 51.562 | 55.406 | −10.036 | 1.00 | 30.99 |
| ATOM | 816 | CA | LYS | 213 | 50.761 | 56.346 | −10.818 | 1.00 | 31.42 |
| ATOM | 817 | C | LYS | 213 | 49.766 | 57.072 | −9.955 | 1.00 | 31.15 |
| ATOM | 818 | O | LYS | 213 | 49.074 | 56.467 | −9.116 | 1.00 | 31.01 |
| ATOM | 819 | CB | LYS | 213 | 49.986 | 55.603 | −11.911 | 1.00 | 30.59 |
| ATOM | 820 | CG | LYS | 213 | 50.911 | 55.017 | −12.959 | 1.00 | 29.40 |
| ATOM | 821 | CD | LYS | 213 | 50.177 | 54.712 | −14.282 | 1.00 | 27.87 |
| ATOM | 822 | CE | LYS | 213 | 51.127 | 54.020 | −15.275 | 1.00 | 29.06 |
| ATOM | 823 | NZ | LYS | 213 | 50.269 | 53.473 | −16.416 | 1.00 | 29.60 |
| ATOM | 824 | N | PHE | 214 | 49.736 | 58.380 | −10.165 | 1.00 | 31.08 |
| ATOM | 825 | CA | PHE | 214 | 48.631 | 59.232 | −9.699 | 1.00 | 31.02 |
| ATOM | 826 | C | PHE | 214 | 47.336 | 58.851 | −10.398 | 1.00 | 29.28 |
| ATOM | 827 | O | PHE | 214 | 47.336 | 58.200 | −11.486 | 1.00 | 28.86 |
| ATOM | 828 | CB | PHE | 214 | 48.962 | 60.715 | −10.011 | 1.00 | 31.33 |
| ATOM | 829 | CG | PHE | 214 | 50.110 | 61.273 | −9.193 | 1.00 | 33.17 |
| ATOM | 830 | CD1 | PHE | 214 | 50.029 | 61.331 | −7.785 | 1.00 | 34.17 |

TABLE 11-continued

Three-Dimensional Coordinates of *Neisseria gonorrhoeae* GCYH-IB·Mn$^{2+}$
(SEQ. ID. No. 8)

| ATOM | 831 | CD2 | PHE | 214 | 51.254 | 61.777 | −9.826 | 1.00 | 31.80 |
|------|-----|-----|-----|-----|--------|--------|--------|------|-------|
| ATOM | 832 | CE1 | PHE | 214 | 51.118 | 61.848 | −7.014 | 1.00 | 36.33 |
| ATOM | 833 | CE2 | PHE | 214 | 52.323 | 62.291 | −9.087 | 1.00 | 32.91 |
| ATOM | 834 | CZ | PHE | 214 | 52.258 | 62.343 | −7.665 | 1.00 | 33.95 |
| ATOM | 835 | N | VAL | 215 | 46.226 | 59.269 | −9.796 | 1.00 | 27.85 |
| ATOM | 836 | CA | VAL | 215 | 44.911 | 59.108 | −10.377 | 1.00 | 28.62 |
| ATOM | 837 | C | VAL | 215 | 44.878 | 59.813 | −11.762 | 1.00 | 28.57 |
| ATOM | 838 | O | VAL | 215 | 44.295 | 59.280 | −12.682 | 1.00 | 27.90 |
| ATOM | 839 | CB | VAL | 215 | 43.749 | 59.519 | −9.352 | 1.00 | 28.94 |
| ATOM | 840 | CG1 | VAL | 215 | 43.721 | 61.018 | −9.060 | 1.00 | 29.40 |
| ATOM | 841 | CG2 | VAL | 215 | 42.428 | 59.073 | −9.813 | 1.00 | 29.76 |
| ATOM | 842 | N | GLU | 216 | 45.546 | 60.970 | −11.872 | 1.00 | 28.34 |
| ATOM | 843 | CA | GLU | 216 | 45.735 | 61.768 | −13.131 | 1.00 | 29.82 |
| ATOM | 844 | C | GLU | 216 | 46.364 | 60.930 | −14.235 | 1.00 | 28.79 |
| ATOM | 845 | O | GLU | 216 | 45.822 | 60.801 | −15.311 | 1.00 | 28.87 |
| ATOM | 846 | CB | GLU | 216 | 46.608 | 63.020 | −12.835 | 1.00 | 28.86 |
| ATOM | 847 | CG | GLU | 216 | 45.872 | 64.035 | −11.934 | 1.00 | 32.94 |
| ATOM | 848 | CD | GLU | 216 | 46.306 | 63.994 | −10.455 | 1.00 | 34.70 |
| ATOM | 849 | OE1 | GLU | 216 | 46.537 | 62.903 | −9.914 | 1.00 | 35.44 |
| ATOM | 850 | OE2 | GLU | 216 | 46.400 | 65.073 | −9.820 | 1.00 | 37.76 |
| ATOM | 851 | N | ASP | 217 | 47.483 | 60.303 | −13.892 | 1.00 | 29.08 |
| ATOM | 852 | CA | ASP | 217 | 48.235 | 59.389 | −14.751 | 1.00 | 28.86 |
| ATOM | 853 | C | ASP | 217 | 47.386 | 58.235 | −15.203 | 1.00 | 28.38 |
| ATOM | 854 | O | ASP | 217 | 47.338 | 57.916 | −16.408 | 1.00 | 27.02 |
| ATOM | 855 | CB | ASP | 217 | 49.437 | 58.850 | −14.000 | 1.00 | 29.76 |
| ATOM | 856 | CG | ASP | 217 | 50.398 | 59.919 | −13.603 | 1.00 | 31.99 |
| ATOM | 857 | OD1 | ASP | 217 | 50.489 | 60.928 | −14.298 | 1.00 | 38.26 |
| ATOM | 858 | OD2 | ASP | 217 | 51.084 | 59.766 | −12.591 | 1.00 | 34.15 |
| ATOM | 859 | N | MET | 218 | 46.696 | 57.589 | −14.261 | 1.00 | 28.36 |
| ATOM | 860 | CA | MET | 218 | 45.812 | 56.492 | −14.647 | 1.00 | 29.64 |
| ATOM | 861 | C | MET | 218 | 44.706 | 56.862 | −15.656 | 1.00 | 28.41 |
| ATOM | 862 | O | MET | 218 | 44.492 | 56.145 | −16.636 | 1.00 | 26.63 |
| ATOM | 863 | CB | MET | 218 | 45.176 | 55.791 | −13.422 | 1.00 | 30.96 |
| ATOM | 864 | CG | MET | 218 | 44.319 | 54.575 | −13.861 | 1.00 | 35.70 |
| ATOM | 865 | SD | MET | 218 | 45.273 | 53.140 | −14.514 | 1.00 | 45.47 |
| ATOM | 866 | CE | MET | 218 | 46.456 | 53.050 | −13.190 | 1.00 | 46.95 |
| ATOM | 867 | N | VAL | 219 | 43.962 | 57.941 | −15.405 | 1.00 | 28.22 |
| ATOM | 868 | CA | VAL | 219 | 42.869 | 58.262 | −16.337 | 1.00 | 28.10 |
| ATOM | 869 | C | VAL | 219 | 43.427 | 58.690 | −17.690 | 1.00 | 27.11 |
| ATOM | 870 | O | VAL | 219 | 42.857 | 58.342 | −18.725 | 1.00 | 27.29 |
| ATOM | 871 | CB | VAL | 219 | 41.773 | 59.259 | −15.749 | 1.00 | 28.69 |
| ATOM | 872 | CG1 | VAL | 219 | 41.164 | 58.645 | −14.457 | 1.00 | 29.54 |
| ATOM | 873 | CG2 | VAL | 219 | 42.347 | 60.643 | −15.445 | 1.00 | 27.60 |
| ATOM | 874 | N | ARG | 220 | 44.529 | 59.424 | −17.692 | 1.00 | 27.25 |
| ATOM | 875 | CA | ARG | 220 | 45.171 | 59.840 | −18.986 | 1.00 | 29.06 |
| ATOM | 876 | C | ARG | 220 | 45.667 | 58.643 | −19.743 | 1.00 | 28.85 |
| ATOM | 877 | O | ARG | 220 | 45.464 | 58.585 | −20.955 | 1.00 | 30.55 |
| ATOM | 878 | CB | ARG | 220 | 46.331 | 60.821 | −18.797 | 1.00 | 27.73 |
| ATOM | 879 | CG | ARG | 220 | 45.901 | 62.272 | −18.483 | 1.00 | 29.78 |
| ATOM | 880 | CD | ARG | 220 | 47.100 | 63.094 | −17.937 | 1.00 | 29.72 |
| ATOM | 881 | NE | ARG | 220 | 46.730 | 64.494 | −18.068 | 1.00 | 33.92 |
| ATOM | 882 | CZ | ARG | 220 | 47.200 | 65.477 | −17.324 | 1.00 | 32.61 |
| ATOM | 883 | NH1 | ARG | 220 | 48.094 | 65.214 | −16.410 | 1.00 | 33.13 |
| ATOM | 884 | NH2 | ARG | 220 | 46.761 | 66.725 | −17.514 | 1.00 | 34.32 |
| ATOM | 885 | N | ASP | 221 | 46.313 | 57.712 | −19.036 | 1.00 | 28.07 |
| ATOM | 886 | CA | ASP | 221 | 46.889 | 56.471 | −19.662 | 1.00 | 28.23 |
| ATOM | 887 | C | ASP | 221 | 45.801 | 55.599 | −20.281 | 1.00 | 27.79 |
| ATOM | 888 | O | ASP | 221 | 45.901 | 55.153 | −21.453 | 1.00 | 28.28 |
| ATOM | 889 | CB | ASP | 221 | 47.746 | 55.697 | −18.645 | 1.00 | 27.76 |
| ATOM | 890 | CG | ASP | 221 | 49.112 | 56.318 | −18.449 | 1.00 | 29.80 |
| ATOM | 891 | OD1 | ASP | 221 | 49.405 | 57.309 | −19.147 | 1.00 | 30.61 |
| ATOM | 892 | OD2 | ASP | 221 | 49.902 | 55.850 | −17.583 | 1.00 | 32.40 |
| ATOM | 893 | N | VAL | 222 | 44.730 | 55.358 | −19.532 | 1.00 | 25.93 |
| ATOM | 894 | CA | VAL | 222 | 43.588 | 54.659 | −20.109 | 1.00 | 25.63 |
| ATOM | 895 | C | VAL | 222 | 42.893 | 55.417 | −21.279 | 1.00 | 26.39 |
| ATOM | 896 | O | VAL | 222 | 42.539 | 54.788 | −22.285 | 1.00 | 26.70 |
| ATOM | 897 | CB | VAL | 222 | 42.517 | 54.272 | −19.058 | 1.00 | 24.90 |
| ATOM | 898 | CG1 | VAL | 222 | 41.313 | 53.621 | −19.773 | 1.00 | 25.51 |
| ATOM | 899 | CG2 | VAL | 222 | 43.098 | 53.309 | −18.028 | 1.00 | 24.07 |
| ATOM | 900 | N | ALA | 223 | 42.664 | 56.732 | −21.126 | 1.00 | 25.77 |
| ATOM | 901 | CA | ALA | 223 | 41.954 | 57.535 | −22.148 | 1.00 | 26.96 |
| ATOM | 902 | C | ALA | 223 | 42.728 | 57.519 | −23.503 | 1.00 | 27.41 |
| ATOM | 903 | O | ALA | 223 | 42.141 | 57.449 | −24.555 | 1.00 | 27.99 |
| ATOM | 904 | CB | ALA | 223 | 41.761 | 58.976 | −21.674 | 1.00 | 24.19 |
| ATOM | 905 | N | THR | 224 | 44.042 | 57.579 | −23.440 | 1.00 | 29.50 |
| ATOM | 906 | CA | THR | 224 | 44.885 | 57.497 | −24.635 | 1.00 | 30.83 |
| ATOM | 907 | C | THR | 224 | 44.640 | 56.163 | −25.358 | 1.00 | 31.18 |

TABLE 11-continued

Three-Dimensional Coordinates of *Neisseria gonorrhoeae* GCYH-IB·Mn$^{2+}$
(SEQ. ID. No. 8)

| ATOM | 908 | O | THR | 224 | 44.426 | 56.153 | −26.568 | 1.00 | 31.47 |
|---|---|---|---|---|---|---|---|---|---|
| ATOM | 909 | CB | THR | 224 | 46.353 | 57.671 | −24.266 | 1.00 | 31.10 |
| ATOM | 910 | OG1 | THR | 224 | 46.515 | 58.940 | −23.611 | 1.00 | 32.84 |
| ATOM | 911 | CG2 | THR | 224 | 47.176 | 57.728 | −25.503 | 1.00 | 32.78 |
| ATOM | 912 | N | SER | 225 | 44.589 | 55.061 | −24.612 | 1.00 | 31.19 |
| ATOM | 913 | CA | SER | 225 | 44.306 | 53.722 | −25.208 | 1.00 | 32.14 |
| ATOM | 914 | C | SER | 225 | 42.957 | 53.650 | −25.930 | 1.00 | 31.64 |
| ATOM | 915 | O | SER | 225 | 42.830 | 53.046 | −26.990 | 1.00 | 32.34 |
| ATOM | 916 | CB | SER | 225 | 44.323 | 52.656 | −24.141 | 1.00 | 32.10 |
| ATOM | 917 | OG | SER | 225 | 45.639 | 52.349 | −23.727 | 1.00 | 33.71 |
| ATOM | 918 | N | LEU | 226 | 41.937 | 54.263 | −25.346 | 1.00 | 31.46 |
| ATOM | 919 | CA | LEU | 226 | 40.571 | 54.266 | −25.908 | 1.00 | 31.10 |
| ATOM | 920 | C | LEU | 226 | 40.437 | 55.192 | −27.121 | 1.00 | 31.71 |
| ATOM | 921 | O | LEU | 226 | 39.721 | 54.868 | −28.084 | 1.00 | 31.22 |
| ATOM | 922 | CB | LEU | 226 | 39.570 | 54.742 | −24.815 | 1.00 | 30.41 |
| ATOM | 923 | CG | LEU | 226 | 39.527 | 53.888 | −23.517 | 1.00 | 28.65 |
| ATOM | 924 | CD1 | LEU | 226 | 38.528 | 54.473 | −22.550 | 1.00 | 26.39 |
| ATOM | 925 | CD2 | LEU | 226 | 39.099 | 52.494 | −23.861 | 1.00 | 26.47 |
| ATOM | 926 | N | ILE | 227 | 41.083 | 56.357 | −27.053 | 1.00 | 32.52 |
| ATOM | 927 | CA | ILE | 227 | 41.131 | 57.262 | −28.223 | 1.00 | 34.66 |
| ATOM | 928 | C | ILE | 227 | 41.711 | 56.576 | −29.449 | 1.00 | 34.68 |
| ATOM | 929 | O | ILE | 227 | 41.198 | 56.725 | −30.533 | 1.00 | 36.02 |
| ATOM | 930 | CB | ILE | 227 | 41.928 | 58.555 | −27.959 | 1.00 | 35.04 |
| ATOM | 931 | CG1 | ILE | 227 | 41.168 | 59.408 | −26.956 | 1.00 | 34.54 |
| ATOM | 932 | CG2 | ILE | 227 | 42.124 | 59.326 | −29.307 | 1.00 | 35.53 |
| ATOM | 933 | CD1 | ILE | 227 | 42.062 | 60.418 | −26.261 | 1.00 | 35.14 |
| ATOM | 934 | N | ALA | 228 | 42.764 | 55.808 | −29.247 | 1.00 | 35.83 |
| ATOM | 935 | CA | ALA | 228 | 43.345 | 54.957 | −30.266 | 1.00 | 36.33 |
| ATOM | 936 | C | ALA | 228 | 42.442 | 53.813 | −30.810 | 1.00 | 36.87 |
| ATOM | 937 | O | ALA | 228 | 42.849 | 53.109 | −31.733 | 1.00 | 36.87 |
| ATOM | 938 | CB | ALA | 228 | 44.625 | 54.367 | −29.715 | 1.00 | 35.72 |
| ATOM | 939 | N | ASP | 229 | 41.284 | 53.556 | −30.200 | 1.00 | 36.77 |
| ATOM | 940 | CA | ASP | 229 | 40.461 | 52.454 | −30.644 | 1.00 | 37.00 |
| ATOM | 941 | C | ASP | 229 | 39.408 | 53.150 | −31.459 | 1.00 | 38.22 |
| ATOM | 942 | O | ASP | 229 | 38.582 | 53.892 | −30.903 | 1.00 | 37.95 |
| ATOM | 943 | CB | ASP | 229 | 39.842 | 51.696 | −29.446 | 1.00 | 36.82 |
| ATOM | 944 | CG | ASP | 229 | 39.075 | 50.427 | −29.856 | 1.00 | 35.61 |
| ATOM | 945 | OD1 | ASP | 229 | 38.303 | 50.430 | −30.845 | 1.00 | 32.28 |
| ATOM | 946 | OD2 | ASP | 229 | 39.234 | 49.400 | −29.166 | 1.00 | 36.47 |
| ATOM | 947 | N | LYS | 230 | 39.439 | 52.952 | −32.785 | 1.00 | 39.74 |
| ATOM | 948 | CA | LYS | 230 | 38.611 | 53.794 | −33.663 | 1.00 | 40.81 |
| ATOM | 949 | C | LYS | 230 | 37.141 | 53.311 | −33.702 | 1.00 | 40.52 |
| ATOM | 950 | O | LYS | 230 | 36.284 | 54.023 | −34.227 | 1.00 | 41.73 |
| ATOM | 951 | CB | LYS | 230 | 39.210 | 53.987 | −35.107 | 1.00 | 41.71 |
| ATOM | 952 | CG | LYS | 230 | 40.744 | 54.405 | −35.297 | 1.00 | 43.63 |
| ATOM | 953 | CD | LYS | 230 | 41.364 | 55.367 | −34.210 | 1.00 | 44.04 |
| ATOM | 954 | CE | LYS | 230 | 42.910 | 55.731 | −34.504 | 1.00 | 40.84 |
| ATOM | 955 | NZ | LYS | 230 | 44.069 | 54.838 | −33.927 | 1.00 | 29.08 |
| ATOM | 956 | N | GLU | 240 | 38.629 | 56.109 | −9.090 | 1.00 | 26.04 |
| ATOM | 957 | CA | GLU | 240 | 38.563 | 56.440 | −7.677 | 1.00 | 25.79 |
| ATOM | 958 | C | GLU | 240 | 39.604 | 55.580 | −6.918 | 1.00 | 26.33 |
| ATOM | 959 | O | GLU | 240 | 39.581 | 54.323 | −7.008 | 1.00 | 26.15 |
| ATOM | 960 | CB | GLU | 240 | 37.133 | 56.189 | −7.133 | 1.00 | 25.72 |
| ATOM | 961 | CG | GLU | 240 | 36.967 | 56.616 | −5.663 | 1.00 | 25.21 |
| ATOM | 962 | CD | GLU | 240 | 35.532 | 56.595 | −5.146 | 1.00 | 26.43 |
| ATOM | 963 | OE1 | GLU | 240 | 34.604 | 56.243 | −5.902 | 1.00 | 27.62 |
| ATOM | 964 | OE2 | GLU | 240 | 35.322 | 56.973 | −3.967 | 1.00 | 26.61 |
| ATOM | 965 | N | ASN | 241 | 40.534 | 56.239 | −6.207 | 1.00 | 26.14 |
| ATOM | 966 | CA | ASN | 241 | 41.553 | 55.525 | −5.458 | 1.00 | 25.32 |
| ATOM | 967 | C | ASN | 241 | 41.235 | 55.691 | −3.974 | 1.00 | 25.25 |
| ATOM | 968 | O | ASN | 241 | 41.123 | 56.826 | −3.494 | 1.00 | 23.38 |
| ATOM | 969 | CB | ASN | 241 | 42.918 | 56.080 | −5.756 | 1.00 | 26.66 |
| ATOM | 970 | CG | ASN | 241 | 43.291 | 55.967 | −7.253 | 1.00 | 29.90 |
| ATOM | 971 | OD1 | ASN | 241 | 44.408 | 56.313 | −7.640 | 1.00 | 36.12 |
| ATOM | 972 | ND2 | ASN | 241 | 42.386 | 55.453 | −8.072 | 1.00 | 27.28 |
| ATOM | 973 | N | PHE | 242 | 41.063 | 54.564 | −3.277 | 1.00 | 23.13 |
| ATOM | 974 | CA | PHE | 242 | 40.624 | 54.548 | −1.896 | 1.00 | 24.91 |
| ATOM | 975 | C | PHE | 242 | 41.842 | 54.769 | −1.023 | 1.00 | 25.54 |
| ATOM | 976 | O | PHE | 242 | 42.315 | 53.851 | −0.388 | 1.00 | 25.14 |
| ATOM | 977 | CB | PHE | 242 | 39.830 | 53.259 | −1.586 | 1.00 | 24.91 |
| ATOM | 978 | CG | PHE | 242 | 38.557 | 53.179 | −2.379 | 1.00 | 25.60 |
| ATOM | 979 | CD1 | PHE | 242 | 37.410 | 53.824 | −1.922 | 1.00 | 26.78 |
| ATOM | 980 | CD2 | PHE | 242 | 38.544 | 52.570 | −3.650 | 1.00 | 25.71 |
| ATOM | 981 | CE1 | PHE | 242 | 36.201 | 53.800 | −2.691 | 1.00 | 29.47 |
| ATOM | 982 | CE2 | PHE | 242 | 37.364 | 52.585 | −4.469 | 1.00 | 24.56 |
| ATOM | 983 | CZ | PHE | 242 | 36.193 | 53.174 | −3.984 | 1.00 | 26.86 |
| ATOM | 984 | N | GLU | 243 | 42.356 | 56.005 | −1.066 | 1.00 | 25.28 |

TABLE 11-continued

Three-Dimensional Coordinates of *Neisseria gonorrhoeae* GCYH-IB·Mn$^{2+}$
(SEQ. ID. No. 8)

| ATOM | 985 | CA | GLU | 243 | 43.638 | 56.383 | −0.503 | 1.00 | 27.20 |
|------|------|-----|-----|-----|--------|--------|--------|------|-------|
| ATOM | 986 | C | GLU | 243 | 43.891 | 55.714 | 0.844 | 1.00 | 26.88 |
| ATOM | 987 | O | GLU | 243 | 43.133 | 55.939 | 1.776 | 1.00 | 27.26 |
| ATOM | 988 | CB | GLU | 243 | 43.754 | 57.907 | −0.342 | 1.00 | 28.44 |
| ATOM | 989 | CG | GLU | 243 | 43.600 | 58.669 | −1.660 | 1.00 | 30.04 |
| ATOM | 990 | CD | GLU | 243 | 44.744 | 58.326 | −2.585 | 1.00 | 32.00 |
| ATOM | 991 | OE1 | GLU | 243 | 44.617 | 57.383 | −3.389 | 1.00 | 30.26 |
| ATOM | 992 | OE2 | GLU | 243 | 45.815 | 58.944 | −2.446 | 1.00 | 35.21 |
| ATOM | 993 | N | SER | 244 | 44.962 | 54.926 | 0.945 | 1.00 | 27.02 |
| ATOM | 994 | CA | SER | 244 | 45.160 | 54.124 | 2.185 | 1.00 | 27.90 |
| ATOM | 995 | C | SER | 244 | 45.582 | 54.978 | 3.363 | 1.00 | 28.54 |
| ATOM | 996 | O | SER | 244 | 45.551 | 54.508 | 4.525 | 1.00 | 29.90 |
| ATOM | 997 | CB | SER | 244 | 46.139 | 52.988 | 1.959 | 1.00 | 26.85 |
| ATOM | 998 | OG | SER | 244 | 47.413 | 53.524 | 1.761 | 1.00 | 25.99 |
| ATOM | 999 | N | ILE | 245 | 45.936 | 56.242 | 3.097 | 1.00 | 28.99 |
| ATOM | 1000 | CA | ILE | 245 | 46.325 | 57.173 | 4.192 | 1.00 | 28.75 |
| ATOM | 1001 | C | ILE | 245 | 45.263 | 58.213 | 4.615 | 1.00 | 28.22 |
| ATOM | 1002 | O | ILE | 245 | 45.454 | 58.973 | 5.589 | 1.00 | 28.72 |
| ATOM | 1003 | CB | ILE | 245 | 47.619 | 57.930 | 3.832 | 1.00 | 28.52 |
| ATOM | 1004 | CG1 | ILE | 245 | 47.395 | 58.849 | 2.619 | 1.00 | 27.33 |
| ATOM | 1005 | CG2 | ILE | 245 | 48.795 | 56.924 | 3.645 | 1.00 | 26.82 |
| ATOM | 1006 | CD1 | ILE | 245 | 48.584 | 59.899 | 2.445 | 1.00 | 28.82 |
| ATOM | 1007 | N | HIS | 246 | 44.184 | 58.275 | 3.849 | 1.00 | 27.14 |
| ATOM | 1008 | CA | HIS | 246 | 43.062 | 59.140 | 4.132 | 1.00 | 26.06 |
| ATOM | 1009 | C | HIS | 246 | 41.827 | 58.311 | 4.349 | 1.00 | 26.53 |
| ATOM | 1010 | O | HIS | 246 | 41.870 | 57.070 | 4.164 | 1.00 | 25.05 |
| ATOM | 1011 | CB | HIS | 246 | 42.806 | 60.041 | 2.962 | 1.00 | 26.37 |
| ATOM | 1012 | CG | HIS | 246 | 43.931 | 60.957 | 2.686 | 1.00 | 27.22 |
| ATOM | 1013 | ND1 | HIS | 246 | 44.492 | 61.076 | 1.432 | 1.00 | 29.18 |
| ATOM | 1014 | CD2 | HIS | 246 | 44.608 | 61.803 | 3.496 | 1.00 | 26.14 |
| ATOM | 1015 | CE1 | HIS | 246 | 45.470 | 61.961 | 1.482 | 1.00 | 27.29 |
| ATOM | 1016 | NE2 | HIS | 246 | 45.572 | 62.409 | 2.722 | 1.00 | 28.61 |
| ATOM | 1017 | N | ASN | 247 | 40.747 | 58.982 | 4.800 | 1.00 | 25.55 |
| ATOM | 1018 | CA | ASN | 247 | 39.419 | 58.329 | 4.806 | 1.00 | 25.30 |
| ATOM | 1019 | C | ASN | 247 | 38.497 | 58.880 | 3.718 | 1.00 | 25.63 |
| ATOM | 1020 | O | ASN | 247 | 37.262 | 58.817 | 3.835 | 1.00 | 24.99 |
| ATOM | 1021 | CB | ASN | 247 | 38.719 | 58.368 | 6.211 | 1.00 | 24.56 |
| ATOM | 1022 | CG | ASN | 247 | 37.661 | 57.281 | 6.348 | 1.00 | 25.15 |
| ATOM | 1023 | OD1 | ASN | 247 | 37.853 | 56.171 | 5.856 | 1.00 | 27.25 |
| ATOM | 1024 | ND2 | ASN | 247 | 36.531 | 57.594 | 6.973 | 1.00 | 25.75 |
| ATOM | 1025 | N | SER | 249 | 38.626 | 59.597 | −0.930 | 1.00 | 24.78 |
| ATOM | 1026 | CA | SER | 249 | 39.213 | 59.045 | −2.180 | 1.00 | 24.32 |
| ATOM | 1027 | C | SER | 249 | 39.808 | 60.130 | −3.013 | 1.00 | 24.05 |
| ATOM | 1028 | O | SER | 249 | 39.310 | 61.225 | −2.945 | 1.00 | 25.10 |
| ATOM | 1029 | CB | SER | 249 | 38.100 | 58.361 | −2.967 | 1.00 | 23.81 |
| ATOM | 1030 | OG | SER | 249 | 37.687 | 57.149 | −2.322 | 1.00 | 24.81 |
| ATOM | 1031 | N | ALA | 250 | 40.875 | 59.846 | −3.763 | 1.00 | 24.15 |
| ATOM | 1032 | CA | ALA | 250 | 41.299 | 60.666 | −4.900 | 1.00 | 24.78 |
| ATOM | 1033 | C | ALA | 250 | 40.460 | 60.222 | −6.086 | 1.00 | 25.30 |
| ATOM | 1034 | O | ALA | 250 | 40.141 | 59.036 | −6.212 | 1.00 | 25.56 |
| ATOM | 1035 | CB | ALA | 250 | 42.799 | 60.442 | −5.181 | 1.00 | 25.32 |
| ATOM | 1036 | N | TYR | 251 | 40.095 | 61.159 | −6.971 | 1.00 | 24.61 |
| ATOM | 1037 | CA | TYR | 251 | 39.171 | 60.879 | −8.041 | 1.00 | 24.59 |
| ATOM | 1038 | C | TYR | 251 | 39.481 | 61.721 | −9.294 | 1.00 | 25.35 |
| ATOM | 1039 | O | TYR | 251 | 39.807 | 62.903 | −9.169 | 1.00 | 25.44 |
| ATOM | 1040 | CB | TYR | 251 | 37.739 | 61.192 | −7.534 | 1.00 | 25.31 |
| ATOM | 1041 | CG | TYR | 251 | 36.650 | 61.072 | −8.575 | 1.00 | 24.55 |
| ATOM | 1042 | CD1 | TYR | 251 | 36.232 | 59.831 | −9.035 | 1.00 | 23.76 |
| ATOM | 1043 | CD2 | TYR | 251 | 36.033 | 62.228 | −9.120 | 1.00 | 27.05 |
| ATOM | 1044 | CE1 | TYR | 251 | 35.218 | 59.714 | −10.015 | 1.00 | 23.94 |
| ATOM | 1045 | CE2 | TYR | 251 | 35.009 | 62.121 | −10.113 | 1.00 | 26.38 |
| ATOM | 1046 | CZ | TYR | 251 | 34.626 | 60.872 | −10.547 | 1.00 | 25.70 |
| ATOM | 1047 | OH | TYR | 251 | 33.644 | 60.763 | −11.508 | 1.00 | 30.46 |
| ATOM | 1048 | MN | MN2 | 258 | 50.065 | 59.976 | −1.837 | 1.00 | 31.39 |
| ATOM | 1049 | N1 | AZI | 261 | 48.108 | 61.800 | −2.111 | 0.50 | 29.51 |
| ATOM | 1050 | N2 | AZI | 261 | 47.484 | 62.346 | −1.282 | 0.50 | 23.78 |
| ATOM | 1051 | N3 | AZI | 261 | 47.000 | 62.868 | −0.349 | 0.50 | 33.34 |
| ATOM | 1052 | N | ARG | 14 | 51.699 | 37.265 | 25.990 | 1.00 | 59.94 |
| ATOM | 1053 | CA | ARG | 14 | 50.569 | 36.319 | 25.839 | 1.00 | 60.10 |
| ATOM | 1054 | C | ARG | 14 | 49.765 | 36.676 | 24.590 | 1.00 | 59.52 |
| ATOM | 1055 | O | ARG | 14 | 49.543 | 37.868 | 24.283 | 1.00 | 59.50 |
| ATOM | 1056 | CB | ARG | 14 | 49.727 | 36.251 | 27.117 | 1.00 | 60.86 |
| ATOM | 1057 | CG | ARG | 14 | 50.102 | 35.088 | 28.041 | 1.00 | 62.47 |
| ATOM | 1058 | CD | ARG | 14 | 51.596 | 34.762 | 28.056 | 1.00 | 66.68 |
| ATOM | 1059 | NE | ARG | 14 | 52.030 | 33.730 | 27.094 | 1.00 | 66.83 |
| ATOM | 1060 | CZ | ARG | 14 | 52.974 | 33.889 | 26.153 | 1.00 | 74.89 |
| ATOM | 1061 | NH1 | ARG | 14 | 53.616 | 35.062 | 25.985 | 1.00 | 70.24 |

TABLE 11-continued

Three-Dimensional Coordinates of *Neisseria gonorrhoeae* GCYH-IB·Mn$^{2+}$
(SEQ. ID. No. 8)

| ATOM | 1062 | NH2 | ARG | 14 | 53.281 | 32.861 | 25.359 | 1.00 | 70.54 |
|------|------|-----|-----|----|--------|--------|--------|------|-------|
| ATOM | 1063 | N   | ASN | 15 | 49.332 | 35.620 | 23.892 | 1.00 | 58.31 |
| ATOM | 1064 | CA  | ASN | 15 | 49.230 | 35.630 | 22.425 | 1.00 | 56.79 |
| ATOM | 1065 | C   | ASN | 15 | 47.825 | 35.751 | 21.839 | 1.00 | 54.53 |
| ATOM | 1066 | O   | ASN | 15 | 47.622 | 36.477 | 20.862 | 1.00 | 55.84 |
| ATOM | 1067 | CB  | ASN | 15 | 49.946 | 34.399 | 21.842 | 1.00 | 57.64 |
| ATOM | 1068 | CG  | ASN | 15 | 51.363 | 34.700 | 21.380 | 1.00 | 58.56 |
| ATOM | 1069 | OD1 | ASN | 15 | 51.644 | 35.764 | 20.812 | 1.00 | 59.64 |
| ATOM | 1070 | ND2 | ASN | 15 | 52.266 | 33.739 | 21.597 | 1.00 | 59.50 |
| ATOM | 1071 | N   | LEU | 16 | 46.876 | 35.046 | 22.445 | 1.00 | 50.71 |
| ATOM | 1072 | CA  | LEU | 16 | 45.451 | 35.154 | 22.128 | 1.00 | 45.72 |
| ATOM | 1073 | C   | LEU | 16 | 45.008 | 34.361 | 20.897 | 1.00 | 42.62 |
| ATOM | 1074 | O   | LEU | 16 | 45.480 | 34.571 | 19.781 | 1.00 | 41.21 |
| ATOM | 1075 | CB  | LEU | 16 | 44.990 | 36.597 | 22.066 | 1.00 | 46.03 |
| ATOM | 1076 | CG  | LEU | 16 | 44.014 | 37.291 | 23.024 | 1.00 | 45.53 |
| ATOM | 1077 | CD1 | LEU | 16 | 44.094 | 36.865 | 24.479 | 1.00 | 46.94 |
| ATOM | 1078 | CD2 | LEU | 16 | 44.289 | 38.762 | 22.907 | 1.00 | 42.24 |
| ATOM | 1079 | N   | PRO | 17 | 44.091 | 33.421 | 21.118 | 1.00 | 39.73 |
| ATOM | 1080 | CA  | PRO | 17 | 43.589 | 32.688 | 19.976 | 1.00 | 37.59 |
| ATOM | 1081 | C   | PRO | 17 | 42.594 | 33.628 | 19.285 | 1.00 | 35.06 |
| ATOM | 1082 | O   | PRO | 17 | 41.991 | 34.512 | 19.928 | 1.00 | 34.66 |
| ATOM | 1083 | CB  | PRO | 17 | 42.862 | 31.506 | 20.612 | 1.00 | 37.49 |
| ATOM | 1084 | CG  | PRO | 17 | 42.391 | 32.059 | 21.904 | 1.00 | 38.46 |
| ATOM | 1085 | CD  | PRO | 17 | 43.431 | 33.025 | 22.375 | 1.00 | 39.21 |
| ATOM | 1086 | N   | ILE | 18 | 42.450 | 33.455 | 17.988 | 1.00 | 32.48 |
| ATOM | 1087 | CA  | ILE | 18 | 41.485 | 34.246 | 17.234 | 1.00 | 29.75 |
| ATOM | 1088 | C   | ILE | 18 | 40.315 | 33.372 | 16.866 | 1.00 | 28.71 |
| ATOM | 1089 | O   | ILE | 18 | 40.492 | 32.282 | 16.313 | 1.00 | 29.46 |
| ATOM | 1090 | CB  | ILE | 18 | 42.172 | 34.915 | 16.010 | 1.00 | 29.27 |
| ATOM | 1091 | CG1 | ILE | 18 | 43.186 | 35.933 | 16.555 | 1.00 | 28.75 |
| ATOM | 1092 | CG2 | ILE | 18 | 41.139 | 35.601 | 15.144 | 1.00 | 26.93 |
| ATOM | 1093 | CD1 | ILE | 18 | 44.188 | 36.399 | 15.568 | 1.00 | 29.65 |
| ATOM | 1094 | N   | ASN | 19 | 39.124 | 33.832 | 17.218 | 1.00 | 27.84 |
| ATOM | 1095 | CA  | ASN | 19 | 37.917 | 33.088 | 17.011 | 1.00 | 28.72 |
| ATOM | 1096 | C   | ASN | 19 | 37.791 | 32.671 | 15.535 | 1.00 | 29.30 |
| ATOM | 1097 | O   | ASN | 19 | 37.556 | 31.519 | 15.230 | 1.00 | 29.67 |
| ATOM | 1098 | CB  | ASN | 19 | 36.692 | 33.897 | 17.443 | 1.00 | 27.56 |
| ATOM | 1099 | CG  | ASN | 19 | 36.566 | 34.037 | 18.934 | 1.00 | 30.11 |
| ATOM | 1100 | OD1 | ASN | 19 | 35.628 | 33.510 | 19.537 | 1.00 | 35.03 |
| ATOM | 1101 | ND2 | ASN | 19 | 37.457 | 34.803 | 19.541 | 1.00 | 26.59 |
| ATOM | 1102 | N   | GLN | 20 | 37.946 | 33.633 | 14.625 | 1.00 | 28.21 |
| ATOM | 1103 | CA  | GLN | 20 | 37.823 | 33.346 | 13.200 | 1.00 | 27.61 |
| ATOM | 1104 | C   | GLN | 20 | 38.739 | 34.277 | 12.456 | 1.00 | 26.93 |
| ATOM | 1105 | O   | GLN | 20 | 38.727 | 35.468 | 12.704 | 1.00 | 25.53 |
| ATOM | 1106 | CB  | GLN | 20 | 36.387 | 33.587 | 12.738 | 1.00 | 27.40 |
| ATOM | 1107 | CG  | GLN | 20 | 35.289 | 32.662 | 13.323 | 1.00 | 28.89 |
| ATOM | 1108 | CD  | GLN | 20 | 35.392 | 31.156 | 12.907 | 1.00 | 29.01 |
| ATOM | 1109 | OE1 | GLN | 20 | 36.015 | 30.793 | 11.917 | 1.00 | 24.93 |
| ATOM | 1110 | NE2 | GLN | 20 | 34.725 | 30.299 | 13.677 | 1.00 | 33.39 |
| ATOM | 1111 | N   | VAL | 21 | 39.523 | 33.726 | 11.534 | 1.00 | 28.44 |
| ATOM | 1112 | CA  | VAL | 21 | 40.353 | 34.521 | 10.641 | 1.00 | 28.39 |
| ATOM | 1113 | C   | VAL | 21 | 40.302 | 33.901 | 9.231  | 1.00 | 28.96 |
| ATOM | 1114 | O   | VAL | 21 | 40.332 | 32.653 | 9.084  | 1.00 | 28.04 |
| ATOM | 1115 | CB  | VAL | 21 | 41.813 | 34.603 | 11.139 | 1.00 | 29.27 |
| ATOM | 1116 | CG1 | VAL | 21 | 42.432 | 33.163 | 11.302 | 1.00 | 30.86 |
| ATOM | 1117 | CG2 | VAL | 21 | 42.630 | 35.412 | 10.182 | 1.00 | 26.64 |
| ATOM | 1118 | N   | GLY | 22 | 40.265 | 34.772 | 8.214  | 1.00 | 25.74 |
| ATOM | 1119 | CA  | GLY | 22 | 40.312 | 34.315 | 6.847  | 1.00 | 25.43 |
| ATOM | 1120 | C   | GLY | 22 | 39.912 | 35.415 | 5.893  | 1.00 | 25.13 |
| ATOM | 1121 | O   | GLY | 22 | 40.462 | 36.563 | 5.962  | 1.00 | 24.40 |
| ATOM | 1122 | N   | ILE | 23 | 39.006 | 35.087 | 4.967  | 1.00 | 24.91 |
| ATOM | 1123 | CA  | ILE | 23 | 38.654 | 36.061 | 3.894  | 1.00 | 24.29 |
| ATOM | 1124 | C   | ILE | 23 | 37.205 | 36.429 | 3.946  | 1.00 | 24.19 |
| ATOM | 1125 | O   | ILE | 23 | 36.368 | 35.647 | 4.382  | 1.00 | 22.43 |
| ATOM | 1126 | CB  | ILE | 23 | 39.055 | 35.617 | 2.460  | 1.00 | 24.57 |
| ATOM | 1127 | CG1 | ILE | 23 | 38.314 | 34.325 | 2.043  | 1.00 | 25.55 |
| ATOM | 1128 | CG2 | ILE | 23 | 40.562 | 35.500 | 2.383  | 1.00 | 27.03 |
| ATOM | 1129 | CD1 | ILE | 23 | 38.356 | 33.909 | 0.539  | 1.00 | 26.06 |
| ATOM | 1130 | N   | THR | 48 | 36.553 | 31.379 | 7.054  | 1.00 | 25.33 |
| ATOM | 1131 | CA  | THR | 48 | 37.449 | 31.661 | 8.177  | 1.00 | 26.30 |
| ATOM | 1132 | C   | THR | 48 | 37.736 | 30.379 | 8.969  | 1.00 | 27.67 |
| ATOM | 1133 | O   | THR | 48 | 36.880 | 29.443 | 8.981  | 1.00 | 27.40 |
| ATOM | 1134 | CB  | THR | 48 | 36.811 | 32.640 | 9.156  | 1.00 | 25.92 |
| ATOM | 1135 | OG1 | THR | 48 | 35.570 | 32.127 | 9.604  | 1.00 | 27.43 |
| ATOM | 1136 | CG2 | THR | 48 | 36.580 | 34.048 | 8.541  | 1.00 | 25.73 |
| ATOM | 1137 | N   | VAL | 49 | 38.895 | 30.322 | 9.648  | 1.00 | 28.21 |
| ATOM | 1138 | CA  | VAL | 49 | 39.164 | 29.202 | 10.595 | 1.00 | 27.79 |

TABLE 11-continued

Three-Dimensional Coordinates of *Neisseria gonorrhoeae* GCYH-IB·Mn$^{2+}$
(SEQ. ID. No. 8)

| ATOM | 1139 | C   | VAL | 49 | 39.600 | 29.805 | 11.956 | 1.00 | 29.96 |
|------|------|-----|-----|----|--------|--------|--------|------|-------|
| ATOM | 1140 | O   | VAL | 49 | 39.931 | 30.991 | 12.055 | 1.00 | 29.84 |
| ATOM | 1141 | CB  | VAL | 49 | 40.301 | 28.306 | 10.065 | 1.00 | 27.06 |
| ATOM | 1142 | CG1 | VAL | 49 | 39.910 | 27.547 | 8.745  | 1.00 | 24.24 |
| ATOM | 1143 | CG2 | VAL | 49 | 41.593 | 29.120 | 9.884  | 1.00 | 26.20 |
| ATOM | 1144 | N   | TYR | 50 | 39.658 | 28.969 | 12.980 | 1.00 | 30.77 |
| ATOM | 1145 | CA  | TYR | 50 | 40.097 | 29.355 | 14.333 | 1.00 | 31.30 |
| ATOM | 1146 | C   | TYR | 50 | 41.584 | 29.365 | 14.291 | 1.00 | 31.89 |
| ATOM | 1147 | O   | TYR | 50 | 42.174 | 28.503 | 13.663 | 1.00 | 31.71 |
| ATOM | 1148 | CB  | TYR | 50 | 39.619 | 28.292 | 15.301 | 1.00 | 32.58 |
| ATOM | 1149 | CG  | TYR | 50 | 40.188 | 28.329 | 16.695 | 1.00 | 33.26 |
| ATOM | 1150 | CD1 | TYR | 50 | 39.629 | 29.138 | 17.651 | 1.00 | 32.16 |
| ATOM | 1151 | CD2 | TYR | 50 | 41.235 | 27.478 | 17.067 | 1.00 | 34.15 |
| ATOM | 1152 | CE1 | TYR | 50 | 40.135 | 29.166 | 18.975 | 1.00 | 35.06 |
| ATOM | 1153 | CE2 | TYR | 50 | 41.748 | 27.488 | 18.387 | 1.00 | 34.47 |
| ATOM | 1154 | CZ  | TYR | 50 | 41.182 | 28.336 | 19.318 | 1.00 | 34.05 |
| ATOM | 1155 | OH  | TYR | 50 | 41.636 | 28.362 | 20.629 | 1.00 | 36.34 |
| ATOM | 1156 | N   | LEU | 51 | 42.199 | 30.356 | 14.925 | 1.00 | 32.43 |
| ATOM | 1157 | CA  | LEU | 51 | 43.649 | 30.425 | 15.047 | 1.00 | 33.24 |
| ATOM | 1158 | C   | LEU | 51 | 44.061 | 30.272 | 16.526 | 1.00 | 33.57 |
| ATOM | 1159 | O   | LEU | 51 | 43.695 | 31.115 | 17.330 | 1.00 | 31.07 |
| ATOM | 1160 | CB  | LEU | 51 | 44.161 | 31.778 | 14.528 | 1.00 | 32.42 |
| ATOM | 1161 | CG  | LEU | 51 | 45.656 | 31.778 | 14.277 | 1.00 | 33.30 |
| ATOM | 1162 | CD1 | LEU | 51 | 46.001 | 30.774 | 13.207 | 1.00 | 32.77 |
| ATOM | 1163 | CD2 | LEU | 51 | 46.156 | 33.169 | 13.840 | 1.00 | 33.73 |
| ATOM | 1164 | N   | PRO | 52 | 44.803 | 29.180 | 16.884 | 1.00 | 35.48 |
| ATOM | 1165 | CA  | PRO | 52 | 45.196 | 29.027 | 18.303 | 1.00 | 36.24 |
| ATOM | 1166 | C   | PRO | 52 | 46.242 | 30.079 | 18.713 | 1.00 | 37.08 |
| ATOM | 1167 | O   | PRO | 52 | 46.981 | 30.616 | 17.867 | 1.00 | 35.03 |
| ATOM | 1168 | CB  | PRO | 52 | 45.803 | 27.620 | 18.378 | 1.00 | 36.44 |
| ATOM | 1169 | CG  | PRO | 52 | 46.191 | 27.268 | 16.968 | 1.00 | 37.84 |
| ATOM | 1170 | CD  | PRO | 52 | 45.255 | 28.059 | 16.042 | 1.00 | 35.65 |
| ATOM | 1171 | N   | ALA | 53 | 46.312 | 30.352 | 20.008 | 1.00 | 39.26 |
| ATOM | 1172 | CA  | ALA | 53 | 47.259 | 31.342 | 20.509 | 1.00 | 41.52 |
| ATOM | 1173 | C   | ALA | 53 | 48.632 | 31.262 | 19.902 | 1.00 | 43.70 |
| ATOM | 1174 | O   | ALA | 53 | 49.213 | 32.300 | 19.542 | 1.00 | 44.05 |
| ATOM | 1175 | CB  | ALA | 53 | 47.343 | 31.295 | 22.028 | 1.00 | 41.87 |
| ATOM | 1176 | N   | GLU | 54 | 49.176 | 30.051 | 19.770 | 1.00 | 46.18 |
| ATOM | 1177 | CA  | GLU | 54 | 50.595 | 29.947 | 19.416 | 1.00 | 48.84 |
| ATOM | 1178 | C   | GLU | 54 | 50.950 | 30.189 | 17.960 | 1.00 | 48.48 |
| ATOM | 1179 | O   | GLU | 54 | 52.143 | 30.310 | 17.626 | 1.00 | 48.68 |
| ATOM | 1180 | CB  | GLU | 54 | 51.290 | 28.679 | 19.988 | 1.00 | 49.42 |
| ATOM | 1181 | CG  | GLU | 54 | 50.930 | 27.304 | 19.376 | 1.00 | 51.16 |
| ATOM | 1182 | CD  | GLU | 54 | 51.905 | 26.157 | 19.853 | 1.00 | 52.55 |
| ATOM | 1183 | OE1 | GLU | 54 | 51.600 | 24.953 | 19.611 | 1.00 | 55.01 |
| ATOM | 1184 | OE2 | GLU | 54 | 52.984 | 26.456 | 20.462 | 1.00 | 56.97 |
| ATOM | 1185 | N   | GLN | 55 | 49.943 | 30.264 | 17.098 | 1.00 | 47.97 |
| ATOM | 1186 | CA  | GLN | 55 | 50.192 | 30.396 | 15.657 | 1.00 | 48.24 |
| ATOM | 1187 | C   | GLN | 55 | 50.070 | 31.860 | 15.229 | 1.00 | 47.26 |
| ATOM | 1188 | O   | GLN | 55 | 49.114 | 32.533 | 15.588 | 1.00 | 46.59 |
| ATOM | 1189 | CB  | GLN | 55 | 49.222 | 29.500 | 14.877 | 1.00 | 48.23 |
| ATOM | 1190 | CG  | GLN | 55 | 49.460 | 29.483 | 13.359 | 1.00 | 49.79 |
| ATOM | 1191 | CD  | GLN | 55 | 48.669 | 28.396 | 12.661 | 1.00 | 49.97 |
| ATOM | 1192 | OE1 | GLN | 55 | 48.367 | 27.375 | 13.266 | 1.00 | 53.57 |
| ATOM | 1193 | NE2 | GLN | 55 | 48.337 | 28.601 | 11.382 | 1.00 | 50.86 |
| ATOM | 1194 | N   | LYS | 56 | 51.043 | 32.352 | 14.471 | 1.00 | 47.46 |
| ATOM | 1195 | CA  | LYS | 56 | 51.091 | 33.769 | 14.130 | 1.00 | 48.23 |
| ATOM | 1196 | C   | LYS | 56 | 49.978 | 34.132 | 13.149 | 1.00 | 47.43 |
| ATOM | 1197 | O   | LYS | 56 | 49.311 | 35.150 | 13.323 | 1.00 | 47.38 |
| ATOM | 1198 | CB  | LYS | 56 | 52.461 | 34.174 | 13.542 | 1.00 | 48.49 |
| ATOM | 1199 | CG  | LYS | 56 | 52.559 | 35.701 | 13.239 | 1.00 | 50.23 |
| ATOM | 1200 | CD  | LYS | 56 | 53.838 | 36.104 | 12.483 | 1.00 | 51.07 |
| ATOM | 1201 | CE  | LYS | 56 | 54.040 | 35.276 | 11.199 | 1.00 | 54.39 |
| ATOM | 1202 | NZ  | LYS | 56 | 55.448 | 35.366 | 10.676 | 1.00 | 56.64 |
| ATOM | 1203 | N   | GLY | 57 | 49.801 | 33.300 | 12.124 | 1.00 | 46.67 |
| ATOM | 1204 | CA  | GLY | 57 | 48.811 | 33.554 | 11.099 | 1.00 | 46.24 |
| ATOM | 1205 | C   | GLY | 57 | 48.282 | 32.313 | 10.412 | 1.00 | 46.03 |
| ATOM | 1206 | O   | GLY | 57 | 48.843 | 31.208 | 10.570 | 1.00 | 46.27 |
| ATOM | 1207 | N   | THR | 58 | 47.195 | 32.509 | 9.654  | 1.00 | 45.17 |
| ATOM | 1208 | CA  | THR | 58 | 46.597 | 31.483 | 8.810  | 1.00 | 43.95 |
| ATOM | 1209 | C   | THR | 58 | 47.170 | 31.556 | 7.387  | 1.00 | 43.93 |
| ATOM | 1210 | O   | THR | 58 | 48.149 | 32.270 | 7.156  | 1.00 | 43.84 |
| ATOM | 1211 | CB  | THR | 58 | 45.031 | 31.554 | 8.784  | 1.00 | 43.76 |
| ATOM | 1212 | OG1 | THR | 58 | 44.529 | 30.341 | 8.239  | 1.00 | 42.58 |
| ATOM | 1213 | CG2 | THR | 58 | 44.481 | 32.757 | 7.957  | 1.00 | 41.26 |
| ATOM | 1214 | N   | HIS | 59 | 46.542 | 30.830 | 6.456  | 1.00 | 42.61 |
| ATOM | 1215 | CA  | HIS | 59 | 47.038 | 30.691 | 5.097  | 1.00 | 42.55 |

TABLE 11-continued

Three-Dimensional Coordinates of *Neisseria gonorrhoeae* GCYH-IB·Mn$^{2+}$
(SEQ. ID. No. 8)

| ATOM | 1216 | C | HIS | 59 | 46.006 | 31.176 | 4.075 | 1.00 | 41.58 |
|------|------|------|-----|----|--------|--------|--------|------|-------|
| ATOM | 1217 | O | HIS | 59 | 45.185 | 30.402 | 3.565 | 1.00 | 40.93 |
| ATOM | 1218 | CB | HIS | 59 | 47.431 | 29.246 | 4.868 | 1.00 | 43.03 |
| ATOM | 1219 | CG | HIS | 59 | 48.369 | 28.732 | 5.915 | 1.00 | 46.13 |
| ATOM | 1220 | ND1 | HIS | 59 | 47.926 | 28.125 | 7.076 | 1.00 | 48.89 |
| ATOM | 1221 | CD2 | HIS | 59 | 49.716 | 28.810 | 6.019 | 1.00 | 48.32 |
| ATOM | 1222 | CE1 | HIS | 59 | 48.966 | 27.827 | 7.840 | 1.00 | 48.82 |
| ATOM | 1223 | NE2 | HIS | 59 | 50.063 | 28.233 | 7.222 | 1.00 | 50.35 |
| ATOM | 1224 | N | MET | 60 | 46.054 | 32.471 | 3.790 | 1.00 | 40.23 |
| ATOM | 1225 | CA | MET | 60 | 44.936 | 33.167 | 3.145 | 1.00 | 38.85 |
| ATOM | 1226 | C | MET | 60 | 44.631 | 32.729 | 1.718 | 1.00 | 37.25 |
| ATOM | 1227 | O | MET | 60 | 43.465 | 32.717 | 1.303 | 1.00 | 37.16 |
| ATOM | 1228 | CB | MET | 60 | 45.147 | 34.686 | 3.231 | 1.00 | 40.07 |
| ATOM | 1229 | CG | MET | 60 | 45.182 | 35.218 | 4.688 | 1.00 | 40.71 |
| ATOM | 1230 | SD | MET | 60 | 43.511 | 35.600 | 5.252 | 1.00 | 45.21 |
| ATOM | 1231 | CE | MET | 60 | 43.801 | 36.421 | 6.813 | 1.00 | 42.50 |
| ATOM | 1232 | N | SER | 61 | 45.652 | 32.353 | 0.956 | 1.00 | 36.21 |
| ATOM | 1233 | CA | SER | 61 | 45.423 | 31.968 | −0.429 | 1.00 | 35.39 |
| ATOM | 1234 | C | SER | 61 | 44.706 | 30.631 | −0.540 | 1.00 | 35.50 |
| ATOM | 1235 | O | SER | 61 | 44.116 | 30.325 | −1.581 | 1.00 | 35.82 |
| ATOM | 1236 | CB | SER | 61 | 46.719 | 31.901 | −1.204 | 1.00 | 36.22 |
| ATOM | 1237 | OG | SER | 61 | 47.456 | 30.721 | −0.911 | 1.00 | 36.27 |
| ATOM | 1238 | N | ARG | 62 | 44.724 | 29.844 | 0.533 | 1.00 | 34.65 |
| ATOM | 1239 | CA | ARG | 62 | 44.188 | 28.474 | 0.507 | 1.00 | 34.67 |
| ATOM | 1240 | C | ARG | 62 | 42.670 | 28.505 | 0.519 | 1.00 | 33.66 |
| ATOM | 1241 | O | ARG | 62 | 42.029 | 27.568 | 0.064 | 1.00 | 33.93 |
| ATOM | 1242 | CB | ARG | 62 | 44.700 | 27.655 | 1.718 | 1.00 | 35.39 |
| ATOM | 1243 | CG | ARG | 62 | 46.213 | 27.392 | 1.757 | 1.00 | 35.71 |
| ATOM | 1244 | CD | ARG | 62 | 46.596 | 26.539 | 2.992 | 1.00 | 36.59 |
| ATOM | 1245 | NE | ARG | 62 | 48.060 | 26.429 | 3.152 | 1.00 | 40.81 |
| ATOM | 1246 | CZ | ARG | 62 | 48.673 | 25.627 | 4.030 | 1.00 | 42.85 |
| ATOM | 1247 | NH1 | ARG | 62 | 47.947 | 24.852 | 4.833 | 1.00 | 42.89 |
| ATOM | 1248 | NH2 | ARG | 62 | 50.010 | 25.591 | 4.101 | 1.00 | 39.58 |
| ATOM | 1249 | N | PHE | 63 | 42.080 | 29.569 | 1.073 | 1.00 | 31.76 |
| ATOM | 1250 | CA | PHE | 63 | 40.621 | 29.735 | 1.039 | 1.00 | 29.77 |
| ATOM | 1251 | C | PHE | 63 | 40.169 | 29.909 | −0.413 | 1.00 | 29.97 |
| ATOM | 1252 | O | PHE | 63 | 39.205 | 29.299 | −0.833 | 1.00 | 29.60 |
| ATOM | 1253 | CB | PHE | 63 | 40.155 | 30.970 | 1.815 | 1.00 | 29.04 |
| ATOM | 1254 | CG | PHE | 63 | 40.440 | 30.918 | 3.280 | 1.00 | 24.94 |
| ATOM | 1255 | CD1 | PHE | 63 | 39.661 | 30.140 | 4.105 | 1.00 | 25.06 |
| ATOM | 1256 | CD2 | PHE | 63 | 41.475 | 31.662 | 3.828 | 1.00 | 25.62 |
| ATOM | 1257 | CE1 | PHE | 63 | 39.904 | 30.068 | 5.464 | 1.00 | 25.26 |
| ATOM | 1258 | CE2 | PHE | 63 | 41.738 | 31.610 | 5.202 | 1.00 | 27.19 |
| ATOM | 1259 | CZ | PHE | 63 | 40.938 | 30.802 | 6.022 | 1.00 | 26.37 |
| ATOM | 1260 | N | VAL | 64 | 40.880 | 30.729 | −1.178 | 1.00 | 29.57 |
| ATOM | 1261 | CA | VAL | 64 | 40.513 | 30.944 | −2.578 | 1.00 | 29.55 |
| ATOM | 1262 | C | VAL | 64 | 40.837 | 29.671 | −3.361 | 1.00 | 30.87 |
| ATOM | 1263 | O | VAL | 64 | 40.065 | 29.310 | −4.227 | 1.00 | 30.92 |
| ATOM | 1264 | CB | VAL | 64 | 41.256 | 32.114 | −3.207 | 1.00 | 29.58 |
| ATOM | 1265 | CG1 | VAL | 64 | 40.690 | 32.383 | −4.582 | 1.00 | 30.02 |
| ATOM | 1266 | CG2 | VAL | 64 | 41.126 | 33.412 | −2.311 | 1.00 | 27.42 |
| ATOM | 1267 | N | ALA | 65 | 41.967 | 29.005 | −3.068 | 1.00 | 31.39 |
| ATOM | 1268 | CA | ALA | 65 | 42.338 | 27.724 | −3.733 | 1.00 | 32.56 |
| ATOM | 1269 | C | ALA | 65 | 41.193 | 26.703 | −3.642 | 1.00 | 33.22 |
| ATOM | 1270 | O | ALA | 65 | 40.842 | 26.021 | −4.620 | 1.00 | 33.73 |
| ATOM | 1271 | CB | ALA | 65 | 43.688 | 27.119 | −3.097 | 1.00 | 32.21 |
| ATOM | 1272 | N | LEU | 66 | 40.610 | 26.591 | −2.448 | 1.00 | 33.30 |
| ATOM | 1273 | CA | LEU | 66 | 39.528 | 25.660 | −2.226 | 1.00 | 32.82 |
| ATOM | 1274 | C | LEU | 66 | 38.364 | 25.915 | −3.196 | 1.00 | 33.60 |
| ATOM | 1275 | O | LEU | 66 | 37.849 | 24.996 | −3.856 | 1.00 | 32.31 |
| ATOM | 1276 | CB | LEU | 66 | 39.061 | 25.758 | −0.775 | 1.00 | 31.90 |
| ATOM | 1277 | CG | LEU | 66 | 37.995 | 24.752 | −0.377 | 1.00 | 32.41 |
| ATOM | 1278 | CD1 | LEU | 66 | 38.590 | 23.305 | −0.361 | 1.00 | 35.12 |
| ATOM | 1279 | CD2 | LEU | 66 | 37.421 | 25.135 | 0.955 | 1.00 | 31.49 |
| ATOM | 1280 | N | GLU | 68 | 38.341 | 27.610 | −6.063 | 1.00 | 37.55 |
| ATOM | 1281 | CA | GLU | 68 | 38.771 | 27.390 | −7.422 | 1.00 | 40.89 |
| ATOM | 1282 | C | GLU | 68 | 38.784 | 25.887 | −7.739 | 1.00 | 43.79 |
| ATOM | 1283 | O | GLU | 68 | 38.320 | 25.502 | −8.793 | 1.00 | 42.72 |
| ATOM | 1284 | CB | GLU | 68 | 40.128 | 28.049 | −7.679 | 1.00 | 40.31 |
| ATOM | 1285 | CG | GLU | 68 | 40.090 | 29.562 | −7.438 | 1.00 | 38.64 |
| ATOM | 1286 | CD | GLU | 68 | 39.309 | 30.285 | −8.518 | 1.00 | 38.78 |
| ATOM | 1287 | OE1 | GLU | 68 | 39.045 | 29.632 | −9.551 | 1.00 | 36.65 |
| ATOM | 1288 | OE2 | GLU | 68 | 38.971 | 31.505 | −8.366 | 1.00 | 38.57 |
| ATOM | 1289 | N | GLN | 69 | 39.247 | 25.068 | −6.786 | 1.00 | 47.57 |
| ATOM | 1290 | CA | GLN | 69 | 39.388 | 23.612 | −6.988 | 1.00 | 52.47 |
| ATOM | 1291 | C | GLN | 69 | 38.048 | 22.908 | −7.080 | 1.00 | 53.85 |
| ATOM | 1292 | O | GLN | 69 | 37.912 | 21.936 | −7.810 | 1.00 | 54.85 |

TABLE 11-continued

Three-Dimensional Coordinates of *Neisseria gonorrhoeae* GCYH-IB·Mn$^{2+}$
(SEQ. ID. No. 8)

| ATOM | 1293 | CB | GLN | 69 | 40.200 | 22.961 | −5.857 | 1.00 | 52.64 |
|---|---|---|---|---|---|---|---|---|---|
| ATOM | 1294 | CG | GLN | 69 | 41.709 | 22.868 | −6.141 | 1.00 | 55.16 |
| ATOM | 1295 | CD | GLN | 69 | 42.618 | 22.724 | −4.878 | 1.00 | 55.40 |
| ATOM | 1296 | OE1 | GLN | 69 | 42.147 | 22.602 | −3.726 | 1.00 | 59.00 |
| ATOM | 1297 | NE2 | GLN | 69 | 43.931 | 22.746 | −5.114 | 1.00 | 57.66 |
| ATOM | 1298 | N | GLU | 85 | 36.599 | 20.020 | 4.284 | 1.00 | 34.50 |
| ATOM | 1299 | CA | GLU | 85 | 37.788 | 20.139 | 3.477 | 1.00 | 36.41 |
| ATOM | 1300 | C | GLU | 85 | 38.564 | 21.421 | 3.793 | 1.00 | 35.63 |
| ATOM | 1301 | O | GLU | 85 | 39.804 | 21.403 | 3.868 | 1.00 | 36.27 |
| ATOM | 1302 | CB | GLU | 85 | 37.430 | 20.063 | 2.005 | 1.00 | 37.22 |
| ATOM | 1303 | CG | GLU | 85 | 38.661 | 19.976 | 1.159 | 1.00 | 44.97 |
| ATOM | 1304 | CD | GLU | 85 | 38.432 | 19.342 | −0.195 | 1.00 | 52.91 |
| ATOM | 1305 | OE1 | GLU | 85 | 37.489 | 18.508 | −0.323 | 1.00 | 54.95 |
| ATOM | 1306 | OE2 | GLU | 85 | 39.214 | 19.693 | −1.131 | 1.00 | 55.69 |
| ATOM | 1307 | N | MET | 86 | 37.842 | 22.524 | 4.012 | 1.00 | 33.82 |
| ATOM | 1308 | CA | MET | 86 | 38.514 | 23.766 | 4.412 | 1.00 | 33.23 |
| ATOM | 1309 | C | MET | 86 | 39.369 | 23.647 | 5.676 | 1.00 | 34.16 |
| ATOM | 1310 | O | MET | 86 | 40.527 | 24.057 | 5.679 | 1.00 | 34.95 |
| ATOM | 1311 | CB | MET | 86 | 37.507 | 24.910 | 4.647 | 1.00 | 32.36 |
| ATOM | 1312 | CG | MET | 86 | 38.202 | 26.275 | 4.769 | 1.00 | 31.48 |
| ATOM | 1313 | SD | MET | 86 | 37.050 | 27.565 | 5.210 | 1.00 | 29.78 |
| ATOM | 1314 | CE | MET | 86 | 36.275 | 27.008 | 6.773 | 1.00 | 22.03 |
| ATOM | 1315 | N | VAL | 87 | 38.796 | 23.174 | 6.771 | 1.00 | 36.21 |
| ATOM | 1316 | CA | VAL | 87 | 39.569 | 23.133 | 8.040 | 1.00 | 37.84 |
| ATOM | 1317 | C | VAL | 87 | 40.803 | 22.254 | 7.905 | 1.00 | 39.36 |
| ATOM | 1318 | O | VAL | 87 | 41.838 | 22.528 | 8.531 | 1.00 | 40.24 |
| ATOM | 1319 | CB | VAL | 87 | 38.730 | 22.674 | 9.245 | 1.00 | 38.61 |
| ATOM | 1320 | CG1 | VAL | 87 | 37.639 | 23.672 | 9.519 | 1.00 | 37.63 |
| ATOM | 1321 | CG2 | VAL | 87 | 38.122 | 21.273 | 9.011 | 1.00 | 37.58 |
| ATOM | 1322 | N | ALA | 88 | 40.699 | 21.210 | 7.071 | 1.00 | 39.92 |
| ATOM | 1323 | CA | ALA | 88 | 41.823 | 20.292 | 6.824 | 1.00 | 40.37 |
| ATOM | 1324 | C | ALA | 88 | 42.893 | 20.943 | 5.987 | 1.00 | 40.95 |
| ATOM | 1325 | O | ALA | 88 | 44.082 | 20.856 | 6.326 | 1.00 | 41.91 |
| ATOM | 1326 | CB | ALA | 88 | 41.339 | 19.022 | 6.156 | 1.00 | 40.29 |
| ATOM | 1327 | N | LEU | 89 | 42.467 | 21.627 | 4.917 | 1.00 | 40.06 |
| ATOM | 1328 | CA | LEU | 89 | 43.380 | 22.334 | 4.017 | 1.00 | 40.50 |
| ATOM | 1329 | C | LEU | 89 | 44.174 | 23.435 | 4.745 | 1.00 | 39.98 |
| ATOM | 1330 | O | LEU | 89 | 45.363 | 23.668 | 4.462 | 1.00 | 38.44 |
| ATOM | 1331 | CB | LEU | 89 | 42.588 | 22.951 | 2.848 | 1.00 | 40.68 |
| ATOM | 1332 | CG | LEU | 89 | 43.370 | 23.782 | 1.820 | 1.00 | 41.74 |
| ATOM | 1333 | CD1 | LEU | 89 | 44.363 | 22.868 | 1.059 | 1.00 | 44.04 |
| ATOM | 1334 | CD2 | LEU | 89 | 42.426 | 24.484 | 0.818 | 1.00 | 40.51 |
| ATOM | 1335 | N | LEU | 90 | 43.494 | 24.101 | 5.678 | 1.00 | 40.31 |
| ATOM | 1336 | CA | LEU | 90 | 44.053 | 25.240 | 6.402 | 1.00 | 40.41 |
| ATOM | 1337 | C | LEU | 90 | 44.739 | 24.813 | 7.709 | 1.00 | 41.69 |
| ATOM | 1338 | O | LEU | 90 | 45.256 | 25.655 | 8.483 | 1.00 | 40.27 |
| ATOM | 1339 | CB | LEU | 90 | 42.955 | 26.234 | 6.699 | 1.00 | 39.60 |
| ATOM | 1340 | CG | LEU | 90 | 43.070 | 27.082 | 5.455 | 1.00 | 38.10 |
| ATOM | 1341 | CD1 | LEU | 90 | 41.936 | 26.856 | 4.502 | 1.00 | 33.65 |
| ATOM | 1342 | CD2 | LEU | 90 | 43.272 | 28.457 | 5.834 | 1.00 | 34.46 |
| ATOM | 1343 | N | ASP | 91 | 44.738 | 23.494 | 7.925 | 1.00 | 41.99 |
| ATOM | 1344 | CA | ASP | 91 | 45.381 | 22.868 | 9.110 | 1.00 | 42.31 |
| ATOM | 1345 | C | ASP | 91 | 44.863 | 23.449 | 10.409 | 1.00 | 41.35 |
| ATOM | 1346 | O | ASP | 91 | 45.669 | 23.923 | 11.225 | 1.00 | 42.00 |
| ATOM | 1347 | CB | ASP | 91 | 46.900 | 23.075 | 9.073 | 1.00 | 42.72 |
| ATOM | 1348 | CG | ASP | 91 | 47.545 | 22.472 | 7.880 | 1.00 | 46.18 |
| ATOM | 1349 | OD1 | ASP | 91 | 47.169 | 21.337 | 7.503 | 1.00 | 52.04 |
| ATOM | 1350 | OD2 | ASP | 91 | 48.439 | 23.124 | 7.313 | 1.00 | 48.88 |
| ATOM | 1351 | N | SER | 92 | 43.543 | 23.426 | 10.605 | 1.00 | 40.27 |
| ATOM | 1352 | CA | SER | 92 | 42.920 | 24.003 | 11.793 | 1.00 | 39.39 |
| ATOM | 1353 | C | SER | 92 | 41.864 | 23.088 | 12.372 | 1.00 | 40.36 |
| ATOM | 1354 | O | SER | 92 | 41.378 | 22.183 | 11.699 | 1.00 | 42.15 |
| ATOM | 1355 | CB | SER | 92 | 42.236 | 25.342 | 11.488 | 1.00 | 39.41 |
| ATOM | 1356 | OG | SER | 92 | 41.483 | 25.795 | 12.630 | 1.00 | 34.46 |
| ATOM | 1357 | N | ARG | 93 | 41.454 | 23.378 | 13.594 | 1.00 | 40.29 |
| ATOM | 1358 | CA | ARG | 93 | 40.521 | 22.535 | 14.309 | 1.00 | 42.05 |
| ATOM | 1359 | C | ARG | 93 | 39.068 | 22.948 | 14.088 | 1.00 | 40.68 |
| ATOM | 1360 | O | ARG | 93 | 38.152 | 22.193 | 14.428 | 1.00 | 41.97 |
| ATOM | 1361 | CB | ARG | 93 | 40.847 | 22.576 | 15.799 | 1.00 | 42.19 |
| ATOM | 1362 | CG | ARG | 93 | 39.854 | 23.386 | 16.613 | 1.00 | 45.63 |
| ATOM | 1363 | CD | ARG | 93 | 40.382 | 23.916 | 17.978 | 1.00 | 46.18 |
| ATOM | 1364 | NE | ARG | 93 | 39.617 | 25.125 | 18.363 | 1.00 | 54.20 |
| ATOM | 1365 | CZ | ARG | 93 | 38.309 | 25.154 | 18.680 | 1.00 | 54.69 |
| ATOM | 1366 | NH1 | ARG | 93 | 37.576 | 24.036 | 18.686 | 1.00 | 58.29 |
| ATOM | 1367 | NH2 | ARG | 93 | 37.720 | 26.307 | 18.984 | 1.00 | 56.33 |
| ATOM | 1368 | N | ALA | 94 | 38.842 | 24.151 | 13.541 | 1.00 | 37.80 |
| ATOM | 1369 | CA | ALA | 94 | 37.501 | 24.726 | 13.516 | 1.00 | 35.70 |

TABLE 11-continued

Three-Dimensional Coordinates of *Neisseria gonorrhoeae* GCYH-IB·$Mn^{2+}$ (SEQ. ID. No. 8)

| ATOM | 1370 | C   | ALA | 94  | 37.410 | 25.833 | 12.474 | 1.00 | 34.21 |
|------|------|-----|-----|-----|--------|--------|--------|------|-------|
| ATOM | 1371 | O   | ALA | 94  | 38.389 | 26.471 | 12.193 | 1.00 | 33.40 |
| ATOM | 1372 | CB  | ALA | 94  | 37.134 | 25.284 | 14.843 | 1.00 | 34.97 |
| ATOM | 1373 | N   | LYS | 106 | 38.708 | 65.977 | 15.909 | 1.00 | 31.12 |
| ATOM | 1374 | CA  | LYS | 106 | 39.798 | 66.800 | 15.380 | 1.00 | 32.80 |
| ATOM | 1375 | C   | LYS | 106 | 41.145 | 66.122 | 15.628 | 1.00 | 32.96 |
| ATOM | 1376 | O   | LYS | 106 | 41.449 | 65.723 | 16.783 | 1.00 | 33.18 |
| ATOM | 1377 | CB  | LYS | 106 | 39.757 | 68.191 | 16.041 | 1.00 | 34.65 |
| ATOM | 1378 | CG  | LYS | 106 | 40.696 | 69.235 | 15.401 | 1.00 | 39.55 |
| ATOM | 1379 | CD  | LYS | 106 | 40.008 | 70.188 | 14.406 | 1.00 | 47.35 |
| ATOM | 1380 | CE  | LYS | 106 | 38.963 | 71.096 | 15.070 | 1.00 | 49.33 |
| ATOM | 1381 | NZ  | LYS | 106 | 39.461 | 71.819 | 16.300 | 1.00 | 54.56 |
| ATOM | 1382 | N   | LYS | 107 | 41.930 | 65.936 | 14.557 | 1.00 | 31.08 |
| ATOM | 1383 | CA  | LYS | 107 | 43.263 | 65.361 | 14.676 | 1.00 | 30.55 |
| ATOM | 1384 | C   | LYS | 107 | 44.327 | 66.386 | 14.279 | 1.00 | 30.89 |
| ATOM | 1385 | O   | LYS | 107 | 44.023 | 67.385 | 13.627 | 1.00 | 31.02 |
| ATOM | 1386 | CB  | LYS | 107 | 43.437 | 64.118 | 13.789 | 1.00 | 30.30 |
| ATOM | 1387 | CG  | LYS | 107 | 42.291 | 63.137 | 13.910 | 1.00 | 30.97 |
| ATOM | 1388 | CD  | LYS | 107 | 42.610 | 61.772 | 13.245 | 1.00 | 29.55 |
| ATOM | 1389 | CE  | LYS | 107 | 43.721 | 61.074 | 13.925 | 1.00 | 27.26 |
| ATOM | 1390 | NZ  | LYS | 107 | 43.937 | 59.742 | 13.259 | 1.00 | 25.91 |
| ATOM | 1391 | N   | THR | 108 | 45.561 | 66.081 | 14.645 | 1.00 | 31.14 |
| ATOM | 1392 | CA  | THR | 108 | 46.746 | 66.902 | 14.404 | 1.00 | 32.51 |
| ATOM | 1393 | C   | THR | 108 | 47.714 | 66.097 | 13.548 | 1.00 | 32.54 |
| ATOM | 1394 | O   | THR | 108 | 48.188 | 65.028 | 13.983 | 1.00 | 33.24 |
| ATOM | 1395 | CB  | THR | 108 | 47.397 | 67.166 | 15.779 | 1.00 | 32.61 |
| ATOM | 1396 | OG1 | THR | 108 | 46.422 | 67.786 | 16.589 | 1.00 | 35.34 |
| ATOM | 1397 | CG2 | THR | 108 | 48.586 | 68.069 | 15.699 | 1.00 | 33.31 |
| ATOM | 1398 | N   | ALA | 109 | 48.002 | 66.566 | 12.335 | 1.00 | 33.07 |
| ATOM | 1399 | CA  | ALA | 109 | 49.018 | 65.906 | 11.498 | 1.00 | 33.80 |
| ATOM | 1400 | C   | ALA | 109 | 50.355 | 65.718 | 12.250 | 1.00 | 34.89 |
| ATOM | 1401 | O   | ALA | 109 | 50.734 | 66.564 | 13.083 | 1.00 | 34.88 |
| ATOM | 1402 | CB  | ALA | 109 | 49.209 | 66.686 | 10.195 | 1.00 | 34.10 |
| ATOM | 1403 | N   | PRO | 110 | 51.057 | 64.576 | 11.991 | 1.00 | 35.11 |
| ATOM | 1404 | CA  | PRO | 110 | 52.171 | 64.180 | 12.837 | 1.00 | 35.19 |
| ATOM | 1405 | C   | PRO | 110 | 53.463 | 64.984 | 12.693 | 1.00 | 35.83 |
| ATOM | 1406 | O   | PRO | 110 | 54.287 | 64.898 | 13.615 | 1.00 | 36.44 |
| ATOM | 1407 | CB  | PRO | 110 | 52.426 | 62.722 | 12.426 | 1.00 | 35.24 |
| ATOM | 1408 | CG  | PRO | 110 | 51.888 | 62.618 | 11.047 | 1.00 | 35.53 |
| ATOM | 1409 | CD  | PRO | 110 | 50.757 | 63.576 | 10.945 | 1.00 | 33.91 |
| ATOM | 1410 | N   | VAL | 111 | 53.642 | 65.732 | 11.579 | 1.00 | 34.87 |
| ATOM | 1411 | CA  | VAL | 111 | 54.845 | 66.561 | 11.401 | 1.00 | 34.55 |
| ATOM | 1412 | C   | VAL | 111 | 54.480 | 68.049 | 11.361 | 1.00 | 34.44 |
| ATOM | 1413 | O   | VAL | 111 | 54.889 | 68.807 | 12.217 | 1.00 | 34.73 |
| ATOM | 1414 | CB  | VAL | 111 | 55.721 | 66.104 | 10.201 | 1.00 | 35.20 |
| ATOM | 1415 | CG1 | VAL | 111 | 56.926 | 67.053 | 10.018 | 1.00 | 35.13 |
| ATOM | 1416 | CG2 | VAL | 111 | 56.258 | 64.662 | 10.458 | 1.00 | 33.36 |
| ATOM | 1417 | N   | SER | 112 | 53.644 | 68.445 | 10.411 | 1.00 | 34.36 |
| ATOM | 1418 | CA  | SER | 112 | 53.171 | 69.829 | 10.301 | 1.00 | 33.65 |
| ATOM | 1419 | C   | SER | 112 | 52.276 | 70.296 | 11.430 | 1.00 | 34.37 |
| ATOM | 1420 | O   | SER | 112 | 52.205 | 71.522 | 11.716 | 1.00 | 34.40 |
| ATOM | 1421 | CB  | SER | 112 | 52.457 | 70.035 | 8.980  | 1.00 | 33.85 |
| ATOM | 1422 | OG  | SER | 112 | 51.195 | 69.359 | 8.954  | 1.00 | 32.93 |
| ATOM | 1423 | N   | GLY | 113 | 51.573 | 69.348 | 12.067 | 1.00 | 33.94 |
| ATOM | 1424 | CA  | GLY | 113 | 50.585 | 69.684 | 13.125 | 1.00 | 32.54 |
| ATOM | 1425 | C   | GLY | 113 | 49.345 | 70.397 | 12.624 | 1.00 | 33.41 |
| ATOM | 1426 | O   | GLY | 113 | 48.569 | 70.950 | 13.442 | 1.00 | 32.86 |
| ATOM | 1427 | N   | ILE | 114 | 49.131 | 70.384 | 11.289 | 1.00 | 33.45 |
| ATOM | 1428 | CA  | ILE | 114 | 47.931 | 70.990 | 10.697 | 1.00 | 34.24 |
| ATOM | 1429 | C   | ILE | 114 | 46.768 | 70.138 | 11.217 | 1.00 | 34.53 |
| ATOM | 1430 | O   | ILE | 114 | 46.890 | 68.901 | 11.331 | 1.00 | 33.15 |
| ATOM | 1431 | CB  | ILE | 114 | 47.910 | 70.965 | 9.134  | 1.00 | 35.17 |
| ATOM | 1432 | CG1 | ILE | 114 | 49.151 | 71.641 | 8.519  | 1.00 | 38.77 |
| ATOM | 1433 | CG2 | ILE | 114 | 46.701 | 71.682 | 8.582  | 1.00 | 33.39 |
| ATOM | 1434 | CD1 | ILE | 114 | 49.226 | 73.088 | 8.731  | 1.00 | 42.74 |
| ATOM | 1435 | N   | ARG | 115 | 45.664 | 70.796 | 11.562 | 1.00 | 34.61 |
| ATOM | 1436 | CA  | ARG | 115 | 44.558 | 70.079 | 12.189 | 1.00 | 35.62 |
| ATOM | 1437 | C   | ARG | 115 | 43.499 | 69.759 | 11.134 | 1.00 | 33.87 |
| ATOM | 1438 | O   | ARG | 115 | 43.329 | 70.512 | 10.171 | 1.00 | 32.92 |
| ATOM | 1439 | CB  | ARG | 115 | 43.976 | 70.844 | 13.399 | 1.00 | 35.86 |
| ATOM | 1440 | CG  | ARG | 115 | 45.049 | 71.225 | 14.495 | 1.00 | 39.50 |
| ATOM | 1441 | CD  | ARG | 115 | 44.457 | 71.218 | 15.918 | 1.00 | 41.37 |
| ATOM | 1442 | NE  | ARG | 115 | 44.156 | 69.839 | 16.349 | 1.00 | 49.17 |
| ATOM | 1443 | CZ  | ARG | 115 | 43.421 | 69.486 | 17.420 | 1.00 | 50.07 |
| ATOM | 1444 | NH1 | ARG | 115 | 42.877 | 70.418 | 18.205 | 1.00 | 52.25 |
| ATOM | 1445 | NH2 | ARG | 115 | 43.228 | 68.182 | 17.705 | 1.00 | 50.44 |
| ATOM | 1446 | N   | SER | 116 | 42.829 | 68.612 | 11.305 | 1.00 | 32.49 |

TABLE 11-continued

Three-Dimensional Coordinates of *Neisseria gonorrhoeae* GCYH-IB·Mn$^{2+}$
(SEQ. ID. No. 8)

| ATOM | 1447 | CA  | SER | 116 | 41.712 | 68.256 | 10.444 | 1.00 | 31.24 |
|------|------|-----|-----|-----|--------|--------|--------|------|-------|
| ATOM | 1448 | C   | SER | 116 | 40.804 | 67.204 | 11.123 | 1.00 | 30.84 |
| ATOM | 1449 | O   | SER | 116 | 41.201 | 66.486 | 12.080 | 1.00 | 31.63 |
| ATOM | 1450 | CB  | SER | 116 | 42.218 | 67.835 |  9.021 | 1.00 | 31.35 |
| ATOM | 1451 | OG  | SER | 116 | 42.970 | 66.625 |  9.062 | 1.00 | 29.62 |
| ATOM | 1452 | N   | PRO | 142 | 38.636 | 53.573 | 10.939 | 1.00 | 23.23 |
| ATOM | 1453 | CA  | PRO | 142 | 39.398 | 53.247 |  9.753 | 1.00 | 23.79 |
| ATOM | 1454 | C   | PRO | 142 | 40.866 | 53.611 |  9.963 | 1.00 | 24.65 |
| ATOM | 1455 | O   | PRO | 142 | 41.162 | 54.667 | 10.563 | 1.00 | 25.09 |
| ATOM | 1456 | CB  | PRO | 142 | 38.715 | 54.125 |  8.699 | 1.00 | 24.09 |
| ATOM | 1457 | CG  | PRO | 142 | 38.391 | 55.456 |  9.539 | 1.00 | 23.27 |
| ATOM | 1458 | CD  | PRO | 142 | 37.978 | 54.901 | 10.870 | 1.00 | 23.22 |
| ATOM | 1459 | N   | VAL | 143 | 41.771 | 52.733 |  9.512 | 1.00 | 24.51 |
| ATOM | 1460 | CA  | VAL | 143 | 43.210 | 52.865 |  9.769 | 1.00 | 25.26 |
| ATOM | 1461 | C   | VAL | 143 | 43.912 | 52.341 |  8.527 | 1.00 | 26.54 |
| ATOM | 1462 | O   | VAL | 143 | 43.270 | 51.805 |  7.611 | 1.00 | 25.34 |
| ATOM | 1463 | CB  | VAL | 143 | 43.698 | 52.054 | 11.032 | 1.00 | 24.57 |
| ATOM | 1464 | CG1 | VAL | 143 | 42.985 | 52.533 | 12.322 | 1.00 | 25.48 |
| ATOM | 1465 | CG2 | VAL | 143 | 43.463 | 50.510 | 10.826 | 1.00 | 23.63 |
| ATOM | 1466 | N   | THR | 144 | 45.225 | 52.542 |  8.503 | 1.00 | 27.67 |
| ATOM | 1467 | CA  | THR | 144 | 46.106 | 51.971 |  7.510 | 1.00 | 27.19 |
| ATOM | 1468 | C   | THR | 144 | 46.653 | 50.618 |  8.005 | 1.00 | 27.74 |
| ATOM | 1469 | O   | THR | 144 | 47.110 | 50.536 |  9.150 | 1.00 | 27.09 |
| ATOM | 1470 | CB  | THR | 144 | 47.302 | 52.895 |  7.281 | 1.00 | 27.10 |
| ATOM | 1471 | OG1 | THR | 144 | 46.827 | 54.201 |  6.909 | 1.00 | 24.38 |
| ATOM | 1472 | CG2 | THR | 144 | 48.174 | 52.329 |  6.162 | 1.00 | 28.95 |
| ATOM | 1473 | N   | SER | 145 | 46.572 | 49.569 |  7.157 | 1.00 | 26.89 |
| ATOM | 1474 | CA  | SER | 145 | 47.241 | 48.293 |  7.442 | 1.00 | 27.89 |
| ATOM | 1475 | C   | SER | 145 | 48.318 | 48.049 |  6.381 | 1.00 | 28.66 |
| ATOM | 1476 | O   | SER | 145 | 48.130 | 48.418 |  5.237 | 1.00 | 28.16 |
| ATOM | 1477 | CB  | SER | 145 | 46.217 | 47.132 |  7.504 | 1.00 | 28.02 |
| ATOM | 1478 | OG  | SER | 145 | 45.570 | 46.960 |  6.232 | 1.00 | 26.68 |
| ATOM | 1479 | N   | LEU | 146 | 49.460 | 47.468 |  6.756 | 1.00 | 29.89 |
| ATOM | 1480 | CA  | LEU | 146 | 50.545 | 47.208 |  5.789 | 1.00 | 29.68 |
| ATOM | 1481 | C   | LEU | 146 | 51.070 | 45.787 |  5.993 | 1.00 | 30.59 |
| ATOM | 1482 | O   | LEU | 146 | 51.229 | 45.362 |  7.132 | 1.00 | 28.81 |
| ATOM | 1483 | CB  | LEU | 146 | 51.662 | 48.237 |  5.962 | 1.00 | 29.41 |
| ATOM | 1484 | CG  | LEU | 146 | 52.892 | 48.155 |  5.020 | 1.00 | 29.93 |
| ATOM | 1485 | CD1 | LEU | 146 | 53.407 | 49.526 |  4.667 | 1.00 | 27.71 |
| ATOM | 1486 | CD2 | LEU | 146 | 54.018 | 47.284 |  5.659 | 1.00 | 28.67 |
| ATOM | 1487 | N   | CYS | 147 | 51.337 | 45.045 |  4.903 | 1.00 | 31.66 |
| ATOM | 1488 | CA  | CYS | 147 | 51.527 | 43.581 |  5.043 | 1.00 | 31.98 |
| ATOM | 1489 | C   | CYS | 147 | 52.968 | 43.149 |  5.421 | 1.00 | 31.99 |
| ATOM | 1490 | O   | CYS | 147 | 53.908 | 43.398 |  4.649 | 1.00 | 31.52 |
| ATOM | 1491 | CB  | CYS | 147 | 51.081 | 42.864 |  3.767 | 1.00 | 31.07 |
| ATOM | 1492 | SG  | CYS | 147 | 51.160 | 41.046 |  3.962 | 1.00 | 34.30 |
| ATOM | 1493 | N   | PRO | 148 | 53.160 | 42.488 |  6.599 | 1.00 | 32.55 |
| ATOM | 1494 | CA  | PRO | 148 | 54.563 | 42.078 |  6.962 | 1.00 | 33.44 |
| ATOM | 1495 | C   | PRO | 148 | 55.189 | 41.064 |  5.986 | 1.00 | 34.23 |
| ATOM | 1496 | O   | PRO | 148 | 56.410 | 41.057 |  5.794 | 1.00 | 34.47 |
| ATOM | 1497 | CB  | PRO | 148 | 54.420 | 41.429 |  8.350 | 1.00 | 33.47 |
| ATOM | 1498 | CG  | PRO | 148 | 53.058 | 41.894 |  8.878 | 1.00 | 33.36 |
| ATOM | 1499 | CD  | PRO | 148 | 52.191 | 42.134 |  7.641 | 1.00 | 32.15 |
| ATOM | 1500 | N   | CYS | 149 | 54.353 | 40.234 |  5.358 | 1.00 | 35.48 |
| ATOM | 1501 | CA  | CYS | 149 | 54.815 | 39.212 |  4.420 | 1.00 | 34.64 |
| ATOM | 1502 | C   | CYS | 149 | 55.291 | 39.887 |  3.120 | 1.00 | 33.98 |
| ATOM | 1503 | O   | CYS | 149 | 56.400 | 39.584 |  2.588 | 1.00 | 33.37 |
| ATOM | 1504 | CB  | CYS | 149 | 53.683 | 38.205 |  4.164 | 1.00 | 34.81 |
| ATOM | 1505 | SG  | CYS | 149 | 54.068 | 36.986 |  2.863 | 1.00 | 41.23 |
| ATOM | 1506 | N   | SER | 150 | 54.474 | 40.834 |  2.636 | 1.00 | 32.17 |
| ATOM | 1507 | CA  | SER | 150 | 54.840 | 41.677 |  1.498 | 1.00 | 31.42 |
| ATOM | 1508 | C   | SER | 150 | 56.187 | 42.422 |  1.673 | 1.00 | 31.54 |
| ATOM | 1509 | O   | SER | 150 | 57.066 | 42.369 |  0.783 | 1.00 | 31.16 |
| ATOM | 1510 | CB  | SER | 150 | 53.698 | 42.692 |  1.218 | 1.00 | 31.09 |
| ATOM | 1511 | OG  | SER | 150 | 54.012 | 43.515 |  0.114 | 1.00 | 28.82 |
| ATOM | 1512 | N   | LYS | 151 | 56.340 | 43.137 |  2.787 | 1.00 | 30.89 |
| ATOM | 1513 | CA  | LYS | 151 | 57.609 | 43.773 |  3.108 | 1.00 | 32.75 |
| ATOM | 1514 | C   | LYS | 151 | 58.783 | 42.735 |  3.082 | 1.00 | 34.08 |
| ATOM | 1515 | O   | LYS | 151 | 59.806 | 42.922 |  2.380 | 1.00 | 35.64 |
| ATOM | 1516 | CB  | LYS | 151 | 57.521 | 44.443 |  4.506 | 1.00 | 31.90 |
| ATOM | 1517 | CG  | LYS | 151 | 58.790 | 45.152 |  4.942 | 1.00 | 31.20 |
| ATOM | 1518 | CD  | LYS | 151 | 58.619 | 45.793 |  6.326 | 1.00 | 31.30 |
| ATOM | 1519 | CE  | LYS | 151 | 59.952 | 46.371 |  6.776 | 1.00 | 33.03 |
| ATOM | 1520 | NZ  | LYS | 151 | 59.848 | 47.112 |  8.026 | 1.00 | 30.24 |
| ATOM | 1521 | N   | GLU | 152 | 58.639 | 41.671 |  3.850 | 1.00 | 35.50 |
| ATOM | 1522 | CA  | GLU | 152 | 59.707 | 40.675 |  4.032 | 1.00 | 38.06 |
| ATOM | 1523 | C   | GLU | 152 | 60.216 | 40.033 |  2.718 | 1.00 | 38.25 |

TABLE 11-continued

Three-Dimensional Coordinates of *Neisseria gonorrhoeae* GCYH-IB·Mn$^{2+}$
(SEQ. ID. No. 8)

| ATOM | 1524 | O | GLU | 152 | 61.426 | 39.897 | 2.526 | 1.00 | 39.41 |
|------|------|-----|-----|-----|--------|--------|--------|------|-------|
| ATOM | 1525 | CB | GLU | 152 | 59.253 | 39.597 | 5.017 | 1.00 | 39.11 |
| ATOM | 1526 | CG | GLU | 152 | 60.091 | 38.324 | 4.985 | 1.00 | 45.31 |
| ATOM | 1527 | CD | GLU | 152 | 59.694 | 37.369 | 6.069 | 1.00 | 52.84 |
| ATOM | 1528 | OE1 | GLU | 152 | 58.956 | 36.401 | 5.769 | 1.00 | 57.04 |
| ATOM | 1529 | OE2 | GLU | 152 | 60.086 | 37.614 | 7.237 | 1.00 | 57.07 |
| ATOM | 1530 | N | ILE | 153 | 59.302 | 39.645 | 1.824 | 1.00 | 37.49 |
| ATOM | 1531 | CA | ILE | 153 | 59.688 | 38.928 | 0.608 | 1.00 | 37.01 |
| ATOM | 1532 | C | ILE | 153 | 60.152 | 39.898 | −0.517 | 1.00 | 37.61 |
| ATOM | 1533 | O | ILE | 153 | 60.871 | 39.477 | −1.429 | 1.00 | 37.14 |
| ATOM | 1534 | CB | ILE | 153 | 58.543 | 37.957 | 0.113 | 1.00 | 37.48 |
| ATOM | 1535 | CG1 | ILE | 153 | 57.332 | 38.750 | −0.436 | 1.00 | 37.02 |
| ATOM | 1536 | CG2 | ILE | 153 | 58.110 | 36.947 | 1.257 | 1.00 | 35.87 |
| ATOM | 1537 | CD1 | ILE | 153 | 56.064 | 37.955 | −0.708 | 1.00 | 36.43 |
| ATOM | 1538 | N | SER | 154 | 59.742 | 41.184 | −0.451 | 1.00 | 36.39 |
| ATOM | 1539 | CA | SER | 154 | 59.982 | 42.125 | −1.561 | 1.00 | 36.06 |
| ATOM | 1540 | C | SER | 154 | 61.247 | 42.893 | −1.398 | 1.00 | 36.42 |
| ATOM | 1541 | O | SER | 154 | 61.594 | 43.277 | −0.288 | 1.00 | 36.52 |
| ATOM | 1542 | CB | SER | 154 | 58.810 | 43.104 | −1.733 | 1.00 | 34.92 |
| ATOM | 1543 | OG | SER | 154 | 57.623 | 42.347 | −1.874 | 1.00 | 34.60 |
| ATOM | 1544 | N | GLN | 155 | 61.952 | 43.146 | −2.491 | 1.00 | 37.31 |
| ATOM | 1545 | CA | GLN | 155 | 63.209 | 43.910 | −2.338 | 1.00 | 39.20 |
| ATOM | 1546 | C | GLN | 155 | 62.959 | 45.361 | −2.004 | 1.00 | 38.30 |
| ATOM | 1547 | O | GLN | 155 | 63.840 | 46.057 | −1.475 | 1.00 | 37.74 |
| ATOM | 1548 | CB | GLN | 155 | 64.129 | 43.785 | −3.565 | 1.00 | 40.45 |
| ATOM | 1549 | CG | GLN | 155 | 63.556 | 44.240 | −4.895 | 1.00 | 42.35 |
| ATOM | 1550 | CD | GLN | 155 | 64.560 | 44.047 | −6.021 | 1.00 | 42.99 |
| ATOM | 1551 | OE1 | GLN | 155 | 65.753 | 44.345 | −5.856 | 1.00 | 45.28 |
| ATOM | 1552 | NE2 | GLN | 155 | 64.086 | 43.541 | −7.171 | 1.00 | 46.69 |
| ATOM | 1553 | N | TYR | 156 | 61.739 | 45.810 | −2.305 | 1.00 | 37.89 |
| ATOM | 1554 | CA | TYR | 156 | 61.285 | 47.172 | −1.997 | 1.00 | 36.80 |
| ATOM | 1555 | C | TYR | 156 | 59.761 | 47.230 | −2.042 | 1.00 | 36.04 |
| ATOM | 1556 | O | TYR | 156 | 59.130 | 46.344 | −2.647 | 1.00 | 36.63 |
| ATOM | 1557 | CB | TYR | 156 | 61.934 | 48.202 | −2.936 | 1.00 | 36.72 |
| ATOM | 1558 | CG | TYR | 156 | 62.101 | 47.789 | −4.392 | 1.00 | 36.70 |
| ATOM | 1559 | CD1 | TYR | 156 | 61.034 | 47.312 | −5.141 | 1.00 | 37.81 |
| ATOM | 1560 | CD2 | TYR | 156 | 63.346 | 47.894 | −5.026 | 1.00 | 38.83 |
| ATOM | 1561 | CE1 | TYR | 156 | 61.201 | 46.948 | −6.492 | 1.00 | 37.24 |
| ATOM | 1562 | CE2 | TYR | 156 | 63.520 | 47.546 | −6.405 | 1.00 | 38.26 |
| ATOM | 1563 | CZ | TYR | 156 | 62.456 | 47.086 | −7.110 | 1.00 | 37.10 |
| ATOM | 1564 | OH | TYR | 156 | 62.629 | 46.764 | −8.447 | 1.00 | 37.14 |
| ATOM | 1565 | N | GLY | 157 | 59.159 | 48.216 | −1.365 | 1.00 | 34.75 |
| ATOM | 1566 | CA | GLY | 157 | 57.687 | 48.263 | −1.303 | 1.00 | 33.03 |
| ATOM | 1567 | C | GLY | 157 | 57.048 | 47.295 | −0.316 | 1.00 | 31.76 |
| ATOM | 1568 | O | GLY | 157 | 57.700 | 46.349 | 0.178 | 1.00 | 30.74 |
| ATOM | 1569 | N | ALA | 158 | 55.778 | 47.550 | −0.010 | 1.00 | 30.83 |
| ATOM | 1570 | CA | ALA | 158 | 54.967 | 46.646 | 0.799 | 1.00 | 31.12 |
| ATOM | 1571 | C | ALA | 158 | 53.511 | 46.998 | 0.556 | 1.00 | 30.73 |
| ATOM | 1572 | O | ALA | 158 | 53.158 | 48.186 | 0.675 | 1.00 | 31.76 |
| ATOM | 1573 | CB | ALA | 158 | 55.327 | 46.795 | 2.295 | 1.00 | 30.85 |
| ATOM | 1574 | N | HIS | 159 | 52.661 | 46.030 | 0.177 | 1.00 | 28.96 |
| ATOM | 1575 | CA | HIS | 159 | 51.271 | 46.418 | −0.084 | 1.00 | 27.54 |
| ATOM | 1576 | C | HIS | 159 | 50.593 | 46.832 | 1.198 | 1.00 | 26.90 |
| ATOM | 1577 | O | HIS | 159 | 50.909 | 46.304 | 2.264 | 1.00 | 27.11 |
| ATOM | 1578 | CB | HIS | 159 | 50.445 | 45.374 | −0.843 | 1.00 | 27.56 |
| ATOM | 1579 | CG | HIS | 159 | 49.942 | 44.219 | −0.023 | 1.00 | 27.53 |
| ATOM | 1580 | ND1 | HIS | 159 | 48.771 | 44.283 | 0.707 | 1.00 | 28.80 |
| ATOM | 1581 | CD2 | HIS | 159 | 50.386 | 42.937 | 0.080 | 1.00 | 25.15 |
| ATOM | 1582 | CE1 | HIS | 159 | 48.537 | 43.109 | 1.261 | 1.00 | 26.96 |
| ATOM | 1583 | NE2 | HIS | 159 | 49.509 | 42.275 | 0.905 | 1.00 | 27.80 |
| ATOM | 1584 | N | ASN | 160 | 49.683 | 47.794 | 1.076 | 1.00 | 25.77 |
| ATOM | 1585 | CA | ASN | 160 | 49.021 | 48.415 | 2.233 | 1.00 | 24.99 |
| ATOM | 1586 | C | ASN | 160 | 47.670 | 48.860 | 1.744 | 1.00 | 25.23 |
| ATOM | 1587 | O | ASN | 160 | 47.413 | 48.871 | 0.501 | 1.00 | 25.07 |
| ATOM | 1588 | CB | ASN | 160 | 49.886 | 49.533 | 2.882 | 1.00 | 24.72 |
| ATOM | 1589 | CG | ASN | 160 | 50.412 | 50.583 | 1.905 | 1.00 | 26.68 |
| ATOM | 1590 | OD1 | ASN | 160 | 51.537 | 50.449 | 1.397 | 1.00 | 31.21 |
| ATOM | 1591 | ND2 | ASN | 160 | 49.665 | 51.679 | 1.721 | 1.00 | 22.78 |
| ATOM | 1592 | N | GLN | 161 | 46.763 | 49.133 | 2.659 | 1.00 | 24.62 |
| ATOM | 1593 | CA | GLN | 161 | 45.373 | 49.346 | 2.282 | 1.00 | 25.62 |
| ATOM | 1594 | C | GLN | 161 | 44.660 | 49.983 | 3.461 | 1.00 | 25.75 |
| ATOM | 1595 | O | GLN | 161 | 45.160 | 49.911 | 4.567 | 1.00 | 25.66 |
| ATOM | 1596 | CB | GLN | 161 | 44.663 | 48.030 | 1.948 | 1.00 | 24.86 |
| ATOM | 1597 | CG | GLN | 161 | 44.856 | 46.908 | 3.004 | 1.00 | 25.88 |
| ATOM | 1598 | CD | GLN | 161 | 46.155 | 46.130 | 2.795 | 1.00 | 26.01 |
| ATOM | 1599 | OE1 | GLN | 161 | 46.542 | 45.812 | 1.652 | 1.00 | 25.80 |
| ATOM | 1600 | NE2 | GLN | 161 | 46.835 | 45.811 | 3.899 | 1.00 | 24.43 |

TABLE 11-continued

Three-Dimensional Coordinates of *Neisseria gonorrhoeae* GCYH-IB·Mn$^{2+}$
(SEQ. ID. No. 8)

| ATOM | 1601 | N | ARG | 162 | 43.511 | 50.606 | 3.202 | 1.00 | 25.37 |
|------|------|-----|-----|-----|--------|--------|--------|------|-------|
| ATOM | 1602 | CA  | ARG | 162 | 42.654 | 51.021 | 4.265  | 1.00 | 26.23 |
| ATOM | 1603 | C   | ARG | 162 | 42.032 | 49.766 | 4.913  | 1.00 | 26.60 |
| ATOM | 1604 | O   | ARG | 162 | 41.775 | 48.749 | 4.252  | 1.00 | 25.80 |
| ATOM | 1605 | CB  | ARG | 162 | 41.556 | 51.925 | 3.741  | 1.00 | 26.40 |
| ATOM | 1606 | CG  | ARG | 162 | 40.992 | 52.868 | 4.879  | 1.00 | 29.11 |
| ATOM | 1607 | CD  | ARG | 162 | 39.866 | 53.804 | 4.360  | 1.00 | 27.52 |
| ATOM | 1608 | NE  | ARG | 162 | 40.374 | 54.762 | 3.381  | 1.00 | 26.18 |
| ATOM | 1609 | CZ  | ARG | 162 | 39.603 | 55.301 | 2.453  | 1.00 | 19.53 |
| ATOM | 1610 | NH1 | ARG | 162 | 38.283 | 54.963 | 2.374  | 1.00 | 23.76 |
| ATOM | 1611 | NH2 | ARG | 162 | 40.179 | 56.167 | 1.612  | 1.00 | 23.47 |
| ATOM | 1612 | N   | SER | 163 | 41.787 | 49.876 | 6.208  | 1.00 | 26.65 |
| ATOM | 1613 | CA  | SER | 163 | 41.244 | 48.793 | 6.987  | 1.00 | 27.57 |
| ATOM | 1614 | C   | SER | 163 | 40.155 | 49.368 | 7.909  | 1.00 | 26.82 |
| ATOM | 1615 | O   | SER | 163 | 40.152 | 50.577 | 8.235  | 1.00 | 26.70 |
| ATOM | 1616 | CB  | SER | 163 | 42.423 | 48.044 | 7.657  | 1.00 | 27.35 |
| ATOM | 1617 | OG  | SER | 163 | 42.151 | 47.777 | 9.023  | 1.00 | 35.69 |
| ATOM | 1618 | N   | ILE | 181 | 38.506 | 54.867 | 20.151 | 1.00 | 22.91 |
| ATOM | 1619 | CA  | ILE | 181 | 39.317 | 55.319 | 18.995 | 1.00 | 23.75 |
| ATOM | 1620 | C   | ILE | 181 | 40.825 | 55.261 | 19.310 | 1.00 | 26.04 |
| ATOM | 1621 | O   | ILE | 181 | 41.638 | 54.746 | 18.478 | 1.00 | 27.11 |
| ATOM | 1622 | CB  | ILE | 181 | 38.911 | 56.790 | 18.555 | 1.00 | 23.88 |
| ATOM | 1623 | CG1 | ILE | 181 | 37.430 | 56.843 | 18.071 | 1.00 | 21.17 |
| ATOM | 1624 | CG2 | ILE | 181 | 39.925 | 57.390 | 17.477 | 1.00 | 21.79 |
| ATOM | 1625 | CD1 | ILE | 181 | 36.943 | 58.289 | 17.780 | 1.00 | 20.98 |
| ATOM | 1626 | N   | ASP | 182 | 41.225 | 55.777 | 20.488 | 1.00 | 26.54 |
| ATOM | 1627 | CA  | ASP | 182 | 42.657 | 55.804 | 20.814 | 1.00 | 26.69 |
| ATOM | 1628 | C   | ASP | 182 | 43.199 | 54.396 | 20.957 | 1.00 | 25.88 |
| ATOM | 1629 | O   | ASP | 182 | 44.296 | 54.134 | 20.514 | 1.00 | 26.00 |
| ATOM | 1630 | CB  | ASP | 182 | 42.995 | 56.648 | 22.070 | 1.00 | 27.60 |
| ATOM | 1631 | CG  | ASP | 182 | 42.783 | 58.157 | 21.860 | 1.00 | 30.47 |
| ATOM | 1632 | OD1 | ASP | 182 | 42.991 | 58.661 | 20.746 | 1.00 | 31.48 |
| ATOM | 1633 | OD2 | ASP | 182 | 42.373 | 58.844 | 22.814 | 1.00 | 33.73 |
| ATOM | 1634 | N   | TYR | 183 | 42.452 | 53.490 | 21.589 | 1.00 | 26.54 |
| ATOM | 1635 | CA  | TYR | 183 | 42.882 | 52.083 | 21.703 | 1.00 | 26.51 |
| ATOM | 1636 | C   | TYR | 183 | 43.281 | 51.500 | 20.323 | 1.00 | 27.37 |
| ATOM | 1637 | O   | TYR | 183 | 44.284 | 50.774 | 20.180 | 1.00 | 28.29 |
| ATOM | 1638 | CB  | TYR | 183 | 41.761 | 51.248 | 22.358 | 1.00 | 27.89 |
| ATOM | 1639 | CG  | TYR | 183 | 41.688 | 51.296 | 23.877 | 1.00 | 27.72 |
| ATOM | 1640 | CD1 | TYR | 183 | 42.832 | 51.358 | 24.634 | 1.00 | 31.11 |
| ATOM | 1641 | CD2 | TYR | 183 | 40.457 | 51.235 | 24.546 | 1.00 | 27.18 |
| ATOM | 1642 | CE1 | TYR | 183 | 42.777 | 51.366 | 26.075 | 1.00 | 32.80 |
| ATOM | 1643 | CE2 | TYR | 183 | 40.377 | 51.263 | 25.943 | 1.00 | 31.64 |
| ATOM | 1644 | CZ  | TYR | 183 | 41.555 | 51.318 | 26.706 | 1.00 | 31.01 |
| ATOM | 1645 | OH  | TYR | 183 | 41.507 | 51.305 | 28.099 | 1.00 | 33.34 |
| ATOM | 1646 | N   | VAL | 184 | 42.476 | 51.794 | 19.307 | 1.00 | 26.40 |
| ATOM | 1647 | CA  | VAL | 184 | 42.668 | 51.208 | 17.997 | 1.00 | 24.57 |
| ATOM | 1648 | C   | VAL | 184 | 43.796 | 51.942 | 17.240 | 1.00 | 25.20 |
| ATOM | 1649 | O   | VAL | 184 | 44.694 | 51.321 | 16.708 | 1.00 | 25.99 |
| ATOM | 1650 | CB  | VAL | 184 | 41.309 | 51.223 | 17.190 | 1.00 | 23.34 |
| ATOM | 1651 | CG1 | VAL | 184 | 41.538 | 50.986 | 15.671 | 1.00 | 24.07 |
| ATOM | 1652 | CG2 | VAL | 184 | 40.331 | 50.125 | 17.729 | 1.00 | 21.77 |
| ATOM | 1653 | N   | GLU | 185 | 43.711 | 53.261 | 17.177 | 1.00 | 25.17 |
| ATOM | 1654 | CA  | GLU | 185 | 44.647 | 54.082 | 16.391 | 1.00 | 25.55 |
| ATOM | 1655 | C   | GLU | 185 | 46.078 | 53.861 | 16.857 | 1.00 | 27.14 |
| ATOM | 1656 | O   | GLU | 185 | 47.019 | 53.873 | 16.027 | 1.00 | 26.38 |
| ATOM | 1657 | CB  | GLU | 185 | 44.185 | 55.548 | 16.421 | 1.00 | 25.17 |
| ATOM | 1658 | CG  | GLU | 185 | 42.920 | 55.799 | 15.549 | 1.00 | 23.68 |
| ATOM | 1659 | CD  | GLU | 185 | 42.609 | 57.281 | 15.318 | 1.00 | 26.50 |
| ATOM | 1660 | OE1 | GLU | 185 | 42.984 | 58.100 | 16.171 | 1.00 | 24.21 |
| ATOM | 1661 | OE2 | GLU | 185 | 41.987 | 57.636 | 14.288 | 1.00 | 26.85 |
| ATOM | 1662 | N   | THR | 186 | 46.230 | 53.597 | 18.172 | 1.00 | 27.44 |
| ATOM | 1663 | CA  | THR | 186 | 47.548 | 53.360 | 18.780 | 1.00 | 29.10 |
| ATOM | 1664 | C   | THR | 186 | 48.130 | 52.082 | 18.223 | 1.00 | 28.82 |
| ATOM | 1665 | O   | THR | 186 | 49.335 | 51.950 | 18.137 | 1.00 | 29.57 |
| ATOM | 1666 | CB  | THR | 186 | 47.488 | 53.171 | 20.331 | 1.00 | 28.74 |
| ATOM | 1667 | OG1 | THR | 186 | 46.989 | 54.361 | 20.926 | 1.00 | 31.76 |
| ATOM | 1668 | CG2 | THR | 186 | 48.900 | 52.980 | 20.950 | 1.00 | 31.01 |
| ATOM | 1669 | N   | GLN | 187 | 47.266 | 51.138 | 17.880 | 1.00 | 27.63 |
| ATOM | 1670 | CA  | GLN | 187 | 47.734 | 49.838 | 17.463 | 1.00 | 27.72 |
| ATOM | 1671 | C   | GLN | 187 | 47.895 | 49.701 | 15.963 | 1.00 | 27.83 |
| ATOM | 1672 | O   | GLN | 187 | 48.495 | 48.744 | 15.524 | 1.00 | 29.63 |
| ATOM | 1673 | CB  | GLN | 187 | 46.797 | 48.744 | 17.974 | 1.00 | 27.75 |
| ATOM | 1674 | CG  | GLN | 187 | 46.783 | 48.579 | 19.519 | 1.00 | 26.73 |
| ATOM | 1675 | CD  | GLN | 187 | 48.157 | 48.394 | 20.097 | 1.00 | 27.76 |
| ATOM | 1676 | OE1 | GLN | 187 | 49.015 | 47.700 | 19.533 | 1.00 | 30.15 |
| ATOM | 1677 | NE2 | GLN | 187 | 48.378 | 48.979 | 21.239 | 1.00 | 28.32 |

TABLE 11-continued

Three-Dimensional Coordinates of *Neisseria gonorrhoeae* GCYH-IB·Mn$^{2+}$ (SEQ. ID. No. 8)

| ATOM | 1678 | N | ALA | 188 | 47.356 | 50.625 | 15.176 | 1.00 | 27.23 |
|---|---|---|---|---|---|---|---|---|---|
| ATOM | 1679 | CA | ALA | 188 | 47.369 | 50.474 | 13.725 | 1.00 | 27.88 |
| ATOM | 1680 | C | ALA | 188 | 48.791 | 50.622 | 13.135 | 1.00 | 28.74 |
| ATOM | 1681 | O | ALA | 188 | 49.614 | 51.334 | 13.715 | 1.00 | 28.55 |
| ATOM | 1682 | CB | ALA | 188 | 46.445 | 51.517 | 13.118 | 1.00 | 27.58 |
| ATOM | 1683 | N | SER | 189 | 49.102 | 49.935 | 12.010 | 1.00 | 28.35 |
| ATOM | 1684 | CA | SER | 189 | 50.358 | 50.217 | 11.299 | 1.00 | 28.39 |
| ATOM | 1685 | C | SER | 189 | 50.551 | 51.741 | 11.159 | 1.00 | 28.75 |
| ATOM | 1686 | O | SER | 189 | 51.626 | 52.259 | 11.474 | 1.00 | 29.75 |
| ATOM | 1687 | CB | SER | 189 | 50.435 | 49.501 | 9.947 | 1.00 | 28.00 |
| ATOM | 1688 | OG | SER | 189 | 50.545 | 48.071 | 10.203 | 1.00 | 31.33 |
| ATOM | 1689 | N | CYS | 190 | 49.503 | 52.434 | 10.730 | 1.00 | 28.89 |
| ATOM | 1690 | CA | CYS | 190 | 49.416 | 53.884 | 10.865 | 1.00 | 29.72 |
| ATOM | 1691 | C | CYS | 190 | 47.958 | 54.324 | 10.868 | 1.00 | 29.12 |
| ATOM | 1692 | O | CYS | 190 | 47.134 | 53.764 | 10.176 | 1.00 | 29.39 |
| ATOM | 1693 | CB | CYS | 190 | 50.183 | 54.607 | 9.738 | 1.00 | 29.28 |
| ATOM | 1694 | SG | CYS | 190 | 50.602 | 56.361 | 10.127 | 1.00 | 31.60 |
| ATOM | 1695 | N | GLN | 191 | 47.637 | 55.341 | 11.649 | 1.00 | 28.56 |
| ATOM | 1696 | CA | GLN | 191 | 46.306 | 55.907 | 11.624 | 1.00 | 28.62 |
| ATOM | 1697 | C | GLN | 191 | 46.093 | 56.881 | 10.431 | 1.00 | 28.18 |
| ATOM | 1698 | O | GLN | 191 | 47.055 | 57.305 | 9.816 | 1.00 | 30.09 |
| ATOM | 1699 | CB | GLN | 191 | 46.007 | 56.587 | 12.982 | 1.00 | 27.91 |
| ATOM | 1700 | CG | GLN | 191 | 46.917 | 57.763 | 13.269 | 1.00 | 29.69 |
| ATOM | 1701 | CD | GLN | 191 | 46.745 | 58.292 | 14.681 | 1.00 | 28.05 |
| ATOM | 1702 | OE1 | GLN | 191 | 45.815 | 59.041 | 14.953 | 1.00 | 26.08 |
| ATOM | 1703 | NE2 | GLN | 191 | 47.663 | 57.940 | 15.563 | 1.00 | 27.88 |
| ATOM | 1704 | N | LEU | 192 | 44.838 | 57.261 | 10.165 | 1.00 | 27.13 |
| ATOM | 1705 | CA | LEU | 192 | 44.458 | 58.173 | 9.084 | 1.00 | 26.58 |
| ATOM | 1706 | C | LEU | 192 | 44.288 | 59.643 | 9.519 | 1.00 | 26.86 |
| ATOM | 1707 | O | LEU | 192 | 43.984 | 59.927 | 10.665 | 1.00 | 26.33 |
| ATOM | 1708 | CB | LEU | 192 | 43.123 | 57.728 | 8.459 | 1.00 | 25.94 |
| ATOM | 1709 | CG | LEU | 192 | 42.975 | 56.272 | 8.007 | 1.00 | 25.68 |
| ATOM | 1710 | CD1 | LEU | 192 | 41.595 | 56.059 | 7.442 | 1.00 | 24.34 |
| ATOM | 1711 | CD2 | LEU | 192 | 44.038 | 55.909 | 6.967 | 1.00 | 25.68 |
| ATOM | 1712 | N | TYR | 193 | 44.460 | 60.540 | 8.550 | 1.00 | 26.29 |
| ATOM | 1713 | CA | TYR | 193 | 44.264 | 62.010 | 8.677 | 1.00 | 27.06 |
| ATOM | 1714 | C | TYR | 193 | 43.652 | 62.508 | 7.373 | 1.00 | 27.76 |
| ATOM | 1715 | O | TYR | 193 | 43.991 | 61.962 | 6.293 | 1.00 | 28.41 |
| ATOM | 1716 | CB | TYR | 193 | 45.624 | 62.683 | 8.820 | 1.00 | 26.43 |
| ATOM | 1717 | CG | TYR | 193 | 46.409 | 62.194 | 10.009 | 1.00 | 26.85 |
| ATOM | 1718 | CD1 | TYR | 193 | 46.305 | 62.834 | 11.260 | 1.00 | 26.58 |
| ATOM | 1719 | CD2 | TYR | 193 | 47.243 | 61.076 | 9.887 | 1.00 | 28.66 |
| ATOM | 1720 | CE1 | TYR | 193 | 47.035 | 62.375 | 12.367 | 1.00 | 24.85 |
| ATOM | 1721 | CE2 | TYR | 193 | 47.967 | 60.602 | 10.959 | 1.00 | 26.95 |
| ATOM | 1722 | CZ | TYR | 193 | 47.841 | 61.248 | 12.187 | 1.00 | 26.61 |
| ATOM | 1723 | OH | TYR | 193 | 48.580 | 60.752 | 13.189 | 1.00 | 26.01 |
| ATOM | 1724 | N | GLY | 194 | 42.805 | 63.541 | 7.430 | 1.00 | 27.45 |
| ATOM | 1725 | CA | GLY | 194 | 42.219 | 64.052 | 6.211 | 1.00 | 28.39 |
| ATOM | 1726 | C | GLY | 194 | 43.250 | 64.943 | 5.558 | 1.00 | 29.37 |
| ATOM | 1727 | O | GLY | 194 | 43.404 | 64.987 | 4.351 | 1.00 | 29.71 |
| ATOM | 1728 | N | LEU | 195 | 43.997 | 65.660 | 6.377 | 1.00 | 30.72 |
| ATOM | 1729 | CA | LEU | 195 | 44.913 | 66.671 | 5.828 | 1.00 | 30.71 |
| ATOM | 1730 | C | LEU | 195 | 46.347 | 66.356 | 6.172 | 1.00 | 29.77 |
| ATOM | 1731 | O | LEU | 195 | 46.736 | 66.317 | 7.330 | 1.00 | 28.47 |
| ATOM | 1732 | CB | LEU | 195 | 44.495 | 68.064 | 6.282 | 1.00 | 30.93 |
| ATOM | 1733 | CG | LEU | 195 | 44.897 | 69.300 | 5.459 | 1.00 | 33.19 |
| ATOM | 1734 | CD1 | LEU | 195 | 44.301 | 70.553 | 6.174 | 1.00 | 33.40 |
| ATOM | 1735 | CD2 | LEU | 195 | 46.381 | 69.408 | 5.430 | 1.00 | 35.11 |
| ATOM | 1736 | N | LEU | 196 | 47.125 | 66.119 | 5.120 | 1.00 | 29.88 |
| ATOM | 1737 | CA | LEU | 196 | 48.509 | 65.742 | 5.234 | 1.00 | 31.16 |
| ATOM | 1738 | C | LEU | 196 | 49.300 | 66.583 | 4.255 | 1.00 | 32.87 |
| ATOM | 1739 | O | LEU | 196 | 48.981 | 66.596 | 3.049 | 1.00 | 31.79 |
| ATOM | 1740 | CB | LEU | 196 | 48.716 | 64.262 | 4.891 | 1.00 | 30.65 |
| ATOM | 1741 | CG | LEU | 196 | 48.111 | 63.218 | 5.856 | 1.00 | 31.74 |
| ATOM | 1742 | CD1 | LEU | 196 | 48.363 | 61.876 | 5.281 | 1.00 | 32.71 |
| ATOM | 1743 | CD2 | LEU | 196 | 48.735 | 63.288 | 7.252 | 1.00 | 32.09 |
| ATOM | 1744 | N | LYS | 197 | 50.312 | 67.269 | 4.790 | 1.00 | 33.78 |
| ATOM | 1745 | CA | LYS | 197 | 51.318 | 67.927 | 3.980 | 1.00 | 36.74 |
| ATOM | 1746 | C | LYS | 197 | 52.431 | 66.910 | 3.573 | 1.00 | 36.95 |
| ATOM | 1747 | O | LYS | 197 | 52.487 | 65.762 | 4.085 | 1.00 | 37.20 |
| ATOM | 1748 | CB | LYS | 197 | 51.883 | 69.166 | 4.722 | 1.00 | 37.53 |
| ATOM | 1749 | CG | LYS | 197 | 50.885 | 70.341 | 4.822 | 1.00 | 39.92 |
| ATOM | 1750 | CD | LYS | 197 | 50.542 | 70.745 | 3.378 | 1.00 | 44.49 |
| ATOM | 1751 | CE | LYS | 197 | 49.503 | 71.820 | 3.289 | 1.00 | 49.11 |
| ATOM | 1752 | NZ | LYS | 197 | 50.033 | 73.137 | 3.746 | 1.00 | 51.33 |
| ATOM | 1753 | N | ARG | 198 | 53.316 | 67.333 | 2.673 | 1.00 | 36.70 |
| ATOM | 1754 | CA | ARG | 198 | 54.337 | 66.444 | 2.112 | 1.00 | 37.70 |

TABLE 11-continued

Three-Dimensional Coordinates of *Neisseria gonorrhoeae* GCYH-IB·Mn$^{2+}$
(SEQ. ID. No. 8)

| ATOM | 1755 | C | ARG | 198 | 55.200 | 65.833 | 3.247 | 1.00 | 36.39 |
|------|------|-----|-----|-----|--------|--------|--------|------|-------|
| ATOM | 1756 | O | ARG | 198 | 55.469 | 64.629 | 3.250 | 1.00 | 35.97 |
| ATOM | 1757 | CB | ARG | 198 | 55.148 | 67.195 | 1.021 | 1.00 | 37.77 |
| ATOM | 1758 | CG | ARG | 198 | 56.366 | 66.474 | 0.404 | 1.00 | 40.32 |
| ATOM | 1759 | CD | ARG | 198 | 57.175 | 67.441 | −0.517 | 1.00 | 41.88 |
| ATOM | 1760 | NE | ARG | 198 | 58.574 | 67.027 | −0.649 | 1.00 | 49.67 |
| ATOM | 1761 | CZ | ARG | 198 | 59.170 | 66.702 | −1.802 | 1.00 | 51.87 |
| ATOM | 1762 | NH1 | ARG | 198 | 58.489 | 66.743 | −2.947 | 1.00 | 53.30 |
| ATOM | 1763 | NH2 | ARG | 198 | 60.453 | 66.333 | −1.808 | 1.00 | 51.58 |
| ATOM | 1764 | N | PRO | 199 | 55.623 | 66.644 | 4.241 | 1.00 | 35.71 |
| ATOM | 1765 | CA | PRO | 199 | 56.383 | 65.975 | 5.318 | 1.00 | 34.81 |
| ATOM | 1766 | C | PRO | 199 | 55.516 | 64.977 | 6.110 | 1.00 | 35.08 |
| ATOM | 1767 | O | PRO | 199 | 56.055 | 63.974 | 6.651 | 1.00 | 34.43 |
| ATOM | 1768 | CB | PRO | 199 | 56.823 | 67.129 | 6.208 | 1.00 | 34.84 |
| ATOM | 1769 | CG | PRO | 199 | 55.836 | 68.250 | 5.874 | 1.00 | 35.30 |
| ATOM | 1770 | CD | PRO | 199 | 55.517 | 68.099 | 4.440 | 1.00 | 35.36 |
| ATOM | 1771 | N | ASP | 200 | 54.201 | 65.247 | 6.175 | 1.00 | 34.66 |
| ATOM | 1772 | CA | ASP | 200 | 53.252 | 64.371 | 6.906 | 1.00 | 35.25 |
| ATOM | 1773 | C | ASP | 200 | 53.062 | 63.072 | 6.146 | 1.00 | 35.17 |
| ATOM | 1774 | O | ASP | 200 | 53.055 | 61.983 | 6.722 | 1.00 | 35.34 |
| ATOM | 1775 | CB | ASP | 200 | 51.908 | 65.054 | 7.035 | 1.00 | 35.09 |
| ATOM | 1776 | CG | ASP | 200 | 51.976 | 66.311 | 7.874 | 1.00 | 35.57 |
| ATOM | 1777 | OD1 | ASP | 200 | 52.551 | 66.260 | 8.989 | 1.00 | 33.86 |
| ATOM | 1778 | OD2 | ASP | 200 | 51.410 | 67.331 | 7.420 | 1.00 | 35.70 |
| ATOM | 1779 | N | GLU | 201 | 52.943 | 63.196 | 4.831 | 1.00 | 35.17 |
| ATOM | 1780 | CA | GLU | 201 | 52.823 | 62.023 | 3.976 | 1.00 | 34.49 |
| ATOM | 1781 | C | GLU | 201 | 54.086 | 61.136 | 4.066 | 1.00 | 34.61 |
| ATOM | 1782 | O | GLU | 201 | 53.997 | 59.913 | 4.171 | 1.00 | 32.47 |
| ATOM | 1783 | CB | GLU | 201 | 52.492 | 62.398 | 2.523 | 1.00 | 34.51 |
| ATOM | 1784 | CG | GLU | 201 | 52.407 | 61.131 | 1.648 | 1.00 | 34.40 |
| ATOM | 1785 | CD | GLU | 201 | 51.698 | 61.348 | 0.353 | 1.00 | 36.89 |
| ATOM | 1786 | OE1 | GLU | 201 | 51.475 | 62.494 | −0.017 | 1.00 | 40.24 |
| ATOM | 1787 | OE2 | GLU | 201 | 51.344 | 60.361 | −0.298 | 1.00 | 36.83 |
| ATOM | 1788 | N | LYS | 202 | 55.260 | 61.764 | 4.042 | 1.00 | 34.91 |
| ATOM | 1789 | CA | LYS | 202 | 56.499 | 61.051 | 4.256 | 1.00 | 35.18 |
| ATOM | 1790 | C | LYS | 202 | 56.511 | 60.265 | 5.589 | 1.00 | 34.53 |
| ATOM | 1791 | O | LYS | 202 | 56.870 | 59.085 | 5.584 | 1.00 | 33.52 |
| ATOM | 1792 | CB | LYS | 202 | 57.704 | 62.016 | 4.144 | 1.00 | 36.19 |
| ATOM | 1793 | CG | LYS | 202 | 58.953 | 61.532 | 4.837 | 1.00 | 36.45 |
| ATOM | 1794 | CD | LYS | 202 | 60.187 | 62.464 | 4.538 | 1.00 | 36.73 |
| ATOM | 1795 | CE | LYS | 202 | 61.352 | 62.086 | 5.420 | 1.00 | 38.08 |
| ATOM | 1796 | NZ | LYS | 202 | 62.094 | 60.862 | 5.001 | 1.00 | 38.27 |
| ATOM | 1797 | N | TYR | 203 | 56.132 | 60.924 | 6.695 | 1.00 | 34.14 |
| ATOM | 1798 | CA | TYR | 203 | 56.081 | 60.343 | 8.049 | 1.00 | 34.26 |
| ATOM | 1799 | C | TYR | 203 | 55.182 | 59.058 | 8.081 | 1.00 | 33.41 |
| ATOM | 1800 | O | TYR | 203 | 55.545 | 58.012 | 8.591 | 1.00 | 32.66 |
| ATOM | 1801 | CB | TYR | 203 | 55.507 | 61.380 | 9.034 | 1.00 | 34.85 |
| ATOM | 1802 | CG | TYR | 203 | 55.420 | 60.870 | 10.446 | 1.00 | 36.49 |
| ATOM | 1803 | CD1 | TYR | 203 | 56.444 | 61.128 | 11.371 | 1.00 | 37.59 |
| ATOM | 1804 | CD2 | TYR | 203 | 54.323 | 60.087 | 10.869 | 1.00 | 36.73 |
| ATOM | 1805 | CE1 | TYR | 203 | 56.386 | 60.629 | 12.694 | 1.00 | 38.56 |
| ATOM | 1806 | CE2 | TYR | 203 | 54.267 | 59.579 | 12.195 | 1.00 | 38.63 |
| ATOM | 1807 | CZ | TYR | 203 | 55.309 | 59.874 | 13.091 | 1.00 | 37.44 |
| ATOM | 1808 | OH | TYR | 203 | 55.280 | 59.398 | 14.372 | 1.00 | 40.73 |
| ATOM | 1809 | N | VAL | 204 | 54.002 | 59.204 | 7.518 | 1.00 | 32.56 |
| ATOM | 1810 | CA | VAL | 204 | 52.952 | 58.186 | 7.520 | 1.00 | 32.86 |
| ATOM | 1811 | C | VAL | 204 | 53.349 | 56.948 | 6.664 | 1.00 | 32.32 |
| ATOM | 1812 | O | VAL | 204 | 53.162 | 55.792 | 7.075 | 1.00 | 32.22 |
| ATOM | 1813 | CB | VAL | 204 | 51.675 | 58.966 | 7.117 | 1.00 | 33.17 |
| ATOM | 1814 | CG1 | VAL | 204 | 50.933 | 58.449 | 5.882 | 1.00 | 33.70 |
| ATOM | 1815 | CG2 | VAL | 204 | 50.855 | 59.467 | 8.375 | 1.00 | 31.96 |
| ATOM | 1816 | N | THR | 205 | 53.936 | 57.206 | 5.498 | 1.00 | 32.24 |
| ATOM | 1817 | CA | THR | 205 | 54.428 | 56.161 | 4.608 | 1.00 | 31.51 |
| ATOM | 1818 | C | THR | 205 | 55.481 | 55.291 | 5.321 | 1.00 | 31.55 |
| ATOM | 1819 | O | THR | 205 | 55.359 | 54.032 | 5.363 | 1.00 | 30.90 |
| ATOM | 1820 | CB | THR | 205 | 54.970 | 56.812 | 3.295 | 1.00 | 31.73 |
| ATOM | 1821 | OG1 | THR | 205 | 53.875 | 57.474 | 2.591 | 1.00 | 30.86 |
| ATOM | 1822 | CG2 | THR | 205 | 55.646 | 55.761 | 2.411 | 1.00 | 31.29 |
| ATOM | 1823 | N | GLU | 206 | 56.491 | 55.966 | 5.892 | 1.00 | 31.37 |
| ATOM | 1824 | CA | GLU | 206 | 57.593 | 55.325 | 6.652 | 1.00 | 32.61 |
| ATOM | 1825 | C | GLU | 206 | 57.142 | 54.659 | 7.949 | 1.00 | 32.07 |
| ATOM | 1826 | O | GLU | 206 | 57.573 | 53.565 | 8.226 | 1.00 | 31.97 |
| ATOM | 1827 | CB | GLU | 206 | 58.753 | 56.297 | 6.930 | 1.00 | 32.31 |
| ATOM | 1828 | CG | GLU | 206 | 59.419 | 56.801 | 5.654 | 1.00 | 33.50 |
| ATOM | 1829 | CD | GLU | 206 | 60.435 | 57.936 | 5.897 | 1.00 | 34.50 |
| ATOM | 1830 | OE1 | GLU | 206 | 60.604 | 58.380 | 7.066 | 1.00 | 38.19 |
| ATOM | 1831 | OE2 | GLU | 206 | 61.035 | 58.388 | 4.917 | 1.00 | 31.10 |

TABLE 11-continued

Three-Dimensional Coordinates of *Neisseria gonorrhoeae* GCYH-IB·Mn$^{2+}$
(SEQ. ID. No. 8)

| ATOM | 1832 | N   | LYS | 207 | 56.281 | 55.310 | 8.721  | 1.00 | 31.90 |
|------|------|-----|-----|-----|--------|--------|--------|------|-------|
| ATOM | 1833 | CA  | LYS | 207 | 55.750 | 54.708 | 9.952  | 1.00 | 32.07 |
| ATOM | 1834 | C   | LYS | 207 | 55.029 | 53.371 | 9.645  | 1.00 | 32.17 |
| ATOM | 1835 | O   | LYS | 207 | 55.321 | 52.339 | 10.253 | 1.00 | 32.06 |
| ATOM | 1836 | CB  | LYS | 207 | 54.804 | 55.688 | 10.670 | 1.00 | 32.80 |
| ATOM | 1837 | CG  | LYS | 207 | 54.356 | 55.265 | 12.090 | 1.00 | 36.71 |
| ATOM | 1838 | CD  | LYS | 207 | 55.577 | 54.891 | 12.935 | 1.00 | 43.40 |
| ATOM | 1839 | CE  | LYS | 207 | 55.461 | 55.312 | 14.453 | 1.00 | 46.89 |
| ATOM | 1840 | NZ  | LYS | 207 | 56.763 | 55.097 | 15.135 | 1.00 | 47.00 |
| ATOM | 1841 | N   | ALA | 208 | 54.094 | 53.390 | 8.690  | 1.00 | 30.86 |
| ATOM | 1842 | CA  | ALA | 208 | 53.376 | 52.163 | 8.340  | 1.00 | 30.32 |
| ATOM | 1843 | C   | ALA | 208 | 54.366 | 51.055 | 7.984  | 1.00 | 30.56 |
| ATOM | 1844 | O   | ALA | 208 | 54.272 | 49.920 | 8.483  | 1.00 | 29.36 |
| ATOM | 1845 | CB  | ALA | 208 | 52.364 | 52.415 | 7.163  | 1.00 | 28.98 |
| ATOM | 1846 | N   | TYR | 209 | 55.321 | 51.403 | 7.116  | 1.00 | 31.34 |
| ATOM | 1847 | CA  | TYR | 209 | 56.333 | 50.475 | 6.618  | 1.00 | 32.07 |
| ATOM | 1848 | C   | TYR | 209 | 57.240 | 49.938 | 7.739  | 1.00 | 32.83 |
| ATOM | 1849 | O   | TYR | 209 | 57.700 | 48.783 | 7.691  | 1.00 | 32.54 |
| ATOM | 1850 | CB  | TYR | 209 | 57.154 | 51.167 | 5.554  | 1.00 | 32.73 |
| ATOM | 1851 | CG  | TYR | 209 | 58.158 | 50.285 | 4.853  | 1.00 | 33.75 |
| ATOM | 1852 | CD1 | TYR | 209 | 57.787 | 49.556 | 3.703  | 1.00 | 34.84 |
| ATOM | 1853 | CD2 | TYR | 209 | 59.483 | 50.197 | 5.299  | 1.00 | 33.51 |
| ATOM | 1854 | CE1 | TYR | 209 | 58.718 | 48.758 | 3.031  | 1.00 | 34.86 |
| ATOM | 1855 | CE2 | TYR | 209 | 60.438 | 49.371 | 4.623  | 1.00 | 34.90 |
| ATOM | 1856 | CZ  | TYR | 209 | 60.032 | 48.661 | 3.486  | 1.00 | 33.05 |
| ATOM | 1857 | OH  | TYR | 209 | 60.932 | 47.845 | 2.791  | 1.00 | 35.66 |
| ATOM | 1858 | N   | GLU | 210 | 57.463 | 50.754 | 8.762  | 1.00 | 34.05 |
| ATOM | 1859 | CA  | GLU | 210 | 58.206 | 50.296 | 9.956  | 1.00 | 34.62 |
| ATOM | 1860 | C   | GLU | 210 | 57.331 | 49.457 | 10.902 | 1.00 | 35.41 |
| ATOM | 1861 | O   | GLU | 210 | 57.848 | 48.791 | 11.824 | 1.00 | 34.97 |
| ATOM | 1862 | CB  | GLU | 210 | 58.758 | 51.496 | 10.696 | 1.00 | 35.86 |
| ATOM | 1863 | CG  | GLU | 210 | 59.770 | 52.335 | 9.883  | 1.00 | 36.13 |
| ATOM | 1864 | CD  | GLU | 210 | 59.917 | 53.774 | 10.388 | 1.00 | 38.52 |
| ATOM | 1865 | OE1 | GLU | 210 | 59.209 | 54.198 | 11.326 | 1.00 | 38.33 |
| ATOM | 1866 | OE2 | GLU | 210 | 60.761 | 54.497 | 9.805  | 1.00 | 40.89 |
| ATOM | 1867 | N   | ASN | 211 | 56.010 | 49.495 | 10.701 | 1.00 | 34.65 |
| ATOM | 1868 | CA  | ASN | 211 | 55.071 | 48.805 | 11.625 | 1.00 | 35.17 |
| ATOM | 1869 | C   | ASN | 211 | 54.033 | 47.949 | 10.929 | 1.00 | 33.23 |
| ATOM | 1870 | O   | ASN | 211 | 52.844 | 48.101 | 11.179 | 1.00 | 34.24 |
| ATOM | 1871 | CB  | ASN | 211 | 54.387 | 49.764 | 12.597 | 1.00 | 35.24 |
| ATOM | 1872 | CG  | ASN | 211 | 55.388 | 50.549 | 13.414 | 1.00 | 38.14 |
| ATOM | 1873 | OD1 | ASN | 211 | 55.927 | 51.587 | 12.954 | 1.00 | 41.46 |
| ATOM | 1874 | ND2 | ASN | 211 | 55.681 | 50.053 | 14.617 | 1.00 | 36.20 |
| ATOM | 1875 | N   | PRO | 212 | 54.503 | 46.993 | 10.110 | 1.00 | 32.10 |
| ATOM | 1876 | CA  | PRO | 212 | 53.583 | 46.146 | 9.385  | 1.00 | 31.76 |
| ATOM | 1877 | C   | PRO | 212 | 52.823 | 45.257 | 10.356 | 1.00 | 31.38 |
| ATOM | 1878 | O   | PRO | 212 | 53.380 | 44.787 | 11.353 | 1.00 | 30.16 |
| ATOM | 1879 | CB  | PRO | 212 | 54.490 | 45.317 | 8.486  | 1.00 | 30.78 |
| ATOM | 1880 | CG  | PRO | 212 | 55.845 | 45.286 | 9.224  | 1.00 | 31.04 |
| ATOM | 1881 | CD  | PRO | 212 | 55.922 | 46.619 | 9.893  | 1.00 | 31.09 |
| ATOM | 1882 | N   | LYS | 213 | 51.562 | 45.014 | 10.036 | 1.00 | 30.99 |
| ATOM | 1883 | CA  | LYS | 213 | 50.761 | 44.074 | 10.818 | 1.00 | 31.42 |
| ATOM | 1884 | C   | LYS | 213 | 49.766 | 43.348 | 9.955  | 1.00 | 31.15 |
| ATOM | 1885 | O   | LYS | 213 | 49.074 | 43.953 | 9.116  | 1.00 | 31.01 |
| ATOM | 1886 | CB  | LYS | 213 | 49.986 | 44.817 | 11.911 | 1.00 | 30.59 |
| ATOM | 1887 | CG  | LYS | 213 | 50.911 | 45.403 | 12.959 | 1.00 | 29.40 |
| ATOM | 1888 | CD  | LYS | 213 | 50.177 | 45.708 | 14.282 | 1.00 | 27.87 |
| ATOM | 1889 | CE  | LYS | 213 | 51.127 | 46.400 | 15.275 | 1.00 | 29.06 |
| ATOM | 1890 | NZ  | LYS | 213 | 50.269 | 46.947 | 16.416 | 1.00 | 29.60 |
| ATOM | 1891 | N   | PHE | 214 | 49.736 | 42.040 | 10.165 | 1.00 | 31.08 |
| ATOM | 1892 | CA  | PHE | 214 | 48.631 | 41.188 | 9.699  | 1.00 | 31.02 |
| ATOM | 1893 | C   | PHE | 214 | 47.336 | 41.569 | 10.398 | 1.00 | 29.28 |
| ATOM | 1894 | O   | PHE | 214 | 47.336 | 42.220 | 11.486 | 1.00 | 28.86 |
| ATOM | 1895 | CB  | PHE | 214 | 48.962 | 39.705 | 10.011 | 1.00 | 31.33 |
| ATOM | 1896 | CG  | PHE | 214 | 50.110 | 39.147 | 9.193  | 1.00 | 33.17 |
| ATOM | 1897 | CD1 | PHE | 214 | 50.029 | 39.089 | 7.785  | 1.00 | 34.17 |
| ATOM | 1898 | CD2 | PHE | 214 | 51.254 | 38.643 | 9.826  | 1.00 | 31.80 |
| ATOM | 1899 | CE1 | PHE | 214 | 51.118 | 38.572 | 7.014  | 1.00 | 36.33 |
| ATOM | 1900 | CE2 | PHE | 214 | 52.323 | 38.129 | 9.087  | 1.00 | 32.91 |
| ATOM | 1901 | CZ  | PHE | 214 | 52.258 | 38.077 | 7.665  | 1.00 | 33.95 |
| ATOM | 1902 | N   | VAL | 215 | 46.226 | 41.151 | 9.796  | 1.00 | 27.85 |
| ATOM | 1903 | CA  | VAL | 215 | 44.911 | 41.312 | 10.377 | 1.00 | 28.62 |
| ATOM | 1904 | C   | VAL | 215 | 44.878 | 40.607 | 11.762 | 1.00 | 28.57 |
| ATOM | 1905 | O   | VAL | 215 | 44.295 | 41.140 | 12.682 | 1.00 | 27.90 |
| ATOM | 1906 | CB  | VAL | 215 | 43.749 | 40.901 | 9.352  | 1.00 | 28.94 |
| ATOM | 1907 | CG1 | VAL | 215 | 43.721 | 39.402 | 9.060  | 1.00 | 29.40 |
| ATOM | 1908 | CG2 | VAL | 215 | 42.428 | 41.347 | 9.813  | 1.00 | 29.76 |

TABLE 11-continued

Three-Dimensional Coordinates of *Neisseria gonorrhoeae* GCYH-IB·Mn$^{2+}$
(SEQ. ID. No. 8)

| ATOM | 1909 | N | GLU | 216 | 45.546 | 39.450 | 11.872 | 1.00 | 28.34 |
|---|---|---|---|---|---|---|---|---|---|
| ATOM | 1910 | CA | GLU | 216 | 45.735 | 38.652 | 13.131 | 1.00 | 29.82 |
| ATOM | 1911 | C | GLU | 216 | 46.364 | 39.490 | 14.235 | 1.00 | 28.79 |
| ATOM | 1912 | O | GLU | 216 | 45.822 | 39.619 | 15.311 | 1.00 | 28.87 |
| ATOM | 1913 | CB | GLU | 216 | 46.608 | 37.400 | 12.835 | 1.00 | 28.86 |
| ATOM | 1914 | CG | GLU | 216 | 45.872 | 36.385 | 11.934 | 1.00 | 32.94 |
| ATOM | 1915 | CD | GLU | 216 | 46.306 | 36.426 | 10.455 | 1.00 | 34.70 |
| ATOM | 1916 | OE1 | GLU | 216 | 46.537 | 37.517 | 9.914 | 1.00 | 35.44 |
| ATOM | 1917 | OE2 | GLU | 216 | 46.400 | 35.347 | 9.820 | 1.00 | 37.76 |
| ATOM | 1918 | N | ASP | 217 | 47.483 | 40.117 | 13.892 | 1.00 | 29.08 |
| ATOM | 1919 | CA | ASP | 217 | 48.235 | 41.031 | 14.751 | 1.00 | 28.86 |
| ATOM | 1920 | C | ASP | 217 | 47.386 | 42.185 | 15.203 | 1.00 | 28.38 |
| ATOM | 1921 | O | ASP | 217 | 47.338 | 42.504 | 16.408 | 1.00 | 27.02 |
| ATOM | 1922 | CB | ASP | 217 | 49.437 | 41.570 | 14.000 | 1.00 | 29.76 |
| ATOM | 1923 | CG | ASP | 217 | 50.398 | 40.501 | 13.603 | 1.00 | 31.99 |
| ATOM | 1924 | OD1 | ASP | 217 | 50.489 | 39.492 | 14.298 | 1.00 | 38.26 |
| ATOM | 1925 | OD2 | ASP | 217 | 51.084 | 40.654 | 12.591 | 1.00 | 34.15 |
| ATOM | 1926 | N | MET | 218 | 46.696 | 42.831 | 14.261 | 1.00 | 28.36 |
| ATOM | 1927 | CA | MET | 218 | 45.812 | 43.928 | 14.647 | 1.00 | 29.64 |
| ATOM | 1928 | C | MET | 218 | 44.706 | 43.558 | 15.656 | 1.00 | 28.41 |
| ATOM | 1929 | O | MET | 218 | 44.492 | 44.275 | 16.636 | 1.00 | 26.63 |
| ATOM | 1930 | CB | MET | 218 | 45.176 | 44.629 | 13.422 | 1.00 | 30.96 |
| ATOM | 1931 | CG | MET | 218 | 44.319 | 45.845 | 13.861 | 1.00 | 35.70 |
| ATOM | 1932 | SD | MET | 218 | 45.273 | 47.280 | 14.514 | 1.00 | 45.47 |
| ATOM | 1933 | CE | MET | 218 | 46.456 | 47.370 | 13.190 | 1.00 | 46.95 |
| ATOM | 1934 | N | VAL | 219 | 43.962 | 42.479 | 15.405 | 1.00 | 28.22 |
| ATOM | 1935 | CA | VAL | 219 | 42.869 | 42.158 | 16.337 | 1.00 | 28.10 |
| ATOM | 1936 | C | VAL | 219 | 43.427 | 41.730 | 17.690 | 1.00 | 27.11 |
| ATOM | 1937 | O | VAL | 219 | 42.857 | 42.078 | 18.725 | 1.00 | 27.29 |
| ATOM | 1938 | CB | VAL | 219 | 41.773 | 41.161 | 15.749 | 1.00 | 28.69 |
| ATOM | 1939 | CG1 | VAL | 219 | 41.164 | 41.775 | 14.457 | 1.00 | 29.54 |
| ATOM | 1940 | CG2 | VAL | 219 | 42.347 | 39.777 | 15.445 | 1.00 | 27.60 |
| ATOM | 1941 | N | ARG | 220 | 44.529 | 40.996 | 17.692 | 1.00 | 27.25 |
| ATOM | 1942 | CA | ARG | 220 | 45.171 | 40.580 | 18.986 | 1.00 | 29.06 |
| ATOM | 1943 | C | ARG | 220 | 45.667 | 41.777 | 19.743 | 1.00 | 28.85 |
| ATOM | 1944 | O | ARG | 220 | 45.464 | 41.835 | 20.955 | 1.00 | 30.55 |
| ATOM | 1945 | CB | ARG | 220 | 46.331 | 39.599 | 18.797 | 1.00 | 27.73 |
| ATOM | 1946 | CG | ARG | 220 | 45.901 | 38.148 | 18.483 | 1.00 | 29.78 |
| ATOM | 1947 | CD | ARG | 220 | 47.100 | 37.326 | 17.937 | 1.00 | 29.72 |
| ATOM | 1948 | NE | ARG | 220 | 46.730 | 35.926 | 18.068 | 1.00 | 33.92 |
| ATOM | 1949 | CZ | ARG | 220 | 47.200 | 34.943 | 17.324 | 1.00 | 32.61 |
| ATOM | 1950 | NH1 | ARG | 220 | 48.094 | 35.206 | 16.410 | 1.00 | 33.13 |
| ATOM | 1951 | NH2 | ARG | 220 | 46.761 | 33.695 | 17.514 | 1.00 | 34.32 |
| ATOM | 1952 | N | ASP | 221 | 46.313 | 42.708 | 19.036 | 1.00 | 28.07 |
| ATOM | 1953 | CA | ASP | 221 | 46.889 | 43.949 | 19.662 | 1.00 | 28.23 |
| ATOM | 1954 | C | ASP | 221 | 45.801 | 44.821 | 20.281 | 1.00 | 27.79 |
| ATOM | 1955 | O | ASP | 221 | 45.901 | 45.267 | 21.453 | 1.00 | 28.28 |
| ATOM | 1956 | CB | ASP | 221 | 47.746 | 44.723 | 18.645 | 1.00 | 27.76 |
| ATOM | 1957 | CG | ASP | 221 | 49.112 | 44.102 | 18.449 | 1.00 | 29.80 |
| ATOM | 1958 | OD1 | ASP | 221 | 49.405 | 43.111 | 19.147 | 1.00 | 30.61 |
| ATOM | 1959 | OD2 | ASP | 221 | 49.902 | 44.570 | 17.583 | 1.00 | 32.40 |
| ATOM | 1960 | N | VAL | 222 | 44.730 | 45.062 | 19.532 | 1.00 | 25.93 |
| ATOM | 1961 | CA | VAL | 222 | 43.588 | 45.761 | 20.109 | 1.00 | 25.63 |
| ATOM | 1962 | C | VAL | 222 | 42.893 | 45.003 | 21.279 | 1.00 | 26.39 |
| ATOM | 1963 | O | VAL | 222 | 42.539 | 45.632 | 22.285 | 1.00 | 26.70 |
| ATOM | 1964 | CB | VAL | 222 | 42.517 | 46.148 | 19.058 | 1.00 | 24.90 |
| ATOM | 1965 | CG1 | VAL | 222 | 41.313 | 46.799 | 19.773 | 1.00 | 25.51 |
| ATOM | 1966 | CG2 | VAL | 222 | 43.098 | 47.111 | 18.028 | 1.00 | 24.07 |
| ATOM | 1967 | N | ALA | 223 | 42.664 | 43.688 | 21.126 | 1.00 | 25.77 |
| ATOM | 1968 | CA | ALA | 223 | 41.954 | 42.885 | 22.148 | 1.00 | 26.96 |
| ATOM | 1969 | C | ALA | 223 | 42.728 | 42.901 | 23.503 | 1.00 | 27.41 |
| ATOM | 1970 | O | ALA | 223 | 42.141 | 42.971 | 24.555 | 1.00 | 27.99 |
| ATOM | 1971 | CB | ALA | 223 | 41.761 | 41.444 | 21.674 | 1.00 | 24.19 |
| ATOM | 1972 | N | THR | 224 | 44.042 | 42.841 | 23.440 | 1.00 | 29.50 |
| ATOM | 1973 | CA | THR | 224 | 44.885 | 42.923 | 24.635 | 1.00 | 30.83 |
| ATOM | 1974 | C | THR | 224 | 44.640 | 44.257 | 25.358 | 1.00 | 31.18 |
| ATOM | 1975 | O | THR | 224 | 44.426 | 44.267 | 26.568 | 1.00 | 31.47 |
| ATOM | 1976 | CB | THR | 224 | 46.353 | 42.749 | 24.266 | 1.00 | 31.10 |
| ATOM | 1977 | OG1 | THR | 224 | 46.515 | 41.480 | 23.611 | 1.00 | 32.84 |
| ATOM | 1978 | CG2 | THR | 224 | 47.176 | 42.692 | 25.503 | 1.00 | 32.78 |
| ATOM | 1979 | N | SER | 225 | 44.589 | 45.359 | 24.612 | 1.00 | 31.19 |
| ATOM | 1980 | CA | SER | 225 | 44.306 | 46.698 | 25.208 | 1.00 | 32.14 |
| ATOM | 1981 | C | SER | 225 | 42.957 | 46.770 | 25.930 | 1.00 | 31.64 |
| ATOM | 1982 | O | SER | 225 | 42.830 | 47.374 | 26.990 | 1.00 | 32.34 |
| ATOM | 1983 | CB | SER | 225 | 44.323 | 47.764 | 24.141 | 1.00 | 32.10 |
| ATOM | 1984 | OG | SER | 225 | 45.639 | 48.071 | 23.727 | 1.00 | 33.71 |
| ATOM | 1985 | N | LEU | 226 | 41.937 | 46.157 | 25.346 | 1.00 | 31.46 |

TABLE 11-continued

Three-Dimensional Coordinates of *Neisseria gonorrhoeae* GCYH-IB·$Mn^{2+}$
(SEQ. ID. No. 8)

| ATOM | 1986 | CA  | LEU | 226 | 40.571 | 46.154 | 25.908 | 1.00 | 31.10 |
|------|------|-----|-----|-----|--------|--------|--------|------|-------|
| ATOM | 1987 | C   | LEU | 226 | 40.437 | 45.228 | 27.121 | 1.00 | 31.71 |
| ATOM | 1988 | O   | LEU | 226 | 39.721 | 45.552 | 28.084 | 1.00 | 31.22 |
| ATOM | 1989 | CB  | LEU | 226 | 39.570 | 45.678 | 24.815 | 1.00 | 30.41 |
| ATOM | 1990 | CG  | LEU | 226 | 39.527 | 46.532 | 23.517 | 1.00 | 28.65 |
| ATOM | 1991 | CD1 | LEU | 226 | 38.528 | 45.947 | 22.550 | 1.00 | 26.39 |
| ATOM | 1992 | CD2 | LEU | 226 | 39.099 | 47.926 | 23.861 | 1.00 | 26.47 |
| ATOM | 1993 | N   | ILE | 227 | 41.083 | 44.063 | 27.053 | 1.00 | 32.52 |
| ATOM | 1994 | CA  | ILE | 227 | 41.131 | 43.158 | 28.223 | 1.00 | 34.66 |
| ATOM | 1995 | C   | ILE | 227 | 41.711 | 43.844 | 29.449 | 1.00 | 34.68 |
| ATOM | 1996 | O   | ILE | 227 | 41.198 | 43.695 | 30.533 | 1.00 | 36.02 |
| ATOM | 1997 | CB  | ILE | 227 | 41.928 | 41.865 | 27.959 | 1.00 | 35.04 |
| ATOM | 1998 | CG1 | ILE | 227 | 41.168 | 41.012 | 26.956 | 1.00 | 34.54 |
| ATOM | 1999 | CG2 | ILE | 227 | 42.124 | 41.094 | 29.307 | 1.00 | 35.53 |
| ATOM | 2000 | CD1 | ILE | 227 | 42.062 | 40.002 | 26.261 | 1.00 | 35.14 |
| ATOM | 2001 | N   | ALA | 228 | 42.764 | 44.612 | 29.247 | 1.00 | 35.83 |
| ATOM | 2002 | CA  | ALA | 228 | 43.345 | 45.463 | 30.266 | 1.00 | 36.33 |
| ATOM | 2003 | C   | ALA | 228 | 42.442 | 46.607 | 30.810 | 1.00 | 36.87 |
| ATOM | 2004 | O   | ALA | 228 | 42.849 | 47.311 | 31.733 | 1.00 | 36.87 |
| ATOM | 2005 | CB  | ALA | 228 | 44.625 | 46.053 | 29.715 | 1.00 | 35.72 |
| ATOM | 2006 | N   | ASP | 229 | 41.284 | 46.864 | 30.200 | 1.00 | 36.77 |
| ATOM | 2007 | CA  | ASP | 229 | 40.461 | 47.966 | 30.644 | 1.00 | 37.00 |
| ATOM | 2008 | C   | ASP | 229 | 39.408 | 47.270 | 31.459 | 1.00 | 38.22 |
| ATOM | 2009 | O   | ASP | 229 | 38.582 | 46.528 | 30.903 | 1.00 | 37.95 |
| ATOM | 2010 | CB  | ASP | 229 | 39.842 | 48.724 | 29.446 | 1.00 | 36.82 |
| ATOM | 2011 | CG  | ASP | 229 | 39.075 | 49.993 | 29.856 | 1.00 | 35.61 |
| ATOM | 2012 | OD1 | ASP | 229 | 38.303 | 49.990 | 30.845 | 1.00 | 32.28 |
| ATOM | 2013 | OD2 | ASP | 229 | 39.234 | 51.020 | 29.166 | 1.00 | 36.47 |
| ATOM | 2014 | N   | GLU | 240 | 38.629 | 44.311 | 9.090  | 1.00 | 26.04 |
| ATOM | 2015 | CA  | GLU | 240 | 38.563 | 43.980 | 7.677  | 1.00 | 25.79 |
| ATOM | 2016 | C   | GLU | 240 | 39.604 | 44.840 | 6.918  | 1.00 | 26.33 |
| ATOM | 2017 | O   | GLU | 240 | 39.581 | 46.097 | 7.008  | 1.00 | 26.15 |
| ATOM | 2018 | CB  | GLU | 240 | 37.133 | 44.231 | 7.133  | 1.00 | 25.72 |
| ATOM | 2019 | CG  | GLU | 240 | 36.967 | 43.804 | 5.663  | 1.00 | 25.21 |
| ATOM | 2020 | CD  | GLU | 240 | 35.532 | 43.825 | 5.146  | 1.00 | 26.43 |
| ATOM | 2021 | OE1 | GLU | 240 | 34.604 | 44.177 | 5.902  | 1.00 | 27.62 |
| ATOM | 2022 | OE2 | GLU | 240 | 35.322 | 43.447 | 3.967  | 1.00 | 26.61 |
| ATOM | 2023 | N   | ASN | 241 | 40.534 | 44.181 | 6.207  | 1.00 | 26.14 |
| ATOM | 2024 | CA  | ASN | 241 | 41.553 | 44.895 | 5.458  | 1.00 | 25.32 |
| ATOM | 2025 | C   | ASN | 241 | 41.235 | 44.729 | 3.974  | 1.00 | 25.25 |
| ATOM | 2026 | O   | ASN | 241 | 41.123 | 43.594 | 3.494  | 1.00 | 23.38 |
| ATOM | 2027 | CB  | ASN | 241 | 42.918 | 44.340 | 5.756  | 1.00 | 26.66 |
| ATOM | 2028 | CG  | ASN | 241 | 43.291 | 44.453 | 7.253  | 1.00 | 29.90 |
| ATOM | 2029 | OD1 | ASN | 241 | 44.408 | 44.107 | 7.640  | 1.00 | 36.12 |
| ATOM | 2030 | ND2 | ASN | 241 | 42.386 | 44.967 | 8.072  | 1.00 | 27.28 |
| ATOM | 2031 | N   | PHE | 242 | 41.063 | 45.856 | 3.277  | 1.00 | 23.13 |
| ATOM | 2032 | CA  | PHE | 242 | 40.624 | 45.872 | 1.896  | 1.00 | 24.91 |
| ATOM | 2033 | C   | PHE | 242 | 41.842 | 45.651 | 1.023  | 1.00 | 25.54 |
| ATOM | 2034 | O   | PHE | 242 | 42.315 | 46.569 | 0.388  | 1.00 | 25.14 |
| ATOM | 2035 | CB  | PHE | 242 | 39.830 | 47.161 | 1.586  | 1.00 | 24.91 |
| ATOM | 2036 | CG  | PHE | 242 | 38.557 | 47.241 | 2.379  | 1.00 | 25.60 |
| ATOM | 2037 | CD1 | PHE | 242 | 37.410 | 46.596 | 1.922  | 1.00 | 26.78 |
| ATOM | 2038 | CD2 | PHE | 242 | 38.544 | 47.850 | 3.650  | 1.00 | 25.71 |
| ATOM | 2039 | CE1 | PHE | 242 | 36.201 | 46.620 | 2.691  | 1.00 | 29.47 |
| ATOM | 2040 | CE2 | PHE | 242 | 37.364 | 47.835 | 4.469  | 1.00 | 24.56 |
| ATOM | 2041 | CZ  | PHE | 242 | 36.193 | 47.246 | 3.984  | 1.00 | 26.86 |
| ATOM | 2042 | N   | GLU | 243 | 42.356 | 44.415 | 1.066  | 1.00 | 25.28 |
| ATOM | 2043 | CA  | GLU | 243 | 43.638 | 44.037 | 0.503  | 1.00 | 27.20 |
| ATOM | 2044 | C   | GLU | 243 | 43.891 | 44.706 | −0.844 | 1.00 | 26.88 |
| ATOM | 2045 | O   | GLU | 243 | 43.133 | 44.481 | −1.776 | 1.00 | 27.26 |
| ATOM | 2046 | CB  | GLU | 243 | 43.754 | 42.513 | 0.342  | 1.00 | 28.44 |
| ATOM | 2047 | CG  | GLU | 243 | 43.600 | 41.751 | 1.660  | 1.00 | 30.04 |
| ATOM | 2048 | CD  | GLU | 243 | 44.744 | 42.094 | 2.585  | 1.00 | 32.00 |
| ATOM | 2049 | OE1 | GLU | 243 | 44.617 | 43.037 | 3.389  | 1.00 | 30.26 |
| ATOM | 2050 | OE2 | GLU | 243 | 45.815 | 41.476 | 2.446  | 1.00 | 35.21 |
| ATOM | 2051 | N   | SER | 244 | 44.962 | 45.494 | −0.945 | 1.00 | 27.02 |
| ATOM | 2052 | CA  | SER | 244 | 45.160 | 46.296 | −2.185 | 1.00 | 27.90 |
| ATOM | 2053 | C   | SER | 244 | 45.582 | 45.442 | −3.363 | 1.00 | 28.54 |
| ATOM | 2054 | O   | SER | 244 | 45.551 | 45.912 | −4.525 | 1.00 | 29.90 |
| ATOM | 2055 | CB  | SER | 244 | 46.139 | 47.432 | −1.959 | 1.00 | 26.85 |
| ATOM | 2056 | OG  | SER | 244 | 47.413 | 46.896 | −1.761 | 1.00 | 25.99 |
| ATOM | 2057 | N   | ILE | 245 | 45.936 | 44.178 | −3.097 | 1.00 | 28.99 |
| ATOM | 2058 | CA  | ILE | 245 | 46.325 | 43.247 | −4.192 | 1.00 | 28.75 |
| ATOM | 2059 | C   | ILE | 245 | 45.263 | 42.207 | −4.615 | 1.00 | 28.22 |
| ATOM | 2060 | O   | ILE | 245 | 45.454 | 41.447 | −5.589 | 1.00 | 28.72 |
| ATOM | 2061 | CB  | ILE | 245 | 47.619 | 42.490 | −3.832 | 1.00 | 28.52 |
| ATOM | 2062 | CG1 | ILE | 245 | 47.395 | 41.571 | −2.619 | 1.00 | 27.33 |

TABLE 11-continued

Three-Dimensional Coordinates of *Neisseria gonorrhoeae* GCYH-IB·Mn$^{2+}$
(SEQ. ID. No. 8)

| ATOM | 2063 | CG2 | ILE | 245 | 48.795 | 43.496 | −3.645 | 1.00 | 26.82 |
|---|---|---|---|---|---|---|---|---|---|
| ATOM | 2064 | CD1 | ILE | 245 | 48.584 | 40.521 | −2.445 | 1.00 | 28.82 |
| ATOM | 2065 | N | HIS | 246 | 44.184 | 42.145 | −3.849 | 1.00 | 27.14 |
| ATOM | 2066 | CA | HIS | 246 | 43.062 | 41.280 | −4.132 | 1.00 | 26.06 |
| ATOM | 2067 | C | HIS | 246 | 41.827 | 42.109 | −4.349 | 1.00 | 26.53 |
| ATOM | 2068 | O | HIS | 246 | 41.870 | 43.350 | −4.164 | 1.00 | 25.05 |
| ATOM | 2069 | CB | HIS | 246 | 42.806 | 40.379 | −2.962 | 1.00 | 26.37 |
| ATOM | 2070 | CG | HIS | 246 | 43.931 | 39.463 | −2.686 | 1.00 | 27.22 |
| ATOM | 2071 | ND1 | HIS | 246 | 44.492 | 39.344 | −1.432 | 1.00 | 29.18 |
| ATOM | 2072 | CD2 | HIS | 246 | 44.608 | 38.617 | −3.496 | 1.00 | 26.14 |
| ATOM | 2073 | CE1 | HIS | 246 | 45.470 | 38.459 | −1.482 | 1.00 | 27.29 |
| ATOM | 2074 | NE2 | HIS | 246 | 45.572 | 38.011 | −2.722 | 1.00 | 28.61 |
| ATOM | 2075 | N | ASN | 247 | 40.747 | 41.438 | −4.800 | 1.00 | 25.55 |
| ATOM | 2076 | CA | ASN | 247 | 39.419 | 42.091 | −4.806 | 1.00 | 25.30 |
| ATOM | 2077 | C | ASN | 247 | 38.497 | 41.540 | −3.718 | 1.00 | 25.63 |
| ATOM | 2078 | O | ASN | 247 | 37.262 | 41.603 | −3.835 | 1.00 | 24.99 |
| ATOM | 2079 | CB | ASN | 247 | 38.719 | 42.052 | −6.211 | 1.00 | 24.56 |
| ATOM | 2080 | CG | ASN | 247 | 37.661 | 43.139 | −6.348 | 1.00 | 25.15 |
| ATOM | 2081 | OD1 | ASN | 247 | 37.853 | 44.249 | −5.856 | 1.00 | 27.25 |
| ATOM | 2082 | ND2 | ASN | 247 | 36.531 | 42.826 | −6.973 | 1.00 | 25.75 |
| ATOM | 2083 | N | HIS | 248 | 39.094 | 41.004 | −2.644 | 1.00 | 24.93 |
| ATOM | 2084 | CA | HIS | 248 | 38.331 | 40.606 | −1.484 | 1.00 | 24.20 |
| ATOM | 2085 | C | HIS | 248 | 39.165 | 41.050 | −0.265 | 1.00 | 24.68 |
| ATOM | 2086 | O | HIS | 248 | 40.280 | 41.561 | −0.416 | 1.00 | 23.64 |
| ATOM | 2087 | CB | HIS | 248 | 38.116 | 39.080 | −1.470 | 1.00 | 24.81 |
| ATOM | 2088 | CG | HIS | 248 | 39.397 | 38.297 | −1.527 | 1.00 | 22.23 |
| ATOM | 2089 | ND1 | HIS | 248 | 40.078 | 37.886 | −0.404 | 1.00 | 26.19 |
| ATOM | 2090 | CD2 | HIS | 248 | 40.115 | 37.849 | −2.579 | 1.00 | 22.16 |
| ATOM | 2091 | CE1 | HIS | 248 | 41.186 | 37.259 | −0.757 | 1.00 | 21.82 |
| ATOM | 2092 | NE2 | HIS | 248 | 41.208 | 37.186 | −2.077 | 1.00 | 24.48 |
| ATOM | 2093 | N | SER | 249 | 38.626 | 40.823 | 0.930 | 1.00 | 24.78 |
| ATOM | 2094 | CA | SER | 249 | 39.213 | 41.375 | 2.180 | 1.00 | 24.32 |
| ATOM | 2095 | C | SER | 249 | 39.808 | 40.290 | 3.013 | 1.00 | 24.05 |
| ATOM | 2096 | O | SER | 249 | 39.310 | 39.195 | 2.945 | 1.00 | 25.10 |
| ATOM | 2097 | CB | SER | 249 | 38.100 | 42.059 | 2.967 | 1.00 | 23.81 |
| ATOM | 2098 | OG | SER | 249 | 37.687 | 43.271 | 2.322 | 1.00 | 24.81 |
| ATOM | 2099 | N | ALA | 250 | 40.875 | 40.574 | 3.763 | 1.00 | 24.15 |
| ATOM | 2100 | CA | ALA | 250 | 41.299 | 39.754 | 4.900 | 1.00 | 24.78 |
| ATOM | 2101 | C | ALA | 250 | 40.460 | 40.198 | 6.086 | 1.00 | 25.30 |
| ATOM | 2102 | O | ALA | 250 | 40.141 | 41.384 | 6.212 | 1.00 | 25.56 |
| ATOM | 2103 | CB | ALA | 250 | 42.799 | 39.978 | 5.181 | 1.00 | 25.32 |
| ATOM | 2104 | N | TYR | 251 | 40.095 | 39.261 | 6.971 | 1.00 | 24.61 |
| ATOM | 2105 | CA | TYR | 251 | 39.171 | 39.541 | 8.041 | 1.00 | 24.59 |
| ATOM | 2106 | C | TYR | 251 | 39.481 | 38.699 | 9.294 | 1.00 | 25.35 |
| ATOM | 2107 | O | TYR | 251 | 39.807 | 37.517 | 9.169 | 1.00 | 25.44 |
| ATOM | 2108 | CB | TYR | 251 | 37.739 | 39.228 | 7.534 | 1.00 | 25.31 |
| ATOM | 2109 | CG | TYR | 251 | 36.650 | 39.348 | 8.575 | 1.00 | 24.55 |
| ATOM | 2110 | CD1 | TYR | 251 | 36.232 | 40.589 | 9.035 | 1.00 | 23.76 |
| ATOM | 2111 | CD2 | TYR | 251 | 36.033 | 38.192 | 9.120 | 1.00 | 27.05 |
| ATOM | 2112 | CE1 | TYR | 251 | 35.218 | 40.706 | 10.015 | 1.00 | 23.94 |
| ATOM | 2113 | CE2 | TYR | 251 | 35.009 | 38.299 | 10.113 | 1.00 | 26.38 |
| ATOM | 2114 | CZ | TYR | 251 | 34.626 | 39.548 | 10.547 | 1.00 | 25.70 |
| ATOM | 2115 | OH | TYR | 251 | 33.644 | 39.657 | 11.508 | 1.00 | 30.46 |
| ATOM | 2116 | N | ALA | 252 | 39.332 | 39.252 | 10.484 | 1.00 | 25.78 |
| ATOM | 2117 | CA | ALA | 252 | 39.476 | 38.425 | 11.698 | 1.00 | 26.50 |
| ATOM | 2118 | C | ALA | 252 | 38.616 | 38.996 | 12.773 | 1.00 | 27.38 |
| ATOM | 2119 | O | ALA | 252 | 38.245 | 40.160 | 12.707 | 1.00 | 27.79 |
| ATOM | 2120 | CB | ALA | 252 | 40.915 | 38.388 | 12.137 | 1.00 | 25.42 |
| ATOM | 2121 | MN | MN2 | 258 | 50.065 | 40.444 | 1.837 | 1.00 | 31.39 |
| ATOM | 2122 | N1 | AZI | 261 | 48.108 | 38.620 | 2.111 | 0.50 | 29.51 |
| ATOM | 2123 | N2 | AZI | 261 | 47.484 | 38.074 | 1.282 | 0.50 | 23.78 |
| ATOM | 2124 | N3 | AZI | 261 | 47.000 | 37.552 | 0.349 | 0.50 | 33.34 |
| TER | | | | | | | | | |
| ENDMDL | | | | | | | | | |

Example 10

Metal Dependencies of GCYH-IB

Enzyme Activity Assays: All chemicals were of analytical, metal-free grade from Sigma or Fisher. All solutions were prepared with Milli-Q water (18.2 MΩ) and treated with Chelex-100 (BioRad) to remove contaminating metals. Glassware were soaked in nitric acid (10%), then EDTA (5 mM) and rinsed liberally with Chelex-treated Milli-Q water before use. Activity assays were conducted as described previously (El Yacoubi et al, 2006) using either variable concentrations of metal or EDTA (5 mM), and 0.1 mM GTP.

Apoenzyme Preparation: Metal ions were removed from *B. subtilis* and *N. gonorrhoeae* GCYH-IB by incubating the purified, recombinant protein (0.5 ml) with EDTA (5 mM, 1 hr, 21° C.) followed by dialysis thrice against a 4-liter solution of Tris-HCl (50 mM, pH 8.0), KCl (50 mM), EDTA (5 mM)

and a few grams of Chelex-100. The resulting apoenzyme was dialyzed thrice against 3 L of Tris-HCl (50 mM, pH 8.0), KCl (50 mM), and Chelex-100 to remove EDTA and passed through Chelex-100 resin (5 ml protein solution per 3 ml resin) prior to activity assays. Protein concentrations were determined spectrophotometrically.

Metal Activation Studies: The *B. subtilis* apoenzyme (2 μM) was incubated with varying concentrations (0.1 μM-4 mM) of metal chlorides (MnCl2, ZnCl2, MgCl2, NiCl2, CaCl2, CdCl2, CoCl2, CuCl2, CoCl3, FeCl3) or Fe(SO4) in standard buffer (100 mM HEPES, pH 8.0, 100 mM KCl) for 10 min at 37 C, and assayed for activity as described above. All assays involving $Fe^{2+}$ were conducted in an anaerobic chamber with degassed and N2-purged buffers.

Reconstitution of *N. gonorrhoeae* GCYH-IB with Mn: The apoenzyme was incubated in the presence of 2-7 molar equivalents of MnCl2 in standard buffer containing 2 mM DTT for 60 min at 25° C. Loosely bound metal was removed either by dialysis twice against Tris-HCl (50 mM, pH 8.0), KCl (50 mM) and DTT (1 mM) for 4 hr at 4° C., filtration on a Sephadex G-25 column, or extensive washing with buffer in an Amicon ultra-centrifugal device. The enzyme was assayed for activity as described above and the metal content analyzed by ICP-MS.

Example 11

Zinc-Dependent Regulation of GCYH-IB

Bioinformatics: Analysis of the folE/folE2 gene distribution was performed using the SEED annotation environment. The results of the analysis are provided by Table I. Candidate Zur binding sites were identified using the Genome Explorer software (Mironov et al., 2000) by scanning bacterial genomes with two PWMs constructed using the training sets of two different sets of known Zur binding sites in proteobacteria and firmicutes. Panina et al. 100 *Proc. Natl. Acad. Sci. USA*, 9912-9917 (2003).

*B. subtilis* strain construction and growth conditions: All strains were derived from the *B. subtilis* 168 trpc2attSPβwild-type strain, CU1065, and were grown in LB. Growth curves were done using a Bioscreen CMBR system for 24 hours with OD600 measurements every 10 min. Liquid overnight cultures with antibiotics were used to start pre-cultures that were diluted at mid-log to a normalized OD600 of 0.01 in a volume of 200 μl in a 100-well honeycomb microtiter plate at which point the growth curve was started. Cultures were incubated at 37° C. with shaking at 200 rpm. For selection, antibiotics were added at the following concentrations: erythromycin (1 μg/ml) and lincomycin (25 μg/ml) (for selecting for macrolide-lincosamide-streptogramin B resistance), spectinomycin (100 μg/ml), kanamycin (15 μg/ml).

Mutants in folE, folE2 and zur were constructed using long-flanking-homology polymerase chain reaction (LFH-PCR) as previously described (Butcher & Helmann, 2006). LFH-PCR and chromosomal DNA transformation were used to generate strains expressing various combinations of GCYH-I enzymes. Specifically, strain HB6788 CU1065folE::mls) lacks GCYH-IA while its GCYH-IB is repressed, but its gene is still present (designated ΔfolE). This strain was used for construction of other strains. Strain HB6791 (CU1065 folE::mls zur::kan) expresses only GCYH-IB (designated ΔfolE Δzur). Strain HB6852 (CU1065 folE::mls zur::kan folE2::spc) lacks both GCYH-I isozymes (designated ΔfolE Δzur ΔfolE2).

The invention claimed is:

1. A crystal of a GTP Cyclohydrolase Type-IB (GCYH-IB) polypeptide, wherein the GCYH-IB polypeptide comprises the amino acid sequence of SEQ ID NO: 8, wherein the GCYH-IB crystal is characterized by space group $C222_1$ and unit cell dimension values: a=91.7 Å; b=100.3 Å; and c=114.1 Å.

2. A crystal of a GCYH-IB polypeptide in complex with $Mn^{2+}$ (GCYH-IB.$Mn^{2+}$), wherein the GCYH-IB polypeptide comprises the amino acid sequence of SEQ ID NO: 8, wherein the GCYH-IB.$Mn^{2+}$ crystal is characterized by space group $C222_1$ and unit cell dimension values: a=92.2 Å; b=100.4 Å; and c=113.9 Å.

3. A method of preparing a crystal of a GCYH-IB polypeptide, comprising the steps of:
   a) preparing a crystallizable composition that comprises a solution comprising: a selenomethionine (SeMet)-labeled GCYH-IB polypeptide that comprises the amino acid sequence of SEQ ID NO: 8; 10-16% polyethylene glycol 6000; 1-1.4 M LiCl; 50 mM Tris buffer, pH 9.0; and 50 mM Tris-HCl buffer, pH 7.0,
   b) subjecting the crystallizable composition to conditions which promote crystallization, and
   c) obtaining a crystal having space group $C222_1$ and the unit cell dimension values: a=91.7 Å; b=100.3 Å; and c=114.1 Å.

4. The method of claim 3, wherein the SeMet-labeled GCYH-IB polypeptide is added to the crystallizable composition from a solution comprising 9 mg/ml of SeMet-labeled GCYH-IB polypeptide, 50 mM Tris-Acetate, 100 mM KCl, and 5 mM 2-mercaptoethanol (BME), and wherein the solution has a pH of 8.0.

5. A method of preparing a crystal of a GCYH-IB polypeptide in complex with $Mn^{2+}$ (GCYH-IB.$Mn^{2+}$), comprising the steps of:
   a) preparing a crystallizable composition that comprises a solution comprising: a GCYH-IB polypeptide that comprises the amino acid sequence of SEQ ID NO: 8; 10-16% polyethylene glycol 6000; 1-1.4 M LiCl; 50 mM Tris buffer, pH 9.0; 50 mM Tris-HCl buffer, pH 7.0; and $MnCl_2$,
   b) subjecting the crystallizable composition to conditions which promote crystallization, and
   c) obtaining a crystal that forms in space group $C222_1$ and the unit cell dimension values: a=92.2 Å; b=100.4 Å; and c=113.9 Å.

6. The method of claim 5, wherein the GCYH-IB polypeptide is added to the crystallizable composition from a solution comprising 10 mg/ml of GCYH-IB polypeptide, 50 mM Tris-HCl, 50 mM KCl, and 1 mM dithiothreitol (DTT), and 1 to 10 mM $MnCl_2$, and wherein the solution has a pH of 8.0.

* * * * *